United States Patent
Macleod et al.

(10) Patent No.: US 10,100,349 B2
(45) Date of Patent: Oct. 16, 2018

(54) METHODS OF DETERMINING POLYMORPHISMS

(71) Applicant: President and Fellows of Harvard College, Cambridge, MA (US)

(72) Inventors: Iain J. Macleod, Boston, MA (US); Christopher F. Rowley, Boston, MA (US); Max Essex, Sharon, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 110 days.

(21) Appl. No.: 15/026,031

(22) PCT Filed: Sep. 30, 2014

(86) PCT No.: PCT/US2014/058278
§ 371 (c)(1),
(2) Date: Mar. 30, 2016

(87) PCT Pub. No.: WO2015/048730
PCT Pub. Date: Apr. 2, 2015

(65) Prior Publication Data
US 2016/0244817 A1    Aug. 25, 2016

Related U.S. Application Data

(60) Provisional application No. 61/945,187, filed on Feb. 27, 2014, provisional application No. 61/884,352, filed on Sep. 30, 2013.

(51) Int. Cl.
*C12Q 1/68*   (2018.01)
*C12Q 1/6827*   (2018.01)
*C12Q 1/70*   (2006.01)

(52) U.S. Cl.
CPC ........... *C12Q 1/6827* (2013.01); *C12Q 1/703* (2013.01); *C12Q 2600/106* (2013.01); *C12Q 2600/156* (2013.01)

(58) Field of Classification Search
CPC .................................. C12Q 1/68; C07H 21/00
See application file for complete search history.

(56) References Cited

U.S. PATENT DOCUMENTS

| | | | | |
|---|---|---|---|---|
| 5,437,975 A | * | 8/1995 | McClelland | C12Q 1/6858 435/6.1 |
| 6,528,288 B2 | * | 3/2003 | Senapathy | C12Q 1/6853 435/6.1 |
| 2005/0118623 A1 | * | 6/2005 | Belousov | C12Q 1/6827 435/6.14 |
| 2005/0123980 A1 | | 6/2005 | Senapathy | |
| 2005/0196750 A1 | * | 9/2005 | Elagin | C12Q 1/6883 435/5 |
| 2006/0057561 A1 | | 3/2006 | Hart | |
| 2010/0173795 A1 | | 7/2010 | Kozal | |
| 2012/0244523 A1 | * | 9/2012 | St. John | C12Q 1/703 435/5 |

FOREIGN PATENT DOCUMENTS

EP           2322668 A2     5/2011
WO    WO 2006/031870    *  3/2006

OTHER PUBLICATIONS

Kant et al. Avian Pathology 26 :837 (1997).*
Abravaya et al. Nucleic Acids Research 23(4) :675 (Year: 1995).*
Girgis et al. Nucleic Acids Research 16(21) : 10371 (Year: 1988).*
Mack et al. PNAS 85 :6977 (Year: 1988).*
Nunberg et al., J. of Virology 63(8) : 3240 (Year: 1989).*
Rowley et al., J. of Virological Methods 149 :69 (Year: 2008).*
Saiki et al., Nature 324 :163 (Year: 1986).*
Agilent. Introduction to Quantitative PCR [online] 2012 (retrieved Apr. 13, 2015]. Available on 19-22 the internet: <http://www.google.com/url?sa=t&rct=j&q=&esrc=s&source=web&cd=5&ved=OCDwQFjAE&url=http%3A%2F%2Fwww.chem.agilent.com%2FLibrary%2Fbrochures%2FBrochure_Guide%2520to%2520QPCR_IN70200C.pdf&ei=Cv4pVc3_1M6gugSRuYDwBw&usg=AFQjCNEXAA7b7-IUJaCTcGE2ToxQPScjow&sig2=HIRxVSD8vFxIn5ttQdKBtO&bvm=bv.90491159,d.c2E>.
Buonaguro et al. Human immunodeficiency virus type 1 subtype distribution in the worldwide epidemic: pathogenetic and therapeutic implications. Oct. 2007 vol. 81 No. 19, pp. 10209-10219.
Burucoa et al.. Ouadruplex real-time PCR assay using allele-specific scorpion primers for detection of mutations conferring clarithromycin resistance to Helicobacter pylori. J Clin Microbial Jul. 2008 vol. 46 No. 7 pp. 2320-2326.

* cited by examiner

*Primary Examiner* — Ethan C Whisenant
(74) *Attorney, Agent, or Firm* — Banner & Witcoff, Ltd.

(57) ABSTRACT

Methods and compositions for determining the presence of a polymorphism at a target nucleotide position in a plurality of target nucleic acid sequences is provided.

47 Claims, 18 Drawing Sheets

Specification includes a Sequence Listing.

FIG. 3

① Probe Binding Site / 103

The fluorescent probe is a perfect match for ~63% of patient *pol* sequences. A single mismatch has the potential to completely abrogate probe binding.

Forward 100-102

Reverse 104-107

② 103

Primers that exactly match the probe sequence flank the 103 region and alter the amplicon to remove any polymorphisms not associated with drug resistance

③ 103

After a single round of PCR only one region will have been altered on separate PCR product DNA strands.

④ 103

After 10 rounds of PCR, there will be an excess of PCR amplicons that contain a nucleotide sequence flanking both sides of the 103 position that perfectly match the probe binding site

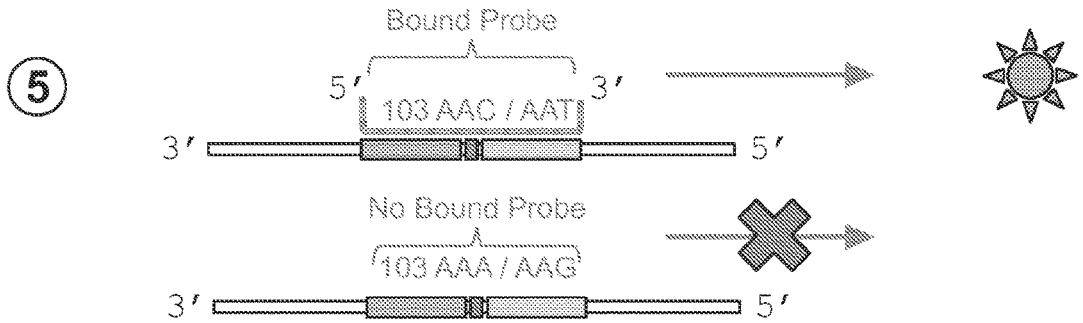

Upon binding to the perfectly matched sequence, the 5' flurophore on the probe is cleaved by the DNA polymerase enzyme and is irreversible released into the reaction whereby fluorescence is detected and quantified.

⑥

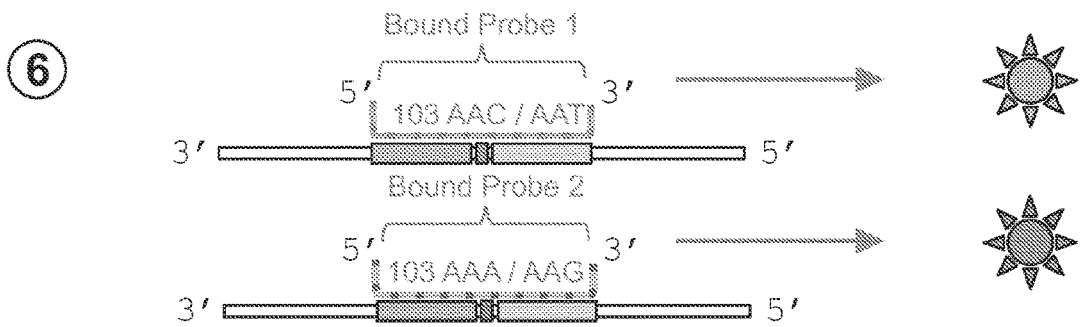

The same reaction can be multiplexed with probes specific for the wild-type and mutant targets that will be conjugated with a different fluorescent molecule. These probes will compete for the same template, and only the perfectly-matched probe will bind and emit fluorescence.

⑦

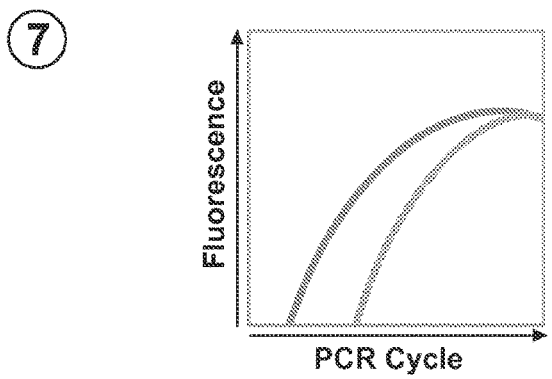

As the PCR product concentration doubles with each cycle, there is a corresponding exponential increase in fluorescence from the probes. The difference in probe fluorescence at any given cycle can be used to determine the relative abundance of the wild-type vs. mutant template.

① A primer with no 5' complementary GC sequence will form primer dimers that are extended by DNA polymerase in the qPCR and will act as templates in the next PCR cycles.

5'-TYTGGGAAGTTCAATTAGGAATACRCATCCMGCAGGKTAAAAAAG-3'
      ||||||
3'-GAAAAAATTKGGACGMCCTACRCCATAAGGATTAACTTGAAGGGTYT-5'

DNA polymerase will extend in 5'-3' direction
DNA polymerase will extend in 5'-3' direction ② A primer with a 5' complementary GC sequence will form primer dimers at the 5' that cannot be extended by DNA polymerase 8bp GC
5'-CGCGCGGCGTYTGGGAAGTTCAATTAGGAATACRCATCCMGCAGGKTAAAAAAG-3'
         ||||||
3'-GAAAAAATTKGGACGMCCTACRCCATAAGGATTAACTTGAAGGGTYTGCGCGCGC-5'
                                                   8bp GC DNA polymerase cannot extend in 3'-5' direction
DNA polymerase will extend in 5'-3' direction ③ A primer with a 5' complementary GC sequence may still form a primer dimer similar to (1) and will be extended by DNA polymerase 8bp GC
5'-CGCGCGGCGTYTGGGAAGTTCAATTAGGAATACRCATCCMGCAGGKTAAAAAAG-3'
         ||||||
3'-GAAAAAATTKGGACGMCCTACRCCATAAGGATTAACTTGAAGGGTYTGCGCGCGC-5'
                                                   8bp GC DNA polymerase will extend in 5'-3' direction
                                    Synthesized primer dimer product   8bp GC ④ The synthesized primer dimer product will contain a 3' region complementary to the 5' GC sequence 5'-CGCGCGGCGTYTGGGAAGMCCTACRCCATAAGGATGYGGTATTCCTAATTGAACTTCCCAPACGCCGCGCG-3'
         ||||||
3'-GAAAAAATTKGGACGMCCTACRCCATAAGGATTAACTTGAAGGGTYTGCGCGCGC-5'
                                                   8bp GC

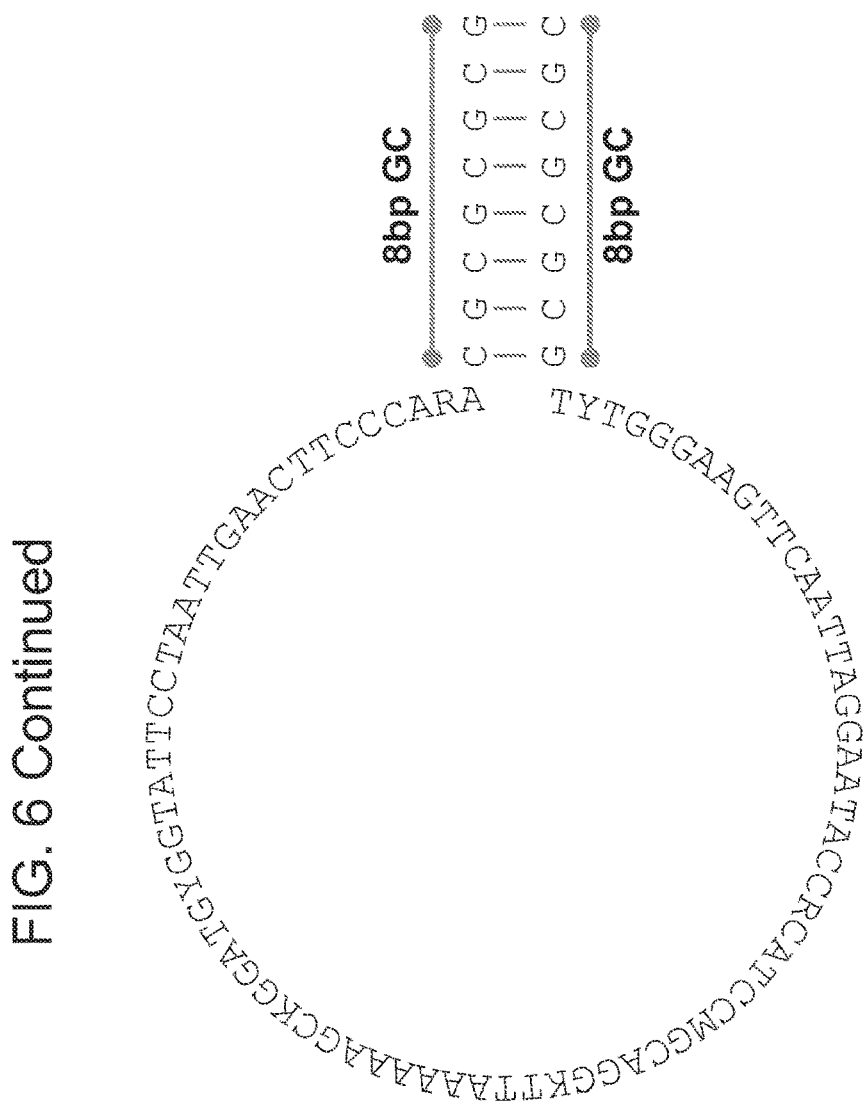

FIG. 9

| Forward Primer | 5' GGG ANG TYC ANY TAG GRA TAC CDC AYC CHG CRG GDY THA AAA AG 3' |
|---|---|
| Subtype A   | 5' ... .A. ... .T. .AT ... .A. ... .A. .T. .A. .G. .TT .A. ... 3' |
| Subtype AE  | 5' ... .A. ... .T. .AT ... .A. ... .G. .T. .A. .A. .TT .A. ... 3' |
| Subtype B   | 5' ... .A. ... .T. .AT ... .A. ... .A. .T. .C. .A. .GT .A. ... 3' |
| Subtype C   | 5' ... .G. ... .T. .AT ... .A. ... .G. .C. .A. .A. .GT .A. ... 3' |
| Subtype D   | 5' ... .A. ... .T. .AC ... .A. ... .A. .T. .T. .A. .GC .A. ... 3' |

| Reverse Primer | 3' AAA TCA GTR ACA GTR YTR GAT GTR GGD GAT GCA TAV TTV TCA GTV CCY–5' |
|---|---|
| Subtype A   | 3' ... ... .A. ... ..A C.A ... ..G ..G ... ..C ... ..T ... ..T ..T 5' |
| Subtype AE  | 3' ... ... .A. ... ..A C.A ... ..G ..A ... ... ... ..T ... ..T ..T 5' |
| Subtype B   | 3' ... ... .A. ... ..A C.G ... ..G ..T ... ... ... ..T ... ..T ..C 5' |
| Subtype C   | 3' ... ... .A. ... ..A T.A ... ..G ..G ... ... ... ..T ... ..T ..T 5' |
| Subtype D   | 3' ... ... .A. ... ..A C.G ... ..G ..T ... ... ... ..T ... ..T ..C 5' |

FIG. 11
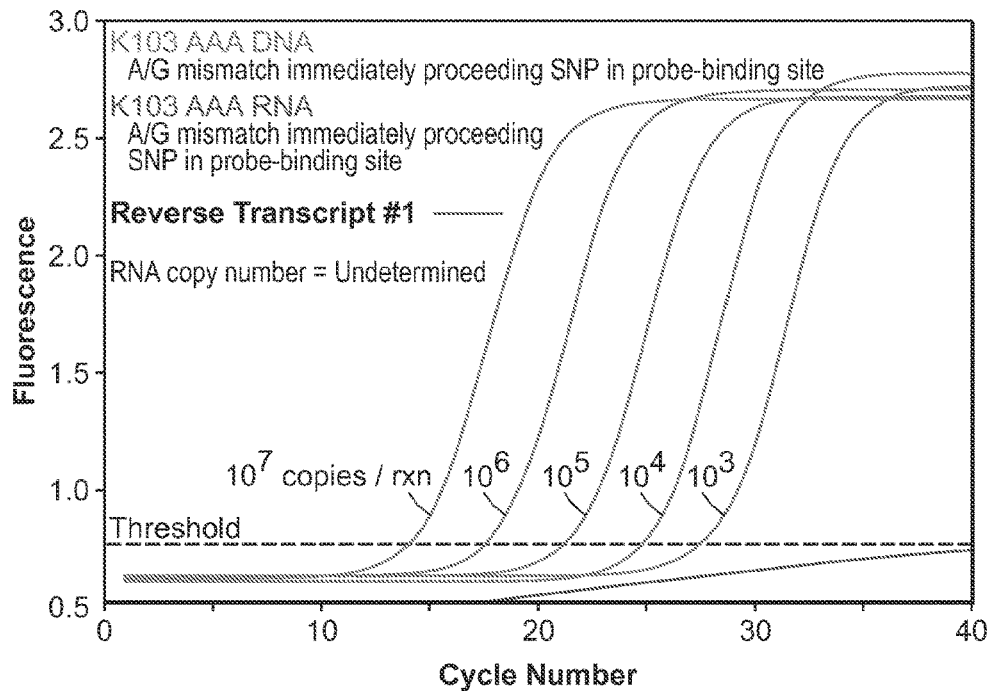
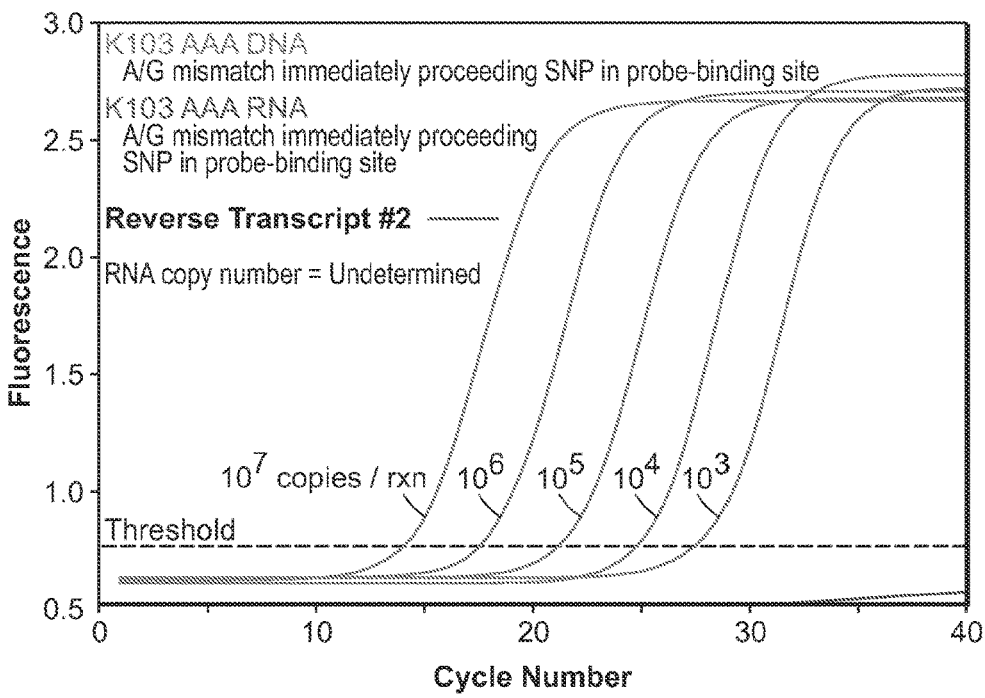

FIG. 11 Continued
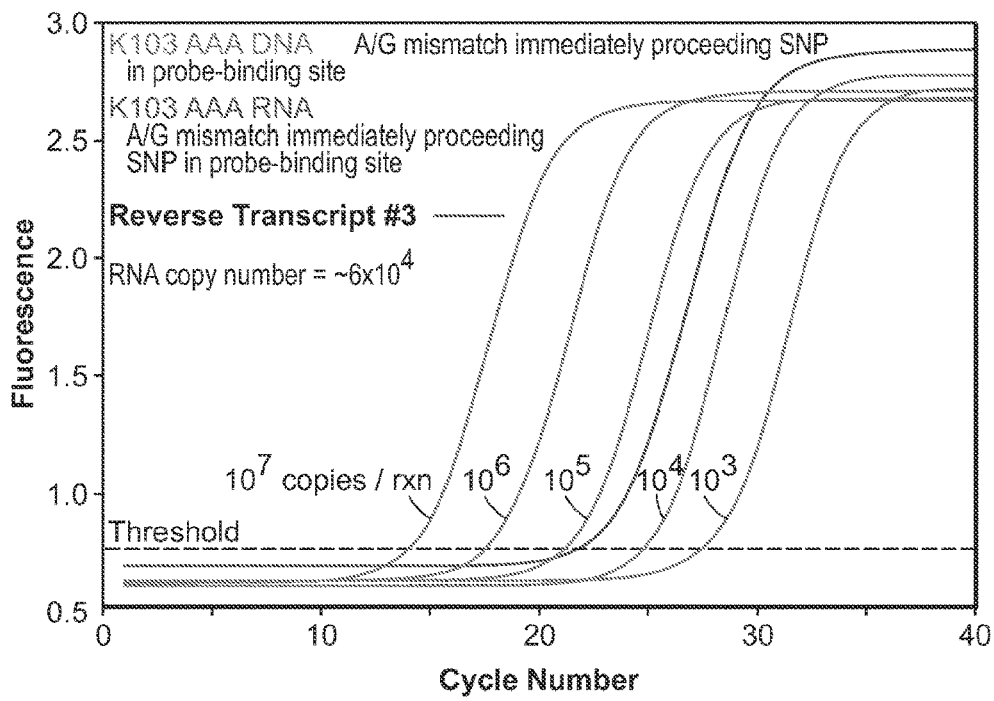
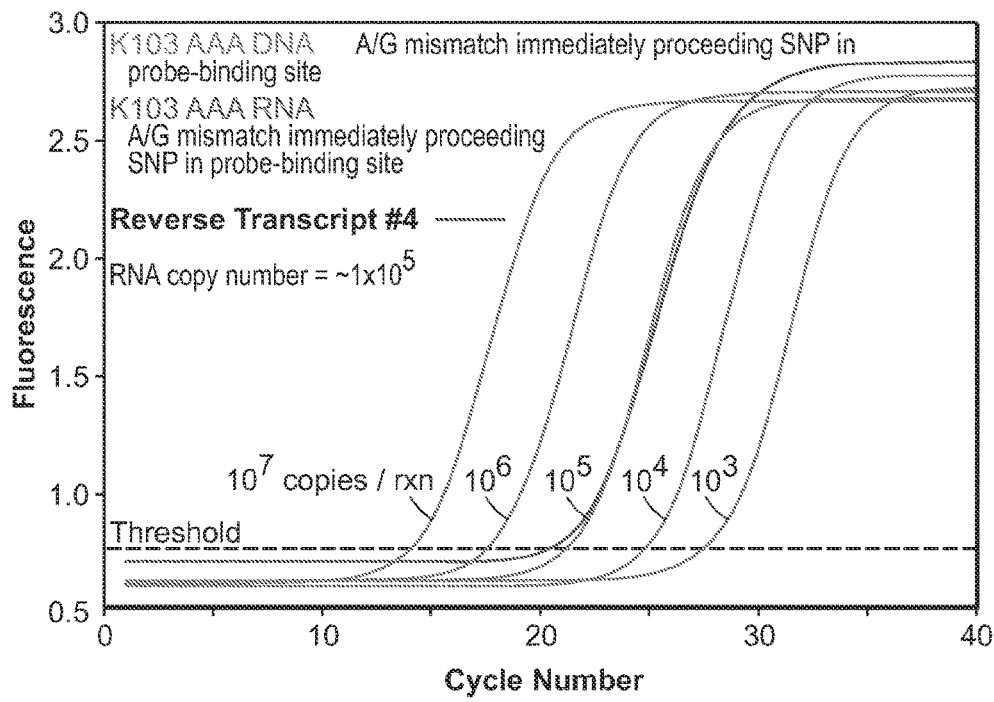

FIG. 11 Continued
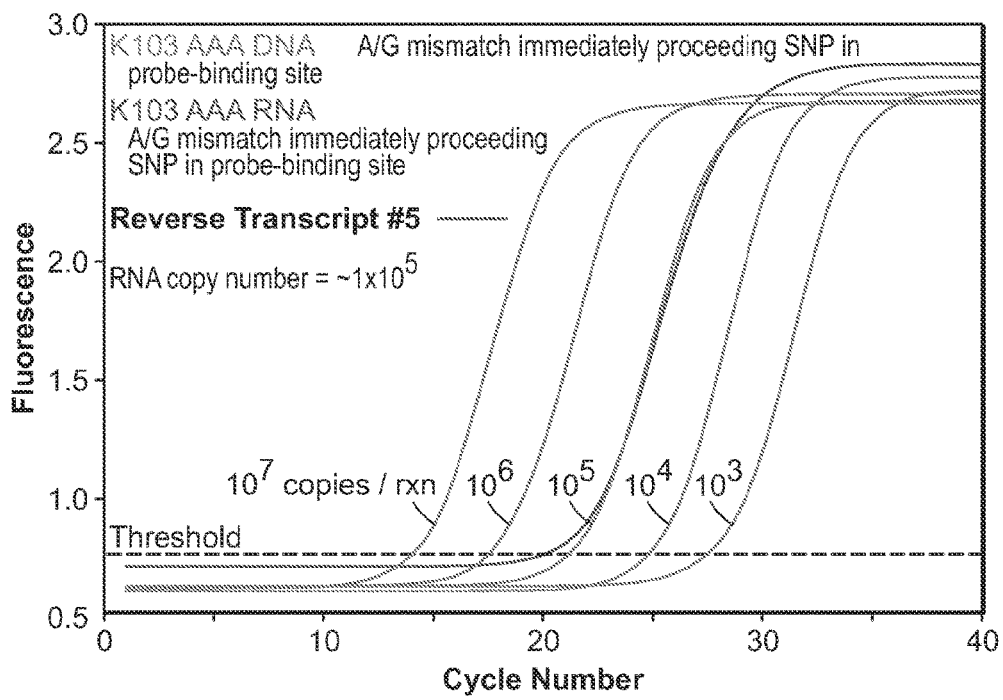
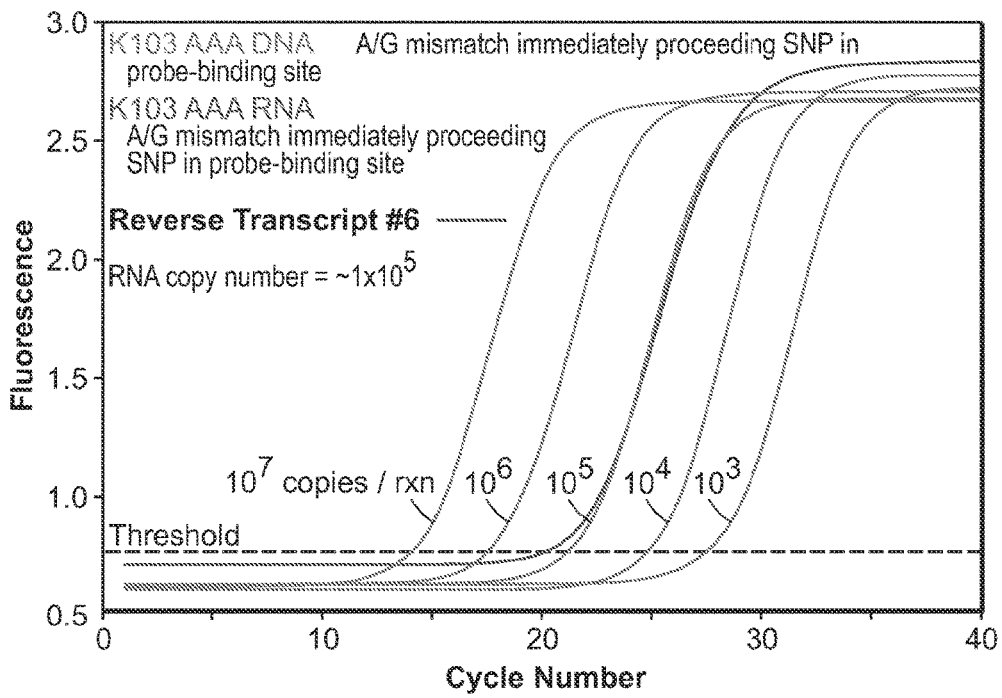

FIG. 14
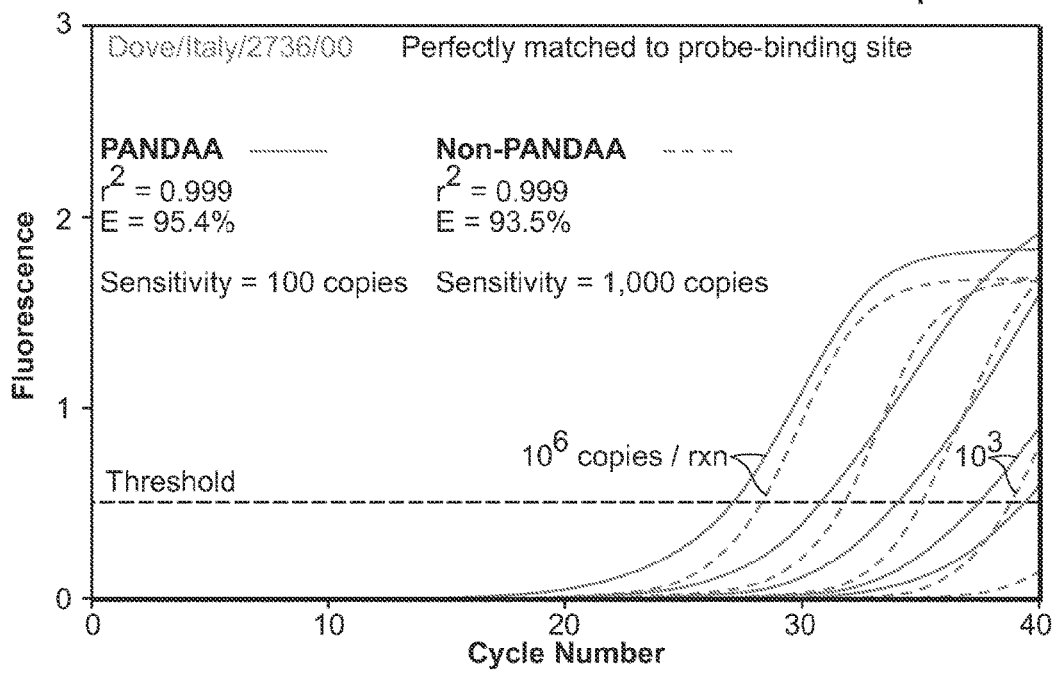
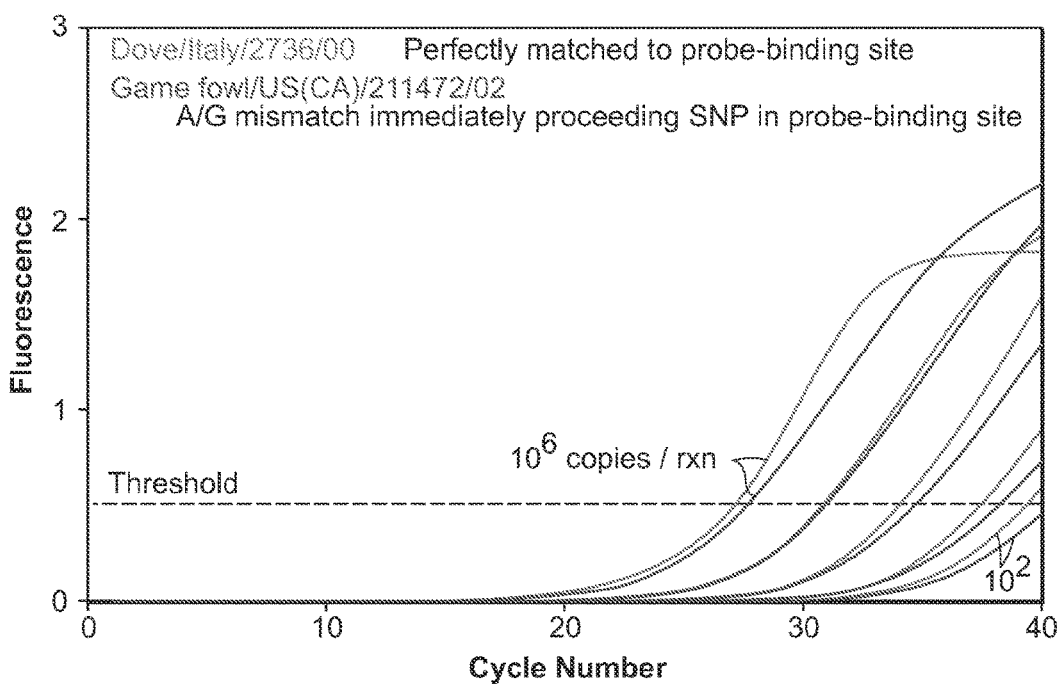

FIG. 14 Continued
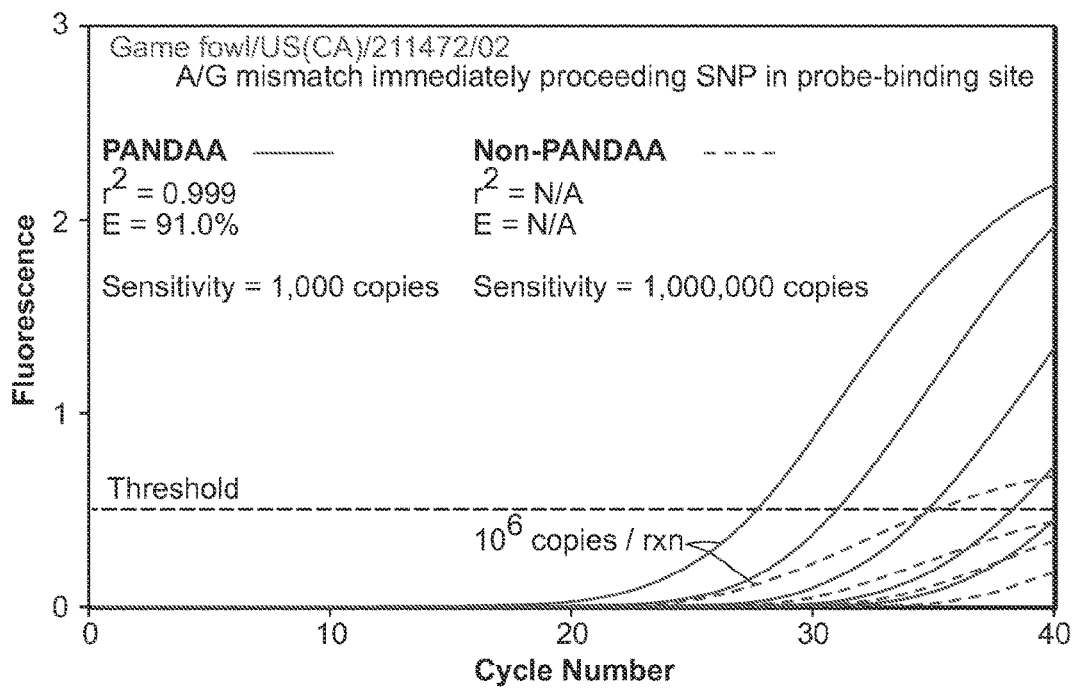
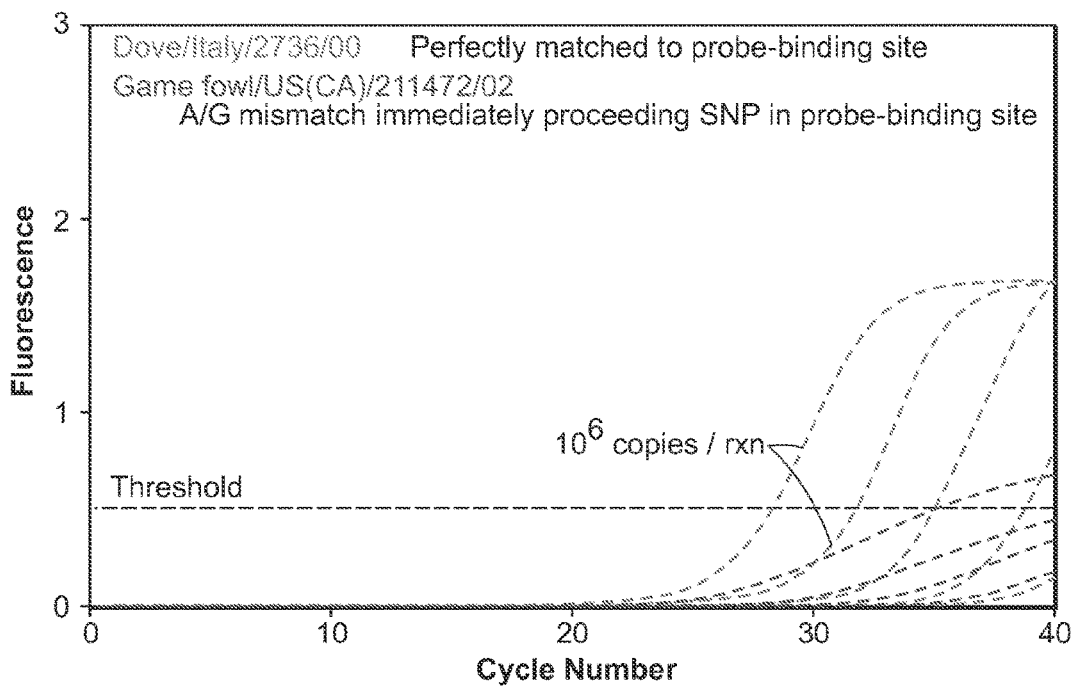

METHODS OF DETERMINING POLYMORPHISMS

RELATED APPLICATION DATA

This application is a National Stage Application under 35 U.S.C. 371 of co-pending PCT application number PCT/US14/58278 designating the United States and filed Sep. 30, 2014; which claims the benefit of U.S. provisional application No. 61/945,187 and filed Feb. 27, 2014 and U.S. provisional application No. 61/884,352 and filed Sep. 30, 2013 each of which are hereby incorporated by reference in their entireties.

REFERENCE TO SEQUENCE LISTING

This application includes as part of its subject matter a Sequence Listing electronically submitted via EFS-Web on Feb. 16, 2018, as a single text file named "Sequence_Listing_ST25.txt". The Sequence listing text file was created on Feb. 15, 2018 and is 10.9 Mb in size. The contents of the Sequence Listing are hereby incorporated by reference.

STATEMENT OF GOVERNMENT INTERESTS

This invention was made with government support under 1 R01 AI089350-03 awarded by the National Institutes of Health/National Institute of Allergy and Infectious Diseases. The government has certain rights in the invention.

BACKGROUND

Field of the Invention

Embodiments of the present disclosure relate in general to methods for determining the presence of a polymorphism at a target nucleotide position. Embodiments of the present disclosure also relate in general to methods of introducing known sequences flanking a target nucleotide position into amplicons of a target nucleic acid sequence. A probe complementary to the known sequences flanking the target nucleotide position can then be used to identify the presence of a polymorphism at the target nucleotide position.

Description of Related Art

Methods exist to identify polymorphisms in target nucleic acid sequences. See U.S. Pat. No. 7,368,242; U.S. Pat. No. 6,830,887; US 20030054339; U.S. Pat. No. 8,318,428; U.S. Pat. No. 7,115,364; U.S. Pat. No. 6,410,231; US 20120088246; US 20100009355; US 20130045881; WO1999016910; Billard et al., Appl. Environ. Microbiol. (2012); 78(4):1063-8; Hymas et al., J. Virol. Methods (2007); 142(1-2): 10-14; Rowley et al., AIDS Res. Hum. retroviruses (2010); 26(3):293-300; Rowley et al., J. Virol. methods (2008); 149(1): 69-75; Stevenson et al., J. Clin. Microbiol. (2005); 43(5):2391-98; and Whiley et al., J. Clin. Virol. (2006); 35(1): 81-83.

However, in certain replicating organisms, one or more secondary polymorphisms may be present near a primary polymorphism in a target nucleic acid sequence which may prevent or inhibit probe binding to the target probe binding site, thereby resulting in a false negative.

SUMMARY

Methods of the present disclosure take into consideration the possible presence of one or more secondary polymorphisms in a target nucleic acid sequence which may inhibit binding of a nucleic acid probe to a target probe binding site including a primary polymorphism. A primary polymorphism is a polymorphism of interest which is the target of being identified using the methods described herein. Accordingly, there is no particular limit to a particular polymorphism which is the subject of the methods described herein. Methods of the present disclosure produce amplicons having known 5' and 3' flanking regions to a target nucleotide position having a target nucleotide, such as a wild type nucleotide or a polymorphism or to a target nucleotide sequence including polymorphisms and one or more wild type nucleotides. In this manner, secondary polymorphisms on either the 5' or 3' side of the target nucleotide position or nucleotide positions in a sequence which may be present in the original target nucleic acid before amplification and which may inhibit probe binding are not present in amplicons which retain the target nucleotide or nucleotide positions in a sequence. Instead, known flanking regions are introduced into the amplicons. According to one aspect, the known flanking regions are based on the consensus or average sequence from known variants of the target genome. The probe binding site of the amplicons is therefore known or can readily be determined. In this manner, the original 5' and 3' flanking sequences in the original target nucleic acid may be referred to herein as being mutated to the determined consensus or average sequences of the 5' and 3' flanking sequences from known variants. Accordingly, the 5' and 3' flanking regions of the amplicons are known. Accordingly, the probe binding site of the amplicons is known or can be readily determined. A probe may be designed having a probe sequence which is complementary to the exact sequence of a known probe binding site which includes the target nucleotide, for example a known polymorphism, and the known 5' flanking region and the known 3' flanking region. Accordingly, one aspect of the present disclosure is directed to mutating the 5' and 3' flanking regions of a target nucleotide in a target nucleic acid to known 5' and 3' flanking regions, thereby reducing or eliminating probe binding inhibition which may result from the presence of secondary polymorphisms. In this manner, the probe is designed to be an exact match for the mutated probe binding region in the amplicons. Because the probe is an exact match for the mutated probe binding region in the amplicons, probe binding efficiency to the probe binding region is increased thereby reducing false negatives and improving identification of target nucleic acids having one or more primary polymorphisms.

Methods of the disclosure can be used to detect drug resistant or drug sensitive viruses such as, e.g., HIV-1, using genotyping. In certain aspects, methods for identifying drug resistant HIV-1 comprising identifying one or more mutations (e.g., substitutions, insertions and/or deletions) at specific amino acid positions of HIV-1 reverse transcriptase protein, HIV-1 integrase protein, and/or HIV-1 protease protein are provided. Kits for detecting mutations in HIV-1 reverse transcriptase protein, HIV-1 integrase protein, and/or HIV-1 protease protein using any of the method described herein are provided.

Further features and advantages of certain embodiments of the present invention will become more fully apparent in the following description of the embodiments and drawings thereof, and from the claims.

BRIEF DESCRIPTION OF THE DRAWINGS

FIG. 3 is a schematic of various method steps where primers are used to create amplicons having known 5' and 3' flanking regions to a target nucleotide position and a known probe sequence is used to identify the presence of a polymorphism.

FIG. 4 depicts that in putative primer-binding regions for the detection of SNPs at the 103 position of HIV-1 reverse transcriptase, variations in the primer-binding, and probe-binding, regions are shown as nucleotides A, C, T or G. Nucleotides that match the primer are given as dots. Positions within each HIV sequence that are identical to the primers/probe are shown as a dot.

FIG. 5 depicts that in putative primer-binding regions for the detection of SNPs at the fusion cleavage site of NDV, variations in the primer-binding region are shown as nucleotides A, C, T or G. Nucleotides that match the primer are given as dots. Positions within each NDV sequence that are identical to the primer are shown as a dot.

FIG. 6 depicts in schematic primer design that reduced dimer formation.

FIG. 7A is a graph showing primers designed using the majority consensus of HIV sequences.

FIG. 7B is a graph showing pan degenerate primers designed using the 95% consensus sequence.

FIG. 8A is a graph showing sensitivity of pan degenerate primers designed using the 95% consensus sequence.

FIG. 8B is a graph showing sensitivity of pan degenerate primers designed using the 95% consensus sequence in a multiplex qPCR using differentially labeled probes for the wild-type and drug resistance mutants.

FIG. 9 is a comparison of the pan degenerate primers for the detection of the K103 SNP with the corresponding primer binding regions in five of the most prevalent HIV subtypes. The adaptor regions (overlap with probe-binding regions) are shown in red, and the degenerate bases are highlighted in blue, where the mismatches are concentrated.

FIG. 10 is a graph showing that using a standard copy number of template per reaction, PANDAA methods described herein were able to detect the wild-type K103 codon with similar sensitivity across multiple HIV subtypes.

FIG. 11 are graphs showing SNP detection with various commercial reverse transcriptase enzymes.

FIG. 12 is a schematic showing that PCR product from a PANDAA reaction described herein, using primers with adaptor regions that introduced an intentional mismatch into the probe-binding region, was sequenced and that the alignment shows that the template was successfully altered to introduce an A to G mutation in the 104 codon, thus abrogating probe binding.

FIG. 13 is a schematic of an alignment of the PANDAA primers and probe with the genomes from two pathogenic NDV strains, with an additional alignment to the forward and reverse primers used by a USDA assay.

FIG. 14 are graphs showing a in the upper panels a comparison of the sensitivity and efficiency of PANDAA primers vs. USDA primers for the Dove/Italy/2736/00 and Game fowl/US(CA)/211472/02 NDV strains, respectively, and for the lower panels, a comparison per primer set for both NDV strains.

DETAILED DESCRIPTION

The present invention provides methods for the identification of one or more polymorphisms in a target nucleic acid of interest, such as a target nucleic acid from a virus, bacteria or fungus. A virus, bacteria or fungus can lead to detrimental health conditions in humans and animals, and the methods described herein can be used with a virus, bacteria or fungus associate with or otherwise infecting either a human or an animal. Polymorphisms can result in mutant strains having characteristics which differ from the wild type, such as drug resistance. It is advantageous for diagnosis or treatment of an individual or an animal to identify whether mutant strains including one or more polymorphisms of interest are present within an individual or an animal.

According to certain aspects, quickly replicating organisms such as viruses, bacteria and fungi introduce secondary polymorphisms near primary polymorphisms of interest. The secondary polymorphisms at or near a primary polymorphism of interest may reduce or inhibit probe binding at the probe binding site including the primary polymorphism of interest. Methods of the present disclosure are particularly advantageous in identifying the presence of one or more polymorphisms in a target nucleic acid in quickly replicating organisms which may have one or more secondary polymorphisms introduced into their genome. The methods disclosed herein introduce known 5' and 3' flanking regions to a target nucleotide position into amplicons of the original target nucleic acid. Since the 5' and 3' flanking regions of the original target nucleic acid are replaced with known 5' and 3' flanking regions in the amplicon, the detrimental effect of secondary polymorphisms in inhibiting probe binding to a probe binding site including the target nucleotide position is removed as the secondary polymorphisms which may be present are removed.

According to one aspect, a method is provided for determining the presence of a polymorphism at one or more of a target nucleotide position in a plurality of target nucleic acid sequences, with each target nucleic acid sequence having a sense strand sequence and an antisense strand sequence, wherein the one or more of a target nucleotide position is flanked by a 5' flanking region and a 3' flanking region in each of the sense strand sequence and the antisense strand sequence. According to one aspect, two or more or a plurality of polymorphisms may occur directly adjacent to each other or polymorphisms may be separated by one or more wild type nucleotides. Accordingly, one of skill in the art will readily understand that the methods described herein include detecting polymorphisms where two or more or a plurality of nucleotide positions have nucleotides that differ from the wild type. The 5' and 3' flanking regions flank the two or more or a plurality of polymorphisms. According to one exemplary aspect, the 5' and 3' flanking regions are immediately flanking a single nucleotide polymorphism. "Immediately flanking" refers to the flanking region being immediately adjacent to a single nucleotide polymorphism, i.e. the next nucleotide away from a single nucleotide polymorphism in either the 5' or 3' direction is a nucleotide in the 5' or 3' flanking region. According to an additional exemplary aspect, the polymorphism includes a series of nucleotide positions wherein two or more single nucleotide polymorphisms exist, i.e. a polymorphic sequence, and the 5' and 3' flanking regions are immediately flanking the polymorphic sequence. The polymorphic sequence can include between about 2 to about 5 nucleotides. According to one aspect, the end nucleotides in the polymorphic sequence are single nucleotide polymorphisms. According to one aspect, the polymorphic sequence can include one or more wild type nucleotides. According to one aspect, the end nucleotides in the polymorphic sequence are single nucleotide polymorphisms and the polymorphic sequence can include one or more wild type nucleotides.

Figure 1:
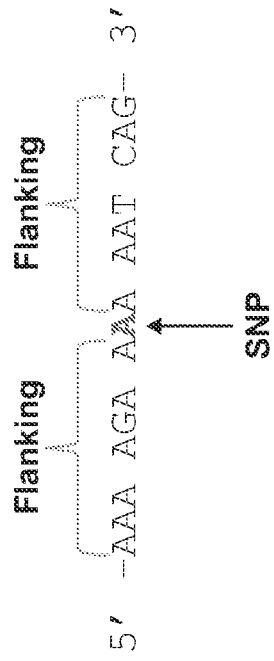
FIG. 1 is a schematic of a putative probe for the detection of the 103 SNP of HIV-1. The SNP is centered in the probe sequenced and is flanked by 7 nucleotides.
Figure 2:
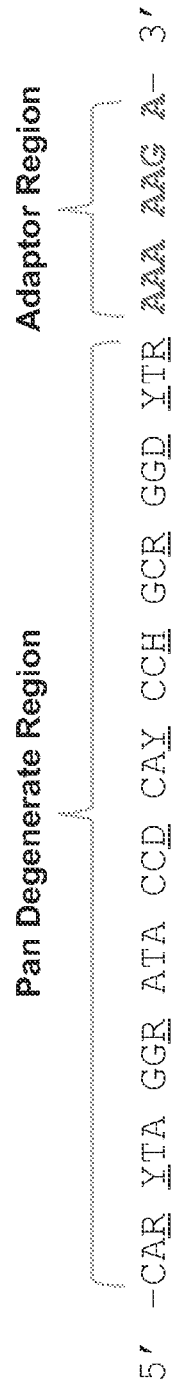
FIG. 2 is a schematic of a basic design of a primer for the pan degenerate amplification and adaptation assay described herein which includes a degenerate region that is complementary to multiple related polymorphic templates (i.e., a pan degenerate region), and an adaptor region that matches the probe-binding region.

The target nucleic acid sequences are amplified to produce amplicons using a forward primer and a reverse primer. The forward primer includes a 3' adaptor region. The 3' adaptor region is a determined consensus sequence for the 5' flanking region of the sense strand. The reverse primer includes a 3' adaptor region, wherein the 3' adaptor region is complementary to a determined consensus sequence for the 3' flanking region of the sense strand. One of skill in the art will readily understand how to determine a consensus sequence based on the present disclosure.

The amplicons resulting from amplification have an amplicon sense strand and an amplicon antisense strand. The amplicon sense strand includes a probe binding site including one or more of a target nucleotide at the one or more of a target nucleotide position with a 5' flanking region being the 3' adapter region sequence of the forward primer and with a 3' flanking region being the complement of the 3' adapter region sequence of the reverse primer. The amplicon antisense strand includes a probe binding site including one or more of a target nucleotide at the one or more of a target nucleotide position with a 5' flanking region being the 3' adapter region sequence of the reverse primer and with a 3' flanking region being the complement of the 3' adaptor region of the forward primer.

The method further includes contacting the amplicons with sense-oriented nucleic acid probes including a label or antisense-oriented nucleic acid probes including a label. According to one aspect, the probes have a probe sequence identical to the complement of the probe binding site. The probes hybridize to the probe binding site of the amplicons and the label of the bound probe can be detected.

Terms and symbols of nucleic acid chemistry, biochemistry, genetics, and molecular biology used herein follow those of standard treatises and texts in the field, e.g., Komberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

Polymorphisms within the scope of the present disclosure include any desired polymorphism which can be identified using a nucleic acid probe. Polymorphisms, in general, refer to changes of a nucleotide at a single base-pair location on a nucleic acid. A polymorphism means a substitution, inversion, insertion, or deletion of one or more nucleotides at a genetic locus, or a translocation of DNA from one genetic locus to another genetic locus. In one aspect, polymorphism means one of multiple alternative nucleotide sequences that may be present at a genetic locus and that may comprise a nucleotide substitution, insertion, or deletion with respect to other sequences at the same locus. In one aspect, insertions or deletions at a genetic locus comprises the addition or the absence of from 1 to 10 nucleotides at such locus, in comparison with the same locus in another organism of a population. According to one aspect, the polymorphism is a substitution at a target nucleotide position.

Such polymorphisms can occur in organisms with highly variable genomes, such as pathogens in general. One of skill will readily understand and identify pathogens in general and those characterized with highly variable genomes. Such pathogens include such as viruses, bacteria, parasites and fungi. One of ordinary skill in the art will readily understand and appreciate that the methods described herein are not limited to any particular polymorphism, as the methods described herein are intended to determine the presence of a particular polymorphism known to those of skill in the art. Polymorphisms can readily be identified in literature in various organisms. Such organisms include pathogens in general which are well known to those of skill in the art. Target nucleic acids may include one or more primary polymorphisms. Primary polymorphisms are those which are of interest to be detected. Such primary polymorphisms may result in a change in the characteristics of the organism, such as a pathogen. However, a primary polymorphisms may not alter or change the phenotype of the organism, but may still be of interest to be detected. For organisms that quickly replicate, like viruses, bacteria, parasites and fungi, primary polymorphisms can result in drug resistance, virulent forms, and other detrimental characteristics. For organisms that quickly replicate, one or more secondary polymorphisms can also result in the genome. Secondary polymorphisms are those which are not of primary interest to be detected. One or more secondary polymorphisms are in proximity to the primary polymorphism to the extent that they are within sufficient distance to a primary polymorphism to inhibit a probe binding to a target probe binding site including the primary polymorphism. The one or more secondary polymorphisms may be in close proximity, for example within about 5 to about 10 nucleotides of the primary polymorphism. Secondary polymorphisms may not alter the characteristics or phenotype of the organism. However, secondary polymorphisms may alter the characteristics or phenotype of the organism. Secondary polymorphisms, however, can inhibit a nucleic acid probe if present in the probe binding site that includes the primary polymorphism. This is so because probes may be designed based on the known 5' and 3' flanking sequences to the target nucleotide position where a polymorphism can reside. If secondary polymorphisms are present in the 5' or 3' flanking region, the designed probe is not a perfect match for the probe binding site and the probe may fail to bind, thereby resulting in a false negative.

According to certain aspects, once an organism is selected, target nucleic acid sequences for the organism, for example a "genetic locus" or "locus", may be readily determined as being known in the literature or may be determined by sequencing methods known to those of skill in the art. Polymorphisms known to occur in the organism may also be readily determined as being known in the literature. Since the target nucleic acid sequence including a polymorphism for a particular organism is known, the 5' and 3' flanking sequences are also known or can be readily determined. A 5' flanking region is a nucleic acid sequence which lies 5' to a target nucleotide position. A 3' flanking region is a nucleic acid sequence which lies 3' to a target nucleotide position. According to one aspect, the 5' flanking region is immediately adjacent to the target nucleotide position. According to one aspect, the 3' flanking region is immediately adjacent to the target nucleotide position. From the sequence information of the target nucleotide at the target nucleotide position and the 5' and 3' flanking regions, a probe including a label can be designed as described herein. According to certain aspects, the methods are not limited to a single target nucleotide position. Rather, two or more or a plurality of nucleotide positions adjacent to one another can form a polymorphic sequence. A polymorphic sequence may be a series of nucleotides wherein two or more nucleotide positions within the series are single nucleotide polymorphisms. A polymorphic sequence may be a series of nucleotides wherein two or more nucleotide positions within the series are single nucleotide polymorphisms and wherein the polymorphic series can also include one or more wild type nucleotides. Accordingly, methods described herein may target more than one polymorphism where the polymorphic nucleotides are grouped together. For example, where there are three nucleotides of interest, i.e. three polymorphisms represented by "X", the three nucleotides, i.e. polymorphic sequence, would be grouped together and immediately flanked by the 5' and 3' flanking regions as follows: 5' flanking region ----->XXX<----- 3' flanking region. In another example, two nucleotides of interest may be separated by a nucleotide which has not changed from the wild type. The three nucleotides, i.e. polymorphic sequence, are immediately flanked by the 5' and 3' flanking regions as follows: 5' flanking region ----->X-X<----- 3' flanking region, where X represents the polymorphisms. In this example, two variable nucleotides, i.e. polymorphisms, are separated by a nucleotide that doesn't change.

"Genetic locus," or "locus" refers to a contiguous subregion or segment of a genome. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length. Usually, a particular genetic locus may be identified by its nucleotide sequence, or the nucleotide sequence, or sequences, of one or both adjacent or flanking regions. In another aspect, a genetic locus refers to the expressed nucleic acid product of a gene, such as an RNA molecule or a cDNA copy thereof.

Target nucleic acid sequences include genomic nucleic acids of a particular organism. Such target nucleic acid sequences may be single stranded or double stranded and may include a sense strand and/or an antisense strand. Such target nucleic acid sequences may be a deoxyribonucleic acid ("DNA") or a ribonucleic acid ("RNA").

The target nucleic acid sequences may be amplified using methods known to those of skill in the art. Such methods include using a polymerase, primers and nucleotides. "Amplifying" includes the production of copies of a nucleic acid molecule via repeated rounds of primed enzymatic synthesis. Amplification can take place in solution or on a support. "In situ" amplification indicates that the amplification takes place with the template nucleic acid molecule positioned on a support or a bead, rather than in solution. In situ amplification methods are described in U.S. Pat. No. 6,432,360.

Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) Cold Spring Harb. Symp. Quant. Biol. 51 Pt 1:263 and Cleary et al. (2004) Nature Methods 1:241; and U.S. Pat. Nos. 4,683,195 and 4,683,202), anchor PCR, RACE PCR, ligation chain reaction (LCR) (see, e.g., Landegran et al. (1988) Science 241:1077-1080; and Nakazawa et al. (1994) Proc. Natl. Acad. Sci. U.S.A. 91:360-364), self sustained sequence replication (Guatelli et al. (1990) Proc. Natl. Acad. Sci. U.S.A. 87:1874), transcriptional amplification system (Kwoh et al. (1989) Proc. Natl. Acad. Sci. U.S.A. 86:1173), Q-Beta Replicase (Lizardi et al. (1988) BioTechnology 6:1197), recursive PCR (Jaffe et al. (2000) J. Biol. Chem. 275:2619; and Williams et al. (2002) J. Biol. Chem. 277:7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification.

In certain exemplary embodiments, methods for amplifying nucleic acid sequences are provided. Exemplary methods for amplifying nucleic acids include the polymerase chain reaction (PCR) (see, e.g., Mullis et al. (1986) Cold Spring Harb. Symp. Quant. Biol. 51 Pt 1:263 and Cleary et al. (2004) Nature Methods 1:241; and U.S. Pat. Nos. 4,683, 195 and 4,683,202), anchor PCR, RACE PCR, ligation chain reaction (LCR) (see, e.g., Landegran et al. (1988) Science 241:1077-1080; and Nakazawa et al. (1994) Proc. Natl. Acad. Sci. U.S.A. 91:360-364), self-sustained sequence replication (Guatelli et al. (1990) Proc. Natl. Acad. Sci. U.S.A. 87:1874), transcriptional amplification system (Kwoh et al. (1989) Proc. Natl. Acad. Sci. U.S.A. 86:1173), Q-Beta Replicase (Lizardi et al. (1988) BioTechnology 6:1197), recursive PCR (Jaffe et al. (2000) J. Biol. Chem. 275:2619; and Williams et al. (2002) J. Biol. Chem. 277: 7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach* and *PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

"Oligonucleotide" or "polynucleotide," which are used synonymously, means a linear polymer of natural or modified nucleosidic monomers linked by phosphodiester bonds or analogs thereof. Accordingly the oligonucleotide or polynucleotide may be considered a polymer of natural or modified nucleotides. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers usually have a length in the range of between 3 to 36 nucleotides, also 5 to 24 nucleotides, also from 14 to 36 nucleotides. Primers within the scope of the invention include orthogonal primers, amplification primers, constructions primers and the like. Pairs of primers can flank a sequence of interest or a set of sequences of interest. Primers and probes can be degenerate in sequence. Primers within the scope of the present invention bind adjacent to a target sequence (e.g., an oligonucleotide sequence of an oligonucleotide set or a nucleic acid sequence of interest).

Primers suitable for use in the methods disclosed herein may be designed with the aid of a computer program, such as, for example, DNAWorks, Gene2Oligo, or using the parameters software described herein. Typically, primers are from about 5 to about 500, about 10 to about 100, about 10 to about 50, or about 10 to about 30 nucleotides in length. In certain exemplary embodiments, a set of primers is designed so as to have substantially similar melting temperatures to facilitate manipulation of a complex reaction mixture. The melting temperature may be influenced, for example, by primer length and nucleotide composition.

"Specific" or "specificity" in reference to the binding of one molecule to another molecule, such as a target sequence to a probe, means the recognition, contact, and formation of a stable complex between the two molecules, together with substantially less recognition, contact, or complex formation of that molecule with other molecules.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid or between an oligonucleotide probe and a probe binding site on a single stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. According to certain aspects, probes described herein have 100% complementarity with their corresponding probe binding site. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucl. Acids Res.* 12:203.

"Duplex" refers to at least two oligonucleotides and/or polynucleotides that are fully or partially complementary undergo Watson-Crick type base pairing among all or most of their nucleotides so that a stable complex is formed of a sense strand and an antisense strand. The sense strand may be identified as the strand in the 5' to 3' direction in the hybridized duplex while the antisense strand may be identified as the strand in the 3' to 5' direction in the hybridized duplex. The terms "annealing" and "hybridization" are used interchangeably to mean the formation of a stable duplex. In one aspect, stable duplex means that a duplex structure is not destroyed by a stringent wash, e.g., conditions including temperature of about 5° C. less that the $T_m$ of a strand of the duplex and low monovalent salt concentration, e.g., less than 0.2 M, or less than 0.1 M. "Perfectly matched" or "100% complementarity" in reference to a duplex means that the polynucleotide or oligonucleotide strands making up the duplex form a double stranded structure with one another such that every nucleotide in each strand undergoes Watson- Crick base pairing with a nucleotide in the other strand, i.e. every nucleotide in a shorter strand undergoes Watson-Crick base pairing with a nucleotide in the other longer strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* 1$^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"$T_m$" is used in reference to "melting temperature." Melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation. $T_m=81.5+0.41$ (% G+C), when a nucleic acid is in aqueous solution at 1 M NaCl (see e.g., Anderson and Young, "Quantitative Filter Hybridization," in *Nucleic Acid Hybridization* (1985). Other references (e.g., Allawi, H. T. & Santa Lucia, J., Jr., *Biochemistry* 36, 10581-94 (1997)) include alternative methods of computation which take structural and environmental, as well as sequence characteristics into account for the calculation of $T_m$.

Probes according to the present disclosure include nucleic acid sequences having a detectable label attached thereto. A probe according to the present disclosure may be referred to as a hybridization probe which is a fragment of DNA or RNA of variable length which is used in DNA or RNA samples to detect the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. According to certain aspects, the labeled probe is first denatured (by heating or under alkaline conditions such as exposure to sodium hydroxide) into single stranded DNA (ssDNA) and then hybridized to the target ssDNA (Southern blotting) or RNA (Northern blotting) immobilized on a membrane or in situ.

To detect hybridization of the probe to its target sequence, the probe is tagged (or "labeled") with a molecular marker or label, for example a fluorescent marker or other detectable moiety such as a radioactive moiety. DNA sequences or RNA transcripts that have moderate to high sequence similarity to the probe are then detected by visualizing the hybridized probe via autoradiography or other imaging techniques. Normally, either X-ray pictures are taken of the filter, or the filter is placed under UV light. Detection of sequences with moderate or high similarity depends on how stringent the hybridization conditions were applied—high stringency, such as high hybridization temperature and low salt in hybridization buffers, permits only hybridization between nucleic acid sequences that are highly similar, whereas low stringency, such as lower temperature and high salt, allows hybridization when the sequences are less similar.

Depending on the method, the probe may be synthesized using the phosphoramidite method, or it can be generated and labeled by PCR amplification or cloning. Methods of making nucleic acid probes are known to those of skill in the art. Exemplary probes include Scorpion® probes, Molecular Beacon probes, TaqMan® probes, LNA® (Locked Nucleic Acid) probes and Cycling Probe Technology (CPT). Molecular beacons according to the present disclosure include those known to exist to those of skill in the art and in the literature. Molecular beacons are hairpin-shaped nucleic acid probes functionalized with a label, such as a fluorophore, and a quencher on opposing ends. See Tyagi S, Kramer F R., Molecular beacons: probes that fluoresce upon hybridization, *Nature Biotechnology,* 14:303-8 (1996) hereby incorporated by reference in its entirety. The loop region of the probe is complimentary to a nucleic acid sequence of interest. In the absence of the target sequence, the probe retains its stem-loop structure and fluorescence is quenched. When the target sequence is bound by the loop region, the stem unfolds, affording fluorescence. Molecular beacons have been used in many capacities, including single nucleotide polymorphism (SNP) detection, real-time PCR applications, and many live cell imaging applications. See Manganelli R, Tyagi S, Smith I., Real Time PCR Using Molecular Beacons: A New Tool to Identify Point Mutations and to Analyze Gene Expression in *Mycobacterium tuberculosis, Methods in Molecular Medicine.* 54:295-310 (2001), Mhlanga M M, Vargas D Y, Fung C W, Kramer F R, Tyagi S., tRNA-linked molecular beacons for imaging mRNAs in the cytoplasm of living cells, *Nucleic Acids Research,* 33:1902-12 (2005), Rhee W J, Bao G., Simultaneous detection of mRNA and protein stem cell markers in live cells, *BMC Biotechnology,* 9:30 (2009), Santangelo P J, Nix B, Tsourkas A, Bao G., Dual FRET molecular beacons for mRNA detection in living cells, Nucleic Acids Research, 32:e57 (2004), Tsourkas A, Bao G., Shedding light on health and disease using molecular beacons, Briefings in Functional Genomics & Proteomics, 1:372-84 (2003), and Baker M B, Bao G, Searles C D., In vitro quantification of specific microRNA using molecular beacons, Nucleic Acids Research, 40:e13 (2012) each of which is hereby incorporated by refernece in its entirety.

Visually detectable markers suitable for use in the probes such as molecular beacons described herein include various enzymes, prosthetic groups, fluorescent markers, luminescent markers, bioluminescent markers, and the like. Examples of suitable fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride, phycoerythrin and the like. Examples of suitable bioluminescent markers include, but are not limited to, luciferase (e.g., bacterial, firefly, click beetle and the like), luciferin, aequorin and the like. Examples of suitable enzyme systems having visually detectable signals include, but are not limited to, galactosidases, glucorinidases, phosphatases, peroxidases, cholinesterases and the like. Other suitable markers useful for molecular beacon design and probe design in general, are known to those of skill in the art.

Methods for incorporating detectable labels into nucleic acid probes are well known. Typically, detectable labels (e.g., as hapten- or fluorochrome-conjugated deoxyribonucleotides) are incorporated into a nucleic acid probe during a polymerization or amplification step, e.g., by PCR, nick translation, random primer labeling, terminal transferase tailing (e.g., one or more labels can be added after cleavage of the primer sequence), and others (see Ausubel et al., 1997, Current Protocols In Molecular Biology, Greene Publishing and Wiley-Interscience, New York).

Fluorescent labels and their attachment to oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); Wetmur, *Critical Reviews in Biochemistry and Molecular Biology*, 26:227-259 (1991); and the like. Particular methodologies are disclosed in the following sample of references: Fung et al., U.S. Pat. No. 4,757,141; Hobbs, Jr., et al. U.S. Pat. No. 5,151,507; Cruickshank, U.S. Pat. No. 5,091,519. In one embodiment, one or more fluorescent dyes are used as labels, e.g., as disclosed by Menchen et al., U.S. Pat. No. 5,188,934 (4,7-dichlorofluorscein dyes); Begot et al., U.S. Pat. No. 5,366,860 (spectrally resolvable rhodamine dyes); Lee et al., U.S. Pat. No. 5,847,162 (4,7-dichlororhodamine dyes); Khanna et al., U.S. Pat. No. 4,318,846 (ether-substituted fluorescein dyes); Lee et al., U.S. Pat. No. 5,800,996 (energy transfer dyes); Lee et al., U.S. Pat. No. 5,066,580 (xanthine dyes): Mathies et al., U.S. Pat. No. 5,688,648 (energy transfer dyes); and the like. Labelling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. Amines can be incorporated into nucleic acid probes, and labels can be added via the amines using methods known in the art. As used herein, the term "fluorescent label" includes a signaling moiety that conveys information through the fluorescent absorption and/or emission properties of one or more molecules. Such fluorescent properties include fluorescence intensity, fluorescence life time, emission spectrum characteristics, energy transfer and the like. Exemplary labels include fluorescein amidite (FAM) and VIC which is a proprietary probe to Applera/Applied Biosystems.

Commercially available fluorescent nucleotide analogues readily incorporated into nucleic acid probes include, for example, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHODAMINE GREEN™-5-UTP, ALEXA FLUOR™ 488-5-UTP, ALEXA FLUOR™ 546-14-UTP (Molecular Probes, Inc. Eugene, Oreg.). Protocols are available for custom synthesis of nucleotides having other fluorophores. Henegariu et al., "Custom Fluorescent-Nucleotide Synthesis as an Alternative Method for Nucleic Acid Labeling," *Nature Biotechnol*. 18:345-348 (2000).

Other fluorophores available for post-synthetic attachment include, inter alia, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like) (available from Thermo Fisher Scientific, Rockford, Ill.), Texas Red (available from Molecular Probes, Inc., Eugene, Oreg.), and Cy2, Cy3.5, Cy5.5, and Cy7 (available from Amersham Biosciences, Piscataway, N.J. USA, and others).

FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes.

Detection method(s) used will depend on the particular detectable labels used in the nucleic acid probes. In certain exemplary embodiments, labels may be detected by a microscope, a spectrophotometer, a tube luminometer or plate luminometer, x-ray film, a scintillator, a fluorescence activated cell sorting (FACS) apparatus, a microfluidics apparatus or the like.

When fluorescently labeled nucleic acid probes are used, fluorescence photomicroscopy can be used to detect and record the results of hybridization using routine methods known in the art. Alternatively, digital (computer implemented) fluorescence microscopy with image-processing capability may be used.

In certain exemplary embodiments, images of fluorescently labeled nucleic acid probes are detected and recorded using a computerized imaging system such as the Applied Imaging Corporation CytoVision System (Applied Imaging Corporation, Santa Clara, Calif.) with modifications (e.g., software, Chroma 84000 filter set, and an enhanced filter wheel). Other suitable systems include a computerized imaging system using a cooled CCD camera (Photometrics, NU200 series equipped with Kodak KAF 1400 CCD) coupled to a Zeiss Axiophot microscope, with images processed as described by Ried et al. (1992) *Proc. Natl. Acad. Sci. USA* 89:1388). Other suitable imaging and analysis systems are described by Schrock et al., supra; and Speicher et al., supra.

"Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in *Flow Cytometry: Instrumentation and Data Analysis* (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

Methods described herein are useful in determining the presence of organisms having one or more polymorphisms within a population of organisms which include wild type organisms or organisms without the one or more polymorphisms. Organisms within the scope of the present disclosure include viruses, bacteria and fungi. Exemplary viruses include Influenza viruses, Hepatitis C virus, Dengue virus, West Nile virus, Ebola virus, Lassa virus and the like. One of skill will readily understand that this list is exemplary only and that other viruses are well known to and can be readily identified by those of skill in the art. Exemplary bacteria include *Staphylococcus aureus*/methicillin-resistant *S. aureus, Neisseria meningitides, Mycobacterium tuberculosis, Borrelia* species, *Streptococcus Pneumoniae, Chlamydia Trachomatis, Neisseria Gonorrhoeae* and the like. One of skill will readily understand that this list is exemplary only and that other bacteria are well known to and can be readily identified by those of skill in the art. Exemplary fungi include *Candida* species, *Aspergillus* species, *Histoplasma capsulatum, Cryptococcus neoformans, Cryptococcus gattii, Coccidioides immitis* and the like. One of skill will readily understand that this list is exemplary only and that other fungi are well known to and can be readily identified by those of skill in the art.

"Kit" refers to any system, materials or reagents for carrying out a method of the present disclosure. In the context of method described herein, a kit for identifying a particular polymorphism within a population of particular organisms may include assays, reaction reagents (e.g., primers, enzymes, etc. in the appropriate containers) and/or supporting materials (e.g., buffers, written instructions for performing the assay etc.). For example, kits include one or more enclosures (e.g., boxes) containing the relevant reaction reagents and/or supporting materials for assays or methods of the invention. Such contents may be delivered to the intended recipient together or separately. For example, a first container may contain an enzyme for use in an assay, while a second container contains primers.

In certain embodiments, methods of determining the sequence of one or more nucleic acid sequences of interest, if desired, are provided. Determination of the sequence of a nucleic acid sequence of interest can be performed using a variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, AB-SOLiD, Helicos, Polonator platforms and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmacogenomics* 1:95-100; and Shi (2001) *Clin. Chem.* 47:164-172).

According to certain aspects of the present disclosure, primers include forward primers and reverse primers. Each primer includes an adaptor region. Each primer may include a pan degenerate region. The adaptor region is a nucleic acid sequence which is the consensus sequence of the target nucleic acid of the organism of interest that is adjacent to a target nucleotide position, such as a polymorphism at the position, or a polymorphic sequence, such as a series of polymorphic nucleotides which may also include one or more wild type nucleotides. Consensus sequences can be determined using methods known to those of skill in the art. Briefly, a consensus may be constructed from the most frequent residues at each site (alignment column), so that the total fraction of rows represented by the selected residues in that column reaches at least a specified threshold. IUPAC ambiguity codes (such as R for an A or G nucleotide) are counted as fractional support for each nucleotide in the ambiguity set (A and G, in this case), thus two rows with R are counted the same as one row with A and one row with G. When more than one nucleotide is necessary to reach the desired threshold, this is represented by the best-fit ambiguity symbol in the consensus; for protein sequences, this will always be an X. In the case of ties, either all or none of the involved residues will be selected. Hence, an alignment column with only A's and G's in equal number will be represented as an R in the consensus sequence regardless of the consensus threshold. See also additional information on determining a consensus sequence at world wide website assets.geneious.com/documentation/geneious/Geneious-Manual.pdf. Software for use in determining a consensus sequence is provided with reference to Bioinformatics, 2012 Jun. 15; 28(12):1647-9. doi: 10.1093/bioinformatics/bts199, Epub 2012 Apr. 27, Geneious Basic: an integrated and extendable desktop software platform for the organization and analysis of sequence data, Kearse M, Moir R, Wilson A, Stones-Havas S, Cheung M, Sturrock S, Buxton S, Cooper A, Markowitz S, Duran C, Thierer T, Ashton B, Meintjes P, Drummond A., Biomatters Ltd., 2/76 Anzac Avenue, Auckland, 1010, New Zealand and at world wide website ncbi.nlm.nih.gov/pubmed/22543367.

For a forward primer, the adaptor region is the consensus sequence of the sense strand of the target nucleic acid of the organism that is 5' to the target nucleotide. For the reverse primer, the adaptor region is the complement of the consensus sequence of the sense strand of the target nucleic acid of the organism that is 3' to the target nucleotide. According to certain aspects, the adaptor region includes between about 5 and about 10 nucleotides or between about 6 and about 9 nucleotides. According to one aspect, the adaptor region includes about 7 nucleotides.

According to one aspect, the pan degenerate region of the probes described herein includes a nucleic acid sequence which includes one or more degenerate nucleotides. Degenerate nucleotides or bases are well known to those of skill in the art. Exemplary degenerate bases are identified herein and in the literature.

According to certain aspects, a method of determining the presence of a polymorphism at one or more of a target nucleotide position in a plurality of target nucleic acid sequences, with each target nucleic acid sequence having a sense strand sequence and an antisense strand sequence, wherein the one or more of a target nucleotide position is flanked by a 5' flanking region and a 3' flanking region in each of the sense strand sequence and the antisense strand sequence including amplifying the target nucleic acid sequences to produce amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the amplicons have a sense strand amplicon and an antisense strand amplicon, wherein the sense strand amplicon includes a probe binding site including one or more of a target nucleotide at the one or more of a target nucleotide position with a 5' flanking region being the 3' adapter region sequence of the forward primer and with a 3' flanking region being the complement of the 3' adapter region sequence of the reverse primer, wherein the antisense strand amplicon includes a probe binding site including one or more of a target nucleotide at the one or more of a target nucleotide position with a 5' flanking region being the 3' adapter region sequence of the reverse primer and with a 3' flanking region being the complement of the 3' adaptor region of the forward primer, contacting the amplicons with sense-oriented nucleic acid probes or antisense-oriented nucleic acid probes including a label and having a probe sequence identical to the complement of the probe binding site, and detecting the label of hybridized nucleic acid probes.

According to certain aspects, the forward primer includes a pan degenerate region. According to certain aspects, the reverse primer further includes a pan degenerate region.

According to certain aspects, the plurality of target nucleotide sequences is a population of viral nucleic acids, bacterial nucleic acids, or fungal nucleic acids. According to certain aspects, the viral nucleic acids are viral RNA or viral DNA. According to certain aspects, the bacterial nucleic acids are bacterial RNA or bacterial DNA. According to certain aspects, the fungal nucleic acids are fungal RNA or fungal DNA.

According to certain aspects, the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position.

According to certain aspects, the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position, wherein the polymorphism provides drug resistance.

According to certain aspects, the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position, and wherein the sense oriented nucleic acid probes or the antisense oriented nucleic acid probes include wild type probes with a first label and mutant detecting probes with a second label and where the first label and the second label are spectrally resolvable.

According to certain aspects, the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position, and wherein the sense oriented nucleic acid probes or the antisense oriented nucleic acid probes include wild type probes with a first label and mutant detecting probes with a second label and where the first label and the second label are spectrally resolvable, wherein the method further includes determining the relative amount of the wild type viral nucleic acids versus the mutated viral nucleic acids by comparing the detected labels.

According to certain aspects, the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position, and wherein the sense oriented nucleic acid probes or the antisense oriented nucleic acid probes include wild type probes with a first label and mutant detecting probes with a second label and where the first label and the second label are spectrally resolvable, wherein the method further includes determining the relative amount of the wild type viral nucleic acids versus the mutated viral nucleic acids by comparing the detected labels, wherein the relative amount is indicative of drug resistance of the population of viral nucleic acids.

According to certain aspects, the plurality of target nucleotide sequences is a population of viral nucleic acids including wild type viral nucleic acids with a wild type nucleotide at the one or more of a target nucleotide position and mutated viral nucleic acid with the polymorphism at the one or more of a target nucleotide position, and wherein the sense oriented nucleic acid probes or the antisense oriented nucleic acid probes include wild type probes with a first label and mutant detecting probes with a second label and where the first label and the second label are spectrally resolvable, wherein the method further includes determining the relative amount of the wild type viral nucleic acids versus the mutated viral nucleic acids by comparing the detected labels, wherein the relative amount is indicative of the presence of virulent versus non-virulent strains of virus.

According to certain aspects, the plurality of target nucleotide sequences is a population of viral nucleic acids with first viral nucleic acids having a first nucleotide at the one or more of a target nucleotide position indicative of a non-virulent strain of virus and mutated viral nucleic acids with the polymorphism at the one or more of a target nucleotide position indicative of a virulent strain of virus, and wherein the sense oriented nucleic acid probes or the antisense oriented nucleic acid probes include mutant detecting probes with a first label and wherein detecting the first label is indicative of the presence of the virulent strain of virus.

According to certain aspects, the forward primers and the reverse primers have constant adaptor regions and variable pan degenerate regions.

According to certain aspects, the nucleic acid probes include molecular beacons, hydrolysis probes, locked nucleic acid probes, FRET probes, scorpion probes and the like. One of skill will readily understand that this list is exemplary only and that other probes are well known to and can be readily identified by those of skill in the art.

According to certain aspects, the plurality of target nucleotide sequences is a population of HIV viral nucleic acid, HIV viral RNA, Newcastle disease viral DNA, hepatitis C viral DNA and the like. One of skill will readily understand that this list is exemplary only and that other target nucleotide sequences are well known to and can be readily identified by those of skill in the art.

According to certain aspects, the polymorphism at the one or more of a target nucleotide position is a single nucleotide polymorphism. According to certain aspects, the polymorphism at the one or more of a target nucleotide position is a substitution. According to certain aspects, the polymorphism at the target nucleotide position is a single nucleotide polymorphism. According to certain aspects, the polymorphism at the target nucleotide position is a substitution.

According to certain aspects, the 5' flanking region to the one or more of a target nucleotide position is between about 1 to about 10 nucleotides in length and wherein the 3' flanking region to the one or more of a target nucleotide position is between about 1 to about 10 nucleotides in length. According to one aspect, the 5' flanking region to the one or more of a target nucleotide position is between about 3 to about 8 nucleotides in length and wherein the 3' flanking region to the one or more of a target nucleotide position is between about 3 to about 8 nucleotides in length. According to certain aspects, the 5' flanking region to the one or more of a target nucleotide position is between about 6 to about 8 nucleotides in length and wherein the 3' flanking region to the one or more of a target nucleotide position is between about 6 to about 8 nucleotides in length. According to certain aspects, the 5' flanking region to the one or more of a target nucleotide position is about 7 nucleotides in length and wherein the 3' flanking region to the one or more of a target nucleotide position is about 7 nucleotides in length. According to one exemplary aspect, a flanking region of 10 nucleotides on either side of a primary polymorphism would designates a probe binding region of between 21 to 23 nucleotides, depending if the primary polymorphism is a substitution at 1, 2 or 3 nucleotide positions.

According to certain aspects, the sense oriented nucleic acid probe or the antisense oriented nucleic acid probe includes a complement to the nucleotide at the one or more of a target nucleotide position which is flanked by a 5' flanking region and a 3' flanking region. According to certain aspects, the sense oriented nucleic acid probe or the antisense oriented nucleic acid probe is an exact complement of the probe binding site of the amplicons.

According to certain aspects, the sense oriented nucleic acid probe or the antisense oriented nucleic acid probe is about 10 to about 20 nucleotides in length. According to certain aspects, the sense oriented nucleic acid probe or the antisense oriented nucleic acid probe is about 12 to about 15 nucleotides in length. According to certain aspects, the sense oriented nucleic acid probe or the antisense oriented nucleic acid probe is about 15 nucleotides in length.

According to certain aspects, the pan degenerate region can be any length depending on the complexity and GC content of the target nucleic acid and/or amplicon. According to one aspect, the pan degenerate region is between about 25 to about 50 nucleotides in length. According to certain aspects, the pan degenerate region is between about 28 to about 32 nucleotides in length. According to certain aspects, the pan degenerate region is about 30 nucleotides in length.

According to certain aspects, the label is a detectable label. According to certain aspects, the label is a fluorescent label. According to certain aspects, a plurality of spectrally resolvable labels are provide on a plurality of probes.

According to certain aspects, a method of mutating flanking regions of one or more of a target nucleotide position in a plurality of target nucleic acid sequences to provide a known probe binding site on amplicons, with each target nucleic acid sequence having a sense strand sequence and an antisense strand sequence, wherein the one or more of a target nucleotide position is flanked by a 5' flanking region and a 3' flanking region in each of the sense strand sequence and the antisense strand sequence including amplifying the target nucleic acid sequence to produce the amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the amplicons have the known probe binding site determined by the determined consensus sequences from the forward and reverse primers and the target nucleotide at the one or more of a target nucleotide position.

According to certain aspects, the forward primer further includes a pan degenerate region. According to certain aspects, the reverse primer further includes a pan degenerate region.

According to certain aspects, a polymorphism is present at the one or more of a target nucleotide position. According to certain aspects, a single nucleotide polymorphism is present at the one or more of a target nucleotide position.

According to certain aspects, a method of providing a known probe binding site sequence including one or more of a target nucleotide in amplicons of a plurality of target nucleic acid sequences, with each target nucleic acid sequence having a sense strand sequence and an antisense strand sequence, wherein one or more of a target nucleotide position is flanked by a 5' flanking region and a 3' flanking region in each of the sense strand sequence and the antisense strand sequence including amplifying the target nucleic acid sequence to produce the amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the known probe binding site of the amplicons is determined by the determined consensus sequences from the forward and reverse primers and the target nucleotide at the one or more of a target nucleotide position.

According to certain aspects, the forward primer further includes a pan degenerate region. According to certain aspects, the reverse primer further includes a pan degenerate region.

According to certain aspects, the one or more of a target nucleotide is a polymorphism. According to certain aspects, the one or more of a target nucleotide is a single nucleotide polymorphism.

According to certain aspects, a method of removing secondary polymorphisms flanking one or more of a target nucleotide position in a plurality of target nucleic acid sequences to provide a known probe binding site in amplicons, with each target nucleic acid sequence having a sense strand sequence and an antisense strand sequence, wherein the target nucleotide position is flanked by a 5' flanking region and a 3' flanking region in each of the sense strand sequence and the antisense strand sequence including amplifying the target nucleic acid sequence to produce the amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the amplicons have the known probe binding site determined by the determined consensus sequences from the forward and reverse primers and the target nucleotide at the one or more of a target nucleotide position.

According to certain aspects, the forward primer further includes a pan degenerate region. According to certain aspects, the reverse primer further includes a pan degenerate region.

According to certain aspects, a polymorphism is present at the one or more of a target nucleotide position. According to certain aspects, a single nucleotide polymorphism is present at the one or more of a target nucleotide position.

According to certain aspects, a method of determining drug resistance of a plurality of target nucleic acid sequences of viral nucleic acids wherein the presence of a polymorphism at one or more of a target nucleotide position indicates a drug resistant strain and wherein the viral nucleic acids including wild type viral nucleic acids, with each target nucleic acid sequence having a sense strand sequence and an antisense strand sequence, wherein the target nucleotide position is flanked by a 5' flanking region and a 3' flanking region in each of the sense strand sequence and the antisense strand sequence including amplifying the target nucleic acid sequence to produce amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the amplicons have a known probe binding site determined by the determined consensus sequences from the forward and reverse primers and the target nucleotide at the one or more of a target nucleotide position, contacting the amplicons with wild type sense oriented probes with a first label and mutant detecting probes with a second label and where the first label and the second label are spectrally resolvable, wherein the method further includes determining the relative amount of the wild type viral nucleic acids versus the mutated viral nucleic acids by comparing the detected labels of hybridized wild type sense oriented probes and hybridized mutant detecting probes, wherein the relative amount is indicative of drug resistance of the population of viral nucleic acids.

According to certain aspects, the forward primer further includes a pan degenerate region. According to certain aspects, the reverse primer further includes a pan degenerate region.

According to certain aspects, a method of characterizing mutant strains of a plurality of target nucleic acid sequences of viral nucleic acids wherein the presence of a polymorphism at one or more of a target nucleotide position indicates a mutant strain and wherein the viral nucleic acids including wild type viral nucleic acids, with each target nucleic acid sequence having a sense strand sequence and an antisense strand sequence, wherein the target nucleotide position is flanked by a 5' flanking region and a 3' flanking region in each of the sense strand sequence and the antisense strand sequence including amplifying the target nucleic acid sequence to produce amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the amplicons have a known probe binding site determined by the determined consensus sequences from the forward and reverse primers and the target nucleotide at the one or more of a target nucleotide position, contacting the amplicons with mutant detecting probes with a label, and detecting the label to indicate the presence of a mutant strain.

According to certain aspects, the forward primer further includes a pan degenerate region. According to certain aspects, the reverse primer further includes a pan degenerate region.

According to certain aspects, a probe is provided having a nucleic acid sequence identical to a target sequence of a target nucleotide, a 5' flanking region and a 3' flanking region, wherein the 5' flanking region is a consensus sequence for a 5' flanking region of a target nucleotide position in a viral nucleic acid and wherein the 3' flanking region is a consensus sequence for a 3' flanking region of the target nucleotide position in the viral nucleic acid. According to certain aspects, the target nucleotide is a polymorphism. According to certain aspects, the target nucleotide is a single nucleotide polymorphism.

According to certain aspects, a forward primer for nucleic acid amplification is provided having a 3' adaptor region, wherein the 3' adaptor region is a determined consensus sequence for a 5' flanking region of a target nucleotide position in a sense strand. According to certain aspects, the forward primer includes a pan degenerate region.

According to certain aspects, a reverse primer for nucleic acid amplification is provided having a 3' adaptor region, wherein the 3' adaptor region is complementary to a determined consensus sequence for a 3' flanking region of a target nucleotide position in a sense strand. According to certain aspects, the reverse primer includes a pan degenerate region.

According to certain aspects, primers for nucleic acid amplification are provided including a forward primer having a 3' adaptor region and a pan degenerate region, wherein the 3' adaptor region is a determined consensus sequence for a 5' flanking region of a target nucleotide position in a sense strand, and a reverse primer for nucleic acid amplification including a 3' adaptor region and a pan degenerate region, wherein the 3' adaptor region is complementary to a determined consensus sequence for a 3' flanking region of a target nucleotide position in the sense strand.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures tables and accompanying claims.

Example I

Standard Criteria for Probe Design

According to certain aspects, a molecular probe can be used in the methods described herein with the molecular probe incorporating one or more modifications that permit a high $T_m$ for short oligonucleotides. An exemplary molecular probe is a TaqMan probe with a minor grove binding protein, or a probe that includes one or more locked nucleic acids (LNAs).

An optimal length for a probe is about 12 to 15 nucleotides, but depending on the GC % of the probe sequence, the length of the probe may fall outside of this range in order to achieve a $T_m$ between 60° C. and 65° C. The $T_m$ of the probe may also fall outside of this range, but the $T_m$ at which probe sensitivity and specificity are adversely affected is determined empirically.

According to one aspect, where the target nucleotide is a single nucleotide polymorphism ("SNP"), the SNP may be placed in the center of the probe, but may also be placed towards or at the 3' end of the probe. Placement at the 5' end may be disadvantageous as mismatches in this region are more likely to be tolerated which may result in reducing probe specificity.

To maximize the probability of the probe being completely complementary for the target probe binding site, the SNP flanking regions should be chosen based on the consensus sequence of all available target/pathogen genomes.

Depending on the fluorescence detection equipment, between 4 and 6 fluorophores can be used with a plurality of probes, allowing up to 6 target-specific molecular probes per each sample, e.g. a single sample can be used to detect drug resistance polymorphisms at three different codon positions simultaneously. For example a probe with label 1 is provided that detects the wild-type nucleotide at codon A, a probe with label 2 is provided that detects the drug resistance nucleotide at codon A, a probe with label 3 is provided that detects the wild-type nucleotide at codon B, a probe with label 4 is provided that detects the drug resistance nucleotide at codon B, a probe with label 5 is provided that detects the wild-type nucleotide at codon C, and a probe with label 6 is provided that detects the drug resistance nucleotide at codon C.

Example II

Standard Criteria for Primer Design

By using forward and reverse (sense and antisense) primers that overlap at their 3' termini with the probe flanking region immediately adjacent to the SNP, and are identical/complementary to the probe sequence (whether the 3' overlapping sequence is identical/complementary depends on the orientation of the primer and probe, e.g. a forward (sense) primer will have an identical sequence at its 3' end to the 5' flanking region of a sense oriented probe, and the reverse (antisense) primer will have a complementary sequence at its 3' end to the 3' flanking region of the same sense oriented probe. Ultimately the primers will perform mutagenesis on the flanking regions of the probe-binding site, altering them such that there are no secondary polymorphisms that could impact probe hybridization.

Furthermore, the primers will attempt to bind to a highly polymorphic template containing mismatches that constrain primer/template hybridization. To account for: 1) the adaptation of the template to match the probe sequence and 2) the high degree of variability that will occur in the primer-binding sites, primer design includes an adaptor region and a pan degenerate region.

The adaptor region includes nucleotides of the primer that overlap with the site on the template/PCR amplicon where the molecular probe binds. Dependent on the orientation of the primer and probe (sense or antisense), the overlap sequence in the adaptor region will be identical to, or complementary to, the probe sequence.

The nucleotides in the adaptor region of the primer may not be complementary to the template. The purpose of the adaptor region is to mutagenize the template so that newly synthesized amplicons contain a probe-binding site that is perfectly complementary to the probe sequence.

Ultimately this compensates for any secondary polymorphisms that may be present in the probe-binding region of the template, which might otherwise prevent hybridization. By using both forward and reverse primers that perfectly match the SNP flanking regions of the probe, a schematic example of which is shown in FIG. 1, the forward and reverse primers will alter the template and subsequently provide a perfect match for the probe, without altering the SNP of interest. An exemplary process is shown and described in FIG. 3.

The 3' adaptor region of the primer may contain mismatches with the template, which are necessary for its function. Although mismatches between the 3' adaptor region of the primer and the 5' flanking region of the target nucleic acid generally prevent oligonucleotide binding, a longer primer including mixed or degenerate bases, referred to herein pan degenerate primers, can overcome this unfavorable binding. Generally speaking, if the 3' ends of the primers match the probe sequence, and the probe sequence (and therefore the primers) is mismatched to target, secondary polymorphisms could theoretically also prevent primer binding.

As generally known, longer oligonucleotides may tolerate mismatches with the target. Therefore, to compensate for the mismatches in the probe-binding region between the primers and template, the primer can be lengthened to make hybridization more favorable.

Although lengthening the primer increases the possibility of encountering additional polymorphic nucleotides, such polymorphic nucleotides are inconsequential in terms of probe hybridization as they lie outside of the probe-binding region. Also, degenerate bases are used to accommodate polymorphisms which may be present outside of probe binding site. For example, if a particular nucleotide in the primer-binding region, but not the probe-binding region, is a C in one strain and a T in another, we can introduce the base Y into the primer design. It is common practice by which to identify that a synthesized oligonucleotide will contain 50% T at that position and 50% C-essentially two identical primers would be synthesized that differ only at the single polymorphic position, resulting in a pool with a 1:1 ratio of primers containing C or T. Exemplary degenerate bases are identified in the table below and are known to those of skill in the art.

a particular position. For example: if 96% of sequences contain A at a given position, and 4% contain G, the 95% consensus will encode for A. If 94% of sequences contain A, and 6% contain G, the 95% consensus will encode R, representing the presence of both bases. With the 95% consensus, any nucleotide present at a given position with ≥5% frequency will be included in the final sequence. Other consensus sequence variations e.g. 90%, 85%, could be used, and their efficiency can be determined empirically. Accordingly, one of skill will be able to utilize a consensus sequence of various percentages so long as the primer degenerate region sufficiently binds to the template to help stabilize the binding of the adaptor region to the template, if needed. A majority consensus sequence will give one the most frequent nucleotide, at any given position on a nucleic acid strand, from an alignment of sequences from the same species. A 95% consensus sequence will provide one with the nucleotide at each position which is present in at least 95% of sequences from the same species. An 85% consensus

TABLE 1

Degenerate Bases Code Table

| Code | N | V | B | H | D | K | S | W | M | Y | R |
|---|---|---|---|---|---|---|---|---|---|---|---|
| Bases | A/C/G/T | G/A/C | G/T/C | A/T/C | G/A/T | G/T | G/C | A/T | A/C | C/T | A/G |

By analyzing sequencing databases known to those of skill in the art for particular target nucleic acids, the frequency of various polymorphisms can be calculated and where degenerate bases are to be introduced can be accurately determined. According to one aspect, a pool of degenerate primers is provided that are all identical in their 3' adaptor region to match the probe, while being polymorphic in their pan degenerate region. According to this aspect, the pan degenerate region helps to stabilize binding of the 3' adaptor region should there be mismatches between the 3' adaptor region and the template. Primers described herein having a degenerate region or sequence, which is understood to be a sequence having one or more degenerate bases, improve primer binding.

Using as an example the primer 5'-CAR YTA GGR ATA CCD CAY CCH GCR GGD YTR-3' (SEQ ID NO:19,249), the degeneracy of the primers (i.e. the number of different primer combinations that are possible using degenerate bases) is calculated by multiplying degenerate base frequency by the number of nucleotides that the degenerate base can result in. For the degeneracy of the example primer, it contains 4 different positions with R, 3 with Y, 2 with D, and 1 with H. R can be 2 nucleotides ("nts") (A or G); Y can be 2 nts (C or T); D can be 3 nts (G, A, or T); H can be 3nts (A, C, or T). Therefore, this exemplary primer has: (4×2)×(3×2)×(2×3)×(1×3)=8×6×6×3=864-fold degeneracy. As such, a synthesized primer would be a pool of 864 oligonucleotides corresponding to each of the possible combination of degenerate bases.

However, the introduction of a large number of degenerate bases may result in a primer combination that is complementary to other regions within the target genome. Such unintentional hybridization may consume reaction components, thereby reducing the efficiency of the amplification, such as by PCR, for the intended target. To address this issue according to one aspect, a consensus sequence is chosen, for example, the 95% consensus sequence is chosen—that is, the sequence representing 95% of the most frequent bases at sequence will provide one with the nucleotide at each position which is present in at least 85% of sequences from the same species.

According to one aspect, the primer and probe design advantageously avoids or reduced primer binding to probe. For example, as shown in FIG. 3, the SNP of interest is positioned in the middle of the probe. The forward and reverse primers alter different ends of the template, so there is only ever a partial overlap between the primer and the probe, with the overlap being insufficient for hybridization of the primer to the probe under hybridization conditions utilized in the method and described herein. For example, with a maximum of a 7 nucleotide match between the forward or reverse primer and probe, this length is too short to allow hybridization between oligonucleotides at the assay annealing temperature.

Given that the primers and probes compete at varying times for the same region of the target nucleic acid sequence in the methods described herein, a higher concentration of primers is used during the initial cycles of the amplification (for example by PCR) which allow the primers to bind more favorably than the probe. As the primers are depleted, the binding of the probe will increase. Also, the shorter probe may more easily hybridize to the target nucleic acid than the longer primer, so as the assay progresses the probe hybridization will increase.

According to one design consideration, the adaptor region, corresponding to the flanking regions of the probe-binding site, should be placed at the 3' termini of the forward (sense) and reverse (antisense) primers.

According to one design consideration, the sequence of the pan degenerate region should be designed to reflect the 95% consensus of target genome sequences. Alternatively, the sequence of the pan degenerate region should be designed to reflect between 80% and 95% consensus of target genome sequences.

According to one design consideration, an optimal primer $T_m$ range is between about 70° C. to about 80° C., but may vary due to primer degeneracy. One of skill will readily be able to determine a sufficient $T_m$ for a given primer sequence. A $T_m$ of the primer may be below 70° C. or above 80° C., as the $T_m$ at which probe sensitivity and specificity are adversely affected is readily determined by one of skill in the art.

According to certain aspects, homo- and hetero-dimers may form between the primers during amplification. The use of degenerate bases may increase dimer formation. Primer dimers can be extended by the DNA polymerase in a PCR reaction, leading to non-specific PCR product accumulation. In addition to consuming reaction components, primer dimer products can serve as templates—sometimes preferentially—in subsequent PCR cycles, which reduces the sensitivity of the PCR for the template of interest. See FIG. 6(1).

One variation of the primer design is the inclusion of a non-specific nucleotide sequence at the 5' terminus of the primer. The effect of this is two-fold: (1) The thermodynamics of hybridization between the 5' complementary sequences is more favorable than hybridization between primers at internal nucleotides. See FIG. 6(2). (2) Should either self-dimers or heterodimers form between the reaction primers, the reverse complement of the 5' non-specific sequence will be present at the 3' terminus of the newly synthesized molecule, which is entirely complementary to the primers present in the reaction. See FIG. 6(3) and FIG. 6(4). As intramolecular hybridization is more thermodynamically favorable than intermolecular hybridization, the product of primer dimerization should form a stem-loop structure that prevents it from further binding, and consuming, primers in the PCR reaction. See FIG. 6(5).

According to certain aspects, the 5' complementary sequence can be 4 to 10 nucleotides. An exemplary length is 5 to 8 nucleotides in length. An exemplary sequence is an 8 nucleotide palindrome CGCGCGCG. The 5' sequence can be any nucleotide sequence that is not complementary to the 5' primer-binding site of the template. A GC-rich sequence is preferable as the stem-loop structure is more likely to be stable at high assay temperatures due to the presence of three hydrogen bonds between guanine and cytidine. This also allows fewer nucleotides to be included in the 5' terminus of the primer, reducing the possibility of complementarity with the template.

Example III

Probe Design for Detection of HIV-1 K103N Polymorphism

Methods described herein are suitable for the detection of drug resistance strains in HIV-1. One of skill will readily understand that the methods described herein can also be used with other viruses such as hepatitis C virus.

The change from AAA to AAC or AAT at the 103 codon of HIV-1 reverse transcriptase confers resistance to the drug nevirapine, which is a non-nucleoside reverse transcriptase inhibitor (NNRTI) in widespread use globally. This single base change results in a substitution of lysine (K) with asparagine (N).

HIV subtypes are defined by their genetic dissimilarities, differing from one another by 10% to 12% of their nucleotides. Globally, subtype C accounts for 50% of infections, whereas subtype A accounts for 12%, subtype B accounts for 10%, subtype G accounts for 6%, and subtype D accounts for 3% of infections.

A 15 nucleotide TaqMan-MGB probe was designed to have a melting temperature ($T_m$) (the temperature at which the probe will dissociate from the target oligonucleotide) of 62° C. to 64° C. The SNP A/C/T was placed in the center of the probe, with 7 nts flanking either side of the SNP.

Given the heterogeneity of HIV genomes, the flanking sequences were determined based on the consensus (most frequently observed) nucleotides at those positions from 4,291 HIV sequences. As shown in the table below, 71.22% (n=4,291) of HIV-1 poi sequences in the Los Alamos database are identical for a 15nt region that covers the 103 SNP (AAA/C/T). 23.91% have 1 mismatch, 4.12% have 2 mismatches, and 0.58% have 3 mismatches. Only 0.16% have >3 mismatches.

Thus, the probe sequence 5'-AAA AGA AAA AAT CAG-3' (SEQ ID NO:19,250) would be a perfect match for >70% of targets. However, almost a third of strains/patients samples would return a false negative result when probing for the drug resistance SNP (A C/T).

TABLE 2

| aaaagaaAaaatcag (SEQ ID NO: 19,251) | n | freq |
|---|---|---|
| ............... | 3056 | 71.22% |
| .........G.... | 210 | 4.89% |
| .G............ | 145 | 3.38% |
| ......G....... | 121 | 2.82% |
| ...G.......... | 65 | 1.51% |
| ..C........... | 64 | 1.49% |
| .........G.... | 62 | 1.44% |
| .......G...... | 51 | 1.19% |
| .......C...... | 43 | 1.00% |
| .............A | 37 | 0.86% |

Example IV

Probe Design for Differentiation of Pathogenic and Non-Pathogenic Newcastle Disease Virus For the detection of pathogens, or differentiation between two strains, where there may be no need to quantify any genetic variability that is present in a sample, then a qualitative approach can be used. Newcastle disease virus outbreaks require the distinction between virulent and non-virulent strains, which are determined by the presence of a particular amino acid conserved in virulent strains but absent in non-virulent strains. One of skill in the art will readily envision it beneficial to identify whether other viruses are virulent or non-virulent and that the present disclosure is not limited to Newcastle disease virus.

The equipment needed for qualitative detection is less specialized, as it does not require a real-time PCR thermal cycler to constantly measure fluorescence as the reaction proceeds. By measuring background fluorescence with a small benchtop fluorometer before performing a standard PCR, the presence or absence of a change in fluorescence after PCR will give a "yes/no" answer for pathogen detection. This approach is advantageous for point-of-care diagnostics.

Newcastle disease virus (NDV) strains can be split into three pathotypes: velogenic and mesogenic, which are highly virulent, and lentogenic, which have low virulence. The presence of virulent strains requires extensive eradication of infected areas as the mortality rate is >90%. Low virulence strains only require additional monitoring as these strains generally cause subclinical disease with very low mortality.

Pathotypes can be distinguished from each other by determining the sequence of the fusion cleavage site. In virulent strains (velogenic and mesogenic), the fusion amino acid sequence is conserved as $^{112}$RRKKRF$^{117}$ (SEQ ID NO:19,252) allowing the differentiation with non-virulent strains. Current qRT-PCR tests demonstrate both efficiency and effectiveness, with good sensitivity and specificity, and can identify most but not all virulent viruses in the test panels used for validation. Upon analysis of sequences from virulent (n=2,217) and non-virulent (n=641) strains of NDV, methods described herein can differentiate between strains, including novel variants that might arise in the future, even where NDV detection may be difficult due to the genomic diversity.

The fusion cleavage point is a suitable region to target to differentiate between virulent (velogenic and mesogenic) and non-virulent (lentogenic) pathotypes. Virulent pathotypes encode a phenylalanine at the cleavage site, of which TTT/C are the only codons, while non-virulent pathotypes encode leucine, encoded by TTA/G and CTA/T/C/G.

To account for the genetic variation in codons for leucine and phenylalanine, there are six possible probes for non-virulent strains, and two for virulent strains. Using the degenerate base code, these probes can be shown as:

```
Pathogenic:
                                    (SEQ ID NO: 19,253)
AAA CGC TTY ATA GGT G Non-pathogenic:
                                    (SEQ ID NO: 19,254)
GGG CGC CTN ATA GG (SEQ ID NO: 19,255)
GGG CGC TTR ATA GG
```

The flanking regions of the probes (underlined) correspond to the most frequently observed nucleotides for pathogenic and non-pathogenic NDV, respectively. The probe for pathogenic NDV is 16 nucleotides, with a $T_m$ of 63° C. for the TTT probe and 66° C. for the TTC probe. For non-pathogenic NDV they are 14 nucleotides, with a $T_m$ range from 65° C. to 69° C. for the CTN probe, and 64° C. to 67° C. for the TTR probe.

Example V

Primer Design for Detection of HIV-1 K103N Polymorphism

Figure 4:
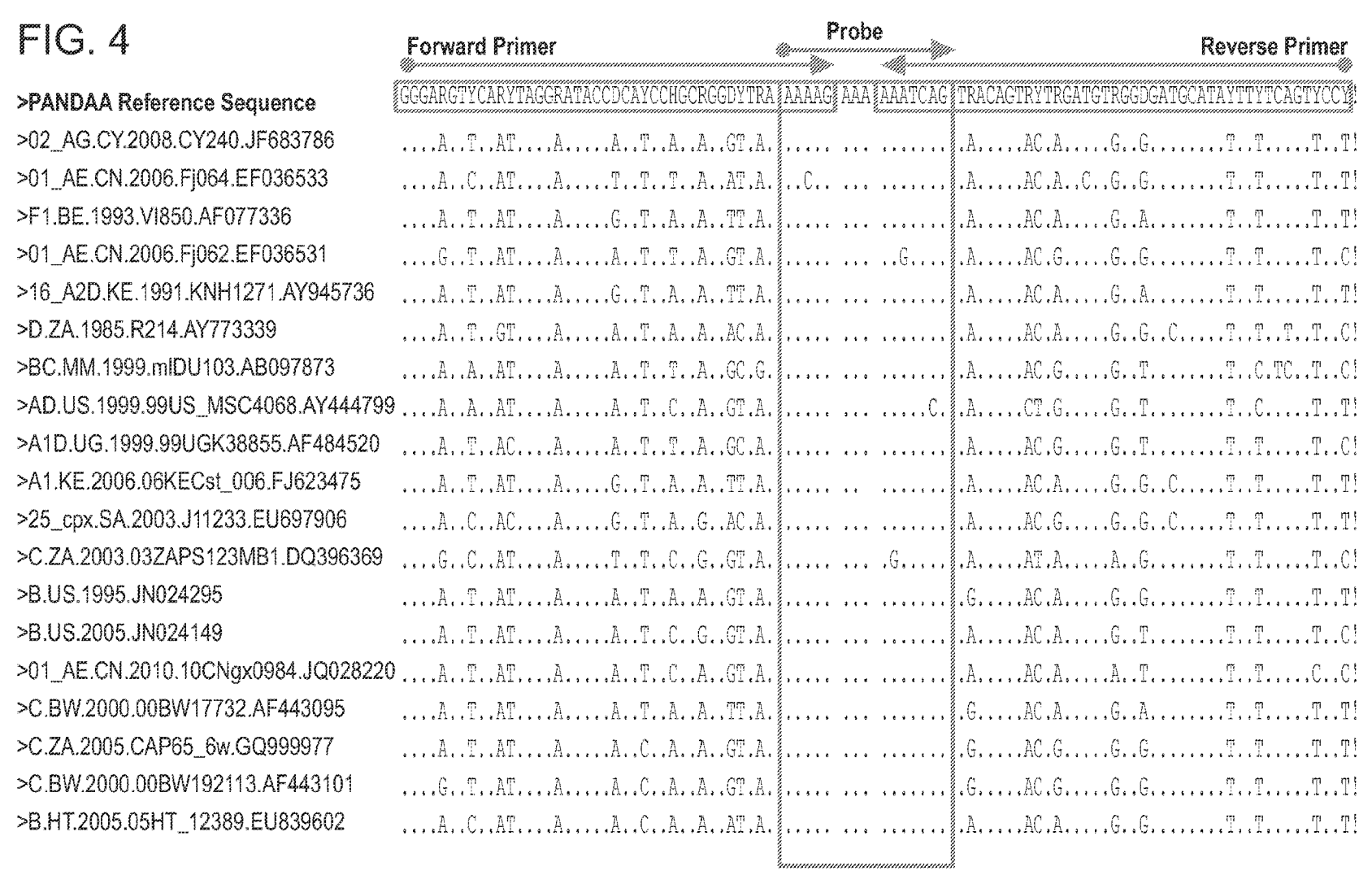

Oligonucleotide primers having an adaptor region and a degenerate region were designed to allow for the template amplification and adaptation of a plurality of HIV subtype as shown in FIG. 4.

As stated, primer design involves a 3' adaptor region overlapping the probe target region, and an extended pan degenerate region that compensates for thermodynamic instability that may arise from 3' mismatches (adaptor regions in bold). The sequences for the PDR are derived from the 95% consensus of sequences publically available from online databases:

```
K103 Forward:
                                    (SEQ ID NO: 19,256)
5'-CAR YTA GGR ATA CCD CAY CCH GCR GGD YTR A
AAAAG-3'

K103 Reverse:
                                    (SEQ ID NO: 19,257)
3'-AAATCAG TR ACA GTR YTR GAT GTR GGD GA-5'
```

For the forward primer degeneracy, it contains 4 different positions with R, 3 with Y, 2 with D, and 1 with H. R can be 2nts (A or G); Y is 2nts (C or T); D is 3nts (G, A, or T); H is 3nts (A, C, or T). Therefore, the forward primer has: (4×2)×(3×2)×(2×3)×(1×3)=8×6×6×3=864 primer variations; the reverse primer has 96 primer variations.

Example VI

Figure 5:
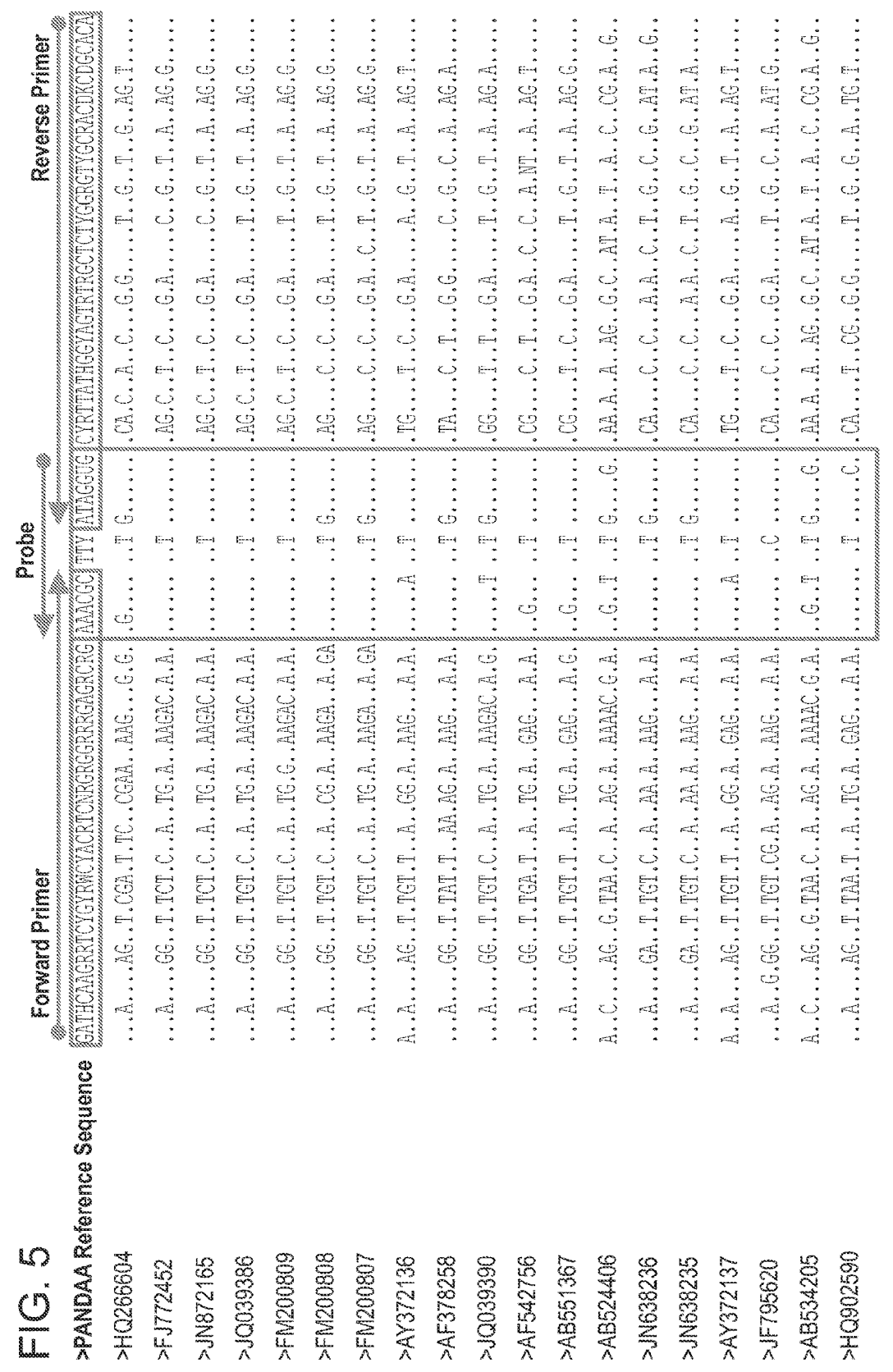

Primer Design for Differentiation of Pathogenic and Non-Pathogenic Newcastle Disease Virus Oligonucleotide primers having an adaptor region and a degenerate region were designed to allow for the template amplification and adaptation. Forward and reverse primers were selected for the template amplification and adaptation of pathogenic (velogenic and mesogenic) strains of NDV (adaptor regions in bold). See FIG. 5.

```
NDV Forward:
                                    (SEQ ID NO: 19,257)
5'-G ATH CAA GRR TCY GYR WCY ACR TCN RGR GGR RRG
AGR CRG AAACGC-3'

NDV Reverse:
                                    (SEQ ID NO: 19,258)
3'-ATAGGTG CY RTT ATH GGY AGT RTR GCT CTY GGR GTY
GCR ACD KCD GCA CA-5'
```

The forward primer has 786,432-fold degeneracy; the reverse primer has 27,648-fold degeneracy.

Example VII

Assay and Reaction Conditions

For the purposes of the experimental results presented here, the following reaction conditions were employed, although these are not absolute and can be further optimized for different conditions: A commercial qPCR master mix, Kapa probe fast qPCR kit master mix (2×) universal, was used in a 20 μl final reaction volume. The final primer concentration for both the forward (sense) and reverse (antisense) primers was 250 nM of each primer. The final probe concentration was 25 nM for each differentially labeled probe (FAM, VIC etc.)

qPCR cycling conditions were 95° C. for 3 minutes, followed by 40 to 50 cycles of 95° C. for 3 seconds and 60° C. for 60 seconds.

Fluorescence was detected during on the 60° C. step of the protocol, and readings were acquired using an ABI 7900HT real-time PCR machine. Fluorescence data were corrected for background fluorescence and the curve fitted with a five-parameter sigmoidal model.

A one-step qRT-PCR, a commercial reverse transcriptase enzyme is added to the final 20 μl reaction. Before the standard qPCR cycling conditions shown above, a 50° C. incubation for 15 minutes is performed so that a complementary DNA template can be synthesized from the input RNA template.

Example VIII

Detecting K103N Drug Resistance Polymorphism in HIV-1 pol

To confirm that the pan degenerate primers were able to bind to templates containing naturally occurring polymorphisms, a template known to contain mismatches to the primer binding sites determined by the majority consensus sequence was used:

```
Forward Standard Primer
                              (SEQ ID NO: 19,259)
5'-GGGAAGTTCAATTAGGAATACCACATCCAGCAGGGTTAAAAA
AG-3'

Template
                              (SEQ ID NO: 19,260)
5'-GGGAGGTTCAATTAGGAATACCGCACCCAGCAGGGTTAAAAA
AG-3'

Reverse Standard Primer
                              (SEQ ID NO: 19,261)
3'-AAATCAGTAACAGTACTGGATGTGGGTGATGCATATTTTCA
GTTCCT-5'

Template
                              (SEQ ID NO: 19,262)
3'-AAATCAGTAACAGTATTAGATGTGGGGGATGCATATTTTCA
GTTCCT-5'
```

The probe-binding region contained the wild-type (AAA) 103 codon, and was perfectly matched to the PANDAA ("Pan Degenerate Amplification and Adaptation) K103 probe used in the methods described herein. Using serial dilutions of the template from $10^7$ to $10^3$ copies/reaction, standard primers were less sensitive at lower template copy numbers than the pan degenerate primers. See Table 3 below.

TABLE 3

|  | Standard | PANDAA | Fold |
|---|---|---|---|
| $10^7$ | 18.99 | 20.63 | 3.10 |
| $10^6$ | 22.27 | 23.89 | 3.08 |
| $10^5$ | 26.07 | 27.36 | 2.45 |
| $10^4$ | 31.69 | 31.16 | −1.45 |
| $10^3$ | 40.47 | 34.87 | −48.72 |

Figure 7A:
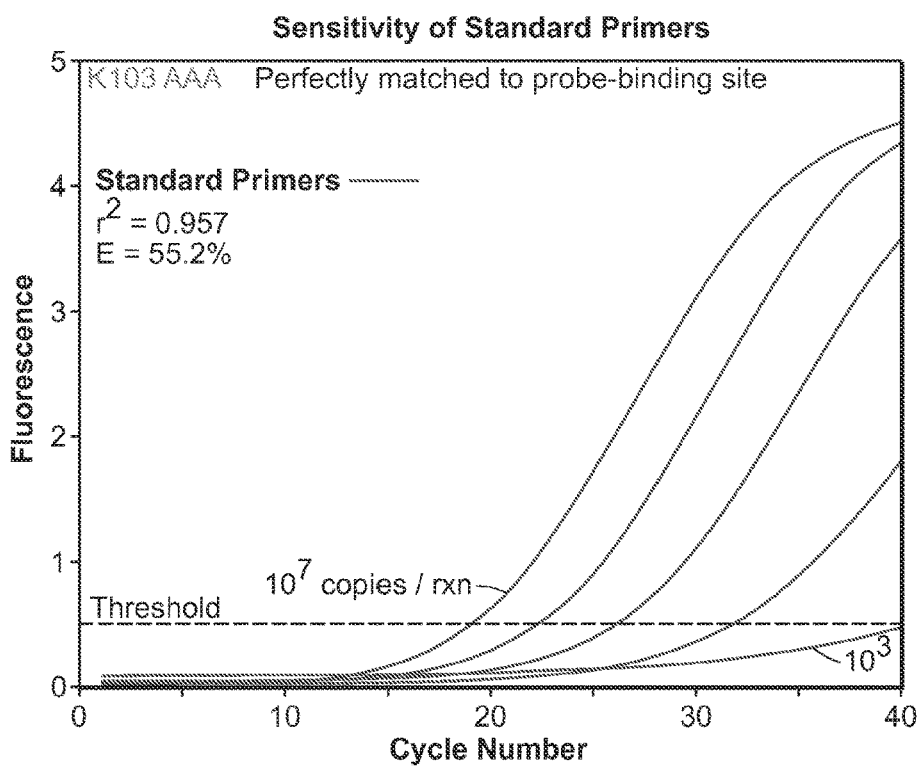

At $10^5$-$10^7$ copies of template per reaction, there was a sufficient concentration of template for the standard primers to overcome the primer/template mismatches, resulting in a ~2-3 fold increase in sensitivity over the PANDAA primers. See FIG. 7a.

Figure 7B:
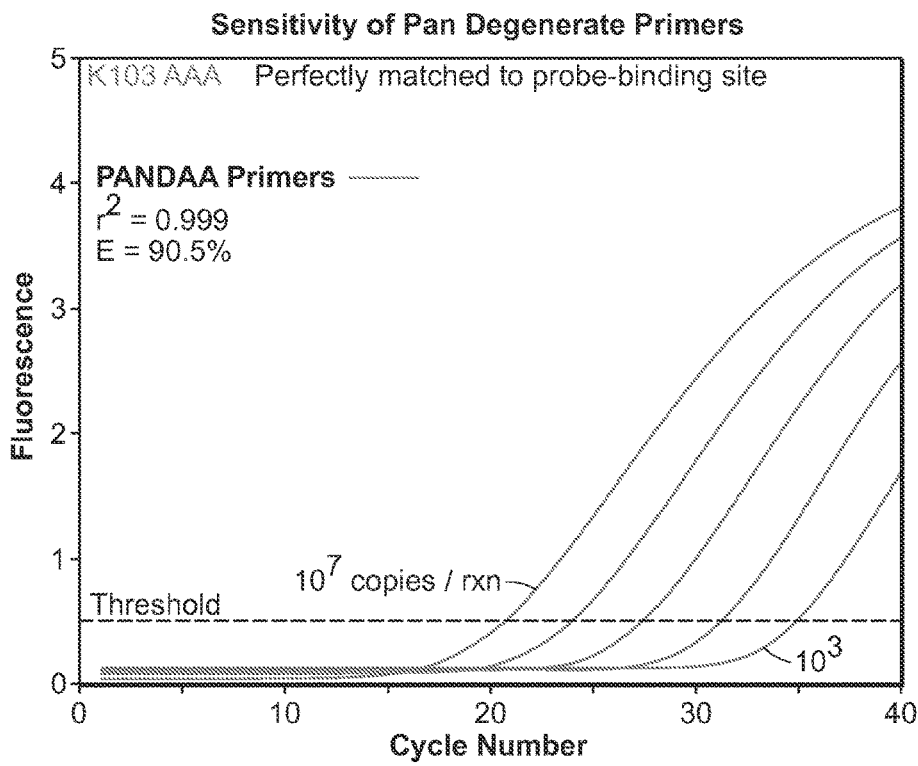
Figure 8A:
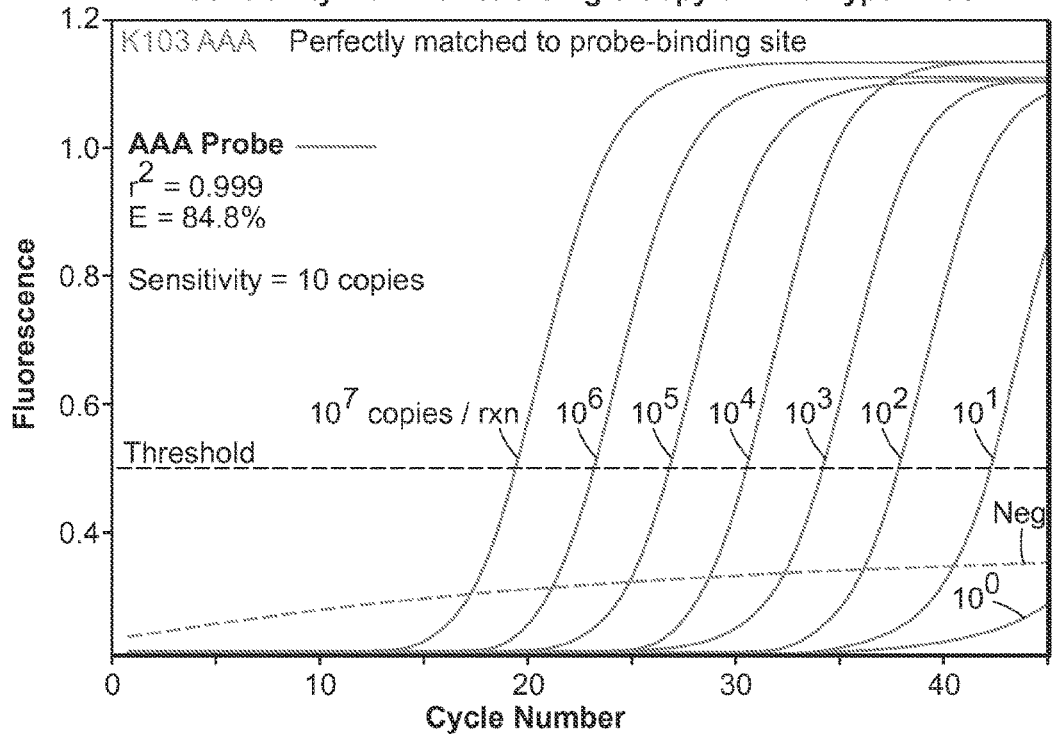
Figure 8B:
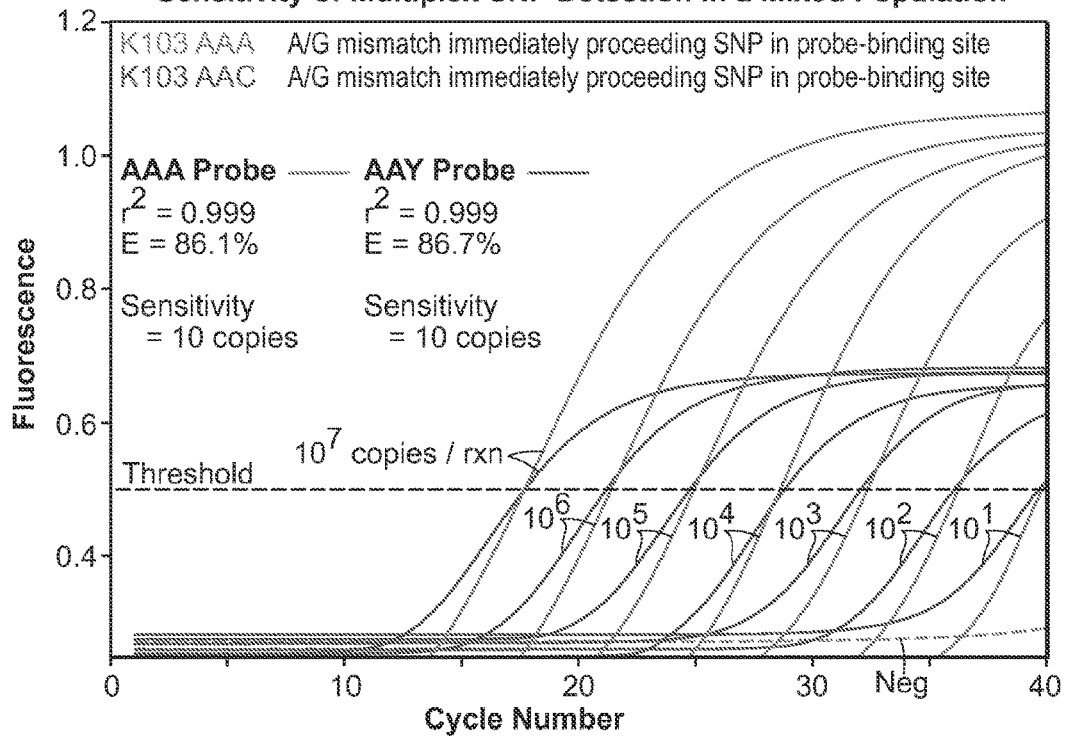
Figure 10:
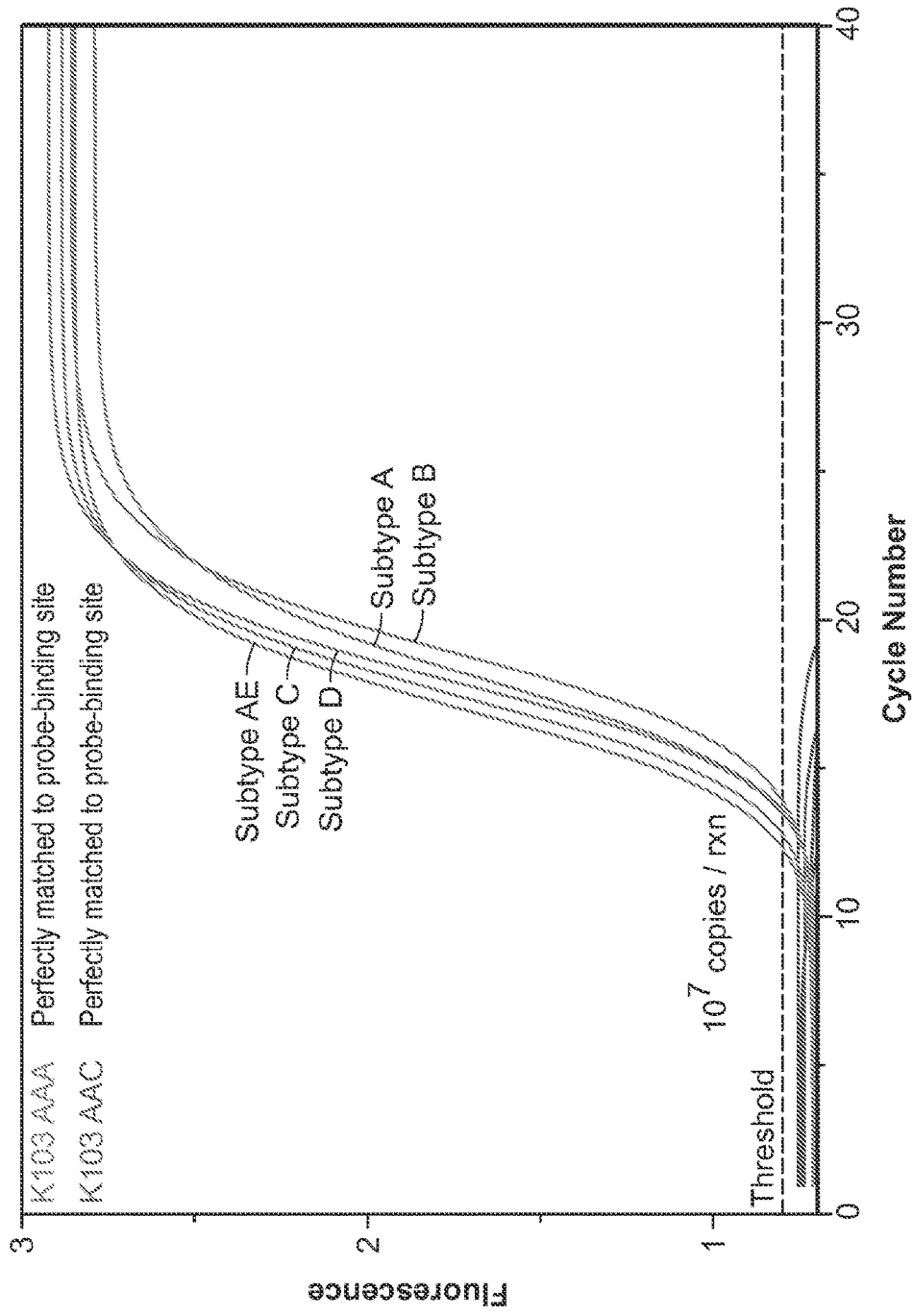
Figure 12:
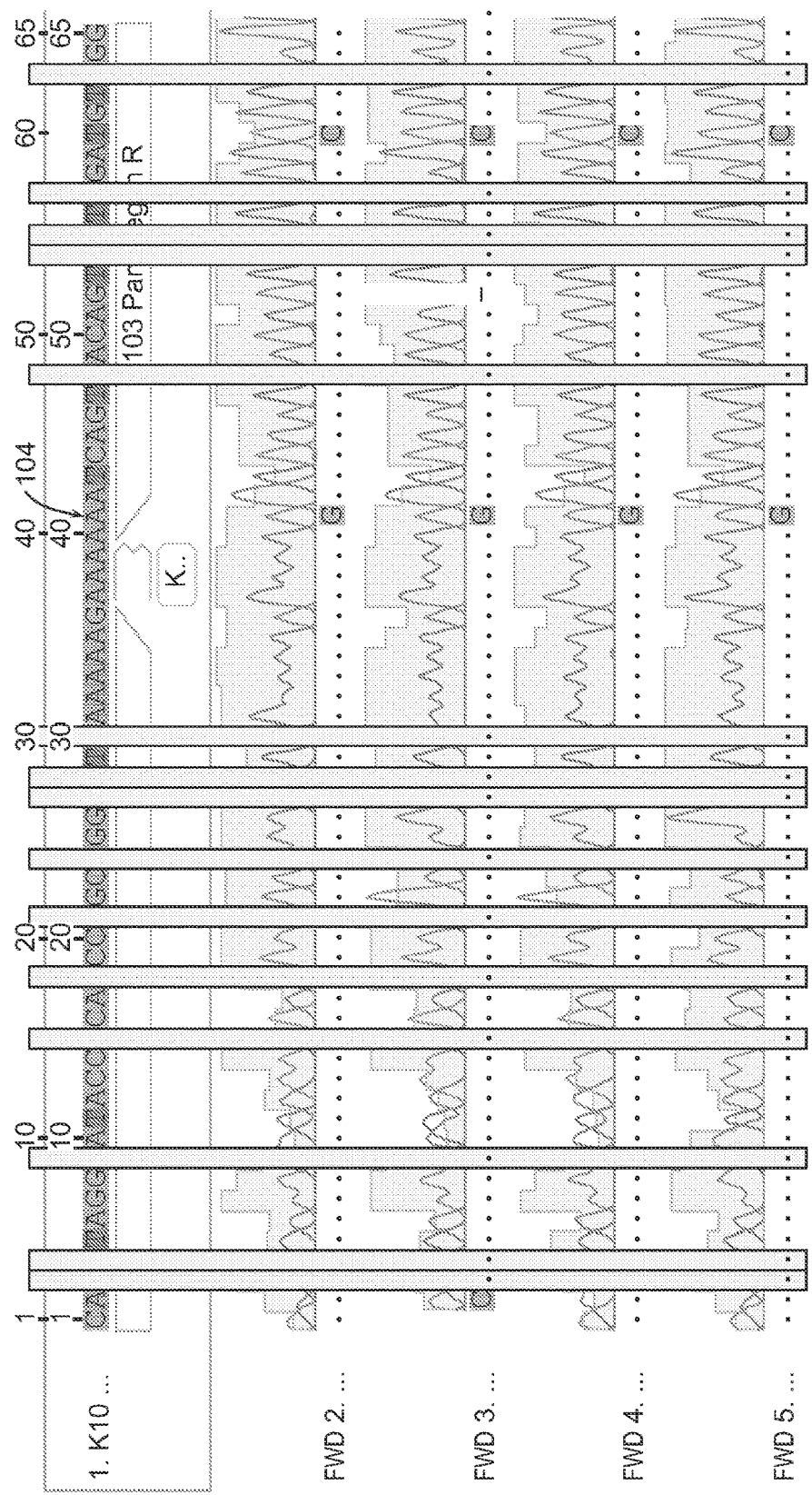

However, at $10^4$ copies/reaction, the efficiency of the standard primers dropped in comparison to the PANDAA primers, and by $10^3$ copies of template, the PANDAA primers were almost 50× more sensitive than the standard primer set. See FIG. 7b.

PANDAA is sensitive to at least 10 copies. Using the same template—with a perfectly complementary probe-binding site but containing mismatches in the primer-binding regions—a wild-type (AAA) template from $10^7$ copies to $10^0$ copies per reaction was titrated.

With a reaction efficiency of ~85%, the wild-type K103 SNP was detected at 10 copies/reaction over 45 cycles of PCR.

To determine whether the wild-type (AAA) and drug resistance mutation (AAC) could be distinguished in the same reaction, an AAA probe labelled with a FAM dye and an AAY (mixed AAC:AAT) probe labelled with a VIC dye were used.

Using a template that contained a mismatch with probe-binding site at codon 104, and also with the same mismatches in the primer-binding regions as previously described, both AAA and AAC was titrated from $10^7$ copies to $10^0$ copies per reaction, and present at a 1:1 ratio wild-type to mutant.

Over 40 cycles of PCR, both the AAA and AAY probes detected their respective templates with equal efficiency and sensitivity.

PANDAA methods described herein can detect multiple HIV subtypes with equal sensitivity. Using templates derived from the majority consensus sequences for HIV-1 subtypes A, AE, B, C, and D, the sensitivity of detection was determined using $10^7$ copies/reaction of each template, in the presence of both AAA and AAY probes, using pan degenerate primers.

As shown in FIG. 9, all nucleotide differences between subtypes—excluding a T/C polymorphism in subtype A found in the reverse primer alignment—occurred at degenerate nucleotides in the pan degenerate primers (highlighted in blue).

Using templates derived from the majority consensus sequences for HIV-1 subtypes A, AE, B, C, and D, the sensitivity of detection was determined using $10^7$ copies/reaction of each template, in the presence of both AAA and AAY probes, using pan degenerate primers.

Using a predetermined fluorescence value as a threshold, the sensitivity is determined by calculating the number of qPCR cycles (the cycle quantification (Cq) value) required for the reaction to reach that level of fluorescence. See Table 4 below.

TABLE 4

| Subtype | Cq |
|---|---|
| Subtype A | 13.49 |
| Subtype AE | 12.30 |
| Subtype B | 13.92 |
| Subtype C | 12.81 |
| Subtype D | 13.47 |

Although the input copy number of template was the same for all subtypes, detection of the target is initiated at different cycles of the qPCR depending on the location and number of polymorphisms for which the pan degenerate primers must compensate.

RNA may be used as a template for the PANDAA methods and reactions described herein which is useful for HIV which has an RNA genome. RNA undergoes an initial reverse transcription step to synthesize complementary DNA (cDNA), which is subsequently used as the template for qPCR.

A one-step qRT-PCR involves including a reverse transcriptase enzyme in the reaction along with the standard qPCR reaction components, and RNA as the template. Using the PANDAA primers described herein, cDNA will be reverse transcribed from the RNA before the reaction subsequently proceeds to qPCR, without any additional handling by the user.

$10^5$ copies of RNA containing the wild-type K103 codon (AAA), a mismatch with probe-binding site at codon 104, and also with the same mismatches in the primer-binding regions as previously described, was used in the one-step qRT-PCR in a parallel with a synthetic DNA template of the same sequence, titrated from $10^7$ copies to $10^3$ copies per reaction. As shown in FIG. 11, reverse transcriptase enzymes from various commercial suppliers performed differently, but 3 of the 6 enzymes resulted in the detection of the AAA K103 codon from RNA with the same sensitivity as using a DNA template.

PANDAA methods described herein can be used to adapt the template to match the probe-binding sequence. Using pan degenerate primers, a mismatch was intentionally introduced in the probe-binding region of a template with a probe-binding site that was completely complementary to the probe. By introducing a change at the 104 codon, the secondary polymorphism abolished probe binding.

No fluorescence was detected using primers that altered the probe-binding sequence to introduce a mismatched nucleotide, compared to primers that perfectly matched the probe sequence.

Upon sequencing of the PCR product, the template had changed to contain a G substitution at the 104 codon position, confirming that PANDAA methods described herein change the probe-binding region.

The use of degenerate primers in the primer-binding region also altered the template. These changes have no impact on probe binding, but recapitulates that use of degenerate bases is an advantageous approach to compensate for intentional mismatches in the 3' end of the primers designed to alter the probe-binding region.

Example IX

Differentiation of Pathogenic and Non-Pathogenic Newcastle Disease Virus

Pan degenerate primers are useful for differentiating between virulent and non-virulent strains. The fusion cleavage point is a region of Newcastle Disease Virus (NDV) that can be targeted to differentiate between virulent (velogenic and mesogenic) and non-virulent (lentogenic) pathotypes. Virulent pathotypes encode a phenylalanine at the cleavage site, of which TTT/C are the only codons, while non-virulent pathotypes encode leucine, encoded by TTA/G and CTA/T/C/G.

To determine the effectiveness of PANDAA methods described herein in detecting NDV, the sensitivity of the assay to detect two strains of pathogenic NDV: Dove/Italy/2736/00 and Game fowl/US(CA)/211472/02 was compared. The Dove strain has a probe-binding site perfectly matched to the PANDAA probe, whereas the Game fowl strain has an A/G mismatch at the nucleotide immediately after the SNP.

Figure 13:
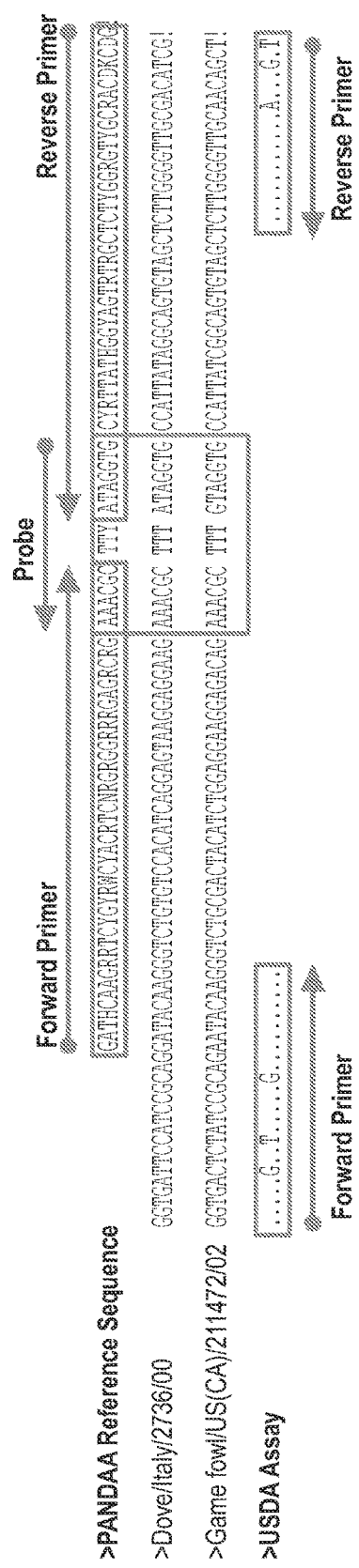

Two primer sets were compared: the PANDAA primers—designed to alter the probe-binding region—and the primers currently used in a US Department of Agriculture (USDA) NDV detection assay, which hybridize outside of the probe-binding region. See FIG. 13.

With the Dove/Italy/2736/00 template, which does not require any adaptation of the probe-binding site to match the probe sequence, both PANDAA and USDA primer sets detected NDV with similar efficiencies, although the PANDAA primers were found to be ~10-fold more sensitive. See FIG. 14.

Game fowl/US(CA)/211472/02, requiring a G to A adaptation in the probe-binding region, was detected by PANDAA methods described herein at a similar reaction efficiency as the Dove/Italy/2736/00 template. However, compared to the USDA primers, the PANDAA method was >1,000-fold more sensitive, detecting as few as 1,000 copies of template. See FIG. 14.

Example X

Primer and Probe Design for 81 Codons in the Reverse Transcriptase, Protease and Integrase Genes of HIV-1

This example discloses 2,701 forward primers, 2,813 reverse primers, 6,691 probes to detect wild-type sequences, and 7,043 probes to detect drug resistance sequences according to certain aspects of the invention. Mutations (e.g., substitutions, deletions and/or additions) at specific amino acid positions of HIV-1 reverse transcriptase protein, HIV-1 integrase protein and/or HIV-1 protease protein described herein can be used to identify HIV-1 drug resistance.

Table 5 depicts forward and reverse primers for the HIV-1 reverse transcriptase gene. A "+" symbol preceding a nucleotide denotes that the nucleotide is an LNA.

TABLE 5

| Codon | Forward Primer (5' to 3') |
|---|---|
| 40 | CCATTRACAGAAGARAAAATAAAAGCMTTARYAGMMATYTGTACA (SEQ ID NO: 1) |
| 40 | CCATTRACAGAAGARAAAATAAAAGCMTTARYAGMMATYTGTACA + N (SEQ ID NO: 2) |
| 41 | AAAATAAAAGCATTARYAGMMATTTGTRMDGAD (SEQ ID NO: 3) |
| 41 | ARAAAATAAAAGCATTARYAGMMATTTGTRMDGAD (SEQ ID NO: 4) |
| 41 | AGAAGARAAAATAAAAGCATTARYAGMMATTTGTRMDGAD (SEQ ID NO: 5) |
| 41 | GCATTARYAGMMATTTGTRMDGAD (SEQ ID NO: 6) |
| 41 | TAAAAGCATTARYAGMMATTTGTRMDGAD (SEQ ID NO: 7) |
| 41 | AAATAAAAGCATTARYAGMMATTTGTRMDGAD (SEQ ID NO: 8) |
| 41 | TTRACAGAAGARAAAATAAAAGCMTTARYAGMMATYTGTACAGAA (SEQ ID NO: 9) |
| 41 | AAAATAAAAGCATTARYAGMMATTTGTRMD GAD + N (SEQ ID NO: 10) |
| 41 | ARAAAATAAAAGCATTARYAGMMATTTGTRMDGAD + N (SEQ ID NO: 11) |
| 41 | AGAAGARAAAATAAAAGCATTARYAGMMATTTGTRMDGAD + N (SEQ ID NO: 12) |

TABLE 5 -continued

| | |
|---|---|
| 41 | GCATTARYAGMMATTTGTRMDGAD + N (SEQ ID NO: 13) |
| 41 | TAAAAGCATTARYAGMMATTTGTRMDGAD + N (SEQ ID NO: 14) |
| 41 | AAATAAAAGCATTARYAGMMATTTGTRMDGAD + N (SEQ ID NO: 15) |
| 41 | TTRACAGAAGARAAAATAAAAGCMTTARYAGMMATYTGTACAGAA + N (SEQ ID NO: 16) |
| 41 | +A + AAATAAAA + GCATTARYAGMMATTTGTRMD GAD (SEQ ID NO: 17) |
| 41 | +AAAA + TAAAA + GCATTARYAGMMATTTGTRMD GAD (SEQ ID NO: 18) |
| 41 | +A + AAA + TAAAAGCATTARYAGMMATTTGTRMDGAD (SEQ ID NO: 19) |
| 41 | +AR + AAAA + TAAAAGCATTARYAGMMATTTGTRMDGAD (SEQ ID NO: 20) |
| 41 | +ARA + AAA + TAAAAGCATTARYAGMMATTTGTRMDGAD (SEQ ID NO: 21) |
| 41 | +AR + A + AAATAAAAGCATTARYAGMMATTTGTRMDGAD (SEQ ID NO: 22) |
| 41 | AGAA + G + ARA + AAATAAAAGCATTARYAGMMATTTGTRMDGAD (SEQ ID NO: 23) |
| 41 | AGAA + GAR + A + AAATAAAAGCATTARYAGMMATTTGTRMDGAD (SEQ ID NO: 24) |
| 41 | +G + CATTARYAGMM + ATTTGTRMDGAD (SEQ ID NO: 25) |
| 41 | +GCAT + TARYAGMM + ATTTGTRMDGAD (SEQ ID NO: 26) |
| 41 | +G + CAT + TARYAGMMATTTGTRMDGAD (SEQ ID NO: 27) |
| 41 | +TAAAA + GCAT + TARYAGMMATTTGTRMDGAD (SEQ ID NO: 28) |
| 41 | +TAAAAG + CAT + TARYAGMMATTTGTRMDGAD (SEQ ID NO: 29) |
| 41 | +TAAAA + G + CATTARYAGMMATTTGTRMDGAD (SEQ ID NO: 30) |
| 41 | +AAA + TAAAAG + CATTARYAGMMATTTGTRMDGAD (SEQ ID NO: 31) |
| 41 | +AAATAAAA + G + CATTARYAGMMATTTGTRMDGAD (SEQ ID NO: 32) |
| 41 | +AAA + TAAAA + GCATTARYAGMMATTTGTRMDGAD (SEQ ID NO: 33) |
| 41 | AGAA + G + AR + AAATAAAAGCATTARYAGMMATTTGTRMDGAD (SEQ ID NO: 34) |
| 44 | CATTARYAGMMATTTGTRMDGADATGGARRARGA (SEQ ID NO: 35) |
| 44 | CATTARYAGMMATTTGTRMDGADATGGARRARG (SEQ ID NO: 36) |
| 44 | GCATTARYAGMMATTTGTRMDGADATGGARRARGA (SEQ ID NO: 37) |
| 44 | GCATTARYAGMMATTTGTRMDGADATGGARRARG (SEQ ID NO: 38) |
| 44 | TAAAAGCATTARYAGMMATTTGTRMDGADATGGARRARGA (SEQ ID NO: 39) |
| 44 | ATAAAAGCATTARYAGMMATTTGTRMDGADATGGARRARG (SEQ ID NO: 40) |
| 44 | TTTGTRMDGADATGGARRARGA (SEQ ID NO: 41) |
| 44 | TTTGTRMDGADATGGARRARG (SEQ ID NO: 42) |
| 44 | ATTTGTRMDGADATGGARRARGA (SEQ ID NO: 43) |
| 44 | ATTTGTRMDGADATGGARRARG (SEQ ID NO: 44) |
| 44 | TARYAGMMATTTGTRMDGADATGGARRARGA (SEQ ID NO: 45) |
| 44 | TARYAGMMATTTGTRMDGADATGGARRARG (SEQ ID NO: 46) |
| 44 | GARAAAATAAAAGCMTTARYAGMMATYTGTRMDGARATGGAAAAG (SEQ ID NO: 47) |
| 44 | CATTARYAGMMATTTGTRMDGADATGGARRARGA + N (SEQ ID NO: 48) |
| 44 | CATTARYAGMMATTTGTRMDGADATGGARRARG + N (SEQ ID NO: 49) |
| 44 | GCATTARYAGMMATTTGTRMDGADATGGARRARGA + N (SEQ ID NO: 50) |
| 44 | GCATTARYAGMMATTTGTRMDGADATGGARRARG + N (SEQ ID NO: 51) |
| 44 | TAAAAGCATTARYAGMMATTTGTRMDGADATGGARRARGA + N (SEQ ID NO: 52) |

TABLE 5 -continued

| | |
|---|---|
| 44 | ATAAAAGCATTARYAGMMATTTGTRMDGADATGGARRARG + N (SEQ ID NO: 53) |
| 44 | TTTGTRMDGADATGGARRARGA + N (SEQ ID NO: 54) |
| 44 | TTTGTRMDGADATGGARRARG + N (SEQ ID NO: 55) |
| 44 | ATTTGTRMDGADATGGARRARGA + N (SEQ ID NO: 56) |
| 44 | ATTTGTRMDGADATGGARRARG + N (SEQ ID NO: 57) |
| 44 | TARYAGMMATTTGTRMDGADATGGARRARGA + N (SEQ ID NO: 58) |
| 44 | TARYAGMMATTTGTRMDGADATGGARRARG + N (SEQ ID NO: 59) |
| 44 | GARAAAATAAAAGCMTTARYAGMMATYTGTRMDGARATGGAAAAG + N (SEQ ID NO: 60) |
| 44 | +CAT + TARYAGMMA + TTTGTRMDGADATGGARRARGA (SEQ ID NO: 61) |
| 44 | +CAT + TARYAGMMA + TTTGTRMDGADATGGARRARG (SEQ ID NO: 62) |
| 44 | +CATTARYAGMM + A + TTTGTRMDGADATGGARRARGA (SEQ ID NO: 63) |
| 44 | +CATTARYAGMM + A + TTTGTRMDGADATGGARRARG (SEQ ID NO: 64) |
| 44 | +CAT + TARYAGMM + ATTTGTRMDGADATGGARRARGA (SEQ ID NO: 65) |
| 44 | +CAT + TARYAGMM + ATTTGTRMDGADATGGARRARG (SEQ ID NO: 66) |
| 44 | +G + CATTARYAGMM + ATTTGTRMDGADATGGARRARGA (SEQ ID NO: 67) |
| 44 | +G + CATTARYAGMM + ATTTGTRMDGADATGGARRARG (SEQ ID NO: 68) |
| 44 | +GCAT + TARYAGMM + ATTTGTRMDGADATGGARRARGA (SEQ ID NO: 69) |
| 44 | +GCAT + TARYAGMM + ATTTGTRMDGADATGGARRARG (SEQ ID NO: 70) |
| 44 | +G + CAT + TARYAGMMATTTGTRMDGADATGGARRARGA (SEQ ID NO: 71) |
| 44 | +G + CAT + TARYAGMMATTTGTRMDGADATGGARRARG (SEQ ID NO: 72) |
| 44 | +TAAAA + GCAT + TARYAGMMATTTGTRMDGADATGGARRARGA (SEQ ID NO: 73) |
| 44 | A + TAAAA + GCAT + TARYAGMMATTTGTRMDGADATGGARRARG (SEQ ID NO: 74) |
| 44 | +TAAAAG + CAT + TARYAGMMATTTGTRMDGADATGGARRARGA (SEQ ID NO: 75) |
| 44 | A + TAAAAG + CAT + TARYAGMMATTTGTRMDGADATGGARRARG (SEQ ID NO: 76) |
| 44 | +TT + TGTRMDGADA + TGGARRARGA (SEQ ID NO: 77) |
| 44 | +TT + TGTRMDGADA + TGGARRARG (SEQ ID NO: 78) |
| 44 | +TTT + GTRMDGADA + TGGARRARGA (SEQ ID NO: 79) |
| 44 | +TTT + GTRMDGADA + TGGARRARG (SEQ ID NO: 80) |
| 44 | +TT + T + GTRMDGADATGGARRARGA (SEQ ID NO: 81) |
| 44 | +TT + T + GTRMDGADATGGARRARG (SEQ ID NO: 82) |
| 44 | +A + TTT + GTRMDGADATGGARRARGA (SEQ ID NO: 83) |
| 44 | +A + TTT + GTRMDGADATGGARRARG (SEQ ID NO: 84) |
| 44 | +ATT + T + GTRMDGADATGGARRARGA (SEQ ID NO: 85) |
| 44 | +ATT + T + GTRMDGADATGGARRARG (SEQ ID NO: 86) |
| 44 | +A + TT + TGTRMDGADATGGARRARGA (SEQ ID NO: 87) |
| 44 | +A + TT + TGTRMDGADATGGARRARG (SEQ ID NO: 88) |
| 44 | +TARYAGMM + ATT + TGTRMDGADATGGARRARGA (SEQ ID NO: 89) |
| 44 | +TARYAGMM + ATT + TGTRMDGADATGGARRARG (SEQ ID NO: 90) |
| 44 | +TARYAGMMA + TT + TGTRMDGADATGGARRARGA (SEQ ID NO: 91) |

TABLE 5 -continued

| | |
|---|---|
| 44 | +TARYAGMMA + TT + TGTRMDGADATGGARRARG (SEQ ID NO: 92) |
| 44 | +TARYAGMM + A + TTTGTRMDGADATGGARRARGA (SEQ ID NO: 93) |
| 44 | +TARYAGMM + A + TTTGTRMDGADATGGARRARG (SEQ ID NO: 94) |
| 44 | +TAAAA + G + CATTARYAGMMATTTGTRMDGADATGGARRARGA (SEQ ID NO: 95) |
| 44 | A + TAAAA + G + CATTARYAGMMATTTGTRMDGADATGGARRARG (SEQ ID NO: 96) |
| 62 | GGGCCTGAAAAYCCATAYAAYACTCCARTATTTG (SEQ ID NO: 97) |
| 62 | TTGGGCCTGAAAAYCCATAYAAYACTCCARTATTTG (SEQ ID NO: 98) |
| 62 | ARAATTGGGCCTGAAAAYCCATAYAAYACTCCARTATTTG (SEQ ID NO: 99) |
| 62 | CTGAAAAYCCATAYAAYACTCCARTATTTG (SEQ ID NO: 100) |
| 62 | CCTGAAAAYCCATAYAAYACTCCARTATTTG (SEQ ID NO: 101) |
| 62 | GGCCTGAAAAYCCATAYAAYACTCCARTATTTG (SEQ ID NO: 102) |
| 62 | ATYWCAARAATYGGGCCTGARAAYCCATAYAAYACTCCAGTATTT (SEQ ID NO: 103) |
| 62 | GGGCCTGAAAAYCCATAYAAYACTCCARTATTTG + N (SEQ ID NO: 104) |
| 62 | TTGGGCCTGAAAAYCCATAYAAYACTCCARTATTTG + N (SEQ ID NO: 105) |
| 62 | ARAATTGGGCCTGAAAAYCCATAYAAYACTCCARTATTTG + N (SEQ ID NO: 106) |
| 62 | CTGAAAAYCCATAYAAYACTCCARTATTTG + N (SEQ ID NO: 107) |
| 62 | CCTGAAAAYCCATAYAAYACTCCARTATTTG + N (SEQ ID NO: 108) |
| 62 | GGCCTGAAAAYCCATAYAAYACTCCARTATTTG + N (SEQ ID NO: 109) |
| 62 | ATYWCAARAATYGGGCCTGARAAYCCATAYAAYACTCCAGTATTT + N (SEQ ID NO: 110) |
| 62 | +G + GGC + CTGAAAAYCCATAYAAYACTCCARTATTTG (SEQ ID NO: 111) |
| 62 | +GGG + C + CTGAAAAYCCATAYAAYACTCCARTATTTG (SEQ ID NO: 112) |
| 62 | +G + GG + CCTGAAAAYCCATAYAAYACTCCARTATTTG (SEQ ID NO: 113) |
| 62 | +TT + GGG + CCTGAAAAYCCATAYAAYACTCCARTATTTG (SEQ ID NO: 114) |
| 62 | +TTG + GG + CCTGAAAAYCCATAYAAYACTCCARTATTTG (SEQ ID NO: 115) |
| 62 | +TT + G + GGCCTGAAAAYCCATAYAAYACTCCARTATTTG (SEQ ID NO: 116) |
| 62 | +ARAA + TTG + GGCCTGAAAAYCCATAYAAYACTCCARTATTTG (SEQ ID NO: 117) |
| 62 | +ARAATT + G + GGCCTGAAAAYCCATAYAAYACTCCARTATTTG (SEQ ID NO: 118) |
| 62 | +CT + GAA + AAYCCATAYAAYACTCCARTATTTG (SEQ ID NO: 119) |
| 62 | +CTG + AA + AAYCCATAYAAYACTCCARTATTTG (SEQ ID NO: 120) |
| 62 | +CT + G + AAAAYCCATAYAAYACTCCARTATTTG (SEQ ID NO: 121) |
| 62 | +C + CTG + AAAAYCCATAYAAYACTCCARTATTTG (SEQ ID NO: 122) |
| 62 | +CCT + G + AAAAYCCATAYAAYACTCCARTATTTG (SEQ ID NO: 123) |
| 62 | +C + CT + GAAAAYCCATAYAAYACTCCARTATTTG (SEQ ID NO: 124) |
| 62 | +GG + CCT + GAAAAYCCATAYAAYACTCCARTATTTG (SEQ ID NO: 125) |
| 62 | +GGC + CT + GAAAAYCCATAYAAYACTCCARTATTTG (SEQ ID NO: 126) |
| 62 | +GG + C + CTGAAAAYCCATAYAAYACTCCARTATTTG (SEQ ID NO: 127) |
| 62 | +ARAA + TT + GGGCCTGAAAAYCCATAYAAYACTCCARTATTTG (SEQ ID NO: 128) |
| 65 | GAAAAYCCATAYAAYACTCCARTATTTGCYATAAARA (SEQ ID NO: 129) |

TABLE 5 -continued

| 65 | AAAAYCCATAYAAYACTCCARTATTTGCYATAAARAA (SEQ ID NO: 130) |
| 65 | CTGAAAAYCCATAYAAYACTCCARTATTTGCYATAAARA (SEQ ID NO: 131) |
| 65 | GAAAAYCCATAYAAYACTCCARTATTTGCYATAAARAA (SEQ ID NO: 132) |
| 65 | CCTGAAAAYCCATAYAAYACTCCARTATTTGCYATAAARA (SEQ ID NO: 133) |
| 65 | CTGAAAAYCCATAYAAYACTCCARTATTTGCYATAAARAA (SEQ ID NO: 134) |
| 65 | AYCCATAYAAYACTCCARTATTTGCYATAAARA (SEQ ID NO: 135) |
| 65 | CCATAYAAYACTCCARTATTTGCYATAAARAA (SEQ ID NO: 136) |
| 65 | AAYCCATAYAAYACTCCARTATTTGCYATAAARA (SEQ ID NO: 137) |
| 65 | AYCCATAYAAYACTCCARTATTTGCYATAAARAA (SEQ ID NO: 138) |
| 65 | AAAAYCCATAYAAYACTCCARTATTTGCYATAAARA (SEQ ID NO: 139) |
| 65 | AAYCCATAYAAYACTCCARTATTTGCYATAAARAA (SEQ ID NO: 140) |
| 65 | ATYGGGCCTGARAAYCCATAYAAYACTCCARTATTTGCYATAAAG (SEQ ID NO: 141) |
| 65 | GAAAAYCCATAYAAYACTCCARTATTTGCYATAAARA + N (SEQ ID NO: 142) |
| 65 | AAAAYCCATAYAAYACTCCARTATTTGCYATAAARAA + N (SEQ ID NO: 143) |
| 65 | CTGAAAAYCCATAYAAYACTCCARTATTTGCYATAAARA + N (SEQ ID NO: 144) |
| 65 | GAAAAYCCATAYAAYACTCCARTATTTGCYATAAARAA + N (SEQ ID NO: 145) |
| 65 | CCTGAAAAYCCATAYAAYACTCCARTATTTGCYATAAARA + N (SEQ ID NO: 146) |
| 65 | CTGAAAAYCCATAYAAYACTCCARTATTTGCYATAAARAA + N (SEQ ID NO: 147) |
| 65 | AYCCATAYAAYACTCCARTATTTGCYATAAARA + N (SEQ ID NO: 148) |
| 65 | CCATAYAAYACTCCARTATTTGCYATAAARAA + N (SEQ ID NO: 149) |
| 65 | AAYCCATAYAAYACTCCARTATTTGCYATAAARA + N (SEQ ID NO: 150) |
| 65 | AYCCATAYAAYACTCCARTATTTGCYATAAARAA + N (SEQ ID NO: 151) |
| 65 | AAAAYCCATAYAAYACTCCARTATTTGCYATAAARA + N (SEQ ID NO: 152) |
| 65 | AAYCCATAYAAYACTCCARTATTTGCYATAAARAA + N (SEQ ID NO: 153) |
| 65 | ATYGGGCCTGARAAYCCATAYAAYACTCCARTATTTGCYATAAAG + N (SEQ ID NO: 154) |
| 65 | +G + AAA + AYCCATAYAAYACTCCARTATTTGCYATAAARA (SEQ ID NO: 155) |
| 65 | +AA + AAY + CCATAYAAYACTCCARTATTTGCYATAAARAA (SEQ ID NO: 156) |
| 65 | +GAA + A + AYCCATAYAAYACTCCARTATTTGCYATAAARAA (SEQ ID NO: 157) |
| 65 | +AAA + AY + CCATAYAAYACTCCARTATTTGCYATAAARAA (SEQ ID NO: 158) |
| 65 | +G + AA + AAYCCATAYAAYACTCCARTATTTGCYATAAARA (SEQ ID NO: 159) |
| 65 | +AA + A + AYCCATAYAAYACTCCARTATTTGCYATAAARAA (SEQ ID NO: 160) |
| 65 | +CT + GAA + AAYCCATAYAAYACTCCARTATTTGCYATAAARA (SEQ ID NO: 161) |
| 65 | +G + AAA + AYCCATAYAAYACTCCARTATTTGCYATAAARAA (SEQ ID NO: 162) |
| 65 | +CTG + AA + AAYCCATAYAAYACTCCARTATTTGCYATAAARA (SEQ ID NO: 163) |
| 65 | +GAA + A + AYCCATAYAAYACTCCARTATTTGCYATAAARAA (SEQ ID NO: 164) |
| 65 | +CT + G + AAAAYCCATAYAAYACTCCARTATTTGCYATAAARA (SEQ ID NO: 165) |
| 65 | +G + AA + AAYCCATAYAAYACTCCARTATTTGCYATAAARAA (SEQ ID NO: 166) |

TABLE 5 -continued

| | | |
|---|---|---|
| 65 | +C + CTG + AAAAYCCATAYAAYACTCCARTATTTGCYATAAARA | (SEQ ID NO: 167) |
| 65 | +CT + GAA + AAYCCATAYAAYACTCCARTATTTGCYATAAARAA | (SEQ ID NO: 168) |
| 65 | +CCT + G + AAAAYCCATAYAAYACTCCARTATTTGCYATAAARA | (SEQ ID NO: 169) |
| 65 | +CTG + AA + AAYCCATAYAAYACTCCARTATTTGCYATAAARAA | (SEQ ID NO: 170) |
| 65 | +AY + CCA + TAYAAYACTCCARTATTTGCYATAAARA | (SEQ ID NO: 171) |
| 65 | +C + CAT + AYAAYACTCCARTATTTGCYATAAARAA | (SEQ ID NO: 172) |
| 65 | +AYC + CA + TAYAAYACTCCARTATTTGCYATAAARA | (SEQ ID NO: 173) |
| 65 | +CCA + T + AYAAYACTCCARTATTTGCYATAAARAA | (SEQ ID NO: 174) |
| 65 | +AY + C + CATAYAAYACTCCARTATTTGCYATAAARA | (SEQ ID NO: 175) |
| 65 | +C + CA + TAYAAYACTCCARTATTTGCYATAAARAA | (SEQ ID NO: 176) |
| 65 | +A + AYC + CATAYAAYACTCCARTATTTGCYATAAARA | (SEQ ID NO: 177) |
| 65 | +AY + CCA + TAYAAYACTCCARTATTTGCYATAAARAA | (SEQ ID NO: 178) |
| 65 | +AAY + C + CATAYAAYACTCCARTATTTGCYATAAARA | (SEQ ID NO: 179) |
| 65 | +AYC + CA + TAYAAYACTCCARTATTTGCYATAAARAA | (SEQ ID NO: 180) |
| 65 | +A + AY + CCATAYAAYACTCCARTATTTGCYATAAARA | (SEQ ID NO: 181) |
| 65 | +AY + C + CATAYAAYACTCCARTATTTGCYATAAARAA | (SEQ ID NO: 182) |
| 65 | +AA + AAY + CCATAYAAYACTCCARTATTTGCYATAAARA | (SEQ ID NO: 183) |
| 65 | +A + AYC + CATAYAAYACTCCARTATTTGCYATAAARAA | (SEQ ID NO: 184) |
| 65 | +AAA + AY + CCATAYAAYACTCCARTATTTGCYATAAARA | (SEQ ID NO: 185) |
| 65 | +AAY + C + CATAYAAYACTCCARTATTTGCYATAAARAA | (SEQ ID NO: 186) |
| 65 | +AA + A + AYCCATAYAAYACTCCARTATTTGCYATAAARA | (SEQ ID NO: 187) |
| 65 | +A + AY + CCATAYAAYACTCCARTATTTGCYATAAARAA | (SEQ ID NO: 188) |
| 65 | +C + CT + GAAAAYCCATAYAAYACTCCARTATTTGCYATAAARA | (SEQ ID NO: 189) |
| 65 | +CT + G + AAAAYCCATAYAAYACTCCARTATTTGCYATAAARAA | (SEQ ID NO: 190) |
| 67 | CCATAYAAYACTCCARTATTTGCYATAAARAARAAR | (SEQ ID NO: 191) |
| 67 | CCATAYAAYACTCCARTATTTGCYATAAARAARAARG | (SEQ ID NO: 192) |
| 67 | CATAYAAYACTCCARTATTTGCYATAAARAARAARGA | (SEQ ID NO: 193) |
| 67 | AYCCATAYAAYACTCCARTATTTGCYATAAARAARAAR | (SEQ ID NO: 194) |
| 67 | AYCCATAYAAYACTCCARTATTTGCYATAAARAARAARG | (SEQ ID NO: 195) |
| 67 | CCATAYAAYACTCCARTATTTGCYATAAARAARAARGA | (SEQ ID NO: 196) |
| 67 | AAAYCCATAYAAYACTCCARTATTTGCYATAAARAARAAR | (SEQ ID NO: 197) |
| 67 | AAYCCATAYAAYACTCCARTATTTGCYATAAARAARAARG | (SEQ ID NO: 198) |
| 67 | AYCCATAYAAYACTCCARTATTTGCYATAAARAARAARGA | (SEQ ID NO: 199) |
| 67 | AYAAYACTCCARTATTTGCYATAAARAARAARAAR | (SEQ ID NO: 200) |
| 67 | AYAAYACTCCARTATTTGCYATAAARAARAARAARG | (SEQ ID NO: 201) |
| 67 | AAYACTCCARTATTTGCYATAAARAARAARAARGA | (SEQ ID NO: 202) |

TABLE 5-continued

| 67 | TAYAAYACTCCARTATTTGCYATAAARAARAAR (SEQ ID NO: 203) |
| --- | --- |
| 67 | TAYAAYACTCCARTATTTGCYATAAARAARAARG (SEQ ID NO: 204) |
| 67 | AYAAYACTCCARTATTTGCYATAAARAARAARGA (SEQ ID NO: 205) |
| 67 | CATAYAAYACTCCARTATTTGCYATAAARAARAAR (SEQ ID NO: 206) |
| 67 | CATAYAAYACTCCARTATTTGCYATAAARAARAARG (SEQ ID NO: 207) |
| 67 | TAYAAYACTCCARTATTTGCYATAAARAARAARGA (SEQ ID NO: 208) |
| 67 | CCTGARAAYCCATAYAAYACTCCARTATTTGCYATAAAGAAAAAA (SEQ ID NO: 209) |
| 67 | CCATAYAAYACTCCARTATTTGCYATAAARAARAAR + N (SEQ ID NO: 210) |
| 67 | CCATAYAAYACTCCARTATTTGCYATAAARAARAARG + N (SEQ ID NO: 211) |
| 67 | CATAYAAYACTCCARTATTTGCYATAAARAARAARGA + N (SEQ ID NO: 212) |
| 67 | AYCCATAYAAYACTCCARTATTTGCYATAAARAARAAR + N (SEQ ID NO: 213) |
| 67 | AYCCATAYAAYACTCCARTATTTGCYATAAARAARAARG + N (SEQ ID NO: 214) |
| 67 | CCATAYAAYACTCCARTATTTGCYATAAARAARAARGA + N (SEQ ID NO: 215) |
| 67 | AAAYCCATAYAAYACTCCARTATTTGCYATAAARAARAAR + N (SEQ ID NO: 216) |
| 67 | AAYCCATAYAAYACTCCARTATTTGCYATAAARAARAARG + N (SEQ ID NO: 217) |
| 67 | AYCCATAYAAYACTCCARTATTTGCYATAAARAARAARGA + N (SEQ ID NO: 218) |
| 67 | AYAAYACTCCARTATTTGCYATAAARAARAAR + N (SEQ ID NO: 219) |
| 67 | AYAAYACTCCARTATTTGCYATAAARAARAARG + N (SEQ ID NO: 220) |
| 67 | AAYACTCCARTATTTGCYATAAARAARAARGA + N (SEQ ID NO: 221) |
| 67 | TAYAAYACTCCARTATTTGCYATAAARAARAAR + N (SEQ ID NO: 222) |
| 67 | TAYAAYACTCCARTATTTGCYATAAARAARAARG + N (SEQ ID NO: 223) |
| 67 | AYAAYACTCCARTATTTGCYATAAARAARAARGA + N (SEQ ID NO: 224) |
| 67 | CATAYAAYACTCCARTATTTGCYATAAARAARAAR + N (SEQ ID NO:225) |
| 67 | CATAYAAYACTCCARTATTTGCYATAAARAARAARG + N (SEQ ID NO: 226) |
| 67 | TAYAAYACTCCARTATTTGCYATAAARAARAARGA + N (SEQ ID NO: 227) |
| 67 | CCTGARAAYCCATAYAAYACTCCARTATTTGCYATAAAGAAAAAA + N (SEQ ID NO: 228) |
| 67 | +C + CAT + AYAAYACTCCARTATTTGCYATAAARAARAAR (SEQ ID NO: 229) |
| 67 | +C + CAT + AYAAYACTCCARTATTTGCYATAAARAARAARG (SEQ ID NO: 230) |
| 67 | +CA + TAY + AAYACTCCARTATTTGCYATAAARAARAARGA (SEQ ID NO: 231) |
| 67 | +CCA + T + AYAAYACTCCARTATTTGCYATAAARAARAAR (SEQ ID NO: 232) |
| 67 | +CCA + T + AYAAYACTCCARTATTTGCYATAAARAARAARG (SEQ ID NO: 233) |
| 67 | +CAT + AY + AAYACTCCARTATTTGCYATAAARAARAARGA (SEQ ID NO: 234) |
| 67 | +C + CA + TAYAAYACTCCARTATTTGCYATAAARAARAAR (SEQ ID NO: 235) |
| 67 | +C + CA + TAYAAYACTCCARTATTTGCYATAAARAARAARG (SEQ ID NO: 236) |
| 67 | +CA + T + AYAAYACTCCARTATTTGCYATAAARAARAARGA (SEQ ID NO: 237) |
| 67 | +AY + CCA + TAYAAYACTCCARTATTTGCYATAAARAARAAR (SEQ ID NO: 238) |
| 67 | +AY + CCA + TAYAAYACTCCARTATTTGCYATAAARAARAARG (SEQ ID NO: 239) |
| 67 | +C + CAT + AYAAYACTCCARTATTTGCYATAAARAARAARGA (SEQ ID NO: 240) |

TABLE 5 -continued

| | |
|---|---|
| 67 | +AYC + CA + TAYAAYACTCCARTATTTGCYATAAARAARAAR (SEQ ID NO: 241) |
| 67 | +AYC + CA + TAYAAYACTCCARTATTTGCYATAAARAARAARG (SEQ ID NO: 242) |
| 67 | +CCA + T + AYAAYACTCCARTATTTGCYATAAARAARAARGA (SEQ ID NO: 243) |
| 67 | +AY + C + CATAYAAYACTCCARTATTTGCYATAAARAARAAR (SEQ ID NO: 244) |
| 67 | +AY + C + CATAYAAYACTCCARTATTTGCYATAAARAARAARG (SEQ ID NO: 245) |
| 67 | +C + CA + TAYAAYACTCCARTATTTGCYATAAARAARAARGA (SEQ ID NO: 246) |
| 67 | A + A + AYC + CATAYAAYACTCCARTATTTGCYATAAARAARAAR (SEQ ID NO: 247) |
| 67 | +A + AYC + CATAYAAYACTCCARTATTTGCYATAAARAARAARG (SEQ ID NO: 248) |
| 67 | +AY + CCA + TAYAAYACTCCARTATTTGCYATAAARAARAARGA (SEQ ID NO: 249) |
| 67 | A + AAY + C + CATAYAAYACTCCARTATTTGCYATAAARAARAAR (SEQ ID NO: 250) |
| 67 | +AAY + C + CATAYAAYACTCCARTATTTGCYATAAARAARAARG (SEQ ID NO: 251) |
| 67 | +AYC + CA + TAYAAYACTCCARTATTTGCYATAAARAARAARGA (SEQ ID NO: 252) |
| 67 | +AY + AAY + ACTCCARTATTTGCYATAAARAARAAR (SEQ ID NO: 253) |
| 67 | +AY + AAY + ACTCCARTATTTGCYATAAARAARAARG (SEQ ID NO: 254) |
| 67 | +A + AYA + CTCCARTATTTGCYATAAARAARAARGA (SEQ ID NO: 255) |
| 67 | +AYA + AY + ACTCCARTATTTGCYATAAARAARAAR (SEQ ID NO: 256) |
| 67 | +AYA + AY + ACTCCARTATTTGCYATAAARAARAARG (SEQ ID NO: 257) |
| 67 | +AAY + A + CTCCARTATTTGCYATAAARAARAARGA (SEQ ID NO: 258) |
| 67 | +AY + A + AYACTCCARTATTTGCYATAAARAARAAR (SEQ ID NO: 259) |
| 67 | +AY + A + AYACTCCARTATTTGCYATAAARAARAARG (SEQ ID NO: 260) |
| 67 | +A + AY + ACTCCARTATTTGCYATAAARAARAARGA (SEQ ID NO: 261) |
| 67 | +T + AYA + AYACTCCARTATTTGCYATAAARAARAAR (SEQ ID NO: 262) |
| 67 | +T + AYA + AYACTCCARTATTTGCYATAAARAARAARG (SEQ ID NO: 263) |
| 67 | +AY + AAY + ACTCCARTATTTGCYATAAARAARAARGA (SEQ ID NO: 264) |
| 67 | +TAY + A + AYACTCCARTATTTGCYATAAARAARAAR (SEQ ID NO: 265) |
| 67 | +TAY + A + AYACTCCARTATTTGCYATAAARAARAARG (SEQ ID NO: 266) |
| 67 | +AYA + AY + ACTCCARTATTTGCYATAAARAARAARGA (SEQ ID NO: 267) |
| 67 | +T + AY + AAYACTCCARTATTTGCYATAAARAARAAR (SEQ ID NO: 268) |
| 67 | +T + AY + AAYACTCCARTATTTGCYATAAARAARAARG (SEQ ID NO: 269) |
| 67 | +AY + A + AYACTCCARTATTTGCYATAAARAARAARGA (SEQ ID NO: 270) |
| 67 | +CA + TAY + AAYACTCCARTATTTGCYATAAARAARAAR (SEQ ID NO: 271) |
| 67 | +CA + TAY + AAYACTCCARTATTTGCYATAAARAARAARG (SEQ ID NO: 272) |
| 67 | +T + AYA + AYACTCCARTATTTGCYATAAARAARAARGA (SEQ ID NO: 273) |
| 67 | +CAT + AY + AAYACTCCARTATTTGCYATAAARAARAAR (SEQ ID NO: 274) |
| 67 | +CAT + AY + AAYACTCCARTATTTGCYATAAARAARAARG (SEQ ID NO: 275) |
| 67 | +TAR + A + AYACTCCARTATTTGCYATAAARAARAARGA (SEQ ID NO: 276) |

TABLE 5 -continued

| | |
|---|---|
| 67 | +CA + T + AYAAYACTCCARTATTTGCYATAAARAARAAR (SEQ ID NO: 277) |
| 67 | +CA + T + AYAAYACTCCARTATTTGCYATAAARAARAARG (SEQ ID NO: 278) |
| 67 | +T + AY + AAYACTCCARTATTTGCYATAAARAARAARGA (SEQ ID NO: 279) |
| 67 | A + A + AY + CCATAYAAYACTCCARTATTTGCYATAAARAARAAR (SEQ ID NO: 280) |
| 67 | +A + AY + CCATAYAAYACTCCARTATTTGCYATAAARAARAARG (SEQ ID NO: 281) |
| 67 | +AY + C + CATAYAAYACTCCARTATTTGCYATAAARAARAARGA (SEQ ID NO: 282) |
| 69 | AAYCCATAYAAYACTCCARTATTTGCYATAAARAARAARGACAGT (SEQ ID NO: 283) |
| 69 | AAYCCATAYAAYACTCCARTATTTGCYATAAARAARAARGACAGT + N (SEQ ID NO: 284) |
| 70 | ACTCCARTATTTGCYATAAARAARAARGAYAGYACY (SEQ ID NO: 285) |
| 70 | ACTCCARTATTTGCYATAAARAARAARGAYAGYACYA (SEQ ID NO: 286) |
| 70 | AYACTCCARTATTTGCYATAAARAARAARGAYAGYACY (SEQ ID NO: 287) |
| 70 | AYACTCCARTATTTGCYATAAARAARAARGAYAGYACYA (SEQ ID NO: 288) |
| 70 | YAAYACTCCARTATTTGCYATAAARAARAARGAYAGYACY (SEQ ID NO: 289) |
| 70 | AAYACTCCARTATTTGCYATAAARAARAARGAYAGYACYA (SEQ ID NO: 290) |
| 70 | CARTATTTGCYATAAARAARAARGAYAGYACY (SEQ ID NO: 291) |
| 70 | CARTATTTGCYATAAARAARAARGAYAGYACYA (SEQ ID NO: 292) |
| 70 | CCARTATTTGCYATAAARAARAARGAYAGYACY (SEQ ID NO: 293) |
| 70 | CCARTATTTGCYATAAARAARAARGAYAGYACYA (SEQ ID NO: 294) |
| 70 | CTCCARTATTTGCYATAAARAARAARGAYAGYACY (SEQ ID NO: 295) |
| 70 | CTCCARTATTTGCYATAAARAARAARGAYAGYACYA (SEQ ID NO: 296) |
| 70 | CCATAYAAYACTCCARTATTTGCYATAAARAARAARGACAGTACT (SEQ ID NO: 297) |
| 70 | ACTCCARTATTTGCYATAAARAARAARGAYAGYACY + N (SEQ ID NO: 298) |
| 70 | ACTCCARTATTTGCYATAAARAARAARGAYAGYACYA + N (SEQ ID NO: 299) |
| 70 | AYACTCCARTATTTGCYATAAARAARAARGAYAGYACY + N (SEQ ID NO: 300) |
| 70 | AYACTCCARTATTTGCYATAAARAARAARGAYAGYACYA + N (SEQ ID NO: 301) |
| 70 | YAAYACTCCARTATTTGCYATAAARAARAARGAYAGYACY + N (SEQ ID NO: 302) |
| 70 | AAYACTCCARTATTTGCYATAAARAARAARGAYAGYACYA + N (SEQ ID NO: 303) |
| 70 | CARTATTTGCYATAAARAARAARGAYAGYACY + N (SEQ ID NO: 304) |
| 70 | CARTATTTGCYATAAARAARAARGAYAGYACYA + N (SEQ ID NO: 305) |
| 70 | CCARTATTTGCYATAAARAARAARGAYAGYACY + N (SEQ ID NO: 306) |
| 70 | CCARTATTTGCYATAAARAARAARGAYAGYACYA + N (SEQ ID NO: 307) |
| 70 | CTCCARTATTTGCYATAAARAARAARGAYAGYACY + N (SEQ ID NO: 308) |
| 70 | CTCCARTATTTGCYATAAARAARAARGAYAGYACYA + N (SEQ ID NO: 309) |
| 70 | CCATAYAAYACTCCARTATTTGCYATAAARAARAARGACAGTACT + N (SEQ ID NO: 310) |
| 70 | +A + CTC + CARTATTTGCYATAAARAARAARGAYAGYACY (SEQ ID NO: 311) |

TABLE 5 -continued

| | | |
|---|---|---|
| 70 | +A + CTC + CARTATTTGCYATAAARAARAARGAYAGYACYA | (SEQ ID NO: 312) |
| 70 | +ACT + C + CARTATTTGCYATAAARAARAARGAYAGYACY | (SEQ ID NO: 313) |
| 70 | +ACT + C + CARTATTTGCYATAAARAARAARGAYAGYACYA | (SEQ ID NO: 314) |
| 70 | +A + CT + CCARTATTTGCYATAAARAARAARGAYAGYACY | (SEQ ID NO: 315) |
| 70 | +A + CT + CCARTATTTGCYATAAARAARAARGAYAGYACYA | (SEQ ID NO: 316) |
| 70 | +AY + ACT + CCARTATTTGCYATAAARAARAARGAYAGYACY | (SEQ ID NO: 317) |
| 70 | +AY + ACT + CCARTATTTGCYATAAARAARAARGAYAGYACYA | (SEQ ID NO: 318) |
| 70 | +AYA + CT + CCARTATTTGCYATAAARAARAARGAYAGYACY | (SEQ ID NO: 319) |
| 70 | +AYA + CT + CCARTATTTGCYATAAARAARAARGAYAGYACYA | (SEQ ID NO: 320) |
| 70 | +AY + A + CTCCARTATTTGCYATAAARAARAARGAYAGYACY | (SEQ ID NO: 321) |
| 70 | +AY + A + CTCCARTATTTGCYATAAARAARAARGAYAGYACYA | (SEQ ID NO: 322) |
| 70 | Y + A + AYA + CTCCARTATTTGCYATAAARAARAARGAYAGYACY | (SEQ ID NO: 323) |
| 70 | +A + AYA + CTCCARTATTTGCYATAAARAARAARGAYAGYACYA | (SEQ ID NO: 324) |
| 70 | Y+AAY + A + CTCCARTATTTGCYATAAARAARAARGAYAGYACY | (SEQ ID NO: 325) |
| 70 | +AAY + A + CTCCARTATTTGCYATAAARAARAARGAYAGYACYA | (SEQ ID NO: 326) |
| 70 | +CAR + TAT + TTGCYATAAARAARAARGAYAGYACY | (SEQ ID NO: 327) |
| 70 | +CAR + TAT + TTGCYATAAARAARAARGAYAGYACYA | (SEQ ID NO: 328) |
| 70 | +CARTA + T + TTGCYATAAARAARAARGAYAGYACY | (SEQ ID NO: 329) |
| 70 | +CARTA + T + TTGCYATAAARAARAARGAYAGYACYA | (SEQ ID NO: 330) |
| 70 | +CAR + TA + TTTGCYATAAARAARAARGAYAGYACY | (SEQ ID NO: 331) |
| 70 | +CAR + TA + TTTGCYATAAARAARAARGAYAGYACYA | (SEQ ID NO: 332) |
| 70 | +C + CARTA + TTTGCYATAAARAARAARGAYAGYACY | (SEQ ID NO: 333) |
| 70 | +C + CARTA + TTTGCYATAAARAARAARGAYAGYACYA | (SEQ ID NO: 334) |
| 70 | +CCAR + TA + TTTGCYATAAARAARAARGAYAGYACY | (SEQ ID NO: 335) |
| 70 | +CCAR + TA + TTTGCYATAAARAARAARGAYAGYACYA | (SEQ ID NO: 336) |
| 70 | +C + CAR + TATTTGCYATAAARAARAARGAYAGYACY | (SEQ ID NO: 337) |
| 70 | +C + CAR + TATTTGCYATAAARAARAARGAYAGYACYA | (SEQ ID NO: 338) |
| 70 | +CT + CCAR + TATTTGCYATAAARAARAARGAYAGYACY | (SEQ ID NO: 339) |
| 70 | +CT + CCAR + TATTTGCYATAAARAARAARGAYAGYACYA | (SEQ ID NO: 340) |
| 70 | +CTC + CAR + TATTTGCYATAAARAARAARGAYAGYACY | (SEQ ID NO: 341) |
| 70 | +CTC + CAR + TATTTGCYATAAARAARAARGAYAGYACYA | (SEQ ID NO: 342) |
| 70 | +CT + C + CARTATTTGCYATAAARAARAARGAYAGYACY | (SEQ ID NO: 343) |
| 70 | +CT + C + CARTATTTGCYATAAARAARAARGAYAGYACYA | (SEQ ID NO: 344) |
| 70 | Y + A + AY + ACTCCARTATTTGCYATAAARAARAARGAYAGYACY | (SEQ ID NO: 345) |

TABLE 5 -continued

| | | |
|---|---|---|
| 70 | +A + AY + ACTCCARTATTTGCYATAAARAARAARGAYAGYACYA (SEQ ID NO: 346) | |
| 74 | GCYATAAARAARAARGAYAGYACYAARTGGAGRAAA (SEQ ID NO: 347) | |
| 74 | TTGCYATAAARAARAARGAYAGYACYAARTGGAGRAAA (SEQ ID NO: 348) | |
| 74 | ATTTGCYATAAARAARAARGAYAGYACYAARTGGAGRAAA (SEQ ID NO: 349) | |
| 74 | AARAARAARGAYAGYACYAARTGGAGRAAA (SEQ ID NO: 350) | |
| 74 | TAAARAARAARGAYAGYACYAARTGGAGRAAA (SEQ ID NO: 351) | |
| 74 | ATAAARAARAARGAYAGYACYAARTGGAGRAAA (SEQ ID NO: 352) | |
| 74 | CCARTATTTGCYATAAARAARAARGAYAGYACYAARTGGAGAAAA (SEQ ID NO: 353) | |
| 74 | GCYATAAARAARAARGAYAGYACYAARTGGAGRAAA + N (SEQ ID NO: 354) | |
| 74 | TTGCYATAAARAARAARGAYAGYACYAARTGGAGRAAA + N (SEQ ID NO: 355) | |
| 74 | ATTTGCYATAAARAARAARGAYAGYACYAARTGGAGRAAA + N (SEQ ID NO: 356) | |
| 74 | AARAARAARGAYAGYACYAARTGGAGRAAA + N (SEQ ID NO: 357) | |
| 74 | TAAARAARAARGAYAGYACYAARTGGAGRAAA + N (SEQ ID NO: 358) | |
| 74 | ATAAARAARAARGAYAGYACYAARTGGAGRAAA + N (SEQ ID NO: 359) | |
| 74 | CCARTATTTGCYATAAARAARAARGAYAGYACYAARTGGAGAAAA + N (SEQ ID NO: 360) | |
| 74 | +GCY + ATA + AARAARAARGAYAGYACYAARTGGAGRAAA (SEQ ID NO: 361) | |
| 74 | +GCYA + TA + AARAARAARGAYAGYACYAARTGGAGRAAA (SEQ ID NO: 362) | |
| 74 | +GCY + A + TAAARAARAARGAYAGYACYAARTGGAGRAAA (SEQ ID NO: 363) | |
| 74 | +TT + GCYA + TAAARAARAARGAYAGYACYAARTGGAGRAAA (SEQ ID NO: 364) | |
| 74 | +TTGCY + A + TAAARAARAARGAYAGYACYAARTGGAGRAAA (SEQ ID NO: 365) | |
| 74 | +TT + GCY + ATAAARAARAARGAYAGYACYAARTGGAGRAAA (SEQ ID NO: 366) | |
| 74 | A + T + TTGCY + ATAAARAARAARGAYAGYACYAARTGGAGRAAA (SEQ ID NO: 367) | |
| 74 | A + TTT + GCY + ATAAARAARAARGAYAGYACYAARTGGAGRAAA (SEQ ID NO: 368) | |
| 74 | +AAR + AARA + ARGAYAGYACYAARTGGAGRAAA (SEQ ID NO: 369) | |
| 74 | +AARAAR + A + ARGAYAGYACYAARTGGAGRAAA (SEQ ID NO: 370) | |
| 74 | +AAR + AAR + AARGAYAGYACYAARTGGAGRAAA (SEQ ID NO: 371) | |
| 74 | +TA + AARAAR + AARGAYAGYACYAARTGGAGRAAA (SEQ ID NO: 372) | |
| 74 | +TAAAR + AAR + AARGAYAGYACYAARTGGAGRAAA (SEQ ID NO: 373) | |
| 74 | +TA + AAR + AARAARGAYAGYACYAARTGGAGRAAA (SEQ ID NO: 374) | |
| 74 | +A + TAAAR + AARAARGAYAGYACYAARTGGAGRAAA (SEQ ID NO: 375) | |
| 74 | +ATA + AAR + AARAARGAYAGYACYAARTGGAGRAAA (SEQ ID NO: 376) | |
| 74 | +A + TA + AARAARAARGAYAGYACYAARTGGAGRAAA (SEQ ID NO: 377) | |
| 74 | A + T + TT + GCYATAAARAARAARGAYAGYACYAARTGGAGRAAA (SEQ ID NO: 378) | |
| 75 | TAAARAARAARGAYAGYACYAARTGGAGRAAATTA (SEQ ID NO: 379) | |
| 75 | TAAARAARAARGAYAGYACYAARTGGAGRAAATTAG (SEQ ID NO: 380) | |
| 75 | ATAAARAARAARGAYAGYACYAARTGGAGRAAATTA (SEQ ID NO: 381) | |
| 75 | ATAAARAARAARGAYAGYACYAARTGGAGRAAATTAG (SEQ ID NO: 382) | |

TABLE 5 -continued

| 75 | TGCYATAAARAARAARGAYAGYACYAARTGGAGRAAATTA (SEQ ID NO: 383) |
| --- | --- |
| 75 | GCYATAAARAARAARGAYAGYACYAARTGGAGRAAATTAG (SEQ ID NO: 384) |
| 75 | AARGAYAGYACYAARTGGAGRAAATTA (SEQ ID NO: 385) |
| 75 | AARGAYAGYACYAARTGGAGRAAATTAG (SEQ ID NO: 386) |
| 75 | AARAARGAYAGYACYAART GGAGRAAATTA (SEQ ID NO: 387) |
| 75 | AARAARGAYAGYACYAART GGAGRAAATTAG (SEQ ID NO: 388) |
| 75 | AARAARAARGAYAGYACYAARTGGAGRAAATTA (SEQ ID NO: 389) |
| 75 | AARAARAARGAYAGYACYAARTGGAGRAAATTAG (SEQ ID NO: 390) |
| 75 | RTATTTGCYATAAARAARAARGAYAGYACYAARTGGAGRAAATTA (SEQ ID NO: 391) |
| 75 | TAAARAARAARGAYAGYACYAARTGGAGRAAATTA + N (SEQ ID NO: 392) |
| 75 | TAAARAARAARGAYAGYACYAARTGGAGRAAATTAG + N (SEQ ID NO: 393) |
| 75 | ATAAARAARAARGAYAGYACYAARTGGAGRAAATTA + N (SEQ ID NO: 394) |
| 75 | ATAAARAARAARGAYAGYACYAARTGGAGRAAATTAG + N (SEQ ID NO: 395) |
| 75 | TGCYATAAARAARAARGAYAGYACYAARTGGAGRAAATTA + N (SEQ ID NO: 396) |
| 75 | GCYATAAARAARAARGAYAGYACYAARTGGAGRAAATTAG + N (SEQ ID NO: 397) |
| 75 | AARGAYAGYACYAARTGGAGRAAATTA + N (SEQ ID NO: 398) |
| 75 | AARGAYAGYACYAARTGGAGRAAATTAG + N (SEQ ID NO: 399) |
| 75 | AARAARGAYAGYACYAARTGGAGRAAATTA + N (SEQ ID NO: 400) |
| 75 | AARAARGAYAGYACYAARTGGAGRAAATTAG + N (SEQ ID NO: 401) |
| 75 | AARAARAARGAYAGYACYAARTGGAGRAAATTA + N (SEQ ID NO: 402) |
| 75 | AARAARAARGAYAGYACYAARTGGAGRAAATTAG + N (SEQ ID NO: 403) |
| 75 | RTATTTGCYATAAARAARAARGAYAGYACYAARTGGAGRAAATTA + N (SEQ ID NO: 404) |
| 75 | +TA + AARAAR + AARGAYAGYACYAARTGGAGRAAATTA (SEQ ID NO: 405) |
| 75 | +TA + AARAAR + AARGAYAGYACYAARTGGAGRAAATTAG (SEQ ID NO: 406) |
| 75 | +TAAAR + AAR + AARGAYAGYACYAARTGGAGRAAATTA (SEQ ID NO: 407) |
| 75 | +TAAAR + AAR + AARGAYAGYACYAARTGGAGRAAATTAG (SEQ ID NO: 408) |
| 75 | +TA + AAR + AARAARGAYAGYACYAARTGGAGRAAATTA (SEQ ID NO: 409) |
| 75 | +TA + AAR + AARAARGAYAGYACYAARTGGAGRAAATTAG (SEQ ID NO: 410) |
| 75 | +A + TAAAR + AARAARGAYAGYACYAARTGGAGRAAATTA (SEQ ID NO: 411) |
| 75 | +A + TAAAR + AARAARGAYAGYACYAARTGGAGRAAATTAG (SEQ ID NO: 412) |
| 75 | +ATA + AAR + AARAARGAYAGYACYAARTGGAGRAAATTA (SEQ ID NO: 413) |
| 75 | +ATA + AAR + AARAARGAYAGYACYAARTGGAGRAAATTAG (SEQ ID NO: 414) |
| 75 | +A + TA + AARAARAARGAYAGYACYAARTGGAGRAAATTA (SEQ ID NO: 415) |
| 75 | +A + TA + AARAARAARGAYAGYACYAARTGGAGRAAATTAG (SEQ ID NO: 416) |
| 75 | T + GCY + ATA + AARAARAARGAYAGYACYAARTGGAGRAAATTA (SEQ ID NO: 417) |
| 75 | +GCY + ATA + AARAARAARGAYAGYACYAARTGGAGRAAATTAG (SEQ ID NO: 418) |

TABLE 5 -continued

| 75 | T + GCYA + TA + AARAARAARGAYAGYACYAARTGGAGRAAATTA (SEQ ID NO: 419) |
| 75 | +GCYA + TA + AARAARAARGAYAGYACYAARTGGAGRAAATTAG (SEQ ID NO: 420) |
| 75 | +A + ARGAYAGYACYAAR + TGGAGRAAATTA (SEQ ID NO: 421) |
| 75 | +A + ARGAYAGYACYAAR + TGGAGRAAATTAG (SEQ ID NO: 422) |
| 75 | +AARGAYAGYACY + AAR + TGGAGRAAATTA (SEQ ID NO: 423) |
| 75 | +AARGAYAGYACY + AAR + TGGAGRAAATTAG (SEQ ID NO: 424) |
| 75 | +A + ARGAYAGYACY + AARTGGAGRAAATTA (SEQ ID NO: 425) |
| 75 | +A + ARGAYAGYACY + AARTGGAGRAAATTAG (SEQ ID NO: 426) |
| 75 | +AAR + AARGAYAGYACY + AARTGGAGRAAATTA (SEQ ID NO: 427) |
| 75 | +AAR + AARGAYAGYACY + AARTGGAGRAAATTAG (SEQ ID NO: 428) |
| 75 | +AARA + ARGAYAGYACY + AARTGGAGRAAATTA (SEQ ID NO: 429) |
| 75 | +AARA + ARGAYAGYACY + AARTGGAGRAAATTAG (SEQ ID NO: 430) |
| 75 | +AAR + A + ARGAYAGYACYAARTGGAGRAAATTA (SEQ ID NO: 431) |
| 75 | +AAR + A + ARGAYAGYACYAARTGGAGRAAATTAG (SEQ ID NO: 432) |
| 75 | +AAR + AARA + ARGAYAGYACYAARTGGAGRAAATTA (SEQ ID NO: 433) |
| 75 | +AAR + AARA + ARGAYAGYACYAARTGGAGRAAATTAG (SEQ ID NO: 434) |
| 75 | +AARAAR + A + ARGAYAGYACYAARTGGAGRAAATTA (SEQ ID NO:435) |
| 75 | +AARAAR + A + ARGAYAGYACYAARTGGAGRAAATTAG (SEQ ID NO: 436) |
| 75 | +AAR + AAR + AARGAYAGYACYAARTGGAGRAAATTA (SEQ ID NO: 437) |
| 75 | +AAR + AAR + AARGAYAGYACYAARTGGAGRAAATTAG (SEQ ID NO: 438) |
| 75 | T + GCY + A + TAAARAARAARGAYAGYACYAARTGGAGRAAATTA (SEQ ID NO: 439) |
| 75 | +GCY + A + TAAARAARAARGAYAGYACYAARTGGAGRAAATTAG (SEQ ID NO: 440) |
| 77 | ARGAYAGYACYAARTGGAGRAAATTAGTAGAYTT (SEQ ID NO: 441) |
| 77 | AARGAYAGYACYAARTGGAGRAAATTAGTAGAYTT (SEQ ID NO: 442) |
| 77 | ARAARAARGAYAGYACYAARTGGAGRAAATTAGTAGAYTT (SEQ ID NO: 443) |
| 77 | AARTGGAGRAAATTAGTAGAYTT (SEQ ID NO: 444) |
| 77 | GCYATAAARAARAARGAYAGYACYAARTGGAGRAAATTAGTAGAT (SEQ ID NO: 445) |
| 77 | ARGAYAGYACYAARTGGAGRAAATTAGTAGAYTT + N (SEQ ID NO: 446) |
| 77 | AARGAYAGYACYAARTGGAGRAAATTAGTAGAYTT + N (SEQ ID NO: 447) |
| 77 | ARAARAARGAYAGYACYAARTGGAGRAAATTAGTAGAYTT + N (SEQ ID NO: 448) |
| 77 | AARTGGAGRAAATTAGTAGAYTT + N (SEQ ID NO: 449) |
| 77 | GCYATAAARAARAARGAYAGYACYAARTGGAGRAAATTAGTAGAT + N (SEQ ID NO: 450) |
| 77 | +ARGAYAGYACY + AART + GGAGRAAATTAGTAGAYTT (SEQ ID NO: 451) |
| 77 | +ARGAYAGYACYAAR + T + GGAGRAAATTAGTAGAYTT (SEQ ID NO: 452) |
| 77 | +ARGAYAGYACY + AAR + TGGAGRAAATTAGTAGAYTT (SEQ ID NO: 453) |
| 77 | +A + ARGAYAGYACYAAR + TGGAGRAAATTAGTAGAYTT (SEQ ID NO: 454) |
| 77 | +AARGAYAGYACY + AAR + TGGAGRAAATTAGTAGAYTT (SEQ ID NO: 455) |

TABLE 5 -continued

| | |
|---|---|
| 77 | +A + ARGAYAGYACY + AARTGGAGRAAATTAGTAGAYTT (SEQ ID NO: 456) |
| 77 | AR + AAR + AARGAYAGYACY + AARTGGAGRAAATTAGTAGAYTT (SEQ ID NO: 457) |
| 77 | AR + AARA + ARGAYAGYACY + AARTGGAGRAAATTAGTAGAYTT (SEQ ID NO: 458) |
| 77 | +AAR + TG + GAGRAAATTAGTAGAYTT (SEQ ID NO: 459) |
| 77 | +AART + G + GAGRAAATTAGTAGAYTT (SEQ ID NO: 460) |
| 77 | +AAR + T + GGAGRAAATTAGTAGAYTT (SEQ ID NO: 461) |
| 77 | AR + AAR + A + ARGAYAGYACYAARTGGAGRAAATTAGTAGAYTT (SEQ ID NO: 462) |
| 90 | GARCTYAATAARAGAACTCARGAYTTYTGGGAR (SEQ ID NO: 463) |
| 90 | GRGARCTYAATAARAGAACTCARGAYTTYTGGGAR (SEQ ID NO: 464) |
| 90 | YTTYAGRGARCTYAATAARAGAACTCARGAYTTYTGGGAR (SEQ ID NO: 465) |
| 90 | TYAATAARAGAACTCARGAYTTYTGGGAR (SEQ ID NO: 466) |
| 90 | CTYAATAARAGAACTCARGAYTTYTGGGAR (SEQ ID NO: 467) |
| 90 | ARCTYAATAARAGAACTCARGAYTTYTGGGAR (SEQ ID NO: 468) |
| 90 | GTRGAYTTYAGRGARCTYAATAARARAACTCARGAYTTCTGGGAA (SEQ ID NO: 469) |
| 90 | GARCTYAATAARAGAACTCARGAYTTYTGGGAR + N (SEQ ID NO: 470) |
| 90 | GRGARCTYAATAARAGAACTCARGAYTTYTGGGAR + N (SEQ ID NO: 471) |
| 90 | YTTYAGRGARCTYAATAARAGAACTCARGAYTTYTGGGAR + N (SEQ ID NO: 472) |
| 90 | TYAATAARAGAACTCARGAYTTYTGGGAR + N (SEQ ID NO: 473) |
| 90 | CTYAATAARAGAACTCARGAYTTYTGGGAR + N (SEQ ID NO: 474) |
| 90 | ARCTYAATAARAGAACTCARGAYTTYTGGGAR + N (SEQ ID NO: 475) |
| 90 | GTRGAYTTYAGRGARCTYAATAARARAACTCARGAYTTCTGGGAA + N (SEQ ID NO: 476) |
| 90 | +G + ARC + TYAATAARAGAACTCARGAYTTYTGGGAR (SEQ ID NO: 477) |
| 90 | +GAR + C + TYAATAARAGAACTCARGAYTTYTGGGAR (SEQ ID NO: 478) |
| 90 | +G + AR + CTYAATAARAGAACTCARGAYTTYTGGGAR (SEQ ID NO: 479) |
| 90 | +GR + GAR + CTYAATAARAGAACTCARGAYTTYTGGGAR (SEQ ID NO: 480) |
| 90 | +GRG + AR + CTYAATAARAGAACTCARGAYTTYTGGGAR (SEQ ID NO: 481) |
| 90 | +GR + G + ARCTYAATAARAGAACTCARGAYTTYTGGGAR (SEQ ID NO: 482) |
| 90 | YT + TYA + GRG + ARCTYAATAARAGAACTCARGAYTTYTGGGAR (SEQ ID NO: 483) |
| 90 | YT + TYAGR + G + ARCTYAATAARAGAACTCARGAYTTYTGGGAR (SEQ ID NO: 484) |
| 90 | +TY + AAT + AARAGAACTCARGAYTTYTGGGAR (SEQ ID NO: 485) |
| 90 | +TYA + AT + AARAGAACTCARGAYTTYTGGGAR (SEQ ID NO: 486) |
| 90 | +TY + A + ATAARAGAACTCARGAYTTYTGGGAR (SEQ ID NO: 487) |
| 90 | +C + TYA + ATAARAGAACTCARGAYTTYTGGGAR (SEQ ID NO: 488) |
| 90 | +CTY + A + ATAARAGAACTCARGAYTTYTGGGAR (SEQ ID NO: 489) |
| 90 | +C + TY + AATAARAGAACTCARGAYTTYTGGGAR (SEQ ID NO: 490) |
| 90 | +AR + CTY + AATAARAGAACTCARGAYTTYTGGGAR (SEQ ID NO: 491) |
| 90 | +ARC + TY + AATAARAGAACTCARGAYTTYTGGGAR (SEQ ID NO: 492) |
| 90 | +AR + C + TYAATAARAGAACTCARGAYTTYTGGGAR (SEQ ID NO: 493) |
| 90 | YT + TYA + GR + GARCTYAATAARAGAACTCARGAYTTYTGGGAR (SEQ ID NO: 494) |

TABLE 5 -continued

| | |
|---|---|
| 98 | GAYTTYTGGGARGTYCAATTAGGRATACCNCAYCCHG (SEQ ID NO: 495) |
| 98 | ARGAYTTYTGGGARGTYCAATTAGGRATACCNCAYCCHG (SEQ ID NO: 496) |
| 98 | CARGAYTTYTGGGARGTYCAATTAGGRATACCNCAYCCHG (SEQ ID NO: 497) |
| 98 | TYTGGGARGTYCAATTAGGRATACCNCAYCCHG (SEQ ID NO: 498) |
| 98 | TTYTGGGARGTYCAATTAGGRATACCNCAYCCHG (SEQ ID NO: 499) |
| 98 | AYTTYTGGGARGTYCAATTAGGRATACCNCAYCCHG (SEQ ID NO: 500) |
| 98 | ARAACTCARGAYTTYTGGGARGTYCARTTAGGRATACCDCATCCA (SEQ ID NO: 501) |
| 98 | GAYTTYTGGGARGTYCAATTAGGRATACCNCAYCCHG + N (SEQ ID NO: 502) |
| 98 | ARGAYTTYTGGGARGTYCAATTAGGRATACCNCAYCCHG + N (SEQ ID NO: 503) |
| 98 | CARGAYTTYTGGGARGTYCAATTAGGRATACCNCAYCCHG + N (SEQ ID NO: 504) |
| 98 | TYTGGGARGTYCAATTAGGRATACCNCAYCCHG + N (SEQ ID NO: 505) |
| 98 | TTYTGGGARGTYCAATTAGGRATACCNCAYCCHG + N (SEQ ID NO: 506) |
| 98 | AYTTYTGGGARGTYCAATTAGGRATACCNCAYCCHG + N (SEQ ID NO: 507) |
| 98 | ARAACTCARGAYTTYTGGGARGTYCARTTAGGRATACCDCATCCA + N (SEQ ID NO: 508) |
| 98 | +G + AYT + TYTGGGARGTYCAATTAGGRATACCNCAYCCHG (SEQ ID NO: 509) |
| 98 | +GAY + T + TYTGGGARGTYCAATTAGGRATACCNCAYCCHG (SEQ ID NO: 510) |
| 98 | +G + AY + TTYTGGGARGTYCAATTAGGRATACCNCAYCCHG (SEQ ID NO: 511) |
| 98 | +AR + GAY + TTYTGGGARGTYCAATTAGGRATACCNCAYCCHG (SEQ ID NO: 512) |
| 98 | +ARG + AY + TTYTGGGARGTYCAATTAGGRATACCNCAYCCHG (SEQ ID NO: 513) |
| 98 | +AR + G + AYTTYTGGGARGTYCAATTAGGRATACCNCAYCCHG (SEQ ID NO: 514) |
| 98 | +C + ARG + AYTTYTGGGARGTYCAATTAGGRATACCNCAYCCHG (SEQ ID NO: 515) |
| 98 | +CAR + G + AYTTYTGGGARGTYCAATTAGGRATACCNCAYCCHG (SEQ ID NO: 516) |
| 98 | +TY + TGGG + ARGTYCAATTAGGRATACCNCAYCCHG (SEQ ID NO: 517) |
| 98 | +TYTGG+ +G + ARGTYCAATTAGGRATACCNCAYCCHG (SEQ ID NO: 518) |
| 98 | +TY + TGG + GARGTYCAATTAGGRATACCNCAYCCHG (SEQ ID NO: 519) |
| 98 | +T + TYTGG + GARGTYCAATTAGGRATACCCAYCCHG (SEQ ID NO: 520) |
| 98 | +TTY + TGG + GARGTYCAATTAGGRATACCNCAYCCHG (SEQ ID NO: 521) |
| 98 | +T + TY + TGGGARGTYCAATTAGGRATACCNCAYCCHG (SEQ ID NO: 522) |
| 98 | +AY + TTY + TGGGARGTYCAATTAGGRATACCNCAYCCHG (SEQ ID NO: 523) |
| 98 | +AYT + TY + TGGGARGTYCAATTAGGRATACCNCAYCCHG (SEQ ID NO: 524) |
| 98 | +AY + T + TYTGGGARGTYCAATTAGGRATACCNCAYCCHG (SEQ ID NO: 525) |
| 98 | +C + AR + GAYTTYTGGGARGTYCAATTAGGRATACCNCAYCCHG (SEQ ID NO: 526) |
| 100 | TGGGARGTYCAATTAGGRATACCNCAYCCHGCRGGD (SEQ ID NO: 527) |
| 100 | TYTGGGARGTYCAATTAGGRATACCNCAYCCHGCRGGD (SEQ ID NO: 528) |
| 100 | YTTYTGGGARGTYCAATTAGGRATACCNCAYCCHGCRGGD (SEQ ID NO: 529) |
| 100 | TYCAATTAGGRATACCNCAYCCHGCRGGD (SEQ ID NO: 530) |

TABLE 5 -continued

| | |
|---|---|
| 100 | ARGTYCAATTAGGRATACCNCAYCCHGCRGGD (SEQ ID NO: 531) |
| 100 | GARGTYCAATTAGGRATACCNCAYCCHGCRGGD (SEQ ID NO: 532) |
| 100 | CARGAYTTYTGGGARGTYCARTTAGGRATACCDCAYCCAGCAGGG (SEQ ID NO: 533) |
| 100 | TGGGARGTYCAATTAGGRATACCNCAYCCHGCRGGD + N (SEQ ID NO: 534) |
| 100 | TYTGGGARGTYCAATTAGGRATACCNCAYCCHGCRGGD + N (SEQ ID NO: 535) |
| 100 | YTTYTGGGARGTYCAATTAGGRATACCNCAYCCHGCRGGD + N (SEQ ID NO: 536) |
| 100 | TYCAATTAGGRATACCNCAYCCHGCRGGD + N (SEQ ID NO: 537) |
| 100 | ARGTYCAATTAGGRATACCNCAYCCHGCRGGD + N (SEQ ID NO: 538) |
| 100 | GARGTYCAATTAGGRATACCNCAYCCHGCRGGD + N (SEQ ID NO: 539) |
| 100 | CARGAYTTYTGGGARGTYCARTTAGGRATACCDCAYCCAGCAGGG + N (SEQ ID NO: 540) |
| 100 | +TGG + GARG + TYCAATTAGGRATACCNCAYCCHGCRGGD (SEQ ID NO: 541) |
| 100 | +TGGG + ARG + TYCAATTAGGRATACCNCAYCCHGCRGGD (SEQ ID NO: 542) |
| 100 | +TGG + G + ARGTYCAATTAGGRATACCNCAYCCHGCRGGD (SEQ ID NO: 543) |
| 100 | +TY + TGGG + ARGTYCAATTAGGRATACCNCAYCCHGCRGGD (SEQ ID NO: 544) |
| 100 | +TYTGG + G + ARGTYCAATTAGGRATACCNCAYCCHGCRGGD (SEQ ID NO: 545) |
| 100 | +TY + TGG + GARGTYCAATTAGGRATACCNCAYCCHGCRGGD (SEQ ID NO: 546) |
| 100 | Y + T + TYTGG + GARGTYCAATTAGGRATACCNCAYCCHGCRGGD (SEQ ID NO: 547) |
| 100 | Y + TTY + TGG + GARGTYCAATTAGGRATACCNCAYCCHGCRGGD (SEQ ID NO: 548) |
| 100 | +TY + CAAT + TAGGRATACCNCAYCCHGCRGGD (SEQ ID NO: 549) |
| 100 | +TYC + AAT + TAGGRATACCNCAYCCHGCRGGD (SEQ ID NO: 550) |
| 100 | +TY + C + AATTAGGRATACCNCAYCCHGCRGGD (SEQ ID NO: 551) |
| 100 | +ARG + TYC + AATTAGGRATACCNCAYCCHGCRGGD (SEQ ID NO: 552) |
| 100 | +ARGTY + C + AATTAGGRATACCNCAYCCHGCRGGD (SEQ ID NO: 553) |
| 100 | +ARG + TY + CAATTAGGRATACCNCAYCCHGCRGGD (SEQ ID NO: 554) |
| 100 | +G + ARGTY + CAATTAGGRATACCNCAYCCHGCRGGD (SEQ ID NO: 555) |
| 100 | +GARG + TY + CAATTAGGRATACCNCAYCCHGCRGGD (SEQ ID NO: 556) |
| 100 | +G + ARG + TYCAATTAGGRATACCNCAYCCHGCRGGD (SEQ ID NO: 557) |
| 100 | Y + T + TY + TGGGARGTYCAATTAGGRATACCNCAYCCHGCRGGD (SEQ ID NO: 558) |
| 101 | ARGTYCAATTAGGRATACCNCAYCCHGCRGGDYTA (SEQ ID NO: 559) |
| 101 | GARGTYCAATTAGGRATACCNCAYCCHGCRGGDYTA (SEQ ID NO: 560) |
| 101 | YTGGGARGTYCAATTAGGRATACCNCAYCCHGCRGGDYTA (SEQ ID NO: 561) |
| 101 | AATTAGGRATACCNCAYCCHGCRGGDYTA (SEQ ID NO: 562) |
| 101 | CAATTAGGRATACCNCAYCCHGCRGGDYTA (SEQ ID NO: 563) |
| 101 | TYCAATTAGGRATACCNCAYCCHGCRGGDYTA (SEQ ID NO: 564) |
| 101 | GAYTTYTGGGARGTYCARTTAGGRATACCDCAYCCHGCRGGGTTA (SEQ ID NO: 565) |
| 101 | ARGTYCAATTAGGRATACCNCAYCCHGCRGGDYTA + N (SEQ ID NO: 566) |

TABLE 5 -continued

| | | |
|---|---|---|
| 101 | GARGTYCAATTAGGRATACCNCAYCCHGCRGGDYTA + N | (SEQ ID NO: 567) |
| 101 | YTGGGARGTYCAATTAGGRATACCNCAYCCHGCRGGDYTA + N | (SEQ ID NO: 568) |
| 101 | AATTAGGRATACCNCAYCCHGCRGGDYTA + N | (SEQ ID NO: 569) |
| 101 | CAATTAGGRATACCNCAYCCHGCRGGDYTA + N | (SEQ ID NO: 570) |
| 101 | TYCAATTAGGRATACCNCAYCCHGCRGGDYTA + N | (SEQ ID NO: 571) |
| 101 | GAYTTYTGGGARGTYCARTTAGGRATACCDCAYCCHGCRGGGTTA + N | (SEQ ID NO: 572) |
| 101 | +ARG + TYC + AATTAGGRATACCNCAYCCHGCRGGDYTA | (SEQ ID NO: 573) |
| 101 | +ARGTY + C + AATTAGGRATACCNCAYCCHGCRGGDYTA | (SEQ ID NO: 574) |
| 101 | +ARG + TY + CAATTAGGRATACCNCAYCCHGCRGGDYTA | (SEQ ID NO: 575) |
| 101 | +G + ARGTY + CAATTAGGRATACCNCAYCCHGCRGGDYTA | (SEQ ID NO: 576) |
| 101 | +GARG + TY + CAATTAGGRATACCNCAYCCHGCRGGDYTA | (SEQ ID NO: 577) |
| 101 | +G + ARG + TYCAATTAGGRATACCNCAYCCHGCRGGDYTA | (SEQ ID NO: 578) |
| 101 | Y + TGG + GARG + TYCAATTAGGRATACCNCAYCCHGCRGGDYTA | (SEQ ID NO: 579) |
| 101 | Y + TGGG + ARG + TYCAATTAGGRATACCNCAYCCHGCRGGDYTA | (SEQ ID NO: 580) |
| 101 | +AAT + TAG + GRATACCNCAYCCHGCRGGDYTA | (SEQ ID NO: 581) |
| 101 | +AATTA + G + GRATACCNCAYCCHGCRGGDYTA | (SEQ ID NO: 582) |
| 101 | +AAT + TA + GGRATACCNCAYCCHGCRGGDYTA | (SEQ ID NO: 583) |
| 101 | +C + AATTA + GGRATACCNCAYCCHGCRGGDYTA | (SEQ ID NO: 584) |
| 101 | +CAAT + TA + GGRATACCNCAYCCHGCRGGDYTA | (SEQ ID NO: 585) |
| 101 | +C + AAT + TAGGRATACCNCAYCCHGCRGGDYTA | (SEQ ID NO :586) |
| 101 | +TY + CAAT + TAGGRATACCNCAYCCHGCRGGDYTA | (SEQ ID NO: 587) |
| 101 | +TYC + AAT + TAGGRATACCNCAYCCHGCRGGDYTA | (SEQ ID NO: 588) |
| 101 | +TY + C + AATTAGGRATACCNCAYCCHGCRGGDYTA | (SEQ ID NO: 589) |
| 101 | Y + TGG + G + ARGTYCAATTAGGRATACCNCAYCCHGCRGGDYTA | (SEQ ID NO: 590) |
| 103 | AATTAGGRATACCNCAYCCHGCRGGDYTAAAAAAGAA | (SEQ ID NO: 591) |
| 103 | CAATTAGGRATACCNCAYCCHGCRGGDYTAAAAAAGAA | (SEQ ID NO: 592) |
| 103 | TYCAATTAGGRATACCNCAYCCHGCRGGDYTAAAAAAGAA | (SEQ ID NO: 593) |
| 103 | GRATACCNCAYCCHGCRGGDYTAAAAAAGAA | (SEQ ID NO: 594) |
| 103 | GGRATACCNCAYCCHGCRGGDYTAAAAAAGAA | (SEQ ID NO: 595) |
| 103 | TAGGRATACCNCAYCCHGCRGGDYTAAAAAAGAA | (SEQ ID NO: 596) |
| 103 | TGGGARGTYCARTTAGGRATACCDCAYCCHGCRGGDYTAAAAAG | (SEQ ID NO: 597) |
| 103 | AATTAGGRATACCNCAYCCHGCRGGDYTAAAAAAGAA + N | (SEQ ID NO: 598) |
| 103 | CAATTAGGRATACCNCAYCCHGCRGGDYTAAAAAAGAA + N | (SEQ ID NO: 599) |
| 103 | TYCAATTAGGRATACCNCAYCCHGCRGGDYTAAAAAAGAA + N | (SEQ ID NO: 600) |
| 103 | GRATACCNCAYCCHGCRGGDYTAAAAAAGAA + N | (SEQ ID NO: 601) |
| 103 | GGRATACCNCAYCCHGCRGGDYTAAAAAAGAA + N | (SEQ ID NO: 602) |
| 103 | TAGGRATACCNCAYCCHGCRGGDYTAAAAAAGAA + N | (SEQ ID NO: 603) |

TABLE 5 -continued

| | |
|---|---|
| 103 | TGGGARGTYCARTTAGGRATACCDCAYCCHGCRGGDYTAAAAAG + N (SEQ ID NO: 604) |
| 103 | +AAT + TAG + GRATACCNCAYCCHGCRGGDYTAAAAAAGAA (SEQ ID NO: 605) |
| 103 | +AATTA + G + GRATACCNCAYCCHGCRGGDYTAAAAAAGAA (SEQ ID NO: 606) |
| 103 | +AAT + TA + GGRATACCNCAYCCHGCRGGDYTAAAAAAGAA (SEQ ID NO: 607) |
| 103 | +C + AATTA + GGRATACCNCAYCCHGCRGGDYTAAAAAAGAA (SEQ ID NO: 608) |
| 103 | +CAAT + TA + GGRATACCNCAYCCHGCRGGDYTAAAAAAGAA (SEQ ID NO: 609) |
| 103 | +C + AAT + TAGGRATACCNCAYCCHGCRGGDYTAAAAAAGAA (SEQ ID NO: 610) |
| 103 | +TY + CAAT + TAGGRATACCMCAUCCJGCRGGDUTAAAAAAGAA (SEQ ID NO: 611) |
| 103 | +TYC + AAT + TAGGRATACCNCAYCCHGCRGGDYTAAAAAAGAA (SEQ ID NO: 612) |
| 103 | +GR + ATA + CCNCAYCCHGCRGGDYTAAAAAAGAA (SEQ ID NO: 613) |
| 103 | +GRA + TA + CCNCAYCCHGCRGGDYTAAAAAAGAA (SEQ ID NO: 614) |
| 103 | +GR + A + TACCNCAYCCHGCRGGDYTAAAAAAGAA (SEQ ID NO: 615) |
| 103 | +G + GRA + TACCNCAYCCHGCRGGDYTAAAAAAGAA (SEQ ID NO: 616) |
| 103 | +GGR + A + TACCNCAYCCHGCRGGDYTAAAAAAGAA (SEQ ID NO: 617) |
| 103 | +G + GR + ATACCNCAYCCHGCRGGDYTAAAAAAGAA (SEQ ID NO: 618) |
| 103 | +TA + GGR + ATACCNCAYCCHGCRGGDYTAAAAAAGAA (SEQ ID NO: 619) |
| 103 | +TAG + GR + ATACCNCAYCCHGCRGGDYTAAAAAAGAA (SEQ ID NO: 620) |
| 103 | +TA + G + GRATACCNCAYCCHGCRGGDYTAAAAAAGAA (SEQ ID NO: 621) |
| 103 | +TY + C + AATTAGGRATACCNCAYCCHGCRGGDYTAAAAAAGAA (SEQ ID NO: 622) |
| 106 | ATACCNCAYCCHGCRGGDYTAAAAAAGAAMAAATCAG (SEQ ID NO: 623) |
| 106 | GRATACCNCAYCCHGCRGGDYTAAAAAAGAAMAAATCAG (SEQ ID NO: 624) |
| 106 | GGRATACCNCAYCCHGCRGGDYTAAAAAAGAAMAAATCAG (SEQ ID NO: 625) |
| 106 | CNCAYCCHGCRGGDYTAAAAAAGAAMAAATCAG (SEQ ID NO: 626) |
| 106 | CCNCAYCCHGCRGGDYTAAAAAAGAAMAAATCAG (SEQ ID NO: 627) |
| 106 | TACCNCAYCCHGCRGGDYTAAAAAAGAAMAAATCAG (SEQ ID NO: 628) |
| 106 | CARTTAGGRATACCDCAYCCHGCRGGDYTAAARAAGAARAAATCA (SEQ ID NO: 629) |
| 106 | ATACCNCAYCCHGCRGGDYTAAAAAAGAAMAAATCAG + N (SEQ ID NO: 630) |
| 106 | GRATACCNCAYCCHGCRGGDYTAAAAAAGAAMAAATCAG + N (SEQ ID NO: 631) |
| 106 | GGRATACCNCAYCCHGCRGGDYTAAAAAAGAAMAAATCAG + N (SEQ ID NO: 632) |
| 106 | CNCAYCCHGCRGGDYTAAAAAAGAAMAAATCAG + N (SEQ ID NO: 633) |
| 106 | CCNCAYCCHGCRGGDYTAAAAAAGAAMAAATCAG + N (SEQ ID NO: 634) |
| 106 | TACCNCAYCCHGCRGGDYTAAAAAAGAAMAAATCAG + N (SEQ ID NO: 635) |
| 106 | CARTTAGGRATACCDCAYCCHGCRGGDYTAAARAAGAARAAATCA + N (SEQ ID NO: 636) |

TABLE 5 -continued

| | |
|---|---|
| 106 | +A + TAC + CNCAYCCHGCRGGDYTAAAAAAGAAMAAATCAG (SEQ ID NO: 637) |
| 106 | +ATA + C + CNCAYCCHGCRGGDYTAAAAAAGAAMAAATCAG (SEQ ID NO: 638) |
| 106 | +A + TA + CCNCAYCCHGCRGGDYTAAAAAAGAAMAAATCAG (SEQ ID NO: 639) |
| 106 | +GR + ATA + CCNCAYCCHGCRGGDYTAAAAAAGAAMAAATCAG (SEQ ID NO: 640) |
| 106 | +GRA + TA + CCNCAYCCHGCRGGDYTAAAAAAGAAMAAATCAG (SEQ ID NO: 641) |
| 106 | +GR + A + TACCNCAYCCHGCRGGDYTAAAAAAGAAMAAATCAG (SEQ ID NO: 642) |
| 106 | +G + GRA + TACCNCAYCCHGCRGGDYTAAAAAAGAAMAAATCAG (SEQ ID NO: 643) |
| 106 | +GGR + A + TACCNCAYCCHGCRGGDYTAAAAAAGAAMAAATCAG (SEQ ID NO: 644) |
| 106 | +CN + CAY + CCHGCRGGDYTAAAAAAGAAMAAATCAG (SEQ ID NO: 645) |
| 106 | +CNC + AY + CCHGCRGGDYTAAAAAAGAAMAAATCAG (SEQ ID NO: 646) |
| 106 | +CN + C + AYCCHGCRGGDYTAAAAAAGAAMAAATCAG (SEQ ID NO: 647) |
| 106 | +C + CNC + AYCCHGCRGGDYTAAAAAAGAAMAAATCAG (SEQ ID NO: 648) |
| 106 | +CCN + C + AYCCHGCRGGDYTAAAAAAGAAMAAATCAG (SEQ ID NO: 649) |
| 106 | +C + CN + CAYCCHGCRGGDYTAAAAAAGAAMAAATCAG (SEQ ID NO: 650) |
| 106 | +TA + CCN + CAYCCHGCRGGDYTAAAAAAGAAMAAATCAG (SEQ ID NO: 651) |
| 106 | +TAC + CN + CAYCCHGCRGGDYTAAAAAAGAAMAAATCAG (SEQ ID NO: 652) |
| 106 | +TA + C + CNCAYCCHGCRGGDYTAAAAAAGAAMAAATCAG (SEQ ID NO: 653) |
| 106 | +G + GR + ATACCNCAYCCHGCRGGDYTAAAAAAGAAMAAATCAG (SEQ ID NO: 654) |
| 108 | CAYCCHGCRGGDYTAAAAAAGAAMAAATCAGTRACA (SEQ ID NO: 655) |
| 108 | CNCAYCCHGCRGGDYTAAAAAAGAAMAAATCAGTRACA (SEQ ID NO: 656) |
| 108 | ACCNCAYCCHGCRGGDYTAAAAAAGAAMAAATCAGTRACA (SEQ ID NO: 657) |
| 108 | CHGCRGGDYTAAAAAAGAAMAAATCAGTRACA (SEQ ID NO: 658) |
| 108 | CCHGCRGGDYTAAAAAAGAAMAAATCAGTRACA (SEQ ID NO: 659) |
| 108 | AYCCHGCRGGDYTAAAAAAGAAMAAATCAGTRACA (SEQ ID NO: 660) |
| 108 | GGRATACCDCAYCCHGCRGGDYTAAARAAGAARAARTCWGTAACA (SEQ ID NO: 661) |
| 108 | CAYCCHGCRGGDYTAAAAAAGAAMAAATCAGTRACA + N (SEQ ID NO: 662) |
| 108 | CNCAYCCHGCRGGDYTAAAAAAGAAMAAATCAGTRACA + N (SEQ ID NO: 663) |
| 108 | ACCNCAYCCHGCRGGDYTAAAAAAGAAMAAATCAGTRACA + N (SEQ ID NO: 664) |
| 108 | CHGCRGGDYTAAAAAAGAAMAAATCAGTRACA + N (SEQ ID NO: 665) |
| 108 | CCHGCRGGDYTAAAAAAGAAMAAATCAGTRACA + N (SEQ ID NO: 666) |
| 108 | AYCCHGCRGGDYTAAAAAAGAAMAAATCAGTRACA + N (SEQ ID NO: 667) |
| 108 | GGRATACCDCAYCCHGCRGGDYTAAARAAGAARAARTCWGTAACA + N (SEQ ID NO: 668) |
| 108 | +C + AYC + CHGCRGGDYTAAAAAAGAAMAAATCAGTRACA (SEQ ID NO: 669) |
| 108 | +CAY + C + CHGCRGGDYTAAAAAAGAAMAAATCAGTRACA (SEQ ID NO: 670) |
| 108 | +C + AY + CCHGCRGGDYTAAAAAAGAAMAAATCAGTRACA (SEQ ID NO: 671) |

TABLE 5 -continued

| | |
|---|---|
| 108 | +CN + CAY + CCHGCRGGDYTAAAAAAGAAMAAATCAGTRACA (SEQ ID NO: 672) |
| 108 | +CNC + AY + CCHGCRGGDYTAAAAAAGAAMAAATCAGTRACA (SEQ ID NO: 673) |
| 108 | +CN + C + AYCCHGCRGGDYTAAAAAAGAAMAAATCAGTRACA (SEQ ID NO: 674) |
| 108 | A + C + CNC + AYCCHGCRGGDYTAAAAAAGAAMAAATCAGTRACA (SEQ ID NO: 675) |
| 108 | A + CCN + C + AYCCHGCRGGDYTAAAAAAGAAMAAATCAGTRACA (SEQ ID NO: 676) |
| 108 | +CHGCR + GGDY + TAAAAAAGAAMAAATCAGTRACA (SEQ ID NO: 677) |
| 108 | +CHGCRG + GDY + TAAAAAAGAAMAAATCAGTRACA (SEQ ID NO: 678) |
| 108 | +CHGCR + G + GDYTAAAAAAGAAMAAATCAGTRACA (SEQ ID NO: 679) |
| 108 | +C + CHGCRG + GDYTAAAAAAGAAMAAATCAGTRACA (SEQ ID NO: 680) |
| 108 | +CCHGCR + G + GDYTAAAAAAGAAMAAATCAGTRACA (SEQ ID NO: 681) |
| 108 | +C + CHGCR + GGDYTAAAAAAGAAMAAATCAGTRACA (SEQ ID NO: 682) |
| 108 | +AY + CCHGCR + GGDYTAAAAAAGAAMAAATCAGTRACA (SEQ ID NO: 683) |
| 108 | +AYC + CHGCR + GGDYTAAAAAAGAAMAAATCAGTRACA (SEQ ID NO: 684) |
| 108 | +AY+C + CHGCRG GDYTAAAAAAGAAMAAATCAGTRACA (SEQ ID NO: 685) |
| 108 | A + C + CN + CAYCCHGCRGGDYTAAAAAAGAAMAAATCAGTRACA (SEQ ID NO: 686) |
| 115 | CAGTRACAGTRYTRGATGTRGGDGAYGCAT (SEQ ID NO: 687) |
| 115 | AAATCAGTRACAGTRYTRGATGTRGGDGAYGCAT (SEQ ID NO: 688) |
| 115 | AAGAAMAAATCAGTRACAGTRYTRGATGTRGGDGAYGCAT (SEQ ID NO: 689) |
| 115 | TRYTRGATGTRGGDGAYGCAT (SEQ ID NO: 690) |
| 115 | CAGTRYTRGATGTRGGDGAYGCAT (SEQ ID NO: 691) |
| 115 | YTAAARAAGAARAARTCWGTRACAGTVYTRGATGTRGGDGATGCA (SEQ ID NO: 692) |
| 115 | CAGTRACAGTRYTRGATGTRGGDGAYGCAT + N (SEQ ID NO: 693) |
| 115 | AAATCAGTRACAGTRYTRGATGTRGGDGAYGCAT + N (SEQ ID NO: 694) |
| 115 | AAGAAMAAATCAGTRACAGTRYTRGATGTRGGDGAYGCAT + N (SEQ ID NO: 695) |
| 115 | TRYTRGATGTRGGDGAYGCAT + N (SEQ ID NO: 696) |
| 115 | CAGTRYTRGATGTRGGDGAYGCAT + N (SEQ ID NO: 697) |
| 115 | YTAAARAAGAARAARTCWGTRACAGTVYTRGATGTRGGDGATGCA + N (SEQ ID NO: 698) |
| 115 | +CAGTRA + CAGTRY + TRGATGTRGGDGAYGCAT (SEQ ID NO: 699) |
| 115 | +CAGTRACAG + TRY + TRGATGTRGGDGAYGCAT (SEQ ID NO: 700) |
| 115 | +CAGTRA + CAG + TRYTRGATGTRGGDGAYGCAT (SEQ ID NO: 701) |
| 115 | +AAAT + CAGTRACAG + TRYTRGATGTRGGDGAYGCAT (SEQ ID NO: 702) |
| 115 | +AAATCAGTRA + CAG + TRYTRGATGTRGGDGAYGCAT (SEQ ID NO: 703) |
| 115 | +AAAT + CAGTRA + CAGTRYTRGATGTRGGDGAYGCAT (SEQ ID NO: 704) |
| 115 | AAG + AAM + AAATCAGTRA + CAGTRYTRGATGTRGGDGAYGCAT (SEQ ID NO: 705) |
| 115 | AAG + AAMAAAT + CAGTRA + CAGTRYTRGATGTRGGDGAYGCAT (SEQ ID NO: 706) |
| 115 | +TRY + TRG + ATGTRGGDGAYGCAT (SEQ ID NO: 707) |
| 115 | +TRYTR + G + ATGTRGGDGAYGCAT (SEQ ID NO: 708) |

TABLE 5 -continued

| | |
|---|---|
| 115 | +TRY + TR + GATGTRGGDGAYGCAT (SEQ ID NO: 709) |
| 115 | +CAG + TRYTR + GATGTRGGDGAYGCAT (SEQ ID NO: 710) |
| 115 | +CAGTRY + TR + GATGTRGGDGAYGCAT (SEQ ID NO: 711) |
| 115 | +CAG + TRY + TRGATGTRGGDGAYGCAT (SEQ ID NO: 712) |
| 115 | AAG + AAM + AAAT + CAGTRACAGTRYTRGATGTRGGDGAYGCAT (SEQ ID NO: 713) |
| 116 | CAGTRACAGTRYTRGATGTRGGDGAYGCATAYT (SEQ ID NO: 714) |
| 116 | AAATCAGTRACAGTRYTRGATGTRGGDGAYGCATAYT (SEQ ID NO: 715) |
| 116 | AAMAAATCAGTRACAGTRYTRGATGTRGGDGAYGCATAYT (SEQ ID NO: 716) |
| 116 | TRGATGTRGGDGAYGCATAYT (SEQ ID NO: 717) |
| 116 | TRYTRGATGTRGGDGAYGCATAYT (SEQ ID NO: 718) |
| 116 | CAGTRYTRGATGTRGGDGAYGCATAYT (SEQ ID NO: 719) |
| 116 | AARAAGAARAARTCWGTRACAGTVYTRGATGTRGGDGATGCATAT (SEQ ID NO: 720) |
| 116 | CAGTRACAGTRYTRGATGTRGGDGAYGCATAYT + N (SEQ ID NO: 721) |
| 116 | AAATCAGTRACAGTRYTRGATGTRGGDGAYGCATAYT + N (SEQ ID NO: 722) |
| 116 | AAMAAATCAGTRACAGTRYTRGATGTRGGDGAYGCATAYT + N (SEQ ID NO: 723) |
| 116 | TRGATGTRGGDGAYGCATAYT + N (SEQ ID NO: 724) |
| 116 | TRYTRGATGTRGGDGAYGCATAYT + N (SEQ ID NO: 725) |
| 116 | CAGTRYTRGATGTRGGDGAYGCATAYT + N (SEQ ID NO: 726) |
| 116 | AARAAGAARAARTCWGTRACAGTVYTRGATGTRGGDGATGCATAT + N (SEQ ID NO: 727) |
| 116 | +CAGTRA + CAGTRY + TRGATGTRGGDGAYGCATAYT (SEQ ID NO: 728) |
| 116 | +CAGTRACAG + TRY + TRGATGTRGGDGAYGCATAYT (SEQ ID NO: 729) |
| 116 | +CAGTRA + CAG + TRYTRGATGTRGGDGAYGCATAYT (SEQ ID NO: 730) |
| 116 | +AAAT + CAGTRACAG + TRYTRGATGTRGGDGAYGCATAYT (SEQ ID NO: 731) |
| 116 | +AAATCAGTRA + CAG + TRYTRGATGTRGGDGAYGCATAYT (SEQ ID NO: 732) |
| 116 | +AAAT + CAGTRA + CAGTRYTRGATGTRGGDGAYGCATAYT (SEQ ID NO: 733) |
| 116 | +AAM + AAATCAGTRA + CAGTRYTRGATGTRGGDGAYGCATAYT (SEQ ID NO: 734) |
| 116 | +AAMAAAT + CAGTRA + CAGTRYTRGATGTRGGDGAYGCATAYT (SEQ ID NO: 735) |
| 116 | +TR + GATG + TRGGDGAYGCATAYT (SEQ ID NO: 736) |
| 116 | +TRG + ATG + TRGGDGAYGCATAYT (SEQ ID NO: 737) |
| 116 | +TR + G + ATGTRGGDGAYGCATAYT (SEQ ID NO: 738) |
| 116 | +TRY + TRG + ATGTRGGDGAYGCATAYT (SEQ ID NO: 739) |
| 116 | +TRYTR + G + ATGTRGGDGAYGCATAYT (SEQ ID NO: 740) |
| 116 | +TRY + TR + GATGTRGGDGAYGCATAYT (SEQ ID NO: 741) |
| 116 | +CAG + TRYTR + GATGTRGGDGAYGCATAYT (SEQ ID NO: 742) |
| 116 | +CAGTRY + TR + GATGTRGGDGAYGCATAYT (SEQ ID NO: 743) |
| 116 | +CAG + TRY + TRGATGTRGGDGAYGCATAYT (SEQ ID NO: 744) |
| 116 | +AAM + AAAT + CAGTRACAGTRYTRGATGTRGGDGAYGCATAYT (SEQ ID NO: 745) |

TABLE 5 -continued

| 118 | TRYTRGATGTRGGDGAYGCATAYTTYTCA (SEQ ID NO: 746) |
| --- | --- |
| 118 | CAGTRYTRGATGTRGGDGAYGCATAYTTYTCA (SEQ ID NO: 747) |
| 118 | ATCAGTRACAGTRYTRGATGTRGGDGAYGCATAYTTYTCA (SEQ ID NO: 748) |
| 118 | ATGTRGGDGAYGCATAYTTYTCA (SEQ ID NO: 749) |
| 118 | GATGTRGGDGAYGCATAYTTYTCA (SEQ ID NO: 750) |
| 118 | TRGATGTRGGDGAYGCATAYTTYTCA (SEQ ID NO: 751) |
| 118 | AARAARTCWGTRACAGTVYTRGATGTRGGDGATGCATATTTTTCA (SEQ ID NO: 752) |
| 118 | TRYTRGATGTRGGDGAYGCATAYTTYTCA + N (SEQ ID NO: 753) |
| 118 | CAGTRYTRGATGTRGGDGAYGCATAYTTYTCA + N (SEQ ID NO: 754) |
| 118 | ATCAGTRACAGTRYTRGATGTRGGDGAYGCATAYTTYTCA + N (SEQ ID NO: 755) |
| 118 | ATGTRGGDGAYGCATAYTTYTCA + N (SEQ ID NO: 756) |
| 118 | GATGTRGGDGAYGCATAYTTYTCA + N (SEQ ID NO: 757) |
| 118 | TRGATGTRGGDGAYGCATAYTTYTCA + N (SEQ ID NO: 758) |
| 118 | AARAARTCWGTRACAGTVYTRGATGTRGGDGATGCATATTTTTCA + N (SEQ ID NO: 759) |
| 118 | +TRY + TRG + ATGTRGGDGAYGCATAYTTYTCA (SEQ ID NO: 760) |
| 118 | +TRYTR + G + ATGTRGGDGAYGCATAYTTYTCA (SEQ ID NO: 761) |
| 118 | +TRY + TR + GATGTRGGDGAYGCATAYTTYTCA (SEQ ID NO: 762) |
| 118 | +CAG + TRYTR + GATGTRGGDGAYGCATAYTTYTCA (SEQ ID NO: 763) |
| 118 | +CAGTRY + TR + GATGTRGGDGAYGCATAYTTYTCA (SEQ ID NO: 764) |
| 118 | +CAG + TRY + TRGATGTRGGDGAYGCATAYTTYTCA (SEQ ID NO: 765) |
| 118 | AT + CAGTRA + CAGTRY + TRGATGTRGGDGAYGCATAYTTYTCA (SEQ ID NO: 766) |
| 118 | AT + CAGTRACAG + TRY + TRGATGTRGGDGAYGCATAYTTYTCA (SEQ ID NO: 767) |
| 118 | +ATG + TRG + GDGAYGCATAYTTYTCA (SEQ ID NO: 768) |
| 118 | +ATGTR + G + GDGAYGCATAYTTYTCA (SEQ ID NO: 769) |
| 118 | +ATG + TR + GGDGAYGCATAYTTYTCA (SEQ ID NO: 770) |
| 118 | +G + ATGTR + GGDGAYGCATAYTTYTCA (SEQ ID NO: 771) |
| 118 | +GATG + TR + GGDGAYGCATAYTTYTCA (SEQ ID NO: 772) |
| 118 | +G + ATG + TRGGDGAYGCATAYTTYTCA (SEQ ID NO: 773) |
| 118 | +TR + GATG + TRGGDGAYGCATAYTTYTCA (SEQ ID NO: 774) |
| 118 | +TRG + ATG + TRGGDGAYGCATAYTTYTCA (SEQ ID NO: 775) |
| 118 | +TR + G + ATGTRGGDGAYGCATAYTTYTCA (SEQ ID NO: 776) |
| 118 | AT + CAGTRA + CAG + TRYTRGATGTRGGDGAYGCATAYTTYTCA (SEQ ID NO: 777) |
| 138 | AARTAYACTGCATTYACYATACCTAGTRYAAAYAAT (SEQ ID NO: 778) |
| 138 | AARTAYACTGCATTYACYATACCTAGTRYAAAYAATG (SEQ ID NO: 779) |
| 138 | GRAARTAYACTGCATTYACYATACCTAGTRYAAAYAAT (SEQ ID NO: 780) |
| 138 | GRAARTAYACTGCATTYACYATACCTAGTRYAAAYAATG (SEQ ID NO: 781) |
| 138 | YAGRAARTAYACTGCATTYACYATACCTAGTRYAAAYAAT (SEQ ID NO: 782) |

TABLE 5 -continued

| | | |
|---|---|---|
| 138 | AGRAARTAYACTGCATTYACYATACCTAGTRYAAAYAATG | (SEQ ID NO: 783) |
| 138 | AYACTGCATTYACYATACCTAGTRYAAAYAAT | (SEQ ID NO: 784) |
| 138 | AYACTGCATTYACYATACCTAGTRYAAAYAATG | (SEQ ID NO: 785) |
| 138 | TAYACTGCATTYACYATACCTAGTRYAAAYAAT | (SEQ ID NO: 786) |
| 138 | TAYACTGCATTYACYATACCTAGTRYAAAYAATG | (SEQ ID NO: 787) |
| 138 | ARTAYACTGCATTYACYATACCTAGTRYAAAYAAT | (SEQ ID NO: 788) |
| 138 | ARTAYACTGCATTYACYATACCTAGTRYAAAYAATG | (SEQ ID NO: 789) |
| 138 | RRHTTYAGRAARTAYACTGCATTYACYATACCYAGTRYMAACAAT | (SEQ ID NO: 790) |
| 138 | AARTAYACTGCATTYACYATACCTAGTRYAAAYAAT + N | (SEQ ID NO: 791) |
| 138 | AARTAYACTGCATTYACYATACCTAGTRYAAAYAATG + N | (SEQ ID NO: 792) |
| 138 | GRAARTAYACTGCATTYACYATACCTAGTRYAAAYAAT + N | (SEQ ID NO: 793) |
| 138 | GRAARTAYACTGCATTYACYATACCTAGTRYAAAYAATG + N | (SEQ ID NO: 794) |
| 138 | YAGRAARTAYACTGCATTYACYATACCTAGTRYAAAYAAT + N | (SEQ ID NO: 795) |
| 138 | AGRAARTAYACTGCATTYACYATACCTAGTRYAAAYAATG + N | (SEQ ID NO: 796) |
| 138 | AYACTGCATTYACYATACCTAGTRYAAAYAAT + N | (SEQ ID NO: 797) |
| 138 | AYACTGCATTYACYATACCTAGTRYAAAYAATG + N | (SEQ ID NO: 798) |
| 138 | TAYACTGCATTYACYATACCTAGTRYAAAYAAT + N | (SEQ ID NO: 799) |
| 138 | TAYACTGCATTYACYATACCTAGTRYAAAYAATG + N | (SEQ ID NO: 800) |
| 138 | ARTAYACTGCATTYACYATACCTAGTRYAAAYAAT + N | (SEQ ID NO: 801) |
| 138 | ARTAYACTGCATTYACYATACCTAGTRYAAAYAATG + N | (SEQ ID NO: 802) |
| 138 | RRHTTYAGRAARTAYACTGCATTYACYATACCYAGTRYMAACAAT + N | (SEQ ID NO: 803) |
| 138 | +A + ART + AYACTGCATTYACYATACCTAGTRYAAAYAAT | (SEQ ID NO: 804) |
| 138 | +A + ART + AYACTGCATTYACYATACCTAGTRYAAAYAATG | (SEQ ID NO: 805) |
| 138 | +AAR + T + AYACTGCATTYACYATACCTAGTRYAAAYAAT | (SEQ ID NO: 806) |
| 138 | +AAR + T + AYACTGCATTYACYATACCTAGTRYAAAYAATG | (SEQ ID NO: 807) |
| 138 | +A + AR + TAYACTGCATTYACYATACCTAGTRYAAAYAAT | (SEQ ID NO: 808) |
| 138 | +A + AR + TAYACTGCATTYACYATACCTAGTRYAAAYAATG | (SEQ ID NO: 809) |
| 138 | +GR + AAR + TAYACTGCATTYACYATACCTAGTRYAAAYAAT | (SEQ ID NO: 810) |
| 138 | +GR + AAR + TAYACTGCATTYACYATACCTAGTRYAAAYAATG | (SEQ ID NO: 811) |
| 138 | +GRA + AR + TAYACTGCATTYACYATACCTAGTRYAAAYAAT | (SEQ ID NO: 812) |
| 138 | +GRA + AR + TAYACTGCATTYACYATACCTAGTRYAAAYAATG | (SEQ ID NO: 813) |
| 138 | +GR + A + ARTAYACTGCATTYACYATACCTAGTRYAAAYAAT | (SEQ ID NO: 814) |
| 138 | +GR + A + ARTAYACTGCATTYACYATACCTAGTRYAAAYAATG | (SEQ ID NO: 815) |
| 138 | Y + A + GRA + ARTAYACTGCATTYACYATACCTAGTRYAAAYAAT | (SEQ ID NO: 816) |
| 138 | +A + GRA + ARTAYACTGCATTYACYATACCTAGTRYAAAYAATG | (SEQ ID NO: 817) |
| 138 | Y + AGR + A + ARTAYACTGCATTYACYATACCTAGTRYAAAYAAT | (SEQ ID NO: 818) |

TABLE 5 -continued

| | | |
|---|---|---|
| 138 | +AGR + A + ARTAYACTGCATTYACYATACCTAGTRYAAAYAATG | (SEQ ID NO: 819) |
| 138 | +AY + ACT + GCATTYACYATACCTAGTRYAAAYAAT | (SEQ ID NO: 820) |
| 138 | +AY + ACT + GCATTYACYATACCTAGTRYAAAYAATG | (SEQ ID NO: 821) |
| 138 | +AYA + CT + GCATTYACYATACCTAGTRYAAAYAAT | (SEQ ID NO: 822) |
| 138 | +AYA + CT + GCATTYACYATACCTAGTRYAAAYAATG | (SEQ ID NO: 823) |
| 138 | +AY + A + CTGCATTYACYATACCTAGTRYAAAYAAT | (SEQ ID NO: 824) |
| 138 | +AY + A + CTGCATTYACYATACCTAGTRYAAAYAATG | (SEQ ID NO: 825) |
| 138 | +T + AYA + CTGCATTYACYATACCTAGTRYAAAYAAT | (SEQ ID NO: 826) |
| 138 | +T + AYA+ ACTGCATTYACYATACCTAGTRYAAAYAATG | (SEQ ID NO: 827) |
| 138 | +TAY + A + CTGCATTYACYATACCTAGTRYAAAYAAT | (SEQ ID NO: 828) |
| 138 | +TAY + A + CTGCATTYACYATACCTAGTRYAAAYAATG | (SEQ ID NO: 829) |
| 138 | +T + AY + ACTGCATTYACYATACCTAGTRYAAAYAAT | (SEQ ID NO: 830) |
| 138 | +T + AY + ACTGCATTYACYATACCTAGTRYAAAYAATG | (SEQ ID NO: 831) |
| 138 | +AR + TAY + ACTGCATTYACYATACCTAGTRYAAAYAAT | (SEQ ID NO: 832) |
| 138 | +AR + TAY + ACTGCATTYACYATACCTAGTRYAAAYAATG | (SEQ ID NO: 833) |
| 138 | +ART + AY + ACTGCATTYACYATACCTAGTRYAAAYAAT | (SEQ ID NO: 834) |
| 138 | +ART + AY + ACTGCATTYACYATACCTAGTRYAAAYAATG | (SEQ ID NO: 835) |
| 138 | +AR + T + AYACTGCATTYACYATACCTAGTRYAAAYAAT | (SEQ ID NO: 836) |
| 138 | +AR + T + AYACTGCATTYACYATACCTAGTRYAAAYAATG | (SEQ ID NO: 837) |
| 138 | Y + A + GR + AARTAYACTGCATTYACYATACCTAGTRYAAAYAAT | (SEQ ID NO: 838) |
| 138 | +A + GR + AARTAYACTGCATTYACYATACCTAGTRYAAAYAATG | (SEQ ID NO: 839) |
| 151 | AAYAATGARACACCAGGRRTYAGRTATCARTAYAATGTRCTTCCA | (SEQ ID NO: 840) |
| 151 | AAYAATGARACACCAGGRRTYAGRTATCARTAYAATGTRCTTCCA + N | (SEQ ID NO: 841) |
| 179 | TYTTAGARCCYTTTAGRDHAMAAAAYCCAGAVATRR | (SEQ ID NO: 842) |
| 179 | TYTTAGARCCYTTTAGRDHAMAAAAYCCAGAVATR | (SEQ ID NO: 843) |
| 179 | ATYTTAGARCCYTTTAGRDHAMAAAAYCCAGAVATRR | (SEQ ID NO: 844) |
| 179 | ATYTTAGARCCYTTTAGRDHAMAAAAYCCAGAVATR | (SEQ ID NO: 845) |
| 179 | ARAATYTTAGARCCYTTTAGRDHAMAAAAYCCAGAVATRR | (SEQ ID NO: 846) |
| 179 | AARAATYTTAGARCCYTTTAGRDHAMAAAAYCCAGAVATR | (SEQ ID NO: 847) |
| 179 | CYTTTAGRDHAMAAAAYCCAGAVATRR | (SEQ ID NO: 848) |
| 179 | CYTTTAGRDHAMAAAAYCCAGAVATR | (SEQ ID NO: 849) |
| 179 | CCYTTTAGRDHAMAAAAYCCAGAVATRR | (SEQ ID NO: 850) |
| 179 | CCYTTTAGRDHAMAAAAYCCAGAVATR | (SEQ ID NO: 851) |
| 179 | TAGARCCYTTTAGRDHAMAAAAYCCAGAVATRR | (SEQ ID NO: 852) |
| 179 | TAGARCCYTTTAGRDHAMAAAAYCCAGAVATR | (SEQ ID NO: 853) |
| 179 | ATGACAARAATYTTAGARCCYTTTAGRRHRMARAAYCCAGACATA | (SEQ ID NO: 854) |
| 179 | TYTTAGARCCYTTTAGRDHAMAAAAYCCAGAVATRR + N | (SEQ ID NO: 855) |
| 179 | TYTTAGARCCYTTTAGRDHAMAAAAYCCAGAVATR + N | (SEQ ID NO: 856) |

TABLE 5 -continued

| | |
|---|---|
| 179 | ATYTTAGARCCYTTTAGRDHAMAAAAYCCAGAVATRR + N (SEQ ID NO: 857) |
| 179 | ATYTTAGARCCYTTTAGRDHAMAAAAYCCAGAVATR + N (SEQ ID NO: 858) |
| 179 | ARAATYTTAGARCCYTTTAGRDHAMAAAAYCCAGAVATRR + N (SEQ ID NO: 859) |
| 179 | AARAATYTTAGARCCYTTTAGRDHAMAAAAYCCAGAVATR + N (SEQ ID NO: 860) |
| 179 | CYTTTAGRDHAMAAAAYCCAGAVATRR + N (SEQ ID NO: 861) |
| 179 | CYTTTAGRDHAMAAAAYCCAGAVATR + N (SEQ ID NO: 862) |
| 179 | CCYTTTAGRDHAMAAAAYCCAGAVATRR + N (SEQ ID NO: 863) |
| 179 | CCYTTTAGRDHAMAAAAYCCAGAVATR + N (SEQ ID NO: 864) |
| 179 | TAGARCCYTTTAGRDHAMAAAAYCCAGAVATRR + N (SEQ ID NO: 865) |
| 179 | TAGARCCYTTTAGRDHAMAAAAYCCAGAVATR + N (SEQ ID NO: 866) |
| 179 | ATGACAARAATYTTAGARCCYTTTAGRRHRMARAAYCCAGACATA + N (SEQ ID NO: 867) |
| 179 | +TYT + TAGARC + CYTTTAGRDHAMAAAAYCCAGAVATRR (SEQ ID NO: 868) |
| 179 | +TYT + TAGARC + CYTTAGRDHAMAAAAYCCAGAVATR (SEQ ID NO: 869) |
| 179 | +TYTTAGAR + C + CYTTTAGRDHAMAAAAYCCAGAVATRR (SEQ ID NO: 870) |
| 179 | +TYTTAGAR + C + CYTTTAGRDHAMAAAAYCCAGAVATR (SEQ ID NO: 871) |
| 179 | +TYT + TAGAR + CCYTTTAGRDHAMAAAAYCCAGAVATRR (SEQ ID NO: 872) |
| 179 | +TYT + TAGAR + CCYTTTAGRDHAMAAAAYCCAGAVATR (SEQ ID NO: 873) |
| 179 | +A + TYTTAGAR + CCYTTTAGRDHAMAAAAYCCAGAVATRR (SEQ ID NO: 874) |
| 179 | +A + TYTTAGAR + CCYTTTAGRDHAMAAAAYCCAGAVATR (SEQ ID NO: 875) |
| 179 | +ATYT + TAGAR + CCYTTTAGRDHAMAAAAYCCAGAVATRR (SEQ ID NO: 876) |
| 179 | +ATYT + TAGAR + CCYTTTAGRDHAMAAAAYCCAGAVATR (SEQ ID NO: 877) |
| 179 | +A + TYT + TAGARCCYTTTAGRDHAMAAAAYCCAGAVATRR (SEQ ID NO: 878) |
| 179 | +A + TYT + TAGARCCYTTTAGRDHAMAAAAYCCAGAVATR (SEQ ID NO: 879) |
| 179 | +ARA + ATYT + TAGARCCYTTTAGRDHAMAAAAYCCAGAVATRR (SEQ ID NO: 880) |
| 179 | A + ARA + ATYT + TAGARCCYTTTAGRDHAMAAAAYCCAGAVATR (SEQ ID NO: 881) |
| 179 | +ARAA + TYT + TAGARCCYTTTAGRDHAMAAAAYCCAGAVATRR (SEQ ID NO: 882) |
| 179 | A + ARAA + TYT + TAGARCCYTTTAGRDHAMAAAAYCCAGAVATR (SEQ ID NO: 883) |
| 179 | +CY + TTTAGRDHAMAAA + AYCCAGAVATRR (SEQ ID NO: 884) |
| 179 | +CY + TTTAGRDHAMAAA + AYCCAGAVATR (SEQ ID NO: 885) |
| 179 | +CYTTT + AGRDHAMAAA + AYCCAGAVATRR (SEQ ID NO: 886) |
| 179 | +CYTTT + AGRDHAMAAA + AYCCAGAVATR (SEQ ID NO: 887) |
| 179 | +CY + TTT + AGRDHAMAAAAYCCAGAVATRR (SEQ ID NO: 888) |
| 179 | +CY + TTT + AGRDHAMAAAAYCCAGAVATR (SEQ ID NO: 889) |
| 179 | +C + CYTTT + AGRDHAMAAAAYCCAGAVATRR (SEQ ID NO: 890) |
| 179 | +C + CYTTT + AGRDHAMAAAAYCCAGAVATR (SEQ ID NO: 891) |
| 179 | +CCY + TTT + AGRDHAMAAAAYCCAGAVATRR (SEQ ID NO: 892) |
| 179 | +CCY + TTT + AGRDHAMAAAAYCCAGAVATR (SEQ ID NO: 893) |

TABLE 5 -continued

| | | |
|---|---|---|
| 179 | +C + CY + TTTAGRDHAMAAAAYCCAGAVATRR | (SEQ ID NO: 894) |
| 179 | +C + CY + TTTAGRDHAMAAAAYCCAGAVATR | (SEQ ID NO: 895) |
| 179 | +TAGAR + CCY + TTTAGRDHAMAAAAYCCAGAVATRR | (SEQ ID NO: 896) |
| 179 | +TAGAR + CCY + TTTAGRDHAMAAAAYCCAGAVATR | (SEQ ID NO: 897) |
| 179 | +TAGARC + CY + TTTAGRDHAMAAAAYCCAGAVATRR | (SEQ ID NO: 898) |
| 179 | +TAGARC + CY + TTTAGRDHAMAAAAYCCCAGAVATR | (SEQ ID NO: 899) |
| 179 | +TAGAR + C + CYTTTAGRDHAMAAAAYCCAGAVATRR | (SEQ ID NO: 900) |
| 179 | +TAGAR + C + CYTTTAGRDHAMAAAAYCCAGAVATR | (SEQ ID NO: 901) |
| 179 | +ARA + A + TYTTAGARCCYTTTAGRDHAMAAAAYCCAGAVATRR | (SEQ ID NO: 902) |
| 179 | A + ARA + A + TYTTAGARCCYTTTAGRDHAMAAAAYCCAGAVATR | (SEQ ID NO: 903) |
| 181 | CYTTTAGRDHAMAAAAYCCAGAVATRRTBATYT | (SEQ ID NO: 904) |
| 181 | CCYTTTAGRDHAMAAAAYCCAGAVATRRTBATYT | (SEQ ID NO: 905) |
| 181 | TTAGARCCYTTTAGRDHAMAAAAYCCAGAVATRRTBATYT | (SEQ ID NO: 906) |
| 181 | AGRDHAMAAAAYCCAGAVATRRTBATYT | (SEQ ID NO: 907) |
| 181 | TTTAGRDHAMAAAAYCCAGAVATRRTBATYT | (SEQ ID NO: 908) |
| 181 | ARAATYTTAGARCCYTTTAGRRHRMARAAYCCAGAVMTRRTTATC | (SEQ ID NO: 909) |
| 181 | CYTTTAGRDHAMAAAAYCCAGAVATRRTBATYT + N | (SEQ ID NO: 910) |
| 181 | CCYTTTAGRDHAMAAAAYCCAGAVATRRTBATYT + N | (SEQ ID NO: 911) |
| 181 | TTAGARCCYTTTAGRDHAMAAAAYCCAGAVATRRTBATYT + N | (SEQ ID NO: 912) |
| 181 | AGRDHAMAAAAYCCAGAVATRRTBATYT + N | (SEQ ID NO: 913) |
| 181 | TTTAGRDHAMAAAAYCCAGAVATRRTBATYT + N | (SEQ ID NO: 914) |
| 181 | ARAATYTTAGARCCYTTTAGRRHRMARAAYCCAGAVMTRRTTATC + N | (SEQ ID NO: 915) |
| 181 | +CY + TTTAGRDHAMAAA + AYCCAGAVATRRTBATYT | (SEQ ID NO: 916) |
| 181 | +CYTTT + AGRDHAMAAA + AYCCAGAVATRRTBATYT | (SEQ ID NO: 917) |
| 181 | +CY + TTT + AGRDHAMAAAAYCCAGAVATRRTBATYT | (SEQ ID NO: 918) |
| 181 | +C + CYTTT + AGRDHAMAAAAYCCAGAVATRRTBATYT | (SEQ ID NO: 919) |
| 181 | +CCY + TTT + AGRDHAMAAAAYCCAGAVATRRTBATYT | (SEQ ID NO: 920) |
| 181 | +C + CY + TTTAGRDHAMAAAAYCCAGAVATRRTBATYT | (SEQ ID NO: 921) |
| 181 | T + TAGAR + CCY + TTTAGRDHAMAAAAYCCAGAVATRRTBATYT | (SEQ ID NO: 922) |
| 181 | T + TAGARC + CY + TTTAGRDHAMAAAAYCCAGAVATRRTBATYT | (SEQ ID NO: 923) |
| 181 | +AGRDHAMAAA + AYCCAGAVATRRTBA + TYT | (SEQ ID NO: 924) |
| 181 | +AGRDHAMAAAAYCCAGAVA + TRRTBA + TYT | (SEQ ID NO: 925) |
| 181 | +AGRDHAMAAA + AYCCAGAVA + TRRTBATYT | (SEQ ID NO: 926) |
| 181 | +TTT + AGRDHAMAAAAYCCAGAVA + TRRTBATYT | (SEQ ID NO: 927) |
| 181 | +TTTAGRDHAMAAA + AYCCAGAVA + TRRTBATYT | (SEQ ID NO: 928) |
| 181 | +TTT + AGRDHAMAAA + AYCCAGAVATRRTBATYT | (SEQ ID NO: 929) |

TABLE 5 -continued

| | | |
|---|---|---|
| 181 | T + TAGAR + C + CYTTTAGRDHAMAAAAYCCAGAVATRRTBATYT | (SEQ ID NO: 930) |
| 184 | AYCCAGAVATRRTBATYTAYCAATAY | (SEQ ID NO: 931) |
| 184 | AGRDHAMAAAAYCCAGAVATRRTBATYTAYCAATAY | (SEQ ID NO: 932) |
| 184 | AYCCAGAVATRRTBATYTAYCAATAYRT | (SEQ ID NO: 933) |
| 184 | YTTTAGRDHAMAAAAYCCAGAVATRRTBATYTAYCAATAY | (SEQ ID NO: 934) |
| 184 | TTAGRDHAMAAAAYCCAGAVATRRTBATYTAYCAATAYRT | (SEQ ID NO: 935) |
| 184 | GARCCYTTTAGRRHRMARAAYCCAGAVMTRRTBATYTATCAATAC | (SEQ ID NO: 936) |
| 184 | AYCCAGAVATRRTBATYTAYCAATAY + N | (SEQ ID NO: 937) |
| 184 | AGRDHAMAAAAYCCAGAVATRRTBATYTAYCAATAY + N | (SEQ ID NO: 938) |
| 184 | AYCCAGAVATRRTBATYTAYCAATAYRT + N | (SEQ ID NO: 939) |
| 184 | YTTTAGRDHAMAAAAYCCAGAVATRRTBATYTAYCAATAY + N | (SEQ ID NO: 940) |
| 184 | TTAGRDHAMAAAAYCCAGAVATRRTBATYTAYCAATAYRT + N | (SEQ ID NO: 941) |
| 184 | GARCCYTTTAGRRHRMARAAYCCAGAVMTRRTBATYTATCAATAC + N | (SEQ ID NO: 942) |
| 184 | +AYCCAGAVA + TRRTBATY + TAYCAATAY | (SEQ ID NO: 943) |
| 184 | +AYCCAGAVATRRTBA + TY + TAYCAATAY | (SEQ ID NO: 944) |
| 184 | +AYCCAGAVA + TRRTBA + TYTAYCAATAY | (SEQ ID NO: 945) |
| 184 | +AGRDHAMAAA + AYCCAGAVATRRTBA + TYTAYCAATAY | (SEQ ID NO: 946) |
| 184 | +AYCCAGAVA + TRRTBATY + TAYCAATAYRT | (SEQ ID NO: 947) |
| 184 | +AGRDHAMAAAAYCCAGAVA + TRRTBA + TYTAYCAATAY | (SEQ ID NO: 948) |
| 184 | +AYCCAGAVATRRTBA + TY + TAYCAATAYRT | (SEQ ID NO: 949) |
| 184 | +AGRDHAMAAA + AYCCAGAVA + TRRTBATYTAYCAATAY | (SEQ ID NO: 950) |
| 184 | +AYCCAGAVA + TRRTBA + TYTAYCAATAYRT | (SEQ ID NO: 951) |
| 184 | Y + TTT + AGRDHAMAAAAYCCAGAVA + TRRTBATYTAYCAATAY | (SEQ ID NO: 952) |
| 184 | TT + AGRDHAMAAA + AYCCAGAVATRRTBA + TYTAYCAATAYRT | (SEQ ID NO: 953) |
| 184 | Y + TTTAGRDHAMAAA + AYCCAGAVA + TRRTBATYTAYCAATAY | (SEQ ID NO: 954) |
| 184 | TT + AGRDHAMAAAAYCCAGAVA + TRRTBA + TYTAYCAATAYRT | (SEQ ID NO: 955) |
| 184 | Y + TTT + AGRDHAMAAA + AYCCAGAVATRRTBATYTAYCAATAY | (SEQ ID NO: 956) |
| 184 | TT + AGRDHAMAAA + AYCCAGAVA + TRRTBATYTAYCAATAYRT | (SEQ ID NO: 957) |
| 188 | TYTAYCAATAYRTGGATGAYTTRT | (SEQ ID NO: 958) |
| 188 | TYTAYCAATAYRTGGATGAYTTR | (SEQ ID NO: 959) |
| 188 | TRRTBATYTAYCAATAYRTGGATGAYTTRT | (SEQ ID NO: 960) |
| 188 | TRRTBATYTAYCAATAYRTGGATGAYTTR | (SEQ ID NO: 961) |
| 188 | AAYCCAGAVATRRTBATYTAYCAATAYRTGGATGAYTTRT | (SEQ ID NO: 962) |
| 188 | AAAYCCAGAVATRRTBATYTAYCAATAYRTGGATGAYTTR | (SEQ ID NO: 963) |
| 188 | TAYCAATAYRTGGATGAYTTRT | (SEQ ID NO: 964) |
| 188 | TAYCAATAYRTGGATGAYTTR | (SEQ ID NO: 965) |
| 188 | RHRMARAAYCCAGAVMTRRTBATYTAYCARTAYATGGATGATTTG | (SEQ ID NO: 966) |
| 188 | TYTAYCAATAYRTGGATGAYTTRT + N | (SEQ ID NO: 967) |
| 188 | TYTAYCAATAYRTGGATGAYTTR + N | (SEQ ID NO: 968) |
| 188 | TRRTBATYTAYCAATAYRTGGATGAYTTRT + N | (SEQ ID NO: 969) |

TABLE 5 -continued

| | |
|---|---|
| 188 | TRRTBATYTAYCAATAYRTGGATGAYTTR + N (SEQ ID NO: 970) |
| 188 | AAYCCAGAVATRRTBATYTAYCAATAYRTGGATGAYTTRT + N (SEQ ID NO: 971) |
| 188 | AAAYCCAGAVATRRTBATYTAYCAATAYRTGGATGAYTTR + N (SEQ ID NO: 972) |
| 188 | TAYCAATAYRTGGATGAYTTRT + N (SEQ ID NO: 973) |
| 188 | TAYCAATAYRTGGATGAYTTR + N (SEQ ID NO: 974) |
| 188 | RHRMARAAYCCAGAVMTRRTBATYTAYCARTAYATGGATGATTTG + N (SEQ ID NO: 975) |
| 188 | +TY + TAYC + AATAYRTGGATGAYTTRT (SEQ ID NO: 976) |
| 188 | +TY + TAYC + AATAYRTGGATGAYTTR (SEQ ID NO: 977) |
| 188 | +TYTAY + C + AATAYRTGGATGAYTTRT (SEQ ID NO: 978) |
| 188 | TYTAY + C + AATAYRTGGATGAYTTR (SEQ ID NO: 979) |
| 188 | +TY + TAY + CAATAYRTGGATGAYTTRT (SEQ ID NO: 980) |
| 188 | +TY + TAY + CAATAYRTGGATGAYTTR (SEQ ID NO: 981) |
| 188 | +TRRTBA + TYTAY + CAATAYRTGGATGAYTTRT (SEQ ID NO: 982) |
| 188 | +TRRTBA + TYTAY + CAATAYRTGGATGAYTTR (SEQ ID NO: 983) |
| 188 | +TRRTBATY + TAY + CAATAYRTGGATGAYTTRT (SEQ ID NO: 984) |
| 188 | +TRRTBATY + TAY + CAATAYRTGGATGAYTTR (SEQ ID NO: 985) |
| 188 | +TRRTBA + TY + TAYCAATAYRTGGATGAYTTRT (SEQ ID NO: 986) |
| 188 | +TRRTBA + TY + TAYCAATAYRTGGATGAYTTR (SEQ ID NO: 987) |
| 188 | A + AYCCAGAVA + TRRTBATY + TAYCAATAYRTGGATGAYTTRT (SEQ ID NO: 988) |
| 188 | AA + AYCCAGAVA + TRRTBATY + TAYCAATAYRTGGATGAYTTR (SEQ ID NO: 989) |
| 188 | A + AYCCAGAVATRRTBA + TY + TAYCAATAYRTGGATGAYTTRT (SEQ ID NO: 990) |
| 188 | AA + AYCCAGAVATRRTBA + TY + TAYCAATAYRTGGATGAYTTR (SEQ ID NO: 991) |
| 188 | +TAY + CAA + TAYRTGGATGAYTTRT (SEQ ID NO: 992) |
| 188 | +TAY + CAA + TAYRTGGATGAYTTR (SEQ ID NO: 993) |
| 188 | +TAYC + AA + TAYRTGGATGAYTTRT (SEQ ID NO: 994) |
| 188 | +TARC + AA + TAYRTGGATGAYTTR (SEQ ID NO: 995) |
| 188 | +TAY + C + AATAYRTGGATGAYTTRT (SEQ ID NO: 996) |
| 188 | +TAY + C + AATAYRTGGATGAYTTR (SEQ ID NO: 997) |
| 188 | A + AYCCAGAVA + TRRTBA + TYTAYCAATAYRTGGATGAYTTRT (SEQ ID NO: 998) |
| 188 | AA + AYCCAGAVA + TRRTBA + TYTAYCAATAYRTGGATGAYTTR (SEQ ID NO: 999) |
| 190 | TAYCAATAYRTGGATGAYTTRTATGTAG (SEQ ID NO: 1000) |
| 190 | TAYCAATAYRTGGATGAYTTRTATGTA (SEQ ID NO: 1001) |
| 190 | TYTAYCAATAYRTGGATGAYTTRTATGTAG (SEQ ID NO: 1002) |
| 190 | TYTAYCAATAYRTGGATGAYTTRTATGTA (SEQ ID NO: 1003) |
| 190 | GAVATRRTBATYTAYCAATAYRTGGATGAYTTRTATGTAG (SEQ ID NO: 1004) |
| 190 | AGAVATRRTBATYTAYCAATAYRTGGATGAYTTRTATGTA (SEQ ID NO: 1005) |
| 190 | TAYRTGGATGAYTTRTATGTAG (SEQ ID NO: 1006) |
| 190 | TAYRTGGATGAYTTRTATGTA (SEQ ID NO: 1007) |
| 190 | AATAYRTGGATGAYTTRTATGTAG (SEQ ID NO: 1008) |

TABLE 5 -continued

| | |
|---|---|
| 190 | AATAYRTGGATGAYTTRTATGTA (SEQ ID NO: 1009) |
| 190 | CAATAYRTGGATGAYTTRTATGTAG (SEQ ID NO: 1010) |
| 190 | CAATAYRTGGATGAYTTRTATGTA (SEQ ID NO: 1011) |
| 190 | AAYCCAGAVMTRRTBATYTAYCARTAYATGGATGAYTTRTATGTA (SEQ ID NO: 1012) |
| 190 | TAYCAATAYRTGGATGAYTTRTATGTAG + N (SEQ ID NO: 1013) |
| 190 | TAYCAATAYRTGGATGAYTTRTATGTA + N (SEQ ID NO: 1014) |
| 190 | TYTAYCAATAYRTGGATGAYTTRTATGTAG + N (SEQ ID NO: 1015) |
| 190 | TYTAYCAATAYRTGGATGAYTTRTATGTA + N (SEQ ID NO: 1016) |
| 190 | GAVATRRTBATYTAYCAATAYRTGGATGAYTTRTATGTAG + N (SEQ ID NO: 1017) |
| 190 | AGAVATRRTBATYTAYCAATAYRTGGATGAYTTRTATGTA + N (SEQ ID NO: 1018) |
| 190 | TAYRTGGATGAYTTRTATGTAG + N (SEQ ID NO: 1019) |
| 190 | TAYRTGGATGAYTTRTATGTA + N (SEQ ID NO: 1020) |
| 190 | AATAYRTGGATGAYTTRTATGTAG + N (SEQ ID NO: 1021) |
| 190 | AATAYRTGGATGAYTTRTATGTA + N (SEQ ID NO: 1022) |
| 190 | CAATAYRTGGATGAYTTRTATGTAG + N (SEQ ID NO: 1023) |
| 190 | CAATAYRTGGATGAYTTRTATGTA + N (SEQ ID NO: 1024) |
| 190 | AAYCCAGAVMTRRTBATYTAYCARTAYATGGATGAYTTRTATGTA + N (SEQ ID NO: 1025) |
| 190 | +TAY + CAA + TAYRTGGATGAYTTRTATGTAG (SEQ ID NO: 1026) |
| 190 | +TAY + CAA + TAYRTGGATGAYTTRTATGTA (SEQ ID NO: 1027) |
| 190 | +TAYC + AA + TAYRTGGATGAYTTRTATGTAG (SEQ ID NO: 1028) |
| 190 | +TAYC + AA + TAYRTGGATGAYTTRTATGTA (SEQ ID NO: 1029) |
| 190 | +TAY + C + AATAYRTGGATGAYTTRTATGTAG (SEQ ID NO: 1030) |
| 190 | +TAY + C + AATAYRTGGATGAYTTRTATGTA (SEQ ID NO: 1031) |
| 190 | +TY + TAYC + AATAYRTGGATGAYTTRTATGTAG (SEQ ID NO: 1032) |
| 190 | +TY + TAYC + AATAYRTGGATGAYTTRTATGTA (SEQ ID NO: 1033) |
| 190 | +TYTAY + C + AATAYRTGGATGAYTTRTATGTAG (SEQ ID NO: 1034) |
| 190 | +TYTAY + C + AATAYRTGGATGAYTTRTATGTA (SEQ ID NO: 1035) |
| 190 | +TY + TAY + CAATAYRTGGATGAYTTRTATGTAG (SEQ ID NO: 1036) |
| 190 | +TY + TAY + CAATAYRTGGATGAYTTRTATGTA (SEQ ID NO: 1037) |
| 190 | GAVA + TRRTBA + TYTAY + CAATAYRTGGATGAYTTRTATGTAG (SEQ ID NO: 1038) |
| 190 | AGAVA + TRRTBA + TYTAY + CAATAYRTGGATGAYTTRTATGTA (SEQ ID NO: 1039) |
| 190 | GAVA + TRRTBATY + TAY + CAATAYRTGGATGAYTTRTATGTAG (SEQ ID NO: 1040) |
| 190 | AGAVA + TRRTBATY + TAY + CAATAYRTGGATGAYTTRTATGTA (SEQ ID NO: 1041) |
| 190 | +T + AYRTG + GATGAYTTRTATGTAG (SEQ ID NO: 1042) |
| 190 | +T + AYRTG + GATGAYTTRTATGTA (SEQ ID NO: 1043) |
| 190 | +TAYR + TG + GATGAYTTRTATGTAG (SEQ ID NO: 1044) |
| 190 | +TAYR - TG + GATGAYTTRTATGTA (SEQ ID NO: 1045) |

TABLE 5 -continued

| | | |
|---|---|---|
| 190 | +T + AYR + TGGATGAYTTRTATGTAG (SEQ ID NO: 1046) | |
| 190 | +T + AYR + TGGATGAYTTRTATGTA (SEQ ID NO: 1047) | |
| 190 | +AA + TAYR + TGGATGAYTTRTATGTAG (SEQ ID NO: 1048) | |
| 190 | +AA + TAYR + TGGATGAYTTRTATGTA (SEQ ID NO: 1049) | |
| 190 | +AAT + AYR + TGGATGAYTTRTATGTAG (SEQ ID NO: 1050) | |
| 190 | +AAT + AYR + TGGATGAYTTRTATGTA (SEQ ID NO: 1051) | |
| 190 | +AA + T + AYRTGGATGAYTTRTATGTAG (SEQ ID NO: 1052) | |
| 190 | +AA + T + AYRTGGATGAYTTRTATGTA (SEQ ID NO: 1053) | |
| 190 | +C + AAT + AYRTGGATGAYTTRTATGTAG (SEQ ID NO: 1054) | |
| 190 | +C + AAT + AYRTGGATGAYTTRTATGTA (SEQ ID NO: 1055) | |
| 190 | +CAA + T + AYRTGGATGAYTTRTATGTAG (SEQ ID NO: 1056) | |
| 190 | +CAA + T + AYRTGGATGAYTTRTATGTA (SEQ ID NO: 1057) | |
| 190 | +C + AA + TAYRTGGATGAYTTRTATGTAG (SEQ ID NO: 1058) | |
| 190 | +C + AA + TAYRTGGATGAYTTRTATGTA (SEQ ID NO: 1059) | |
| 190 | GAVA + TRRTBA + TY + TAYCAATAYRTGGATGAYTTRTATGTAG (SEQ ID NO: 1060) | |
| 190 | AGAVA + TRRTBA + TY + TAYCAATAYRTGGATGAYTTRTATGTA (SEQ ID NO: 1061) | |
| 210 | AGARYAAAARTAGARGARYTRAGRVMDCAYYTRY (SEQ ID NO: 1062) | |
| 210 | AYAGARYAAAARTAGARGARYTRAGRVMDCAYYTRY (SEQ ID NO: 1063) | |
| 210 | CARCAYAGARYAAAARTAGARGARYTRAGRVMDCAYYTRY (SEQ ID NO: 1064) | |
| 210 | TAGARGARYTRAGRVMDCAYYTRY (SEQ ID NO: 1065) | |
| 210 | AAARTAGARGARYTRAGRVMDCAYYTRY (SEQ ID NO: 1066) | |
| 210 | GARYAAAARTAGARGARYTRAGRVMDCAYYTRY (SEQ ID NO: 1067) | |
| 210 | ATAGRRCARCAYAGARYAAAARTAGARGARYTRAGRVMDCATCTG (SEQ ID NO: 1068) | |
| 210 | AGARYAAAARTAGARGARYTRAGRVMDCAYYTRY + N (SEQ ID NO: 1069) | |
| 210 | AYAGARYAAAARTAGARGARYTRAGRVMDCAYYTRY + N (SEQ ID NO: 1070) | |
| 210 | CARCAYAGARYAAAARTAGARGARYTRAGRVMDCAYYTRY + N (SEQ ID NO: 1071) | |
| 210 | TAGARGARYTRAGRVMDCAYYTRY + N (SEQ ID NO: 1072) | |
| 210 | AAARTAGARGARYTRAGRVMDCAYYTRY + N (SEQ ID NO: 1073) | |
| 210 | GARYAAAARTAGARGARYTRAGRVMDCAYYTRY + N (SEQ ID NO: 1074) | |
| 210 | ATAGRRCARCAYAGARYAAAARTAGARGARYTRAGRVMDCATCTG + N (SEQ ID NO: 1075) | |
| 210 | +A + GARYAAAAR + TAGARGARYTRAGRVMDCAYYTRY (SEQ ID NO: 1076) | |
| 210 | +AGARYA + AAAR + TAGARGARYTRAGRVMDCAYYTRY (SEQ ID NO: 1077) | |
| 210 | +A + GARYA + AAARTAGARGARYTRAGRVMDCAYYTRY (SEQ ID NO: 1078) | |
| 210 | +AY + AGARYA + AAARTAGARGARYTRAGRVMDCAYYTRY (SEQ ID NO: 1079) | |
| 210 | +AYA + GARYA + AAARTAGARGARYTRAGRVMDCAYYTRY (SEQ ID NO: 1080) | |
| 210 | +AY + A + GARYAAAARTAGARGARYTRAGRVMDCAYYTRY (SEQ ID NO: 1081) | |
| 210 | CAR + C + AYA + GARYAAAARTAGARGARYTRAGRVMDCAYYTRY (SEQ ID NO: 1082) | |

TABLE 5 -continued

| | |
|---|---|
| 210 | CAR + CAY + A + GARYAAAARTAGARGARYTRAGRVMDCAYYTRY (SEQ ID NO: 1083) |
| 210 | +TAG + ARGARY + TRAGRVMDCAYYTRY (SEQ ID NO: 1084) |
| 210 | +TAGARG + ARY + TRAGRVMDCAYYTRY (SEQ ID NO: 1085) |
| 210 | +TAG + ARG + ARYTRAGRVMDCAYYTRY (SEQ ID NO: 1086) |
| 210 | +AAAR + TAGARG + ARYTRAGRVMDCAYYTRY (SEQ ID NO: 1087) |
| 210 | +AAARTAG + ARG + ARYTRAGRVMDCAYYTRY (SEQ ID NO: 1088) |
| 210 | +AAAR + TAG + ARGARYTRAGRVMDCAYYTRY (SEQ ID NO: 1089) |
| 210 | +GARYA + AAARTAG + ARGARYTRAGRVMDCAYYTRY (SEQ ID NO: 1090) |
| 210 | +GARYAAAAR + TAG + ARGARYTRAGRVMDCAYYTRY (SEQ ID NO: 1091) |
| 210 | +GARYA + AAAR + TAGARGARYTRAGRVMDCAYYTRY (SEQ ID NO: 1092) |
| 210 | CAR + C + AY + AGARYAAAARTAGARGARYTRAGRVMDCAYYTRY (SEQ ID NO: 1093) |
| 215 | ARYTRAGRVMDCAYYTRYTRARVTGGGGRYTYW (SEQ ID NO: 1094) |
| 215 | ARGARYTRAGRVMDCAYYTRYTRARVTGGGGRYTYW (SEQ ID NO: 1095) |
| 215 | RTAGARGARYTRAGRVMDCAYYTRYTRARVTGGGGRYTYW (SEQ ID NO: 1096) |
| 215 | GRVMDCAYYTRYTRARVTGGGGRYTYW (SEQ ID NO: 1097) |
| 215 | AGRVMDCAYYTRYTRARVTGGGGRYTYW (SEQ ID NO: 1098) |
| 215 | TRAGRVMDCAYYTRYTRARVTGGGGRYTYW (SEQ ID NO: 1099) |
| 215 | RYAAAARTAGARGARYTRAGRVMDCAYYTRYTRARVTGGGGATTT (SEQ ID NO: 1100) |
| 215 | ARYTRAGRVMDCAYYTRYTRARVTGGGGRYTYW + N (SEQ ID NO: 1101) |
| 215 | ARGARYTRAGRVMDCAYYTRYTRARVTGGGGRYTYW + N (SEQ ID NO: 1102) |
| 215 | RTAGARGARYTRAGRVMDCAYYTRYTRARVTGGGGRYTYW + N (SEQ ID NO: 1103) |
| 215 | GRVMDCAYYTRYTRARVTGGGGRYTYW + N (SEQ ID NO: 1104) |
| 215 | AGRVMDCAYYTRYTRARVTGGGGRYTYW + N (SEQ ID NO: 1105) |
| 215 | TRAGRVMDCAYYTRYTRARVTGGGGRYTYW + N (SEQ ID NO: 1106) |
| 215 | RYAAAARTAGARGARYTRAGRVMDCAYYTRYTRARVTGGGGATTT + N (SEQ ID NO: 1107) |
| 215 | +ARY + TRA + GRVMDCAYYTRYTRARVTGGGGRYTYW (SEQ ID NO: 1108) |
| 215 | +ARYTR + A + GRVMDCAYYTRYTRARVTGGGGRYTYW (SEQ ID NO: 1109) |
| 215 | +ARY + TR + AGRVMDCAYYTRYTRARVTGGGGRYTYW (SEQ ID NO: 1110) |
| 215 | +ARG + ARYTR + AGRVMDCAYYTRYTRARVTGGGGRYTYW (SEQ ID NO: 1111) |
| 215 | +ARGARY + TR + AGRVMDCAYYTRYTRARVTGGGGRYTYW (SEQ ID NO: 1112) |
| 215 | +ARG + ARY + TRAGRVMDCAYYTRYTRARVTGGGGRYTYW (SEQ ID NO: 1113) |
| 215 | R + TAG + ARGARY + TRAGRVMDCAYYTRYTRARVTGGGGRYTYW (SEQ ID NO: 1114) |
| 215 | R + TAGARG + ARY + TRAGRVMDCAYYTRYTRARVTGGGGRYTYW (SEQ ID NO: 1115) |
| 215 | +GRVMDC + AYYTRYTRARV + TGGGGRYTYW (SEQ ID NO: 1116) |
| 215 | +GRVMDCAYY + TRYTRARV + TGGGGRYTYW (SEQ ID NO: 1117) |
| 215 | +GRVMDC + AYY + TRYTRARVTGGGGRYTYW (SEQ ID NO: 1118) |
| 215 | +A + GRVMDCAYY + TRYTRARVTGGGGRYTYW (SEQ ID NO: 1119) |
| 215 | +AGRVMDC + AYY + TRYTRARVTGGGGRYTYW (SEQ ID NO: 1120) |

TABLE 5 -continued

| | |
|---|---|
| 215 | +A + GRVMDC + AYYTRYTRARVTGGGGRYTYW (SEQ ID NO: 1121) |
| 215 | +TR + AGRMVDC + AYYTRYTRARVTGGGGRYTYW (SEQ ID NO: 1122) |
| 215 | +TRA + GRVMDC + AYYTRYTRARVTGGGGRYTYW (SEQ ID NO: 1123) |
| 215 | +TR + A + GRVMDCAYYTRYTRARVTGGGGRYTYW (SEQ ID NO: 1124) |
| 215 | R + TAG + ARG + ARYTRAGRVMDCAYYTRYTRARVTGGGGRYTYW (SEQ ID NO: 1125) |
| 219 | AYYTRYTRARVTGGGGRYTYWCYACACCAGAY (SEQ ID NO: 1126) |
| 219 | TRYTRARVTGGGGRYTYWCYACACCAGAYAA (SEQ ID NO: 1127) |
| 219 | AYYTRYTRARVTGGGGRYTYWCYACACCAGAYA (SEQ ID NO: 1128) |
| 219 | GRVMDCAYYTRYTRARVTGGGGRYTYWCYACACCAGAY (SEQ ID NO: 1129) |
| 219 | AYYTRYTRARVTGGGGRYTYWCYACACCAGAYAA (SEQ ID NO: 1130) |
| 219 | GRVMDCAYYTRYTRARVTGGGGRYTYWCYACACCAGAYA (SEQ ID NO: 1131) |
| 219 | RAGRVMDCAYYTRYTRARVTGGGGRYTYWCYACACCAGAY (SEQ ID NO: 1132) |
| 219 | GRVMDCAYYTRYTRARVTGGGGRYTYWCYACACCAGAYAA (SEQ ID NO: 1133) |
| 219 | AGRVMDCAYYTRYTRARVTGGGGRYTYWCYACACCAGAYA (SEQ ID NO: 1134) |
| 219 | GGGRYTYWCYACACCAGAYAA (SEQ ID NO: 1135) |
| 219 | GGGRYTYWCYACACCAGAYA (SEQ ID NO: 1136) |
| 219 | TGGGGRYTYWCYACACCAGAY (SEQ ID NO: 1137) |
| 219 | GGGGRYTYWCYACACCAGAYAA (SEQ ID NO: 1138) |
| 219 | TGGGGRYTYWCYACACCAGAYA (SEQ ID NO: 1139) |
| 219 | TRYTRARVTGGGGRYTYWCYACACCAGAY (SEQ ID NO: 1140) |
| 219 | TGGGGRYTYWCYACACCAGAYAA (SEQ ID NO: 1141) |
| 219 | TRYTRARVTGGGGRYTYWCYACACCAGAYA (SEQ ID NO: 1142) |
| 219 | GARYTRAGRVMDCAYYTRYTRARVTGGGGRYTYWMYACMCCAGAC (SEQ ID NO: 1143) |
| 219 | AYYTRYTRARVTGGGGRYTYWCYACACCAGAY + N (SEQ ID NO: 1144) |
| 219 | TRYTRARVTGGGGRYTYWCYACACCAGAYAA + N (SEQ ID NO: 1145) |
| 219 | AYYTRYTRARVTGGGGRYTYWCYACACCAGAYA + N (SEQ ID NO: 1146) |
| 219 | GRVMDCAYYTRYTRARVTGGGGRYTYWCYACACCAGAY + N (SEQ ID NO: 1147) |
| 219 | AYYTRYTRARVTGGGGRYTYWCYACACCAGAYAA + N (SEQ ID NO: 1148) |
| 219 | GRVMDCAYYTRYTRARVTGGGGRYTYWCYACACCAGAYA + N (SEQ ID NO: 1149) |
| 219 | RAGRVMDCAYYTRYTRARVTGGGGRYTYWCYACACCAGAY + N (SEQ ID NO: 1150) |
| 219 | GRVMDCAYYTRYTRARVTGGGGRYTYWCYACACCAGAYAA + N (SEQ ID NO: 1151) |
| 219 | AGRVMDCAYYTRYTRARVTGGGGRYTYWCYACACCAGAYA + N (SEQ ID NO: 1152) |
| 219 | GGGRYTYWCYACACCAGAYAA + N (SEQ ID NO: 1153) |
| 219 | GGGGRYTYWCYACACCAGAYA + N (SEQ ID NO: 1154) |
| 219 | TGGGGRYTYWCYACACCAGAY + N (SEQ ID NO: 1155) |

TABLE 5 -continued

| | |
|---|---|
| 219 | GGGGRYTYWCYACACCAGAYAA + N (SEQ ID NO: 1156) |
| 219 | TGGGGRYTYWCYACACCAGAYA + N (SEQ ID NO: 1157) |
| 219 | TRYTRARVTGGGGRYTYWCYACACCAGAY + N (SEQ ID NO: 1158) |
| 219 | TGGGGRYTYWCYACACCAGAYAA + N (SEQ ID NO: 1159) |
| 219 | TRYTRARVTGGGGRYTYWCYACACCAGAYA + N (SEQ ID NO: 1160) |
| 219 | GARYTRAGRVMDCAYYTRYTRARVTGGGGRYTYWMYACMCCAGAC + N (SEQ ID NO: 1161) |
| 219 | +AYY + TRYTRARVT + GGGGRYTYWCYACACCAGAY (SEQ ID NO: 1162) |
| 219 | +TRYTRARV + TG + GGGRYTYWCYACACCAGAYAA (SEQ ID NO: 1163) |
| 219 | +AYY + TRYTRARVT + GGGGRYTYWCYACACCAGAYA (SEQ ID NO: 1164) |
| 219 | +AYYTRYTRARV + T + GGGGRYTYWCYACACCAGAY (SEQ ID NO: 1165) |
| 219 | +TRYTRARVT + G + GGGGRYTYWCYACACCAGAYAA (SEQ ID NO: 1166) |
| 219 | +AYYTRYTRARV + T + GGGGRYTYWCYACACCAGAYA (SEQ ID NO: 1167) |
| 219 | +AYY + TRYTRARV + TGGGGRYTYWCYACACCAGAY (SEQ ID NO: 1168) |
| 219 | +TRYTRARV + T + GGGGRYTYWCYACACCAGAYAA (SEQ ID NO: 1169) |
| 219 | +AYY + TRYTRARV + TGGGGRYTYWCYACACCAGAYA (SEQ ID NO: 1170) |
| 219 | +GRVMDC + AYYTRYTRARV + TGGGGRYTYWCYACACCAGAY (SEQ ID NO: 1171) |
| 219 | +AYY + TRYTRARVT + GGGGRYTYWCYACACCAGAYAA (SEQ ID NO: 1172) |
| 219 | +GRVMDC + AYYTRYTRARV + TGGGGRYTYWCYACACCAGAYA (SEQ ID NO: 1173) |
| 219 | +GRVMDCAYY + TRYTRARV + TGGGGRYTYWCYACACCAGAY (SEQ ID NO: 1174) |
| 219 | +AYYTRYTRARV + T + GGGGRYTYWCYACACCAGAYAA (SEQ ID NO: 1175) |
| 219 | +GRVMDCAYY + TRYTRARV + TGGGGRYTYWCYACACCAGAYA (SEQ ID NO: 1176) |
| 219 | +GRVMDC + AYY + TRYTRARVTGGGGRYTYWCYACACCAGAY (SEQ ID NO: 1177) |
| 219 | +AYY + TRYTRARV + TGGGGRYTYWCYACACCAGAYAA (SEQ ID NO: 1178) |
| 219 | +GRVMDC + AYY + TRYTRARVTGGGGRYTYWCYACACCAGAYA (SEQ ID NO: 1179) |
| 219 | R + A + GRVMDCAYY + TRYTRARVTGGGGRYTYWCYACACCAGAY (SEQ ID NO: 1180) |
| 219 | +GRVMDC + AYYTRYTRARV + TGGGGRYTYWCYACACCAGAYAA (SEQ ID NO: 1181) |
| 219 | +A + GRVMDCAYY + TRYTRARVTGGGGRYTYWCYACACCAGAYA (SEQ ID NO: 1182) |
| 219 | R + AGRVMDC + AYY + TRYTRARVTGGGGRYTYWCYACACCAGAY (SEQ ID NO: 1183) |
| 219 | +GRVMDCAYY + TRYTRARV + TGGGGRYTYWCYACACCAGAYAA (SEQ ID NO: 1184) |
| 219 | +AGRVMDC + AYY + TRYTRARVTGGGGRYTYWCYACACCAGAYA (SEQ ID NO: 1185) |
| 219 | +G + GGRY + TYWCYACACCAGAYAA (SEQ ID NO: 1186) |
| 219 | +G + GG + GRYTYWCYACACCAGAYA (SEQ ID NO: 1187) |
| 219 | +GG + GRY + TYWCYACACCAGAYAA (SEQ ID NO: 1188) |
| 219 | +GG + G + GRYTYWCYACACCAGAYA (SEQ ID NO: 1189) |
| 219 | +G + G + GRYTYWCYACACCAGAYAA (SEQ ID NO: 1190) |
| 219 | +G + G + GGRYTYWCYACACCAGAYA (SEQ ID NO: 1191) |
| 219 | +T + GG + GGRYTYWCYACACCAGAY (SEQ ID NO: 1192) |
| 219 | +G + GG + GRYTYWCYACACCAGAYAA (SEQ ID NO: 1193) |
| 219 | +T + GG + GGRYTYWCYACACCAGAYA (SEQ ID NO: 1194) |

TABLE 5 -continued

| | | |
|---|---|---|
| 219 | +TG + G + GGRYTYWCYACACCAGAY | (SEQ ID NO: 1195) |
| 219 | +GG + G + GRYTYWCYACACCAGAYAA | (SEQ ID NO: 1196) |
| 219 | +TG + G + GGRYTYWCYACACCAGAYA | (SEQ ID NO: 1197) |
| 219 | +T + G + GGGRYTYWCYACACCAGAY | (SEQ ID NO: 1198) |
| 219 | +G + G + GGRYTYWCYACACCAGAYAA | (SEQ ID NO: 1199) |
| 219 | +T + G + GGGRYTYWCYACACCAGAYA | (SEQ ID NO: 1200) |
| 219 | +TRYTRARV + TG + GGGRYTYWCYACACCAGAY | (SEQ ID NO: 1201) |
| 219 | +T + GG + GGRYTYWCYACACCAGAYAA | (SEQ ID NO: 1202) |
| 219 | +TRYTRARV + TG + GGGRYTYWCYACACCAGAYA | (SEQ ID NO: 1203) |
| 219 | +TRYTRARVT + G + GGGRYTYWCYACACCAGAY | (SEQ ID NO: 1204) |
| 219 | +TG + G + GGRYTYWCYACACCAGAYAA | (SEQ ID NO: 1205) |
| 219 | +TRYTRARVT + G + GGGRYTYWCYACACCAGAYA | (SEQ ID NO: 1206) |
| 219 | +TRYTRARV + T + GGGGRYTYWCYACACCAGAY | (SEQ ID NO: 1207) |
| 219 | +T + G + GGGRYTYWCYACACCAGAYAA | (SEQ ID NO: 1208) |
| 219 | +TRYTRARV + T + GGGGRYTYWCYACACCAGAYA | (SEQ ID NO: 1209) |
| 219 | R + A + GRVMDC + AYYTRYTRARVTGGGGRYTYWCYACACCAGAY | (SEQ ID NO: 1210) |
| 219 | +GRVMDC + AYY + TRYTRARVTGGGGRYTYWCYACACCAGAYAA | (SEQ ID NO: 1211) |
| 219 | +A + GRVMDC + AYYTRYTRARVTGGGGRYTYWCYACACCAGAYA | (SEQ ID NO: 1212) |
| 225 | GGGRYTYWCYACACCAGAYAARAARCATCARAARGAAC | (SEQ ID NO: 1213) |
| 225 | GGGGRYTYWCYACACCAGAYAARAARCATCARAARGAAC | (SEQ ID NO: 1214) |
| 225 | TGGGGRYTYWCYACACCAGAYAARAARCATCARAARGAAC | (SEQ ID NO: 1215) |
| 225 | TYWCYACACCAGAYAARAARCATCARAARGAAC | (SEQ ID NO: 1216) |
| 225 | GRYTYWCYACACCAGAYAARAARCATCARAARGAAC | (SEQ ID NO: 1217) |
| 225 | GGRYTYWCYACACCAGAYAARAARCATCARAARGAAC | (SEQ ID NO: 1218) |
| 225 | YTRARVTGGGGRYTYWMYACMCCAGAYAARAARCATCARAAAGAA | (SEQ ID NO: 1219) |
| 225 | GGGRYTYWCYACACCAGAYAARAARCATCARAARGAAC + N | (SEQ ID NO: 1220) |
| 225 | GGGGRYTYWCYACACCAGAYAARAARCATCARAARGAAC + N | (SEQ ID NO: 1221) |
| 225 | TGGGGRYTYWCYACACCAGAYAARAARCATCARAARGAAC + N | (SEQ ID NO: 1222) |
| 225 | TYWCYACACCAGAYAARAARCATCARAARGAAC + N | (SEQ ID NO: 1223) |
| 225 | GRYTYWCYACACCAGAYAARAARCATCARAARGAAC + N | (SEQ ID NO: 1224) |
| 225 | GGRYTYWCYACACCAGAYAARAARCATCARAARGAAC + N | (SEQ ID NO: 1225) |
| 225 | YTRARVTGGGGRYTYWMYACMCCAGAYAARAARCATCARAAAGAA + N | (SEQ ID NO: 1226) |
| 225 | +G + GGRY + TYWCYACACCAGAYAARAARCATCARAARGAAC | (SEQ ID NO: 1227) |
| 225 | +GG + GRY + TYWCYACACCAGAYAARAARCATCARAARGAAC | (SEQ ID NO: 1228) |
| 225 | +G + G + GRYTYWCYACACCAGAYAARAARCATCARAARGAAC | (SEQ ID NO: 1229) |
| 225 | +G + GG + GRYTYWCYACACCAGAYAARAARCATCARAARGAAC | (SEQ ID NO: 1230) |
| 225 | +GG + G + GRYTYWCYACACCAGAYAARAARCATCARAARGAAC | (SEQ ID NO: 1231) |
| 225 | +G + G + GGRYTYWCYACACCAGAYAARAARCATCARAARGAAC | (SEQ ID NO: 1232) |
| 225 | +T + GG + GGRYTYWCYACACCAGAYAARAARCATCARAARGAAC | (SEQ ID NO: 1233) |

TABLE 5 -continued

| 225 | +TG + G + GGRYTYWCYACACCAGAYAARAARCATCARAARGAAC (SEQ ID NO: 1234) |
| --- | --- |
| 225 | +TYWCY + ACA + CCAGAYAARAARCATCARAARGAAC (SEQ ID NO: 1235) |
| 225 | +TYWCYA + CA + CCAGAYAARAARCATCARAARGAAC (SEQ ID NO: 1236) |
| 225 | +TYWCY + A + CACCAGAYAARAARCATCARAARGAAC (SEQ ID NO: 1237) |
| 225 | +GRY + TYWCYA + CACCAGAYAARAARCATCARAARGAAC (SEQ ID NO: 1238) |
| 225 | +GRYTYWCY + A + CACCAGAYAARAARCATCARAARGAAC (SEQ ID NO: 1239) |
| 225 | +GRY + TYWCY + ACACCAGAYAARAARCATCARAARGAAC (SEQ ID NO: 1240) |
| 225 | +G + GRYTYWCY + ACACCAGAYAARAARCATCARAARGAAC (SEQ ID NO: 1241) |
| 225 | +GGRY + TYWCY + ACACCAGAYAARAARCATCARAARGAAC (SEQ ID NO: 1242) |
| 225 | +G + GRY + TYWCYACACCAGAYAARAARCATCARAARGAAC (SEQ ID NO: 1243) |
| 225 | +T + G + GGGRYTYWCYACACCAGAYAARAARCATCARAARGAAAC (SEQ ID NO: 1244) |
| 227 | CACCAGAYAARAARCATCARAARGAACCYCCA (SEQ ID NO: 1245) |
| 227 | CACCAGAYAARAARCATCARAARGAACCYCCAT (SEQ ID NO: 1246) |
| 227 | ACACCAGAYAARAARCATCARAARGAACCYCCA (SEQ ID NO: 1247) |
| 227 | ACACCAGAYAARAARCATCARAARGAACCYCCAT (SEQ ID NO: 1248) |
| 227 | RYTYWCYACACCAGAYAARAARCATCARAARGAACCYCCA (SEQ ID NO: 1249) |
| 227 | YTYWCYACACCAGAYAARAARCATCARAARGAACCYCCAT (SEQ ID NO: 1250) |
| 227 | GAYAARAARCATCARAARGAACCYCCA (SEQ ID NO: 1251) |
| 227 | GAYAARAARCATCARAARGAACCYCCAT (SEQ ID NO: 1252) |
| 227 | CAGAYAARAARCATCARAARGAACCYCCA (SEQ ID NO: 1253) |
| 227 | CAGAYAARAARCATCARAARGAACCYCCAT (SEQ ID NO: 1254) |
| 227 | CCAGAYAARAARCATCARAARGAACCYCCA (SEQ ID NO: 1255) |
| 227 | CCAGAYAARAARCATCARAARGAACCYCCAT (SEQ ID NO: 1256) |
| 227 | TGGGGRYTYWMYACMCCAGAYAARAARCATCARAARGAACCTCCA (SEQ ID NO: 1257) |
| 227 | CACCAGAYAARAARCATCARAARGAACCYCCA + N (SEQ ID NO: 1258) |
| 227 | CACCAGAYAARAARCATCARAARGAACCYCCAT + N (SEQ ID NO: 1259) |
| 227 | ACACCAGAYAARAARCATCARAARGAACCYCCA + N (SEQ ID NO: 1260) |
| 227 | ACACCAGAYAARAARCATCARAARGAACCYCCAT + N (SEQ ID NO:1261) |
| 227 | RYTYWCYACACCAGAYAARAARCATCARAARGAACCYCCA + N (SEQ ID NO: 1262) |
| 227 | YTYWCYACACCAGAYAARAARCATCARAARGAACCYCCAT + N (SEQ ID NO: 1263) |
| 227 | GAYAARAARCATCARAARGAACCYCCA + N (SEQ ID NO: 1264) |
| 227 | GAYAARAARCATCARAARGAACCYCCAT + N (SEQ ID NO: 1265) |
| 227 | CAGAYAARAARCATCARAARGAACCYCCA + N (SEQ ID NO: 1266) |
| 227 | CAGAYAARAARCATCARAARGAACCYCCAT + N (SEQ ID NO: 1267) |
| 227 | CCAGAYAARAARCATCARAARGAACCYCCA + N (SEQ ID NO: 1268) |
| 227 | CCAGAYAARAARCATCARAARGAACCYCCAT + N (SEQ ID NO: 1269) |
| 227 | TGGGGRYTYWMYACMCCAGAYAARAARCATCARAARGAACCTCCA + N (SEQ ID NO: 1270) |
| 227 | +CA + CCA + GAYAARAARCATCARAARGAACCYCCA (SEQ ID NO: 1271) |
| 227 | +CA + CCA + GAYAARAARCATCARAARGAACCYCCAT (SEQ ID NO: 1272) |

TABLE 5 -continued

| | |
|---|---|
| 227 | +CAC + CA + GAYAARAARCATCARAARGAACCYCCA (SEQ ID NO: 1273) |
| 227 | +CAC + CA + GAYAARAARCATCARAARGAACCYCCAT (SEQ ID NO: 1274) |
| 227 | +CA + C + CAGAYAARAARCATCARAARGAACCYCCA (SEQ ID NO: 1275) |
| 227 | +CA + C + CAGAYAARAARCATCARAARGAACCYCCAT (SEQ ID NO: 1276) |
| 227 | +A + CAC + CAGAYAARAARCATCARAARGAACCYCCA (SEQ ID NO: 1277) |
| 227 | +A + CAC + CAGAYAARAARCATCARAARGAACCYCCAT (SEQ ID NO: 1278) |
| 227 | +ACA + C + CAGAYAARAARCATCARAARGAACCYCCA (SEQ ID NO: 1279) |
| 227 | +ACA + C + CAGAYAARAARCATCARAARGAACCYCCAT (SEQ ID NO: 1280) |
| 227 | +A + CA + CCAGAYAARAARCATCARAARGAACCYCCA (SEQ ID NO: 1281) |
| 227 | +A + CA + CCAGAYAARAARCATCARAARGAACCYCCAT (SEQ ID NO: 1282) |
| 227 | RY + TYWCY + ACA + CCAGAYAARAARCATCARAARGAACCYCCA (SEQ ID NO: 1283) |
| 227 | Y + TYWCY + ACA + CCAGAYAARAARCATCARAARGAACCYCCAT (SEQ ID NO: 1284) |
| 227 | RY + TYWCYA + CA + CCAGAYAARAARCATCARAARGAACCYCCA (SEQ ID NO: 1285) |
| 227 | Y + TYWCYA + CA + CCAGAYAARAARCATCARAARGAACCYCCAT (SEQ ID NO: 1286) |
| 227 | +G + AYAARA + ARCATCARAARGAACCYCCA (SEQ ID NO: 1287) |
| 227 | +G + AYAARA + ARCATCARAARGAACCYCCAT (SEQ ID NO: 1288) |
| 227 | +GAYAAR + A + ARCATCARAARGAACCYCCA (SEQ ID NO: 1289) |
| 227 | +GAYAAR + A + ARCATCARAARGAACCYCCAT (SEQ ID NO: 1290) |
| 227 | +G + AYAAR + AARCATCARAARGAACCYCCA (SEQ ID NO: 1291) |
| 227 | +G + AYAAR + AARCATCARAARGAACCYCCAT (SEQ ID NO: 1292) |
| 227 | +CA + GAYAAR + AARCATCARAARGAACCYCCA (SEQ ID NO: 1293) |
| 227 | +CA + GAYAAR + AARCATCARAARGAACCYCCAT (SEQ ID NO: 1294) |
| 227 | +CAG + AYAAR + AARCATCARAARGAACCYCCA (SEQ ID NO: 1295) |
| 227 | +CAG + AYAAR + AARCATCARAARGAACCYCCAT (SEQ ID NO: 1296) |
| 227 | +CA + G + AYAARAARCATCARAARGAACCYCCA (SEQ ID NO: 1297) |
| 227 | +CA + G + AYAARAARCATCARAARGAACCYCCAT (SEQ ID NO: 1298) |
| 227 | +C + CAG + AYAARAARCATCARAARGAACCYCCA (SEQ ID NO: 1299) |
| 227 | +C + CAG + AYAARAARCATCARAARGAACCYCCAT (SEQ ID NO: 1300) |
| 227 | +CCA + G + AYAARAARCATCARAARGAACCYCCA (SEQ ID NO: 1301) |
| 227 | +CCA + G + AYAARAARCATCARAARGAACCYCCAT (SEQ ID NO: 1302) |
| 227 | +C + CA + GAYAARAARCATCARAARGAACCYCCA (SEQ ID NO: 1303) |
| 227 | +C + CA + GAYAARAARCATCARAARGAACCYCCAT (SEQ ID NO: 1304) |
| 227 | RY + TYWCY + A + CACCAGAYAARAARCATCARAARGAACCYCCA (SEQ ID NO: 1305) |
| 227 | Y + TYWCY + A + CACCAGAYAARAARCATCARAARGAACCYCCAT (SEQ ID NO: 1306) |
| 230 | GAYAARAARCATCARAARGAACCYCCATTYCTTTGG (SEQ ID NO: 1307) |
| 230 | CAGAYAARAARCATCARAARGAACCYCCATTYCTTTGG (SEQ ID NO: 1308) |
| 230 | ACCAGAYAARAARCATCARAARGAACCYCCATTYCTTTGG (SEQ ID NO: 1309) |
| 230 | ARCATCARAARGAACCYCCATTYCTTTGG (SEQ ID NO: 1310) |

| | |
|---|---|
| 230 | AARCATCARAARGAACCYCCATTYCTTTGG (SEQ ID NO: 1311) |
| 230 | AYAARAARCATCARAARGAACCYCCATTYCTTTGG (SEQ ID NO: 1312) |
| 230 | WMYACMCCAGAYAARAARCATCARAARGAACCYCCATTCCTTTGG (SEQ ID NO: 1313) |
| 230 | GAYAARAARCATCARAARGAACCYCCATTYCTTTGG + N (SEQ ID NO: 1314) |
| 230 | CAGAYAARAARCATCARAARGAACCYCCATTYCTTTGG + N (SEQ ID NO: 1315) |
| 230 | ACCAGAYAARAARCATCARAARGAACCYCCATTYCTTTGG + N (SEQ ID NO: 1316) |
| 230 | ARCATCARAARGAACCYCCATTYCTTTGG + N (SEQ ID NO: 1317) |
| 230 | AARCATCARAARGAACCYCCATTYCTTTGG + N (SEQ ID NO: 1318) |
| 230 | AYAARAARCATCARAARGAACCYCCATTYCTTTGG + N (SEQ ID NO: 1319) |
| 230 | WMYACMCCAGAYAARAARCATCARAARGAACCYCCATTCCTTTGG + N (SEQ ID NO: 1320) |
| 230 | +G + AYAARA + ARCATCARAARGAACCYCCATTYCTTTGG (SEQ ID NO: 1321) |
| 230 | +GAYAAR + A + ARCATCARAARGAACCYCCATTYCTTTGG (SEQ ID NO: 1322) |
| 230 | +G + AYAAR + AARCATCARAARGAACCYCCATTYCTTTGG (SEQ ID NO: 1323) |
| 230 | +CA + GAYAAR + AARCATCARAARGAACCYCCATTYCTTTGG (SEQ ID NO: 1324) |
| 230 | +CAG + AYAAR + AARCATCARAARGAACCYCCATTYCTTTGG (SEQ ID NO: 1325) |
| 230 | +CA + G + AYAARAARCATCARAARGAACCYCCATTYCTTTGG (SEQ ID NO: 1326) |
| 230 | A + C + CAG + AYAARAARCATCARAARGAACCYCCATTYCTTTGG (SEQ ID NO: 1327) |
| 230 | A + CCA + G + AYAARAARCATCARAARGAACCYCCATTYCTTTGG (SEQ ID NO: 1328) |
| 230 | +ARC + ATC + ARAARGAACCYCCATTYCTTTGG (SEQ ID NO: 1329) |
| 230 | +ARCAT + C + ARAARGAACCYCCATTYCTTTGG (SEQ ID NO: 1330) |
| 230 | +ARC + AT + CARAARGAACCYCCATTYCTTTGG (SEQ ID NO: 1331) |
| 230 | +A + ARCAT + CARAARGAACCYCCATTYCTTTGG (SEQ ID NO: 1332) |
| 230 | +AARC + AT + CARAARGAACCYCCATTYCTTTGG (SEQ ID NO: 1333) |
| 230 | +A + ARC + ATCARAARGAACCYCCATTYCTTTGG (SEQ ID NO: 1334) |
| 230 | +AYAAR + AARC + ATCARAARGAACCYCCATTYCTTTGG (SEQ ID NO: 1335) |
| 230 | +AYAARA + ARC + ATCARAARGAACCYCCATTYCTTTGG (SEQ ID NO: 1336) |
| 230 | +AYAAR + A + ARCATCARAARGAACCYCCATTYCTTTGG (SEQ ID NO: 1337) |
| 230 | A + C + CA + GAYAARAARCATCARAARGAACCYCCATTYCTTTGG (SEQ ID NO: 1338) |
| 238 | CATTYCTTTGGATGGGDTATGARCTCCATCCTGAYA (SEQ ID NO: 1339) |
| 238 | CCATTYCTTTGGATGGGDTATGARCTCCATCCTGAYA (SEQ ID NO: 1340) |
| 238 | CCYCCATTYCTTTGGATGGGDTATGARCTCCATCCTGAYA (SEQ ID NO: 1341) |
| 238 | GGATGGGDTATGARCTCCATCCTGAYA (SEQ ID NO: 1342) |
| 238 | TGGATGGGDTATGARCTCCATCCTGAYA (SEQ ID NO: 1343) |
| 238 | TYCTTTGGATGGGDTATGARCTCCATCCTGAYA (SEQ ID NO: 1344) |
| 238 | AARGAACCYCCATTYCTYTGGATGGGDTATGARCTCCATCCTGAT (SEQ ID NO: 1345) |
| 238 | CATTYCTTTGGATGGGDTATGARCTCCATCCTGAYA + N (SEQ ID NO: 1346) |
| 238 | CCATTYCTTTGGATGGGDTATGARCTCCATCCTGAYA + N (SEQ ID NO: 1347) |
| 238 | CCYCCATTYCTTTGGATGGGDTATGARCTCCATCCTGAYA + N (SEQ ID NO: 1348) |

TABLE 5 -continued

| | | |
|---|---|---|
| 238 | GGATGGGDTATGARCTCCATCCTGAYA + N | (SEQ ID NO: 1349) |
| 238 | TGGATGGGDTATGARCTCCATCCTGAYA + N | (SEQ ID NO: 1350) |
| 238 | TYCTTTGGATGGGDTATGARCTCCATCCTGAYA + N | (SEQ ID NO: 1351) |
| 238 | AARGAACCYCCATTYCTYTGGATGGGDTATGARCTCCATCCTGAT + N | (SEQ ID NO: 1352) |
| 238 | +CAT + TYCTTT + GGATGGGDTATGARCTCCATCCTGAYA | (SEQ ID NO: 1353) |
| 238 | +CATTYCTT + T + GGATGGGDTATGARCTCCATCCTGAYA | (SEQ ID NO: 1354) |
| 238 | +CAT + TYCTT + TGGATGGGDTATGARCTCCATCCTGAYA | (SEQ ID NO: 1355) |
| 238 | +C + CATTYCTT + TGGATGGGDTATGARCTCCATCCTGAYA | (SEQ ID NO: 1356) |
| 238 | +CCAT + TYCTT + TGGATGGGDTATGARCTCCATCCTGAYA | (SEQ ID NO: 1357) |
| 238 | +C + CAT + TYCTTTGGATGGGDTATGARCTCCATCCTGAYA | (SEQ ID NO: 1358) |
| 238 | +CCY + CCAT + TYCTTTGGATGGGDTATGARCTCCATCCTGAYA | (SEQ ID NO: 1359) |
| 238 | +CCYC + CAT + TYCTTTGGATGGGDTATGARCTCCATCCTGAYA | (SEQ ID NO: 1360) |
| 238 | +G + GAT + GGGDTATGARCTCCATCCTGAYA | (SEQ ID NO: 1361) |
| 238 | +GGA + T + GGGDTATGARCTCCATCCTGAYA | (SEQ ID NO: 1362) |
| 238 | +G + GA + TGGGDTATGARCTCCATCCTGAYA | (SEQ ID NO: 1363) |
| 238 | +T + GGA + TGGGDTATGARCTCCATCCTGAYA | (SEQ ID NO: 1364) |
| 238 | +TG + GA + TGGGDTATGARCTCCATCCTGAYA | (SEQ ID NO: 1365) |
| 238 | +T + G + GATGGGDTATGARCTCCATCCTGAYA | (SEQ ID NO: 1366) |
| 238 | +TYCTT + TG + GATGGGDTATGARCTCCATCCTGAYA | (SEQ ID NO: 1367) |
| 238 | +TYCTTT + G + GATGGGDTATGARCTCCATCCTGAYA | (SEQ ID NO: 1368) |
| 238 | +TYCTT + T + GGATGGGTATGARCTCCATCCTGAYA | (SEQ ID NO: 1369) |
| 238 | +CCY + C + CATTYCTTTGGATGGGDTATGARCTCCATCCTGAYA | (SEQ ID NO: 1370) |
| 318 | TTYTAARARMMCCWGTRCATGGRGYVTA | (SEQ ID NO: 1371) |
| 318 | AAYAGRGARATTYTAARARMMCCWGTRCATGGRGYVTA | (SEQ ID NO: 1372) |
| 318 | ARAAYAGRGARATTYTAARARMMCCWGTRCATGGRGYVTA | (SEQ ID NO: 1373) |
| 318 | YTRGCRGARAAYAGRGARATTYTRARARMVCCWGTRCATGGAG | (SEQ ID NO: 1374) |
| 318 | TTYTAARARMMCCWGTRCATGGRGYVTA + N | (SEQ ID NO: 1375) |
| 318 | AAYAGRGARATTYTAARARMMCCWGTRCATGGRGYVTA + N | (SEQ ID NO: 1376) |
| 318 | ARAAYAGRGARATTYTAARARMMCCWGTRCATGGRGYVTA + N | (SEQ ID NO: 1377) |
| 318 | YTRGCRGARAAYAGRGARATTYTRARARMVCCWGTRCATGGAG + N | (SEQ ID NO: 1378) |
| 318 | +TTYTAARARMMCCWGTRCATGGRGYV + TA | (SEQ ID NO: 1379) |
| 318 | +TTYTAARARMMCCWGTRCATGGRGYVTA | (SEQ ID NO: 1380) |
| 318 | +AAYAGRGARA + TTYTAARARMMCCWGTRCATGGRGYVTA | (SEQ ID NO: 1381) |
| 318 | +AAYAGRGARATTYTAARARMMCCWGTRCATGGRGYV + TA | (SEQ ID NO: 1382) |
| 318 | +AAYAGRGARA + TTYTAARARMMCCWGTRCATGGRGYV + TA | (SEQ ID NO: 1383) |
| 318 | +AR + AAYAGRGARATTYTAARARMMCCWGTRCATGGRGYV + TA | (SEQ ID NO: 1384) |

TABLE 5 -continued

| | |
|---|---|
| 318 | +ARAAYAGRGARA + TTYTAARARMMCCWGTRCATGGRGYV + TA (SEQ ID NO: 1385) |
| 318 | +AR + AAYAGRGARA + TTYTAARARMMCCWGTRCATGGRGYVTA (SEQ ID NO: 1386) |

| Codon | Reverse Primer (5' to 3') |
|---|---|
| 40 | RTTRTATGGRTTYTCAGGCCCRATTYTTGWRATTTTYCCTTCYTYTTCCAT (SEQ ID NO: 1387) |
| 40 | RTTRTATGGRTTYTCAGGCCCRATTYTTGWRATTTTYCCTTCYTYTTCCAT + N (SEQ ID NO: 1388) |
| 41 | TCAGGCCCAATTYTTGWRATTTTYCCTTCYTYYTCCA (SEQ ID NO: 1389) |
| 41 | TTCAGGCCCAATTYTTGWRATTTTYCCTTCYTYYTCCA (SEQ ID NO: 1390) |
| 41 | TTTTCAGGCCCAATTYTTGWRATTTTYCCTTCYTYYTCCA (SEQ ID NO: 1391) |
| 41 | AATTYTTGWRATTTTYCCTTCYTYYTCCA (SEQ ID NO: 1392) |
| 41 | CCAATTYTTGWRATTTTYCCTTCYTYYTCCA (SEQ ID NO: 1393) |
| 41 | CCCAATTYTTGWRATTTTYCCTTCYTYYTCCA (SEQ ID NO: 1394) |
| 41 | GTRTTRTATGGRTTYTCAGGCCCRATTYTTGWRATTTTYCCTTCYTTTTC (SEQ ID NO: 1395) |
| 41 | TCAGGCCCAATTYTTGWRATTTTYCCTTCYTYYTCCA + N (SEQ ID NO: 1396) |
| 41 | TTCAGGCCCAATTYTTGWRATTTTYCCTTCYTYYTCCA + N (SEQ ID NO: 1397) |
| 41 | TTTTCAGGCCCAATTYTTGWRATTTTYCCTTCYTYYTCCA + N (SEQ ID NO: 1398) |
| 41 | AATTYTTGWRATTTTYCCTTCYTYYTCCA + N (SEQ ID NO: 1399) |
| 41 | CCAATTYTTGWRATTTTYCCTTCYTYYTCCA + N (SEQ ID NO: 1400) |
| 41 | CCCAATTYTTGWRATTTTYCCTTCYTYYTCCA + N (SEQ ID NO: 1401) |
| 41 | GTRTTRTATGGRTTYTCAGGCCCRATTYTTGWRATTTTYCCTTCYTTTTC + N (SEQ ID NO: 1402) |
| 41 | +TCAGG + CCC + AATTYTTGWRATTTTYCCTTCYTYYTCCA (SEQ ID NO: 1403) |
| 41 | +TCAGGC + CC + AATTYTTGWRATTTTYCCTTCYTYYTCCA (SEQ ID NO: 1404) |
| 41 | +TCAGG + C CCAATTYTTGWRATTTTYCCTTCYTYYTCAA (SEQ ID NO: 1405) |
| 41 | +T + TCAGGC + CCAATTYTTGWRATTTTYCCTTCYTYYTCCA (SEQ ID NO: 1406) |
| 41 | +TTCAGG + C + CCAATTYTTGWRATTTTYCCTTCYTYYTCCA (SEQ ID NO: 1407) |
| 41 | +T + TCAGG + CCCAATTYTTGWRATTTTYCCTTCYTYYTCCA (SEQ ID NO: 1408) |
| 41 | +TT + TTCAGG + CCCAATTYTTGWRATTTTYCCTTCYTYYTCCA (SEQ ID NO: 1409) |
| 41 | +TTT + TCAGG + CCCAATTYTTGWRATTTTYCCTTCYTYYTCCA (SEQ ID NO: 1410) |
| 41 | +A + ATT + YTTGWRATTTTYCCTTCYTYYTCCA (SEQ ID NO: 1411) |
| 41 | +AAT + T + YTTGWRATTTTYCCTTCYTYYTCCA (SEQ ID NO: 1412) |
| 41 | +A + AT + TYTTGWRATTTTYCCTTCYTYYTCCA (SEQ ID NO: 1413) |
| 41 | +CC + AAT + TYTTGWRATTTTYCCTTCYTYYTCCA (SEQ ID NO: 1414) |
| 41 | +CCA + AT + TYTTGWRATTTTYCCTTCYTYYTCCA (SEQ ID NO: 1415) |
| 41 | +CC + A + ATTYTTGWRATTTTYCCTTCYTYYTCCA (SEQ ID NO: 1416) |
| 41 | +C + CCA + ATTYTTGWRATTTTYCCTTCYTYYTCCA (SEQ ID NO: 1417) |
| 41 | +CCC + A + ATTYTTGWRATTTTYCCTTCYTYYTCCA (SEQ ID NO: 1418) |
| 41 | +C + CC + AATTYTTGWRATTTTYCCTTCYTYYTCCA (SEQ ID NO: 1419) |
| 41 | +TT + T + TCAGGCCCAATTYTTGWRATTTTYCCTTCYTYYTCCA (SEQ ID NO: 1420) |
| 44 | TRTATGGRTTTTCAGGCCCAATTYTTGWRATTTTYCC (SEQ ID NO: 1421) |

TABLE 5 -continued

| | | |
|---|---|---|
| 44 | TATGGRTTTTCAGGCCCAATTYTTGWRATTTTYCCT | (SEQ ID NO: 1422) |
| 44 | RTTRTATGGRTTTTCAGGCCCAATTYTTGWRATTTTYCC | (SEQ ID NO: 1423) |
| 44 | TRTATGGRTTTTCAGGCCCAATTYTTGWRATTTTYCCT | (SEQ ID NO: 1424) |
| 44 | TRTTRTATGGRTTTTCAGGCCCAATTYTTGWRATTTTYCC | (SEQ ID NO: 1425) |
| 44 | RTTRTATGGRTTTTCAGGCCCAATTYTTGWRATTTTYCCT | (SEQ ID NO: 1426) |
| 44 | TTTCAGGCCCAATTYTTGWRATTTTYCC | (SEQ ID NO: 1427) |
| 44 | TCAGGCCCAATTYTTGWRATTTTYCCT | (SEQ ID NO: 1428) |
| 44 | TGGRTTTTCAGGCCCAATTYTTGWRATTTTYCC | (SEQ ID NO: 1429) |
| 44 | GRTTTTCAGGCCCAATTYTTGWRATTTTYCCT | (SEQ ID NO: 1430) |
| 44 | RTATGGRTTTTCAGGCCCAATTYTTGWRATTTTYCC | (SEQ ID NO: 1431) |
| 44 | ATGGRTTTTCAGGCCCAATTYTTGWRATTTTYCCT | (SEQ ID NO: 1432) |
| 44 | CAAATAYTGGAGTRTTRTATGGRTTYTCAGGCCCRATTYTTGWRATTTTTCC (SEQ ID NO: 1433) | |
| 44 | TRTATGGRTTTTCAGGCCCAATTYTTGWRATTTTYCC + N | (SEQ ID NO: 1434) |
| 44 | TATGGRTTTTCAGGCCCAATTYTTGWRATTTTYCCT + N | (SEQ ID NO: 1435) |
| 44 | RTTRTATGGRTTTTCAGGCCCAATTYTTGWRATTTTYCC + N (SEQ ID NO: 1436) | |
| 44 | TRTATGGRTTTTCAGGCCCAATTYTTGWRATTTTYCCT + N | (SEQ ID NO: 1437) |
| 44 | TRTTRTATGGRTTTTCAGGCCCAATTYTTGWRATTTTYCC + N | (SEQ ID NO: 1438) |
| 44 | RTTRTATGGRTTTTCAGGCCCAATTYTTGWRATTTTYCCT + N (SEQ ID NO: 1439) | |
| 44 | TTTCAGGCCCAATTYTTGWRATTTTYCC + N | (SEQ ID NO: 1440) |
| 44 | TCAGGCCCAATTYTTGWRATTTTYCCT + N | (SEQ ID NO: 1441) |
| 44 | TGGRTTTTCAGGCCCAATTYTTGWRATTTTYCC + N | (SEQ ID NO: 1442) |
| 44 | GRTTTTCAGGCCCAATTYTTGWRATTTTYCCT + N | (SEQ ID NO: 1443) |
| 44 | RTATGGRTTTTCAGGCCCAATTYTTGWRATTTTYCC + N | (SEQ ID NO: 1444) |
| 44 | ATGGRTTTTCAGGCCCAATTYTTGWRATTTTYCCT + N | (SEQ ID NO: 1445) |
| 44 | CAAATAYTGGAGTRTTRTATGGRTTYTCAGGCCCRATTYTTGWRATTTTTCC + N (SEQ ID NO: 1446) | |
| 44 | +T + RTATGGRT + TTTCAGGCCCAATTYTTGWRATTTTYCC | (SEQ ID NO: 1447) |
| 44 | +T + ATGGRTTT + TCAGGCCCAATTYTTGWRATTTTYCCT | (SEQ ID NO: 1448) |
| 44 | +TRTA + TGGRT + TTTCAGGCCCAATTYTTGWRATTTTYCC | (SEQ ID NO: 1449) |
| 44 | +TARG + GRTTT + TCAGGCCCAATTYTTGWRATTTTYCCT | (SEQ ID NO: 1450) |
| 44 | +T + RTA + TGGRTTTTCAGGCCCAATTYTTGWRATTTTYCC | (SEQ ID NO: 1451) |
| 44 | +T + ATG + GRTTTTCAGGCCCAATTYTTGWRATTTTYCCT | (SEQ ID NO: 1452) |
| 44 | +RT + TRTA + TGGRTTTTCAGGCCCAATTYTTGWRATTTTYCC | (SEQ ID NO: 1453) |
| 44 | +TR + TATG + GRTTTTCAGGCCCAATTYTTGWRATTTTYCCT | (SEQ ID NO: 1454) |
| 44 | +RTT + RTA + TGGRTTTTCAGGCCCAATTYTTGWRATTTTYCC | (SEQ ID NO: 1455) |
| 44 | +TRT + ATG + GRTTTTCAGGCCCAATTYTTGWRATTTTYCCT | (SEQ ID NO: 1456) |
| 44 | +RT + T + RTATGGRTTTTCAGGCCCAATTYTTGWRATTTTYCC | (SEQ ID NO: 1457) |
| 44 | +TR + T + ATGGRTTTTCAGGCCCAATTYTTGWRATTTTYCCT | (SEQ ID NO: 1458) |
| 44 | (SEQ ID NO: 1459) | |

TABLE 5 -continued

| 44 | R + T + TRT + ATGGRTTTTCAGGCCCAATTYTTGWRATTTTYCCT (SEQ ID NO: 1460) |
| 44 | +TRT + T RTATGGRTTTTCAGGCCCAATTYTTGWRATTTTYCC (SEQ ID NO: 1461) |
| 44 | R + TTR + T ATGGRTTTTCAGGCCCAATTYTTGWRATTTTYCCT (SEQ ID NO: 1462) |
| 44 | +TTTC + AGG + CCCAATTYTTGWRATTTTYCC (SEQ ID NO: 1463) |
| 44 | +TCAG + GCC + CAATTYTTGWRATTTTYCCT (SEQ ID NO: 1464) |
| 44 | +TTTCAG + G + CCCAATTYTTGWRATTTTYCC (SEQ ID NO: 1465) |
| 44 | +TCAGGC + C + CAATTYTTGWRATTTTYCCT (SEQ ID NO: 1466) |
| 44 | +TTTC + AG + GCCCAATTYTTGWRATTTTYCC (SEQ ID NO: 1467) |
| 44 | +TCAG + GC + CCAATTYTTGWRATTTTYCCT (SEQ ID NO: 1468) |
| 44 | +TGGRT + TTTCAG + GCCCAATTYTTGWRATTTTYCC (SEQ ID NO: 1469) |
| 44 | +GRTTT + TCAGGC + CCAATTYTTGWRATTTTYCCT (SEQ ID NO: 1470) |
| 44 | +TGGRTTTC + AG + GCCCAATTYTTGWRATTTTYCC (SEQ ID NO: 1471) |
| 44 | +GRTTTCAG + GC + CCAATTYTTGWRATTTTYCCT (SEQ ID NO: 1472) |
| 44 | +TGGRT + TTTC + AGGCCCAATTYTTGWRATTTTYCC (SEQ ID NO: 1473) |
| 44 | +GRTTT + TCAG + GCCCAATTYTTGWRATTTTYCCT (SEQ ID NO: 1474) |
| 44 | +RTA + TGGRTTTTC + AGGCCCAATTYTTGWRATTTTYCC (SEQ ID NO: 1475) |
| 44 | +ATG + GRTTTTCAG + GCCCAATTYTTGWRATTTTYCCT (SEQ ID NO: 1476) |
| 44 | +RTATGGRT + TTTC + AGGCCCAATTYTTGWRATTTTYCC (SEQ ID NO: 1477) |
| 44 | +ATGGRTTT + TCAG + GCCCAATTYTTGWRATTTTYCCT (SEQ ID NO: 1478) |
| 44 | +RTA + TGGRT + TTTCAGGCCCAATTYTTGWRATTTTYCC (SEQ ID NO: 1479) |
| 44 | +ATG + GRTTT + TCAGGCCCAATTYTTGWRATTTTYCCT (SEQ ID NO: 1480) |
| 44 | +T + RT + TRTATGGRTTTTCAGGCCCAATTYTTGWRATTTTYCC (SEQ ID NO: 1481) |
| 44 | R + T + TR + TATGGRTTTTCAGGCCCAATTYTTGWRATTTTYCCT (SEQ ID NO: 1482) |
| 62 | AATTTYCTCCAYTTRGTRCTRTYYTTYTTYTTTATR (SEQ ID NO: 1483) |
| 62 | CTAATTTYCTCCAYTTRGTRCTRTYYTTYTTYTTTATR (SEQ ID NO: 1484) |
| 62 | TACTAATTTYCTCCAYTTRGTRCTRTYYTTYTTYTTTATR (SEQ ID NO: 1485) |
| 62 | TCCAYTTRGTRCTRTYYTTYTTYTTTATR (SEQ ID NO: 1486) |
| 62 | CTCCAYTTRGTRCTRTYYTTYTTYTTTATR (SEQ ID NO: 1487) |
| 62 | TTYCTCCAYTTRGTRCTRTYYTTYTTYTTTATR (SEQ ID NO: 1488) |
| 62 | YTCYCTRAARTCYACTAATTTYCTCCAYTTRGTRCTRTCYTTYTTCTTTAT (SEQ ID NO: 1489) |
| 62 | AATTTYCTCCAYTTRGTRCTRTYYTTYTTYTTTATR + N (SEQ ID NO: 1490) |
| 62 | CTAATTTYCTCCAYTTRGTRCTRTYYTTYTTYTTTATR + N (SEQ ID NO: 1491) |
| 62 | TACTAATTTYCTCCAYTTRGTRCTRTYYTTYTTYTTTATR + N (SEQ ID NO: 1492) |
| 62 | TCCAYTTRGTRCTRTYYTTYTTYTTTATR + N (SEQ ID NO: 1493) |
| 62 | CTCCAYTTRGTRCTRTYYTTYTTYTTTATR + N (SEQ ID NO: 1494) |
| 62 | TTYCTCCAYTTRGTRCTRTYYTTYTTYTTTATR + N (SEQ ID NO: 1495) |
| 62 | YTCYCTRAARTCYACTAATTTYCTCCAYTTRGTRCTRTCYTTYTTCTTTAT + N (SEQ ID NO: 1496) |
| 62 | +AAT + TTYC + TCCAYTTRGTRCTRTYYTTYTTYTTTATR (SEQ ID NO: 1497) |
| 62 | +AATTTY + C + TCCAYTTRGTRCTRTYYTTYTTYTTTATR (SEQ ID NO: 1498) |
| 62 | +AAT + TTY + CTCCAYTTRGTRCTRTYYTTYTTYTTTATR (SEQ ID NO: 1499) |

TABLE 5 -continued

| | | |
|---|---|---|
| 62 | +CT + AATTTY + CTCCAYTTRGTRCTRTYYTTYTTYTTTATR | (SEQ ID NO: 1500) |
| 62 | +CTAAT + TTY + CTCCAYTTRGTRCTRTYYTTYTTYTTTATR | (SEQ ID NO: 1501) |
| 62 | +CT + AAT + TTYCTCCAYTTRGTRCTRTYYTTYTTYTTTATR | (SEQ ID NO: 1502) |
| 62 | T + A + CTAAT + TTYCTCCAYTTRGTRCTRTYYTTYTTYTTTATR | (SEQ ID NO: 1503) |
| 62 | T + ACT + AAT + TTYCTCCAYTTRGTRCTRTYYTTYTTYTTTATR | (SEQ ID NO: 1504) |
| 62 | +TCCAYTTRGTR + CTRT + YYTTYTTYTTTATR | (SEQ ID NO: 1505) |
| 62 | +TCCAYTTRGTRCTR + T + YYTTYTTYTTTATR | (SEQ ID NO: 1506) |
| 62 | +TCCAYTTRGTR + CTR + TYYTTYTTYTTTATR | (SEQ ID NO: 1507) |
| 62 | +C + TCCAYTTRGTRCTR + TYYTTYTTYTTTATR | (SEQ ID NO: 1508) |
| 62 | +CTCCAYTTRGTR + CTR + TYYTTYTTYTTTATR | (SEQ ID NO: 1509) |
| 62 | +C + TCCAYTTRGTR + CTRTYYTTYTTYTTTATR | (SEQ ID NO: 1510) |
| 62 | +TTY + CTCCAYTTRGTR + CTRTYYTTYTTYTTTATR | (SEQ ID NO: 1511) |
| 62 | +TTYC + TCCAYTTRGTR + CTRTYYTTYTTYTTTATR | (SEQ ID NO: 1512) |
| 62 | +TTY + C + TCCAYTTRGTRCTRTYYTTYTTYTTTATR | (SEQ ID NO: 1513) |
| 62 | T + A + CT + AATTTYCTCCAYTTRGTRCTRTYYTTYTTYTTTATR | (SEQ ID NO: 1514) |
| 65 | AATTTYCTCCAYTTRGTRCTRTYYTTY | (SEQ ID NO: 1515) |
| 65 | CTAATTTYCTCCAYTTRGTRCTRTYYTT | (SEQ ID NO: 1516) |
| 65 | TRAARTCTACTAATTTYCTCCAYTTRGTRCTRTYYTTY | (SEQ ID NO: 1517) |
| 65 | YCTRAARTCTACTAATTTYCTCCAYTTRGTRCTRTYYTT | (SEQ ID NO: 1518) |
| 65 | YCTRAARTCTACTAATTTYCTCCAYTTRGTRCTRTYYTTY | (SEQ ID NO: 1519) |
| 65 | CYCTRAARTCTACTAATTTYCTCCAYTTRGTRCTRTYYTT | (SEQ ID NO: 1520) |
| 65 | YCTCCAYTTRGTRCTRTYYTTY | (SEQ ID NO: 1521) |
| 65 | TTYCTCCAYTTRGTRCTRTYYTT | (SEQ ID NO: 1522) |
| 65 | TYCTCCAYTTRGTRCTRTYYTTY | (SEQ ID NO: 1523) |
| 65 | TTTYCTCCAYTTRGTRCTRTYYTT | (SEQ ID NO: 1524) |
| 65 | TTYCTCCAYTTRGTRCTRTYYTTY | (SEQ ID NO: 1525) |
| 65 | ATTTYCTCCAYTTRGTRCTRTYYTT | (SEQ ID NO: 1526) |
| 65 | YTTATTRAGYTCYCTRAARTCYACTAATTTYCTCCAYTTRGTRCTGTCTTT | (SEQ ID NO: 1527) |
| 65 | AATTTYCTCCAYTTRGTRCTRTYYTTY + N | (SEQ ID NO: 1528) |
| 65 | CTAATTTYCTCCAYTTRGTRCTRTYYTT + N | (SEQ ID NO: 1529) |
| 65 | TRAARTCTACTAATTTYCTCCAYTTRGTRCTRTYYTTY + N | (SEQ ID NO: 1530) |
| 65 | YCTRAARTCTACTAATTTYCTCCAYTTRGTRCTRTYYTT + N | (SEQ ID NO: 1531) |
| 65 | YCTRAARTCTACTAATTTYCTCCAYTTRGTRCTRTYYTTY + N | (SEQ ID NO: 1532) |
| 65 | CYCTRAARTCTACTAATTTYCTCCAYTTRGTRCTRTYYTT + N | (SEQ ID NO: 1533) |
| 65 | YCTCCAYTTRGTRCTRTYYTTY + N | (SEQ ID NO: 1534) |
| 65 | TTYCTCCAYTTRGTRCTRTYYTT + N | (SEQ ID NO: 1535) |
| 65 | TYCTCCAYTTRGTRCTRTYYTTY + N | (SEQ ID NO: 1536) |
| 65 | TTTYCTCCAYTTRGTRCTRTYYTT + N | (SEQ ID NO: 1537) |
| 65 | TTYCTCCAYTTRGTRCTRTYYTTY + N | (SEQ ID NO: 1538) |

TABLE 5 -continued

| | |
|---|---|
| 65 | ATTTYCTCCAYTTRGTRCTRTYYTT + N (SEQ ID NO: 1539) |
| 65 | YTTATTRAGYTCYCTRAARTCYACTAATTTYCTCCAYTTRGTRCTGTCTTT + N (SEQ ID NO: 1540) |
| 65 | +AAT + TT + YCTCCAYTTRGTRCTRTYYTTY (SEQ ID NO: 1541) |
| 65 | +CTA + AT + TTYCTCCAYTTRGTRCTRTYYTT (SEQ ID NO: 1542) |
| 65 | +AATT + T + YCTCCAYTTRGTRCTRTYYTTY (SEQ ID NO: 1543) |
| 65 | +CTAA + T + TTYCTCCAYTTRGTRCTRTYYTT (SEQ ID NO: 1544) |
| 65 | +AAT + T + TYCTCCAYTTRGTRCTRTYYTTY (SEQ ID NO: 1545) |
| 65 | +CTA + A + TTTYCTCCAYTTRGTRCTRTYYTT (SEQ ID NO: 1546) |
| 65 | +TRAARTCTACT + AATT + TYCTCCAYTTRGTRCTRTYYTTY (SEQ ID NO: 1547) |
| 65 | +YCTRAARTCTA + CTAA + TTTYCTCCAYTTRGTRCTRTYYTT (SEQ ID NO: 1548) |
| 65 | +TRAARTCTACTAAT + T + TYCTCCAYTTRGTRCTRTYYTTY (SEQ ID NO: 1549) |
| 65 | +YCTRAARTCTACTA + A + TTTYCTCCAYTTRGTRCTRTYYTT (SEQ ID NO: 1550) |
| 65 | +TRAARTCTACT + AAT + TTYCTCCAYTTRGTRCTRTYYTTY (SEQ ID NO: 1551) |
| 65 | +YCTRAARTCTA + CTA + ATTTYCTCCAYTTRGTRCTRTYYTT (SEQ ID NO: 1552) |
| 65 | Y + C + TRAARTCTACTAAT + TTYCTCCAYTTRGTRCTRTYYTTY (SEQ ID NO: 1553) |
| 65 | +C + YCTRAARTCTACTA + ATTTYCTCCAYTTRGTRCTRTYYTT (SEQ ID NO: 1554) |
| 65 | Y + CTRAARTCTACT + AAT + TTYCTCCAYTTRGTRCTRTYYTTY (SEQ ID NO: 1555) |
| 65 | +CYCTRAARTCTA + CTA + ATTTYCTCCAYTTRGTRCTRTYYTT (SEQ ID NO: 1556) |
| 65 | +Y + CTC + CAYTTRGTRCTRTYYTTY (SEQ ID NO: 1557) |
| 65 | +T + TYC + TCCAYTTRGTRCTRTYYTT (SEQ ID NO: 1558) |
| 65 | +YC + TC + CAYTTRGTRCTRTYYTTY (SEQ ID NO: 1559) |
| 65 | +TT + YC + TCCAYTTRGTRCTRTYYTT (SEQ ID NO: 1560) |
| 65 | +Y + C + TCCAYTTRGTRCTRTYYTTY (SEQ ID NO: 1561) |
| 65 | +T + T + YCTCCAYTTRGTRCTRTYYTT (SEQ ID NO: 1562) |
| 65 | +T + YC + TCCAYTTRGTRCTRTYYTTY (SEQ ID NO: 1563) |
| 65 | +T + TT + YCTCCAYTTRGTRCTRTYYTT (SEQ ID NO: 1564) |
| 65 | +TY + C + TCCAYTTRGTRCTRTYYTTY (SEQ ID NO: 1565) |
| 65 | +TT + T + YCTCCAYTTRGTRCTRTYYTT (SEQ ID NO: 1566) |
| 65 | +T + Y + CTCCAYTTRGTRCTRTYYTTY (SEQ ID NO: 1567) |
| 65 | +T + T + TYCTCCAYTTRGTRCTRTYYTT (SEQ ID NO: 1568) |
| 65 | +T + TY + CTCCAYTTRGTRCTRTYYTTY (SEQ ID NO: 1569) |
| 65 | +A + TT + TYCTCCAYTTRGTRCTRTYYTT (SEQ ID NO: 1570) |
| 65 | +TT + Y + CTCCAYTTRGTRCTRTYYTTY (SEQ ID NO: 1571) |
| 65 | +AT + T + TYCTCCAYTTRGTRCTRTYYTT (SEQ ID NO: 1572) |
| 65 | +T + T + YCTCCAYTTRGTRCTRTYYTTY (SEQ ID NO: 1573) |
| 65 | +A + T + TTYCTCCAYTTRGTRCTRTYYTT (SEQ ID NO: 1574) |
| 65 | Y + C + TRAARTCTACT + AATTTYCTCCAYTTRGTRCTRTYYTTY (SEQ ID NO: 1575) |
| 65 | +C + YCTRAARTCTA + CTAATTTYCTCCAYTTRGTRCTRTYYTT (SEQ ID NO: 1576) |
| 67 | TCTACTAATTTYCTCCAYTTRGTRCTRT (SEQ ID NO: 1577) |

TABLE 5 -continued

| | |
|---|---|
| 67 | ARTCTACTAATTTYCTCCAYTTRGTRCTR (SEQ ID NO: 1578) |
| 67 | RAARTCTACTAATTTYCTCCAYTTRGTRCT (SEQ ID NO: 1579) |
| 67 | RTCTACTAATTTYCTCCAYTTRGTRCTRT (SEQ ID NO: 1580) |
| 67 | AARTCTACTAATTTYCTCCAYTTRGTRCTR (SEQ ID NO: 1581) |
| 67 | TRAARTCTACTAATTTYCTCCAYTTRGTRCT (SEQ ID NO: 1582) |
| 67 | AGYTCYCTRAARTCTACTAATTTYCTCCAYTTRGTRCTRT (SEQ ID NO: 1583) |
| 67 | RAGYTCYCTRAARTCTACTAATTTYCTCCAYTTRGTRCTR (SEQ ID NO: 1584) |
| 67 | TRAGYTCYCTRAARTCTACTAATTTYCTCCAYTTRGTRCT (SEQ ID NO: 1585) |
| 67 | ACTAATTTYCTCCAYTTRGTRCTRT (SEQ ID NO: 1586) |
| 67 | CTACTAATTTYCTCCAYTTRGTRCTR (SEQ ID NO: 1587) |
| 67 | RTCTACTAATTTYCTCCAYTTRGTRCT (SEQ ID NO: 1588) |
| 67 | TACTAATTTYCTCCAYTTRGTRCTRT (SEQ ID NO: 1589) |
| 67 | TCTACTAATTTYCTCCAYTTRGTRCTR (SEQ ID NO: 1590) |
| 67 | ARTCTACTAATTTYCTCCAYTTRGTRCT (SEQ ID NO: 1591) |
| 67 | CTACTAATTTYCTCCAYTTRGTRCTRT (SEQ ID NO: 1592) |
| 67 | RTCTACTAATTTYCTCCAYTTRGTRCTR (SEQ ID NO: 1593) |
| 67 | AARTCTACTAATTTYCTCCAYTTRGTRCT (SEQ ID NO: 1594) |
| 67 | GTTYTYTTATTRAGYTCYCTRAARTCYACTAATTTYCTCCAYTTRGTACT (SEQ ID NO: 1595) |
| 67 | TCTACTAATTTYCTCCAYTTRGTRCTRT + N (SEQ ID NO: 1596) |
| 67 | ARTCTACTAATTTYCTCCAYTTRGTRCTR + N (SEQ ID NO: 1597) |
| 67 | RAARTCTACTAATTTYCTCCAYTTRGTRCT + N (SEQ ID NO: 1598) |
| 67 | RTCTACTAATTTYCTCCAYTTRGTRCTRT + N (SEQ ID NO: 1599) |
| 67 | AARTCTACTAATTTYCTCCAYTTRGTRCTR + N (SEQ ID NO: 1600) |
| 67 | TRAARTCTACTAATTTYCTCCAYTTRGTRCT + N (SEQ ID NO: 1601) |
| 67 | AGYTCYCTRAARTCTACTAATTTYCTCCAYTTRGTRCTRT + N (SEQ ID NO: 1602) |
| 67 | RAGYTCYCTRAARTCTACTAATTTYCTCCAYTTRGTRCTR + N (SEQ ID NO: 1603) |
| 67 | TRAGYTCYCTRAARTCTACTAATTTYCTCCAYTTRGTRCT + N (SEQ ID NO: 1604) |
| 67 | ACTAATTTYCTCCAYTTRGTRCTRT + N (SEQ ID NO: 1605) |
| 67 | CTACTAATTTYCTCCAYTTRGTRCTR + N (SEQ ID NO: 1606) |
| 67 | RTCTACTAATTTYCTCCAYTTRGTRCT + N (SEQ ID NO: 1607) |
| 67 | TACTAATTTYCTCCAYTTRGTRCTRT + N (SEQ ID NO: 1608) |
| 67 | TCTACTAATTTYCTCCAYTTRGTRCTR + N (SEQ ID NO: 1609) |
| 67 | ARTCTACTAATTTYCTCCAYTTRGTRCT + N (SEQ ID NO: 1610) |
| 67 | CTACTAATTTYCTCCAYTTRGTRCTRT + N (SEQ ID NO: 1611) |
| 67 | RTCTACTAATTTYCTCCAYTTRGTRCTR + N (SEQ ID NO: 1612) |
| 67 | AARTCTACTAATTTYCTCCAYTTRGTRCT + N (SEQ ID NO: 1613) |
| 67 | GTTYTYTTATTRAGYTCYCTRAARTCYACTAATTTYCTCCAYTTRGTACT + N (SEQ ID NO: 1614) |
| 67 | +T + CT + ACTAATTTYCTCCAYTTRGTRCTRT (SEQ ID NO: 1615) |
| 67 | +A + RT + CTACTAATTTYCTCCAYTTRGTRCTR (SEQ ID NO: 1616) |

TABLE 5 -continued

| 67 | +R + AA + RTCTACTAATTTYCTCCAYTTRGTRCT (SEQ ID NO: 1617) |
| --- | --- |
| 67 | +TC + T + ACTAATTTYCTCCAYTTRGTRCTRT (SEQ ID NO: 1618) |
| 67 | +AR + T + CTACTAATTTYCTCCAYTTRGTRCTR (SEQ ID NO: 1619) |
| 67 | +RA + A + RTCTACTAATTTYCTCCAYTTRGTRCT (SEQ ID NO: 1620) |
| 67 | +T + C + TACTAATTTYCTCCAYTTRGTRCTRT (SEQ ID NO: 1621) |
| 67 | +A + R + TCTACTAATTTYCTCCAYTTRGTRCTR (SEQ ID NO: 1622) |
| 67 | +R + A + ARTCTACTAATTTYCTCCAYTTRGTRCT (SEQ ID NO: 1623) |
| 67 | +R + TC + TACTAATTTYCTCCAYTTRGTRCTRT (SEQ ID NO: 1624) |
| 67 | +A + AR + TCTACTAATTTYCTCCAYTTRGTRCTR (SEQ ID NO: 1625) |
| 67 | +T + RA + ARTCTACTAATTTYCTCCAYTTRGTRCT (SEQ ID NO: 1626) |
| 67 | +RT + C + TACTAATTTYCTCCAYTTRGTRCTRT (SEQ ID NO: 1627) |
| 67 | +AA + R + TCTACTAATTTYCTCCAYTTRGTRCTR (SEQ ID NO: 1628) |
| 67 | +TR + A + ARTCTACTAATTTYCTCCAYTTRGTRCT (SEQ ID NO: 1629) |
| 67 | +R + T + CTACTAATTTYCTCCAYTTRGTRCTRT (SEQ ID NO: 1630) |
| 67 | +A + A + RTCTACTAATTTYCTCCAYTTRGTRCTR (SEQ ID NO: 1631) |
| 67 | +T + R + AARTCTACTAATTTYCTCCAYTTRGTRCT (SEQ ID NO: 1632) |
| 67 | +AGYTCYCT + RAAR + TCTACTAATTTYCTCCAYTTRGTRCTRT (SEQ ID NO: 1633) |
| 67 | RAGYTCY + CTR + AA + RTCTACTAATTTYCTCCAYTTRGTRCTR (SEQ ID NO: 1634) |
| 67 | +TRAGYT + CYCT + RAARTCTACTAATTTYCTCCAYTTRGTRCT (SEQ ID NO: 1635) |
| 67 | RAGYTCY + CTRA + A + RTCTACTAATTTYCTCCAYTTRGTRCTR (SEQ ID NO: 1636) |
| 67 | +AC + TAAT + TTYCTCCAYTTRGTRCTRT (SEQ ID NO: 1637) |
| 67 | +CT + ACTA + ATTTYCTCCAYTTRGTRCTR (SEQ ID NO: 1638) |
| 67 | +RT + CTAC + TAATTTYCTCCAYTTRGTRCT (SEQ ID NO: 1639) |
| 67 | +ACT + AAT + TTYCTCCAYTTRGTRCTRT (SEQ ID NO: 1640) |
| 67 | +CTA + CTA + ATTTYCTCCAYTTRGTRCTR (SEQ ID NO: 1641) |
| 67 | +RTC + TAC + TAATTTYCTCCAYTTRGTRCT (SEQ ID NO: 1642) |
| 67 | +AC + T + AATTTYCTCCAYTTRGTRCTRT (SEQ ID NO: 1643) |
| 67 | +CT + A + CTAATTTYCTCCAYTTRGTRCTR (SEQ ID NO: 1644) |
| 67 | +RT + C + TACTAATTTYCTCCAYTTRGTRCT (SEQ ID NO: 1645) |
| 67 | +T + ACT + AATTTYCTCCAYTTRGTRCTRT (SEQ ID NO: 1646) |
| 67 | +T + CTA + CTAATTTYCTCCAYTTRGTRCTR (SEQ ID NO: 1647) |
| 67 | +A + RTC + TACTAATTTYCTCCAYTTRGTRCT (SEQ ID NO: 1648) |
| 67 | +TAC + T + AATTTYCTCCAYTTRGTRCTRT (SEQ ID NO: 1649) |
| 67 | +TCT + A + CTAATTTYCTCCAYTTRGTRCTR (SEQ ID NO: 1650) |
| 67 | +ART + C + TACTAATTTYCTCCAYTTRGTRCT (SEQ ID NO: 1651) |
| 67 | +TA + AC + TAATTTYCTCCAYTTRGTRCTRT (SEQ ID NO: 1652) |
| 67 | +T + CT + ACTAATTTYCTCCAYTTRGTRCTR (SEQ ID NO: 1653) |
| 67 | +A + RT + CTACTAATTTYCTCCAYTTRGTRCT (SEQ ID NO: 1654) |
| 67 | +C + TAC + TAATTTYCTCCAYTTRGTRCTRT (SEQ ID NO: 1655) |
| 67 | +R + TCT + ACTAATTTYCTCCAYTTRGTRCTR (SEQ ID NO: 1656) |

TABLE 5 -continued

| | | |
|---|---|---|
| 67 | +A + ART + CTACTAATTTYCTCCAYTTRGTRCT (SEQ ID NO: 1657) | |
| 67 | +CT + AC + TAATTTYCTCCAYTTRGTRCTRT (SEQ ID NO: 1658) | |
| 67 | +RT + CT + ACTAATTTYCTCCAYTTRGTRCTR (SEQ ID NO: 1659) | |
| 67 | +AA + RT + CTACTAATTTYCTCCAYTTRGTRCT (SEQ ID NO: 1660) | |
| 67 | +C + T + ACTAATTTYCTCCAYTTRGTRCTRT (SEQ ID NO: 1661) | |
| 67 | +R + T + CTACTAATTTYCTCCAYTTRGTRCTR (SEQ ID NO: 1662) | |
| 67 | +A + A + RTCTACTAATTTYCTCCAYTTRGTRCT (SEQ ID NO: 1663) | |
| 67 | AGYTCYCT + RAA + R + TCTACTAATTTYCTCCAYTTRGTRCTRT (SEQ ID NO: 1664) | |
| 67 | RAGYTCY + CTR + A + ARTCTACTAATTTYCTCCAYTTRGTRCTR (SEQ ID NO: 1665) | |
| 67 | TRAGYT + CYC + T + RAARTCTACTAATTTYCTCCAYTTRGTRCT (SEQ ID NO: 1666) | |
| 69 | RTCYTGAGTTYTYTTATTRAGYTCYCTRAARTCYACTAATTTYCTCCATTT (SEQ ID NO: 1667) | |
| 69 | RTCYTGAGTTYTYTTATTRAGYTCYCTRAARTCYACTAATTTYCTCCATTT + N (SEQ ID NO: 1668) | |
| 70 | TATTRAGYTCYCTRAARTCTACTAATTTYCTCCAYT (SEQ ID NO: 1669) | |
| 70 | YTTATTRAGYTCYCTRAARTCTACTAATTTYCTCCAY (SEQ ID NO: 1670) | |
| 70 | TTATTRAGYTCYCTRAARTCTACTAATTTYCTCCAYT (SEQ ID NO: 1671) | |
| 70 | TYTTATTRAGYTCYCTRAARTCTACTAATTTYCTCCAY (SEQ ID NO: 1672) | |
| 70 | CTYTTATTRAGYTCYCTRAARTCTACTAATTTYCTCCAYT (SEQ ID NO: 1673) | |
| 70 | TCTYTTATTRAGYTCYCTRAARTCTACTAATTTYCTCCAY (SEQ ID NO: 1674) | |
| 70 | RAGYTCYCTRAARTCTACTAATTTYCTCCAYT (SEQ ID NO: 1675) | |
| 70 | TTRAGYTCYCTRAARTCTACTAATTTYCTCCAY (SEQ ID NO: 1676) | |
| 70 | TTRAGYTCYCTRAARTCTACTAATTTYCTCCAYT (SEQ ID NO: 1677) | |
| 70 | TATTRAGYTCYCTRAARTCTACTAATTTYCTCCAY (SEQ ID NO: 1678) | |
| 70 | ATTRAGYTCYCTRAARTCTACTAATTTYCTCCAYT (SEQ ID NO: 1679) | |
| 70 | TTATTRAGYTCYCTRAARTCTACTAATTTYCTCCAY (SEQ ID NO: 1680) | |
| 70 | AARTCYTGAGTTYTYTTATTRAGYTCYCTRAARTCYACTAATTTYCTCCA (SEQ ID NO: 1681) | |
| 70 | TATTRAGYTCYCTRAARTCTACTAATTTYCTCCAYT + N (SEQ ID NO: 1682) | |
| 70 | YTTATTRAGYTCYCTRAARTCTACTAATTTYCTCCAY + N (SEQ ID NO: 1683) | |
| 70 | TTATTRAGYTCYCTRAARTCTACTAATTTYCTCCAYT + N (SEQ ID NO: 1684) | |
| 70 | TYTTATTRAGYTCYCTRAARTCTACTAATTTYCTCCAY + N (SEQ ID NO: 1685) | |
| 70 | CTYTTATTRAGYTCYCTRAARTCTACTAATTTYCTCCAYT + N (SEQ ID NO: 1686) | |
| 70 | TCTYTTATTRAGYTCYCTRAARTCTACTAATTTYCTCCAY + N (SEQ ID NO: 1687) | |
| 70 | RAGYTCYCTRAARTCTACTAATTTYCTCCAYT + N (SEQ ID NO: 1688) | |
| 70 | TTRAGYTCYCTRAARTCTACTAATTTYCTCCAY + N (SEQ ID NO: 1689) | |
| 70 | TTRAGYTCYCTRAARTCTACTAATTTYCTCCAYT + N (SEQ ID NO: 1690) | |
| 70 | TATTRAGYTCYCTRAARTCTACTAATTTYCTCCAY + N (SEQ ID NO: 1691) | |
| 70 | ATTRAGYTCYCTRAARTCTACTAATTTYCTCCAYT + N (SEQ ID NO: 1692) | |
| 70 | TTATTRAGYTCYCTRAARTCTACTAATTTYCTCCAY + N (SEQ ID NO: 1693) | |
| 70 | AARTCYTGAGTTYTYTTATTRAGYTCYCTRAARTCYACTAATTTYCTCCA + N (SEQ ID NO: 1694) | |

TABLE 5 -continued

| | | |
|---|---|---|
| 70 | +T + ATT + RAGYTCYCTRAARTCTACTAATTTYCTCCAYT | (SEQ ID NO: 1695) |
| 70 | +Y + TTA + TTRAGYTCYCTRAARTCTACTAATTTYCTCCAY | (SEQ ID NO: 1696) |
| 70 | +TA + TT + RAGYTCYCTRAARTCTACTAATTTYCTCCAYT | (SEQ ID NO: 1697) |
| 70 | +YT + TA + TTRAGYTCYCTRAARTCTACTAATTTYCTCCAY | (SEQ ID NO: 1698) |
| 70 | +T + A + TTRAGYTCYCTRAARTCTACTAATTTYCTCCAYT | (SEQ ID NO: 1699) |
| 70 | +Y + T + TATTRAGYTCYCTRAARTCTACTAATTTYCTCCAY | (SEQ ID NO: 1700) |
| 70 | +T + TA + TTRAGYTCYCTRAARTCTACTAATTTYCTCCAYT | (SEQ ID NO: 1701) |
| 70 | +T + YT + TATTRAGYTCYCTRAARTCTACTAATTTYCTCCAY | (SEQ ID NO: 1702) |
| 70 | +TT + A + TTRAGYTCYCTRAARTCTACTAATTTYCTCCAYT | (SEQ ID NO: 1703) |
| 70 | +TY + T + TATTRAGYTCYCTRAARTCTACTAATTTYCTCCAY | (SEQ ID NO: 1704) |
| 70 | +T + T + ATTRAGYTCYCTRAARTCTACTAATTTYCTCCAYT | (SEQ ID NO: 1705) |
| 70 | +T + Y + TTATTRAGYTCYCTRAARTCTACTAATTTYCTCCAY | (SEQ ID NO: 1706) |
| 70 | CT + Y + TT + ATTRAGYTCYCTRAARTCTACTAATTTYCTCCAYT | (SEQ ID NO: 1707) |
| 70 | T + C + TY + TTATTRAGYTCYCTRAARTCTACTAATTTYCTCCAY | (SEQ ID NO: 1708) |
| 70 | CT + YT + T + ATTRAGYTCYCTRAARTCTACTAATTTYCTCCAYT | (SEQ ID NO: 1709) |
| 70 | T + CT + Y + TTATTRAGYTCYCTRAARTCTACTAATTTYCTCCAY | (SEQ ID NO: 1710) |
| 70 | +R + AGYTCYCT + RAARTCTACTAATTTYCTCCAYT | (SEQ ID NO: 1711) |
| 70 | +T + TRAGYTCY + CTRAARTCTACTAATTTYCTCCAY | (SEQ ID NO: 1712) |
| 70 | +RAGY + TCYCT + RAARTCTACTAATTTYCTCCAYT | (SEQ ID NO: 1713) |
| 70 | +TTRA + GYTCY + CTRAARTCTACTAATTTYCTCCAY | (SEQ ID NO: 1714) |
| 70 | +R + AGY + TCYCTRAARTCTACTAATTTYCTCCAYT | (SEQ ID NO: 1715) |
| 70 | +T + TRA + GYTCYCTRAARTCTACTAATTTYCTCCAY | (SEQ ID NO: 1716) |
| 70 | +TT + RAGY + TCYCTRAARTCTACTAATTTYCTCCAYT | (SEQ ID NO: 1717) |
| 70 | +TA + TTRA + GYTCYCTRAARTCTACTAATTTYCTCCAY | (SEQ ID NO: 1718) |
| 70 | +TTR + AGY + TCYCTRAARTCTACTAATTTYCTCCAYT | (SEQ ID NO: 1719) |
| 70 | +TAT + TRA + GYTCYCTRAARTCTACTAATTTYCTCCAY | (SEQ ID NO: 1720) |
| 70 | +TT + R + AGYTCYCTRAARTCTACTAATTTYCTCCAYT | (SEQ ID NO: 1721) |
| 70 | +TA + T + TRAGYTCYCTRAARTCTACTAATTTYCTCCAY | (SEQ ID NO: 1722) |
| 70 | +A + TTR + AGYTCYCTRAARTCTACTAATTTYCTCCAYT | (SEQ ID NO: 1723) |
| 70 | +T + TAT + TRAGYTCYCTRAARTCTACTAATTTYCTCCAY | (SEQ ID NO: 1724) |
| 70 | +ATT + R + AGYTCYCTRAARTCTACTAATTTYCTCCAYT | (SEQ ID NO: 1725) |
| 70 | +TTA + T + TRAGYTCYCTRAARTCTACTAATTTYCTCCAY | (SEQ ID NO: 1726) |
| 70 | +A + TT + RAGYTCYCTRAARTCTACTAATTTYCTCCAYT | (SEQ ID NO: 1727) |
| 70 | +T + TA + TTRAGYTCYCTRAARTCTACTAATTTYCTCCAY | (SEQ ID NO: 1728) |
| 70 | CT + Y + T + TATTRAGYTCYCTRAARTCTACTAATTTYCTCCAYT | (SEQ ID NO: 1729) |
| 70 | T + C + T + YTTATTRAGYTCYCTRAARTCTACTAATTTYCTCCAY | (SEQ ID NO: 1730) |
| 74 | TGAGTTCTYTTATTRAGYTCYCTRAARTCTACTA | (SEQ ID NO: 1731) |

TABLE 5 -continued

| | | |
|---|---|---|
| 74 | YTGAGTTCTYTTATTRAGYTCYCTRAARTCTACTA | (SEQ ID NO: 1732) |
| 74 | AARTCYTGAGTTCYTTATTRAGYTCYCTRAARTCTACTA | (SEQ ID NO: 1733) |
| 74 | YTTATTRAGYTCYCTRAARTCTACTA | (SEQ ID NO: 1734) |
| 74 | CTYTTATTRAGYTCYCTRAARTCTACTA | (SEQ ID NO: 1735) |
| 74 | GTTCTYTTATTRAGYTCYCTRAARTCTACTA | (SEQ ID NO: 1736) |
| 74 | YTGRACYTCCCARAARTCYTGAGTTYTYTTATTRAGYTCYCTRAAATCTAC | (SEQ ID NO: 1737) |
| 74 | TGAGTTCTYTTATTRAGYTCYCTRAARTCTACTA + N | (SEQ ID NO: 1738) |
| 74 | YTGAGTTCTYTTATTRAGYTCYCTRAARTCTACTA + N | (SEQ ID NO: 1739) |
| 74 | AARTCYTGAGTTCTYTTATTRAGYTCYCTRAARTCTACTA + N | (SEQ ID NO: 1740) |
| 74 | YTTATTRAGYTCYCTRAARTCTACTA + N | (SEQ ID NO: 1741) |
| 74 | CTYTTATTRAGYTCYCTRAARTCTACTA + N | (SEQ ID NO: 1742) |
| 74 | GTTCTYTTATTRAGYTCYCTRAARTCTACTA + N | (SEQ ID NO: 1743) |
| 74 | YTGRACYTCCCARAARTCYTGAGTTYTYTTATTRAGYTCYCTRAAATCTAC + N | (SEQ ID NO: 1744) |
| 74 | +TGA + GTTCT + YTTATTRAGYTCYCTRAARTCTACTA | (SEQ ID NO: 1745) |
| 74 | +TGAGTT + CT + YTTATTRAGYTCYCTRAARTCTACTA | (SEQ ID NO: 1746) |
| 74 | +TGA + GTT + CTYTTATTRAGYTCYCTRAARTCTACTA | (SEQ ID NO: 1747) |
| 74 | +Y + TGAGTT + CTYTTATTRAGYTCYCTRAARTCTACTA | (SEQ ID NO: 1748) |
| 74 | +YTGA + GTT + CTYTTATTRAGYTCYCTRAARTCTACTA | (SEQ ID NO: 1749) |
| 74 | +Y + TGA + GTTCTYTTATTRAGYTCYCTRAARTCTACTA | (SEQ ID NO: 1750) |
| 74 | +AARTC + YTGA + GTTCTYTTATTRAGYTCYCTRAARTCTACTA | (SEQ ID NO: 1751) |
| 74 | +AARTCY + TGA + GTTCTYTTATTRAGYTCYCTRAARTCTACTA | (SEQ ID NO: 1752) |
| 74 | +Y + TTA + TTRAGYTCYCTRAARTCTACTA | (SEQ ID NO: 1753) |
| 74 | +YTT + A + TTRAGYTCYCTRAARTCTACTA | (SEQ ID NO: 1754) |
| 74 | +Y + TT + ATTRAGYTCYCTRAARTCTACTA | (SEQ ID NO: 1755) |
| 74 | +CT + YTT + ATTRAGYTCYCTRAARTCTACTA | (SEQ ID NO: 1756) |
| 74 | +CTY + TT + ATTRAGYTCYCTRAARTCTACTA | (SEQ ID NO: 1757) |
| 74 | +CT + Y + TTATTRAGYTCYCTRAARTCTACTA | (SEQ ID NO: 1758) |
| 74 | +GTT + CTY + TTATTRAGYTCYCTRAARTCTACTA | (SEQ ID NO: 1759) |
| 74 | +GTTCT + Y + TTATTRAGYTCYCTRAARTCTACTA | (SEQ ID NO: 1760) |
| 74 | +GTT + CT + YTTATTRAGYTCYCTRAARTCTACTA | (SEQ ID NO: 1761) |
| 74 | +AARTC + Y + TGAGTTCTYTTATTRAGYTCYCTRAARTCTACTA | (SEQ ID NO: 1762) |
| 75 | TCYTGAGTTCTYTTATTRAGYTCYCTRAARTCTA | (SEQ ID NO: 1763) |
| 75 | ARTCYTGAGTTCTYTTATTRAGYTCYCTRAARTCT | (SEQ ID NO: 1764) |
| 75 | AARTCYTGAGTTCTYTTATTRAGYTCYCTRAARTCTA | (SEQ ID NO: 1765) |
| 75 | ARAARTCYTGAGTTCTYTTATTRAGYTCYCTRAARTCT | (SEQ ID NO: 1766) |
| 75 | CARAARTCYTGAGTTCTYTTATTRAGYTCYCTRAARTCTA | (SEQ ID NO: 1767) |
| 75 | CCARAARTCYTGAGTTCTYTTATTRAGYTCYCTRAARTCT | (SEQ ID NO: 1768) |
| 75 | GTTCTYTTATTRAGYTCYCTRAARTCTA | (SEQ ID NO: 1769) |

TABLE 5 -continued

| 75 | GAGTTCTYTTATTRAGYTCYCTRAARTCT (SEQ ID NO: 1770) |
| --- | --- |
| 75 | AGTTCTYTTATTRAGYTCYCTRAARTCTA (SEQ ID NO: 1771) |
| 75 | TGAGTTCTYTTATTRAGYTCYCTRAARTCT (SEQ ID NO:1772) |
| 75 | TGAGTTCTYTTATTRAGYTCYCTRAARTCTA (SEQ ID NO: 1773) |
| 75 | CYTGAGTTCTYTTATTRAGYTCYCTRAARTCT (SEQ ID NO: 1774) |
| 75 | TAAYTGRACYTCCCARAARTCYTGAGTTYTYTTATTRAGYTCYCTGAAATC (SEQ ID NO: 1775) |
| 75 | TCYTGAGTTCTYTTATTRAGYTCYCTRAARTCTA + N (SEQ ID NO: 1776) |
| 75 | ARTCYTGAGTTCTYTTATTRAGYTCYCTRAARTCT + N (SEQ ID NO: 1777) |
| 75 | AARTCYTGAGTTCTYTTATTRAGYTCYCTRAARTCTA + N (SEQ ID NO: 1778) |
| 75 | ARAARTCYTGAGTTCTYTTATTRAGYTCYCTRAARTCT + N (SEQ ID NO: 1779) |
| 75 | CARAARTCYTGAGTTCTYTTATTRAGYTCYCTRAARTCTA + N (SEQ ID NO: 1780) |
| 75 | CCARAARTCYTGAGTTCTYTTATTRAGYTCYCTRAARTCT + N (SEQ ID NO: 1781) |
| 75 | GTTCTYTTATTRAGYTCYCTRAARTCTA + N (SEQ ID NO: 1782) |
| 75 | GAGTTCTYTTATTRAGYTCYCTRAARTCT + N (SEQ ID NO: 1783) |
| 75 | AGTTCTYTTATTRAGYTCYCTRAARTCTA + N (SEQ ID NO: 1784) |
| 75 | TGAGTTCTYTTATTRAGYTCYCTRAARTCT + N (SEQ ID NO: 1785) |
| 75 | TGAGTTCTYTTATTRAGYTCYCTRAARTCTA + N (SEQ ID NO: 1786) |
| 75 | CYTGAGTTCTYTTATTRAGYTCYCTRAARTCT + N (SEQ ID NO: 1787) |
| 75 | TAAYTGRACYTCCCARAARTCYTGAGTTYTYTTATTRAGYTCYCTGAAATC + N (SEQ ID NO: 1788) |
| 75 | +TCY + TGA + GTTCTYTTATTRAGYTCYCTRAARTCTA (SEQ ID NO: 1789) |
| 75 | +ART + CYT + GAGTTCTYTTATTRAGYTCYCTRAARTCT (SEQ ID NO: 1790) |
| 75 | +TCYTG + A + GTTCTYTTATTRAGYTCYCTRAARTCTA (SEQ ID NO: 1791) |
| 75 | +ARTCY + T + GAGTTCTYTTATTRAGYTCYCTRAARTCT (SEQ ID NO: 1792) |
| 75 | +TCY + TG + AGTTCTYTTATTRAGYTCYCTRAARTCTA (SEQ ID NO: 1793) |
| 75 | +ART + CY + TGAGTTCTYTTATTRAGYTCYCTRAARTCT (SEQ ID NO: 1794) |
| 75 | +AAR + TCYTG + AGTTCTYTTATTRAGYTCYCTRAARTCTA (SEQ ID NO: 1795) |
| 75 | +ARA + ARTCY + TGAGTTCTYTTATTRAGYTCYCTRAARTCT (SEQ ID NO: 1796) |
| 75 | +AARTCY + TG + AGTTCTYTTATTRAGYTCYCTRAARTCTA (SEQ ID NO: 1797) |
| 75 | +ARAART + CY + TGAGTTCTYTTATTRAGYTCYCTRAARTCT (SEQ ID NO: 1798) |
| 75 | +AAR + TCY + TGAGTTCTYTTATTRAGYTCYCTRAARTCTA (SEQ ID NO: 1799) |
| 75 | +ARA + ART + CYTGAGTTCTYTTATTRAGYTCYCTRAARTCT (SEQ ID NO: 1800) |
| 75 | CA + R + AARTCY + TGAGTTCTYTTATTRAGYTCYCTRAARTCTA (SEQ ID NO: 1801) |
| 75 | C + C + ARAART + CYTGAGTTCTYTTATTRAGYTCYCTRAARTCT (SEQ ID NO: 1802) |
| 75 | CA + RAAR + TCY + TGAGTTCTYTTATTRAGYTCYCTRAARTCTA (SEQ ID NO: 1803) |
| 75 | C + CARA + ART + CYTGAGTTCTYTTATTRAGYTCYCTRAARTCT (SEQ ID NO: 1804) |
| 75 | +GT + TCT + YTTATTRAGYTCYCTRAARTCTA (SEQ ID NO: 1805) |
| 75 | +GA + GTT + CTYTTATTRAGYTCYCTRAARTCT (SEQ ID NO: 1806) |
| 75 | +GTT + CT + YTTATTRAGYTCYCTRAARTCTA (SEQ ID NO: 1807) |
| 75 | +GAG + TT + CTYTTATTRAGYTCYCTRAARTCT (SEQ ID NO: 1808) |

TABLE 5 -continued

| | | |
|---|---|---|
| 75 | +GT + T + CTYTTATTRAGYTCYCTRAARTCTA | (SEQ ID NO: 1809) |
| 75 | +GA + G + TTCTYTTATTRAGYTCYCTRAARTCT | (SEQ ID NO: 1810) |
| 75 | +A + GTT + CTYTTATTRAGYTCYCTRAARTCTA | (SEQ ID NO: 1811) |
| 75 | +T + GAG + TTCTYTTATTRAGYTCYCTRAARTCT | (SEQ ID NO: 1812) |
| 75 | +AGT + T + CTYTTATTRAGYTCYCTRAARTCTA | (SEQ ID NO: 1813) |
| 75 | +TGA + G + TTCTYTTATTRAGYTCYCTRAARTCT | (SEQ ID NO: 1814) |
| 75 | +A + GT + TCTYTTATTRAGYTCYCTRAARTCTA | (SEQ ID NO: 1815) |
| 75 | +T + GA + GTCTYTTATTRAGYTCYCTRAARTCT | (SEQ ID NO: 1816) |
| 75 | +TG + AGT + TCTYTTATTRAGYTCYCTRAARTCTA | (SEQ ID NO: 1817) |
| 75 | +CY + TGA + GTTCTYTTATTRAGYTCYCTRAARTCT | (SEQ ID NO: 1818) |
| 75 | +TGA + GT + TCTYTTATTRAGYTCYCTRAARTCTA | (SEQ ID NO: 1819) |
| 75 | +CYT + GA + GTTCTYTTATTRAGYTCYCTRAARTCT | (SEQ ID NO: 1820) |
| 75 | +TG + A + GTTCTYTTATTRAGYTCYCTRAARTCTA | (SEQ ID NO: 1821) |
| 75 | +CY + T + GAGTTCTYTTATTRAGYTCYCTRAARTCT | (SEQ ID NO: 1822) |
| 75 | CA + R + AAR + TCYTGAGTTCTYTTATTRAGYTCYCTRAARTCTA | (SEQ ID NO: 1823) |
| 75 | C + C + ARA + ARTCYTGAGTTCTYTTATTRAGYTCYCTRAARTCT | (SEQ ID NO: 1824) |
| 77 | YTCCCARAARTCYTGAGTTCTYTTATTRAGYTCYCT | (SEQ ID NO: 1825) |
| 77 | CYTCCCARAARTCYTGAGTTCTYTTATTRAGYTCYCT | (SEQ ID NO: 1826) |
| 77 | GRACYTCCCARAARTCYTGAGTTCTYTTATTRAGYTCYCT | (SEQ ID NO: 1827) |
| 77 | ARAARTCYTGAGTTCTYTTATTRAGYTCYCT | (SEQ ID NO: 1828) |
| 77 | CCARAARTCYTGAGTTCTYTTATTRAGYTCYCT | (SEQ ID NO: 1829) |
| 77 | CCCARAARTCYTGAGTTCTYTTATTRAGYTCYCT | (SEQ ID NO: 1830) |
| 77 | TATYCCTAAYTGRACYTCCCARAARTCYTGAGTTYTYTTATTRAGTTCTCT | (SEQ ID NO: 1831) |
| 77 | YTCCCARAARTCYTGAGTTCTYTTATTRAGYTCYCT + N | (SEQ ID NO: 1832) |
| 77 | CYTCCCARAARTCYTGAGTTCTYTTATTRAGYTCYCT + N | (SEQ ID NO: 1833) |
| 77 | GRACYTCCCARAARTCYTGAGTTCTYTTATTRAGYTCYCT + N | (SEQ ID NO: 1834) |
| 77 | ARAARTCYTGAGTTCTYTTATTRAGYTCYCT + N | (SEQ ID NO: 1835) |
| 77 | CCARAARTCYTGAGTTCTYTTATTRAGYTCYCT + N | (SEQ ID NO: 1836) |
| 77 | CCCARAARTCYTGAGTTCTYTTATTRAGYTCYCT + N | (SEQ ID NO: 1837) |
| 77 | TATYCCTAAYTGRACYTCCCARAARTCYTGAGTTYTYTTATTRAGTTCTCT + N (SEQ ID NO: 1838) | |
| 77 | +YT + CCC + ARAARTCYTGAGTTCTYTTATTRAGYTCYCT | (SEQ ID NO: 1839) |
| 77 | +YTC + CC + ARAARTCYTGAGTTCTYTTATTRAGYTCYCT | (SEQ ID NO: 1840) |
| 77 | +YT + C + CCARAARTCYTGAGTTCTYTTATTRAGYTCYCT | (SEQ ID NO: 1841) |
| 77 | +C + YTC + CCARAARTCYTGAGTTCTYTTATTRAGYTCYCT | (SEQ ID NO: 1842) |
| 77 | +CYT + C + CCARAARTCYTGAGTTCTYTTATTRAGYTCYCT | (SEQ ID NO: 1843) |
| 77 | +C + YT + CCCARAARTCYTGAGTTCTYTTATTRAGYTCYCT | (SEQ ID NO: 1844) |
| 77 | +G + RAC + YTCCCARAARTCYTGAGTTCTYTTATTRAGYTCYCT (SEQ ID NO: 1845) | |
| 77 | +A + RAART + CYTGAGTTCTYTTATTRAGYTCYCT | (SEQ ID NO: 1846) |
| 77 | +ARA + ART + CYTGAGTTCTYTTATTRAGYTCYCT | (SEQ ID NO: 1847) |

TABLE 5 -continued

| | |
|---|---|
| 77 | +A + RA + ARTCYTGAGTTCTYTTATTRAGYTCYCT (SEQ ID NO: 1848) |
| 77 | +CC + ARA + ARTCYTGAGTTCTYTTATTRAGYTCYCT (SEQ ID NO: 1849) |
| 77 | +CCA + RA + ARTCYTGAGTTCTYTTATTRAGYTCYCT (SEQ ID NO: 1850) |
| 77 | +CC + A + RAARTCYTGAGTTCTYTTATTRAGYTCYCT (SEQ ID NO: 1851) |
| 77 | +C + CCA + RAARTCYTGAGTTCTYTTATTRAGYTCYCT (SEQ ID NO: 1852) |
| 77 | +CCC + A + RAARTCYTGAGTTCTYTTATTRAGYTCYCT (SEQ ID NO: 1853) |
| 77 | +C + CC + ARAARTCYTGAGTTCTYTTATTRAGYTCYCT (SEQ ID NO: 1854) |
| 77 | G + RA + C + YTCCCARAARTCYTGAGTTCTYTTATTRAGYTCYCT (SEQ ID NO: 1855) |
| 90 | TTTTTTARHCCYGCDGGRTGNGGTATYCCTAATTGRA (SEQ ID NO: 1856) |
| 90 | CTTTTTTARHCCYGCDGGRTGNGGTATYCCTAATTGRA (SEQ ID NO: 1857) |
| 90 | TTCTTTTTTARHCCYGCDGGRTGNGGTATYCCTAATTGRA (SEQ ID NO: 1858) |
| 90 | ARHCCYGCDGGRTGNGGTATYCCTAATTGRA (SEQ ID NO: 1859) |
| 90 | TARHCCYGCDGGRTGNGGTATYCCTAATTGRA (SEQ ID NO: 1860) |
| 90 | TTTARHCCYGCDGGRTGNGGTATYCCTAATTGRA (SEQ ID NO: 1861) |
| 90 | GTYACWGAYTTYTTCTTYTTTARHCCYGCDGGRTGHGGTATYCCTAATTG (SEQ ID NO: 1862) |
| 90 | TTTTTTARHCCYGCDGGRTGNGGTATYCCTAATTGRA + N (SEQ ID NO: 1863) |
| 90 | CTTTTTTARHCCYGCDGGRTGNGGTATYCCTAATTGRA + N (SEQ ID NO: 1864) |
| 90 | TTCTTTTTTARHCCYGCDGGRTGNGGTATYCCTAATTGRA + N (SEQ ID NO: 1865) |
| 90 | ARHCCYGCDGGRTGNGGTATYCCTAATTGRA + N (SEQ ID NO: 1866) |
| 90 | TARHCCYGCDGGRTGNGGTATYCCTAATTGRA + N (SEQ ID NO: 1867) |
| 90 | TTTARHCCYGCDGGRTGNGGTATYCCTAATTGRA + N (SEQ ID NO: 1868) |
| 90 | GTYACWGAYTTYTTCTTYTTTARHCCYGCDGGRTGHGGTATYCCTAATTG + N (SEQ ID NO: 1869) |
| 90 | GGRTGNGGTATYCCTAATTGRA (SEQ ID NO: 1870) |
| 90 | +TTTTT + T + ARHCCYGCDGGRTGNGGTATYCCTAATTGRA (SEQ ID NO: 1871) |
| 90 | +TTT + TT +TARHCCYGCDGGRTGNGGTATYCCTAATTGRA (SEQ ID NO: 1872) |
| 90 | +C + TTTTT + TARHCCYGCDGGRTGNGGTATYCCTAATTGRA (SEQ ID NO: 1873) |
| 90 | +CTTT + TT + TARHCCYGCDGGRTGNGGTATYCCTAATTGRA (SEQ ID NO: 1874) |
| 90 | +C + TTT + TTTARHCCYGCDGGRTGNGGTATYCCTAATTGRA (SEQ ID NO: 1875) |
| 90 | TT + C + TTTTT + TARHCCYGCDGGRTGNGGTATYCCTAATTGRA (SEQ ID NO: 1876) |
| 90 | TTC + TTT + TT + TARHCCYGCDGGRTGNGGTATYCCTAATTGRA (SEQ ID NO: 1877) |
| 90 | +AR + HCC + YGCDGGRTGNGGTATYCCTAATTGRA (SEQ ID NO: 1878) |
| 90 | +ARH + CC + YGCDGGRTGNGGTATYCCTAATTGRA (SEQ ID NO: 1879) |
| 90 | +AR + H + CCYGCDGGRTGNGGTATYCCTAATTGRA (SEQ ID NO: 1880) |
| 90 | +T + ARH + CCYGCDGGRTGNGGTATYCCTAATTGRA (SEQ ID NO: 1881) |
| 90 | +TAR + H + CCYGCDGGRTGNGGTATYCCTAATTGRA (SEQ ID NO: 1882) |

TABLE 5 -continued

| | |
|---|---|
| 90 | +T + AR + HCCYGCDGGRTGNGGTATYCCTAATTGRA (SEQ ID NO: 1883) |
| 90 | +TT + TAR + HCCYGCDGGRTGNGGTATYCCTAATTGRA (SEQ ID NO: 1884) |
| 90 | +TTT + AR + HCCYGCDGGRTGNGGTATYCCTAATTGRA (SEQ ID NO: 1885) |
| 90 | +TT + T + ARHCCYGCDGGRTGNGGTATYCCTAATTGRA (SEQ ID NO: 1886) |
| 90 | +TT + C + TTTTTTARHCCYGCDGGRTGNGGTATYCCTAATTGRA (SEQ ID NO: 1887) |
| 98 | CYARYACTGTYACTGAYTTKTTCTTTTTTARHCCY (SEQ ID NO: 1888) |
| 98 | CATCYARYACTGTYACTGAYTTKTTCTTTTTTARHCCY (SEQ ID NO: 1889) |
| 98 | YACATCYARYACTGTYACTGAYTTKTTCTTTTTTARHCCY (SEQ ID NO: 1890) |
| 98 | AYTTKTTCTTTTTTARHCCY (SEQ ID NO: 1891) |
| 98 | ACTGAYTTKTTCTTTTTTARHCCY (SEQ ID NO: 1892) |
| 98 | GTYACTGAYTTKTTCTTTTTTARHCCY (SEQ ID NO: 1893) |
| 98 | RTATGCATCHCCYACATCYARBACTGTYACWGAYTTYTTCTTYTTTAACCC (SEQ ID NO: 1894) |
| 98 | CYARYACTGTYACTGAYTTKTTCTTTTTTARHC CY + N (SEQ ID NO: 1895) |
| 98 | CATCYARYACTGTYACTGAYTTKTTCTTTTTTARHC CY + N (SEQ ID NO: 1896) |
| 98 | YACATCYARYACTGTYACTGAYTTKTTCTTTTTTARHCCY + N (SEQ ID NO: 1897) |
| 98 | AYTTKTTCTTTTTTARHC CY + N (SEQ ID NO: 1898) |
| 98 | ACTGAYTTKTTCTTTTTTARHC CY + N (SEQ ID NO: 1899) |
| 98 | GTYACTGAYTTKTTCTTTTTTARHCCY + N (SEQ ID NO: 1900) |
| 98 | RTATGCATCHCCYACATCYARBACTGTYACWGAYTTYTTCTTYTTTAACCC + N (SEQ ID NO: 1901) |
| 98 | +CYARYACT + GTYACTG + AYTTKTTCTTTTTTARHCCY (SEQ ID NO: 1902) |
| 98 | +CYARYACTGTY + ACTG + AYTTKTTCTTTTTTARHCCY (SEQ ID NO: 1903) |
| 98 | +CYARYACT + GTY + ACTGAYTTKTTCTTTTTTARHCCY (SEQ ID NO: 1904) |
| 98 | +CAT + CYARYACTGTY + ACTGAYTTKTTCTTTTTTARHCCY (SEQ ID NO: 1905) |
| 98 | +CATCYARYACT + GTY + ACTGAYTTKTTCTTTTTTARHCCY (SEQ ID NO: 1906) |
| 98 | +CAT + CYARYACT + GTYACTGAYTTKTTCTTTTTTARHCCY (SEQ ID NO: 1907) |
| 98 | Y + A + CATCYARYACT + GTYACTGAYTTKTTCTTTTTTARHCCY (SEQ ID NO: 1908) |
| 98 | Y + ACAT + CYARYACT + GTYACTGAYTTKTTCTTTTTTARHCCY (SEQ ID NO: 1909) |
| 98 | +AYTTKT + TCTTTT + TTARHCCY (SEQ ID NO: 1910) |
| 98 | +AYTTKTTCT + TTT + TTARHCCY (SEQ ID NO: 1911) |
| 98 | +AYTTKT + TCT + TTTTARHCCY (SEQ ID NO: 1912) |
| 98 | +ACTG + AYTTKTTCT + TTTTARHCCY (SEQ ID NO: 1913) |
| 98 | +ACTGAYTTKT + TCT + TTTTARHCCY (SEQ ID NO: 1914) |
| 98 | +ACTG + AYTTKT + TCTTTTTARHCCY (SEQ ID NO: 1915) |
| 98 | +GTY + ACTGAYTTKT + TCTTTTTARHCCY (SEQ ID NO: 1916) |
| 98 | +GTYACTG + AYTTKT + TCTTTTTARHCCY (SEQ ID NO: 1917) |
| 98 | +GTY + ACTG + AYTTKTTCTTTTTTARHCCY (SEQ ID NO: 1918) |
| 98 | Y + A + CAT + CYARYACTGTYACTGAYTTKTTCTTTTTTARHCCY (SEQ ID NO: 1919) |

TABLE 5 -continued

| | |
|---|---|
| 100 | YARYACTGTYACTGAYTTKTTCTTTTTTA (SEQ ID NO: 1920) |
| 100 | ATCYARYACTGTYACTGAYTTKTTCTTTTTTA (SEQ ID NO: 1921) |
| 100 | TCHCCYACATCYARYACTGTYACTGAYTTKTTCTTTTTTA (SEQ ID NO: 1922) |
| 100 | GAYTTKTTCTTTTTTA (SEQ ID NO: 1923) |
| 100 | ACTGAYTTKTTCTTTTTTA (SEQ ID NO: 1924) |
| 100 | ACTGTYACTGAYTTKTTCTTTTTTA (SEQ ID NO: 1925) |
| 100 | GARAARTATGCATCHCCYACATCYARBACTGTYACWGAYTTYTTCTTTTT (SEQ ID NO: 1926) |
| 100 | YARYACTGTYACTGAYTTKTTCTTTTTTA + N (SEQ ID NO: 1927) |
| 100 | ATCYARYACTGTYACTGAYTTKTTCTTTTTTA + N (SEQ ID NO: 1928) |
| 100 | TCHCCYACATCYARYACTGTYACTGAYTTKTTCTTTTTTA + N (SEQ ID NO: 1929) |
| 100 | GAYTTKTTCTTTTTTA + N (SEQ ID NO: 1930) |
| 100 | ACTGAYTTKTTCTTTTTTA + N (SEQ ID NO: 1931) |
| 100 | ACTGTYACTGAYTTKTTCTTTTTTA + N (SEQ ID NO: 1932) |
| 100 | GARAARTATGCATCHCCYACATCYARBACTGTYACWGAYTTYTTCTTTTT + N (SEQ ID NO: 1933) |
| 100 | +YARY + ACTGTYACT + GAYTTKTTCTTTTTTA (SEQ ID NO: 1934) |
| 100 | +YARYACTGTY + ACT + GAYTTKTTCTTTTTTA (SEQ ID NO: 1935) |
| 100 | +YARY + ACTGTY + ACTGAYTTKTTCTTTTTTA (SEQ ID NO: 1936) |
| 100 | +ATC + YARYACTGTY + ACTGAYTTKTTCTTTTTTA (SEQ ID NO: 1937) |
| 100 | +ATCYARY + ACTGTY + ACTGAYTTKTTCTTTTTTA (SEQ ID NO: 1938) |
| 100 | +ATC + YARY + ACTGTYACTGAYTTKTTCTTTTTTA (SEQ ID NO: 1939) |
| 100 | +TCHCCYAC + ATCYART + ACTGTYACTGAYTTKTTCTTTTTTA (SEQ ID NO: 1940) |
| 100 | +TCHCCYACATC + YARY + ACTGTYACTGAYTTKTTCTTTTTTA (SEQ ID NO: 1941) |
| 100 | +GAY + TTK + TTCTTTTTTA (SEQ ID NO: 1942) |
| 100 | +GAYTT + K + TTCTTTTTTA (SEQ ID NO: 1943) |
| 100 | +GAY + TT + KTTCTTTTTTA (SEQ ID NO: 1944) |
| 100 | +ACT + GAYTT + KTTCTTTTTTA (SEQ ID NO: 1945) |
| 100 | +ACTGAY + TT + KTTCTTTTTTA (SEQ ID NO: 1946) |
| 100 | +ACT + GAY + TTKTTCTTTTTTA (SEQ ID NO: 1947) |
| 100 | +ACTGTY + ACTGAY + TTKTTCTTTTTTA (SEQ ID NO: 1948) |
| 100 | +ACTGTYACT + GAY + TTKTTCTTTTTTA (SEQ ID NO: 1949) |
| 100 | +ACTGTY + ACT + GAYTTKTTCTTTTTTA (SEQ ID NO: 1950) |
| 100 | +TCHCCYAC + ATC + YARYACTGTYACTGAYTTKTTCTTTTTTA (SEQ ID NO: 1951) |
| 101 | TCYARYACTGTYACTGAYTTKTTCTTTT (SEQ ID NO: 1952) |
| 101 | YACATCYARYACTGTYACTGAYTTKTTCTTTT (SEQ ID NO: 1953) |
| 101 | GCRTCHCCYACATCYARYACTGTYACTGAYTTKTTCTTTT (SEQ ID NO: 1954) |
| 101 | ACTGAYTTKTTCTTTT (SEQ ID NO: 1955) |
| 101 | GTYACTGAYTTKTTCTTTT (SEQ ID NO: 1956) |
| 101 | ACTGTYACTGAYTTKTTCTTTT (SEQ ID NO: 1957) |

TABLE 5 -continued

| | |
|---|---|
| 101 | DACTGARAARTATGCATCHCCYACATCYARBACTGTYACWGAYTTTTCTT (SEQ ID NO: 1958) |
| 101 | TCYARYACTGTYACTGAYTTKTTCTTTT + N (SEQ ID NO: 1959) |
| 101 | YACATCYARYACTGTYACTGAYTTKTTCTTTT + N (SEQ ID NO: 1960) |
| 101 | GCRTCHCCYACATCYARYACTGTYACTGAYTTKTTCTTTT + N (SEQ ID NO: 1961) |
| 101 | ACTGAYTTKTTCTTTT + N (SEQ ID NO: 1962) |
| 101 | GTYACTGAYTTKTTCTTTT + N (SEQ ID NO: 1963) |
| 101 | ACTGTYACTGAYTTKTTCTTTT + N (SEQ ID NO: 1964) |
| 101 | DACTGARAARTATGCATCHCCYACATCYARBACTGTYACWGAYTTTTCTT + N (SEQ ID NO: 1965) |
| 101 | +TCYARY + ACTGTY + ACTGAYTTKTTCTTTT (SEQ ID NO: 1966) |
| 101 | +TCYARYACT + GTY + ACTGAYTTKTTCTTTT (SEQ ID NO: 1967) |
| 101 | +TCYARY + ACT + GTYACTGAYTTKTTCTTTT (SEQ ID NO: 1968) |
| 101 | +YACA + TCYARYACT + GTYACTGAYTTKTTCTTTT (SEQ ID NO: 1969) |
| 101 | +YACATCYARY + ACT + GTYACTGAYTTKTTCTTTT (SEQ ID NO: 1970) |
| 101 | +YACA + TCYARY + ACTGTYACTGAYTTKTTCTTTT (SEQ ID NO: 1971) |
| 101 | +GCRTC + HCCYACA + TCYARYACTGTYACTGAYTTKTTCTTTT (SEQ ID NO: 1972) |
| 101 | +AC + TGAY + TTKTTCTTTT (SEQ ID NO: 1973) |
| 101 | +ACT + GAY + TTKTTCTTTT (SEQ ID NO: 1974) |
| 101 | +AC + T + GAYTTKTTCTTTT (SEQ ID NO: 1975) |
| 101 | +GTY + ACT + GAYTTKTTCTTTT (SEQ ID NO: 1976) |
| 101 | +GTYAC + T + GAYTTKTTCTTTT (SEQ ID NO: 1977) |
| 101 | +GTY + AC + TGAYTTKTTCTTTT (SEQ ID NO: 1978) |
| 101 | +ACT + GTYAC + TGAYTTKTTCTTTT (SEQ ID NO: 1979) |
| 101 | +ACTGTY + AC + TGAYTTKTTCTTTT (SEQ ID NO: 1980) |
| 101 | +ACT + GTY + ACTGAYTTKTTCTTTT (SEQ ID NO: 1981) |
| 101 | GCRTC + HCC + YACA + TCYARYACTGTYACTGAYTTKTTCTTTT (SEQ ID NO: 1982) |
| 103 | RTCHCCYACATCYARYACTGTYACTGAYTT (SEQ ID NO: 1983) |
| 103 | RTATGCRTCHCCYACATCYARYACTGTYACTGAYTT (SEQ ID NO: 1984) |
| 103 | ARAARTATGCRTCHCCYACATCYARYACTGTYACTGAYTT (SEQ ID NO: 1985) |
| 103 | CATCYARYACTGTYACTGAYTT (SEQ ID NO: 1986) |
| 103 | YACATCYARYACTGTYACTGAYTT (SEQ ID NO: 1987) |
| 103 | HCCYACATCYARYACTGTYACTGAYTT (SEQ ID NO: 1988) |
| 103 | MTAARGGDACTGARAARTATGCATCHCCYACATCYARBACTGTYACTGATTT (SEQ ID NO: 1989) |
| 103 | RTCHCCYACATCYARYACTGTYACTGAYTT + N (SEQ ID NO: 1990) |
| 103 | RTATGCRTCHCCYACATCYARYACTGTYACTGAYTT + N (SEQ ID NO: 1991) |
| 103 | ARAARTATGCRTCHCCYACATCYARYACTGTYACTGAYTT + N (SEQ ID NO: 1992) |
| 103 | CATCYARYACTGTYACTGAYTT + N (SEQ ID NO: 1993) |
| 103 | YACATCYARYACTGTYACTGAYTT + N (SEQ ID NO: 1994) |

TABLE 5 -continued

| | |
|---|---|
| 103 | HCCYACATCYARYACTGTYACTGAYTT + N (SEQ ID NO: 1995) |
| 103 | MTAARGGDACTGARAARTATGCATCHCCYACATCYARBACTGTYACTGATTT + N (SEQ ID NO: 1996) |
| 103 | +RTC + HCCYA + CATCYARYACTGTYACTGAYTT (SEQ ID NO: 1997) |
| 103 | +RTCHCC + YA + CATCYARYACTGTYACTGAYTT (SEQ ID NO: 1998) |
| 103 | +RTC + HCC + YACATCYARYACTGTYACTGAYTT (SEQ ID NO: 1999) |
| 103 | +RTATGC + RTCHCC + YACATCYARYACTGTYACTGAYTT (SEQ ID NO: 2000) |
| 103 | +RTATGCRTC + HCC + YACATCYARYACTGTYACTGAYTT (SEQ ID NO: 2001) |
| 103 | +RTATGC + RTC + HCCYACATCYARYACTGTYACTGAYTT (SEQ ID NO: 2002) |
| 103 | +ARAA + RTATGCRTC + HCCYACATCYARYACTGTYACTGAYTT (SEQ ID NO: 2003) |
| 103 | +ARAARTATGC + RTC + HCCYACATCYARYACTGTYACTGAYTT (SEQ ID NO: 2004) |
| 103 | +C + ATCYA + RYACTGTYACTGAYTT (SEQ ID NO: 2005) |
| 103 | +CATC + YA + RYACTGTYACTGAYTT (SEQ ID NO: 2006) |
| 103 | +C + ATC + YARYACTGTYACTGAYTT (SEQ ID NO: 2007) |
| 103 | +YA + CATC + YARYACTGTYACTGAYTT (SEQ ID NO: 2008) |
| 103 | +YAC + ATC + YARYACTGTYACTGAYTT (SEQ ID NO: 2009) |
| 103 | +YA + C + ATCYARYACTGTYACTGAYTT (SEQ ID NO: 2010) |
| 103 | +HCC + YAC + ATCYARYACTGTYACTGAYTT (SEQ ID NO: 2011) |
| 103 | +TCCYA + C + ATCYARYACTGTYACTGAYTT (SEQ ID NO: 2012) |
| 103 | +TCC + YA + CATCYARYACTGYACTGAYTT (SEQ ID NO: 2013) |
| 103 | +ARAA + RTATGC + RTCHCCYACATCYARYACTGTYACTGAYTT (SEQ ID NO: 2014) |
| 106 | ARAARTATGCRTCHCCYACATCYARYACTGTY (SEQ ID NO: 2015) |
| 106 | CTGARAARTATGCRTCHCCYACATCYARYACTGTY (SEQ ID NO: 2016) |
| 106 | RGGRACTGARAARTATGCRTCHCCYACATCYARYACTGTY (SEQ ID NO: 2017) |
| 106 | ATGCRTCHCCYACATCYARYACTGTY (SEQ ID NO: 2018) |
| 106 | ARTATGCRTCHCCYACATCYARYACTGTY (SEQ ID NO: 2019) |
| 106 | AARTATGCRTCHCCYACATCYARYACTGTY (SEQ ID NO: 2020) |
| 106 | DYYYTYATMTAARGGDACTGARAARTATGCATCHCCYACATCYARTACTGT (SEQ ID NO: 2021) |
| 106 | ARAARTATGCRTCHCCYACATCYARYACTGTY + N (SEQ ID NO: 2022) |
| 106 | CTGARAARTATGCRTCHCCYACATCYARYACTGTY + N (SEQ ID NO: 2023) |
| 106 | RGGRACTGARAARTATGCRTCHCCYACATCYARYACTGTY + N (SEQ ID NO: 2024) |
| 106 | ATGCRTCHCCYACATCYARYACTGTY + N (SEQ ID NO: 2025) |
| 106 | ARTATGCRTCHCCYACATCYARYACTGTY + N (SEQ ID NO: 2026) |
| 106 | AARTATGCRTCHCCYACATCYARYACTGTY + N (SEQ ID NO: 2027) |
| 106 | DYYYTYATMTAARGGDACTGARAARTATGCATCHCCYACATCYARTACTGT + N (SEQ ID NO: 2028) |
| 106 | +AR + AART + ATGCRTCHCCYACATCYARYACTGTY (SEQ ID NO: 2029) |
| 106 | +ARA + ART + ATGCRTCHCCYACATCYARYACTGTY (SEQ ID NO: 2030) |

TABLE 5 -continued

| | |
|---|---|
| 106 | +AR + A + ARTATGCRTCHCCYACATCYARYACTGTY (SEQ ID NO: 2031) |
| 106 | +CTG + ARA + ARTATGCRTCHCCYACATCYARYACTGTY (SEQ ID NO: 2032) |
| 106 | +CTGAR + A + ARTATGCRTCHCCYACATCYARYACTGTY (SEQ ID NO: 2033) |
| 106 | +CTG + AR + AARTATGCRTCHCCYACATCYARYACTGTY (SEQ ID NO: 2034) |
| 106 | RG + GRA + CTGAR + AARTATGCRTCHCCYACATCYARYACTGTY (SEQ ID NO: 2035) |
| 106 | RG + GRACTG + AR + AARTATGCRTCHCCYACATCYARYACTGTY (SEQ ID NO: 2036) |
| 106 | +AT + GCR + TCHCCYACATCYARYACTGTY (SEQ ID NO: 2037) |
| 106 | +ATG + CR + TCHCCYACATCYARYACTGTY (SEQ ID NO: 2038) |
| 106 | +AT + G + CRTCHCCYACATCYARYACTGTY (SEQ ID NO: 2039) |
| 106 | +ART + ATG + CRTCHCCYACATCYARYACTGTY (SEQ ID NO: 2040) |
| 106 | +ARTAT + G + CRTCHCCYACATCYARYACTGTY (SEQ ID NO: 2041) |
| 106 | +ART + AT + GCRTCHCCYACATCYARYACTGTY (SEQ ID NO: 2042) |
| 106 | +A + ARTAT + GCRTCHCCYACATCYARYACTGTY (SEQ ID NO: 2043) |
| 106 | +AART + AT + GCRTCHCCYACATCYARYACTGTY (SEQ ID NO: 2044) |
| 106 | +A + ART + ATGCRTCHCCYACATCYARYACTGTY (SEQ ID NO: 2045) |
| 106 | RG + GRA + CTG + ARAARTATGCRTCHCCYACATCYARYACTGTY (SEQ ID NO: 2046) |
| 108 | RGGRACTGARAARTATGCRTCHCCYACATCYARYA (SEQ ID NO: 2047) |
| 108 | AARGGRACTGARAARTATGCRTCHCCYACATCYARYA (SEQ ID NO: 2048) |
| 108 | TVTAARGGRACTGARAARTATGCRTCHCCYACATCYARYA (SEQ ID NO: 2049) |
| 108 | TGARAARTATGCRTCHCCYACATCYARYA (SEQ ID NO: 2050) |
| 108 | ACTGARAARTATGCRTCHCCYACATCYARYA (SEQ ID NO: 2051) |
| 108 | GGRACTGARAARTATGCRTCHCCYACATCYARYA (SEQ ID NO: 2052) |
| 108 | YCTRAADYYYTYATMTAARGGDACTGARAARTATGCATCHCCYACATCCAG (SEQ ID NO: 2053) |
| 108 | RGGRACTGARAARTATGCRTCHCCYACATCYARYA + N (SEQ ID NO: 2054) |
| 108 | AARGGRACTGARAARTATGCRTCHCCYACATCYARYA + N (SEQ ID NO: 2055) |
| 108 | TVTAARGGRACTGARAARTATGCRTCHCCYACATCYARYA + N (SEQ ID NO: 2056) |
| 108 | TGARAARTATGCRTCHCCYACATCYARYA + N (SEQ ID NO: 2057) |
| 108 | ACTGARAARTATGCRTCHCCYACATCYARYA + N (SEQ ID NO: 2058) |
| 108 | GGRACTGARAARTATGCRTCHCCYACATCYARYA + N (SEQ ID NO: 2059) |
| 108 | YCTRAADYYYTYATMTAARGGDACTGARAARTATGCATCHCCYACATCCAG + N (SEQ ID NO: 2060) |
| 108 | +R + GGRAC + TGARAARTATGCRTCHCCYACATCYARYA (SEQ ID NO: 2061) |
| 108 | +RGGR + AC + TGARAARTATGCRTCHCCYACATCYARYA (SEQ ID NO: 2062) |
| 108 | +R + GGR + ACTGARAARTATGCRTCHCCYACATCYARYA (SEQ ID NO: 2063) |
| 108 | +AA + RGGR + ACTGARAARTATGCRTCHCCYACATCYARYA (SEQ ID NO: 2064) |
| 108 | +AAR + GGR + ACTGARAARTATGCRTCHCCYACATCYARYA (SEQ ID NO: 2065) |

TABLE 5 -continued

| | |
|---|---|
| 108 | +AA + R + GGRACTGARAARTATGCRTCHCCYACATCYARYA (SEQ ID NO: 2066) |
| 108 | TVT + AA + RGGR + ACTGARAARTATGCRTCHCCYACATCYARYA (SEQ ID NO: 2067) |
| 108 | TVTAA + R + GGR + ACTGARAARTATGCRTCHCCYACATCYARYA (SEQ ID NO: 2068) |
| 108 | +T + GAR + AARTATGCRTCHCCYACATCYARYA (SEQ ID NO: 2069) |
| 108 | +TGA + R + AARTATGCRTCHCCYACATCYARYA (SEQ ID NO: 2070) |
| 108 | +T + GA + RAARTATGCRTCHCCYACATCYARYA (SEQ ID NO: 2071) |
| 108 | +AC + TGA + RAARTATGCRTCHCCYACATCYARYA (SEQ ID NO: 2072) |
| 108 | +ACT + GA + RAARTATGCRTCHCCYACATCYARYA (SEQ ID NO: 2073) |
| 108 | +AC + T + GARAARTATGCRTCHCCYACATCYARYA (SEQ ID NO: 2074) |
| 108 | +GGR + ACT + GARAARTATGCRTCHCCYACATCYARYA (SEQ ID NO: 2075) |
| 108 | +GGRAC + T + GARAARTATGCRTCHCCYACATCYARYA (SEQ ID NO: 2076) |
| 108 | +GGR + AC + TGARAARTATGCRTCHCCYACATCYARYA (SEQ ID NO: 2077) |
| 108 | +TVT + AA + RGGRACTGARAARTATGCRTCHCCYACATCYARYA (SEQ ID NO: 2078) |
| 115 | AYTTYCTRAADYYYTYATVTAARGGRACTGARAAR (SEQ ID NO: 2079) |
| 115 | TAYTTYCTRAADYYYTYATVTAARGGRACTGARAAR (SEQ ID NO: 2080) |
| 115 | AGTRTAYTTYCTRAADYYYTYATVTAARGGRACTGARAAR (SEQ ID NO: 2081) |
| 115 | TRAADYYYTYATVTAARGGRACTGARAAR (SEQ ID NO: 2082) |
| 115 | CTRAADYYYTYATVTAARGGRACTGARAAR (SEQ ID NO: 2083) |
| 115 | TYCTRAADYYYTYATVTAARGGRACTGARAAR (SEQ ID NO: 2084) |
| 115 | TATRGTRAATGCAGTRTAYTTYCTRAADYYYTYATMTAARGGDACTGAAAA (SEQ ID NO: 2085) |
| 115 | AYTTYCTRAADYYYTYATVTAARGGRACTGARAAR + N (SEQ ID NO: 2086) |
| 115 | TAYTTYCTRAADYYYTYATVTAARGGRACTGARAAR + N (SEQ ID NO: 2087) |
| 115 | AGTRTAYTTYCTRAADYYYTYATVTAARGGRACTGARAAR + N (SEQ ID NO: 2088) |
| 115 | TRAADYYYTYATVTAARGGRACTGARAAR + N (SEQ ID NO: 2089) |
| 115 | CTRAADYYYTYATVTAARGGRACTGARAAR + N (SEQ ID NO: 2090) |
| 115 | TYCTRAADYYYTYATVTAARGGRACTGARAAR + N (SEQ ID NO: 2091) |
| 115 | TATRGTRAATGCAGTRTAYTTYCTRAADYYYTYATMTAARGGDACTGAAAA + N (SEQ ID NO: 2092) |
| 115 | +AYT + TYC + TRAADYYYTYATVTAARGGRACTGARAAR (SEQ ID NO: 2093) |
| 115 | +AYTTY + C + TRAADYYYTYATVTAARGGRACTGARAAR (SEQ ID NO: 2094) |
| 115 | +AYT + TY + CTRAADYYYTYATVTAARGGRACTGARAAR (SEQ ID NO: 2095) |
| 115 | +T + AYTTY + CTRAADYYYTYATVTAARGGRACTGARAAR (SEQ ID NO: 2096) |
| 115 | +TAYT + TY + CTRAADYYYTYATVTAARGGRACTGARAAR (SEQ ID NO: 2097) |
| 115 | +T + AYT + TYCTRAADYYYTYATVTAARGGRACTGARAAR (SEQ ID NO: 2098) |
| 115 | A + GTR + TAYT + TYCTRAADYYYTYATVTAARGGRACTGARAAR (SEQ ID NO: 2099) |
| 115 | A + GTRT + AYT + TYCTRAADYYYTYATVTAARGGRACTGARAAR (SEQ ID NO: 2100) |
| 115 | +TRA + ADYYYTYATVTA + AGGGRACTGARAAR (SEQ ID NO: 2101) |
| 115 | +TRAADYYYTYATVT + A + ARGGRACTGARAAR (SEQ ID NO: 2102) |
| 115 | +TRA + ADYYYTYATVT + AARGGRACTGARAAR (SEQ ID NO: 2103) |

TABLE 5 -continued

| | |
|---|---|
| 115 | +C + TRAADYYYTYATVT + AARGGRACTGARAAR (SEQ ID NO: 2104) |
| 115 | +CTRA + ADYYYTYATVT + AARGGRACTGARAAR (SEQ ID NO: 2105) |
| 115 | +C + TRA + ADYYYTYATVTAARGGRACTGARAAR (SEQ ID NO: 2106) |
| 115 | +TY + CTRA + ADYYYTYATVTAARGGRACTGARAAR (SEQ ID NO: 2107) |
| 115 | +TYC + TRA + ADYYYTYATVTAARGGRACTGARAAR (SEQ ID NO: 2108) |
| 115 | +TY + C + TRAADYYYTYATVTAARGGRACTGARAAR (SEQ ID NO: 2109) |
| 115 | A + GTR + T + AYTTYCTRAADYYYTYATVTAARGGRACTGARAAR (SEQ ID NO: 2110) |
| 116 | TRTAYTTYCTRAADYYYTYATVTAARGGRACTGAR (SEQ ID NO: 2111) |
| 116 | CAGTRTAYTTYCTRAADYYYTYATVTAARGGRACTGAR (SEQ ID NO: 2112) |
| 116 | TGCAGTRTAYTTYCTRAADYYYTYATVTAARGGRACTGAR (SEQ ID NO: 2113) |
| 116 | TYCTRAADYYYTYATVTAARGGRACTGAR (SEQ ID NO: 2114) |
| 116 | AYTTYCTRAADYYYTYATVTAARGGRACTGAR (SEQ ID NO: 2115) |
| 116 | TAYTTYCTRAADYYYTYATVTAARGGRACTGAR (SEQ ID NO: 2116) |
| 116 | RGGTATRGTRAATGCAGTRTAYTTYCTRAADYYYTYATMTAARGGAACTGA (SEQ ID NO: 2117) |
| 116 | TRTAYTTYCTRAADYYYTYATVTAARGGRACTGAR + N (SEQ ID NO: 2118) |
| 116 | CAGTRTAYTTYCTRAADYYYTYATVTAARGGRACTGAR + N (SEQ ID NO: 2119) |
| 116 | TGCAGTRTAYTTYCTRAADYYYTYATVTAARGGRACTGAR + N (SEQ ID NO: 2120) |
| 116 | TYCTRAADYYYTYATVTAARGGRACTGAR + N (SEQ ID NO: 2121) |
| 116 | AYTTYCTRAADYYYTYATVTAARGGRACTGAR + N (SEQ ID NO: 2122) |
| 116 | TAYTTYCTRAADYYYTYATVTAARGGRACTGAR + N (SEQ ID NO: 2123) |
| 116 | RGGTATRGTRAATGCAGTRTAYTTYCTRAADYYYTYATMTAARGGAACTGA + N (SEQ ID NO: 2124) |
| 116 | +TR + TAYT + TYCTRAADYYYTYATVTAARGGRACTGAR (SEQ ID NO: 2125) |
| 116 | +TRT + AYT + TYCTRAADYYYTYATVTAARGGRACTGAR (SEQ ID NO: 2126) |
| 116 | +TR + T + AYTTYCTRAADYYYTYATVTAARGGRACTGAR (SEQ ID NO: 2127) |
| 116 | +CAG + TRT + AYTTYCTRAADYYYTYATVTAARGGRACTGAR (SEQ ID NO: 2128) |
| 116 | +CAGTR + T + AYTTYCTRAADYYYTYATVTAARGGRACTGAR (SEQ ID NO: 2129) |
| 116 | +CAG + TR + TAYTTYCTRAADYYYTYATVTAARGGRACTGAR (SEQ ID NO: 2130) |
| 116 | T + G + CAGTR + TAYTTYCTRAADYYYTYATVTAARGGRACTGAR (SEQ ID NO: 2131) |
| 116 | T + GCAG + TR + TAYTTYCTRAADYYYTYATVTAARGGRACTGAR (SEQ ID NO: 2132) |
| 116 | +TYCTRAADYYY + TVA + TVTAARGGRACTGAR (SEQ ID NO: 2133) |
| 116 | +TRYTRAADYYYT + YA + TVTAARGGRACTGAR (SEQ ID NO: 2134) |
| 116 | +TYCTRAADYYY + T + YATVTAARGGRACTGAR (SEQ ID NO: 2135) |
| 116 | +AYT + TYCTRAADYYYT + YATVTAARGGRACTGAR (SEQ ID NO: 2136) |
| 116 | +AYTTYCTRAADYYY + T + YATVTAARGGRACTGAR (SEQ ID NO: 2137) |
| 116 | +AYT + TYCTRAADYYY + TYATVTAARGGRACTGAR (SEQ ID NO: 2138) |
| 116 | +T + AYTTYCTRAADYYY + TVATVTAARGGRACTGAR (SEQ ID NO: 2139) |
| 116 | +TAYT + TYCTRAADYYY + TYATVTAARGGRACTGAR (SEQ ID NO: 2140) |
| 116 | +T + AYT + TYCTRAADYYYTYATVTAARGGRACTGAR (SEQ ID NO: 2141) |

TABLE 5 -continued

| | | |
|---|---|---|
| 116 | T + G + CAG + TRTAYTTYCTRAADYYYTYATVTAARGGRACTGAR (SEQ ID NO: 2142) | |
| 118 | AATGCAGTRTAYTTYCTRAADYYYTYATVTAARGGRA (SEQ ID NO: 2143) | |
| 118 | RAATGCAGTRTAYTTYCTRAADYYYTYATVTAARGGRA (SEQ ID NO: 2144) | |
| 118 | GTRAATGCAGTRTAYTTYCTRAADYYYTYATVTAARGGRA (SEQ ID NO: 2145) | |
| 118 | CTRAADYYYTYATVTAARGGRA (SEQ ID NO: 2146) | |
| 118 | YCTRAADYYYTYATVTAARGGRA (SEQ ID NO: 2147) | |
| 118 | GCAGTRTAYTTYCTRAADYYYTYATVTAARGGRA (SEQ ID NO: 2148) | |
| 118 | RYACTRGGTATRGTRAATGCAGTRTAYTTYCTRAADYYYTYATMTAAAGG (SEQ ID NO: 2149) | |
| 118 | AATGCAGTRTAYTTYCTRAADYYYTYATVTAARGGRA + N (SEQ ID NO: 2150) | |
| 118 | RAATGCAGTRTAYTTYCTRAADYYYTYATVTAARGGRA + N (SEQ ID NO: 2151) | |
| 118 | GTRAATGCAGTRTAYTTYCTRAADYYYTYATVTAARGGRA + N (SEQ ID NO: 2152) | |
| 118 | CTRAADYYYTYATVTAARGGRA + N (SEQ ID NO: 2153) | |
| 118 | YCTRAADYYYTYATVTAARGGRA + N (SEQ ID NO: 2154) | |
| 118 | GCAGTRTAYTTYCTRAADYYYTYATVTAARGGRA + N (SEQ ID NO: 2155) | |
| 118 | RYACTRGGTATRGTRAATGCAGTRTAYTTYCTRAADYYYTYATMTAAAGG + N (SEQ ID NO: 2156) | |
| 118 | +AAT + GCAGTRTAYTTY + CTRAADYYYTYATVTAARGGRA (SEQ ID NO: 2157) | |
| 118 | +AATGCAGTRTAYTT + Y + CTRAADYYYTYATVTAARGGRA (SEQ ID NO: 2158) | |
| 118 | +AAT + GCAGTRTAYTT + YCTRAADYYYTYATVTAARGGRA (SEQ ID NO: 2159) | |
| 118 | +R + AATGCAGTRTAYTT + YCTRAADYYYTYATVTAARGGRA (SEQ ID NO: 2160) | |
| 118 | +RAAT + GCAGTRTAYTT + YCTRAADYYYTYATVTAARGGRA (SEQ ID NO: 2161) | |
| 118 | +R + AAT + GCAGTRTAYTTYCTRAADYYYTYATVTAARGGRA (SEQ ID NO: 2162) | |
| 118 | +GT + RAAT + GCAGTRTAYTTYCTRAADYYYTYATVTAARGGRA (SEQ ID NO: 2163) | |
| 118 | +GTR + AAT + GCAGTRTAYTTYCTRAADYYYTYATVTAARGGRA (SEQ ID NO: 2164) | |
| 118 | +CT + RAA + DYYYTYATVTAARGGRA (SEQ ID NO: 2165) | |
| 118 | +CTR + AA + DYYYTYATVTAARGGRA (SEQ ID NO: 2166) | |
| 118 | +CT + R + AADYYYTYATVTAARGGRA (SEQ ID NO: 2167) | |
| 118 | +Y + CTR + AADYYYTYATVTAARGGRA (SEQ ID NO: 2168) | |
| 118 | +YCT + R + AADYYYTYATVTAARGGRA (SEQ ID NO: 2169) | |
| 118 | +Y + CT + RAADYYYTYATVTAARGGRA (SEQ ID NO: 2170) | |
| 118 | +GCAGTRTAYTT + YCT + RAADYYYTYATVTAARGGRA (SEQ ID NO: 2171) | |
| 118 | +GCAGTRTAYTTY + CT + RAADYYYTYATVTAARGGRA (SEQ ID NO: 2172) | |
| 118 | +GCAGTRTAYTT + Y + CTRAADYYYTYATVTAARGGRA (SEQ ID NO: 2173) | |
| 118 | +GT + R + AATGCAGTRTAYTTYCTRAADYYYTYATVTAARGGRA (SEQ ID NO: 2174) | |
| 138 | YACATTRTAYTGRTAYCTRAYYCCTGGTGTYT (SEQ ID NO: 2175) | |
| 138 | AGYACATTRTAYTGRTAYCTRAYYCCTGGTGTY (SEQ ID NO: 2176) | |
| 138 | AGYACATTRTAYTGRTAYCTRAYYCCTGGTGTYT (SEQ ID NO: 2177) | |
| 138 | GNAGYACATTRTAYTGRTAYCTRAYYCCTGGTGTY (SEQ ID NO: 2178) | |
| 138 | TGTGGNAGYACATTRTAYTGRTAYCTRAYYCCTGGTGTYT (SEQ ID NO: 2179) | |

TABLE 5 -continued

| | |
|---|---|
| 138 | YTGTGGNAGYACATTRTAYTGRTAYCTRAYYCCTGGTGTY (SEQ ID NO: 2180) |
| 138 | TAYTGRTAYCTRAYYCCTGGTGTYT (SEQ ID NO: 2181) |
| 138 | TRTAYTGRTAYCTRAYYCCTGGTGTY (SEQ ID NO: 2182) |
| 138 | RTAYTGRTAYCTRAYYCCTGGTGTYT (SEQ ID NO: 2183) |
| 138 | TTRTAYTGRTAYCTRAYYCCTGGTGTY (SEQ ID NO: 2184) |
| 138 | ACATTRTAYTGRTAYCTRAYYCCTGGTGTYT (SEQ ID NO: 2185) |
| 138 | GYACATTRTAYTGRTAYCTRAYYCCTGGTGTY (SEQ ID NO: 2186) |
| 138 | YCCTTTCCATCCYTGTGGVAGYACATTRTAYTGATAYCTRAYYCCTGGTGT (SEQ ID NO: 2187) |
| 138 | YACATTRTAYTGRTAYCTRAYYCCTGGTGTYT + N (SEQ ID NO: 2188) |
| 138 | AGYACATTRTAYTGRTAYCTRAYYCCTGGTGTY + N (SEQ ID NO: 2189) |
| 138 | AGYACATTRTAYTGRTAYCTRAYYCCTGGTGTYT + N (SEQ ID NO: 2190) |
| 138 | GNAGYACATTRTAYTGRTAYCTRAYYCCTGGTGTY + N (SEQ ID NO: 2191) |
| 138 | TGTGGNAGYACATTRTAYTGRTAYCTRAYYCCTGGTGTYT + N (SEQ ID NO: 2192) |
| 138 | YTGTGGNAGYACATTRTAYTGRTAYCTRAYYCCTGGTGTY + N (SEQ ID NO: 2193) |
| 138 | TAYTGRTAYCTRAYYCCTGGTGTYT + N (SEQ ID NO: 2194) |
| 138 | TRTAYTGRTAYCTRAYYCCTGGTGTY + N (SEQ ID NO: 2195) |
| 138 | RTAYTGRTAYCTRAYYCCTGGTGTYT + N (SEQ ID NO: 2196) |
| 138 | TTRTAYTGRTAYCTRAYYCCTGGTGTY + N (SEQ ID NO: 2197) |
| 138 | ACATTRTAYTGRTAYCTRAYYCCTGGTGTYT + N (SEQ ID NO: 2198) |
| 138 | GYACATTRTAYTGRTAYCTRAYYCCTGGTGTY + N (SEQ ID NO: 2199) |
| 138 | YCCTTTCCATCCYTGTGGVAGYACATTRTAYTGATAYCTRAYYCCTGGTGT + N (SEQ ID NO: 2200) |
| 138 | +Y + ACATTR + TAYTGRTAYCTRAYYCCTGGTGTYT (SEQ ID NO: 2201) |
| 138 | +A + GYACAT + TRTAYTGRTAYCTRAYYCCTGGTGTY (SEQ ID NO: 2202) |
| 138 | +YACATT + R + TAYTGRTAYCTRAYYCCTGGTGTYT (SEQ ID NO: 2203) |
| 138 | +AGYACA + T + TRTAYTGRTAYCTRAYYCCTGGTGTY (SEQ ID NO: 2204) |
| 138 | +Y + ACATT + RTAYTGRTAYCTRAYYCCTGGTGTYT (SEQ ID NO: 2205) |
| 138 | +A + GYACA + TTRTAYTGRTAYCTRAYYCCTGGTGTY (SEQ ID NO: 2206) |
| 138 | +AG + YACATT + RTAYTGRTAYCTRAYYCCTGGTGTYT (SEQ ID NO: 2207) |
| 138 | +GN + AGYACA + TTRTAYTGRTAYCTRAYYCCTGGTGTY (SEQ ID NO: 2208) |
| 138 | +AGY + ACATT + RTAYTGRTAYCTRAYYCCTGGTGTYT (SEQ ID NO: 2209) |
| 138 | +GNA + GYACA + TTRTAYTGRTAYCTRAYYCCTGGTGTY (SEQ ID NO: 2210) |
| 138 | +AG + Y + ACATTRTAYTGRTAYCTRAYYCCTGGTGTYT (SEQ ID NO: 2211) |
| 138 | +GN + A + GYACATTRTAYTGRTAYCTRAYYCCTGGTGTY (SEQ ID NO: 2212) |
| 138 | TGTGG + N + AGY + ACATTRTAYTGRTAYCTRAYYCCTGGTGTYT (SEQ ID NO: 2213) |
| 138 | YTGT + G + GNA + GYACATTRTAYTGRTAYCTRAYYCCTGGTGTY (SEQ ID NO: 2214) |
| 138 | TGTGG + NAG + Y + ACATTRTAYTGRTAYCTRAYYCCTGGTGTYT (SEQ ID NO: 2215) |
| 138 | YTGT + GGN + A + GYACATTRTAYTGRTAYCTRAYYCCTGGTGTY (SEQ ID NO: 2216) |
| 138 | +TA + YTGRTA + YCTRAYYCCTGGTGTYT (SEQ ID NO: 2217) |

TABLE 5 -continued

| | |
|---|---|
| 138 | +TR + TAYTGR + TAYCTRAYYCCTGGTGTY (SEQ ID NO: 2218) |
| 138 | +TAY + TGRTA + YCTRAYYCCTGGTGTYT (SEQ ID NO: 2219) |
| 138 | +TRT + AYTGR + TAYCTRAYYCCTGGTGTY (SEQ ID NO: 2220) |
| 138 | +TA + Y + TGRTAYCTRAYYCCTGGTGTYT (SEQ ID NO: 2221) |
| 138 | +TR + T + AYTGRTAYCTRAYYCCTGGTGTY (SEQ ID NO: 2222) |
| 138 | +R + TAY + TGRTAYCTRAYYCCTGGTGTYT (SEQ ID NO: 2223) |
| 138 | +T + TRT + AYTGRTAYCTRAYYCCTGGTGTY (SEQ ID NO: 2224) |
| 138 | +RTA + Y + TGRTAYCTRAYYCCTGGTGTYT (SEQ ID NO: 2225) |
| 138 | +TTR + T + AYTGRTAYCTRAYYCCTGGTGTY (SEQ ID NO: 2226) |
| 138 | +R + TA + YTGRTAYCTRAYYCCTGGTGTYT (SEQ ID NO: 2227) |
| 138 | +T + TR + TAYTGRTAYCTRAYYCCTGGTGTY (SEQ ID NO: 2228) |
| 138 | +ACATT + RTA + YTGRTAYCTRAYYCCTGGTGTYT (SEQ ID NO: 2229) |
| 138 | +GYACA + TTR + TAYTGRTAYCTRAYYCCTGGTGTY (SEQ ID NO: 2230) |
| 138 | +ACATTR + TA + YTGRTAYCTRAYYCCTGGTGTYT (SEQ ID NO: 2231) |
| 138 | +GYACAT + TR + TAYTGRTAYCTRAYYCCTGGTGTY (SEQ ID NO: 2232) |
| 138 | +ACATT + R + TAYTGRTAYCTRAYYCCTGGTGTYT (SEQ ID NO: 2233) |
| 138 | +GYACA + T + TRTAYTGRTAYCTRAYYCCTGGTGTY (SEQ ID NO: 2234) |
| 138 | TGTGG + N + AG + YACATTRTAYTGRTAYCTRAYYCCTGGTGTYT (SEQ ID NO: 2235) |
| 138 | YTGT + G + GN + AGYACATTRTAYTGRTAYCTRAYYCCTGGTGTY (SEQ ID NO: 2236) |
| 151 | TAARATTYTTGTCATRCTRSHYTGRAATATYGCYGGTGAYCCTTTCCATCC (SEQ ID NO: 2237) |
| 151 | TAARATTYTTGTCATRCTRSHYTGRAATATYGCYGGTGAYCCTTTCCATCC + N (SEQ ID NO: 2238) |
| 179 | CTACATAYAARTCATCCAYRTATTGRTARATV (SEQ ID NO: 2239) |
| 179 | ACATAYAARTCATCCAYRTATTGRTARATVA (SEQ ID NO: 2240) |
| 179 | CCTACATAYAARTCATCCAYRTATTGRTARATV (SEQ ID NO: 2241) |
| 179 | TACATAYAARTCATCCAYRTATTGRTARATVA (SEQ ID NO: 2242) |
| 179 | RTCWGAKCCTACATAYAARTCATCCAYRTATTGRTARATV (SEQ ID NO: 2243) |
| 179 | TCWGAKCCTACATAYAARTCATCCAYRTATTGRTARATVA (SEQ ID NO: 2244) |
| 179 | AYAARTCATCCAYRTATTGRTARATV (SEQ ID NO: 2245) |
| 179 | AARTCATCCAYRTATTGRTARATVA (SEQ ID NO: 2246) |
| 179 | CATAYAARTCATCCAYRTATTGRTARATV (SEQ ID NO: 2247) |
| 179 | TAYAARTCATCCAYRTATTGRTARATVA (SEQ ID NO: 2248) |
| 179 | ACATAYAARTCATCCAYRTATTGRTARATV (SEQ ID NO: 2249) |
| 179 | ATAYAARTCATCCAYRTATTGRTARATVA (SEQ ID NO: 2250) |
| 179 | YYCTATYTCTAARTCAGAYCCTACATAYAARTCATCCATRTAYTGATAGAT (SEQ ID NO: 2251) |
| 179 | CTACATAYAARTCATCCAYRTATTGRTARATV + N (SEQ ID NO: 2252) |
| 179 | ACATAYAARTCATCCAYRTATTGRTARATVA + N (SEQ ID NO: 2253) |
| 179 | CCTACATAYAARTCATCCAYRTATTGRTARATV + N (SEQ ID NO: 2254) |
| 179 | TACATAYAARTCATCCAYRTATTGRTARATVA + N (SEQ ID NO: 2255) |
| 179 | RTCWGAKCCTACATAYAARTCATCCAYRTATTGRTARATV + N (SEQ ID NO: 2256) |

TABLE 5 -continued

| | |
|---|---|
| 179 | TCWGAKCCTACATAYAARTCATCCAYRTATTGRTARATVA + N (SEQ ID NO: 2257) |
| 179 | AYAARTCATCCAYRTATTGRTARATV + N (SEQ ID NO: 2258) |
| 179 | AARTCATCCAYRTATTGRTARATVA + N (SEQ ID NO: 2259) |
| 179 | CATAYAARTCATCCAYRTATTGRTARATV + N (SEQ ID NO: 2260) |
| 179 | TAYAARTCATCCAYRTATTGRTARATVA + N (SEQ ID NO: 2261) |
| 179 | ACATAYAARTCATCCAYRTATTGRTARATV + N (SEQ ID NO: 2262) |
| 179 | ATAYAARTCATCCAYRTATTGRTARATVA + N (SEQ ID NO: 2263) |
| 179 | YYCTATYTCTAARTCAGAYCCTACATAYAARTCATCCATRTAYTGATAGAT + N (SEQ ID NO: 2264) |
| 179 | +CT + ACAT + AYAARTCATCCAYRTATTGRTARATV (SEQ ID NO: 2265) |
| 179 | +AC + ATAY + AARTCATCCAYRTATTGRTARATVA (SEQ ID NO: 2266) |
| 179 | +CTA + CAT + AYAARTCATCCAYRTATTGRTARATV (SEQ ID NO: 2267) |
| 179 | +ACA + TAY + AARTCATCCAYRTATTGRTARATVA (SEQ ID NO: 2268) |
| 179 | +CT + A + CATAYAARTCATCCAYRTATTGRTARATV (SEQ ID NO: 2269) |
| 179 | +AC + A + TAYAARTCATCCAYRTATTGRTARATVA (SEQ ID NO: 2270) |
| 179 | +C + CTA + CATAYAARTCATCCAYRTATTGRTARATV (SEQ ID NO: 2271) |
| 179 | +T + ACA + TAYAARTCATCCAYRTATTGRTARATVA (SEQ ID NO: 2272) |
| 179 | +CCT + A + CATAYAARTCATCCAYRTATTGRTARATV (SEQ ID NO: 2273) |
| 179 | +TAC + A + TAYAARTCATCCAYRTATTGRTARATVA (SEQ ID NO: 2274) |
| 179 | +C + CT + ACATAYAARTCATCCAYRTATTGRTARATV (SEQ ID NO: 2275) |
| 179 | +T + AC + ATAYAARTCATCCAYRTATTGRTARATVA (SEQ ID NO: 2276) |
| 179 | RT + CWGAK + CCT + ACATAYAARTCATCCAYRTATTGRTARATV (SEQ ID NO: 2277) |
| 179 | +TCW + GAKCCT + ACATAYAARTCATCCAYRTATTGRTARATVA (SEQ ID NO: 2278) |
| 179 | RT + CWGAKC + CT + ACATAYAARTCATCCAYRTATTGRTARATV (SEQ ID NO: 2279) |
| 179 | +AY + AA + RTCATCCAYRTATTGRTARATV (SEQ ID NO: 2280) |
| 179 | +AA + RT + CATCCAYRTATTGRTARATVA (SEQ ID NO: 2281) |
| 179 | +AYA + A + RTCATCCAYRTATTGRTARATV (SEQ ID NO: 2282) |
| 179 | +AAR + T + CATCCAYRTATTGRTARATVA (SEQ ID NO: 2283) |
| 179 | +AY + A + ARTCATCCAYRTATTGRTARATV (SEQ ID NO: 2284) |
| 179 | +AA + R + TCATCCAYRTATTGRTARATVA (SEQ ID NO: 2285) |
| 179 | +CAT + AYA + ARTCATCCAYRTATTGRTARATV (SEQ ID NO: 2286) |
| 179 | +TAY + AAR + TCATCCAYRTATTGRTARATVA (SEQ ID NO: 2287) |
| 179 | +CATAY + A + ARTCATCCAYRTATTGRTARATV (SEQ ID NO: 2288) |
| 179 | +TAYAA + R + TCATCCAYRTATTGRTARATVA (SEQ ID NO: 2289) |
| 179 | +CAT + AY + AARTCATCCAYRTATTGRTARATV (SEQ ID NO: 2290) |
| 179 | +TAY + AA + RTCATCCAYRTATTGRTARATVA (SEQ ID NO: 2291) |
| 179 | +A + CATAY + AARTCATCCAYRTATTGRTARATV (SEQ ID NO: 2292) |
| 179 | +A + TAYAA + RTCATCCAYRTATTGRTARATVA (SEQ ID NO: 2293) |
| 179 | +ACAT + AY + AARTCATCCAYRTATTGRTARATV (SEQ ID NO: 2294) |
| 179 | +ATAY + AA + RTCATCCAYRTATTGRTARATVA (SEQ ID NO: 2295) |

TABLE 5 -continued

| | |
|---|---|
| 179 | +A + CAT + AYAARTCATCCAYRTATTGRTARATV (SEQ ID NO: 2296) |
| 179 | +A + TAY + AARTCATCCAYRTATTGRTARATVA (SEQ ID NO: 2297) |
| 179 | RT + CWGAK + C + CTACATAYAARTCATCCAYRTATTGRTARATV (SEQ ID NO: 2298) |
| 179 | TCW + GAKCC + T + ACATAYAARTCATCCAYRTATTGRTARATVA (SEQ ID NO: 2299) |
| 181 | AARTCWGAKCCTACATAYAARTCATCCAYRTATTGR (SEQ ID NO: 2300) |
| 181 | CTAARTCWGAKCCTACATAYAARTCATCCAYRTATTGR (SEQ ID NO: 2301) |
| 181 | YTCTAARTCWGAKCCTACATAYAARTCATCCAYRTATTGR (SEQ ID NO: 2302) |
| 181 | GAKCCTACATAYAARTCATCCAYRTATTGR (SEQ ID NO: 2303) |
| 181 | CWGAKCCTACATAYAARTCATCCAYRTATTGR (SEQ ID NO: 2304) |
| 181 | ARTCWGAKCCTACATAYAARTCATCCAYRTATTGR (SEQ ID NO: 2305) |
| 181 | TRTGYTGYYCTATYTCTAARTCAGAYCCTACATAYAARTCATCCATGTATTG (SEQ ID NO: 2306) |
| 181 | AARTCWGAKCCTACATAYAARTCATCCAYRTATTGR + N (SEQ ID NO: 2307) |
| 181 | CTAARTCWGAKCCTACATAYAARTCATCCAYRTATTGR + N (SEQ ID NO: 2308) |
| 181 | YTCTAARTCWGAKCCTACATAYAARTCATCCAYRTATTGR + N (SEQ ID NO: 2309) |
| 181 | GAKCCTACATAYAARTCATCCAYRTATTGR + N (SEQ ID NO: 2310) |
| 181 | CWGAKCCTACATAYAARTCATCCAYRTATTGR + N (SEQ ID NO: 2311) |
| 181 | ARTCWGAKCCTACATAYAARTCATCCAYRTATTGR + N (SEQ ID NO: 2312) |
| 181 | TRTGYTGYYCTATYTCTAARTCAGAYCCTACATAYAARTCATCCATGTATTG + N (SEQ ID NO: 2313) |
| 181 | +A + ARTCW + GAKCCTACATAYAARTCATCCAYRTATTGR (SEQ ID NO: 2314) |
| 181 | +AART + CW + GAKCCTACATAYAARTCATCCAYRTATTGR (SEQ ID NO: 2315) |
| 181 | +A + ART + CWGAKCCTACATAYAARTCATCCAYRTATTGR (SEQ ID NO: 2316) |
| 181 | +CT + AART + CWGAKCCTACATAYAARTCATCCAYRTATTGR (SEQ ID NO: 2317) |
| 181 | +CTA + ART + CWGAKCCTACATAYAARTCATCCAYRTATTGR (SEQ ID NO: 2318) |
| 181 | +CT + A + ARTCWGAKCCTACATAYAARTCATCCAYRTATTGR (SEQ ID NO: 2319) |
| 181 | Y + T + CTA + ARTCWGAKCCTACATAYAARTCATCCAYRTATTGR (SEQ ID NO: 2320) |
| 181 | Y + TCT + A + ARTCWGAKCCTACATAYAARTCATCCAYRTATTGR (SEQ ID NO: 2321) |
| 181 | +G + AK + CCTACATAYAARTCATCCAYRTATTGR (SEQ ID NO: 2322) |
| 181 | +GA + K + CCTACATAYAARTCATCCAYRTATTGR (SEQ ID NO: 2323) |
| 181 | +G + A + KCCTACATAYAARTCATCCAYRTATTGR (SEQ ID NO: 2324) |
| 181 | +CW + GA + KCCTACATAYAARTCATCCAYRTATTGR (SEQ ID NO: 2325) |
| 181 | +CWG + A + KCCTACATAYAARTCATCCAYRTATTGR (SEQ ID NO: 2326) |
| 181 | +CW + G + AKCCTACATAYAARTCATCCAYRTATTGR (SEQ ID NO: 2327) |
| 181 | +ART + CWG + AKCCTACATAYAARTCATCCAYRTATTGR (SEQ ID NO: 2328) |
| 181 | +ARTCW + G + AKCCTACATAYAARTCATCCAYRTATTGR (SEQ ID NO: 2329) |
| 181 | +ART + CW + GAKCCTACATAYAARTCATCCAYRTATTGR (SEQ ID NO: 2330) |
| 181 | Y + T + CT + AARTCWGAKCCTACATAYAARTCATCCAYRTATTGR (SEQ ID NO: 2331) |
| 184 | YCTATYTCTAARTCWGAKCCTACATAYAARTCATCCA (SEQ ID NO: 2332) |
| 184 | TGYYCTATYTCTAARTCWGAKCCTACATAYAARTCATC (SEQ ID NO: 2333) |

TABLE 5 -continued

| | | |
|---|---|---|
| 184 | YYCTATYTCTAARTCWGAKCCTACATAYAARTCATCCA | (SEQ ID NO: 2334) |
| 184 | YTGYYCTATYTCTAARTCWGAKCCTACATAYAARTCATC | (SEQ ID NO: 2335) |
| 184 | TGYYCTATYTCTAARTCWGAKCCTACATAYAARTCATCCA | (SEQ ID NO: 2336) |
| 184 | GYTGYYCTATYTCTAARTCWGAKCCTACATAYAARTCATC | (SEQ ID NO: 2337) |
| 184 | ATYTCTAARTCWGAKCCTACATAYAARTCATCCA | (SEQ ID NO: 2338) |
| 184 | TATYTCTAARTCWGAKCCTACATAYAARTCATC | (SEQ ID NO: 2339) |
| 184 | TATYTCTAARTCWGAKCCTACATAYAARTCATCCA | (SEQ ID NO: 2340) |
| 184 | YYCTATYTCTAARTCWGAKCCTACATAYAARTCATC | (SEQ ID NO: 2341) |
| 184 | CTATYTCTAARTCWGAKCCTACATAYAARTCATCCA | (SEQ ID NO: 2342) |
| 184 | GYYCTATYTCTAARTCWGAKCCTACATAYAARTCATC | (SEQ ID NO: 2343) |
| 184 | TTTRYTCTRTGYTGYYCTATYTCTAARTCAGAYCCTACATAYAARTCATC (SEQ ID NO: 2344) | |
| 184 | YCTATYTCTAARTCWGAKCCTACATAYAARTCATCCA + N | (SEQ ID NO: 2345) |
| 184 | TGYYCTATYTCTAARTCWGAKCCTACATAYAARTCATC + N | (SEQ ID NO: 2346) |
| 184 | YYCTATYTCTAARTCWGAKCCTACATAYAARTCATCCA + N | (SEQ ID NO: 2347) |
| 184 | YTGYYCTATYTCTAARTCWGAKCCTACATAYAARTCATC + N (SEQ ID NO: 2348) | |
| 184 | TGYYCTATYTCTAARTCWGAKCCTACATAYAARTCATCCA + N | (SEQ ID NO: 2349) |
| 184 | GYTGYYCTATYTCTAARTCWGAKCCTACATAYAARTCATC + N | (SEQ ID NO: 2350) |
| 184 | ATYTCTAARTCWGAKCCTACATAYAARTCATCCA + N | (SEQ ID NO: 2351) |
| 184 | TATYTCTAARTCWGAKCCTACATAYAARTCATC + N | (SEQ ID NO: 2352) |
| 184 | TATYTCTAARTCWGAKCCTACATAYAARTCATCCA + N | (SEQ ID NO: 2353) |
| 184 | YYCTATYTCTAARTCWGAKCCTACATAYAARTCATC + N | (SEQ ID NO: 2354) |
| 184 | CTATYTCTAARTCWGAKCCTACATAYAARTCATCCA + N | (SEQ ID NO: 2355) |
| 184 | GYYCTATYTCTAARTCWGAKCCTACATAYAARTCATC + N | (SEQ ID NO: 2356) |
| 184 | TTTRYTCTRTGYTGYYCTATYTCTAARTCAGAYCCTACATAYAARTCATC + N (SEQ ID NO: 2357) | |
| 184 | +Y + CT + ATYTCTAARTCWGAKCCTACATAYAARTCATCCA | (SEQ ID NO: 2358) |
| 184 | | (SEQ ID NO: 2359) |
| 184 | +YC + T + ATYTCTAARTCWGAKCCTACATAYAARTCATCCA | (SEQ ID NO: 2360) |
| 184 | +TG + YYC + TATYTCTAARTCWGAKCCTACATAYAARTCATC (SEQ ID NO: 2361) | |
| 184 | +Y + C + TATYTCTAARTCWGAKCCTACATAYAARTCATCCA (SEQ ID NO: 2362) | |
| 184 | +T + G + YYCTATYTCTAARTCWGAKCCTACATAYAARTCATC | (SEQ ID NO: 2363) |
| 184 | +Y + YC + TATYTCTAARTCWGAKCCTACATAYAARTCATCCA (SEQ ID NO: 2364) | |
| 184 | +Y + TG + YYCTATYTCTAARTCWGAKCCTACATAYAARTCATC | (SEQ ID NO: 2365) |
| 184 | +YY + C + TATYTCTAARTCWGAKCCTACATAYAARTCATCCA | (SEQ ID NO: 2366) |
| 184 | +YT + G + YYCTATYTCTAARTCWGAKCCTACATAYAARTCATC | (SEQ ID NO: 2367) |
| 184 | +Y + Y + CTATYTCTAARTCWGAKCCTACATAYAARTCATCCA | (SEQ ID NO: 2368) |
| 184 | +Y + T + GYYCTATYTCTAARTCWGAKCCTACATAYAARTCATC | (SEQ ID NO: 2369) |
| 184 | TG + Y + YC + TATYTCTAARTCWGAKCCTACATAYAARTCATCCA | (SEQ ID NO: 2370) |

TABLE 5 -continued

| 184 | +G + YT + GYYCTATYTCTAARTCWGAKCCTACATAYAARTCATC (SEQ ID NO: 2371) |
| --- | --- |
| 184 | TGY + Y + C + TATYTCTAARTCWGAKCCTACATAYAARTCATCCA (SEQ ID NO: 2372) |
| 184 | +GY + T + GYYCTATYTCTAARTCWGAKCCTACATAYAARTCATC (SEQ ID NO: 2373) |
| 184 | +ATY + TCTAARTCWGA + KCCTACATAYAARTCATCCA (SEQ ID NO: 2374) |
| 184 | +TATYTC + TAARTC + WGAKCCTACATAYAARTCATC (SEQ ID NO: 2375) |
| 184 | +ATYTCTAAR + TCWGA + KCCTACATAYAARTCATCCA (SEQ ID NO: 2376) |
| 184 | +TATYTCTAART + C + WGAKCCTACATAYAARTCATC (SEQ ID NO: 2377) |
| 184 | +ATY + TCTAAR + TCWGAKCCTACATAYAARTCATCCA (SEQ ID NO: 2378) |
| 184 | +TATYTC + TAART + CWGAKCCTACATAYAARTCATC (SEQ ID NO: 2379) |
| 184 | +T + ATYTCTAAR + TCWGAKCCTACATAYAARTCATCCA (SEQ ID NO: 2380) |
| 184 | +YYC + TATYTCTAART + CWGAKCCTACATAYAARTCATC (SEQ ID NO: 2381) |
| 184 | +TATY + TCTAAR + TCWGAKCCTACATAYAARTCATCCA (SEQ ID NO: 2382) |
| 184 | +YYCTATYTC + TAART + CWGAKCCTACATAYAARTCATC (SEQ ID NO: 2383) |
| 184 | +T + ATY + TCTAARTCWGAKCCTACATAYAARTCATCCA (SEQ ID NO: 2384) |
| 184 | +YYC + TATYTC + TAARTCWGAKCCTACATAYAARTCATC (SEQ ID NO: 2385) |
| 184 | +C + TATY + TCTAART CWGAKCCTACATAYAARTCATCCA (SEQ ID NO: 2386) |
| 184 | +G + YYCTATYTC + TAARTCWGAKCCTACATAYAARTCATC (SEQ ID NO: 2387) |
| 184 | +CT + ATY + TCTAARTCWGAKCCTACATAYAARTCATCCA (SEQ ID NO: 2388) |
| 184 | +GYYC + TATYTC + TAARTCWGAKCCTACATAYAARTCATC (SEQ ID NO: 2389) |
| 184 | +C + T + ATYTCTAARTCWGAKCCTACATAYAARTCATCCA (SEQ ID NO: 2390) |
| 184 | +G + YYC + TATYTCTAARTCWGAKCCTACATAYAARTCATC (SEQ ID NO: 2391) |
| 184 | +TG + Y + YCTATYTCTAARTCWGAKCCTACATAYAARTCATCCA (SEQ ID NO: 2392) |
| 184 | +G + Y + TGYYCTATYTCTAARTCWGAKCCTACATAYAARTCATC (SEQ ID NO: 2393) |
| 188 | TRTGYTGYYCTATYTCTAARTCWGAKCCTACA (SEQ ID NO: 2394) |
| 188 | TGYTGYYCTATYTCTAARTCWGAKCCTACAT (SEQ ID NO: 2395) |
| 188 | CTRTGYTGYYCTATYTCTAARTCWGAKCCTACA (SEQ ID NO: 2396) |
| 188 | RTGYTGYYCTATYTCTAARTCWGAKCCTACAT (SEQ ID NO: 2397) |
| 188 | TTTTRYTCTRTGYTGYYCTATYTCTAARTCWGAKCCTACA (SEQ ID NO: 2398) |
| 188 | TTTRYTCTRTGYTGYYCTATYTCTAARTCWGAKCCTACAT (SEQ ID NO: 2399) |
| 188 | GYYCTATYTCTAARTCWGAKCCTACA (SEQ ID NO: 2400) |
| 188 | YCTATYTCTAARTCWGAKCCTACAT (SEQ ID NO: 2401) |
| 188 | GYTGYYCTATYTCTAARTCWGAKCCTACA (SEQ ID NO: 2402) |
| 188 | TGYYCTATYTCTAARTCWGAKCCTACAT (SEQ ID NO: 2403) |
| 188 | TGYTGYYCTATYTCTAARTCWGAKCCTACA (SEQ ID NO: 2404) |
| 188 | YTGYYCTATYTCTAARTCWGAKCCTACAT (SEQ ID NO: 2405) |
| 188 | YARYTCYTCTAYTTTTRYTCTRTGYTGYYCTATYTCTAARTCAGATCCTAC (SEQ ID NO: 2406) |
| 188 | TRTGYTGYYCTATYTCTAARTCWGAKCCTACA + N (SEQ ID NO: 2407) |
| 188 | TGYTGYYCTATYTCTAARTCWGAKCCTACAT + N (SEQ ID NO: 2408) |
| 188 | CTRTGYTGYYCTATYTCTAARTCWGAKCCTACA + N (SEQ ID NO: 2409) |

TABLE 5 -continued

| | | |
|---|---|---|
| 188 | RTGYTGYYCTATYTCTAARTCWGAKCCTACAT + N (SEQ ID NO: 2410) | |
| 188 | TTTTRYTCTRTGYTGYYCTATYTCTAARTCWGAKCCTACA + N (SEQ ID NO: 2411) | |
| 188 | TTTRYTCTRTGYTGYYCTATYTCTAARTCWGAKCCTACAT + N (SEQ ID NO: 2412) | |
| 188 | GYYCTATYTCTAARTCWGAKCCTACA + N (SEQ ID NO: 2413) | |
| 188 | YCTATYTCTAARTCWGAKCCTACAT + N (SEQ ID NO: 2414) | |
| 188 | GYTGYYCTATYTCTAARTCWGAKCCTACA + N (SEQ ID NO: 2415) | |
| 188 | TGYYCTATYTCTAARTCWGAKCCTACAT + N (SEQ ID NO: 2416) | |
| 188 | TGYTGYYCTATYTCTAARTCWGAKCCTACA + N (SEQ ID NO: 2417) | |
| 188 | YTGYYCTATYTCTAARTCWGAKCCTACAT + N (SEQ ID NO: 2418) | |
| 188 | YARYTCYTCTAYTTTTRYTCTRTGYTGYYCTATYTCTAARTCAGATCCTAC + N (SEQ ID NO: 2419) | |
| 188 | +TR + TGYT + GYYCTATYTCTAARTCWGAKCCTACA (SEQ ID NO: 2420) | |
| 188 | +TG + YTGY + YCTATYTCTAARTCWGAKCCTACAT (SEQ ID NO: 2421) | |
| 188 | +TRT + GYT + GYYCTATYTCTAARTCWGAKCCTACA (SEQ ID NO: 2422) | |
| 188 | +TGY + TGY + YCTATYTCTAARTCWGAKCCTACAT (SEQ ID NO: 2423) | |
| 188 | +TR + T + GYTGYYCTATYTCTAARTCWGAKCCTACA (SEQ ID NO: 2424) | |
| 188 | +TG + Y + TGYYCTATYTCTAARTCWGAKCCTACAT (SEQ ID NO: 2425) | |
| 188 | +C + TRT + GYTGYYCTATYTCTAARTCWGAKCCTACA (SEQ ID NO: 2426) | |
| 188 | +R + TGY + TGYYCTATYTCTAARTCWGAKCCTACAT (SEQ ID NO: 2427) | |
| 188 | +CTR + T + GYTGYYCTATYTCTAARTCWGAKCCTACA (SEQ ID NO: 2428) | |
| 188 | +RTG + Y + TGYYCTATYTCTAARTCWGAKCCTACAT (SEQ ID NO: 2429) | |
| 188 | +C + TR + TGYTGYYCTATYTCTAARTCWGAKCCTACA (SEQ ID NO: 2430) | |
| 188 | +R + TG + YTGYYCTATYTCTAARTCWGAKCCTACAT (SEQ ID NO: 2431) | |
| 188 | TT + TTRYT + CTR + TGYTGYYCTATYTCTAARTCWGAKCCTACA (SEQ ID NO: 2432) | |
| 188 | TTT + RYTCT + RTG + YTGYYCTATYTCTAARTCWGAKCCTACAT (SEQ ID NO: 2433) | |
| 188 | TT + TTRYTC + TR + TGYTGYYCTATYTCTAARTCWGAKCCTACA (SEQ ID NO: 2434) | |
| 188 | TTT + RYTCTR + TG + YTGYYCTATYTCTAARTCWGAKCCTACAT (SEQ ID NO: 2435) | |
| 188 | +GYY + CTATYTCTAART + CWGAKCCTACA (SEQ ID NO: 2436) | |
| 188 | +YCT + ATYTCTAARTCW + GAKCCTACAT (SEQ ID NO: 2437) | |
| 188 | +GYYCTATYTCTAAR + T + CWGAKCCTACA (SEQ ID NO: 2438) | |
| 188 | +YCTATYTCTAARTC + W + GAKCCTACAT (SEQ ID NO: 2439) | |
| 188 | +GYY + CTATYTCTAAR + TCWGAKCCTACA (SEQ ID NO: 2440) | |
| 188 | +YCT + ATYTCTAARTC + WGAKCCTACAT (SEQ ID NO: 2441) | |
| 188 | +GYT + GYYCTATYTCTAAR + TCWGAKCCTACA (SEQ ID NO: 2442) | |
| 188 | +TGY + YCTATYTCTAARTC + WGAKCCTACAT (SEQ ID NO: 2443) | |
| 188 | +GYTGYY + CTATYTCTAAR + TCWGAKCCTACA (SEQ ID NO: 2444) | |
| 188 | +TGYYCT + ATYTCTAARTC + WGAKCCTACAT (SEQ ID NO: 2445) | |
| 188 | +GYT + GYY + CTATYTCTAARTCWGAKCCTACA (SEQ ID NO: 2446) | |
| 188 | +TGY + YCT + ATYTCTAARTCWGAKCCTACAT (SEQ ID NO: 2447) | |
| 188 | +T + GYTGYY + CTATYTCTAARTCWGAKCCTACA (SEQ ID NO: 2448) | |
| 188 | +Y + TGYYCT + ATYTCTAARTCWGAKCCTACAT (SEQ ID NO: 2449) | |

TABLE 5 -continued

| | |
|---|---|
| 188 | +TGYT + GYY + CTATYTCTAARTCWGAKCCTACA (SEQ ID NO: 2450) |
| 188 | +YTGY + YCT + ATYTCTAARTCWGAKCCTACAT (SEQ ID NO: 2451) |
| 188 | +T + GYT + GYYCTATYTCTAARTCWGAKCCTACA (SEQ ID NO: 2452) |
| 188 | +Y + TGY + YCTATYTCTAARTCWGAKCCTACAT (SEQ ID NO: 2453) |
| 188 | TT + TTRYT + C + TRTGYTGYYCTATYTCTAARTCWGAKCCTACA (SEQ ID NO: 2454) |
| 188 | TTT + RYTCT + R + TGYTGYYCTATYTCTAARTCWGAKCCTACAT (SEQ ID NO: 2455) |
| 190 | AYTTTTRYTCTRTGYTGYYCTATYTCTAARTCWGAK (SEQ ID NO: 2456) |
| 190 | TTTTRYTCTRTGYTGYYCTATYTCTAARTCWGAKC (SEQ ID NO: 2457) |
| 190 | CTAYTTTTRYTCTRTGYTGYYCTATYTCTAARTCWGAK (SEQ ID NO: 2458) |
| 190 | AYTTTTRYTCTRTGYTGYYCTATYTCTAARTCWGAKC (SEQ ID NO: 2459) |
| 190 | YTCTAYTTTTRYTCTRTGYTGYYCTATYTCTAARTCWGAK (SEQ ID NO: 2460) |
| 190 | TCTAYTTTTRYTCTRTGYTGYYCTATYTCTAARTCWGAKC (SEQ ID NO: 2461) |
| 190 | YTCTRTGYTGYYCTATYTCTAARTCWGAK (SEQ ID NO: 2462) |
| 190 | CTRTGYTGYYCTATYTCTAARTCWGAKC (SEQ ID NO: 2463) |
| 190 | TTRYTCTRTGYTGYYCTATYTCTAARTCWGAK (SEQ ID NO: 2464) |
| 190 | RYTCTRTGYTGYYCTATYTCTAARTCWGAKC (SEQ ID NO: 2465) |
| 190 | YTTTTRYTCTRTGYTGYYCTATYTCTAARTCWGAK (SEQ ID NO: 2466) |
| 190 | TTTRYTCTRTGYTGYYCTATYTCTAARTCWGAKC (SEQ ID NO: 2467) |
| 190 | HKBYCTYARYTCYTCTAYTTTTRYTCTRTGYTGYYCTATYTCTAAGTCAGA (SEQ ID NO: 2468) |
| 190 | AYTTTTRYTCTRTGYTGYYCTATYTCTAARTCWGAK + N (SEQ ID NO: 2469) |
| 190 | TTTTRYTCTRTGYTGYYCTATYTCTAARTCWGAKC + N (SEQ ID NO: 2470) |
| 190 | CTAYTTTTRYTCTRTGYTGYYCTATYTCTAARTCWGAK + N (SEQ ID NO: 2471) |
| 190 | AYTTTTRYTCTRTGYTGYYCTATYTCTAARTCWGAKC + N (SEQ ID NO: 2472) |
| 190 | YTCTAYTTTTRYTCTRTGYTGYYCTATYTCTAARTCWGAK + N (SEQ ID NO: 2473) |
| 190 | TCTAYTTTTRYTCTRTGYTGYYCTATYTCTAARTCWGAKC + N (SEQ ID NO: 2474) |
| 190 | YTCTRTGYTGYYCTATYTCTAARTCWGAK + N (SEQ ID NO: 2475) |
| 190 | CTRTGYTGYYCTATYTCTAARTCWGAKC + N (SEQ ID NO: 2476) |
| 190 | TTRYTCTRTGYTGYYCTATYTCTAARTCWGAK + N (SEQ ID NO: 2477) |
| 190 | RYTCTRTGYTGYYCTATYTCTAARTCWGAKC + N (SEQ ID NO: 2478) |
| 190 | YTTTTRYTCTRTGYTGYYCTATYTCTAARTCWGAK + N (SEQ ID NO: 2479) |
| 190 | TTTRYTCTRTGYTGYYCTATYTCTAARTCWGAKC + N (SEQ ID NO: 2480) |
| 190 | HKBYCTYARYTCYTCTAYTTTTRYTCTRTGYTGYYCTATYTCTAAGTCAGA + N (SEQ ID NO: 2481) |
| 190 | +A + YTTTTR + YTCTRTGYTGYYCTATYTCTAARTCWGAK (SEQ ID NO: 2482) |
| 190 | +T + TTTRYT + CTRTGYTGYYCTATYTCTAARTCWGAKC (SEQ ID NO: 2483) |
| 190 | +AYTT + TTR + YTCTRTGYTGYYCTATYTCTAARTCWGAK (SEQ ID NO: 2484) |
| 190 | +TTTT + RYT + CTRTGYTGYYCTATYTCTAARTCWGAKC (SEQ ID NO: 2485) |

TABLE 5 -continued

| | |
|---|---|
| 190 | +A + YTT + TTRYTCTRTGYTGYYCTATYTCTAARTCWGAK (SEQ ID NO: 2486) |
| 190 | +T + TTT + TRYCTRTGYTGYYCTATYTCTAARTCWGAKC (SEQ ID NO: 2487) |
| 190 | +CT + AYTT + TTRYTCTRTGYTGYYCTATYTCTAARTCWGAK (SEQ ID NO: 2488) |
| 190 | +AY + TTTT + RYTCTRTGYTGYYCTATYTCTAARTCWGAKC (SEQ ID NO: 2489) |
| 190 | +CTA + YTT + TTRYTCTRTGYTGYYCTATYTCTAARTCWGAK (SEQ ID NO: 2490) |
| 190 | +AYT + TTT + RYTCTRTGYTGYYCTATYTCTAARTCWGAKC (SEQ ID NO: 2491) |
| 190 | +CT + A + YTTTTRYTCTRTGYTGYYCTATYTCTAARTCWGAK (SEQ ID NO: 2492) |
| 190 | +AY + T + TTTRYTCTRTGYTGYYCTATYTCTAARTCWGAKC (SEQ ID NO: 2493) |
| 190 | Y + T + CTA + YTTTTRYTCTRTGYTGYYCTATYTCTAARTCWGAK (SEQ ID NO: 2494) |
| 190 | TC + T + AYT + TTTRYTCTRTGYTGYYCTATYTCTAARTCWGAKC (SEQ ID NO: 2495) |
| 190 | Y + TCT + A + YTTTTRYTCTRTGYTGYYCTATYTCTAARTCWGAK (SEQ ID NO: 2496) |
| 190 | TC + TAY + T + TTTRYTCTRTGYTGYYCTATYTCTAARTCWGAKC (SEQ ID NO: 2497) |
| 190 | +YTCTRTGYTGY + YCT + ATYTCTAARTCWGAK (SEQ ID NO: 2498) |
| 190 | +CTRTGYTGYYC + TAT + YTCTAARTCWGAKC (SEQ ID NO: 2499) |
| 190 | +YTCTRTGYTGYY + CT + ATYTCTAARTCWGAK (SEQ ID NO: 2500) |
| 190 | +CTRTGYTGYYCT + AT + YTCTAARTCWGAKC (SEQ ID NO: 2501) |
| 190 | +YTCTRTGYTGY + Y + CTATYTCTAARTCWGAK (SEQ ID NO: 2502) |
| 190 | +CTRTGYTGYYC + T + ATYTCTAARTCWGAKC (SEQ ID NO: 2503) |
| 190 | +TTR + YTCTRTGYTGYY + CTATYTCTAARTCWGAK (SEQ ID NO: 2504) |
| 190 | +RYT + CTRTGYTGYYCT + ATYTCTAARTCWGAKC (SEQ ID NO: 2505) |
| 190 | +TTRYTCTRTGYTGY + Y + CTATYTCTAARTCWGAK (SEQ ID NO: 2506) |
| 190 | +RYTCTRTGYTGYYC + T + ATYTCTAARTCWGAKC (SEQ ID NO: 2507) |
| 190 | +TTR + YTCTRTGYTGY + YCTATYTCTAARTCWGAK (SEQ ID NO: 2508) |
| 190 | +RYT + CTRTGYTGYYC + TATYTCTAARTCWGAKC (SEQ ID NO: 2509) |
| 190 | +YTT + TTRYTCTRTGYTGY + YCTATYTCTAARTCWGAK (SEQ ID NO: 2510) |
| 190 | +TTT + RYTCTRTGYTGYYC + TATYTCTAARTCWGAKC (SEQ ID NO: 2511) |
| 190 | +YTTTTR + YTCTRTGYTGY + YCTATYTCTAARTCWGAK (SEQ ID NO: 2512) |
| 190 | +TTTRYT + CTRTGYTGYYC + TATYTCTAARTCWGAKC (SEQ ID NO: 2513) |
| 190 | +YTT + TTR + YTCTRTGYTGYYCTATYTCTAARTCWGAK (SEQ ID NO: 2514) |
| 190 | +TTT + RYT + CTRTGYTGYYCTATYTCTAARTCWGAKC (SEQ ID NO: 2515) |
| 190 | Y + T + CT + AYTTTTRYTCTRTGYTGYYCTATYTCTAARTCWGAK (SEQ ID NO: 2516) |
| 190 | TC + T + AY + TTTTRYTCTRTGYTGYYCTATYTCTAARTCWGAKC (SEQ ID NO: 2517) |
| 210 | ATGYTTYTTRTCTGGTGTRGWRARYCCCCABYTY (SEQ ID NO: 2518) |
| 210 | GATGYTTYTTRTCTGGTGTRGWRARYCCCCABYTY (SEQ ID NO: 2519) |
| 210 | YTTYTGATGYTTYTTRTCTGGTGTRGWRARYCCCCABYTY (SEQ ID NO: 2520) |
| 210 | TYTTRTCTGGTGTRGWRARYCCCCABYTY (SEQ ID NO: 2521) |
| 210 | GYTTYTTRTCTGGTGTRGWRARYCCCCABYTY (SEQ ID NO: 2522) |
| 210 | TGYTTYTTRTCTGGTGTRGWRARYCCCCABYTY (SEQ ID NO: 2523) |
| 210 | RAATGGRGGTTCYTTYTGATGYTTYTTRTCTGGKGTRKWRARYCCCCACCT (SEQ ID NO: 2524) |
| 210 | ATGYTTYTTRTCTGGTGTRGWRARYCCCCABYTY + N (SEQ ID NO: 2525) |

TABLE 5 -continued

| | |
|---|---|
| 210 | GATGYTTYTTRTCTGGTGTRGWRARYCCCCABYTY + N (SEQ ID NO: 2526) |
| 210 | YTTYTGATGYTTYTTRTCTGGTGTRGWRARYCCCCABYTY + N (SEQ ID NO: 2527) |
| 210 | TYTTRTCTGGTGTRGWRARYCCCCABYTY + N (SEQ ID NO: 2528) |
| 210 | GYTTYTTRTCTGGTGTRGWRARYCCCCABYTY + N (SEQ ID NO: 2529) |
| 210 | TGYTTYTTRTCTGGTGTRGWRARYCCCCABYTY + N (SEQ ID NO: 2530) |
| 210 | RAATGGRGGTTCYTTYTGATGYTTYTTRTCTGGKGTRKWRARYCCCCACCT + N (SEQ ID NO: 2531) |
| 210 | +A + TGYT + TYTTRTCTGGTGTRGWRARYCCCCABYTY (SEQ ID NO: 2532) |
| 210 | +AT + GYT + TYTTRTCTGGTGTRGWRARYCCCCABYTY (SEQ ID NO: 2533) |
| 210 | +A + T + GYTTYTTRTCTGGTGTRGWRARYCCCCABYTY (SEQ ID NO: 2534) |
| 210 | +G + AT + GYTTYTTRTCTGGTGTRGWRARYCCCCABYTY (SEQ ID NO: 2535) |
| 210 | +GA + T + GYTTYTTRTCTGGTGTRGWRARYCCCCABYTY (SEQ ID NO: 2536) |
| 210 | +G + A + TGYTTYTTRTCTGGTGTRGWRARYCCCCABYTY (SEQ ID NO: 2537) |
| 210 | YTTY + T + GA + TGYTTYTTRTCTGGTGTRGWRARYCCCCABYTY (SEQ ID NO: 2538) |
| 210 | YTTY + TG + A + TGYTTYTTRTCTGGTGTRGWRARYCCCCABYTY (SEQ ID NO: 2539) |
| 210 | +TYTTR + TCT + GGTGTRGWRARYCCCCABYTY (SEQ ID NO: 2540) |
| 210 | +TYTTRT + CT + GGTGTRGWRARYCCCCABYTY (SEQ ID NO: 2541) |
| 210 | +TYTTR + T + CTGGTGTRGWRARYCCCCABYTY (SEQ ID NO: 2542) |
| 210 | +GYT + TYTTRT + CTGGTGTRGWRARYCCCCABYTY (SEQ ID NO: 2543) |
| 210 | +GYTTYTTR + T + CTGGTGTRGWRARYCCCCABYTY (SEQ ID NO: 2544) |
| 210 | +GYT + TYTTR + TCTGGTGTRGWRARYCCCCABYTY (SEQ ID NO: 2545) |
| 210 | +T + GYTTYTTR + TCTGGTGTRGWRARYCCCCABYTY (SEQ ID NO: 2546) |
| 210 | +TGYT + TYTTR + TCTGGTGTRGWRARYCCCCABYTY (SEQ ID NO: 2547) |
| 210 | +T + GYT + TYTTRTCTGGTGTRGWRARYCCCCABYTY (SEQ ID NO: 2548) |
| 210 | YTTY + T + G + ATGYTTYTTRTCTGGTGTRGWRARYCCCCABYTY (SEQ ID NO: 2549) |
| 215 | AATGGRGGTTCYTTYTGATGYTTYTTRTCTGGTGTR (SEQ ID NO: 2550) |
| 215 | GRAATGGRGGTTCYTTYTGATGYTTYTTRTCTGGTGTR (SEQ ID NO: 2551) |
| 215 | AAGRAATGGRGGTTCYTTYTGATGYTTYTTRTCTGGTGTR (SEQ ID NO: 2552) |
| 215 | GRGGTTCYTTYTGATGYTTYTTRTCTGGTGTR (SEQ ID NO: 2553) |
| 215 | GGRGGTTCYTTYTGATGYTTYTTRTCTGGTGTR (SEQ ID NO: 2554) |
| 215 | ATGGRGGTTCYTTYTGATGYTTYTTRTCTGGTGTR (SEQ ID NO: 2555) |
| 215 | ATAHCCCATCCARAGRAATGGRGGTTCYTTYTGATGYTTYTTRTCTGGTGT (SEQ ID NO: 2556) |
| 215 | AATGGRGGTTCYTTYTGATGYTTYTTRTCTGGTGTR + N (SEQ ID NO: 2557) |
| 215 | GRAATGGRGGTTCYTTYTGATGYTTYTTRTCTGGTGTR + N (SEQ ID NO: 2558) |
| 215 | AAGRAATGGRGGTTCYTTYTGATGYTTYTTRTCTGGTGTR + N (SEQ ID NO: 2559) |
| 215 | GRGGTTCYTTYTGATGYTTYTTRTCTGGTGTR + N (SEQ ID NO: 2560) |
| 215 | GGRGGTTCYTTYTGATGYTTYTTRTCTGGTGTR + N (SEQ ID NO: 2561) |
| 215 | ATGGRGGTTCYTTYTGATGYTTYTTRTCTGGTGTR + N (SEQ ID NO: 2562) |
| 215 | ATAHCCCATCCARAGRAATGGRGGTTCYTTYTGATGYTTYTTRTCTGGTGT + N (SEQ ID NO: 2563) |

TABLE 5 -continued

| | | |
|---|---|---|
| 215 | +A + ATG + GRGGTTCYTTYTGATGYTTYTTRTCTGGTGTR | (SEQ ID NO: 2564) |
| 215 | +AAT + G + GRGGTTCYTTYTGATGYTTYTTRTCTGGTGTR | (SEQ ID NO: 2565) |
| 215 | +A + AT + GGRGGTTCYTTYTGATGYTTYTTRTCTGGTGTR | (SEQ ID NO: 2566) |
| 215 | +GR + AAT + GGRGGTTCYTTYTGATGYTTYTTRTCTGGTGTR | (SEQ ID NO: 2567) |
| 215 | +GRA + AT + GGRGGTTCYTTYTGATGYTTYTTRTCTGGTGTR | (SEQ ID NO: 2568) |
| 215 | +GR + A + ATGGRGGTTCYTTYTGATGYTTYTTRTCTGGTGTR | (SEQ ID NO: 2569) |
| 215 | A + A + GRA + ATGGRGGTTCYTTYTGATGYTTYTTRTCTGGTGTR | (SEQ ID NO: 2570) |
| 215 | A + AGR + A + ATGGRGGTTCYTTYTGATGYTTYTTRTCTGGTGTR | (SEQ ID NO: 2571) |
| 215 | +GRGGT + TCYT + TYTGATGYTTYTTRTCTGGTGTR | (SEQ ID NO: 2572) |
| 215 | +GRGGTT + CYT + TYTGATGYTTYTTRTCTGGTGTR | (SEQ ID NO: 2573) |
| 215 | +GRGGT + T + CYTTYTGATGYTTYTTRTCTGGTGTR | (SEQ ID NO: 2574) |
| 215 | +G + GRGGTT + CYTTYTGATGYTTYTTRTCTGGTGTR | (SEQ ID NO: 2575) |
| 215 | +GGRGGT + T + CYTTYTGATGYTTYTTRTCTGGTGTR | (SEQ ID NO: 2576) |
| 215 | +G + GRGGT + TCYTTYTGATGYTTYTTRTCTGGTGTR | (SEQ ID NO: 2577) |
| 215 | +AT + GGRGGT + TCYTTYTGATGYTTYTTRTCTGGTGTR | (SEQ ID NO: 2578) |
| 215 | +ATG + GRGGT + TCYTTYTGATGYTTYTTRTCTGGTGTR | (SEQ ID NO: 2579) |
| 215 | +AT + G + GRGGTTCYTTYTGATGYTTYTTRTCTGGTGTR | (SEQ ID NO: 2580) |
| 215 | A + A + GR + AATGGRGGTTCYTTYTGATGYTTYTTRTCTGGTGTR | (SEQ ID NO: 2581) |
| 219 | ATCCAAAGRAATGGRGGTTCYTTYTGATGYTTYT | (SEQ ID NO: 2582) |
| 219 | HCCCATCCAAAGRAATGGRGGTTCYTTYTGATGYTT | (SEQ ID NO: 2583) |
| 219 | CCATCCAAAGRAATGGRGGTTCYTTYTGATGYTTY | (SEQ ID NO: 2584) |
| 219 | CCCATCCAAAGRAATGGRGGTTCYTTYTGATGYTTYT | (SEQ ID NO: 2585) |
| 219 | ATAHCCCATCCAAAGRAATGGRGGTTCYTTYTGATGYTT | (SEQ ID NO: 2586) |
| 219 | AHCCCATCCAAAGRAATGGRGGTTCYTTYTGATGYTTY | (SEQ ID NO: 2587) |
| 219 | TAHCCCATCCAAAGRAATGGRGGTTCYTTYTGATGYTTYT | (SEQ ID NO: 2588) |
| 219 | CATAHCCCATCCAAAGRAATGGRGGTTCYTTYTGATGYTT | (SEQ ID NO: 2589) |
| 219 | ATAHCCCATCCAAAGRAATGGRGGTTCYTTYTGATGYTTY | (SEQ ID NO: 2590) |
| 219 | AGRAATGGRGGTTCYTTYTGATGYTTYT | (SEQ ID NO: 2591) |
| 219 | CCAAAGRAATGGRGGTTCYTTYTGATGYTT | (SEQ ID NO: 2592) |
| 219 | AAAGRAATGGRGGTTCYTTYTGATGYTTY | (SEQ ID NO: 2593) |
| 219 | CAAAGRAATGGRGGTTCYTTYTGATGYTTYT | (SEQ ID NO: 2594) |
| 219 | CATCCAAAGRAATGGRGGTTCYTTYTGATGYTT | (SEQ ID NO: 2595) |
| 219 | TCCAAAGRAATGGRGGTTCYTTYTGATGYTTY | (SEQ ID NO: 2596) |
| 219 | CCAAAGRAATGGRGGTTCYTTYTGATGYTTYT | (SEQ ID NO: 2597) |
| 219 | CCATCCAAAGRAATGGRGGTTCYTTYTGATGYTT | (SEQ ID NO: 2598) |
| 219 | ATCCAAAGRAATGGRGGTTCYTTYTGATGYTTY | (SEQ ID NO: 2599) |
| 219 | AGGATGGAGYTCATAHCCCATCCARAGRAATGGRGGTTCYTTYTGATGTTT | (SEQ ID NO: 2600) |
| 219 | ATCCAAAGRAATGGRGGTTCYTTYTGATGYTTYT + N | (SEQ ID NO: 2601) |
| 219 | HCCCATCCAAAGRAATGGRGGTTCYTTYTGATGYTT + N | (SEQ ID NO: 2602) |

TABLE 5 -continued

| | |
|---|---|
| 219 | CCATCCAAAGRAATGGRGGTTCYTTYTGATGYTTY + N (SEQ ID NO: 2603) |
| 219 | CCCATCCAAAGRAATGGRGGTTCYTTYTGATGYTTYT + N (SEQ ID NO: 2604) |
| 219 | ATAHCCCATCCAAAGRAATGGRGGTTCYTTYTGATGYTT + N (SEQ ID NO: 2605) |
| 219 | AHCCCATCCAAAGRAATGGRGGTTCYTTYTGATGYTTY + N (SEQ ID NO: 2606) |
| 219 | TAHCCCATCCAAAGRAATGGRGGTTCYTTYTGATGYTTYT + N (SEQ ID NO: 2607) |
| 219 | CATAHCCCATCCAAAGRAATGGRGGTTCYTTYTGATGYTT + N (SEQ ID NO: 2608) |
| 219 | ATAHCCCATCCAAAGRAATGGRGGTTCYTTYTGATGYTTY + N (SEQ ID NO: 2609) |
| 219 | AGRAATGGRGGTTCYTTYTGATGYTTYT + N (SEQ ID NO: 2610) |
| 219 | CCAAAGRAATGGRGGTTCYTTYTGATGYTT + N (SEQ ID NO: 2611) |
| 219 | AAAGRAATGGRGGTTCYTTYTGATGYTTY + N (SEQ ID NO: 2612) |
| 219 | CAAAGRAATGGRGGTTCYTTYTGATGYTTYT + N (SEQ ID NO: 2613) |
| 219 | CATCCAAAGRAATGGRGGTTCYTTYTGATGYTT + N (SEQ ID NO: 2614) |
| 219 | TCCAAAGRAATGGRGGTTCYTTYTGATGYTTY + N (SEQ ID NO: 2615) |
| 219 | CCAAAGRAATGGRGGTTCYTTYTGATGYTTYT + N (SEQ ID NO: 2616) |
| 219 | CCATCCAAAGRAATGGRGGTTCYTTYTGATGYTT + N (SEQ ID NO: 2617) |
| 219 | ATCCAAAGRAATGGRGGTTCYTTYTGATGYTTY + N (SEQ ID NO: 2618) |
| 219 | AGGATGGAGYTCATAHCCCATCCARAGRAATGGRGGTTCYTTYTGATGTTT + N (SEQ ID NO: 2619) |
| 219 | +AT + CCAA + AGRAATGGRGGTTCYTTYTGATGYTTYT (SEQ ID NO: 2620) |
| 219 | +HC + CCAT + CCAAAGRAATGGRGGTTCYTTYTGATGYTT (SEQ ID NO: 2621) |
| 219 | +CC + ATCC + AAAGRAATGGRGGTTCYTTYTGATGYTTY (SEQ ID NO: 2622) |
| 219 | +ATC + CAA + AGRAATGGRGGTTCYTTYTGATGYTTYT (SEQ ID NO: 2623) |
| 219 | +HCC + CAT + CCAAAGRAATGGRGGTTCYTTYTGATGYTT (SEQ ID NO: 2624) |
| 219 | +CCA + TCC + AAAGRAATGGRGGTTCYTTYTGATGYTTY (SEQ ID NO: 2625) |
| 219 | +AT + C + CAAAGRAATGGRGGTTCYTTYTGATGYTTYT (SEQ ID NO: 2626) |
| 219 | +HC + C + CATCCAAAGRAATGGRGGTTCYTTYTGATGYTT (SEQ ID NO: 2627) |
| 219 | +CC + A + TCCAAAGRAATGGRGGTTCYTTYTGATGYTTY (SEQ ID NO: 2628) |
| 219 | +CCC + ATC + CAAAGRAATGGRGGTTCYTTYTGATGYTTYT (SEQ ID NO: 2629) |
| 219 | +ATA + HCC + CATCCAAAGRAATGGRGGTTCYTTYTGATGYTT (SEQ ID NO: 2630) |
| 219 | +AHC + CCA + TCCAAAGRAATGGRGGTTCYTTYTGATGYTTY (SEQ ID NO: 2631) |
| 219 | +CCCAT + C + CAAAGRAATGGRGGTTCYTTYTGATGYTTYT (SEQ ID NO: 2632) |
| 219 | +ATAHC + C + CATCCAAAGRAATGGRGGTTCYTTYTGATGYTT (SEQ ID NO: 2633) |
| 219 | +AHCCC + A + TCCAAAGRAATGGRGGTTCYTTYTGATGYTTY (SEQ ID NO: 2634) |
| 219 | +CCC + AT + CCAAAGRAATGGRGGTTCYTTYTGATGYTTYT (SEQ ID NO: 2635) |
| 219 | +ATA + HC + CCATCCAAAGRAATGGRGGTTCYTTYTGATGYTT (SEQ ID NO: 2636) |
| 219 | +AHC + CC + ATCCAAAGRAATGGRGGTTCYTTYTGATGYTTY (SEQ ID NO: 2637) |
| 219 | +TA + HCCC + ATCCAAAGRAATGGRGGTTCYTTYTGATGYTTYT (SEQ ID NO: 2638) |

TABLE 5 -continued

| | | |
|---|---|---|
| 219 | +C + ATAHC + CCATCCAAAGRAATGGRGGTTCYTTYTGATGYTT (SEQ ID NO: 2639) | |
| 219 | A + T + AHCCC + ATCCAAAGRAATGGRGGTTCYTTYTGATGYTTY (SEQ ID NO: 2640) | |
| 219 | +CATA + HC + CCATCCAAAGRAATGGRGGTTCYTTYTGATGYTT (SEQ ID NO: 2641) | |
| 219 | A + TAHC + CC + ATCCAAAGRAATGGRGGTTCYTTYTGATGYTTY (SEQ ID NO: 2642) | |
| 219 | +AG + RAA + TGGRGGTTCYTTYTGATGYTTYT (SEQ ID NO: 2643) | |
| 219 | +CC + AAA + GRAATGGRGGTTCYTTYTGATGYTT (SEQ ID NO: 2644) | |
| 219 | +AA + AGR + AATGGRGGTTCYTTYTGATGYTTY (SEQ ID NO: 2645) | |
| 219 | +AGR + AA + TGGRGGTTCYTTYTGATGYTTYT (SEQ ID NO: 2646) | |
| 219 | +CCA + AA + GRAATGGRGGTTCYTTYTGATGYTT (SEQ ID NO: 2647) | |
| 219 | +AAA + GR + AATGGRGGTTCYTTYTGATGYTTY (SEQ ID NO: 2648) | |
| 219 | +AG + R + AATGGRGGTTCYTTYTGATGYTTYT (SEQ ID NO: 2649) | |
| 219 | +CC + A + AAGRAATGGRGGTTCYTTYTGATGYTT (SEQ ID NO: 2650) | |
| 219 | +AA + A + GRAATGGRGGTTCYTTYTGATGYTTY (SEQ ID NO: 2651) | |
| 219 | +CAA + AGR + AATGGRGGTTCYTTYTGATGYTTYT (SEQ ID NO: 2652) | |
| 219 | +CAT + CCA + AAGRAATGGRGGTTCYTTYTGATGYTT (SEQ ID NO: 2653) | |
| 219 | +TCC + AAA + GRAATGGRGGTTCYTTYTGATGYTTY (SEQ ID NO: 2654) | |
| 219 | +CAAAG + R + AATGGRGGTTCYTTYTGATGYTTYT (SEQ ID NO: 2655) | |
| 219 | +CATCC + A + AAGRAATGGRGGTTCYTTYTGATGYTT (SEQ ID NO: 2656) | |
| 219 | +TCCAA + A + GRAATGGRGGTTCYTTYTGATGYTTY (SEQ ID NO: 2657) | |
| 219 | +CAA + AG + RAATGGRGGTTCYTTYTGATGYTTYT (SEQ ID NO: 2658) | |
| 219 | +CAT + CC + AAAGRAATGGRGGTTCYTTYTGATGYTT (SEQ ID NO: 2659) | |
| 219 | +TCC + AA + AGRAATGGRGGTTCYTTYTGATGYTTY (SEQ ID NO: 2660) | |
| 219 | +C + CAAAG + RAATGGRGGTTCYTTYTGATGYTTYT (SEQ ID NO: 2661) | |
| 219 | +C + CATCC + AAAGRAATGGRGGTTCYTTYTGATGYTT (SEQ ID NO: 2662) | |
| 219 | +A + TCCAA + AGRAATGGRGGTTCYTTYTGATGYTTY (SEQ ID NO: 2663) | |
| 219 | +CCAA + AG + RAATGGRGGTTCYTTYTGATGYTTYT (SEQ ID NO: 2664) | |
| 219 | +CCAT + CC + AAAGRAATGGRGGTTCYTTYTGATGYTT (SEQ ID NO: 2665) | |
| 219 | +ATCC + AA + AGRAATGGRGGTTCYTTYTGATGYTTY (SEQ ID NO: 2666) | |
| 219 | +C + CAA + AGRAATGGRGGTTCYTTYTGATGYTTYT (SEQ ID NO: 2667) | |
| 219 | +C + CAT + CCAAAGRAATGGRGGTTCYTTYTGATGYTT (SEQ ID NO: 2668) | |
| 219 | +A + TCC + AAAGRAATGGRGGTTCYTTYTGATGYTTY (SEQ ID NO: 2669) | |
| 219 | TA + H + CCC + ATCCAAAGRAATGGRGGTTCYTTYTGATGYTTYT (SEQ ID NO: 2670) | |
| 219 | +C + ATA + HCCCATCCAAAGRAATGGRGGTTCYTTYTGATGYTT (SEQ ID NO: 2671) | |
| 219 | A + T + AHC + CCATCCAAAGRAATGGRGGTTCYTTYTGATGYTTY (SEQ ID NO: 2672) | |
| 225 | CAGGATGGAGYTCATAHCCCATCCAAAGRAATGGR (SEQ ID NO: 2673) | |
| 225 | TRTCAGGATGGAGYTCATAHCCCATCCAAAGRAATGGR (SEQ ID NO: 2674) | |

TABLE 5 -continued

| | |
|---|---|
| 225 | YTTRTCAGGATGGAGYTCATAHCCCATCCAAAGRAATGGR (SEQ ID NO: 2675) |
| 225 | GAGYTCATAHCCCATCCAAAGRAATGGR (SEQ ID NO: 2676) |
| 225 | GGAGYTCATAHCCCATCCAAAGRAATGGR (SEQ ID NO: 2677) |
| 225 | TGGAGYTCATAHCCCATCCAAAGRAATGGR (SEQ ID NO: 2678) |
| 225 | YTGBACTGTCCAYYTRTCAGGATGGAGYTCATAHCCCATCCARAGGAATGG (SEQ ID NO: 2679) |
| 225 | CAGGATGGAGYTCATAHCCCATCCAAAGRAATGGR + N (SEQ ID NO: 2680) |
| 225 | TRTCAGGATGGAGYTCATAHCCCATCCAAAGRAATGGR + N (SEQ ID NO: 2681) |
| 225 | YTTRTCAGGATGGAGYTCATAHCCCATCCAAAGRAATGGR + N (SEQ ID NO: 2682) |
| 225 | GAGYTCATAHCCCATCCAAAGRAATGGR + N (SEQ ID NO: 2683) |
| 225 | GGAGYTCATAHCCCATCCAAAGRAATGGR + N (SEQ ID NO: 2684) |
| 225 | TGGAGYTCATAHCCCATCCAAAGRAATGGR + N (SEQ ID NO: 2685) |
| 225 | YTGBACTGTCCAYYTRTCAGGATGGAGYTCATAHCCCATCCARAGGAATGG + N (SEQ ID NO: 2686) |
| 225 | +CAGGA + TG + GAGYTCATAHCCCATCCAAAGRAATGGR (SEQ ID NO: 2687) |
| 225 | +CAGGAT + G + GAGYTCATAHCCCATCCAAAGRAATGGR (SEQ ID NO: 2688) |
| 225 | +CAGGA + T + GGAGYTCATAHCCCATCCAAAGRAATGGR (SEQ ID NO: 2689) |
| 225 | +TRT + CAGGAT + GGAGYTCATAHCCCATCCAAAGRAATGGR (SEQ ID NO: 2690) |
| 225 | +TRTCAGGA + GGAGYTCATAHCCCATCCAAAGRAATGGR (SEQ ID NO: 2691) |
| 225 | +TRT + CAGGA + TGGAGYTCATAHCCCATCCAAAGRAATGGR (SEQ ID NO: 2692) |
| 225 | Y + T + TRTCAGGA + TGGAGYTCATAHCCCATCCAAAGRAATGGR (SEQ ID NO: 2693) |
| 225 | Y + TTRT + CAGGA + TGGAGYTCATAHCCCATCCAAAGRAATGGR (SEQ ID NO: 2694) |
| 225 | +GA + GY + TCATAHCCCATCCAAAGRAATGGR (SEQ ID NO: 2695) |
| 225 | +GAG + Y + TCATAHCCCATCCAAAGRAATGGR (SEQ ID NO: 2696) |
| 225 | +GA + G + YTCATAHCCCATCCAAAGRAATGGR (SEQ ID NO: 2697) |
| 225 | +G + GAG + YTCATAHCCCATCCAAAGRAATGGR (SEQ ID NO: 2698) |
| 225 | +GGA + G + YTCATAHCCCATCCAAAGRAATGGR (SEQ ID NO: 2699) |
| 225 | +G + GA + GYTCATAHCCCATCCAAAGRAATGGR (SEQ ID NO: 2700) |
| 225 | +T + GGA + GYTCATAHCCCATCCAAAGRAATGGR (SEQ ID NO: 2701) |
| 225 | +TG + GA + GYTCATAHCCCATCCAAAGRAATGGR (SEQ ID NO: 2702) |
| 225 | +T + G + GAGYTCATAHCCCATCCAAAGRAATGGR (SEQ ID NO: 2703) |
| 225 | Y + T + TRT + CAGGATGGAGYTCATAHCCCATCCAAAGRAATGGR (SEQ ID NO: 2704) |
| 227 | TTRTCAGGATGGAGYTCATAHCCCATCCAAAGRA (SEQ ID NO: 2705) |
| 227 | YTTRTCAGGATGGAGYTCATAHCCCATCCAAAGR (SEQ ID NO: 2706) |
| 227 | YTTRTCAGGATGGAGYTCATAHCCCATCCAAAGRA (SEQ ID NO: 2707) |
| 227 | AYTTRTCAGGATGGAGYTCATAHCCCATCCAAAGR (SEQ ID NO: 2708) |
| 227 | GTCCAYTTRTCAGGATGGAGYTCATAHCCCATCCAAAGRA (SEQ ID NO: 2709) |
| 227 | TGTCCAYTTRTCAGGATGGAGYTCATAHCCCATCCAAAGR (SEQ ID NO: 2710) |
| 227 | CAGGATGGAGYTCATAHCCCATCCAAAGRA (SEQ ID NO: 2711) |
| 227 | TCAGGATGGAGYTCATAHCCCATCCAAAGR (SEQ ID NO: 2712) |

TABLE 5 -continued

| 227 | TCAGGATGGAGYTCATAHCCCATCCAAAGRA (SEQ ID NO: 2713) |
| --- | --- |
| 227 | RTCAGGATGGAGYTCATAHCCCATCCAAAGR (SEQ ID NO: 2714) |
| 227 | TRTCAGGATGGAGYTCATAHCCCATCCAAAGRA (SEQ ID NO: 2715) |
| 227 | TRTCAGGATGGAGYTCATAHCCCATCCAAAGR (SEQ ID NO: 2716) |
| 227 | TATAGGYTGBACTGTCCAYYTRTCAGGATGGAGYTCATAHCCCATCCAAAG (SEQ ID NO: 2717) |
| 227 | TTRTCAGGATGGAGYTCATAHCCCATCCAAAGRA + N (SEQ ID NO: 2718) |
| 227 | YTTRTCAGGATGGAGYTCATAHCCCATCCAAAGR + N (SEQ ID NO: 2719) |
| 227 | YTTRTCAGGATGGAGYTCATAHCCCATCCAAAGRA + N (SEQ ID NO: 2720) |
| 227 | AYTTRTCAGGATGGAGYTCATAHCCCATCCAAAGR + N (SEQ ID NO: 2721) |
| 227 | GTCCAYTTRTCAGGATGGAGYTCATAHCCCATCCAAAGRA + N (SEQ ID NO: 2722) |
| 227 | TGTCCAYTTRTCAGGATGGAGYTCATAHCCCATCCAAAGR + N (SEQ ID NO: 2723) |
| 227 | CAGGATGGAGYTCATAHCCCATCCAAAGRA + N (SEQ ID NO: 2724) |
| 227 | TCAGGATGGAGYTCATAHCCCATCCAAAGR + N (SEQ ID NO: 2725) |
| 227 | TCAGGATGGAGYTCATAHCCCATCCAAAGRA + N (SEQ ID NO: 2726) |
| 227 | RTCAGGATGGAGYTCATAHCCCATCCAAAGR + N (SEQ ID NO: 2727) |
| 227 | TRTCAGGATGGAGYTCATAHCCCATCCAAAGRA + N (SEQ ID NO: 2728) |
| 227 | TRTCAGGATGGAGYTCATAHCCCATCCAAAGR + N (SEQ ID NO:2729) |
| 227 | TATAGGYTGBACTGTCCAYYTRTCAGGATGGAGYTCATAHCCCATCCAAAG + N (SEQ ID NO: 2730) |
| 227 | +T + TRT + CAGGATGGAGYTCATAHCCCATCCAAAGRA (SEQ ID NO: 2731) |
| 227 | +YT + TR + TCAGGATGGAGYTCATAHCCCATCCAAAGR (SEQ ID NO: 2732) |
| 227 | +TTR + T + CAGGATGGAGYTCATAHCCCATCCAAAGRA (SEQ ID NO: 2733) |
| 227 | +YTT + R + TCAGGATGGAGYTCATAHCCCATCCAAAGR (SEQ ID NO: 2734) |
| 227 | +T + TR + TCAGGATGGAGYTCATAHCCCATCCAAAGRA (SEQ ID NO: 2735) |
| 227 | +YT + T + RTCAGGATGGAGYTCATAHCCCATCCAAAGR (SEQ ID NO: 2736) |
| 227 | +Y + TTR + TCAGGATGGAGYTCATAHCCCATCCAAAGRA (SEQ ID NO: 2737) |
| 227 | +A + YTT + RTCAGGATGGAGYTCATAHCCCATCCAAAGR (SEQ ID NO: 2738) |
| 227 | +YT + TR + TCAGGATGGAGYTCATAHCCCATCCAAAGRA (SEQ ID NO: 2739) |
| 227 | +AYT + T + RTCAGGATGGAGYTCATAHCCCATCCAAAGR (SEQ ID NO: 2740) |
| 227 | +Y + T + TRTCAGGATGGAGYTCATAHCCCATCCAAAGRA (SEQ ID NO: 2741) |
| 227 | +A + YT + TRTCAGGATGGAGYTCATAHCCCATCCAAAGR (SEQ ID NO: 2742) |
| 227 | +GTCCA + YT + TRTCAGGATGGAGYTCATAHCCCATCCAAAGRA (SEQ ID NO: 2743) |
| 227 | TGTC + C + AYT + TRTCAGGATGGAGYTCATAHCCCATCCAAAGR (SEQ ID NO: 2744) |
| 227 | +GTCCAY + T + TRTCAGGATGGAGYTCATAHCCCATCCAAAGRA (SEQ ID NO: 2745) |
| 227 | TGTC + CA + YT + TRTCAGGATGGAGYTCATAHCCCATCCAAAGR (SEQ ID NO: 2746) |
| 227 | +C + AGG + ATGGAGYTCATAHCCCATCCAAAGRA (SEQ ID NO: 2747) |
| 227 | +T + CAG + GATGGAGYTCATAHCCCATCCAAAGR (SEQ ID NO: 2748) |
| 227 | +CA + GG + ATGGAGYTCATAHCCCATCCAAAGRA (SEQ ID NO: 2749) |

TABLE 5-continued

| | | |
|---|---|---|
| 227 | +TCA + G + GATGGAGYTCATAHCCCATCCAAAGR (SEQ ID NO: 2750) | |
| 227 | +C + A + GGATGGAGYTCATAHCCCATCCAAAGRA (SEQ ID NO: 2751) | |
| 227 | +T + CA + GGATGGAGYTCATAHCCCATCCAAAGR (SEQ ID NO: 2752) | |
| 227 | +T + CA + GGATGGAGYTCATAHCCCATCCAAAGRA (SEQ ID NO: 2753) | |
| 227 | +R + TCA + GGATGGAGYTCATAHCCCATCCAAAGR (SEQ ID NO: 2754) | |
| 227 | +TC + A + GGATGGAGYTCATAHCCCATCCAAAGRA (SEQ ID NO: 2755) | |
| 227 | +RT + CA + GGATGGAGYTCATAHCCCATCCAAAGR (SEQ ID NO: 2756) | |
| 227 | +T + C + AGGATGGAGYTCATAHCCCATCCAAAGRA (SEQ ID NO: 2757) | |
| 227 | +R + T + CAGGATGGAGYTCATAHCCCATCCAAAGR (SEQ ID NO: 2758) | |
| 227 | +TR + TC + AGGATGGAGYTCATAHCCCATCCAAAGRA (SEQ ID NO: 2759) | |
| 227 | +T + RT + CAGGATGGAGYTCATAHCCCATCCAAAGR (SEQ ID NO: 2760) | |
| 227 | +TRT + C AGGATGGAGYTCATAHCCCATCCAAAGRA (SEQ ID NO: 2761) | |
| 227 | +TR + T + CAGGATGGAGYTCATAHCCCATCCAAAGR (SEQ ID NO: 2762) | |
| 227 | +TR + T CAGGATGGAGYCATAHCCCATCCAAAGRA (SEQ ID NO: 2763) | |
| 227 | +T + R + TCAGGATGGAGYTCATAHCCCATCCAAAGR (SEQ ID NO: 2764) | |
| 227 | +GTCCA + Y + TTRTCAGGATGGAGYTCATAHCCCATCCAAAGRA (SEQ ID NO: 2765) | |
| 227 | TGTC + C + A + YTTRTCAGGATGGAGYTCATAHCCCATCCAAAGR (SEQ ID NO: 2766) | |
| 230 | YTGKACTGTCCAYTTRTCAGGATGGAGYTCATAHCCCA (SEQ ID NO: 2767) | |
| 230 | GYTGKACTGTCCAYTTRTCAGGATGGAGYTCATAHCCCA (SEQ ID NO: 2768) | |
| 230 | GGYTGKACTGTCCAYTTRTCAGGATGGAGYTCATAHCCCA (SEQ ID NO: 2769) | |
| 230 | ACTGTCCAYTTRTCAGGATGGAGYTCATAHCCCA (SEQ ID NO: 2770) | |
| 230 | KACTGTCCAYTTRTCAGGATGGAGYTCATAHCCCA (SEQ ID NO: 2771) | |
| 230 | TGKACTGTCCAYTTRTCAGGATGGAGYTCATAHCCCA (SEQ ID NO: 2772) | |
| 230 | GGYARYWBTATAGGYTGBACTGTCCAYYTRTCAGGATGGAGYTCATAACC (SEQ ID NO: 2773) | |
| 230 | YTGKACTGTCCAYTTRTCAGGATGGAGYTCATAHCCCA + N (SEQ ID NO: 2774) | |
| 230 | GYTGKACTGTCCAYTTRTCAGGATGGAGYTCATAHCCCA + N (SEQ ID NO: 2775) | |
| 230 | GGYTGKACTGTCCAYTTRTCAGGATGGAGYTCATAHCCCA + N (SEQ ID NO: 2776) | |
| 230 | ACTGTCCAYTTRTCAGGATGGAGYTCATAHCCCA + N (SEQ ID NO: 2777) | |
| 230 | KACTGTCCAYTTRTCAGGATGGAGYTCATAHCCCA + N (SEQ ID NO: 2778) | |
| 230 | TGKACTGTCCAYTTRTCAGGATGGAGYTCATAHCCCA + N (SEQ ID NO: 2779) | |
| 230 | GGYARYWBTATAGGYTGBACTGTCCAYYTRTCAGGATGGAGYTCATAACC + N (SEQ ID NO: 2780) | |
| 230 | +Y + TGK + ACTGTCCAYTTRTCAGGATGGAGYTCATAHCCCA (SEQ ID NO: 2781) | |
| 230 | +YTG + K + ACTGTCCAYTTRTCAGGATGGAGYTCATAHCCCA (SEQ ID NO: 2782) | |
| 230 | +Y + TG + KACTGTCCAYTTRTCAGGATGGAGYTCATAHCCCA (SEQ ID NO: 2783) | |
| 230 | +G + YTG + KACTGTCCAYTTRTCAGGATGGAGYTCATAHCCCA (SEQ ID NO: 2784) | |

TABLE 5 -continued

| | |
|---|---|
| 230 | +GY + TG + KACTGTCCAYTTRTCAGGATGGAGYTCATAHCCCA (SEQ ID NO: 2785) |
| 230 | +G + Y + TGKACTGTCCAYTTRTCAGGATGGAGYTCATAHCCCA (SEQ ID NO: 2786) |
| 230 | G + G + YTG + KACTGTCCAYTTRTCAGGATGGAGYTCATAHCCCA (SEQ ID NO: 2787) |
| 230 | GG + Y + TG + KACTGTCCAYTTRTCAGGATGGAGYTCATAHCCCA (SEQ ID NO: 2788) |
| 230 | +AC + TGT + CCAYTTRTCAGGATGGAGYTCATAHCCCA (SEQ ID NO: 2789) |
| 230 | +ACT + GT + CCAYTTRTCAGGATGGAGYTCATAHCCCA (SEQ ID NO: 2790) |
| 230 | +AC + T + GTCCAYTTRTCAGGATGGAGYTCATAHCCCA (SEQ ID NO: 2791) |
| 230 | +K + ACT + GTCCAYTTRTCAGGATGGAGYTCATAHCCCA (SEQ ID NO: 2792) |
| 230 | +KAC + T + GTCCAYTTRTCAGGATGGAGYTCATAHCCCA (SEQ ID NO: 2793) |
| 230 | +K + AC + TGTCCAYTTRTCAGGATGGAGYTCATAHCCCA (SEQ ID NO: 2794) |
| 230 | +TG + KAC + TGTCCAYTTRTCAGGATGGAGYTCATAHCCCA (SEQ ID NO: 2795) |
| 230 | +TGK + AC + TGTCCAYTTRTCAGGATGGAGYTCATAHCCCA (SEQ ID NO: 2796) |
| 230 | +TG + K + ACTGTCCAYTTRTCAGGATGGAGYTCATAHCCCA (SEQ ID NO: 2797) |
| 230 | +G + G + YTGKACTGTCCAYTTRTCAGGATGGAGYTCATAHCCCA (SEQ ID NO: 2798) |
| 238 | NTCYTTDTCTGGYARYWBTATAGGYTGKACTGTCCAY (SEQ ID NO: 2799) |
| 238 | TNTCYTTDTCTGGYARYWBTATAGGYTGKACTGTCCAY (SEQ ID NO: 2800) |
| 238 | GCTNTCYTTDTCTGGYARYWBTATAGGYTGKACTGTCCAY (SEQ ID NO: 2801) |
| 238 | TDTCTGGYARYWBTATAGGYTGKACTGTCCAY (SEQ ID NO: 2802) |
| 238 | CYTTDTCTGGYARYWBTATAGGYTGKACTGTCCAY (SEQ ID NO: 2803) |
| 238 | TCYTTDTCTGGYARYWBTATAGGYTGKACTGTCCAY (SEQ ID NO: 2804) |
| 238 | ATTGACAGTCCAGCTDTCYTTKTCTGGYARYWBTATAGGYTGBACTGTCCA (SEQ ID NO: 2805) |
| 238 | NTCYTTDTCTGGYARYWBTATAGGYTGKACTGTCCAY + N (SEQ ID NO: 2806) |
| 238 | TNTCYTTDTCTGGYARYWBTATAGGYTGKACTGTCCAY + N (SEQ ID NO: 2807) |
| 238 | GCTNTCYTTDTCTGGYARYWBTATAGGYTGKACTGTCCAY + N (SEQ ID NO: 2808) |
| 238 | TDTCTGGYARYWBTATAGGYTGKACTGTCCAY + N (SEQ ID NO: 2809) |
| 238 | CYTTDTCTGGYARYWBTATAGGYTGKACTGTCCAY + N (SEQ ID NO: 2810) |
| 238 | TCYTTDTCTGGYARYWBTATAGGYTGKACTGTCCAY + N (SEQ ID NO: 2811) |
| 238 | ATTGACAGTCCAGCTDTCYTTKTCTGGYARYWBTATAGGYTGBACTGTCCA + N (SEQ ID NO: 2812) |
| 238 | +N + TCYT + TDTCTGGYARYWBTATAGGYTGKACTGTCCAY (SEQ ID NO: 2813) |
| 238 | +NT + CYT + TDTCTGGYARYWBTATAGGYTGKACTGTCCAY (SEQ ID NO: 2814) |
| 238 | +N + T + CYTTDTCTGGYARYWBTATAGGYTGKACTGTCCAY (SEQ ID NO: 2815) |
| 238 | +T + NT + CYTTDTCTGGYARYWBTATAGGYTGKACTGTCCAY (SEQ ID NO: 2816) |

TABLE 5 -continued

| | |
|---|---|
| 238 | +TN + T + CYTTDTCTGGYARYWBTATAGGYTGKACTGTCCAY (SEQ ID NO: 2817) |
| 238 | +T + N + TCYTTDTCTGGYARYWBTATAGGYTGKACTGTCCAY (SEQ ID NO: 2818) |
| 238 | G + C + TN + TCYTTDTCTGGYARYWBTATAGGYTGKACTGTCCAY (SEQ ID NO: 2819) |
| 238 | G + CT + N + TCYTTDTCTGGYARYWBTATAGGYTGKACTGTCCAY (SEQ ID NO: 2820) |
| 238 | +TD + TCTGGYA + RYWBTATAGGYTGKACTGTCCAY (SEQ ID NO: 2821) |
| 238 | +TDT + CTGGYA + RYWBTATAGGYTGKACTGTCCAY (SEQ ID NO: 2822) |
| 238 | +TD + T + CTGGYARYWBTATAGGYTGKACTGTCCAY (SEQ ID NO: 2823) |
| 238 | +CYT + TDT + CTGGYARYWBTATAGGYTGKACTGTCCAY (SEQ ID NO: 2824) |
| 238 | +CYTTD + T + CTGGYARYWBTATAGGYTGKACTGTCCAY (SEQ ID NO: 2825) |
| 238 | +CYT + TD + TCTGGYARYWBTATAGGYTGKACTGTCCAY (SEQ ID NO: 2826) |
| 238 | +T + CYTTD + TCTGGYARYWBTATAGGYTGKACTGTCCAY (SEQ ID NO: 2827) |
| 238 | +TCYT + TD + TCTGGYARYWBTATAGGYTGKACTGTCCAY (SEQ ID NO: 2828) |
| 238 | +T + CYT + TDTCTGGYARYWBTATAGGYTGKACTGTCCAY (SEQ ID NO: 2829) |
| 238 | G + C + T + NTCYTTDTCTGGYARYWBTATAGGYTGKACTGTCCAY (SEQ ID NO: 2830) |
| 318 | TAYYTCWGCTAYYAADTCTTTTGWTGGRTCATA (SEQ ID NO: 2831) |
| 318 | YTTYTGTAYYTCWGCTAYYAADTCTTTTGWTGGRTCATA (SEQ ID NO: 2832) |
| 318 | GYTTYTGTAYYTCWGCTAYYAADTCTTTTGWTGGRTCATA (SEQ ID NO: 2833) |
| 318 | YCHWBYCCYTGYTTYTGTABTTCWGCTAYYAADTCTTTTGWTGGRTCATAAT (SEQ ID NO: 2834) |
| 318 | TAYYTCWGCTAYYAADTCTTTTGWTGGRTCATA + N (SEQ ID NO: 2835) |
| 318 | YTTYTGTAYYTCWGCTAYYAADTCTTTTGWTGGRTCATA + N (SEQ ID NO: 2836) |
| 318 | GYTTYTGTAYYTCWGCTAYYAADTCTTTTGWTGGRTCATA + N (SEQ ID NO: 2837) |
| 318 | YCHWBYCCYTGYTTYTGTABTTCWGCTAYYAADTCTTTTGWTGGRTCATAAT + N (SEQ ID NO: 2838) |
| 318 | +TAYYTCWGCTAYYAADTCTTTTGWTGGRTCATA (SEQ ID NO: 2839) |
| 318 | +YTTYTG + TAYYTCWGCTAYYAADTCTTTTGWTGGRTCATA (SEQ ID NO: 2840) |
| 318 | +YTTYTGTAYYTCWGCTAYYAADTCTTTTGWTGGRTCATA (SEQ ID NO: 2841) |
| 318 | G + YTTYTG + TAYYTCWGCTAYYAADTCTTTTGWTGGRTCATA (SEQ ID NO: 2842) |
| 318 | GYTTYTG + TAYYTCWGCTAYYAADTCTTTTGWTGGRTCATA (SEQ ID NO: 2843) |
| 318 | +G + YTTYTG + TAYYTCWGCTAYYAADTCTTTTGWTGGRTCATA (SEQ ID NO: 2844) |

Table 6 depicts amino acid substitutions in HIV-1 reverse transcriptase protein.

TABLE 6

| Codon | Single Letter Amino Acid Code | Amino Acid |
|---|---|---|
| 40 | F | Phenylalanine |
| 41 | L | Leucine |
| 44 | D | Aspartic acid |
| 44 | A | Alanine |
| 62 | V | Valine |
| 65 | R | Arginine |
| 65 | N | Asparagine |
| 67 | N | Asparagine |
| 67 | G | Glycine |
| 67 | E | Glutamic acid |
| 69 | ins | INSERTION |
| 69 | D | Aspartic acid |
| 69 | del | DELETION |
| 70 | E | Glutamic acid |
| 70 | G | Glycine |
| 70 | Q | Glutamine |
| 74 | V | Valine |
| 74 | I | Isoleucine |
| 75 | M | Methionine |
| 75 | T | Threonine |
| 75 | A | Alanine |
| 75 | S | Serine |
| 75 | I | Isoleucine |
| 77 | L | Leucine |
| 90 | I | Isoleucine |
| 98 | G | Glycine |
| 100 | I | Isoleucine |
| 101 | P | Proline |
| 101 | E | Glutamic acid |
| 101 | H | Histidine |
| 103 | N | Asparagine |
| 103 | S | Serine |
| 106 | A | Alanine |
| 106 | M | Methionine |
| 108 | I | Isoleucine |
| 115 | F | Phenylalanine |
| 116 | Y | Tyrosine |
| 118 | I | Isoleucine |
| 138 | K | Lysine |
| 138 | A | Alanine |
| 138 | G | Glycine |
| 138 | Q | Glutamine |
| 151 | M | Methionine |
| 179 | D | Aspartic acid |
| 179 | E | Glutamic acid |
| 179 | F | Phenylalanine |

TABLE 6-continued

| Codon | Single Letter Amino Acid Code | Amino Acid |
|---|---|---|
| 179 | T | Threonine |
| 179 | K | Lysine |
| 181 | C | Cysteine |
| 181 | I | Isoleucine |
| 181 | V | Valine |
| 184 | V | Valine |
| 184 | I | Isoleucine |
| 188 | L | Leucine |
| 188 | C | Cysteine |
| 188 | H | Histidine |
| 190 | A | Alanine |
| 190 | S | Serine |
| 190 | E | Glutamic acid |
| 190 | Q | Glutamine |
| 210 | W | Tryptophan |
| 215 | Y | Tyrosine |
| 215 | F | Phenylalanine |
| 215 | S | Serine |
| 215 | C | Cysteine |
| 215 | D | Aspartic acid |
| 215 | E | Glutamic acid |
| 215 | I | Isoleucine |
| 215 | V | Valine |
| 219 | Q | Glutamine |
| 219 | E | Glutamic acid |
| 219 | N | Asparagine |
| 219 | R | Arginine |
| 225 | H | Histidine |
| 227 | L | Leucine |
| 227 | C | Cysteine |
| 230 | L | Leucine |
| 238 | T | Threonine |
| 318 | F | Phenylalanine |

Table 7 depicts wild-type and mutant probes for the HIV-1 reverse transcriptase protein. A "+" symbol preceding a nucleotide denotes that the nucleotide is an LNA.

Lengthy table referenced here

US10100349-20181016-T00001

Please refer to the end of the specification for access instructions.

Table 8 depicts forward and reverse primers for the HIV-1 protease gene. A "+" symbol preceding a nucleotide denotes that the nucleotide is an LNA.

TABLE 8

| Codon | Forward Primer (5' to 3') |
|---|---|
| 10 | NHHRTATCCYTYRRCYTCCCTCARATCACTCTTTGGCARCGACCC (SEQ ID NO: 9976) |
| 10 | NHHRTATCCYTYRRCYTCCCTCARATCACTCTTTGGCARCGACCC + N (SEQ ID NO: 9977) |
| 11 | RTATCCYTYRRCYTCCCTCARATCACTCTTTGGCARCGACCCCTC (SEQ ID NO: 9978) |
| 11 | RTATCCYTYRRCYTCCCTCARATCACTCTTTGGCARCGACCCCTC + N (SEQ ID NO: 9979) |
| 20 | CTTTGGCARCGACCMNTHGTYDCARTAARRRTAGRRGGVCAACTA (SEQ ID NO: 9980) |
| 20 | CTTTGGCARCGACCMNTHGTYDCARTAARRRTAGRRGGVCAACTA + N (SEQ ID NO: 9981) |
| 23 | CGACCMNTHGTYDCARTAARRRTAGRRGGVCARHYRADRGAAGCT (SEQ ID NO: 9982) |
| 23 | CGACCMNTHGTYDCARTAARRRTAGRRGGVCARHYRADRGAAGCT + N (SEQ ID NO: 9983) |
| 24 | CCMNTHGTYDCARTAARRRTAGRRGGVCARHYRADRGARGCTCTA (SEQ ID NO: 9984) |

TABLE 8-continued

| Codon | |
|---|---|
| 24 | CCMNTHGTYDCARTAARRRTAGRRGGVCARHYRADRGARGCTCTA + N (SEQ ID NO: 9985) |
| 30 | RTAGRRGGVCARHYRADRGARGCYCTMTTAGAYACAGGAGCAGAT (SEQ ID NO: 9986) |
| 30 | RTAGRRGGVCARHYRADRGARGCYCTMTTAGAYACAGGAGCAGAT + N (SEQ ID NO: 9987) |
| 32 | GGVCARHYRADRGARGCYCTMTTAGAYACAGGAGCAGATGATACA (SEQ ID NO: 9988) |
| 32 | GGVCARHYRADRGARGCYCTMTTAGAYACAGGAGCAGATGATACA + N (SEQ ID NO: 9989) |
| 33 | CARHYRADRGARGCYCTMTTAGAYACAGGAGCAGATGATACAGTA (SEQ ID NO: 9990) |
| 33 | CARHYRADRGARGCYCTMTTAGAYACAGGAGCAGATGATACAGTA + N (SEQ ID NO: 9991) |
| 43 | GCAGATGATACAGTATTAGAAGAHATRRRKTTRCCAGGRAAATGG (SEQ ID NO: 9992) |
| 43 | GCAGATGATACAGTATTAGAAGAHATRRRKTTRCCAGGRAAATGG + N (SEQ ID NO: 9993) |
| 46 | ACAGTATTAGAAGAHATRRRKTTRCCAGGRARATGGAARCCAAAA (SEQ ID NO: 9994) |
| 46 | ACAGTATTAGAAGAHATRRRKTTRCCAGGRARATGGAARCCAAAA + N (SEQ ID NO: 9995) |
| 47 | AGAAGAHATRRRWT + TRCCA + G + GRARATGGAAACCAARAATG (SEQ ID NO: 9996) |
| 47 | AGAAGAHATRRRWT + TRCCAG + GRARA + TGGAAACCAARAATG (SEQ ID NO: 9997) |
| 47 | AGAAGAHATRRRWT + TRCCA + GGRARA + TGGAAACCAARAATG (SEQ ID NO: 9998) |
| 47 | +G + GRARA + TGGAAACCAARAATG (SEQ ID NO: 9999) |
| 47 | +GGRARA + T + GGAAACCAARAATG (SEQ ID NO: 10000) |
| 47 | +G + GRARAT + GGAAACCAARAATG (SEQ ID NO: 10001) |
| 47 | AGAAGAHATRRRWTTRCCAGGRARATGGAAACCAARAATG (SEQ ID NO: 10002) |
| 47 | GGRARATGGAAACCAARAATG (SEQ ID NO: 10003) |
| 47 | GTATTAGAAGAHATRRRKTTRCCAGGRARATGGAARCCAAAAATG (SEQ ID NO: 10004) |
| 47 | AGAAGAHATRRRWTTRCCAGGRARATGGAAACCAARAATG + N (SEQ ID NO: 10005) |
| 47 | GGRARATGGAAACCAARAATG + N (SEQ ID NO: 10006) |
| 47 | GTATTAGAAGAHATRRRKTTRCCAGGRARATGGAARCCAAAAATG + N (SEQ ID NO: 10007) |
| 48 | TTAGAAGAHATRRRKTTRCCAGGRARATGGAARCCAAAAATGATA (SEQ ID NO: 10008) |
| 48 | TTAGAAGAHATRRRKTTRCCAGGRARATGGAARCCAAAAATGATA + N (SEQ ID NO: 10009) |
| 50 | RRRWT + TRCCA + G + GRARATGGAAACCAARAATGATAGGRGGA (SEQ ID NO: 10010) |
| 50 | RRRWT + TRCCAG + GRARA + TGGAAACCAARAATGATAGGRGGA (SEQ ID NO: 10011) |
| 50 | RRRWT + TRCCA + GGRARA + TGGAAACCAARAATGATAGGRGGA (SEQ ID NO: 10012) |
| 50 | +G + GRARA + TGGAAACCAARAATGATAGGRGGA (SEQ ID NO: 10013) |
| 50 | +GGRARA + T + GGAAACCAARAATGATAGGRGGA (SEQ ID NO: 10014) |
| 50 | +G + GRARAT + GGAAACCAARAATGATAGGRGGA (SEQ ID NO: 10015) |
| 50 | +GRARA + T + GGAAACCAARAATGATAGGRGGA (SEQ ID NO: 10016) |
| 50 | +GRARAT + G + GAAACCAARAATGATAGGRGGA (SEQ ID NO: 10017) |
| 50 | +GRARA + TG + GAAACCAARAATGATAGGRGGA (SEQ ID NO: 10018) |
| 50 | +T + G + GAAACCAARAATGATAGGRGGA (SEQ ID NO: 10019) |
| 50 | +TG + G + AAACCAARAATGATAGGRGGA (SEQ ID NO: 10020) |
| 50 | +T + GG + AAACCAARAATGATAGGRGGA (SEQ ID NO: 10021) |
| 50 | +G + G + AAACCAARAATGATAGGRGGA (SEQ ID NO: 10022) |
| 50 | +GG + AAA + CCAARAATGATAGGRGGA (SEQ ID NO: 10023) |

TABLE 8-continued

| Codon | |
|---|---|
| 50 | +G + GAAA + CCAARAATGATAGGRGGA (SEQ ID NO: 10024) |
| 50 | +G + AAA + CCAARAATGATAGGRGGA (SEQ ID NO: 10025) |
| 50 | +GAAA + C + CAARAATGATAGGRGGA (SEQ ID NO: 10026) |
| 50 | +G + AAAC + CAARAATGATAGGRGGA (SEQ ID NO: 10027) |
| 50 | RRRWTTRCCAGGRARATGGAAACCAARAATGATAGGRGGA (SEQ ID NO: 10028) |
| 50 | GGRARATGGAAACCAARAATGATAGGRGGA (SEQ ID NO: 10029) |
| 50 | GRARATGGAAACCAARAATGATAGGRGGA (SEQ ID NO: 10030) |
| 50 | TGGAAACCAARAATGATAGGRGGA (SEQ ID NO: 10031) |
| 50 | GGAAACCAARAATGATAGGRGGA (SEQ ID NO: 10032) |
| 50 | GAAACCAARAATGATAGGRGGA (SEQ ID NO: 10033) |
| 50 | GAHATRRRKTTRCCAGGRARATGGAARCCAAAAATRATAGGGGGA (SEQ ID NO: 10034) |
| 50 | RRRWTTRCCAGGRARATGGAAACCAARAATGATAGGRGGA + N (SEQ ID NO: 10035) |
| 50 | GGRARATGGAAACCAARAATGATAGGRGGA + N (SEQ ID NO: 10036) |
| 50 | GRARATGGAAACCAARAATGATAGGRGGA + N (SEQ ID NO: 10037) |
| 50 | TGGAAACCAARAATGATAGGRGGA + N (SEQ ID NO: 10038) |
| 50 | GGAAACCAARAATGATAGGRGGA + N (SEQ ID NO: 10039) |
| 50 | GAAACCAARAATGATAGGRGGA + N (SEQ ID NO: 10040) |
| 50 | GAHATRRRKTTRCCAGGRARATGGAARCCAAAAATRATAGGGGGA + N (SEQ ID NO: 10041) |
| 53 | +GRARA + T + GGAAACCAARAATGATAGGRGGAATTGGAGGYTT (SEQ ID NO: 10042) |
| 53 | +GRARAT + G + GAAACCAARAATGATAGGRGGAATTGGAGGYTT (SEQ ID NO: 10043) |
| 53 | +GRARA + TG + GAAACCAARAATGATAGGRGGAATTGGAGGYTT (SEQ ID NO: 10044) |
| 53 | +T + G + GAAACCAARAATGATAGGRGGAATTGGAGGYTT (SEQ ID NO: 10045) |
| 53 | +TG + G + AAACCAARAATGATAGGRGGAATTGGAGGYTT (SEQ ID NO: 10046) |
| 53 | +T + GG + AAACCAARAATGATAGGRGGAATTGGAGGYTT (SEQ ID NO: 10047) |
| 53 | +G + G + AAACCAARAATGATAGGRGGAATTGGAGGYTT (SEQ ID NO: 10048) |
| 53 | +GG + AAA + CCAARAATGATAGGRGGAATTGGAGGYTT (SEQ ID NO: 10049) |
| 53 | +G + GAAA + CCAARAATGATAGGRGGAATTGGAGGYTT (SEQ ID NO: 10050) |
| 53 | +G + AAA + CCAARAATGATAGGRGGAATTGGAGGYTT (SEQ ID NO: 10051) |
| 53 | +GAAA + C + CAARAATGATAGGRGGAATTGGAGGYTT (SEQ ID NO: 10052) |
| 53 | +G + AAAC + CAARAATGATAGGRGGAATTGGAGGYTT (SEQ ID NO: 10053) |
| 53 | +AAA + C + CAARAATGATAGGRGGAATTGGAGGYTT (SEQ ID NO: 10054) |
| 53 | +AAAC + CA + ARAATGATAGGRGGAATTGGAGGYTT (SEQ ID NO: 10055) |
| 53 | +AAA + CCA + ARAATGATAGGRGGAATTGGAGGYTT (SEQ ID NO: 10056) |
| 53 | +C + CA + ARAATGATAGGRGGAATTGGAGGYTT (SEQ ID NO: 10057) |
| 53 | +CCA + ARAA + TGATAGGRGGAATTGGAGGYTT (SEQ ID NO: 10058) |
| 53 | +C + CAARAA + TGATAGGRGGAATTGGAGGYTT (SEQ ID NO: 10059) |
| 53 | +G + GRARA + TGGAAACCAARAATGATAGGRGGAATTGGAGGYT (SEQ ID NO: 10060) |
| 53 | +GGRARA + T + GGAAACCAARAATGATAGGRGGAATTGGAGGYT (SEQ ID NO: 10061) |
| 53 | +G + GRARAT + GGAAACCAARAATGATAGGRGGAATTGGAGGYT (SEQ ID NO: 10062) |

TABLE 8-continued

| Codon | |
|---|---|
| 53 | +GRARA + T + GGAAACCAARAATGATAGGRGGAATTGGAGGYT (SEQ ID NO: 10063) |
| 53 | +GRARAT + G + GAAACCAARAATGATAGGRGGAATTGGAGGYT (SEQ ID NO: 10064) |
| 53 | +GRARA + TG + GAAACCAARAATGATAGGRGGAATTGGAGGYT (SEQ ID NO: 10065) |
| 53 | +T + G + GAAACCAARAATGATAGGRGGAATTGGAGGYT (SEQ ID NO: 10066) |
| 53 | +TG + G + AAACCAARAATGATAGGRGGAATTGGAGGYT (SEQ ID NO: 10067) |
| 53 | +T + GG + AAACCAARAATGATAGGRGGAATTGGAGGYT (SEQ ID NO: 10068) |
| 53 | +G + G + AAACCAARAATGATAGGRGGAATTGGAGGYT (SEQ ID NO: 10069) |
| 53 | +GG + AAA + CCAARAATGATAGGRGGAATTGGAGGYT (SEQ ID NO: 10070) |
| 53 | +G + GAAA + CCAARAATGATAGGRGGAATTGGAGGYT (SEQ ID NO: 10071) |
| 53 | +G + AAA + CCAARAATGATAGGRGGAATTGGAGGYT (SEQ ID NO: 10072) |
| 53 | +GAAA + C + CAARAATGATAGGRGGAATTGGAGGYT (SEQ ID NO: 10073) |
| 53 | +G + AAAC + CAARAATGATAGGRGGAATTGGAGGYT (SEQ ID NO: 10074) |
| 53 | +AAA + C + CAARAATGATAGGRGGAATTGGAGGYT (SEQ ID NO: 10075) |
| 53 | +AAAC + CA + ARAATGATAGGRGGAATTGGAGGYT (SEQ ID NO: 10076) |
| 53 | +AAA + CCA + ARAATGATAGGRGGAATTGGAGGYT (SEQ ID NO: 10077) |
| 53 | GRARATGGAAACCAARAATGATAGGRGGAATTGGAGGYTT (SEQ ID NO: 10078) |
| 53 | TGGAAACCAARAATGATAGGRGGAATTGGAGGYTT (SEQ ID NO: 10079) |
| 53 | GGAAACCAARAATGATAGGRGGAATTGGAGGYTT (SEQ ID NO: 10080) |
| 53 | GAAACCAARAATGATAGGRGGAATTGGAGGYTT (SEQ ID NO: 10081) |
| 53 | AAACCAARAATGATAGGRGGAATTGGAGGYTT (SEQ ID NO: 10082) |
| 53 | CCAARAATGATAGGRGGAATTGGAGGYTT (SEQ ID NO: 10083) |
| 53 | GGRARATGGAAACCAARAATGATAGGRGGAATTGGAGGYT (SEQ ID NO: 10084) |
| 53 | GRARATGGAAACCAARAATGATAGGRGGAATTGGAGGYT (SEQ ID NO: 10085) |
| 53 | TGGAAACCAARAATGATAGGRGGAATTGGAGGYT (SEQ ID NO: 10086) |
| 53 | GGAAACCAARAATGATAGGRGGAATTGGAGGYT (SEQ ID NO: 10087) |
| 53 | GAAACCAARAATGATAGGRGGAATTGGAGGYT (SEQ ID NO: 10088) |
| 53 | AAACCAARAATGATAGGRGGAATTGGAGGYT (SEQ ID NO: 10089) |
| 53 | TTRCCAGGRARATGGAARCCAAAAATRATAGGRGGAATTGGAGGT (SEQ ID NO: 10090) |
| 53 | GRARATGGAAACCAARAATGATAGGRGGAATTGGAGGYTT + N (SEQ ID NO: 10091) |
| 53 | TGGAAACCAARAATGATAGGRGGAATTGGAGGYTT + N (SEQ ID NO: 10092) |
| 53 | GGAAACCAARAATGATAGGRGGAATTGGAGGYTT + N (SEQ ID NO: 10093) |
| 53 | GAAACCAARAATGATAGGRGGAATTGGAGGYTT + N (SEQ ID NO: 10094) |
| 53 | AAACCAARAATGATAGGRGGAATTGGAGGYTT + N (SEQ ID NO: 10095) |
| 53 | CCAARAATGATAGGRGGAATTGGAGGYTT + N (SEQ ID NO: 10096) |
| 53 | GGRARATGGAAACCAARAATGATAGGRGGAATTGGAGGYT + N (SEQ ID NO: 10097) |
| 53 | GRARATGGAAACCAARAATGATAGGRGGAATTGGAGGYT + N (SEQ ID NO: 10098) |
| 53 | TGGAAACCAARAATGATAGGRGGAATTGGAGGYT + N (SEQ ID NO: 10099) |
| 53 | GGAAACCAARAATGATAGGRGGAATTGGAGGYT + N (SEQ ID NO: 10100) |
| 53 | GAAACCAARAATGATAGGRGGAATTGGAGGYT + N (SEQ ID NO: 10101) |

TABLE 8-continued

| Codon | |
|---|---|
| 53 | AAACCAARAATGATAGGRGGAATTGGAGGYT + N (SEQ ID NO: 10102) |
| 53 | TTRCCAGGRARATGGAARCCAAAAATRATAGGRGGAATTGGAGGT + N (SEQ ID NO: 10103) |
| 54 | RA + T + G + GAAACCAARAATGATAGGRGGAATTGGAGGYTTTAT (SEQ ID NO: 10104) |
| 54 | RA + TG + G + AAACCAARAATGATAGGRGGAATTGGAGGYTTTAT (SEQ ID NO: 10105) |
| 54 | RA + T + GG + AAACCAARAATGATAGGRGGAATTGGAGGYTTTAT (SEQ ID NO: 10106) |
| 54 | +G + G + AAACCAARAATGATAGGRGGAATTGGAGGYTTTAT (SEQ ID NO: 10107) |
| 54 | +GG + AAA + CCAARAATGATAGGRGGAATTGGAGGYTTTAT (SEQ ID NO: 10108) |
| 54 | +G + GAAA + CCAARAATGATAGGRGGAATTGGAGGYTTTAT (SEQ ID NO: 10109) |
| 54 | +G + AAA + CCAARAATGATAGGRGGAATTGGAGGYTTTAT (SEQ ID NO: 10110) |
| 54 | +GAAA + C + CAARAATGATAGGRGGAATTGGAGGYTTTAT (SEQ ID NO: 10111) |
| 54 | +G + AAAC + CAARAATGATAGGRGGAATTGGAGGYTTTAT (SEQ ID NO: 10112) |
| 54 | +AAA + C + CAARAATGATAGGRGGAATTGGAGGYTTTAT (SEQ ID NO: 10113) |
| 54 | +AAAC + CA + ARAATGATAGGRGGAATTGGAGGYTTTAT (SEQ ID NO: 10114) |
| 54 | +AAA + CCA + ARAATGATAGGRGGAATTGGAGGYTTTAT (SEQ ID NO: 10115) |
| 54 | +C + CA + ARAATGATAGGRGGAATTGGAGGYTTTAT (SEQ ID NO: 10116) |
| 54 | +CCA + ARAA + TGATAGGRGGAATTGGAGGYTTTAT (SEQ ID NO: 10117) |
| 54 | +C + CAARAA + TGATAGGRGGAATTGGAGGYTTTAT (SEQ ID NO: 10118) |
| 54 | +CA + ARAA + TGATAGGRGGAATTGGAGGYTTTAT (SEQ ID NO: 10119) |
| 54 | +CAARAA + TG + ATAGGRGGAATTGGAGGYTTTAT (SEQ ID NO: 10120) |
| 54 | +CA + ARAATG + ATAGGRGGAATTGGAGGYTTTAT (SEQ ID NO: 10121) |
| 54 | ARA + T + G + GAAACCAARAATGATAGGRGGAATTGGAGGYTTTA (SEQ ID NO: 10122) |
| 54 | ARA + TG + G + AAACCAARAATGATAGGRGGAATTGGAGGYTTTA (SEQ ID NO: 10123) |
| 54 | ARA + T + GG + AAACCAARAATGATAGGRGGAATTGGAGGYTTTA (SEQ ID NO: 10124) |
| 54 | +G + G + AAACCAARAATGATAGGRGGAATTGGAGGYTTTA (SEQ ID NO: 10125) |
| 54 | +GG + AAA + CCAARAATGATAGGRGGAATTGGAGGYTTTA (SEQ ID NO: 10126) |
| 54 | +G + GAAA + CCAARAATGATAGGRGGAATTGGAGGYTTTA (SEQ ID NO: 10127) |
| 54 | +G + AAA + CCAARAATGATAGGRGGAATTGGAGGYTTTA (SEQ ID NO: 10128) |
| 54 | +GAAA + C + CAARAATGATAGGRGGAATTGGAGGYTTTA (SEQ ID NO: 10129) |
| 54 | +G + AAAC + CAARAATGATAGGRGGAATTGGAGGYTTTA (SEQ ID NO: 10130) |
| 54 | +AAA + C + CAARAATGATAGGRGGAATTGGAGGYTTTA (SEQ ID NO: 10131) |
| 54 | +AAAC + CA + ARAATGATAGGRGGAATTGGAGGYTTTA (SEQ ID NO: 10132) |
| 54 | +AAA + CCA + ARAATGATAGGRGGAATTGGAGGYTTTA (SEQ ID NO: 10133) |
| 54 | +C + CA + ARAATGATAGGRGGAATTGGAGGYTTTA (SEQ ID NO: 10134) |
| 54 | +CCA + ARAA + TGATAGGRGGAATTGGAGGYTTTA (SEQ ID NO: 10135) |
| 54 | +C + CAARAA + TGATAGGRGGAATTGGAGGYTTTA (SEQ ID NO: 10136) |
| 54 | +CA + ARAA + TGATAGGRGGAATTGGAGGYTTTA (SEQ ID NO: 10137) |
| 54 | +CAARAA + TG + ATAGGRGGAATTGGAGGYTTTA (SEQ ID NO: 10138) |
| 54 | +CA + ARAATG + ATAGGRGGAATTGGAGGYTTTA (SEQ ID NO: 10139) |
| 54 | RARA + T + G + GAAACCAARAATGATAGGRGGAATTGGAGGYTTT (SEQ ID NO: 10140) |

TABLE 8-continued

| Codon | |
|---|---|
| 54 | RARA + TG + G + AAACCAARAATGATAGGRGGAATTGGAGGYTTT (SEQ ID NO: 10141) |
| 54 | RARA + T + GG + AAACCAARAATGATAGGRGGAATTGGAGGYTTT (SEQ ID NO: 10142) |
| 54 | +G + G + AAACCAARAATGATAGGRGGAATTGGAGGYTTT (SEQ ID NO: 10143) |
| 54 | +GG + AAA + CCAARAATGATAGGRGGAATTGGAGGYTTT (SEQ ID NO: 10144) |
| 54 | +G + GAAA + CCAARAATGATAGGRGGAATTGGAGGYTTT (SEQ ID NO: 10145) |
| 54 | +G + AAA + CCAARAATGATAGGRGGAATTGGAGGYTTT (SEQ ID NO: 10146) |
| 54 | +GAAA + C + CAARAATGATAGGRGGAATTGGAGGYTTT (SEQ ID NO: 10147) |
| 54 | +G + AAAC + CAARAATGATAGGRGGAATTGGAGGYTTT (SEQ ID NO: 10148) |
| 54 | +AAA + C + CAARAATGATAGGRGGAATTGGAGGYTTT (SEQ ID NO: 10149) |
| 54 | +AAAC + CA + ARAATGATAGGRGGAATTGGAGGYTTT (SEQ ID NO: 10150) |
| 54 | +AAA + CCA + ARAATGATAGGRGGAATTGGAGGYTTT (SEQ ID NO: 10151) |
| 54 | +C + CA + ARAATGATAGGRGGAATTGGAGGYTTT (SEQ ID NO: 10152) |
| 54 | +CCA + ARAA + TGATAGGRGGAATTGGAGGYTTT (SEQ ID NO: 10153) |
| 54 | +C + CAARAA + TGATAGGRGGAATTGGAGGYTTT (SEQ ID NO: 10154) |
| 54 | +CA + ARAA + TGATAGGRGGAATTGGAGGYTTT (SEQ ID NO: 10155) |
| 54 | +CAARAA + TG + ATAGGRGGAATTGGAGGYTTT (SEQ ID NO: 10156) |
| 54 | +CA + ARAATG + ATAGGRGGAATTGGAGGYTTT (SEQ ID NO: 10157) |
| 54 | RATGGAAACCAARAATGATAGGRGGAATTGGAGGYTTTAT (SEQ ID NO: 10158) |
| 54 | GGAAACCAARAATGATAGGRGGAATTGGAGGYTTTAT (SEQ ID NO: 10159) |
| 54 | GAAACCAARAATGATAGGRGGAATTGGAGGYTTTAT (SEQ ID NO: 10160) |
| 54 | AAACCAARAATGATAGGRGGAATTGGAGGYTTTAT (SEQ ID NO: 10161) |
| 54 | CCAARAATGATAGGRGGAATTGGAGGYTTTAT (SEQ ID NO: 10162) |
| 54 | CAARAATGATAGGRGGAATTGGAGGYTTTAT (SEQ ID NO: 10163) |
| 54 | ARATGGAAACCAARAATGATAGGRGGAATTGGAGGYTTTA (SEQ ID NO: 10164) |
| 54 | GGAAACCAARAATGATAGGRGGAATTGGAGGYTTTA (SEQ ID NO: 10165) |
| 54 | GAAACCAARAATGATAGGRGGAATTGGAGGYTTTA (SEQ ID NO: 10166) |
| 54 | AAACCAARAATGATAGGRGGAATTGGAGGYTTTA (SEQ ID NO: 10167) |
| 54 | CCAARAATGATAGGRGGAATTGGAGGYTTTA (SEQ ID NO: 10168) |
| 54 | CAARAATGATAGGRGGAATTGGAGGYTTTA (SEQ ID NO: 10169) |
| 54 | RARATGGAAACCAARAATGATAGGRGGAATTGGAGGYTTT (SEQ ID NO: 10170) |
| 54 | GGAAACCAARAATGATAGGRGGAATTGGAGGYTTT (SEQ ID NO: 10171) |
| 54 | GAAACCAARAATGATAGGRGGAATTGGAGGYTTT (SEQ ID NO: 10172) |
| 54 | AAACCAARAATGATAGGRGGAATTGGAGGYTTT (SEQ ID NO: 10173) |
| 54 | CCAARAATGATAGGRGGAATTGGAGGYTTT (SEQ ID NO: 10174) |
| 54 | CAARAATGATAGGRGGAATTGGAGGYTTT (SEQ ID NO: 10175) |
| 54 | CCAGGRARATGGAARCCAAAAATRATAGGRGGAATTGGAGGTTTT (SEQ ID NO: 10176) |
| 54 | RATGGAAACCAARAATGATAGGRGGAATTGGAGGYTTTAT + N (SEQ ID NO: 10177) |
| 54 | GGAAACCAARAATGATAGGRGGAATTGGAGGYTTTAT + N (SEQ ID NO: 10178) |
| 54 | GAAACCAARAATGATAGGRGGAATTGGAGGYTTTAT + N (SEQ ID NO: 10179) |

TABLE 8-continued

| Codon | |
|---|---|
| 54 | AAACCAARAATGATAGGRGGAATTGGAGGYTTTAT + N (SEQ ID NO: 10180) |
| 54 | CCAARAATGATAGGRGGAATTGGAGGYTTTAT + N (SEQ ID NO: 10181) |
| 54 | CAARAATGATAGGRGGAATTGGAGGYTTTAT + N (SEQ ID NO: 10182) |
| 54 | ARATGGAAACCAARAATGATAGGRGGAATTGGAGGYTTTA + N (SEQ ID NO: 10183) |
| 54 | GGAAACCAARAATGATAGGRGGAATTGGAGGYTTTA + N (SEQ ID NO: 10184) |
| 54 | GAAACCAARAATGATAGGRGGAATTGGAGGYTTTA + N (SEQ ID NO: 10185) |
| 54 | AAACCAARAATGATAGGRGGAATTGGAGGYTTTA + N (SEQ ID NO: 10186) |
| 54 | CCAARAATGATAGGRGGAATTGGAGGYTTTA + N (SEQ ID NO: 10187) |
| 54 | CAARAATGATAGGRGGAATTGGAGGYTTTA + N (SEQ ID NO: 10188) |
| 54 | RARATGGAAACCAARAATGATAGGRGGAATTGGAGGYTTT + N (SEQ ID NO: 10189) |
| 54 | GGAAACCAARAATGATAGGRGGAATTGGAGGYTTT + N (SEQ ID NO: 10190) |
| 54 | GAAACCAARAATGATAGGRGGAATTGGAGGYTTT + N (SEQ ID NO: 10191) |
| 54 | AAACCAARAATGATAGGRGGAATTGGAGGYTTT + N (SEQ ID NO: 10192) |
| 54 | CCAARAATGATAGGRGGAATTGGAGGYTTT + N (SEQ ID NO: 10193) |
| 54 | CAARAATGATAGGRGGAATTGGAGGYTTT + N (SEQ ID NO: 10194) |
| 54 | CCAGGRARATGGAARCCAAAAATRATAGGRGGAATTGGAGGTTTT + N (SEQ ID NO: 10195) |
| 58 | A + ARAA + TG + ATAGGRGGAATTGGAGGYTTTATYAARGTAARR (SEQ ID NO: 10196) |
| 58 | A + ARAATG + A + TAGGRGGAATTGGAGGYTTTATYAARGTAARR (SEQ ID NO: 10197) |
| 58 | A + ARAA + TGA + TAGGRGGAATTGGAGGYTTTATYAARGTAARR (SEQ ID NO: 10198) |
| 58 | +TG + A + TAGGRGGAATTGGAGGYTTTATYAARGTAARR (SEQ ID NO: 10199) |
| 58 | +TGA + T + AGGRGGAATTGGAGGYTTTATYAARGTAARR (SEQ ID NO: 10200) |
| 58 | +TG + AT + AGGRGGAATTGGAGGYTTTATYAARGTAARR (SEQ ID NO: 10201) |
| 58 | +A + T + AGGRGGAATTGGAGGYTTTATYAARGTAARR (SEQ ID NO: 10202) |
| 58 | +AT + A + GGRGGAATTGGAGGYTTTATYAARGTAARR (SEQ ID NO: 10203) |
| 58 | +A + TA + GGRGGAATTGGAGGYTTTATYAARGTAARR (SEQ ID NO: 10204) |
| 58 | +T + A + GGRGGAATTGGAGGYTTTATYAARGTAARR (SEQ ID NO: 10205) |
| 58 | +TA + G + GRGGAATTGGAGGYTTTATYAARGTAARR (SEQ ID NO: 10206) |
| 58 | +T + AG + GRGGAATTGGAGGYTTTATYAARGTAARR (SEQ ID NO: 10207) |
| 58 | +A + G + GRGGAATTGGAGGYTTTATYAARGTAARR (SEQ ID NO: 10208) |
| 58 | +AG + GR + GGAATTGGAGGYTTTATYAARGTAARR (SEQ ID NO: 10209) |
| 58 | +A + GGR + GGAATTGGAGGYTTTATYAARGTAARR (SEQ ID NO: 10210) |
| 58 | +G + GR + GGAATTGGAGGYTTTATYAARGTAARR (SEQ ID NO: 10211) |
| 58 | +GGR + G + GAATTGGAGGYTTTATYAARGTAARR (SEQ ID NO: 10212) |
| 58 | +G + GRG + GAATTGGAGGYTTTATYAARGTAARR (SEQ ID NO: 10213) |
| 58 | AARAATGATAGGRGGAATTGGAGGYTTTATYAARGTAARR (SEQ ID NO: 10214) |
| 58 | TGATAGGRGGAATTGGAGGYTTTATYAARGTAARR (SEQ ID NO: 10215) |
| 58 | ATAGGRGGAATTGGAGGYTTTATYAARGTAARR (SEQ ID NO: 10216) |
| 58 | TAGGRGGAATTGGAGGYTTTATYAARGTAARR (SEQ ID NO: 10217) |
| 58 | AGGRGGAATTGGAGGYTTTATYAARGTAARR (SEQ ID NO: 10218) |

TABLE 8-continued

| Codon | |
|---|---|
| 58 | GGRGGAATTGGAGGYTTTATYAARGTAARR (SEQ ID NO: 10219) |
| 58 | AARCCAAAAATRATAGGRGGAATTGGAGGYTTTRTYAAAGTAAGA (SEQ ID NO: 10220) |
| 58 | AARAATGATAGGRGGAATTGGAGGYTTTATYAARGTAARR + N (SEQ ID NO: 10221) |
| 58 | TGATAGGRGGAATTGGAGGYTTTATYAARGTAARR + N (SEQ ID NO: 10222) |
| 58 | ATAGGRGGAATTGGAGGYTTTATYAARGTAARR + N (SEQ ID NO: 10223) |
| 58 | TAGGRGGAATTGGAGGYTTTATYAARGTAARR + N (SEQ ID NO: 10224) |
| 58 | AGGRGGAATTGGAGGYTTTATYAARGTAARR + N (SEQ ID NO: 10225) |
| 58 | GGRGGAATTGGAGGYTTTATYAARGTAARR + N (SEQ ID NO: 10226) |
| 58 | AARCCAAAAATRATAGGRGGAATTGGAGGYTTTRTYAAAGTAAGA + N (SEQ ID NO: 10227) |
| 71 | RC + AR + T + ATGAKSARRTANYYATAGAAATYTGTGGRMAWARR (SEQ ID NO: 10228) |
| 71 | RC + ART + AT + GAKSARRTANYYATAGAAATYTGTGGRMAWARR (SEQ ID NO: 10229) |
| 71 | RC + AR + TAT + GAKSARRTANYYATAGAAATYTGTGGRMAWARR (SEQ ID NO: 10230) |
| 71 | +T + AT + GAKSARRTANYYATAGAAATYTGTGGRMAWARR (SEQ ID NO: 10231) |
| 71 | +TAT + G + AKSARRTANYYATAGAAATYTGTGGRMAWARR (SEQ ID NO: 10232) |
| 71 | +T + ATG + AKSARRTANYYATAGAAATYTGTGGRMAWARR (SEQ ID NO: 10233) |
| 71 | +AT + G + AKSARRTANYYATAGAAATYTGTGGRMAWARR (SEQ ID NO: 10234) |
| 71 | +ATG + AKS + ARRTANYYATAGAAATYTGTGGRMAWARR (SEQ ID NO: 10235) |
| 71 | +AT + GAKS + ARRTANYYATAGAAATYTGTGGRMAWARR (SEQ ID NO: 10236) |
| 71 | +G + AKS + ARRTANYYATAGAAATYTGTGGRMAWARR (SEQ ID NO: 10237) |
| 71 | +GAKS + ARR + TANYYATAGAAATYTGTGGRMAWARR (SEQ ID NO: 10238) |
| 71 | +G + AKSARR + TANYYATAGAAATYTGTGGRMAWARR (SEQ ID NO: 10239) |
| 71 | +AKS + ARR + TANYYATAGAAATYTGTGGRMAWARR (SEQ ID NO: 10240) |
| 71 | +AKSARR + TANYYA + TAGAAATYTGTGGRMAWARR (SEQ ID NO: 10241) |
| 71 | +AKS + ARRTANYYA + TAGAAATYTGTGGRMAWARR (SEQ ID NO: 10242) |
| 71 | +ARR + TANYYA + TAGAAATYTGTGGRMAWARR (SEQ ID NO: 10243) |
| 71 | +ARRTANYYA + TA + GAAATYTGTGGRMAWARR (SEQ ID NO: 10244) |
| 71 | +ARR + TANYYATA + GAAATYTGTGGRMAWARR (SEQ ID NO: 10245) |
| 71 | RCARTATGAKSARRTANYYATAGAAATYTGTGGRMAWARR (SEQ ID NO: 10246) |
| 71 | TATGAKSARRTANYYATAGAAATYTGTGGRMAWARR (SEQ ID NO: 10247) |
| 71 | ATGAKSARRTANYYATAGAAATYTGTGGRMAWARR (SEQ ID NO: 10248) |
| 71 | GAKSARRTANYYATAGAAATYTGTGGRMAWARR (SEQ ID NO: 10249) |
| 71 | AKSARRTANYYATAGAAATYTGTGGRMAWARR (SEQ ID NO: 10250) |
| 71 | ARRTANYYATAGAAATYTGTGGRMAWARR (SEQ ID NO: 10251) |
| 71 | GTAARRCARTATGAKSAVRTANHHRTAGARATYTGYGGRCATAAA (SEQ ID NO: 10252) |
| 71 | RCARTATGAKSARRTANYYATAGAAATYTGTGGRMAWARR + N (SEQ ID NO: 10253) |
| 71 | TATGAKSARRTANYYATAGAAATYTGTGGRMAWARR + N (SEQ ID NO: 10254) |
| 71 | ATGAKSARRTANYYATAGAAATYTGTGGRMAWARR + N (SEQ ID NO: 10255) |
| 71 | GAKSARRTANYYATAGAAATYTGTGGRMAWARR + N (SEQ ID NO: 10256) |
| 71 | AKSARRTANYYATAGAAATYTGTGGRMAWARR + N (SEQ ID NO: 10257) |

TABLE 8-continued

| Codon | |
|---|---|
| 71 | ARRTANYYATAGAAATYTGTGGRMAWARR + N (SEQ ID NO: 10258) |
| 71 | GTAARRCARTATGAKSAVRTANHHRTAGARATYTGYGGRCATAAA + N (SEQ ID NO: 10259) |
| 73 | +G + AKS + ARRTANYYATAGAAATYTGTGGRMAWARRGCYATAG (SEQ ID NO: 10260) |
| 73 | +GAKS + ARR + TANYYATAGAAATYTGTGGRMAWARRGCYATAG (SEQ ID NO: 10261) |
| 73 | +G + AKSARR + TANYYATAGAAATYTGTGGRMAWARRGCYATAG (SEQ ID NO: 10262) |
| 73 | +AKS + ARR + TANYYATAGAAATYTGTGGRMAWARRGCYATAG (SEQ ID NO: 10263) |
| 73 | +AKSARR + TANYYA + TAGAAATYTGTGGRMAWARRGCYATAG (SEQ ID NO: 10264) |
| 73 | +AKS + ARRTANYYA + TAGAAATYTGTGGRMAWARRGCYATAG (SEQ ID NO: 10265) |
| 73 | +ARR + TANYYA + TAGAAATYTGTGGRMAWARRGCYATAG (SEQ ID NO: 10266) |
| 73 | +ARRTANYYA + TA + GAAATYTGTGGRMAWARRGCYATAG (SEQ ID NO: 10267) |
| 73 | +ARR + TANYYATA + GAAATYTGTGGRMAWARRGCYATAG (SEQ ID NO: 10268) |
| 73 | +TANYYA + TA + GAAATYTGTGGRMAWARRGCYATAG (SEQ ID NO: 10269) |
| 73 | +TANYYATA + G + AAATYTGTGGRMAWARRGCYATAG (SEQ ID NO: 10270) |
| 73 | +TANYYA + TAG + AAATYTGTGGRMAWARRGCYATAG (SEQ ID NO: 10271) |
| 73 | +TA + G + AAATYTGTGGRMAWARRGCYATAG (SEQ ID NO: 10272) |
| 73 | +TAG + AAA + TYTGTGGRMAWARRGCYATAG (SEQ ID NO: 10273) |
| 73 | +TA + GAAA + TYTGTGGRMAWARRGCYATAG (SEQ ID NO: 10274) |
| 73 | +G + AAA + TYTGTGGRMAWARRGCYATAG (SEQ ID NO: 10275) |
| 73 | +GAAA + TYTGT + GGRMAWARRGCYATAG (SEQ ID NO: 10276) |
| 73 | +G + AAATYTGT + GGRMAWARRGCYATAG (SEQ ID NO: 10277) |
| 73 | T + G + AKS + ARRTANYYATAGAAATYTGTGGRMAWARRGCYATA (SEQ ID NO: 10278) |
| 73 | T + GAKS + ARR + TANYYATAGAAATYTGTGGRMAWARRGCYATA (SEQ ID NO: 10279) |
| 73 | T + G + AKSARR + TANYYATAGAAATYTGTGGRMAWARRGCYATA (SEQ ID NO: 10280) |
| 73 | +AKS + ARR + TANYYATAGAAATYTGTGGRMAWARRGCYATA (SEQ ID NO: 10281) |
| 73 | +AKSARR + TANYYA + TAGAAATYTGTGGRMAWARRGCYATA (SEQ ID NO: 10282) |
| 73 | +AKS + ARRTANYYA + TAGAAATYTGTGGRMAWARRGCYATA (SEQ ID NO: 10283) |
| 73 | +ARR + TANYYA + TAGAAATYTGTGGRMAWARRGCYATA (SEQ ID NO: 10284) |
| 73 | +ARRTANYYA + TA + GAAATYTGTGGRMAWARRGCYATA (SEQ ID NO: 10285) |
| 73 | +ARR + TANYYATA + GAAATYTGTGGRMAWARRGCYATA (SEQ ID NO: 10286) |
| 73 | +TANYYA + TA + GAAATYTGTGGRMAWARRGCYATA (SEQ ID NO: 10287) |
| 73 | +TANYYATA + G + AAATYTGTGGRMAWARRGCYATA (SEQ ID NO: 10288) |
| 73 | +TANYYA + TAG + AAATYTGTGGRMAWARRGCYATA (SEQ ID NO: 10289) |
| 73 | +TA + G + AAATYTGTGGRMAWARRGCYATA (SEQ ID NO: 10290) |
| 73 | +TAG + AAA + TYTGTGGRMAWARRGCYATA (SEQ ID NO: 10291) |
| 73 | +TA + GAAA + TYTGTGGRMAWARRGCYATA (SEQ ID NO: 10292) |
| 73 | +G + AAA + TYTGTGGRMAWARRGCYATA (SEQ ID NO: 10293) |
| 73 | +GAAA + TYTGT + GGRMAWARRGCYATA (SEQ ID NO: 10294) |
| 73 | +G + AAATYTGT + GGRMAWARRGCYATA (SEQ ID NO: 10295) |
| 73 | GAKSARRTANYYATAGAAATYTGTGGRMAWARRGCYATAG (SEQ ID NO: 10296) |

TABLE 8-continued

| Codon | |
|---|---|
| 73 | AKSARRTANYYATAGAAATYTGTGGRMAWARRGCYATAG (SEQ ID NO: 10297) |
| 73 | ARRTANYYATAGAAATYTGTGGRMAWARRGCYATAG (SEQ ID NO: 10298) |
| 73 | TANYYATAGAAATYTGTGGRMAWARRGCYATAG (SEQ ID NO: 10299) |
| 73 | TAGAAATYTGTGGRMAWARRGCYATAG (SEQ ID NO: 10300) |
| 73 | GAAATYTGTGGRMAWARRGCYATAG (SEQ ID NO: 10301) |
| 73 | TGAKSARRTANYYATAGAAATYTGTGGRMAWARRGCYATA (SEQ ID NO: 10302) |
| 73 | AKSARRTANYYATAGAAATYTGTGGRMAWARRGCYATA (SEQ ID NO: 10303) |
| 73 | ARRTANYYATAGAAATYTGTGGRMAWARRGCYATA (SEQ ID NO: 10304) |
| 73 | TANYYATAGAAATYTGTGGRMAWARRGCYATA (SEQ ID NO: 10305) |
| 73 | TAGAAATYTGTGGRMAWARRGCYATA (SEQ ID NO: 10306) |
| 73 | GAAATYTGTGGRMAWARRGCYATA (SEQ ID NO: 10307) |
| 73 | CARTATGAKSAVRTANHHRTAGARATYTGYGGRMAHARRGCTATA (SEQ ID NO: 10308) |
| 73 | GAKSARRTANYYATAGAAATYTGTGGRMAWARRGCYATAG + N (SEQ ID NO: 10309) |
| 73 | AKSARRTANYYATAGAAATYTGTGGRMAWARRGCYATAG + N (SEQ ID NO: 10310) |
| 73 | ARRTANYYATAGAAATYTGTGGRMAWARRGCYATAG + N (SEQ ID NO: 10311) |
| 73 | TANYYATAGAAATYTGTGGRMAWARRGCYATAG + N (SEQ ID NO: 10312) |
| 73 | TAGAAATYTGTGGRMAWARRGCYATAG + N (SEQ ID NO: 10313) |
| 73 | GAAATYTGTGGRMAWARRGCYATAG + N (SEQ ID NO: 10314) |
| 73 | TGAKSARRTANYYATAGAAATYTGTGGRMAWARRGCYATA + N (SEQ ID NO: 10315) |
| 73 | AKSARRTANYYATAGAAATYTGTGGRMAWARRGCYATA + N (SEQ ID NO: 10316) |
| 73 | ARRTANYYATAGAAATYTGTGGRMAWARRGCYATA + N (SEQ ID NO: 10317) |
| 73 | TANYYATAGAAATYTGTGGRMAWARRGCYATA + N (SEQ ID NO: 10318) |
| 73 | TAGAAATYTGTGGRMAWARRGCYATA + N (SEQ ID NO: 10319) |
| 73 | GAAATYTGTGGRMAWARRGCYATA + N (SEQ ID NO: 10320) |
| 73 | CARTATGAKSAVRTANHHRTAGARATYTGYGGRMAHARRGCTATA + N (SEQ ID NO: 10321) |
| 74 | KS + ARR + TANYYA + TAGAAATYTGTGGRMAWARRGCYATAGGK (SEQ ID NO: 10322) |
| 74 | KS + ARRTANYYA + TA + GAAATYTGTGGRMAWARRGCYATAGGK (SEQ ID NO: 10323) |
| 74 | KS + ARR + TANYYATA + GAAATYTGTGGRMAWARRGCYATAGGK (SEQ ID NO: 10324) |
| 74 | +TANYYA + TA + GAAATYTGTGGRMAWARRGCYATAGGK (SEQ ID NO: 10325) |
| 74 | +TANYYATA + G + AAATYTGTGGRMAWARRGCYATAGGK (SEQ ID NO: 10326) |
| 74 | +TANYYA + TAG + AAATYTGTGGRMAWARRGCYATAGGK (SEQ ID NO: 10327) |
| 74 | +TA + G + AAATYTGTGGRMAWARRGCYATAGGK (SEQ ID NO: 10328) |
| 74 | +TAG + AAA + TYTGTGGRMAWARRGCYATAGGK (SEQ ID NO: 10329) |
| 74 | +TA + GAAA + TYTGTGGRMAWARRGCYATAGGK (SEQ ID NO: 10330) |
| 74 | +G + AAA + TYTGTGGRMAWARRGCYATAGGK (SEQ ID NO: 10331) |
| 74 | +GAAA + TYTGT + GGRMAWARRGCYATAGGK (SEQ ID NO: 10332) |
| 74 | +G + AAATYTGT + GGRMAWARRGCYATAGGK (SEQ ID NO: 10333) |
| 74 | +AAA + TYTGT + GGRMAWARRGCYATAGGK (SEQ ID NO: 10334) |
| 74 | +AAATYTGT + GGRMAWARRGCYATAG + GK (SEQ ID NO: 10335) |

TABLE 8-continued

| Codon | |
|---|---|
| 74 | +AAA + TYTGTGGRMAWARRGCYATAG + GK (SEQ ID NO: 10336) |
| 74 | +TYTGT + GGRMAWARRGCYATAG + GK (SEQ ID NO: 10337) |
| 74 | +TYTGTGGRMAWARRGCYATAG + GK (SEQ ID NO: 10338) |
| 74 | +TYTGT + GGRMAWARRGCYATAGGK (SEQ ID NO: 10339) |
| 74 | KSARRTANYYATAGAAATYTGTGGRMAWARRGCYATAGGK (SEQ ID NO: 10340) |
| 74 | TANYYATAGAAATYTGTGGRMAWARRGCYATAGGK (SEQ ID NO: 10341) |
| 74 | TAGAAATYTGTGGRMAWARRGCYATAGGK (SEQ ID NO: 10342) |
| 74 | GAAATYTGTGGRMAWARRGCYATAGGK (SEQ ID NO: 10343) |
| 74 | AAATYTGTGGRMAWARRGCYATAGGK (SEQ ID NO: 10344) |
| 74 | TYTGTGGRMAWARRGCYATAGGK (SEQ ID NO: 10345) |
| 74 | TATGAKSAVRTANHHRTAGARATYTGYGGRMAHARRRYYATAGGT (SEQ ID NO: 10346) |
| 74 | KSARRTANYYATAGAAATYTGTGGRMAWARRGCYATAGGK + N (SEQ ID NO: 10347) |
| 74 | TANYYATAGAAATYTGTGGRMAWARRGCYATAGGK + N (SEQ ID NO: 10348) |
| 74 | TAGAAATYTGTGGRMAWARRGCYATAGGK + N (SEQ ID NO: 10349) |
| 74 | GAAATYTGTGGRMAWARRGCYATAGGK + N (SEQ ID NO: 10350) |
| 74 | AAATYTGTGGRMAWARRGCYATAGGK + N (SEQ ID NO: 10351) |
| 74 | TYTGTGGRMAWARRGCYATAGGK + N (SEQ ID NO: 10352) |
| 74 | TATGAKSAVRTANHHRTAGARATYTGYGGRMAHARRRYYATAGGT + N (SEQ ID NO: 10353) |
| 76 | ANYYA + TA + G + AAATYTGTGGRMAWARRGCYATAGGKWCAGTR (SEQ ID NO: 10354) |
| 76 | ANYYA + TAG + AAA + TYTGTGGRMAWARRGCYATAGGKWCAGTR (SEQ ID NO: 10355) |
| 76 | ANYYA + TA + GAAA + TYTGTGGRMAWARRGCYATAGGKWCAGTR (SEQ ID NO: 10356) |
| 76 | +G + AAA + TYTGTGGRMAWARRGCYATAGGKWCAGTR (SEQ ID NO: 10357) |
| 76 | +GAAA + TYTGT + GGRMAWARRGCYATAGGKWCAGTR (SEQ ID NO: 10358) |
| 76 | +G + AAATYTGT + GGRMAWARRGCYATAGGKWCAGTR (SEQ ID NO: 10359) |
| 76 | +AAA + TYTGT + GGRMAWARRGCYATAGGKWCAGTR (SEQ ID NO: 10360) |
| 76 | +AAATYTGT + GGRMAWARRGCYATAG + GKWCAGTR (SEQ ID NO: 10361) |
| 76 | +AAA + TYTGTGGRMAWARRGCYATAG + GKWCAGTR (SEQ ID NO: 10362) |
| 76 | +TYTGT + GGRMAWARRGCYATAG + GKWCAGTR (SEQ ID NO: 10363) |
| 76 | +TYTGTGGRMAWARRGCYATAG + GKW + CAGTR (SEQ ID NO: 10364) |
| 76 | +TYTGT + GGRMAWARRGCYATAGGKW + CAGTR (SEQ ID NO: 10365) |
| 76 | +GGRMAWARRGCYATAG + GKW + CAGTR (SEQ ID NO: 10366) |
| 76 | +GGRMAWARRGCYATAGGKW + CAG + TR (SEQ ID NO: 10367) |
| 76 | +GGRMAWARRGCYATAG + GKWCAG + TR (SEQ ID NO: 10368) |
| 76 | ANYYATAGAAATYTGTGGRMAWARRGCYATAGGKWCAGTR (SEQ ID NO: 10369) |
| 76 | GAAATYTGTGGRMAWARRGCYATAGGKWCAGTR (SEQ ID NO: 10370) |
| 76 | AAATYTGTGGRMAWARRGCYATAGGKWCAGTR (SEQ ID NO: 10371) |
| 76 | TYTGTGGRMAWARRGCYATAGGKWCAGTR (SEQ ID NO: 10372) |
| 76 | GGRMAWARRGCYATAGGKWCAGTR (SEQ ID NO: 10373) |
| 76 | SAVRTANHHRTAGARATYTGYGGRMAHARRRYYRYAGGTACAGTA (SEQ ID NO: 10374) |

TABLE 8-continued

| Codon | |
|---|---|
| 76 | ANYYATAGAAATYTGTGGRMAWARRGCYATAGGKWCAGTR + N (SEQ ID NO: 10375) |
| 76 | GAAATYTGTGGRMAWARRGCYATAGGKWCAGTR + N (SEQ ID NO: 10376) |
| 76 | AAATYTGTGGRMAWARRGCYATAGGKWCAGTR + N (SEQ ID NO: 10377) |
| 76 | TYTGTGGRMAWARRGCYATAGGKWCAGTR + N (SEQ ID NO: 10378) |
| 76 | GGRMAWARRGCYATAGGKWCAGTR + N (SEQ ID NO: 10379) |
| 76 | SAVRTANHHRTAGARATYTGYGGRMAHARRRYYRYAGGTACAGTA + N (SEQ ID NO: 10380) |
| 82 | MAWARRGCYATAG + GKW + CAG + TRYTRRTGGRCCYACACCTR (SEQ ID NO: 10381) |
| 82 | MAWARRGCYATAG + GKWCAG + TRY + TRRTGGRCCYACACCTR (SEQ ID NO: 10382) |
| 82 | MAWARRGCYATAG + GKW + CAGTRY + TRRTGGRCCYACACCTR (SEQ ID NO: 10383) |
| 82 | +CAG + TRY + TRRTGGRCCYACACCTR (SEQ ID NO: 10384) |
| 82 | +CAGTRY + TRR + TGGRCCYACACCTR (SEQ ID NO: 10385) |
| 82 | +CAG + TRYTRR + TGGRCCYACACCTR (SEQ ID NO: 10386) |
| 82 | +TRY + TRR + TGGRCCYACACCTR (SEQ ID NO: 10387) |
| 82 | +TRYTRR + TR + GGRCCYACACCTR (SEQ ID NO: 10388) |
| 82 | +TRY + TRRTR + GGRCCYACACCTR (SEQ ID NO: 10389) |
| 82 | RMAWARRGCYATAG + GKW + CAG + TRYTRRTGGRCCYACACCT (SEQ ID NO: 10390) |
| 82 | RMAWARRGCYATAG + GKWCAG + TRY + TRRTGGRCCYACACCT (SEQ ID NO: 10391) |
| 82 | RMAWARRGCYATAG + GKW + CAGTRY + TRRTGGRCCYACACCT (SEQ ID NO: 10392) |
| 82 | +CAG + TRY + TRRTGGRCCYACACCT (SEQ ID NO: 10393) |
| 82 | +CAGTRY + TRR + TGGRCCYACACCT (SEQ ID NO: 10394) |
| 82 | +CAG + TRYTRR + TGGRCCYACACCT (SEQ ID NO: 10395) |
| 82 | MAWARRGCYATAGGKWCAGTRYTRRTGGRCCYACACCTR (SEQ ID NO: 10396) |
| 82 | CAGTRYTRRTGGRCCYACACCTR (SEQ ID NO: 10397) |
| 82 | TRYTRRTGGRCCYACACCTR (SEQ ID NO: 10398) |
| 82 | RMAWARRGCYATAGGKWCAGTRYTRRTGGRCCYACACCT (SEQ ID NO: 10399) |
| 82 | CAGTRYTRRTGGRCCYACACCT (SEQ ID NO: 10400) |
| 82 | TGYGGRMAHARRRYYRYAGGTACAGTRTTRRTAGGRCCYACACCT (SEQ ID NO: 10401) |
| 82 | MAWARRGCYATAGGKWCAGTRYTRRTGGRCCYACACCTR + N (SEQ ID NO: 10402) |
| 82 | CAGTRYTRRTGGRCCYACACCTR + N (SEQ ID NO: 10403) |
| 82 | TRYTRRTGGRCCYACACCTR + N (SEQ ID NO: 10404) |
| 82 | RMAWARRGCYATAGGKWCAGTRYTRRTGGRCCYACACCT + N (SEQ ID NO: 10405) |
| 82 | CAGTRYTRRTGGRCCYACACCT + N (SEQ ID NO: 10406) |
| 82 | TGYGGRMAHARRRYYRYAGGTACAGTRTTRRTAGGRCCYACACCT + N (SEQ ID NO: 10407) |
| 83 | WARRGCYATAG + GKW + CAG + TRYTRRTGGRCCYACACCTRTC (SEQ ID NO: 10408) |
| 83 | WARRGCYATAG + GKWCAG + TRY + TRRTGGRCCYACACCTRTC (SEQ ID NO: 10409) |
| 83 | WARRGCYATAG + GKW + CAGTRY + TRRTGGRCCYACACCTRTC (SEQ ID NO: 10410) |
| 83 | +CAG + TRY + TRRTGGRCCYACACCTRTC (SEQ ID NO: 10411) |
| 83 | +CAGTRY + TRR + TGGRCCYACACCTRTC (SEQ ID NO: 10412) |
| 83 | +CAG + TRYTRR + TGGRCCYACACCTRTC (SEQ ID NO: 10413) |

TABLE 8-continued

| Codon | |
|---|---|
| 83 | +TRY + TRR + TRGGRCCYACACCTRTC (SEQ ID NO: 10414) |
| 83 | +TRYTRR + TR + GGRCCYACACCTRTC (SEQ ID NO: 10415) |
| 83 | +TRY + TRRTR + GGRCCYACACCTRTC (SEQ ID NO: 10416) |
| 83 | WARRGCYATAGGKWCAGTRYTRRTGGRCCYACACCTRTC (SEQ ID NO: 10417) |
| 83 | CAGTRYTRRTGGRCCYACACCTRTC (SEQ ID NO: 10418) |
| 83 | TRYTRRTGGRCCYACACCTRTC (SEQ ID NO: 10419) |
| 83 | GGRMAHARRRYYRYAGGTACAGTRTTRRTAGGRCCYACACCTGTC (SEQ ID NO: 10420) |
| 83 | WARRGCYATAGGKWCAGTRYTRRTGGRCCYACACCTRTC + N (SEQ ID NO: 10421) |
| 83 | CAGTRYTRRTGGRCCYACACCTRTC + N (SEQ ID NO: 10422) |
| 83 | TRYTRRTGGRCCYACACCTRTC + N (SEQ ID NO: 10423) |
| 83 | GGRMAHARRRYYRYAGGTACAGTRTTRRTAGGRCCYACACCTGTC + N (SEQ ID NO: 10424) |
| 84 | RGCYATAG + GKW + CAG + TRYTRRTGGRCCYACACCTRTCAAC (SEQ ID NO: 10425) |
| 84 | RGCYATAG + GKWCAG + TRY + TRRTGGRCCYACACCTRTCAAC (SEQ ID NO: 10426) |
| 84 | RGCYATAG + GKW + CAGTRY + TRRTGGRCCYACACCTRTCAAC (SEQ ID NO: 10427) |
| 84 | +CAG + TRY + TRRTGGRCCYACACCTRTCAAC (SEQ ID NO: 10428) |
| 84 | +CAGTRY + TRR + TGGRCCYACACCTRTCAAC (SEQ ID NO: 10429) |
| 84 | +CAG + TRYTRR + TGGRCCYACACCTRTCAAC (SEQ ID NO: 10430) |
| 84 | +TRY + TRR + TGGRCCYACACCTRTCAAC (SEQ ID NO: 10431) |
| 84 | +TRYTRR + TR + GGRCCYACACCTRTCAAC (SEQ ID NO: 10432) |
| 84 | +TRY + TRRTR + GGRCCYACACCTRTCAAC (SEQ ID NO: 10433) |
| 84 | +TRR + TR + GGRCCYACACCTRTCAAC (SEQ ID NO: 10434) |
| 84 | +TRRTR + G + GRCCYACACCTRTCAAC (SEQ ID NO: 10435) |
| 84 | +TRR + TRG + GRCCYACACCTRTCAAC (SEQ ID NO: 10436) |
| 84 | RGCYATAGGKWCAGTRYTRRTGGRCCYACACCTRTCAAC (SEQ ID NO: 10437) |
| 84 | CAGTRYTRRTGGRCCYACACCTRTCAAC (SEQ ID NO: 10438) |
| 84 | TRYTRRTGGRCCYACACCTRTCAAC (SEQ ID NO: 10439) |
| 84 | TRRTGGRCCYACACCTRTCAAC (SEQ ID NO: 10440) |
| 84 | MAHARRRYYRYAGGTACAGTRTTRRTAGGRCCYACMCCTGTCAAC (SEQ ID NO: 10441) |
| 84 | RGCYATAGGKWCAGTRYTRRTGGRCCYACACCTRTCAAC + N (SEQ ID NO: 10442) |
| 84 | CAGTRYTRRTGGRCCYACACCTRTCAAC + N (SEQ ID NO: 10443) |
| 84 | TRYTRRTGGRCCYACACCTRTCAAC + N (SEQ ID NO: 10444) |
| 84 | TRRTGGRCCYACACCTRTCAAC + N (SEQ ID NO: 10445) |
| 84 | MAHARRRYYRYAGGTACAGTRTTRRTAGGRCCYACMCCTGTCAAC + N (SEQ ID NO: 10446) |
| 88 | G + TRY + TRR + TRGGRCCYACACCTRTCAACATAATTGGRMGRA (SEQ ID NO: 10447) |
| 88 | G + TRYTRR + TR + GGRCCYACACCTRTCAACATAATTGGRMGRA (SEQ ID NO: 10448) |
| 88 | G + TRY + TRRTR + GGRCCYACACCTRTCAACATAATTGGRMGRA (SEQ ID NO: 10449) |
| 88 | +TRR + TR + GGRCCYACACCTRTCAACATAATTGGRMGRA (SEQ ID NO: 10450) |
| 88 | +TRRTR + G + GRCCYACACCTRTCAACATAATTGGRMGRA (SEQ ID NO: 10451) |
| 88 | +TRR + TRG + GRCCYACACCTRTCAACATAATTGGRMGRA (SEQ ID NO: 10452) |

TABLE 8-continued

| Codon | |
|---|---|
| 88 | +TR + G + GRCCYACACCTRTCAACATAATTGGRMGRA (SEQ ID NO: 10453) |
| 88 | +TRG + GRC + CYACACCTRTCAACATAATTGGRMGRA (SEQ ID NO: 10454) |
| 88 | +TR + GGRC + CYACACCTRTCAACATAATTGGRMGRA (SEQ ID NO: 10455) |
| 88 | +G + GRC + CYACACCTRTCAACATAATTGGRMGRA (SEQ ID NO: 10456) |
| 88 | +GGRC + CY + ACACCTRTCAACATAATTGGRMGRA (SEQ ID NO: 10457) |
| 88 | +G + GRCCY + ACACCTRTCAACATAATTGGRMGRA (SEQ ID NO: 10458) |
| 88 | +GRC + CY + ACACCTRTCAACATAATTGGRMGRA (SEQ ID NO: 10459) |
| 88 | +GRCCY + A + CACCTRTCAACATAATTGGRMGRA (SEQ ID NO: 10460) |
| 88 | +GRC + CYA + CACCTRTCAACATAATTGGRMGRA (SEQ ID NO: 10461) |
| 88 | +CY + A + CACCTRTCAACATAATTGGRMGRA (SEQ ID NO: 10462) |
| 88 | +CYA + CA + CCTRTCAACATAATTGGRMGRA (SEQ ID NO: 10463) |
| 88 | +CY + ACA + CCTRTCAACATAATTGGRMGRA (SEQ ID NO: 10464) |
| 88 | GTRYTRRTRGGRCCYACACCTRTCAACATAATTGGRMGRA (SEQ ID NO: 10465) |
| 88 | TRRTRGGRCCYACACCTRTCAACATAATTGGRMGRA (SEQ ID NO: 10466) |
| 88 | TRGGRCCYACACCTRTCAACATAATTGGRMGRA (SEQ ID NO: 10467) |
| 88 | GGRCCYACACCTRTCAACATAATTGGRMGRA (SEQ ID NO: 10468) |
| 88 | GRCCYACACCTRTCAACATAATTGGRMGRA (SEQ ID NO: 10469) |
| 88 | CYACACCTRTCAACATAATTGGRMGRA (SEQ ID NO: 10470) |
| 88 | GGTACAGTRTTRRTAGGRCCYACMCCTRYCAACATAATTGGAAGA (SEQ ID NO: 10471) |
| 88 | GTRYTRRTRGGRCCYACACCTRTCAACATAATTGGRMGRA + N (SEQ ID NO: 10472) |
| 88 | TRRTRGGRCCYACACCTRTCAACATAATTGGRMGRA + N (SEQ ID NO: 10473) |
| 88 | TRGGRCCYACACCTRTCAACATAATTGGRMGRA + N (SEQ ID NO: 10474) |
| 88 | GGRCCYACACCTRTCAACATAATTGGRMGRA + N (SEQ ID NO: 10475) |
| 88 | GRCCYACACCTRTCAACATAATTGGRMGRA + N (SEQ ID NO: 10476) |
| 88 | CYACACCTRTCAACATAATTGGRMGRA + N (SEQ ID NO: 10477) |
| 88 | GGTACAGTRTTRRTAGGRCCYACMCCTRYCAACATAATTGGAAGA + N (SEQ ID NO: 10478) |
| 89 | RY + TRR + TR + GGRCCYACACCTRTCAACATAATTGGRMGRAAY (SEQ ID NO: 10479) |
| 89 | RY + TRRTR + G + GRCCYACACCTRTCAACATAATTGGRMGRAAY (SEQ ID NO: 10480) |
| 89 | RY + TRR + TRG + GRCCYACACCTRTCAACATAATTGGRMGRAAY (SEQ ID NO: 10481) |
| 89 | +TR + G + GRCCYACACCTRTCAACATAATTGGRMGRAAY (SEQ ID NO: 10482) |
| 89 | +TRG + GRC + CYACACCTRTCAACATAATTGGRMGRAAY (SEQ ID NO: 10483) |
| 89 | +TR + GGRC + CYACACCTRTCAACATAATTGGRMGRAAY (SEQ ID NO: 10484) |
| 89 | +G + GRC + CYACACCTRTCAACATAATTGGRMGRAAY (SEQ ID NO: 10485) |
| 89 | +GGRC + CY + ACACCTRTCAACATAATTGGRMGRAAY (SEQ ID NO: 10486) |
| 89 | +G + GRCCY + ACACCTRTCAACATAATTGGRMGRAAY (SEQ ID NO: 10487) |
| 89 | +GRC + CY + ACACCTRTCAACATAATTGGRMGRAAY (SEQ ID NO: 10488) |
| 89 | +GRCCY + A + CACCTRTCAACATAATTGGRMGRAAY (SEQ ID NO: 10489) |
| 89 | +GRC + CYA + CACCTRTCAACATAATTGGRMGRAAY (SEQ ID NO: 10490) |
| 89 | +CY + A + CACCTRTCAACATAATTGGRMGRAAY (SEQ ID NO: 10491) |

TABLE 8-continued

| Codon | |
|---|---|
| 89 | +CYA + CA + CCTRTCAACATAATTGGRMGRAAY (SEQ ID NO: 10492) |
| 89 | +CY + ACA + CCTRTCAACATAATTGGRMGRAAY (SEQ ID NO: 10493) |
| 89 | +A + CA + CCTRTCAACATAATTGGRMGRAAY (SEQ ID NO: 10494) |
| 89 | +ACA + C + CTRTCAACATAATTGGRMGRAAY (SEQ ID NO: 10495) |
| 89 | +A + CAC + CTRTCAACATAATTGGRMGRAAY (SEQ ID NO: 10496) |
| 89 | RYTRRTRGGRCCYACACCTRTCAACATAATTGGRMGRAAY (SEQ ID NO: 10497) |
| 89 | TRGGRCCYACACCTRTCAACATAATTGGRMGRAAY (SEQ ID NO: 10498) |
| 89 | GGRCCYACACCTRTCAACATAATTGGRMGRAAY (SEQ ID NO: 10499) |
| 89 | GRCCYACACCTRTCAACATAATTGGRMGRAAY (SEQ ID NO: 10500) |
| 89 | CYACACCTRTCAACATAATTGGRMGRAAY (SEQ ID NO: 10501) |
| 89 | ACACCTRTCAACATAATTGGRMGRAAY (SEQ ID NO: 10502) |
| 89 | ACAGTRTTRRTAGGRCCYACMCCTRYCAACATAATTGGAAGAAAT (SEQ ID NO: 10503) |
| 89 | RYTRRTRGGRCCYACACCTRTCAACATAATTGGRMGRAAY + N (SEQ ID NO: 10504) |
| 89 | TRGGRCCYACACCTRTCAACATAATTGGRMGRAAY + N (SEQ ID NO: 10505) |
| 89 | GGRCCYACACCTRTCAACATAATTGGRMGRAAY + N (SEQ ID NO: 10506) |
| 89 | GRCCYACACCTRTCAACATAATTGGRMGRAAY + N (SEQ ID NO: 10507) |
| 89 | CYACACCTRTCAACATAATTGGRMGRAAY + N (SEQ ID NO: 10508) |
| 89 | ACACCTRTCAACATAATTGGRMGRAAY + N (SEQ ID NO: 10509) |
| 89 | ACAGTRTTRRTAGGRCCYACMCCTRYCAACATAATTGGAAGAAAT + N (SEQ ID NO: 10510) |
| 90 | RR + TR + G + GRCCYACACCTRTCAACATAATTGGRMGRAAYHTG (SEQ ID NO: 10511) |
| 90 | RR + TRG + GRC + CYACACCTRTCAACATAATTGGRMGRAAYHTG (SEQ ID NO: 10512) |
| 90 | RR + TR + GGRC + CYACACCTRTCAACATAATTGGRMGRAAYHTG (SEQ ID NO: 10513) |
| 90 | +G + GRC + CYACACCTRTCAACATAATTGGRMGRAAYHTG (SEQ ID NO: 10514) |
| 90 | +GGRC + CY + ACACCTRTCAACATAATTGGRMGRAAYHTG (SEQ ID NO: 10515) |
| 90 | +G + GRCCY + ACACCTRTCAACATAATTGGRMGRAAYHTG (SEQ ID NO: 10516) |
| 90 | +GRC + CY + ACACCTRTCAACATAATTGGRMGRAAYHTG (SEQ ID NO: 10517) |
| 90 | +GRCCY + A + CACCTRTCAACATAATTGGRMGRAAYHTG (SEQ ID NO: 10518) |
| 90 | +GRC + CYA + CACCTRTCAACATAATTGGRMGRAAYHTG (SEQ ID NO: 10519) |
| 90 | +CY + A + CACCTRTCAACATAATTGGRMGRAAYHTG (SEQ ID NO: 10520) |
| 90 | +CYA + CA + CCTRTCAACATAATTGGRMGRAAYHTG (SEQ ID NO: 10521) |
| 90 | +CY + ACA + CCTRTCAACATAATTGGRMGRAAYHTG (SEQ ID NO: 10522) |
| 90 | +A + CA + CCTRTCAACATAATTGGRMGRAAYHTG (SEQ ID NO: 10523) |
| 90 | +ACA + C + CTRTCAACATAATTGGRMGRAAYHTG (SEQ ID NO: 10524) |
| 90 | +A + CAC + CTRTCAACATAATTGGRMGRAAYHTG (SEQ ID NO: 10525) |
| 90 | +CA + C + CTRTCAACATAATTGGRMGRAAYHTG (SEQ ID NO: 10526) |
| 90 | +CAC + CTRTC + AACATAATTGGRMGRAAYHTG (SEQ ID NO: 10527) |
| 90 | +CA + CCTRTC + AACATAATTGGRMGRAAYHTG (SEQ ID NO: 10528) |
| 90 | RRTRGGRCCYACACCTRTCAACATAATTGGRMGRAAYHTG (SEQ ID NO: 10529) |
| 90 | GGRCCYACACCTRTCAACATAATTGGRMGRAAYHTG (SEQ ID NO: 10530) |

TABLE 8-continued

| Codon | |
|---|---|
| 90 | GRCCYACACCTRTCAACATAATTGGRMGRAAYHTG (SEQ ID NO: 10531) |
| 90 | CYACACCTRTCAACATAATTGGRMGRAAYHTG (SEQ ID NO: 10532) |
| 90 | ACACCTRTCAACATAATTGGRMGRAAYHTG (SEQ ID NO: 10533) |
| 90 | CACCTRTCAACATAATTGGRMGRAAYHTG (SEQ ID NO: 10534) |
| 90 | GTRTTRRTAGGRCCYACMCCTRYCAACATAATTGGRMGAAATCTG (SEQ ID NO: 10535) |
| 90 | RRTRGGRCCYACACCTRTCAACATAATTGGRMGRAAYHTG + N (SEQ ID NO: 10536) |
| 90 | GGRCCYACACCTRTCAACATAATTGGRMGRAAYHTG + N (SEQ ID NO: 10537) |
| 90 | GRCCYACACCTRTCAACATAATTGGRMGRAAYHTG + N (SEQ ID NO: 10538) |
| 90 | CYACACCTRTCAACATAATTGGRMGRAAYHTG + N (SEQ ID NO: 10539) |
| 90 | ACACCTRTCAACATAATTGGRMGRAAYHTG + N (SEQ ID NO: 10540) |
| 90 | CACCTRTCAACATAATTGGRMGRAAYHTG + N (SEQ ID NO: 10541) |

| Reverse Primer (5' to 3') | |
|---|---|
| 90 | GTRTTRRTAGGRCCYACMCCTRYCAACATAATTGGRMGAAATCTG + N (SEQ ID NO: 10542) |
| 10 | TCCTGTRTCTAAKAGRGCYTCYHTYRDYTGBCCYYCTAYYYTTAYTGTGAC (SEQ ID NO: 10543) |
| 10 | TCCTGTRTCTAAKAGRGCYTCYHTYRDYTGBCCYYCTAYYYTTAYTGTGAC + N (SEQ ID NO: 10544) |
| 11 | TGCTCCTGTRTCTAAKAGRGCYTCYHTYRDYTGBCCYYCTAYYYTTATTGT (SEQ ID NO: 10545) |
| 11 | TGCTCCTGTRTCTAAKAGRGCYTCYHTYRDYTGBCCYYCTAYYYTTATTGT + N (SEQ ID NO: 10546) |
| 20 | MYYYATDTCTTCTAATACTGTATCATCTGCTCCTGTRTCTAAKAGAGCTTC (SEQ ID NO: 10547) |
| 20 | MYYYATDTCTTCTAATACTGTATCATCTGCTCCTGTRTCTAAKAGAGCTTC + N (SEQ ID NO: 10548) |
| 23 | YCCTGGYAAMYYYATDTCTTCTAATACTGTATCATCTGCTCCTGTATCTAA (SEQ ID NO: 10549) |
| 23 | YCCTGGYAAMYYYATDTCTTCTAATACTGTATCATCTGCTCCTGTATCTAA + N (SEQ ID NO: 10550) |
| 24 | TYTYCCTGGYAAMYYYATDTCTTCTAATACTGTATCATCTGCTCCTGTATC (SEQ ID NO: 10551) |
| 24 | TYTYCCTGGYAAMYYYATDTCTTCTAATACTGTATCATCTGCTCCTGTATC + N (SEQ ID NO: 10552) |
| 30 | TATYATTTTTGGYTTCCATYTYCCTGGYAAMYYYATDTCTTCTAATACTGT (SEQ ID NO: 10553) |
| 30 | TATYATTTTTGGYTTCCATYTYCCTGGYAAMYYYATDTCTTCTAATACTGT + N (SEQ ID NO: 10554) |
| 32 | TCCYCCTATYATTTTTGGYTTCCATYTYCCTGGYAAMYYYATDTCTTCTAA (SEQ ID NO: 10555) |
| 32 | TCCYCCTATYATTTTTGGYTTCCATYTYCCTGGYAAMYYYATDTCTTCTAA + N (SEQ ID NO: 10556) |
| 33 | AATTCCYCCTATYATTTTTGGYTTCCATYTYCCTGGYAAMYYYATTTCTTC (SEQ ID NO: 10557) |
| 33 | AATTCCYCCTATYATTTTTGGYTTCCATYTYCCTGGYAAMYYYATTTCTTC + N (SEQ ID NO: 10558) |
| 43 | MTCATAYTGYYTTACYTTRAYAAARCCTCCAATTCCYCCTATYATTTTTGG (SEQ ID NO: 10559) |
| 43 | MTCATAYTGYYTTACYTTRAYAAARCCTCCAATTCCYCCTATYATTTTTGG + N (SEQ ID NO: 10560) |
| 46 | DDNTAYBTSMTCATAYTGYYTTACYTTRAYAAARCCTCCAATTCCCCCTAT (SEQ ID NO: 10561) |
| 46 | DDNTAYBTSMTCATAYTGYYTTACYTTRAYAAARCCTCCAATTCCCCCTAT + N (SEQ ID NO: 10562) |
| 47 | +T + C + ATAYTGYYTTACYTTRATAAARCCTCCAATTCCYCCTA (SEQ ID NO: 10563) |

TABLE 8-continued

| Codon | |
|---|---|
| 47 | +TC + A + TAYTGYYTTACYTTRATAAARCCTCCAATTCCYCCTA (SEQ ID NO: 10564) |
| 47 | +T + CA + TAYTGYYTTACYTTRATAAARCCTCCAATTCCYCCTA (SEQ ID NO: 10565) |
| 47 | +C + A + TAYTGYYTTACYTTRATAAARCCTCCAATTCCYCCTA (SEQ ID NO: 10566) |
| 47 | +CA + TA + YTGYYTTACYTTRATAAARCCTCCAATTCCYCCTA (SEQ ID NO: 10567) |
| 47 | +C + ATA + YTGYYTTACYTTRATAAARCCTCCAATTCCYCCTA (SEQ ID NO: 10568) |
| 47 | +A + TA + YTGYYTTACYTTRATAAARCCTCCAATTCCYCCTA (SEQ ID NO: 10569) |
| 47 | +ATA + Y + TGYYTTACYTTRATAAARCCTCCAATTCCYCCTA (SEQ ID NO: 10570) |
| 47 | +A + TAY + TGYYTTACYTTRATAAARCCTCCAATTCCYCCTA (SEQ ID NO: 10571) |
| 47 | +TA + Y + TGYYTTACYTTRATAAARCCTCCAATTCCYCCTA (SEQ ID NO: 10572) |
| 47 | +TAY + TG + YYTTACYTTRATAAARCCTCCAATTCCYCCTA (SEQ ID NO: 10573) |
| 47 | +TA + YTG + YYTTACYTTRATAAARCCTCCAATTCCYCCTA (SEQ ID NO: 10574) |
| 47 | +Y + TG + YYTTACYTTRATAAARCCTCCAATTCCYCCTA (SEQ ID NO: 10575) |
| 47 | +YTG + Y + YTTACYTTRATAAARCCTCCAATTCCYCCTA (SEQ ID NO: 10576) |
| 47 | +Y + TGY + YTTACYTTRATAAARCCTCCAATTCCYCCTA (SEQ ID NO: 10577) |
| 47 | +TG + Y + YTTACYTTRATAAARCCTCCAATTCCYCCTA (SEQ ID NO: 10578) |
| 47 | +TGY + YT + TACYTTRATAAARCCTCCAATTCCYCCTA (SEQ ID NO: 10579) |
| 47 | +TG + YYT + TACYTTRATAAARCCTCCAATTCCYCCTA (SEQ ID NO: 10580) |
| 47 | TCATAYTGYYTTACYTTRATAAARCCTCCAATTCCYCCTA (SEQ ID NO: 10581) |
| 47 | CATAYTGYYTTACYTTRATAAARCCTCCAATTCCYCCTA (SEQ ID NO: 10582) |
| 47 | ATAYTGYYTTACYTTRATAAARCCTCCAATTCCYCCTA (SEQ ID NO: 10583) |
| 47 | TAYTGYYTTACYTTRATAAARCCTCCAATTCCYCCTA (SEQ ID NO: 10584) |
| 47 | YTGYYTTACYTTRATAAARCCTCCAATTCCYCCTA (SEQ ID NO: 10585) |
| 47 | TGYYTTACYTTRATAAARCCTCCAATTCCYCCTA (SEQ ID NO: 10586) |
| 47 | TAYDDNTAYBTSMTCATAYTGYYTTACYTTRAYAAARCCTCCAATTCCCCC (SEQ ID NO: 10587) |
| 47 | TCATAYTGYYTTACYTTRATAAARCCTCCAATTCCYCCTA + N (SEQ ID NO: 10588) |
| 47 | CATAYTGYYTTACYTTRATAAARCCTCCAATTCCYCCTA + N (SEQ ID NO: 10589) |
| 47 | ATAYTGYYTTACYTTRATAAARCCTCCAATTCCYCCTA + N (SEQ ID NO: 10590) |
| 47 | TAYTGYYTTACYTTRATAAARCCTCCAATTCCYCCTA + N (SEQ ID NO: 10591) |
| 47 | YTGYYTTACYTTRATAAARCCTCCAATTCCYCCTA + N (SEQ ID NO: 10592) |
| 47 | TGYYTTACYTTRATAAARCCTCCAATTCCYCCTA + N (SEQ ID NO: 10593) |
| 47 | TAYDDNTAYBTSMTCATAYTGYYTTACYTTRAYAAARCCTCCAATTCCCCC + N (SEQ ID NO: 10594) |
| 48 | YTCTAYDDNTAYBTSMTCATAYTGYYTTACYTTRAYAAARCCTCCAATTCC (SEQ ID NO: 10595) |
| 48 | YTCTAYDDNTAYBTSMTCATAYTGYYTTACYTTRAYAAARCCTCCAATTCC + N (SEQ ID NO: 10596) |
| 50 | +RB + T + AYYTSHTCATAYTGYYTTACYTTRATAAARCCTCCAA (SEQ ID NO: 10597) |
| 50 | RBT + AY + Y + TSHTCATAYTGYYTTACYTTRATAAARCCTCCAA (SEQ ID NO: 10598) |
| 50 | RB + T + AYY + TSHTCATAYTGYYTTACYTTRATAAARCCTCCAA (SEQ ID NO: 10599) |
| 50 | +T + AY + YTSHTCATAYTGYYTTACYTTRATAAARCCTCCAA (SEQ ID NO: 10600) |
| 50 | +TAY + Y + TSHTCATAYTGYYTTACYTTRATAAARCCTCCAA (SEQ ID NO: 10601) |

TABLE 8-continued

| Codon | |
|---|---|
| 50 | +T + AYY + TSHTCATAYTGYYTTACYTTRATAAARCCTCCAA (SEQ ID NO: 10602) |
| 50 | +AY + Y + TSHTCATAYTGYYTTACYTTRATAAARCCTCCAA (SEQ ID NO: 10603) |
| 50 | +AYY + TS + HTCATAYTGYYTTACYTTRATAAARCCTCCAA (SEQ ID NO: 10604) |
| 50 | +AY + YTS + HTCATAYTGYYTTACYTTRATAAARCCTCCAA (SEQ ID NO: 10605) |
| 50 | +Y + TS + HTCATAYTGYYTTACYTTRATAAARCCTCCAA (SEQ ID NO: 10606) |
| 50 | +YTS + H + TCATAYTGYYTTACYTTRATAAARCCTCCAA (SEQ ID NO: 10607) |
| 50 | +Y + TSH + TCATAYTGYYTTACYTTRATAAARCCTCCAA (SEQ ID NO: 10608) |
| 50 | +TS + H + TCATAYTGYYTTACYTTRATAAARCCTCCAA (SEQ ID NO: 10609) |
| 50 | +TSH + TCA + TAYTGYYTTACYTTRATAAARCCTCCAA (SEQ ID NO: 10610) |
| 50 | +TS + HTCA + TAYTGYYTTACYTTRATAAARCCTCCAA (SEQ ID NO: 10611) |
| 50 | +H + TCA + TAYTGYYTTACYTTRATAAARCCTCCAA (SEQ ID NO: 10612) |
| 50 | +HTCA + TA + YTGYYTTACYTTRATAAARCCTCCAA (SEQ ID NO: 10613) |
| 50 | +H + TCATA + YTGYYTTACYTTRATAAARCCTCCAA (SEQ ID NO: 10614) |
| 50 | RBTAYYTSHTCATAYTGYYTTACYTTRATAAARCCTCCAA (SEQ ID NO: 10615) |
| 50 | TAYYTSHTCATAYTGYYTTACYTTRATAAARCCTCCAA (SEQ ID NO: 10616) |
| 50 | AYYTSHTCATAYTGYYTTACYTTRATAAARCCTCCAA (SEQ ID NO: 10617) |
| 50 | YTSHTCATAYTGYYTTACYTTRATAAARCCTCCAA (SEQ ID NO: 10618) |
| 50 | TSHTCATAYTGYYTTACYTTRATAAARCCTCCAA (SEQ ID NO: 10619) |
| 50 | HTCATAYTGYYTTACYTTRATAAARCCTCCAA (SEQ ID NO: 10620) |
| 50 | RCARATYTCTAYDDNTAYBTSMTCATAYTGYYTTACYTTRAYAAAACCTCC (SEQ ID NO: 10621) |
| 50 | RBTAYYTSHTCATAYTGYYTTACYTTRATAAARCCTCCAA + N (SEQ ID NO: 10622) |
| 50 | TAYYTSHTCATAYTGYYTTACYTTRATAAARCCTCCAA + N (SEQ ID NO: 10623) |
| 50 | AYYTSHTCATAYTGYYTTACYTTRATAAARCCTCCAA + N (SEQ ID NO: 10624) |
| 50 | YTSHTCATAYTGYYTTACYTTRATAAARCCTCCAA + N (SEQ ID NO: 10625) |
| 50 | TSHTCATAYTGYYTTACYTTRATAAARCCTCCAA + N (SEQ ID NO: 10626) |
| 50 | HTCATAYTGYYTTACYTTRATAAARCCTCCAA + N (SEQ ID NO: 10627) |
| 50 | RCARATYTCTAYDDNTAYBTSMTCATAYTGYYTTACYTTRAYAAAACCTCC + N (SEQ ID NO: 10628) |
| 53 | A + RA + TTT + CTATRRBTAYYTSHTCATAYTGYYTTACYTTRAT (SEQ ID NO: 10629) |
| 53 | A + RATTT + C + TATRRBTAYYTSHTCATAYTGYYTTACYTTRAT (SEQ ID NO: 10630) |
| 53 | A + RA + TTTC + TATRRBTAYYTSHTCATAYTGYYTTACYTTRAT (SEQ ID NO: 10631) |
| 53 | +TTT + C + TATRRBTAYYTSHTCATAYTGYYTTACYTTRAT (SEQ ID NO: 10632) |
| 53 | +TTTC + TA + TRRBTAYYTSHTCATAYTGYYTTACYTTRAT (SEQ ID NO: 10633) |
| 53 | +TTT + CTA + TRRBTAYYTSHTCATAYTGYYTTACYTTRAT (SEQ ID NO: 10634) |
| 53 | +C + TA + TRRBTAYYTSHTCATAYTGYYTTACYTTRAT (SEQ ID NO: 10635) |
| 53 | +CTA + TRRB + TAYYTSHTCATAYTGYYTTACYTTRAT (SEQ ID NO: 10636) |
| 53 | +C + TATRRB + TAYYTSHTCATAYTGYYTTACYTTRAT (SEQ ID NO: 10637) |
| 53 | +TA + TRRB + TAYYTSHTCATAYTGYYTTACYTTRAT (SEQ ID NO: 10638) |
| 53 | +TATRRB + TA + YYTSHTCATAYTGYYTTACYTTRAT (SEQ ID NO: 10639) |

TABLE 8-continued

| Codon | |
|---|---|
| 53 | +TA + TRRBTA + YYTSHTCATAYTGYYTTACYTTRAT (SEQ ID NO: 10640) |
| 53 | +TRRB + TA + YYTSHTCATAYTGYYTTACYTTRAT (SEQ ID NO: 10641) |
| 53 | +TRRBTA + Y + YTSHTCATAYTGYYTTACYTTRAT (SEQ ID NO: 10642) |
| 53 | +TRRB + TAY + YTSHTCATAYTGYYTTACYTTRAT (SEQ ID NO: 10643) |
| 53 | +TA + Y + YTSHTCATAYTGYYTTACYTTRAT (SEQ ID NO: 10644) |
| 53 | +TAY + YTS + HTCATAYTGYYTTACYTTRAT (SEQ ID NO: 10645) |
| 53 | +TA + YYTS + HTCATAYTGYYTTACYTTRAT (SEQ ID NO: 10646) |
| 53 | RA + TT + TCT + ATRRBTAYYTSHTCATAYTGYYTTACYTTRATA (SEQ ID NO: 10647) |
| 53 | RA + TTTCT + A + TRRBTAYYTSHTCATAYTGYYTTACYTTRATA (SEQ ID NO: 10648) |
| 53 | RA + TT + TCTA + TRRBTAYYTSHTCATAYTGYYTTACYTTRATA (SEQ ID NO: 10649) |
| 53 | +TCT + A + TRRBTAYYTSHTCATAYTGYYTTACYTTRATA (SEQ ID NO: 10650) |
| 53 | +TCTA + TR + RBTAYYTSHTCATAYTGYYTTACYTTRATA (SEQ ID NO: 10651) |
| 53 | +TCT + ATR + RBTAYYTSHTCATAYTGYYTTACYTTRATA (SEQ ID NO: 10652) |
| 53 | +A + TR + RBTAYYTSHTCATAYTGYYTTACYTTRATA (SEQ ID NO: 10653) |
| 53 | +ATR + RBTA + YYTSHTCATAYTGYYTTACYTTRATA (SEQ ID NO: 10654) |
| 53 | +A + TRRBTA + YYTSHTCATAYTGYYTTACYTTRATA (SEQ ID NO: 10655) |
| 53 | +TR + RBTA + YYTSHTCATAYTGYYTTACYTTRATA (SEQ ID NO: 10656) |
| 53 | +TRRBTA + YY + TSHTCATAYTGYYTTACYTTRATA (SEQ ID NO: 10657) |
| 53 | +TR + RBTAYY + TSHTCATAYTGYYTTACYTTRATA (SEQ ID NO: 10658) |
| 53 | +RBTA + YY + TSHTCATAYTGYYTTACYTTRATA (SEQ ID NO: 10659) |
| 53 | +RBTAYY + T + SHTCATAYTGYYTTACYTTRATA (SEQ ID NO: 10660) |
| 53 | +RBTA + YYT + SHTCATAYTGYYTTACYTTRATA (SEQ ID NO: 10661) |
| 53 | +YY + T + SHTCATAYTGYYTTACYTTRATA (SEQ ID NO: 10662) |
| 53 | +YYT + SHT + CATAYTGYYTTACYTTRATA (SEQ ID NO: 10663) |
| 53 | +YY + TSHT + CATAYTGYYTTACYTTRATA (SEQ ID NO: 10664) |
| 53 | ARATTTCTATRRBTAYYTSHTCATAYTGYYTTACYTTRAT (SEQ ID NO: 10665) |
| 53 | TTTCTATRRBTAYYTSHTCATAYTGYYTTACYTTRAT (SEQ ID NO: 10666) |
| 53 | CTATRRBTAYYTSHTCATAYTGYYTTACYTTRAT (SEQ ID NO: 10667) |
| 53 | TATRRBTAYYTSHTCATAYTGYYTTACYTTRAT (SEQ ID NO: 10668) |
| 53 | TRRBTAYYTSHTCATAYTGYYTTACYTTRAT (SEQ ID NO: 10669) |
| 53 | TAYYTSHTCATAYTGYYTTACYTTRAT (SEQ ID NO: 10670) |
| 53 | RATTTCTATRRBTAYYTSHTCATAYTGYYTTACYTTRATA (SEQ ID NO: 10671) |
| 53 | TCTATRRBTAYYTSHTCATAYTGYYTTACYTTRATA (SEQ ID NO: 10672) |
| 53 | ATRRBTAYYTSHTCATAYTGYYTTACYTTRATA (SEQ ID NO: 10673) |
| 53 | TRRBTAYYTSHTCATAYTGYYTTACYTTRATA (SEQ ID NO: 10674) |
| 53 | RBTAYYTSHTCATAYTGYYTTACYTTRATA (SEQ ID NO: 10675) |
| 53 | YYTSHTCATAYTGYYTTACYTTRATA (SEQ ID NO: 10676) |
| 53 | YYTDTKYCCRCARATYTCTAYDDNTAYBTSMTCATAYTGYYTTACTTTGAT (SEQ ID NO: 10677) |
| 53 | ARATTTCTATRRBTAYYTSHTCATAYTGYYTTACYTTRAT + N (SEQ ID NO: 10678) |

TABLE 8-continued

| Codon | |
|---|---|
| 53 | TTTCTATRRBTAYYTSHTCATAYTGYYTTACYTTRAT + N (SEQ ID NO: 10679) |
| 53 | CTATRRBTAYYTSHTCATAYTGYYTTACYTTRAT + N (SEQ ID NO: 10680) |
| 53 | TATRRBTAYYTSHTCATAYTGYYTTACYTTRAT + N (SEQ ID NO: 10681) |
| 53 | TRRBTAYYTSHTCATAYTGYYTTACYTTRAT + N (SEQ ID NO: 10682) |
| 53 | TAYYTSHTCATAYTGYYTTACYTTRAT + N (SEQ ID NO: 10683) |
| 53 | RATTTCTATRRBTAYYTSHTCATAYTGYYTTACYTTRATA + N (SEQ ID NO: 10684) |
| 53 | TCTATRRBTAYYTSHTCATAYTGYYTTACYTTRATA + N (SEQ ID NO: 10685) |
| 53 | ATRRBTAYYTSHTCATAYTGYYTTACYTTRATA + N (SEQ ID NO: 10686) |
| 53 | TRRBTAYYTSHTCATAYTGYYTTACYTTRATA + N (SEQ ID NO: 10687) |
| 53 | RBTAYYTSHTCATAYTGYYTTACYTTRATA + N (SEQ ID NO: 10688) |
| 53 | YYTSHTCATAYTGYYTTACYTTRATA + N (SEQ ID NO: 10689) |
| 53 | YYTDTKYCCRCARATYTCTAYDDNTAYBTSMTCATAYTGYYTTACTTTGAT + N (SEQ ID NO: 10690) |
| 54 | +CAC + A + RATTTCTATRRBTAYYTSHTCATAYTGYYTTACYTT (SEQ ID NO: 10691) |
| 54 | +CACA + RA + TTTCTATRRBTAYYTSHTCATAYTGYYTTACYTT (SEQ ID NO: 10692) |
| 54 | +CAC + ARA + TTTCTATRRBTAYYTSHTCATAYTGYYTTACYTT (SEQ ID NO: 10693) |
| 54 | +A + RA + TTTCTATRRBTAYYTSHTCATAYTGYYTTACYTT (SEQ ID NO: 10694) |
| 54 | +ARA + TTTC + TATRRBTAYYTSHTCATAYTGYYTTACYTT (SEQ ID NO: 10695) |
| 54 | +A + RATTTC + TATRRBTAYYTSHTCATAYTGYYTTACYTT (SEQ ID NO: 10696) |
| 54 | +RA + TTTC + TATRRBTAYYTSHTCATAYTGYYTTACYTT (SEQ ID NO: 10697) |
| 54 | +RATTTC + TA + TRRBTAYYTSHTCATAYTGYYTTACYTT (SEQ ID NO: 10698) |
| 54 | +RA + TTTCTA + TRRBTAYYTSHTCATAYTGYYTTACYTT (SEQ ID NO: 10699) |
| 54 | +TTTC + TA + TRRBTAYYTSHTCATAYTGYYTTACYTT (SEQ ID NO: 10700) |
| 54 | +TTTCTA + T + RRBTAYYTSHTCATAYTGYYTTACYTT (SEQ ID NO: 10701) |
| 54 | +TTTC + TAT + RRBTAYYTSHTCATAYTGYYTTACYTT (SEQ ID NO: 10702) |
| 54 | +TA + T + RRBTAYYTSHTCATAYTGYYTTACYTT (SEQ ID NO: 10703) |
| 54 | +TAT + RRB + TAYYTSHTCATAYTGYYTTACYTT (SEQ ID NO: 10704) |
| 54 | +TA + TRRB + TAYYTSHTCATAYTGYYTTACYTT (SEQ ID NO: 10705) |
| 54 | +T + RRB + TAYYTSHTCATAYTGYYTTACYTT (SEQ ID NO: 10706) |
| 54 | +TRRB + TAY + YTSHTCATAYTGYYTTACYTT (SEQ ID NO: 10707) |
| 54 | +T + RRBTAY + YTSHTCATAYTGYYTTACYTT (SEQ ID NO: 10708) |
| 54 | A + CAR + A + TTTCTATRRBTAYYTSHTCATAYTGYYTTACYTTR (SEQ ID NO: 10709) |
| 54 | A + CARA + TT + TCTATRRBTAYYTSHTCATAYTGYYTTACYTTR (SEQ ID NO: 10710) |
| 54 | A + CAR + ATT + TCTATRRBTAYYTSHTCATAYTGYYTTACYTTR (SEQ ID NO: 10711) |
| 54 | +A + TT + TCTATRRBTAYYTSHTCATAYTGYYTTACYTTR (SEQ ID NO: 10712) |
| 54 | +ATT + TCTA + TRRBTAYYTSHTCATAYTGYYTTACYTTR (SEQ ID NO: 10713) |
| 54 | +A + TTTCTA + TRRBTAYYTSHTCATAYTGYYTTACYTTR (SEQ ID NO: 10714) |
| 54 | +TT + TCTA + TRRBTAYYTSHTCATAYTGYYTTACYTTR (SEQ ID NO: 10715) |
| 54 | +TTTCTA + TR + RBTAYYTSHTCATAYTGYYTTACYTTR (SEQ ID NO: 10716) |
| 54 | +TT + TCTATR + RBTAYYTSHTCATAYTGYYTTACYTTR (SEQ ID NO: 10717) |

TABLE 8-continued

| Codon | |
|---|---|
| 54 | +TCTA + TR + RBTAYYTSHTCATAYTGYYTTACYTTR (SEQ ID NO: 10718) |
| 54 | +TCTATR + R + BTAYYTSHTCATAYTGYYTTACYTTR (SEQ ID NO: 10719) |
| 54 | +TCTA + TRR + BTAYYTSHTCATAYTGYYTTACYTTR (SEQ ID NO: 10720) |
| 54 | +TR + R + BTAYYTSHTCATAYTGYYTTACYTTR (SEQ ID NO: 10721) |
| 54 | +TRR + BTA + YYTSHTCATAYTGYYTTACYTTR (SEQ ID NO: 10722) |
| 54 | +TR + RBTA + YYTSHTCATAYTGYYTTACYTTR (SEQ ID NO: 10723) |
| 54 | +R + BTA + YYTSHTCATAYTGYYTTACYTTR (SEQ ID NO: 10724) |
| 54 | +RBTA + YYT + SHTCATAYTGYYTTACYTTR (SEQ ID NO: 10725) |
| 54 | +R + BTAYYT + SHTCATAYTGYYTTACYTTR (SEQ ID NO: 10726) |
| 54 | +CA + RAT + TTCTATRRBTAYYTSHTCATAYTGYYTTACYTTRA (SEQ ID NO: 10727) |
| 54 | CARAT + T + TC + TATRRBTAYYTSHTCATAYTGYYTTACYTTRA (SEQ ID NO: 10728) |
| 54 | CA + RAT + TTC + TATRRBTAYYTSHTCATAYTGYYTTACYTTRA (SEQ ID NO: 10729) |
| 54 | +RAT + T + TCTATRRBTAYYTSHTCATAYTGYYTTACYTTRA (SEQ ID NO: 10730) |
| 54 | +RATT + TC + TATRRBTAYYTSHTCATAYTGYYTTACYTTRA (SEQ ID NO: 10731) |
| 54 | +RAT + TTC + TATRRBTAYYTSHTCATAYTGYYTTACYTTRA (SEQ ID NO: 10732) |
| 54 | +T + TC + TATRRBTAYYTSHTCATAYTGYYTTACYTTRA (SEQ ID NO: 10733) |
| 54 | +TTC + TATR + RBTAYYTSHTCATAYTGYYTTACYTTRA (SEQ ID NO: 10734) |
| 54 | +T + TCTATR + RBTAYYTSHTCATAYTGYYTTACYTTRA (SEQ ID NO: 10735) |
| 54 | +TC + TATR + RBTAYYTSHTCATAYTGYYTTACYTTRA (SEQ ID NO: 10736) |
| 54 | +TCTATR + RB + TAYYTSHTCATAYTGYYTTACYTTRA (SEQ ID NO: 10737) |
| 54 | +TC + TATRRB + TAYYTSHTCATAYTGYYTTACYTTRA (SEQ ID NO: 10738) |
| 54 | +TATR + RB + TAYYTSHTCATAYTGYYTTACYTTRA (SEQ ID NO: 10739) |
| 54 | +TATRRB + T + AYYTSHTCATAYTGYYTTACYTTRA (SEQ ID NO: 10740) |
| 54 | +TATR + RBT + AYYTSHTCATAYTGYYTTACYTTRA (SEQ ID NO: 10741) |
| 54 | +RB + T + AYYTSHTCATAYTGYYTTACYTTRA (SEQ ID NO: 10742) |
| 54 | +RBT + AYY + TSHTCATAYTGYYTTACYTTRA (SEQ ID NO: 10743) |
| 54 | +RB + TAYY + TSHTCATAYTGYYTTACYTTRA (SEQ ID NO: 10744) |
| 54 | CACARATTTCTATRRBTAYYTSHTCATAYTGYYTTACYTT (SEQ ID NO: 10745) |
| 54 | ARATTTCTATRRBTAYYTSHTCATAYTGYYTTACYTT (SEQ ID NO: 10746) |
| 54 | RATTTCTATRRBTAYYTSHTCATAYTGYYTTACYTT (SEQ ID NO: 10747) |
| 54 | TTTCTATRRBTAYYTSHTCATAYTGYYTTACYTT (SEQ ID NO: 10748) |
| 54 | TATRRBTAYYTSHTCATAYTGYYTTACYTT (SEQ ID NO: 10749) |
| 54 | TRRBTAYYTSHTCATAYTGYYTTACYTT (SEQ ID NO: 10750) |
| 54 | ACARATTTCTATRRBTAYYTSHTCATAYTGYYTTACYTTR (SEQ ID NO: 10751) |
| 54 | ATTTCTATRRBTAYYTSHTCATAYTGYYTTACYTTR (SEQ ID NO: 10752) |
| 54 | TTTCTATRRBTAYYTSHTCATAYTGYYTTACYTTR (SEQ ID NO: 10753) |
| 54 | TCTATRRBTAYYTSHTCATAYTGYYTTACYTTR (SEQ ID NO: 10754) |
| 54 | TRRBTAYYTSHTCATAYTGYYTTACYTTR (SEQ ID NO: 10755) |
| 54 | RBTAYYTSHTCATAYTGYYTTACYTTR (SEQ ID NO: 10756) |

TABLE 8-continued

| Codon | |
|---|---|
| 54 | CARATTTCTATRRBTAYYTSHTCATAYTGYYTTACYTTRA (SEQ ID NO: 10757) |
| 54 | RATTTCTATRRBTAYYTSHTCATAYTGYYTTACYTTRA (SEQ ID NO: 10758) |
| 54 | TTCTATRRBTAYYTSHTCATAYTGYYTTACYTTRA (SEQ ID NO: 10759) |
| 54 | TCTATRRBTAYYTSHTCATAYTGYYTTACYTTRA (SEQ ID NO: 10760) |
| 54 | TATRRBTAYYTSHTCATAYTGYYTTACYTTRA (SEQ ID NO: 10761) |
| 54 | RBTAYYTSHTCATAYTGYYTTACYTTRA (SEQ ID NO: 10762) |
| 54 | RRYYYTDTKYCCRCARATYTCTAYDDNTAYBTSMTCATAYTGYYTTACTTT (SEQ ID NO: 10763) |
| 54 | CACARATTTCTATRRBTAYYTSHTCATAYTGYYTTACYTT + N (SEQ ID NO: 10764) |
| 54 | ARATTTCTATRRBTAYYTSHTCATAYTGYYTTACYTT + N (SEQ ID NO: 10765) |
| 54 | RATTTCTATRRBTAYYTSHTCATAYTGYYTTACYTT + N (SEQ ID NO: 10766) |
| 54 | TTTCTATRRBTAYYTSHTCATAYTGYYTTACYTT + N (SEQ ID NO: 10767) |
| 54 | TATRRBTAYYTSHTCATAYTGYYTTACYTT + N (SEQ ID NO: 10768) |
| 54 | TRRBTAYYTSHTCATAYTGYYTTACYTT + N (SEQ ID NO: 10769) |
| 54 | ACARATTTCTATRRBTAYYTSHTCATAYTGYYTTACYTTR + N (SEQ ID NO: 10770) |
| 54 | ATTTCTATRRBTAYYTSHTCATAYTGYYTTACYTTR + N (SEQ ID NO: 10771) |
| 54 | TTTCTATRRBTAYYTSHTCATAYTGYYTTACYTTR + N (SEQ ID NO: 10772) |
| 54 | TCTATRRBTAYYTSHTCATAYTGYYTTACYTTR + N (SEQ ID NO: 10773) |
| 54 | TRRBTAYYTSHTCATAYTGYYTTACYTTR + N (SEQ ID NO: 10774) |
| 54 | RBTAYYTSHTCATAYTGYYTTACYTTR + N (SEQ ID NO: 10775) |
| 54 | CARATTTCTATRRBTAYYTSHTCATAYTGYYTTACYTTRA + N (SEQ ID NO: 10776) |
| 54 | RATTTCTATRRBTAYYTSHTCATAYTGYYTTACYTTRA + N (SEQ ID NO: 10777) |
| 54 | TTCTATRRBTAYYTSHTCATAYTGYYTTACYTTRA + N (SEQ ID NO: 10778) |
| 54 | TCTATRRBTAYYTSHTCATAYTGYYTTACYTTRA + N (SEQ ID NO: 10779) |
| 54 | TATRRBTAYYTSHTCATAYTGYYTTACYTTRA + N (SEQ ID NO: 10780) |
| 54 | RBTAYYTSHTCATAYTGYYTTACYTTRA + N (SEQ ID NO: 10781) |
| 54 | RRYYYTDTKYCCRCARATYTCTAYDDNTAYBTSMTCATAYTGYYTTACTTT + N(SEQ ID NO: 10782) |
| 58 | +GC + Y + YTWTKYCCACARATTTCTATRRBTAYYTSHTCATAYT (SEQ ID NO: 10783) |
| 58 | GCY + YTW + TKY + CCACARATTTCTATRRBTAYYTSHTCATAYT (SEQ ID NO: 10784) |
| 58 | GC + Y + YTWTKY + CCACARATTTCTATRRBTAYYTSHTCATAYT (SEQ ID NO: 10785) |
| 58 | +Y + YTW + TKYCCACARATTTCTATRRBTAYYTSHTCATAYT (SEQ ID NO: 10786) |
| 58 | +YYTW + TKY + CCACARATTTCTATRRBTAYYTSHTCATAYT (SEQ ID NO: 10787) |
| 58 | +Y + YTWTKY + CCACARATTTCTATRRBTAYYTSHTCATAYT (SEQ ID NO: 10788) |
| 58 | +YTW + TKY + CCACARATTTCTATRRBTAYYTSHTCATAYT (SEQ ID NO: 10789) |
| 58 | +YTWTKY + CCA + CARATTTCTATRRBTAYYTSHTCATAYT (SEQ ID NO: 10790) |
| 58 | +YTW + TKYCCA + CARATTTCTATRRBTAYYTSHTCATAYT (SEQ ID NO: 10791) |
| 58 | +TKY + CCA + CARATTTCTATRRBTAYYTSHTCATAYT (SEQ ID NO: 10792) |
| 58 | +TKYCCA + CARATT + TCTATRRBTAYYTSHTCATAYT (SEQ ID NO: 10793) |
| 58 | +TKY + CCACARATT + TCTATRRBTAYYTSHTCATAYT (SEQ ID NO: 10794) |
| 58 | +CCA + CARATT + TCTATRRBTAYYTSHTCATAYT (SEQ ID NO: 10795) |

TABLE 8-continued

| Codon | |
|---|---|
| 58 | +CCACARATT + TC + TATRRBTAYYTSHTCATAYT (SEQ ID NO: 10796) |
| 58 | +CCA + CARATTTC + TATRRBTAYYTSHTCATAYT (SEQ ID NO: 10797) |
| 58 | +CARATT + TC + TATRRBTAYYTSHTCATAYT (SEQ ID NO: 10798) |
| 58 | +CARATTTC + T + ATRRBTAYYTSHTCATAYT (SEQ ID NO: 10799) |
| 58 | +CARATT + TCT + ATRRBTAYYTSHTCATAYT (SEQ ID NO: 10800) |
| 58 | GCYYTWTKYCCACARATTTCTATRRBTAYYTSHTCATAYT (SEQ ID NO: 10801) |
| 58 | YYTWTKYCCACARATTTCTATRRBTAYYTSHTCATAYT (SEQ ID NO: 10802) |
| 58 | YTWTKYCCACARATTTCTATRRBTAYYTSHTCATAYT (SEQ ID NO: 10803) |
| 58 | TKYCCACARATTTCTATRRBTAYYTSHTCATAYT (SEQ ID NO: 10804) |
| 58 | CCACARATTTCTATRRBTAYYTSHTCATAYT (SEQ ID NO: 10805) |
| 58 | CARATTTCTATRRBTAYYTSHTCATAYT (SEQ ID NO: 10806) |
| 58 | ACTGTACCTRYRRYYYTDTKYCCRCARATYTCTAYDDNTAYBTSMTCATA (SEQ ID NO: 10807) |
| 58 | GCYYTWTKYCCACARATTTCTATRRBTAYYTSHTCATAYT + N (SEQ ID NO: 10808) |
| 58 | YYTWTKYCCACARATTTCTATRRBTAYYTSHTCATAYT + N (SEQ ID NO: 10809) |
| 58 | YTWTKYCCACARATTTCTATRRBTAYYTSHTCATAYT + N (SEQ ID NO: 10810) |
| 58 | TKYCCACARATTTCTATRRBTAYYTSHTCATAYT + N (SEQ ID NO: 10811) |
| 58 | CCACARATTTCTATRRBTAYYTSHTCATAYT + N (SEQ ID NO: 10812) |
| 58 | CARATTTCTATRRBTAYYTSHTCATAYT + N (SEQ ID NO: 10813) |
| 58 | ACTGTACCTRYRRYYYTDTKYCCRCARATYTCTAYDDNTAYBTSMTCATA + N (SEQ ID NO: 10814) |
| 71 | ATGTTG + AYA + GGT + GTRGGYCCYAYYARYACTGWACCTATRG (SEQ ID NO: 10815) |
| 71 | +ATGTTG + AYAGGT + GTRGGYCCYAYYARYACTGWACCTATRG (SEQ ID NO: 10816) |
| 71 | +ATGTTG + AYAGGT + GTRGGYCCYAYYARYACTGWACCTATRG (SEQ ID NO: 10817) |
| 71 | +GGT + GTR + GGYCCYAYYARYACTGWACCTATRG (SEQ ID NO: 10818) |
| 71 | +GGTGTR + GGY + CCYAYYARYACTGWACCTATRG (SEQ ID NO: 10819) |
| 71 | +GGT + GTRGGY + CCYAYYARYACTGWACCTATRG (SEQ ID NO: 10820) |
| 71 | +GTR + GGY + CCYAYYARYACTGWACCTATRG (SEQ ID NO: 10821) |
| 71 | +GTRGGY + CC + YAYYARYACTGWACCTATRG (SEQ ID NO: 10822) |
| 71 | +GTR + GGYCC + YAYYARYACTGWACCTATRG (SEQ ID NO: 10823) |
| 71 | +GGY + CC + YAYYARYACTGWACCTATRG (SEQ ID NO: 10824) |
| 71 | +GGYCC + Y + AYYARYACTGWACCTATRG (SEQ ID NO: 10825) |
| 71 | +GGY + CCY + AYYARYACTGWACCTATRG (SEQ ID NO: 10826) |
| 71 | +CC + Y + AYYARYACTGWACCTATRG (SEQ ID NO: 10827) |
| 71 | +CCY + AYY + ARYACTGWACCTATRG (SEQ ID NO: 10828) |
| 71 | +CC + YAYY + ARYACTGWACCTATRG (SEQ ID NO: 10829) |
| 71 | +Y + AYY + ARYACTGWACCTATRG (SEQ ID NO: 10830) |
| 71 | +YAYY + AR + YACTGWACCTATRG (SEQ ID NO: 10831) |
| 71 | +Y + AYYAR + YACTGWACCTATRG (SEQ ID NO: 10832) |
| 71 | ATGTTGAYAGGTGTRGGYCCYAYYARYACTGWACCTATRG (SEQ ID NO: 10833) |
| 71 | GGTGTRGGYCCYAYYARYACTGWACCTATRG (SEQ ID NO: 10834) |

TABLE 8-continued

| Codon | |
|---|---|
| 71 | GTRGGYCCYAYYARYACTGWACCTATRG (SEQ ID NO: 10835) |
| 71 | GGYCCYAYYARYACTGWACCTATRG (SEQ ID NO: 10836) |
| 71 | CCYAYYARYACTGWACCTATRG (SEQ ID NO: 10837) |
| 71 | YAYYARYACTGWACCTATRG (SEQ ID NO: 10838) |
| 71 | RTTYCKYCCAATTATGTTGRYAGGKGTRGGYCCTAYYAAYACTGTACCTAT (SEQ ID NO: 10839) |
| 71 | ATGTTGAYAGGTGTRGGYCCYAYYARYACTGWACCTATRG + N (SEQ ID NO: 10840) |
| 71 | GGTGTRGGYCCYAYYARYACTGWACCTATRG + N (SEQ ID NO: 10841) |
| 71 | GTRGGYCCYAYYARYACTGWACCTATRG + N (SEQ ID NO: 10842) |
| 71 | GGYCCYAYYARYACTGWACCTATRG + N (SEQ ID NO: 10843) |
| 71 | CCYAYYARYACTGWACCTATRG + N (SEQ ID NO: 10844) |
| 71 | YAYYARYACTGWACCTATRG + N (SEQ ID NO: 10845) |
| 71 | RTTYCKYCCAATTATGTTGRYAGGKGTRGGYCCTAYYAAYACTGTACCTAT + N(SEQ ID NO: 10846) |
| 73 | YC + CAA + TTA + TGTTGAYAGGTGTRGGYCCYAYYARYACTGWA (SEQ ID NO: 10847) |
| 73 | YC + CAATTA + TGT + TGAYAGGTGTRGGYCCYAYYARYACTGWA (SEQ ID NO: 10848) |
| 73 | YC + CAA + TTATGT + TGAYAGGTGTRGGYCCYAYYARYACTGWA (SEQ ID NO: 10849) |
| 73 | +TTA + TGT + TGAYAGGTGTRGGYCCYAYYARYACTGWA (SEQ ID NO: 10850) |
| 73 | +TTATGT + TG + AYAGGTGTRGGYCCYAYYARYACTGWA (SEQ ID NO: 10851) |
| 73 | +TTA + TGTTG + AYAGGTGTRGGYCCYAYYARYACTGWA (SEQ ID NO: 10852) |
| 73 | +TGT + TG + AYAGGTGTRGGYCCYAYYARYACTGWA (SEQ ID NO: 10853) |
| 73 | +TGTTG + A + YAGGTGTRGGYCCYAYYARYACTGWA (SEQ ID NO: 10854) |
| 73 | +TGT + TGA + YAGGTGTRGGYCCYAYYARYACTGWA (SEQ ID NO: 10855) |
| 73 | +TG + A + YAGGTGTRGGYCCYAYYARYACTGWA (SEQ ID NO: 10856) |
| 73 | +TGA + YAG + GTGTRGGYCCYAYYARYACTGWA (SEQ ID NO: 10857) |
| 73 | +TG + AYAG + GTGTRGGYCCYAYYARYACTGWA (SEQ ID NO: 10858) |
| 73 | +A + YAG + GTGTRGGYCCYAYYARYACTGWA (SEQ ID NO: 10859) |
| 73 | +AYAG + GT + GTRGGYCCYAYYARYACTGWA (SEQ ID NO: 10860) |
| 73 | +A + YAGGT + GTRGGYCCYAYYARYACTGWA (SEQ ID NO: 10861) |
| 73 | +YAG + GT + GTRGGYCCYAYYARYACTGWA (SEQ ID NO: 10862) |
| 73 | +YAGGT + G + TRGGYCCYAYYARYACTGWA (SEQ ID NO: 10863) |
| 73 | +YAG + GTG + TRGGYCCYAYYARYACTGWA (SEQ ID NO: 10864) |
| 73 | +CCA + ATT + ATGTTGAYAGGTGTRGGYCCYAYYARYACTGWAC (SEQ ID NO: 10865) |
| 73 | +CCAATT + ATG + TTGAYAGGTGTRGGYCCYAYYARYACTGWAC (SEQ ID NO: 10866) |
| 73 | +CCA + ATTATG + TTGAYAGGTGTRGGYCCYAYYARYACTGWAC (SEQ ID NO: 10867) |
| 73 | +ATT + ATG + TTGAYAGGTGTRGGYCCYAYYARYACTGWAC (SEQ ID NO: 10868) |
| 73 | +ATTATG + TTG + AYAGGTGTRGGYCCYAYYARYACTGWAC (SEQ ID NO: 10869) |
| 73 | +ATT + ATGTTG + AYAGGTGTRGGYCCYAYYARYACTGWAC (SEQ ID NO: 10870) |
| 73 | +ATG + TTG + AYAGGTGTRGGYCCYAYYARYACTGWAC (SEQ ID NO: 10871) |
| 73 | +ATGTTG + AY + AGGTGTRGGYCCYAYYARYACTGWAC (SEQ ID NO: 10872) |
| 73 | +ATG + TTGAY + AGGTGTRGGYCCYAYYARYACTGWAC (SEQ ID NO: 10873) |

TABLE 8-continued

| Codon | |
|---|---|
| 73 | +TTG + AY + AGGTGTRGGYCCYAYYARYACTGWAC (SEQ ID NO: 10874) |
| 73 | +TTGAY + A + GGTGTRGGYCCYAYYARYACTGWAC (SEQ ID NO: 10875) |
| 73 | +TTG + AYA + GGTGTRGGYCCYAYYARYACTGWAC (SEQ ID NO: 10876) |
| 73 | +AY + A + GGTGTRGGYCCYAYYARYACTGWAC (SEQ ID NO: 10877) |
| 73 | +AYA + GGT + GTRGGYCCYAYYARYACTGWAC (SEQ ID NO: 10878) |
| 73 | +AY + AGGT + GTRGGYCCYAYYARYACTGWAC (SEQ ID NO: 10879) |
| 73 | +A + GGT + GTRGGYCCYAYYARYACTGWAC (SEQ ID NO: 10880) |
| 73 | +AGGT + GT + RGGYCCYAYYARYACTGWAC (SEQ ID NO: 10881) |
| 73 | +A + GGTGT + RGGYCCYAYYARYACTGWAC (SEQ ID NO: 10882) |
| 73 | YCCAATTATGTTGAYAGGTGTRGGYCCYAYYARYACTGWA (SEQ ID NO: 10883) |
| 73 | TTATGTTGAYAGGTGTRGGYCCYAYYARYACTGWA (SEQ ID NO: 10884) |
| 73 | TGTTGAYAGGTGTRGGYCCYAYYARYACTGWA (SEQ ID NO: 10885) |
| 73 | TGAYAGGTGTRGGYCCYAYYARYACTGWA (SEQ ID NO: 10886) |
| 73 | AYAGGTGTRGGYCCYAYYARYACTGWA (SEQ ID NO: 10887) |
| 73 | YAGGTGTRGGYCCYAYYARYACTGWA (SEQ ID NO: 10888) |
| 73 | CCAATTATGTTGAYAGGTGTRGGYCCYAYYARYACTGWAC (SEQ ID NO: 10889) |
| 73 | ATTATGTTGAYAGGTGTRGGYCCYAYYARYACTGWAC (SEQ ID NO: 10890) |
| 73 | ATGTTGAYAGGTGTRGGYCCYAYYARYACTGWAC (SEQ ID NO: 10891) |
| 73 | TTGAYAGGTGTRGGYCCYAYYARYACTGWAC (SEQ ID NO: 10892) |
| 73 | AYAGGTGTRGGYCCYAYYARYACTGWAC (SEQ ID NO: 10893) |
| 73 | AGGTGTRGGYCCYAYYARYACTGWAC (SEQ ID NO: 10894) |
| 73 | CAWCADRTTYCKYCCAATTATGTTGRYAGGKGTRGGYCCTAYYAATACTGT (SEQ ID NO: 10895) |
| 73 | YCCAATTATGTTGAYAGGTGTRGGYCCYAYYARYACTGWA + N (SEQ ID NO: 10896) |
| 73 | TTATGTTGAYAGGTGTRGGYCCYAYYARYACTGWA + N (SEQ ID NO: 10897) |
| 73 | TGTTGAYAGGTGTRGGYCCYAYYARYACTGWA + N (SEQ ID NO: 10898) |
| 73 | TGAYAGGTGTRGGYCCYAYYARYACTGWA + N (SEQ ID NO: 10899) |
| 73 | AYAGGTGTRGGYCCYAYYARYACTGWA + N (SEQ ID NO: 10900) |
| 73 | YAGGTGTRGGYCCYAYYARYACTGWA + N (SEQ ID NO: 10901) |
| 73 | CCAATTATGTTGAYAGGTGTRGGYCCYAYYARYACTGWAC + N (SEQ ID NO: 10902) |
| 73 | ATTATGTTGAYAGGTGTRGGYCCYAYYARYACTGWAC + N (SEQ ID NO: 10903) |
| 73 | ATGTTGAYAGGTGTRGGYCCYAYYARYACTGWAC + N (SEQ ID NO: 10904) |
| 73 | TTGAYAGGTGTRGGYCCYAYYARYACTGWAC + N (SEQ ID NO: 10905) |
| 73 | AYAGGTGTRGGYCCYAYYARYACTGWAC + N (SEQ ID NO: 10906) |
| 73 | AGGTGTRGGYCCYAYYARYACTGWAC + N (SEQ ID NO: 10907) |
| 73 | CAWCADRTTYCKYCCAATTATGTTGRYAGGKGTRGGYCCTAYYAATACTGT + N (SEQ ID NO: 10908) |
| 74 | +CKY + CCA + ATTATGTTGAYAGGTGTRGGYCCYAYYARYACTG (SEQ ID NO: 10909) |
| 74 | +CKYCCA + ATT + ATGTTGAYAGGTGTRGGYCCYAYYARYACTG (SEQ ID NO: 10910) |
| 74 | +CKY + CCAATT + ATGTTGAYAGGTGTRGGYCCYAYYARYACTG (SEQ ID NO: 10911) |

TABLE 8-continued

| Codon | |
|---|---|
| 74 | +CCA + ATT + ATGTTGAYAGGTGTRGGYCCYAYYARYACTG (SEQ ID NO: 10912) |
| 74 | +CCAATT + AT + GTTGAYAGGTGTRGGYCCYAYYARYACTG (SEQ ID NO: 10913) |
| 74 | +CCA + ATTAT + GTTGAYAGGTGTRGGYCCYAYYARYACTG (SEQ ID NO: 10914) |
| 74 | +ATT + AT + GTTGAYAGGTGTRGGYCCYAYYARYACTG (SEQ ID NO: 10915) |
| 74 | +ATTAT + G + TTGAYAGGTGTRGGYCCYAYYARYACTG (SEQ ID NO: 10916) |
| 74 | +ATT + ATG + TTGAYAGGTGTRGGYCCYAYYARYACTG (SEQ ID NO: 10917) |
| 74 | +AT + G + TTGAYAGGTGTRGGYCCYAYYARYACTG (SEQ ID NO: 10918) |
| 74 | +ATG + TTG + AYAGGTGTRGGYCCYAYYARYACTG (SEQ ID NO: 10919) |
| 74 | +AT + GTTG + AYAGGTGTRGGYCCYAYYARYACTG (SEQ ID NO: 10920) |
| 74 | +G + TTG + AYAGGTGTRGGYCCYAYYARYACTG (SEQ ID NO: 10921) |
| 74 | +GTTG + AY + AGGTGTRGGYCCYAYYARYACTG (SEQ ID NO: 10922) |
| 74 | +G + TTGAY + AGGTGTRGGYCCYAYYARYACTG (SEQ ID NO: 10923) |
| 74 | +TTG + AY + AGGTGTRGGYCCYAYYARYACTG (SEQ ID NO: 10924) |
| 74 | +TTGAY + A + GGTGTRGGYCCYAYYARYACTG (SEQ ID NO: 10925) |
| 74 | +TTG + AYA + GGTGTRGGYCCYAYYARYACTG (SEQ ID NO: 10926) |
| 74 | CKYCCAATTATGTTGAYAGGTGTRGGYCCYAYYARYACTG (SEQ ID NO: 10927) |
| 74 | CCAATTATGTTGAYAGGTGTRGGYCCYAYYARYACTG (SEQ ID NO: 10928) |
| 74 | ATTATGTTGAYAGGTGTRGGYCCYAYYARYACTG (SEQ ID NO: 10929) |
| 74 | ATGTTGAYAGGTGTRGGYCCYAYYARYACTG (SEQ ID NO: 10930) |
| 74 | GTTGAYAGGTGTRGGYCCYAYYARYACTG (SEQ ID NO: 10931) |
| 74 | TTGAYAGGTGTRGGYCCYAYYARYACTG (SEQ ID NO: 10932) |
| 74 | RGTCAWCADRTTYCKYCCAATTATGTTGRYAGGKGTRGGYCCTAYTAATAC (SEQ ID NO: 10933) |
| 74 | CKYCCAATTATGTTGAYAGGTGTRGGYCCYAYYARYACTG + N (SEQ ID NO: 10934) |
| 74 | CCAATTATGTTGAYAGGTGTRGGYCCYAYYARYACTG + N (SEQ ID NO: 10935) |
| 74 | ATTATGTTGAYAGGTGTRGGYCCYAYYARYACTG + N (SEQ ID NO: 10936) |
| 74 | ATGTTGAYAGGTGTRGGYCCYAYYARYACTG + N (SEQ ID NO: 10937) |
| 74 | GTTGAYAGGTGTRGGYCCYAYYARYACTG + N (SEQ ID NO: 10938) |
| 74 | TTGAYAGGTGTRGGYCCYAYYARYACTG + N (SEQ ID NO: 10939) |
| 74 | RGTCAWCADRTTYCKYCCAATTATGTTGRYAGGKGTRGGYCCTAYTAATAC + N (SEQ ID NO: 10940) |
| 76 | +ADR + TT + YCKYCCAATTATGTTGAYAGGTGTRGGYCCYAYYA (SEQ ID NO: 10941) |
| 76 | +ADRTT + Y + CKYCCAATTATGTTGAYAGGTGTRGGYCCYAYYA (SEQ ID NO: 10942) |
| 76 | +ADR + TTY + CKYCCAATTATGTTGAYAGGTGTRGGYCCYAYYA (SEQ ID NO: 10943) |
| 76 | +TT + Y + CKYCCAATTATGTTGAYAGGTGTRGGYCCYAYYA (SEQ ID NO: 10944) |
| 76 | +TTY + CKY + CCAATTATGTTGAYAGGTGTRGGYCCYAYYA (SEQ ID NO: 10945) |
| 76 | +TT + YCKY + CCAATTATGTTGAYAGGTGTRGGYCCYAYYA (SEQ ID NO: 10946) |
| 76 | +Y + CKY + CCAATTATGTTGAYAGGTGTRGGYCCYAYYA (SEQ ID NO: 10947) |
| 76 | +YCKY + CC + AATTATGTTGAYAGGTGTRGGYCCYAYYA (SEQ ID NO: 10948) |
| 76 | +Y + CKYCC + AATTATGTTGAYAGGTGTRGGYCCYAYYA (SEQ ID NO: 10949) |
| 76 | +CKY + CC + AATTATGTTGAYAGGTGTRGGYCCYAYYA (SEQ ID NO: 10950) |

TABLE 8-continued

| Codon | |
|---|---|
| 76 | +CKYCC + A + ATTATGTTGAYAGGTGTRGGYCCYAYYA (SEQ ID NO: 10951) |
| 76 | +CKY + CCA + ATTATGTTGAYAGGTGTRGGYCCYAYYA (SEQ ID NO: 10952) |
| 76 | +CC + A + ATTATGTTGAYAGGTGTRGGYCCYAYYA (SEQ ID NO: 10953) |
| 76 | +CCA + AT + TATGTTGAYAGGTGTRGGYCCYAYYA (SEQ ID NO: 10954) |
| 76 | +CC + AAT + TATGTTGAYAGGTGTRGGYCCYAYYA (SEQ ID NO: 10955) |
| 76 | +A + AT + TATGTTGAYAGGTGTRGGYCCYAYYA (SEQ ID NO: 10956) |
| 76 | +AAT + T + ATGTTGAYAGGTGTRGGYCCYAYYA (SEQ ID NO: 10957) |
| 76 | +A + ATT + ATGTTGAYAGGTGTRGGYCCYAYYA (SEQ ID NO: 10958) |
| 76 | ADRTTYCKYCCAATTATGTTGAYAGGTGTRGGYCCYAYYA (SEQ ID NO: 10959) |
| 76 | TTYCKYCCAATTATGTTGAYAGGTGTRGGYCCYAYYA (SEQ ID NO: 10960) |
| 76 | YCKYCCAATTATGTTGAYAGGTGTRGGYCCYAYYA (SEQ ID NO: 10961) |
| 76 | CKYCCAATTATGTTGAYAGGTGTRGGYCCYAYYA (SEQ ID NO: 10962) |
| 76 | CCAATTATGTTGAYAGGTGTRGGYCCYAYYA (SEQ ID NO: 10963) |
| 76 | AATTATGTTGAYAGGTGTRGGYCCYAYYA (SEQ ID NO: 10964) |
| 76 | AAKYTGRGTCAWCADRTTYCKYCCAATTATGTTGRYAGGKGTRGGTCCTAC (SEQ ID NO: 10965) |
| 76 | ADRTTYCKYCCAATTATGTTGAYAGGTGTRGGYCCYAYYA + N (SEQ ID NO: 10966) |
| 76 | TTYCKYCCAATTATGTTGAYAGGTGTRGGYCCYAYYA + N (SEQ ID NO: 10967) |
| 76 | YCKYCCAATTATGTTGAYAGGTGTRGGYCCYAYYA + N (SEQ ID NO: 10968) |
| 76 | CKYCCAATTATGTTGAYAGGTGTRGGYCCYAYYA + N (SEQ ID NO: 10969) |
| 76 | CCAATTATGTTGAYAGGTGTRGGYCCYAYYA + N (SEQ ID NO: 10970) |
| 76 | AATTATGTTGAYAGGTGTRGGYCCYAYYA + N (SEQ ID NO: 10971) |
| 76 | AAKYTGRGTCAWCADRTTYCKYCCAATTATGTTGRYAGGKGTRGGTCCTAC + N (SEQ ID NO: 10972) |
| 82 | R + C + ADC + CAAKYTGRGTCAACADRTTYCKYCCAATTATGTTG (SEQ ID NO: 10973) |
| 82 | R + CADC + CAA + KYTGRGTCAACADRTTYCKYCCAATTATGTTG (SEQ ID NO: 10974) |
| 82 | R + C + ADCCAA + KYTGRGTCAACADRTTYCKYCCAATTATGTTG (SEQ ID NO: 10975) |
| 82 | +ADC + CAA + KYTGRGTCAACADRTTYCKYCCAATTATGTTG (SEQ ID NO: 10976) |
| 82 | +ADCCAA + KY + TGRGTCAACADRTTYCKYCCAATTATGTTG (SEQ ID NO: 10977) |
| 82 | +ADC + CAAKY + TGRGTCAACADRTTYCKYCCAATTATGTTG (SEQ ID NO: 10978) |
| 82 | +CAA + KY + TGRGTCAACADRTTYCKYCCAATTATGTTG (SEQ ID NO: 10979) |
| 82 | +CAAKY + T + GRGTCAACADRTTYCKYCCAATTATGTTG (SEQ ID NO: 10980) |
| 82 | +CAA + KYT + GRGTCAACADRTTYCKYCCAATTATGTTG (SEQ ID NO: 10981) |
| 82 | +KY + T + GRGTCAACADRTTYCKYCCAATTATGTTG (SEQ ID NO: 10982) |
| 82 | +KYT + GRG + TCAACADRTTYCKYCCAATTATGTTG (SEQ ID NO: 10983) |
| 82 | +KY + TGRG + TCAACADRTTYCKYCCAATTATGTTG (SEQ ID NO: 10984) |
| 82 | +T + GRG + TCAACADRTTYCKYCCAATTATGTTG (SEQ ID NO: 10985) |
| 82 | +TGRG + TCA + ACADRTTYCKYCCAATTATGTTG (SEQ ID NO: 10986) |
| 82 | +T + GRGTCA + ACADRTTYCKYCCAATTATGTTG (SEQ ID NO: 10987) |
| 82 | +GRG + TCA + ACADRTTYCKYCCAATTATGTTG (SEQ ID NO: 10988) |

TABLE 8-continued

| Codon | |
|---|---|
| 82 | +GRGTCA + ACA + DRTTYCKYCCAATTATGTTG (SEQ ID NO: 10989) |
| 82 | +GRG + TCAACA + DRTTYCKYCCAATTATGTTG (SEQ ID NO: 10990) |
| 82 | CA + D + CCA + AKYTGRGTCAACADRTTYCKYCCAATTATGTTGA (SEQ ID NO: 10991) |
| 82 | +CA + DCCA + AKYTGRGTCAACADRTTYCKYCCAATTATGTTGA (SEQ ID NO: 10992) |
| 82 | +CA + DCCA + AKYTGRGTCAACADRTTYCKYCCAATTATGTTGA (SEQ ID NO: 10993) |
| 82 | +CCA + AKY + TGRGTCAACADRTTYCKYCCAATTATGTTGA (SEQ ID NO: 10994) |
| 82 | +CCAAKY + TG + RGTCAACADRTTYCKYCCAATTATGTTGA (SEQ ID NO: 10995) |
| 82 | +CCA + AKYTG + RGTCAACADRTTYCKYCCAATTATGTTGA (SEQ ID NO: 10996) |
| 82 | +AKY + TG + RGTCAACADRTTYCKYCCAATTATGTTGA (SEQ ID NO: 10997) |
| 82 | +AKYTG + R + GTCAACADRTTYCKYCCAATTATGTTGA (SEQ ID NO: 10998) |
| 82 | +AKY + TGR + GTCAACADRTTYCKYCCAATTATGTTGA (SEQ ID NO: 10999) |
| 82 | +TG + R + GTCAACADRTTYCKYCCAATTATGTTGA (SEQ ID NO: 11000) |
| 82 | +TGR + GTC + AACADRTTYCKYCCAATTATGTTGA (SEQ ID NO: 11001) |
| 82 | +TG + RGTC + AACADRTTYCKYCCAATTATGTTGA (SEQ ID NO: 11002) |
| 82 | +R + GTC + AACADRTTYCKYCCAATTATGTTGA (SEQ ID NO: 11003) |
| 82 | +RGTC + AAC + ADRTTYCKYCCAATTATGTTGA (SEQ ID NO: 11004) |
| 82 | +R + GTCAAC + ADRTTYCKYCCAATTATGTTGA (SEQ ID NO: 11005) |
| 82 | +GTC + AAC + ADRTTYCKYCCAATTATGTTGA (SEQ ID NO: 11006) |
| 82 | +GTCAAC + ADR + TTYCKYCCAATTATGTTGA (SEQ ID NO: 11007) |
| 82 | +GTC + AACADR + TTYCKYCCAATTATGTTGA (SEQ ID NO: 11008) |
| 82 | RCADCCAAKYTGRGTCAACADRTTYCKYCCAATTATGTTG (SEQ ID NO: 11009) |
| 82 | ADCCAAKYTGRGTCAACADRTTYCKYCCAATTATGTTG (SEQ ID NO: 11010) |
| 82 | CAAKYTGRGTCAACADRTTYCKYCCAATTATGTTG (SEQ ID NO: 11011) |
| 82 | KYTGRGTCAACADRTTYCKYCCAATTATGTTG (SEQ ID NO: 11012) |
| 82 | TGRGTCAACADRTTYCKYCCAATTATGTTG (SEQ ID NO: 11013) |
| 82 | GRGTCAACADRTTYCKYCCAATTATGTTG (SEQ ID NO: 11014) |
| 82 | CADCCAAKYTGRGTCAACADRTTYCKYCCAATTATGTTGA (SEQ ID NO: 11015) |
| 82 | CCAAKYTGRGTCAACADRTTYCKYCCAATTATGTTGA (SEQ ID NO: 11016) |
| 82 | AKYTGRGTCAACADRTTYCKYCCAATTATGTTGA (SEQ ID NO: 11017) |
| 82 | TGRGTCAACADRTTYCKYCCAATTATGTTGA (SEQ ID NO: 11018) |
| 82 | RGTCAACADRTTYCKYCCAATTATGTTGA (SEQ ID NO: 11019) |
| 82 | GTCAACADRTTYCKYCCAATTATGTTGA (SEQ ID NO: 11020) |
| 82 | RAAATTTARWGTRCANCCAAKYTGRGTCAWCADRTTYCKYCCAATTATGTT (SEQ ID NO: 11021) |
| 82 | RCADCCAAKYTGRGTCAACADRTTYCKYCCAATTATGTTG + N (SEQ ID NO: 11022) |
| 82 | ADCCAAKYTGRGTCAACADRTTYCKYCCAATTATGTTG + N (SEQ ID NO: 11023) |
| 82 | CAAKYTGRGTCAACADRTTYCKYCCAATTATGTTG + N (SEQ ID NO: 11024) |
| 82 | KYTGRGTCAACADRTTYCKYCCAATTATGTTG + N (SEQ ID NO: 11025) |
| 82 | TGRGTCAACADRTTYCKYCCAATTATGTTG + N (SEQ ID NO: 11026) |
| 82 | GRGTCAACADRTTYCKYCCAATTATGTTG + N (SEQ ID NO: 11027) |

TABLE 8-continued

| Codon | |
|---|---|
| 82 | CADCCAAKYTGRGTCAACADRTTYCKYCCAATTATGTTGA + N (SEQ ID NO: 11028) |
| 82 | CCAAKYTGRGTCAACADRTTYCKYCCAATTATGTTGA + N (SEQ ID NO: 11029) |
| 82 | AKYTGRGTCAACADRTTYCKYCCAATTATGTTGA + N (SEQ ID NO: 11030) |
| 82 | TGRGTCAACADRTTYCKYCCAATTATGTTGA + N (SEQ ID NO: 11031) |
| 82 | RGTCAACADRTTYCKYCCAATTATGTTGA + N (SEQ ID NO: 11032) |
| 82 | GTCAACADRTTYCKYCCAATTATGTTGA + N (SEQ ID NO: 11033) |
| 82 | RAAATTTARWGTRCANCCAAKYTGRGTCAWCADRTTYCKYCCAATTATGTT + N (SEQ ID NO: 11034) |
| 83 | +GTR + CAD + CCAAKYTGRGTCAACADRTTYCKYCCAATTATGT (SEQ ID NO: 11035) |
| 83 | +GTRCAD + CC + AAKYTGRGTCAACADRTTYCKYCCAATTATGT (SEQ ID NO: 11036) |
| 83 | +GTR + CADCC + AAKYTGRGTCAACADRTTYCKYCCAATTATGT (SEQ ID NO: 11037) |
| 83 | +CAD + CC + AAKYTGRGTCAACADRTTYCKYCCAATTATGT (SEQ ID NO: 11038) |
| 83 | +CADCC + A + AKYTGRGTCAACADRTTYCKYCCAATTATGT (SEQ ID NO: 11039) |
| 83 | +CAD + CCA + AKYTGRGTCAACADRTTYCKYCCAATTATGT (SEQ ID NO: 11040) |
| 83 | +CC + A + AKYTGRGTCAACADRTTYCKYCCAATTATGT (SEQ ID NO: 11041) |
| 83 | +CCA + AKY + TGRGTCAACADRTTYCKYCCAATTATGT (SEQ ID NO: 11042) |
| 83 | +CC + AAKY + TGRGTCAACADRTTYCKYCCAATTATGT (SEQ ID NO: 11043) |
| 83 | +A + AKY + TGRGTCAACADRTTYCKYCCAATTATGT (SEQ ID NO: 11044) |
| 83 | +AAKY + TGR + GTCAACADRTTYCKYCCAATTATGT (SEQ ID NO: 11045) |
| 83 | +A + AKYTGR + GTCAACADRTTYCKYCCAATTATGT (SEQ ID NO: 11046) |
| 83 | +AKY + TGR + GTCAACADRTTYCKYCCAATTATGT (SEQ ID NO: 11047) |
| 83 | +AKYTGR + GTC + AACADRTTYCKYCCAATTATGT (SEQ ID NO: 11048) |
| 83 | +AKY + TGRGTC + AACADRTTYCKYCCAATTATGT (SEQ ID NO: 11049) |
| 83 | +TGR + GTC + AACADRTTYCKYCCAATTATGT (SEQ ID NO: 11050) |
| 83 | +TGRGTC + AAC + ADRTTYCKYCCAATTATGT (SEQ ID NO: 11051) |
| 83 | +TGR + GTCAAC + ADRTTYCKYCCAATTATGT (SEQ ID NO: 11052) |
| 83 | GTRCADCCAAKYTGRGTCAACADRTTYCKYCCAATTATGT (SEQ ID NO: 11053) |
| 83 | CADCCAAKYTGRGTCAACADRTTYCKYCCAATTATGT (SEQ ID NO: 11054) |
| 83 | CCAAKYTGRGTCAACADRTTYCKYCCAATTATGT (SEQ ID NO: 11055) |
| 83 | AAKYTGRGTCAACADRTTYCKYCCAATTATGT (SEQ ID NO: 11056) |
| 83 | AKYTGRGTCAACADRTTYCKYCCAATTATGT (SEQ ID NO: 11057) |
| 83 | TGRGTCAACADRTTYCKYCCAATTATGT (SEQ ID NO: 11058) |
| 83 | GGRAAATTTARWGTRCANCCAAKYTGRGTCAWCADRTTYCKYCCAATTAT (SEQ ID NO: 11059) |
| 83 | GTRCADCCAAKYTGRGTCAACADRTTYCKYCCAATTATGT + N (SEQ ID NO: 11060) |
| 83 | CADCCAAKYTGRGTCAACADRTTYCKYCCAATTATGT + N (SEQ ID NO: 11061) |
| 83 | CCAAKYTGRGTCAACADRTTYCKYCCAATTATGT + N (SEQ ID NO: 11062) |
| 83 | AAKYTGRGTCAACADRTTYCKYCCAATTATGT + N (SEQ ID NO: 11063) |
| 83 | AKYTGRGTCAACADRTTYCKYCCAATTATGT + N (SEQ ID NO: 11064) |
| 83 | TGRGTCAACADRTTYCKYCCAATTATGT + N (SEQ ID NO: 11065) |
| 83 | GGRAAATTTARWGTRCANCCAAKYTGRGTCAWCADRTTYCKYCCAATTAT + N (SEQ ID NO: 11066) |

TABLE 8-continued

| Codon | |
|---|---|
| 84 | +ARW + GT + RCADCCAAKYTGRGTCAACADRTTYCKYCCAATTA (SEQ ID NO: 11067) |
| 84 | +ARWGT + R + CADCCAAKYTGRGTCAACADRTTYCKYCCAATTA (SEQ ID NO: 11068) |
| 84 | +ARW + GTR + CADCCAAKYTGRGTCAACADRTTYCKYCCAATTA (SEQ ID NO: 11069) |
| 84 | +GT + R + CADCCAAKYTGRGTCAACADRTTYCKYCCAATTA (SEQ ID NO: 11070) |
| 84 | +GTR + CAD + CCAAKYTGRGTCAACADRTTYCKYCCAATTA (SEQ ID NO: 11071) |
| 84 | +GT + RCAD + CCAAKYTGRGTCAACADRTTYCKYCCAATTA (SEQ ID NO: 11072) |
| 84 | +R + CAD + CCAAKYTGRGTCAACADRTTYCKYCCAATTA (SEQ ID NO: 11073) |
| 84 | +RCAD + CCA + AKYTGRGTCAACADRTTYCKYCCAATTA (SEQ ID NO: 11074) |
| 84 | +R + CADCCA + AKYTGRGTCAACADRTTYCKYCCAATTA (SEQ ID NO: 11075) |
| 84 | +CAD + CCA + AKYTGRGTCAACADRTTYCKYCCAATTA (SEQ ID NO: 11076) |
| 84 | +CADCCA + AKY + TGRGTCAACADRTTYCKYCCAATTA (SEQ ID NO: 11077) |
| 84 | +CAD + CCAAKY + TGRGTCAACADRTTYCKYCCAATTA (SEQ ID NO: 11078) |
| 84 | +CCA + AKY + TGRGTCAACADRTTYCKYCCAATTA (SEQ ID NO: 11079) |
| 84 | +CCAAKY + TGR + GTCAACADRTTYCKYCCAATTA (SEQ ID NO: 11080) |
| 84 | +CCA + AKYTGR + GTCAACADRTTYCKYCCAATTA (SEQ ID NO: 11081) |
| 84 | +AKY + TGR + GTCAACADRTTYCKYCCAATTA (SEQ ID NO: 11082) |
| 84 | +AKYTGR + GTCAAC + ADRTTYCKYCCAATTA (SEQ ID NO: 11083) |
| 84 | +AKY + TGRGTCAAC + ADRTTYCKYCCAATTA (SEQ ID NO: 11084) |
| 84 | ARWGTRCADCCAAKYTGRGTCAACADRTTYCKYCCAATTA (SEQ ID NO: 11085) |
| 84 | GTRCADCCAAKYTGRGTCAACADRTTYCKYCCAATTA (SEQ ID NO: 11086) |
| 84 | RCADCCAAKYTGRGTCAACADRTTYCKYCCAATTA (SEQ ID NO: 11087) |
| 84 | CADCCAAKYTGRGTCAACADRTTYCKYCCAATTA (SEQ ID NO: 11088) |
| 84 | CCAAKYTGRGTCAACADRTTYCKYCCAATTA (SEQ ID NO: 11089) |
| 84 | AKYTGRGTCAACADRTTYCKYCCAATTA (SEQ ID NO: 11090) |
| 84 | RATKGGRAAATTTARWGTRCANCCAAKYTGRGTCAWCADRTTYCKTCCAAT (SEQ ID NO: 11091) |
| 84 | ARWGTRCADCCAAKYTGRGTCAACADRTTYCKYCCAATTA + N (SEQ ID NO: 11092) |
| 84 | GTRCADCCAAKYTGRGTCAACADRTTYCKYCCAATTA + N (SEQ ID NO: 11093) |
| 84 | RCADCCAAKYTGRGTCAACADRTTYCKYCCAATTA + N (SEQ ID NO: 11094) |
| 84 | CADCCAAKYTGRGTCAACADRTTYCKYCCAATTA + N (SEQ ID NO: 11095) |
| 84 | CCAAKYTGRGTCAACADRTTYCKYCCAATTA + N (SEQ ID NO: 11096) |
| 84 | AKYTGRGTCAACADRTTYCKYCCAATTA + N (SEQ ID NO: 11097) |
| 84 | RATKGGRAAATTTARWGTRCANCCAAKYTGRGTCAWCADRTTYCKTCCAAT + N (SEQ ID NO: 11098) |
| 88 | DA + TKG + GRAAAT + TTARWGTRCADCCAAKYTGRGTCAACADR (SEQ ID NO: 11099) |
| 88 | DA + TKGGRAAAT + TTA + RWGTRCADCCAAKYTGRGTCAACADR (SEQ ID NO: 11100) |
| 88 | DA + TKG + GRAAATTTA + RWGTRCADCCAAKYTGRGTCAACADR (SEQ ID NO: 11101) |
| 88 | +GRAAAT + TTA + RWGTRCADCCAAKYTGRGTCAACADR (SEQ ID NO: 11102) |
| 88 | +GRAAATTTA + RW + GTRCADCCAAKYTGRGTCAACADR (SEQ ID NO: 11103) |
| 88 | +GRAAAT + TTARW + GTRCADCCAAKYTGRGTCAACADR (SEQ ID NO: 11104) |

TABLE 8-continued

| Codon | |
|---|---|
| 88 | +TTA + RW + GTRCADCCAAKYTGRGTCAACADR (SEQ ID NO: 11105) |
| 88 | +TTARW + G + TRCADCCAAKYTGRGTCAACADR (SEQ ID NO: 11106) |
| 88 | +TTA + RWG + TRCADCCAAKYTGRGTCAACADR (SEQ ID NO: 11107) |
| 88 | +RW + G + TRCADCCAAKYTGRGTCAACADR (SEQ ID NO: 11108) |
| 88 | +RWG + TR + CADCCAAKYTGRGTCAACADR (SEQ ID NO: 11109) |
| 88 | +RW + GTR + CADCCAAKYTGRGTCAACADR (SEQ ID NO: 11110) |
| 88 | +G + TR + CADCCAAKYTGRGTCAACADR (SEQ ID NO: 11111) |
| 88 | +GTR + C + ADCCAAKYTGRGTCAACADR (SEQ ID NO: 11112) |
| 88 | +G + TRC + ADCCAAKYTGRGTCAACADR (SEQ ID NO: 11113) |
| 88 | +TR + C + ADCCAAKYTGRGTCAACADR (SEQ ID NO: 11114) |
| 88 | +TRC + AD + CCAAKYTGRGTCAACADR (SEQ ID NO: 11115) |
| 88 | +TR + CAD + CCAAKYTGRGTCAACADR (SEQ ID NO: 11116) |
| 88 | DATKGGRAAATTTARWGTRCADCCAAKYTGRGTCAACADR (SEQ ID NO: 11117) |
| 88 | GRAAATTTARWGTRCADCCAAKYTGRGTCAACADR (SEQ ID NO: 11118) |
| 88 | TTARWGTRCADCCAAKYTGRGTCAACADR (SEQ ID NO: 11119) |
| 88 | RWGTRCADCCAAKYTGRGTCAACADR (SEQ ID NO: 11120) |
| 88 | GTRCADCCAAKYTGRGTCAACADR (SEQ ID NO: 11121) |
| 88 | TRCADCCAAKYTGRGTCAACADR (SEQ ID NO: 11122) |
| 88 | TCAATRGGRCTRATKGGRAAATTTARWGTRCANCCAAKYTGRGTCAACAG (SEQ ID NO: 11123) |
| 88 | DATKGGRAAATTTARWGTRCADCCAAKYTGRGTCAACADR + N (SEQ ID NO: 11124) |
| 88 | GRAAATTTARWGTRCADCCAAKYTGRGTCAACADR + N (SEQ ID NO: 11125) |
| 88 | TTARWGTRCADCCAAKYTGRGTCAACADR + N (SEQ ID NO: 11126) |
| 88 | RWGTRCADCCAAKYTGRGTCAACADR + N (SEQ ID NO: 11127) |
| 88 | GTRCADCCAAKYTGRGTCAACADR + N (SEQ ID NO: 11128) |
| 88 | TRCADCCAAKYTGRGTCAACADR + N (SEQ ID NO: 11129) |
| 88 | TCAATRGGRCTRATKGGRAAATTTARWGTRCANCCAAKYTGRGTCAACAG + N (SEQ ID NO: 11130) |
| 89 | +CTD + ATKGGR + AAATTTARWGTRCADCCAAKYTGRGTCAACA (SEQ ID NO: 11131) |
| 89 | +CTDATKGGR + AAA + TTTARWGTRCADCCAAKYTGRGTCAACA (SEQ ID NO: 11132) |
| 89 | +CTD + ATKGGRAAA + TTTARWGTRCADCCAAKYTGRGTCAACA (SEQ ID NO: 11133) |
| 89 | +ATKGGR + AAA + TTTARWGTRCADCCAAKYTGRGTCAACA (SEQ ID NO: 11134) |
| 89 | +ATKGGRAAA + TT + TARWGTRCADCCAAKYTGRGTCAACA (SEQ ID NO: 11135) |
| 89 | +ATKGGR + AAATT + TARWGTRCADCCAAKYTGRGTCAACA (SEQ ID NO: 11136) |
| 89 | +AAA + TT + TARWGTRCADCCAAKYTGRGTCAACA (SEQ ID NO: 11137) |
| 89 | +AAATT + T + ARWGTRCADCCAAKYTGRGTCAACA (SEQ ID NO: 11138) |
| 89 | +AAA + TTT + ARWGTRCADCCAAKYTGRGTCAACA (SEQ ID NO: 11139) |
| 89 | +TT + T + ARWGTRCADCCAAKYTGRGTCAACA (SEQ ID NO: 11140) |
| 89 | +TTT + AR + WGTRCADCCAAKYTGRGTCAACA (SEQ ID NO: 11141) |
| 89 | +TT + TAR + WGTRCADCCAAKYTGRGTCAACA (SEQ ID NO: 11142) |
| 89 | +T + AR + WGTRCADCCAAKYTGRGTCAACA (SEQ ID NO: 11143) |

TABLE 8-continued

| Codon | |
|---|---|
| 89 | +TAR + W + GTRCADCCAAKYTGRGTCAACA (SEQ ID NO: 11144) |
| 89 | +T + ARW + GTRCADCCAAKYTGRGTCAACA (SEQ ID NO: 11145) |
| 89 | +AR + W + GTRCADCCAAKYTGRGTCAACA (SEQ ID NO: 11146) |
| 89 | +ARW + GT + RCADCCAAKYTGRGTCAACA (SEQ ID NO: 11147) |
| 89 | +AR + WGT + RCADCCAAKYTGRGTCAACA (SEQ ID NO: 11148) |
| 89 | CTDATKGGRAAATTTARWGTRCADCCAAKYTGRGTCAACA (SEQ ID NO: 11149) |
| 89 | ATKGGRAAATTTARWGTRCADCCAAKYTGRGTCAACA (SEQ ID NO: 11150) |
| 89 | AAATTTARWGTRCADCCAAKYTGRGTCAACA (SEQ ID NO: 11151) |
| 89 | TTTARWGTRCADCCAAKYTGRGTCAACA (SEQ ID NO: 11152) |
| 89 | TARWGTRCADCCAAKYTGRGTCAACA (SEQ ID NO: 11153) |
| 89 | ARWGTRCADCCAAKYTGRGTCAACA (SEQ ID NO: 11154) |
| 89 | GTBTCAATRGGRCTRATKGGRAAATTTARWGTRCANCCAAKYTGRGTCAA (SEQ ID NO: 11155) |
| 89 | CTDATKGGRAAATTTARWGTRCADCCAAKYTGRGTCAACA + N (SEQ ID NO: 11156) |
| 89 | ATKGGRAAATTTARWGTRCADCCAAKYTGRGTCAACA + N (SEQ ID NO: 11157) |
| 89 | AAATTTARWGTRCADCCAAKYTGRGTCAACA + N (SEQ ID NO: 11158) |
| 89 | TTTARWGTRCADCCAAKYTGRGTCAACA + N (SEQ ID NO: 11159) |
| 89 | TARWGTRCADCCAAKYTGRGTCAACA + N (SEQ ID NO: 11160) |
| 89 | ARWGTRCADCCAAKYTGRGTCAACA + N (SEQ ID NO: 11161) |
| 89 | GTBTCAATRGGRCTRATKGGRAAATTTARWGTRCANCCAAKYTGRGTCAA + N (SEQ ID NO: 11162) |
| 90 | +GGRCTD + ATK + GGRAAATTTARWGTRCADCCAAKYTGRGTCA (SEQ ID NO: 11163) |
| 90 | GGRCTDATK + GG + R + AAATTTARWGTRCADCCAAKYTGRGTCA (SEQ ID NO: 11164) |
| 90 | GGRCTD + ATK + GGR + AAATTTARWGTRCADCCAAKYTGRGTCA (SEQ ID NO: 11165) |
| 90 | +ATK + GG + RAAATTTARWGTRCADCCAAKYTGRGTCA (SEQ ID NO: 11166) |
| 90 | +ATKGG + R + AAATTTARWGTRCADCCAAKYTGRGTCA (SEQ ID NO: 11167) |
| 90 | +ATK + GGR + AAATTTARWGTRCADCCAAKYTGRGTCA (SEQ ID NO: 11168) |
| 90 | +GG + R + AAATTTARWGTRCADCCAAKYTGRGTCA (SEQ ID NO: 11169) |
| 90 | +GGR + AA + ATTTARWGTRCADCCAAKYTGRGTCA (SEQ ID NO: 11170) |
| 90 | +GG + RAA + ATTTARWGTRCADCCAAKYTGRGTCA (SEQ ID NO: 11171) |
| 90 | +R + AA + ATTTARWGTRCADCCAAKYTGRGTCA (SEQ ID NO: 11172) |
| 90 | +RAA + A + TTTARWGTRCADCCAAKYTGRGTCA (SEQ ID NO: 11173) |
| 90 | +R + AAA + TTTARWGTRCADCCAAKYTGRGTCA (SEQ ID NO: 11174) |
| 90 | +AA + A + TTTARWGTRCADCCAAKYTGRGTCA (SEQ ID NO: 11175) |
| 90 | +AAA + TT + TARWGTRCADCCAAKYTGRGTCA (SEQ ID NO: 11176) |
| 90 | +AA + ATT + TARWGTRCADCCAAKYTGRGTCA (SEQ ID NO: 11177) |
| 90 | +A + TT + TARWGTRCADCCAAKYTGRGTCA (SEQ ID NO: 11178) |
| 90 | +ATT + T + ARWGTRCADCCAAKYTGRGTCA (SEQ ID NO: 11179) |
| 90 | +A + TTT + ARWGTRCADCCAAKYTGRGTCA (SEQ ID NO: 11180) |
| 90 | GGRCTDATKGGRAAATTTARWGTRCADCCAAKYTGRGTCA (SEQ ID NO: 11181) |
| 90 | ATKGGRAAATTTARWGTRCADCCAAKYTGRGTCA (SEQ ID NO: 11182) |

TABLE 8-continued

| Codon | |
|---|---|
| 90 | GGRAAATTTARWGTRCADCCAAKYTGRGTCA (SEQ ID NO: 11183) |
| 90 | RAAATTTARWGTRCADCCAAKYTGRGTCA (SEQ ID NO: 11184) |
| 90 | AAATTTARWGTRCADCCAAKYTGRGTCA (SEQ ID NO: 11185) |
| 90 | ATTTARWGTRCADCCAAKYTGRGTCA (SEQ ID NO: 11186) |
| 90 | ACAGTBTCAATRGGRCTRATKGGRAAATTTARWGTRCANCCAAKYTGAGT (SEQ ID NO: 11187) |
| 90 | GGRCTDATKGGRAAATTTARWGTRCADCCAAKYTGRGTCA + N (SEQ ID NO: 11188) |
| 90 | ATKGGRAAATTTARWGTRCADCCAAKYTGRGTCA + N (SEQ ID NO: 11189) |
| 90 | GGRAAATTTARWGTRCADCCAAKYTGRGTCA + N (SEQ ID NO: 11190) |
| 90 | RAAATTTARWGTRCADCCAAKYTGRGTCA + N (SEQ ID NO: 11191) |
| 90 | AAATTTARWGTRCADCCAAKYTGRGTCA + N (SEQ ID NO: 11192) |
| 90 | ATTTARWGTRCADCCAAKYTGRGTCA + N (SEQ ID NO: 11193) |
| 90 | ACAGTBTCAATRGGRCTRATKGGRAAATTTARWGTRCANCCAAKYTGAGT + N (SEQ ID NO: 11194) |

Table 9 depicts amino acid substitutions in HIV-1 protease protein.

TABLE 9

| Codon | Single Letter Amino Acid Code | Amino Acid |
|---|---|---|
| 10 | F | Phenylalanine |
| 10 | R | Arginine |
| 10 | Y | Tyrosine |
| 11 | I | Isoleucine |
| 11 | L | Leucine |
| 20 | T | Threonine |
| 20 | V | Valine |
| 23 | I | Isoleucine |
| 24 | I | Isoleucine |
| 24 | F | Phenylalanine |
| 30 | N | Asparagine |
| 32 | I | Isoleucine |
| 33 | F | Phenylalanine |
| 43 | T | Threonine |
| 46 | I | Isoleucine |
| 46 | L | Leucine |
| 46 | V | Valine |
| 47 | V | Valine |
| 47 | A | Alanine |
| 48 | V | Valine |
| 48 | M | Methionine |
| 48 | A | Alanine |
| 48 | S | Serine |
| 48 | T | Threonine |
| 48 | L | Leucine |
| 48 | Q | Glutamine |
| 50 | V | Valine |
| 50 | L | Leucine |
| 53 | L | Leucine |
| 53 | Y | Tyrosine |
| 54 | V | Valine |
| 54 | T | Threonine |

TABLE 9-continued

| Codon | Single Letter Amino Acid Code | Amino Acid |
|---|---|---|
| 54 | A | Alanine |
| 54 | L | Leucine |
| 54 | S | Serine |
| 54 | M | Methionine |
| 58 | E | Glutamic acid |
| 71 | I | Isoleucine |
| 71 | L | Leucine |
| 71 | L | Leucine |
| 73 | S | Serine |
| 73 | T | Threonine |
| 73 | C | Cysteine |
| 73 | A | Alanine |
| 74 | P | Proline |
| 76 | V | Valine |
| 82 | A | Alanine |
| 82 | T | Threonine |
| 82 | S | Serine |
| 82 | F | Phenylalanine |
| 82 | L | Leucine |
| 82 | C | Cysteine |
| 82 | M | Methionine |
| 83 | D | Aspartic acid |
| 84 | V | Valine |
| 84 | A | Alanine |
| 84 | C | Cysteine |
| 88 | D | Aspartic acid |
| 88 | S | Serine |
| 88 | T | Threonine |
| 88 | G | Glycine |
| 89 | V | Valine |
| 90 | M | Methionine |

Table 10 depicts wild-type and mutant probes for the HIV-1 protease protein. A "+" symbol preceding a nucleotide denotes that the nucleotide is an LNA.

TABLE 10

| Codon | Wild-Type Probe (5' to 3') |
|---|---|
| 10 | CGACCCCTHGTCACA (SEQ ID NO: 11195) |
| 10 | CGACCCTTAGTCACA (SEQ ID NO: 11196) |

TABLE 10 -continued

| | | |
|---|---|---|
| 11 | CCCCTCGTYACAATA | (SEQ ID NO: 11197) |
| 20 | CAACTAAARGAAGCT | (SEQ ID NO: 11198) |
| 23 | ATCTAANAGAGCTTC | (SEQ ID NO: 11199) |
| 23 | ATCTAAYAAAGCTTC | (SEQ ID NO: 11200) |
| 24 | TGTATCYARTAGAGC | (SEQ ID NO: 11201) |
| 30 | TACTGTRTCATCTGC | (SEQ ID NO: 11202) |
| 32 | TTCTAAYACTGTATC | (SEQ ID NO: 11203) |
| 33 | ACAGTACTNGAAGAA | (SEQ ID NO: 11204) |
| 33 | ACAGTATTYGAAGAA | (SEQ ID NO: 11205) |
| 43 | AAATGGAARCCAAAA | (SEQ ID NO: 11206) |
| 46 | CCAAAAATGATAGGG | (SEQ ID NO: 11207) |
| 47 | CCAA + RAATGATAGGRGGAAT | (SEQ ID NO: 11208) |
| 47 | CCAARAAT + GATAGGRGGAAT | (SEQ ID NO: 11209) |
| 47 | CC + AARAATGATAGGRGGAAT | (SEQ ID NO: 11210) |
| 47 | CCAARAA + TGATAGGRGGAAT | (SEQ ID NO: 11211) |
| 47 | CCAARAATGATAGG + RGGAAT | (SEQ ID NO: 11212) |
| 47 | CCAARAATGATAGGR + GGAAT | (SEQ ID NO: 11213) |
| 47 | CCAARAATGATAGGRG + GAAT | (SEQ ID NO: 11214) |
| 47 | CCAARAATGATA + GGRGGAAT | (SEQ ID NO: 11215) |
| 47 | CCA + ARAAT + GA + TAGGRGGAAT | (SEQ ID NO: 11216) |
| 47 | CC + AARAAT + GA + TAGGRGGAAT | (SEQ ID NO: 11217) |
| 47 | C + CAARAAT + GA + TAGGRGGAAT | (SEQ ID NO: 11218) |
| 47 | CCAARAA + T + GA + TAGGRGGAAT | (SEQ ID NO: 11219) |
| 47 | CCAARAAT + GA + TA + GGRGGAAT | (SEQ ID NO: 11220) |
| 47 | CCAARAAT + GA + TAGGR + GGAAT | (SEQ ID NO: 11221) |
| 47 | CCAARAAT + GA + TAG + GRGGAAT | (SEQ ID NO: 11222) |
| 47 | CCAARAAT + GA + TAGGRGG + AAT | (SEQ ID NO: 11223) |
| 47 | CCAA + RAATGATAGGRGGAA | (SEQ ID NO: 11224) |
| 47 | CCAARAAT + GATAGGRGGAA | (SEQ ID NO: 11225) |
| 47 | CC + AARAATGATAGGRGGAA | (SEQ ID NO: 11226) |
| 47 | CCAARAA + TGATAGGRGGAA | (SEQ ID NO: 11227) |
| 47 | CCAARAATGATAGG + RGGAA | (SEQ ID NO: 11228) |
| 47 | CCAARAATGATAGGR + GGAA | (SEQ ID NO: 11229) |
| 47 | CCAARAATGATAGGRG + GAA | (SEQ ID NO: 11230) |
| 47 | CCAARAATGATA + GGRGGAA | (SEQ ID NO: 11231) |
| 47 | CCA + ARAAT + GA + TAGGRGGAA | (SEQ ID NO: 11232) |
| 47 | CC + AARAAT + GA + TAGGRGGAA | (SEQ ID NO: 11233) |
| 47 | C + CAARAAT + GA + TAGGRGGAA | (SEQ ID NO: 11234) |
| 47 | CCAARAA + T + GA + TAGGRGGAA | (SEQ ID NO: 11235) |
| 47 | CCAARAAT + GA + TA + GGRGGAA | (SEQ ID NO: 11236) |

TABLE 10 -continued

| 47 | CCAARAAT + GA + TAGGR + GGAA (SEQ ID NO: 11237) |
| 47 | CCAARAAT + GA + TAG + GRGGAA (SEQ ID NO: 11238) |
| 47 | CCAARAAT + GA + TAGGRGG + AA (SEQ ID NO: 11239) |
| 47 | CAA + RAATGATAGGRGGA (SEQ ID NO: 11240) |
| 47 | CAARAAT + GATAGGRGGA (SEQ ID NO: 11241) |
| 47 | C + AARAATGATAGGRGGA (SEQ ID NO: 11242) |
| 47 | CAARAA + TGATAGGRGGA (SEQ ID NO: 11243) |
| 47 | CAARAATGATAGG + RGGA (SEQ ID NO: 11244) |
| 47 | CAARAATGATAGGR + GGA (SEQ ID NO: 11245) |
| 47 | CAARAATGATAGGRG + GA (SEQ ID NO: 11246) |
| 47 | CAARAATGATA + GGRGGA (SEQ ID NO: 11247) |
| 47 | CA + ARAAT + GA + TAGGRGGA (SEQ ID NO: 11248) |
| 47 | C + AARAAT + GA + TAGGRGGA (SEQ ID NO: 11249) |
| 47 | +CAARAAT + GA + TAGGRGGA (SEQ ID NO: 11250) |
| 47 | CAARAA + T + GA + TAGGRGGA (SEQ ID NO: 11251) |
| 47 | CAARAAT + GA + TA + GGRGGA (SEQ ID NO: 11252) |
| 47 | CAARAAT + GA + TAGGR + GGA (SEQ ID NO: 11253) |
| 47 | CAARAAT + GA + TAG + GRGGA (SEQ ID NO: 11254) |
| 47 | CAARAAT + GA + TAGGRGG + A (SEQ ID NO: 11255) |
| 47 | CAA + RAATGATAGGRG (SEQ ID NO: 11256) |
| 47 | CAARAAT + GATAGGRG (SEQ ID NO: 11257) |
| 47 | C + AARAATGATAGGRG (SEQ ID NO: 11258) |
| 47 | CAARAA + TGATAGGRG (SEQ ID NO: 11259) |
| 47 | CAARAATGATAGG + RG (SEQ ID NO: 11260) |
| 47 | CAARAATGATAGGR + G (SEQ ID NO: 11261) |
| 47 | CAARAATGATAGGRG (SEQ ID NO: 11262) |
| 47 | CAARAATGATA + GGRG (SEQ ID NO: 11263) |
| 47 | CA + ARAAT + GA + TAGGRG (SEQ ID NO: 11264) |
| 47 | C + AARAAT + GA + TAGGRG (SEQ ID NO: 11265) |
| 47 | +CAARAAT + GA + TAGGRG (SEQ ID NO: 11266) |
| 47 | CAARAA + T + GA + TAGGRG (SEQ ID NO: 11267) |
| 47 | CAARAAT + GA + TA + GGRG (SEQ ID NO: 11268) |
| 47 | CAARAAT + GA + TAGGR + G (SEQ ID NO: 11269) |
| 47 | CAARAAT + GA + TAG + GRG (SEQ ID NO: 11270) |
| 47 | CAARAAT + GA + TAGGRGG (SEQ ID NO: 11271) |
| 47 | AAAATGATAGGGGGA (SEQ ID NO: 11272) |
| 47 | CCAARAATGATAGGRGGAAT (SEQ ID NO: 11273) |
| 47 | CCAARAATGATAGGRGGAA (SEQ ID NO: 11274) |
| 47 | CAARAATGATAGGRGGA (SEQ ID NO: 11275) |
| 47 | CAARAATGATAGGRG (SEQ ID NO: 11276) |

TABLE 10 -continued

| | | |
|---|---|---|
| 47 | CAARAATGATAGGRGG | (SEQ ID NO: 11277) |
| 48 | ATGATAGGRGGAATT | (SEQ ID NO: 11278) |
| 50 | ATAGGR + GGAATTGGAGGYTT | (SEQ ID NO: 11279) |
| 50 | ATAG + GRGGAATTGGAGGYTT | (SEQ ID NO: 11280) |
| 50 | ATAGGRG + GAATTGGAGGYTT | (SEQ ID NO: 11281) |
| 50 | AT + AGGRGGAATTGGAGGYTT | (SEQ ID NO: 11282) |
| 50 | ATAGGRGGAATT + GGAGGYTT | (SEQ ID NO: 11283) |
| 50 | ATAGGRGGAATTGGAG + GYTT | (SEQ ID NO: 11284) |
| 50 | ATAGGRGGAA + TTGGAGGYTT | (SEQ ID NO: 11285) |
| 50 | ATAGGRGGAATTGG + AGGYTT | (SEQ ID NO: 11286) |
| 50 | ATAGGR + GG + AA + TTGGAGGYTT | (SEQ ID NO: 11287) |
| 50 | ATAGG + RGG + AA + TTGGAGGYTT | (SEQ ID NO: 11288) |
| 50 | A + TAGGRGG + AA + TTGGAGGYTT | (SEQ ID NO: 11289) |
| 50 | AT + AGGRGG + AA + TTGGAGGYTT | (SEQ ID NO: 11290) |
| 50 | ATAGGRGG + AA + TTGGAGG + YTT | (SEQ ID NO: 11291) |
| 50 | ATAGGRGG + AA + TTGGAG + GYTT | (SEQ ID NO: 11292) |
| 50 | ATAGGRGG + AA + TTG + GAGGYTT | (SEQ ID NO: 11293) |
| 50 | ATAGGRGG + AA + TTGGA + GGYTT | (SEQ ID NO: 11294) |
| 50 | ATAGGR + GGAATTGGAGGYT | (SEQ ID NO: 11295) |
| 50 | ATAG + GRGGAATTGGAGGYT | (SEQ ID NO: 11296) |
| 50 | ATAGGRG + GAATTGGAGGYT | (SEQ ID NO: 11297) |
| 50 | AT + AGGRGGAATTGGAGGYT | (SEQ ID NO: 11298) |
| 50 | ATAGGRGGAATT + GGAGGYT | (SEQ ID NO: 11299) |
| 50 | ATAGGRGGAATTGGAG + GYT | (SEQ ID NO: 11300) |
| 50 | ATAGGRGGAA + TTGGAGGYT | (SEQ ID NO: 11301) |
| 50 | ATAGGRGGAATTGG + AGGYT | (SEQ ID NO: 11302) |
| 50 | ATAGGR + GG + AA + TTGGAGGYT | (SEQ ID NO: 11303) |
| 50 | ATAGG + RGG + AA + TTGGAGGYT | (SEQ ID NO: 11304) |
| 50 | A + TAGGRGG + AA + TTGGAGGYT | (SEQ ID NO: 11305) |
| 50 | AT + AGGRGG + AA + TTGGAGGYT | (SEQ ID NO: 11306) |
| 50 | ATAGGRGG + AA + TTGGAGG + YT | (SEQ ID NO: 11307) |
| 50 | ATAGGRGG + AA + TTGGAG + GYT | (SEQ ID NO: 11308) |
| 50 | ATAGGRGG + AA + TTG + GAGGYT | (SEQ ID NO: 11309) |
| 50 | ATAGGRGG + AA + TTGGA + GGYT | (SEQ ID NO: 11310) |
| 50 | TAGGR + GGAATTGGAGGY | (SEQ ID NO: 11311) |
| 50 | TAG + GRGGAATTGGAGGY | (SEQ ID NO: 11312) |
| 50 | TAGGRG + GAATTGGAGGY | (SEQ ID NO: 11313) |
| 50 | T + AGGRGGAATTGGAGGY | (SEQ ID NO: 11314) |
| 50 | TAGGRGGAATT + GGAGGY | (SEQ ID NO: 11315) |
| 50 | TAGGRGGAATTGGAG + GY | (SEQ ID NO: 11316) |

TABLE 10 -continued

| | |
|---|---|
| 50 | TAGGRGGAA + TTGGAGGY (SEQ ID NO: 11317) |
| 50 | TAGGRGGAATTGG + AGGY (SEQ ID NO: 11318) |
| 50 | TAGGR + GG + AA + TTGGAGGY (SEQ ID NO: 11319) |
| 50 | TAGG + RGG + AA + TTGGAGGY (SEQ ID NO: 11320) |
| 50 | +TAGGRGG + AA + TTGGAGGY (SEQ ID NO: 11321) |
| 50 | T + AGGRGG + AA + TTGGAGGY (SEQ ID NO: 11322) |
| 50 | TAGGRGG + AA + TTGGAGG + Y (SEQ ID NO: 11323) |
| 50 | TAGGRGG + AA + TTGGAG + GY (SEQ ID NO: 11324) |
| 50 | TAGGRGG + AA + TTG + GAGGY (SEQ ID NO: 11325) |
| 50 | TAGGRGG + AA + TTGGA + GGY (SEQ ID NO: 11326) |
| 50 | TAGGR + GGAATTGGAG (SEQ ID NO: 11327) |
| 50 | TAG + GRGGAATTGGAG (SEQ ID NO: 11328) |
| 50 | TAGGRG + GAATTGGAG (SEQ ID NO: 11329) |
| 50 | T + AGGRGGAATTGGAG (SEQ ID NO: 11330) |
| 50 | TAGGRGGAATT + GGAG (SEQ ID NO: 11331) |
| 50 | TAGGRGGAATTGGAG (SEQ ID NO: 11332) |
| 50 | TAGGRGGAA + TTGGAG (SEQ ID NO: 11333) |
| 50 | TAGGRGGAATTGG + AG (SEQ ID NO: 11334) |
| 50 | TAGGR + GG + AA + TTGGAG (SEQ ID NO: 11335) |
| 50 | TAGG + RGG + AA + TTGGAG (SEQ ID NO: 11336) |
| 50 | +TAGGRGG + AA + TTGGAG (SEQ ID NO: 11337) |
| 50 | T + AGGRGG + AA + TTGGAG (SEQ ID NO: 11338) |
| 50 | TAGGRGG + AA + TTGGAGG (SEQ ID NO: 11339) |
| 50 | TAGGRGG + AA + TTGGAG (SEQ ID NO: 11340) |
| 50 | TAGGRGG + AA + TTG + GAG (SEQ ID NO: 11341) |
| 50 | TAGGRGG + AA + TTGGA + G (SEQ ID NO: 11342) |
| 50 | ACCTCCAATTCCCCC (SEQ ID NO: 11343) |
| 50 | ATAGGRGGAATTGGAGGYTT (SEQ ID NO: 11344) |
| 50 | ATAGGRGGAATTGGAGGYT (SEQ ID NO: 11345) |
| 50 | TAGGRGGAATTGGAGGY (SEQ ID NO: 11346) |
| 50 | TAGGRGGAATTGGAG (SEQ ID NO: 11347) |
| 50 | TAGGRGGAATTGGAGG (SEQ ID NO: 11348) |
| 53 | TGGAGGY + TTYATYAARGTAA (SEQ ID NO: 11349) |
| 53 | T + GGAGGYTTYATYAARGTAA (SEQ ID NO: 11350) |
| 53 | TGGAGG + YTTYATYAARGTAA (SEQ ID NO: 11351) |
| 53 | TG + GAGGYTTYATYAARGTAA (SEQ ID NO: 11352) |
| 53 | TGGAGGYTTYATYA + ARGTAA (SEQ ID NO: 11353) |
| 53 | TGGAGGYTTYATYAAR + GTAA (SEQ ID NO: 11354) |
| 53 | TGGAGGYTTY + ATYAARGTAA (SEQ ID NO: 11355) |
| 53 | TGGAGGYTTYATY + AARGTAA (SEQ ID NO: 11356) |

TABLE 10 -continued

| | |
|---|---|
| 53 | TGGA + GGYT + TY + ATYAARGTAA (SEQ ID NO: 11357) |
| 53 | TG + GAGGYT + TY + ATYAARGTAA (SEQ ID NO: 11358) |
| 53 | TGGAGGY + T + TY + ATYAARGTAA (SEQ ID NO: 11359) |
| 53 | TGG + AGGYT + TY + ATYAARGTAA (SEQ ID NO: 11360) |
| 53 | TGGAGGYT + TY + ATY + AARGTAA (SEQ ID NO: 11361) |
| 53 | TGGAGGYT + TY + AT + YAARGTAA (SEQ ID NO: 11362) |
| 53 | TGGAGGYT + TY + ATYAA + RGTAA (SEQ ID NO: 11363) |
| 53 | TGGAGGYT + TY + ATYAAR + GTAA (SEQ ID NO: 11364) |
| 53 | TTGGA + GGYTTTATYAARGTA (SEQ ID NO: 11365) |
| 53 | TTGGAGG + YTTTATYAARGTA (SEQ ID NO: 11366) |
| 53 | TTGGAG + GYTTTATYAARGTA (SEQ ID NO: 11367) |
| 53 | TT + GGAGGYTTTATYAARGTA (SEQ ID NO: 11368) |
| 53 | TTGGAGGYTTTATYAA + RGTA (SEQ ID NO: 11369) |
| 53 | TTGGAGGYTTTATYAAR + GTA (SEQ ID NO: 11370) |
| 53 | TTGGAGGYTTT + ATYAARGTA (SEQ ID NO: 11371) |
| 53 | TTGGAGGYTTTAT + YAARGTA (SEQ ID NO: 11372) |
| 53 | T + TGGAGGY + TT + TATYAARGTA (SEQ ID NO: 11373) |
| 53 | TTGGAG + GY + TT + TATYAARGTA (SEQ ID NO: 11374) |
| 53 | TTGG + AGGY + TT + TATYAARGTA (SEQ ID NO: 11375) |
| 53 | TTGGAGG + Y + TT + TATYAARGTA (SEQ ID NO: 11376) |
| 53 | TTGGAGGY + TT + TATYA + ARGTA (SEQ ID NO: 11377) |
| 53 | TTGGAGGY + TT + T + ATYAARGTA (SEQ ID NO: 11378) |
| 53 | TTGGAGGY + TT + TATYAAR + GTA (SEQ ID NO: 11379) |
| 53 | TTGGAGGY + TT + TATY + AARGTA (SEQ ID NO: 11380) |
| 53 | TGGAGGY + TTYATYAARGTA (SEQ ID NO: 11381) |
| 53 | T + GGAGGYTTYATYAARGTA (SEQ ID NO: 11382) |
| 53 | TGGAGG + YTTYATYAARGTA (SEQ ID NO: 11383) |
| 53 | TG + GAGGYTTYATYAARGTA (SEQ ID NO: 11384) |
| 53 | TGGAGGYTTYATYA + ARGTA (SEQ ID NO: 11385) |
| 53 | TGGAGGYTTYATYAAR + GTA (SEQ ID NO: 11386) |
| 53 | TGGAGGYTTY + ATYAARGTA (SEQ ID NO: 11387) |
| 53 | TGGAGGYTTYATY + AARGTA (SEQ ID NO: 11388) |
| 53 | TGGA + GGYT + TY + ATYAARGTA (SEQ ID NO: 11389) |
| 53 | TG + GAGGYT + TY + ATYAARGTA (SEQ ID NO: 11390) |
| 53 | TGGAGGY + T + TY + ATYAARGTA (SEQ ID NO: 11391) |
| 53 | TGG + AGGYT + TY + ATYAARGTA (SEQ ID NO: 11392) |
| 53 | TGGAGGYT + TY + ATY + AARGTA (SEQ ID NO: 11393) |
| 53 | TGGAGGYT + TY + AT + YAARGTA (SEQ ID NO: 11394) |
| 53 | TGGAGGYT + TY + ATYAA + RGTA (SEQ ID NO: 11395) |
| 53 | TGGAGGYT + TY + ATYAAR + GTA (SEQ ID NO: 11396) |

TABLE 10 -continued

| 53 | TTGGA + GGYTTTATYAARGT (SEQ ID NO: 11397) |
| 53 | TTGGAGG + YTTTATYAARGT (SEQ ID NO: 11398) |
| 53 | TTGGAG + GYTTTATYAARGT (SEQ ID NO: 11399) |
| 53 | TT + GGAGGYTTTATYAARGT (SEQ ID NO: 11400) |
| 53 | TTGGAGGYTTTATYAA + RGT (SEQ ID NO: 11401) |
| 53 | TTGGAGGYTTTATYAAR + GT (SEQ ID NO: 11402) |
| 53 | TTGGAGGYTTT + ATYAARGT (SEQ ID NO: 11403) |
| 53 | TTGGAGGYTTTAT + YAARGT (SEQ ID NO: 11404) |
| 53 | T + TGGAGGY + TT + TATYAARGT (SEQ ID NO: 11405) |
| 53 | TTGGAG + GY + TT + TATYAARGT (SEQ ID NO: 11406) |
| 53 | TTGG + AGGY + TT + TATYAARGT (SEQ ID NO: 11407) |
| 53 | TTGGAGG + Y + TT + TATYAARGT (SEQ ID NO: 11408) |
| 53 | TTGGAGGY + TT + TATYA + ARGT (SEQ ID NO: 11409) |
| 53 | TTGGAGGY + TT + T + ATYAARGT (SEQ ID NO: 11410) |
| 53 | TTGGAGGY + TT + TATYAAR + GT (SEQ ID NO: 11411) |
| 53 | TTGGAGGY + TT + TATY + AARGT (SEQ ID NO: 11412) |
| 53 | GGAGGY + TTYATYAARGT (SEQ ID NO: 11413) |
| 53 | +GGAGGYTTYATYAARGT (SEQ ID NO: 11414) |
| 53 | GGAGG + YTTYATYAARGT (SEQ ID NO: 11415) |
| 53 | G + GAGGYTTYATYAARGT (SEQ ID NO: 11416) |
| 53 | GGAGGYTTYATYA + ARGT (SEQ ID NO: 11417) |
| 53 | GGAGGYTTYATYAAR + GT (SEQ ID NO: 11418) |
| 53 | GGAGGYTTY + ATYAARGT (SEQ ID NO: 11419) |
| 53 | GGAGGYTTYATY + AARGT (SEQ ID NO: 11420) |
| 53 | GGA + GGYT + TY + ATYAARGT (SEQ ID NO: 11421) |
| 53 | G + GAGGYT + TY + ATYAARGT (SEQ ID NO: 11422) |
| 53 | GGAGGY + T + TY + ATYAARGT (SEQ ID NO: 11423) |
| 53 | GG + AGGYT + TY + ATYAARGT (SEQ ID NO: 11424) |
| 53 | GGAGGYT + TY + ATY + AARGT (SEQ ID NO: 11425) |
| 53 | GGAGGYT + TY + AT + YAARGT (SEQ ID NO: 11426) |
| 53 | GGAGGYT + TY + ATYAA + RGT (SEQ ID NO: 11427) |
| 53 | GGAGGYT + TY + ATYAAR + GT (SEQ ID NO: 11428) |
| 53 | TGGA + GGYTTTATYAARG (SEQ ID NO: 11429) |
| 53 | TGGAGG + YTTTATYAARG (SEQ ID NO: 11430) |
| 53 | TGGAG + GYTTTATYAARG (SEQ ID NO: 11431) |
| 53 | T + GGAGGYTTTATYAARG (SEQ ID NO: 11432) |
| 53 | TGGAGGYTTTATYAA + RG (SEQ ID NO: 11433) |
| 53 | TGGAGGYTTTATYAAR + G (SEQ ID NO: 11434) |
| 53 | TGGAGGYTTT + ATYAARG (SEQ ID NO: 11435) |
| 53 | TGGAGGYTTTAT + YAARG (SEQ ID NO: 11436) |

TABLE 10 -continued

| | |
|---|---|
| 53 | +TGGAGGY + TT + TATYAARG (SEQ ID NO: 11437) |
| 53 | TGGAG + GY + TT + TATYAARG (SEQ ID NO: 11438) |
| 53 | TGG + AGGY + TT + TATYAARG (SEQ ID NO: 11439) |
| 53 | TGGAGG + Y + TT + TATYAARG (SEQ ID NO: 11440) |
| 53 | TGGAGGY + TT + TATYA + ARG (SEQ ID NO: 11441) |
| 53 | TGGAGGY + TT + T + ATYAARG (SEQ ID NO: 11442) |
| 53 | TGGAGGY + TT + TATYAAR + G (SEQ ID NO: 11443) |
| 53 | TGGAGGY + TT + TATY + AARG (SEQ ID NO: 11444) |
| 53 | GGAGGY + TTYATYAAR (SEQ ID NO: 11445) |
| 53 | +GGAGGYTTYATYAAR (SEQ ID NO: 11446) |
| 53 | GGAGG + YTTYATYAAR (SEQ ID NO: 11447) |
| 53 | G + GAGGYTTYATYAAR (SEQ ID NO: 11448) |
| 53 | GGAGGYTTYATYA + AR (SEQ ID NO: 11449) |
| 53 | GGAGGYTTYATYAAR (SEQ ID NO: 11450) |
| 53 | GGAGGYTTY + ATYAAR (SEQ ID NO: 11451) |
| 53 | GGAGGYTTYATY + AAR (SEQ ID NO: 11452) |
| 53 | GGA + GGYT + TY + ATYAAR (SEQ ID NO: 11453) |
| 53 | G + GAGGYT + TY + ATYAAR (SEQ ID NO: 11454) |
| 53 | GGAGGY + T + TY + ATYAAR (SEQ ID NO: 11455) |
| 53 | GG + AGGYT + TY + ATYAAR (SEQ ID NO: 11456) |
| 53 | GGAGGYT + TY + ATY + AAR (SEQ ID NO: 11457) |
| 53 | GGAGGYT + TY + AT + YAAR (SEQ ID NO: 11458) |
| 53 | GGAGGYT + TY + ATYAA + R (SEQ ID NO: 11459) |
| 53 | GGAGGYT + TY + ATYAAR (SEQ ID NO: 11460) |
| 53 | TGGA + GGYTTTATYAA (SEQ ID NO: 11461) |
| 53 | TGGAGG + YTTTATYAA (SEQ ID NO: 11462) |
| 53 | TGGAG + GYTTTATYAA (SEQ ID NO: 11463) |
| 53 | T + GGAGGYTTTATYAA (SEQ ID NO: 11464) |
| 53 | TGGAGGYTTTATYAA (SEQ ID NO: 11465) |
| 53 | TGGAGGYTTTATYAAR (SEQ ID NO: 11466) |
| 53 | TGGAGGYTTT + ATYAA (SEQ ID NO: 11467) |
| 53 | TGGAGGYTTTAT + YAA (SEQ ID NO: 11468) |
| 53 | +TGGAGGY + TT +TATYAA (SEQ ID NO: 11469) |
| 53 | TGGAG + GY + TT + TATYAA (SEQ ID NO: 11470) |
| 53 | TGG + AGGY + TT + TATYAA (SEQ ID NO: 11471) |
| 53 | TGGAGG + Y + TT + TATYAA (SEQ ID NO: 11472) |
| 53 | TGGAGGY + TT + TATYA + A (SEQ ID NO: 11473) |
| 53 | TGGAGGY + TT + T + ATYAA (SEQ ID NO: 11474) |
| 53 | TGGAGGY + TT + TATYAAR (SEQ ID NO: 11475) |
| 53 | TGGAGGY + TT + TATY + AA (SEQ ID NO: 11476) |

TABLE 10 -continued

| | |
|---|---|
| 53 | TTTGATRAAACCTCC (SEQ ID NO: 11477) |
| 53 | TGGAGGYTTYATYAARGTAA (SEQ ID NO: 11478) |
| 53 | TTGGAGGYTTTATYAARGTA (SEQ ID NO: 11479) |
| 53 | TGGAGGYTTYATYAARGTA (SEQ ID NO: 11480) |
| 53 | TTGGAGGYTTTATYAARGT (SEQ ID NO: 11481) |
| 53 | GGAGGYTTYATYAARGT (SEQ ID NO: 11482) |
| 53 | TGGAGGYTTTATYAARG (SEQ ID NO: 11483) |
| 53 | GGAGGYTTYATYAAR (SEQ ID NO: 11484) |
| 53 | TGGAGGYTTTATYAA (SEQ ID NO: 11485) |
| 54 | AGGYT + TTATYAARGTAARRC (SEQ ID NO: 11486) |
| 54 | AGGYTTTA + TYAARGTAARRC (SEQ ID NO: 11487) |
| 54 | AGGYTT + TATYAARGTAARRC (SEQ ID NO: 11488) |
| 54 | AGGYTTT + ATYAARGTAARRC (SEQ ID NO: 11489) |
| 54 | AGGYTTTATY + AARGTAARRC (SEQ ID NO: 11490) |
| 54 | AGGYTTTATYAARG + TAARRC (SEQ ID NO: 11491) |
| 54 | AGGYTTTATYAARGTA + ARRC (SEQ ID NO: 11492) |
| 54 | AGGYTTTATYAA + RGTAARRC (SEQ ID NO: 11493) |
| 54 | AGGYT + TTA + TY + AARGTAARRC (SEQ ID NO: 11494) |
| 54 | AGGY + TTTA + TY + AARGTAARRC (SEQ ID NO: 11495) |
| 54 | AGG + YTTTA + TY + AARGTAARRC (SEQ ID NO: 11496) |
| 54 | AG + GYTTTA + TY + AARGTAARRC (SEQ ID NO: 11497) |
| 54 | AGGYTTTA + TY + AAR + GTAARRC (SEQ ID NO: 11498) |
| 54 | AGGYTTTA + TY + AARGTAAR + RC (SEQ ID NO: 11499) |
| 54 | AGGYTTTA + TY + AA + RGTAARRC (SEQ ID NO: 11500) |
| 54 | AGGYTTTA + TY + A + ARGTAARRC (SEQ ID NO: 11501) |
| 54 | GAGGYT + TTATYAARGTAARR (SEQ ID NO: 11502) |
| 54 | GA + GGYTTTATYAARGTAARR (SEQ ID NO: 11503) |
| 54 | GAGGYTT + TATYAARGTAARR (SEQ ID NO: 11504) |
| 54 | GAG + GYTTTATYAARGTAARR (SEQ ID NO: 11505) |
| 54 | GAGGYTTTAT + YAARGTAARR (SEQ ID NO: 11506) |
| 54 | GAGGYTTTATYAA + RGTAARR (SEQ ID NO: 11507) |
| 54 | GAGGYTTTATYAARGT + AARR (SEQ ID NO: 11508) |
| 54 | GAGGYTTTATY + AARGTAARR (SEQ ID NO: 11509) |
| 54 | GAGGYT + TT + AT + YAARGTAARR (SEQ ID NO: 11510) |
| 54 | GAG + GYTTT + AT + YAARGTAARR (SEQ ID NO: 11511) |
| 54 | GA + GGYTTT + AT + YAARGTAARR (SEQ ID NO: 11512) |
| 54 | GAGG + YTTT + AT + YAARGTAARR (SEQ ID NO: 11513) |
| 54 | GAGGYTTT + AT + YAARGT + AARR (SEQ ID NO: 11514) |
| 54 | GAGGYTTT + AT + YAARG + TAARR (SEQ ID NO: 11515) |
| 54 | GAGGYTTT + AT + YAA + RGTAARR (SEQ ID NO: 11516) |

TABLE 10 -continued

| | | |
|---|---|---|
| 54 | GAGGYTTT + AT + Y + AARGTAARR | (SEQ ID NO: 11517) |
| 54 | GGA + GGYTTTATYAARGTAAR | (SEQ ID NO: 11518) |
| 54 | G + GAGGYTTTATYAARGTAAR | (SEQ ID NO: 11519) |
| 54 | GG + AGGYTTTATYAARGTAAR | (SEQ ID NO: 11520) |
| 54 | GGAGGY + TTTATYAARGTAAR | (SEQ ID NO: 11521) |
| 54 | GGAGGYTTTATY + AARGTAAR | (SEQ ID NO: 11522) |
| 54 | GGAGGYTTTATYAARGT + AAR | (SEQ ID NO: 11523) |
| 54 | GGAGGYTTTATYAARG + TAAR | (SEQ ID NO: 11524) |
| 54 | GGAGGYTTTATYAARGTA + AR | (SEQ ID NO: 11525) |
| 54 | GG + AGGYTT + TA + TYAARGTAAR | (SEQ ID NO: 11526) |
| 54 | G + GAGGYTT + TA + TYAARGTAAR | (SEQ ID NO: 11527) |
| 54 | GGAGGY + TT + TA + TYAARGTAAR | (SEQ ID NO: 11528) |
| 54 | GGA + GGYTT + TA + TYAARGTAAR | (SEQ ID NO: 11529) |
| 54 | GGAGGYTT + TA + TYAA + RGTAAR | (SEQ ID NO: 11530) |
| 54 | GGAGGYTT + TA + TYA + ARGTAAR | (SEQ ID NO: 11531) |
| 54 | GGAGGYTT + TA + TYAAR + GTAAR | (SEQ ID NO: 11532) |
| 54 | GGAGGYTT + TA + TY + AARGTAAR | (SEQ ID NO: 11533) |
| 54 | AGGYT + TTATYAARGTAARR | (SEQ ID NO: 11534) |
| 54 | AGGYTTTA + TYAARGTAARR | (SEQ ID NO: 11535) |
| 54 | AGGYTT + TATYAARGTAARR | (SEQ ID NO: 11536) |
| 54 | AGGYTTT + ATYAARGTAARR | (SEQ ID NO: 11537) |
| 54 | AGGYTTTATY + AARGTAARR | (SEQ ID NO: 11538) |
| 54 | AGGYTTTATYAARG + TAARR | (SEQ ID NO: 11539) |
| 54 | AGGYTTTATYAARGTA + ARR | (SEQ ID NO: 11540) |
| 54 | AGGYTTTATYAA + RGTAARR | (SEQ ID NO: 11541) |
| 54 | AGGYT + TTA + TY + AARGTAARR | (SEQ ID NO: 11542) |
| 54 | AGGY + TTTA + TY + AARGTAARR | (SEQ ID NO: 11543) |
| 54 | AGG + YTTTA + TY + AARGTAARR | (SEQ ID NO: 11544) |
| 54 | AG + GYTTTA + TY + AARGTAARR | (SEQ ID NO: 11545) |
| 54 | AGGYTTTA + TY + AAR + GTAARR | (SEQ ID NO: 11546) |
| 54 | AGGYTTTA + TY + AARGTAAR + R | (SEQ ID NO: 11547) |
| 54 | AGGYTTTA + TY + AA + RGTAARR | (SEQ ID NO: 11548) |
| 54 | AGGYTTTA + TY + A + ARGTAARR | (SEQ ID NO: 11549) |
| 54 | GAGGYT + TTATYAARGTAAR | (SEQ ID NO: 11550) |
| 54 | GA + GGYTTTATYAARGTAAR | (SEQ ID NO: 11551) |
| 54 | GAGGYTT + TATYAARGTAAR | (SEQ ID NO: 11552) |
| 54 | GAG + GYTTTATYAARGTAAR | (SEQ ID NO: 11553) |
| 54 | GAGGYTTTAT + YAARGTAAR | (SEQ ID NO: 11554) |
| 54 | GAGGYTTTATYAA + RGTAAR | (SEQ ID NO: 11555) |
| 54 | GAGGYTTTATYAARGT + AAR | (SEQ ID NO: 11556) |

TABLE 10 -continued

| | |
|---|---|
| 54 | GAGGYTTTATY + AARGTAAR (SEQ ID NO: 11557) |
| 54 | GAGGYT + TT + AT + YAARGTAAR (SEQ ID NO: 11558) |
| 54 | GAG + GYTTT + AT + YAARGTAAR (SEQ ID NO: 11559) |
| 54 | GA + GGYTT + AT + YAARGTAAR (SEQ ID NO: 11560) |
| 54 | GAGG + YTTT + AT + YAARGTAAR (SEQ ID NO: 11561) |
| 54 | GAGGYTTT + AT + YAARGT + AAR (SEQ ID NO: 11562) |
| 54 | GAGGYTTT + AT + YAARG + TAAR (SEQ ID NO: 11563) |
| 54 | GAGGYTTT + AT + YAA + RGTAAR (SEQ ID NO: 11564) |
| 54 | GAGGYTTT + AT + Y + AARGTAAR (SEQ ID NO: 11565) |
| 54 | GGA + GGYTTTATYAARGTAA (SEQ ID NO: 11566) |
| 54 | G + GAGGYTTTATYAARGTAA (SEQ ID NO: 11567) |
| 54 | GG + AGGYTTTATYAARGTAA (SEQ ID NO: 11568) |
| 54 | GGAGGY + TTTATYAARGTAA (SEQ ID NO: 11569) |
| 54 | GGAGGYTTTATY + AARGTAA (SEQ ID NO: 11570) |
| 54 | GGAGGYTTTATYAARGT + AA (SEQ ID NO: 11571) |
| 54 | GGAGGYTTTATYAARG + TAA (SEQ ID NO: 11572) |
| 54 | GGAGGYTTTATYAARGTA + A (SEQ ID NO: 11573) |
| 54 | GG + AGGYTT + TA + TYAARGTAA (SEQ ID NO: 11574) |
| 54 | G + GAGGYTT + TA + TYAARGTAA (SEQ ID NO: 11575) |
| 54 | GGAGGY + TT + TA + TYAARGTAA (SEQ ID NO: 11576) |
| 54 | GGA + GGYTT + TA + TYAARGTAA (SEQ ID NO: 11577) |
| 54 | GGAGGYTT + TA + TYAA + RGTAA (SEQ ID NO: 11578) |
| 54 | GGAGGYTT + TA + TYA + ARGTAA (SEQ ID NO: 11579) |
| 54 | GGAGGYTT + TA + TYAAR + GTAA (SEQ ID NO: 11580) |
| 54 | GGAGGYTT + TA + TY + AARGTAA (SEQ ID NO: 11581) |
| 54 | GGYT + TTATYAARGTAAR (SEQ ID NO: 11582) |
| 54 | GGYTTTA + TYAARGTAAR (SEQ ID NO: 11583) |
| 54 | GGYTT + TATYAARGTAAR (SEQ ID NO: 11584) |
| 54 | GGYTTT + ATYAARGTAAR (SEQ ID NO: 11585) |
| 54 | GGYTTTATY + AARGTAAR (SEQ ID NO: 11586) |
| 54 | GGYTTTATYAARG + TAAR (SEQ ID NO: 11587) |
| 54 | GGYTTTATYAARGTA + AR (SEQ ID NO: 11588) |
| 54 | GGYTTTATYAA + RGTAAR (SEQ ID NO: 11589) |
| 54 | GGYT + TTA + TY + AARGTAAR (SEQ ID NO: 11590) |
| 54 | GGY + TTTA + TY + AARGTAAR (SEQ ID NO: 11591) |
| 54 | GG + YTTTA + TY + AARGTAAR (SEQ ID NO: 11592) |
| 54 | G + GYTTTA + TY + AARGTAAR (SEQ ID NO: 11593) |
| 54 | GGYTTTA + TY + AAR + GTAAR (SEQ ID NO: 11594) |
| 54 | GGYTTTA + TY + AARGTAAR (SEQ ID NO: 11595) |
| 54 | GGYTTTA + TY + AA + RGTAAR (SEQ ID NO: 11596) |

TABLE 10 -continued

| | |
|---|---|
| 54 | GGYTTTA + TY + A + ARGTAAR (SEQ ID NO: 11597) |
| 54 | AGGYT + TTATYAARGTAA (SEQ ID NO: 11598) |
| 54 | A + GGYTTTATYAARGTAA (SEQ ID NO: 11599) |
| 54 | AGGYTT + TATYAARGTAA (SEQ ID NO: 11600) |
| 54 | AG + GYTTTATYAARGTAA (SEQ ID NO: 11601) |
| 54 | AGGYTTTAT + YAARGTAA (SEQ ID NO: 11602) |
| 54 | AGGYTTTATYAA + RGTAA (SEQ ID NO: 11603) |
| 54 | AGGYTTTATYAARGT + AA (SEQ ID NO: 11604) |
| 54 | AGGYTTTATY + AARGTAA (SEQ ID NO: 11605) |
| 54 | AGGYT + TT + AT + YAARGTAA (SEQ ID NO: 11606) |
| 54 | AG + GYTTT + AT + YAARGTAA (SEQ ID NO: 11607) |
| 54 | A + GGYTTT + AT + YAARGTAA (SEQ ID NO: 11608) |
| 54 | AGG + YTTT + AT + YAARGTAA (SEQ ID NO: 11609) |
| 54 | AGGYTTT + AT + YAARGT + AA (SEQ ID NO: 11610) |
| 54 | AGGYTTT + AT + YAARG + TAA (SEQ ID NO: 11611) |
| 54 | AGGYTTT + AT + YAA + RGTAA (SEQ ID NO: 11612) |
| 54 | AGGYTTT + AT + Y + AARGTAA (SEQ ID NO: 11613) |
| 54 | GA + GGYTTTATYAARGTA (SEQ ID NO: 11614) |
| 54 | +GAGGYTTTATYAARGTA (SEQ ID NO: 11615) |
| 54 | G + AGGYTTTATYAARGTA (SEQ ID NO: 11616) |
| 54 | GAGGY + TTTATYAARGTA (SEQ ID NO: 11617) |
| 54 | GAGGYTTTATY + AARGTA (SEQ ID NO: 11618) |
| 54 | GAGGYTTTATYAARGT + A (SEQ ID NO: 11619) |
| 54 | GAGGYTTTATYAARG + TA (SEQ ID NO: 11620) |
| 54 | GAGGYTTTATYAARGTA (SEQ ID NO: 11621) |
| 54 | G + AGGYTT + TA + TYAARGTA (SEQ ID NO: 11622) |
| 54 | +GAGGYTT + TA + TYAARGTA (SEQ ID NO: 11623) |
| 54 | GAGGY + TT + TA + TYAARGTA (SEQ ID NO: 11624) |
| 54 | GA + GGYTT + TA + TYAARGTA (SEQ ID NO: 11625) |
| 54 | GAGGYTT + TA + TYAA + RGTA (SEQ ID NO: 11626) |
| 54 | GAGGYTT + TA + TYA + ARGTA (SEQ ID NO: 11627) |
| 54 | GAGGYTT + TA + TYAAR + GTA (SEQ ID NO: 11628) |
| 54 | GAGGYTT + TA + TY + AARGTA (SEQ ID NO: 11629) |
| 54 | GGYT + TTATYAARGTA (SEQ ID NO: 11630) |
| 54 | GGYTTTA + TYAARGTA (SEQ ID NO: 11631) |
| 54 | GGYTT + TATYAARGTA (SEQ ID NO: 11632) |
| 54 | GGYTTT + ATYAARGTA (SEQ ID NO: 11633) |
| 54 | GGYTTTATY + AARGTA (SEQ ID NO: 11634) |
| 54 | GGYTTTATYAARG + TA (SEQ ID NO: 11635) |
| 54 | GGYTTTATYAARGTA (SEQ ID NO: 11636) |

TABLE 10 -continued

| | |
|---|---|
| 54 | GGYTTTATYAA + RGTA (SEQ ID NO: 11637) |
| 54 | GGYT + TTA + TY + AARGTA (SEQ ID NO: 11638) |
| 54 | GGY + TTTA + TY + AARGTA (SEQ ID NO: 11639) |
| 54 | GG + YTTTA + TY + AARGTA (SEQ ID NO: 11640) |
| 54 | G + GYTTTA + TY + AARGTA (SEQ ID NO: 11641) |
| 54 | GGYTTTA + TY + AAR + GTA (SEQ ID NO: 11642) |
| 54 | GGYTTTA + TY + AARGTAA (SEQ ID NO: 11643) |
| 54 | GGYTTTA + TY + AA + RGTA (SEQ ID NO: 11644) |
| 54 | GGYTTTA + TY + A + ARGTA (SEQ ID NO: 11645) |
| 54 | AGGYT + TTATYAARGT (SEQ ID NO: 11646) |
| 54 | A + GGYTTTATYAARGT (SEQ ID NO: 11647) |
| 54 | AGGYTT + TATYAARGT (SEQ ID NO: 11648) |
| 54 | AG + GYTTTATYAARGT (SEQ ID NO: 11649) |
| 54 | AGGYTTTAT + YAARGT (SEQ ID NO: 11650) |
| 54 | AGGYTTTATYAA + RGT (SEQ ID NO: 11651) |
| 54 | AGGYTTTATYAARGT (SEQ ID NO: 11652) |
| 54 | AGGYTTTATY + AARGT (SEQ ID NO: 11653) |
| 54 | AGGYT + TT + AT + YAARGT (SEQ ID NO: 11654) |
| 54 | AG + GYTTT + AT + YAARGT (SEQ ID NO: 11655) |
| 54 | A + GGYTTT + AT + YAARGT (SEQ ID NO: 11656) |
| 54 | AGG + YTTT + AT + YAARGT (SEQ ID NO: 11657) |
| 54 | AGGYTTT + AT + YAARGT (SEQ ID NO: 11658) |
| 54 | AGGYTTT + AT + YAARG + T (SEQ ID NO: 11659) |
| 54 | AGGYTTT + AT + YAA + RGT (SEQ ID NO: 11660) |
| 54 | AGGYTTT + AT + Y + AARGT (SEQ ID NO: 11661) |
| 54 | GA + GGYTTTATYAARG (SEQ ID NO: 11662) |
| 54 | +GAGGYTTTATYAARG (SEQ ID NO: 11663) |
| 54 | G + AGGYTTTATYAARG (SEQ ID NO: 11664) |
| 54 | GAGGY + TTTATYAARG (SEQ ID NO: 11665) |
| 54 | GAGGYTTTATY + AARG (SEQ ID NO: 11666) |
| 54 | GAGGYTTTATYAARGT (SEQ ID NO: 11667) |
| 54 | GAGGYTTTATYAARG (SEQ ID NO: 11668) |
| 54 | G + AGGYTT + TA + TYAARG (SEQ ID NO: 11669) |
| 54 | +GAGGYTT + TA + TYAARG (SEQ ID NO: 11670) |
| 54 | GAGGY + TT + TA + TYAARG (SEQ ID NO: 11671) |
| 54 | GA + GGYTT + TA + TYAARG (SEQ ID NO: 11672) |
| 54 | GAGGYTT + TA + TYAA + RG (SEQ ID NO: 11673) |
| 54 | GAGGYTT + TA + TYA + ARG (SEQ ID NO: 11674) |
| 54 | GAGGYTT + TA + TYAAR + G (SEQ ID NO: 11675) |
| 54 | GAGGYTT + TA + TY + AARG (SEQ ID NO: 11676) |

TABLE 10 -continued

| | |
|---|---|
| 54 | TACTTTRATAAAACC (SEQ ID NO: 11677) |
| 54 | AGGYTTTATYAARGTAARRC (SEQ ID NO: 11678) |
| 54 | GAGGYTTTATYAARGTAARR (SEQ ID NO: 11679) |
| 54 | GGAGGYTTTATYAARGTAAR (SEQ ID NO: 11680) |
| 54 | AGGYTTTATYAARGTAARR (SEQ ID NO: 11681) |
| 54 | GAGGYTTTATYAARGTAAR (SEQ ID NO: 11682) |
| 54 | GGAGGYTTTATYAARGTAA (SEQ ID NO: 11683) |
| 54 | GGYTTTATYAARGTAAR (SEQ ID NO: 11684) |
| 54 | AGGYTTTATYAARGTAA (SEQ ID NO: 11685) |
| 54 | GAGGYTTTATYAARGTA (SEQ ID NO: 11686) |
| 54 | GGYTTTATYAARGTA (SEQ ID NO: 11687) |
| 54 | GGYTTTATYAARGTAA (SEQ ID NO: 11688) |
| 54 | AGGYTTTATYAARGT (SEQ ID NO: 11689) |
| 54 | GAGGYTTTATYAARG (SEQ ID NO: 11690) |
| 58 | AA + RGTAARRCARTATGAKSA (SEQ ID NO: 11691) |
| 58 | AARGTAA + RRCARTATGAKSA (SEQ ID NO: 11692) |
| 58 | A + ARGTAARRCARTATGAKSA (SEQ ID NO: 11693) |
| 58 | AARGTAAR + RCARTATGAKSA (SEQ ID NO: 11694) |
| 58 | AARGTAARRCART + ATGAKSA (SEQ ID NO: 11695) |
| 58 | AARGTAARRCARTATGAK + SA (SEQ ID NO: 11696) |
| 58 | AARGTAARRCA + RTATGAKSA (SEQ ID NO: 11697) |
| 58 | AARGTAARRCAR + TATGAKSA (SEQ ID NO: 11698) |
| 58 | AA + RGTAAR + RC + ARTATGAKSA (SEQ ID NO: 11699) |
| 58 | AARG + TAAR + RC + ARTATGAKSA (SEQ ID NO: 11700) |
| 58 | AAR + GTAAR + RC + ARTATGAKSA (SEQ ID NO: 11701) |
| 58 | A + ARGTAAR + RC + ARTATGAKSA (SEQ ID NO: 11702) |
| 58 | AARGTAAR + RC + ARTATGAK + SA (SEQ ID NO: 11703) |
| 58 | AARGTAAR + RC + ARTAT + GAKSA (SEQ ID NO: 11704) |
| 58 | AARGTAAR + RC + ARTA + TGAKSA (SEQ ID NO: 11705) |
| 58 | AARGTAAR + RC + AR + TATGAKSA (SEQ ID NO: 11706) |
| 58 | AA + RGTAARRCARTATGAKS (SEQ ID NO: 11707) |
| 58 | AARGTAA + RRCARTATGAKS (SEQ ID NO: 11708) |
| 58 | A + ARGTAARRCARTATGAKS (SEQ ID NO: 11709) |
| 58 | AARGTAAR + RCARTATGAKS (SEQ ID NO: 11710) |
| 58 | AARGTAARRCART + ATGAKS (SEQ ID NO: 11711) |
| 58 | AARGTAARRCARTATGAK + S (SEQ ID NO: 11712) |
| 58 | AARGTAARRCA + RTATGAKS (SEQ ID NO: 11713) |
| 58 | AARGTAARRCAR + TATGAKS (SEQ ID NO: 11714) |
| 58 | AA + RGTAAR + RC + ARTATGAKS (SEQ ID NO: 11715) |
| 58 | AARG + TAAR + RC + ARTATGAKS (SEQ ID NO: 11716) |

TABLE 10 -continued

| | |
|---|---|
| 58 | AAR + GTAAR + RC + ARTATGAKS (SEQ ID NO: 11717) |
| 58 | A + ARGTAAR + RC + ARTATGAKS (SEQ ID NO: 11718) |
| 58 | AARGTAAR + RC + ARTATGAK + S (SEQ ID NO: 11719) |
| 58 | AARGTAAR + RC + ARTAT + GAKS (SEQ ID NO: 11720) |
| 58 | AARGTAAR + RC + ARTA + TGAKS (SEQ ID NO: 11721) |
| 58 | AARGTAAR + RC + AR + TATGAKS (SEQ ID NO: 11722) |
| 58 | A + RGTAARRCARTATGAK (SEQ ID NO: 11723) |
| 58 | ARGTAA + RRCARTATGAK (SEQ ID NO: 11724) |
| 58 | +ARGTAARRCARTATGAK (SEQ ID NO: 11725) |
| 58 | ARGTAAR + RCARTATGAK (SEQ ID NO: 11726) |
| 58 | ARGTAARRCART + ATGAK (SEQ ID NO: 11727) |
| 58 | ARGTAARRCARTATGAK (SEQ ID NO: 11728) |
| 58 | ARGTAARRCA + RTATGAK (SEQ ID NO: 11729) |
| 58 | ARGTAARRCAR + TATGAK (SEQ ID NO: 11730) |
| 58 | A + RGTAAR + RC + ARTATGAK (SEQ ID NO: 11731) |
| 58 | ARG + TAAR + RC + ARTATGAK (SEQ ID NO: 11732) |
| 58 | AR + GTAAR + RC + ARTATGAK (SEQ ID NO: 11733) |
| 58 | +ARGTAAR + RC + ARTATGAK (SEQ ID NO: 11734) |
| 58 | ARGTAAR + RC + ARTATGAK (SEQ ID NO: 11735) |
| 58 | ARGTAAR + RC + ARTAT + GAK (SEQ ID NO: 11736) |
| 58 | ARGTAAR + RC + ARTA + TGAK (SEQ ID NO: 11737) |
| 58 | ARGTAAR + RC + AR + TATGAK (SEQ ID NO: 11738) |
| 58 | A + RGTAARRCARTATG (SEQ ID NO: 11739) |
| 58 | ARGTAA + RRCARTATG (SEQ ID NO: 11740) |
| 58 | +ARGTAARRCARTATG (SEQ ID NO: 11741) |
| 58 | ARGTAAR + RCARTATG (SEQ ID NO: 11742) |
| 58 | ARGTAARRCART + ATG (SEQ ID NO: 11743) |
| 58 | ARGTAARRCARTATGA (SEQ ID NO: 11744) |
| 58 | ARGTAARRCA + RTATG (SEQ ID NO: 11745) |
| 58 | ARGTAARRCAR + TATG (SEQ ID NO: 11746) |
| 58 | A + RGTAAR + RC + ARTATG (SEQ ID NO: 11747) |
| 58 | ARG + TAAR + RC + ARTATG (SEQ ID NO: 11748) |
| 58 | AR + GTAAR + RC + ARTATG (SEQ ID NO: 11749) |
| 58 | +ARGTAAR + RC + ARTATG (SEQ ID NO: 11750) |
| 58 | ARGTAAR + RC + ARTATGA (SEQ ID NO: 11751) |
| 58 | ARGTAAR + RC + ARTAT + G (SEQ ID NO: 11752) |
| 58 | ARGTAAR + RC + ARTA + TG (SEQ ID NO: 11753) |
| 58 | ARGTAAR + RC + AR + TATG (SEQ ID NO: 11754) |
| 58 | AGTAAGACARTATGA (SEQ ID NO: 11755) |
| 58 | AARGTAARRCARTATGAKSA (SEQ ID NO: 11756) |

TABLE 10 -continued

| | |
|---|---|
| 58 | AARGTAARRCARTATGAKS (SEQ ID NO: 11757) |
| 58 | ARGTAARRCARTATGAK (SEQ ID NO: 11758) |
| 58 | ARGTAARRCARTATG (SEQ ID NO: 11759) |
| 71 | G + GRMAWARRGCYATAGGKWC (SEQ ID NO: 11760) |
| 71 | GGRMAW + ARRGCYATAGGKWC (SEQ ID NO: 11761) |
| 71 | GGR + MAWARRGCYATAGGKWC (SEQ ID NO: 11762) |
| 71 | GGRM + AWARRGCYATAGGKWC (SEQ ID NO: 11763) |
| 71 | GGRMAWARRGCYATA + GGKWC (SEQ ID NO: 11764) |
| 71 | GGRMAWARRGCYATAG + GKWC (SEQ ID NO: 11765) |
| 71 | GGRMAWARRG + CYATAGGKWC (SEQ ID NO: 11766) |
| 71 | GGRMAWARRGC + YATAGGKWC (SEQ ID NO: 11767) |
| 71 | G + GRMAWAR + RG + CYATAGGKWC (SEQ ID NO: 11768) |
| 71 | GGRMAWA + R + RG + CYATAGGKWC (SEQ ID NO: 11769) |
| 71 | GG + RMAWAR + RG + CYATAGGKWC (SEQ ID NO: 11770) |
| 71 | GGRMAW + AR + RG + CYATAGGKWC (SEQ ID NO: 11771) |
| 71 | GGRMAWAR + RG + C + YATAGGKWC (SEQ ID NO: 11772) |
| 71 | GGRMAWAR + RG + CYAT + AGGKWC (SEQ ID NO: 11773) |
| 71 | GGRMAWAR + RG + CYATAGG + KWC (SEQ ID NO: 11774) |
| 71 | GGRMAWAR + RG + CYA + TAGGKWC (SEQ ID NO: 11775) |
| 71 | G + GRMAWARRGCYATAGGKW (SEQ ID NO: 11776) |
| 71 | GGRMAW + ARRGCYATAGGKW (SEQ ID NO: 11777) |
| 71 | GGR + MAWARRGCYATAGGKW (SEQ ID NO: 11778) |
| 71 | GGRM + AWARRGCYATAGGKW (SEQ ID NO: 11779) |
| 71 | GGRMAWARRGCYATA + GGKW (SEQ ID NO: 11780) |
| 71 | GGRMAWARRGCYATAG + GKW (SEQ ID NO: 11781) |
| 71 | GGRMAWARRG + CYATAGGKW (SEQ ID NO: 11782) |
| 71 | GGRMAWARRGC + YATAGGKW (SEQ ID NO: 11783) |
| 71 | G + GRMAWAR + RG + CYATAGGKW (SEQ ID NO: 11784) |
| 71 | GGRMAWA + R + RG + CYATAGGKW (SEQ ID NO: 11785) |
| 71 | GG + RMAWAR + RG + CYATAGGKW (SEQ ID NO: 11786) |
| 71 | GGRMAW + AR + RG + CYATAGGKW (SEQ ID NO: 11787) |
| 71 | GGRMAWAR + RG + C + YATAGGKW (SEQ ID NO: 11788) |
| 71 | GGRMAWAR + RG + CYAT + AGGKW (SEQ ID NO: 11789) |
| 71 | GGRMAWAR + RG + CYATAGG + KW (SEQ ID NO: 11790) |
| 71 | GGRMAWAR + RG + CYA + TAGGKW (SEQ ID NO: 11791) |
| 71 | +GRMAWARRGCYATAGGK (SEQ ID NO: 11792) |
| 71 | GRMAW + ARRGCYATAGGK (SEQ ID NO: 11793) |
| 71 | GR + MAWARRGCYATAGGK (SEQ ID NO: 11794) |
| 71 | GRM + AWARRGCYATAGGK (SEQ ID NO: 11795) |
| 71 | GRMAWARRGCYATA + GGK (SEQ ID NO: 11796) |

TABLE 10 -continued

| | |
|---|---|
| 71 | GRMAWARRGCYATAG + GK (SEQ ID NO: 11797) |
| 71 | GRMAWARRG + CYATAGGK (SEQ ID NO: 11798) |
| 71 | GRMAWARRGC + YATAGGK (SEQ ID NO: 11799) |
| 71 | +GRMAWAR + RG + CYATAGGK (SEQ ID NO: 11800) |
| 71 | GRMAWA + R + RG + CYATAGGK (SEQ ID NO: 11801) |
| 71 | G + RMAWAR + RG + CYATAGGK (SEQ ID NO: 11802) |
| 71 | GRMAW + AR + RG + CYATAGGK (SEQ ID NO: 11803) |
| 71 | GRMAWAR + RG + C + YATAGGK (SEQ ID NO: 11804) |
| 71 | GRMAWAR + RG + CYAT + AGGK (SEQ ID NO: 11805) |
| 71 | GRMAWAR + RG + CYATAGG + K (SEQ ID NO: 11806) |
| 71 | GRMAWAR + RG + CYA + TAGGK (SEQ ID NO: 11807) |
| 71 | +GRMAWARRGCYATAG (SEQ ID NO: 11808) |
| 71 | GRMAW + ARRGCYATAG (SEQ ID NO: 11809) |
| 71 | GR + MAWARRGCYATAG (SEQ ID NO: 11810) |
| 71 | GRM + AWARRGCYATAG (SEQ ID NO: 11811) |
| 71 | GRMAWARRGCYATA + G (SEQ ID NO: 11812) |
| 71 | GRMAWARRGCYATAG (SEQ ID NO: 11813) |
| 71 | GRMAWARRG + CYATAG (SEQ ID NO: 11814) |
| 71 | GRMAWARRGC + YATAG (SEQ ID NO: 11815) |
| 71 | +GRMAWAR + RG + CYATAG (SEQ ID NO: 11816) |
| 71 | GRMAWA + R + RG + CYATAG (SEQ ID NO: 11817) |
| 71 | G + RMAWAR + RG + CYATAG (SEQ ID NO: 11818) |
| 71 | GRMAW + AR + RG + CYATAG (SEQ ID NO: 11819) |
| 71 | GRMAWAR + RG + C + YATAG (SEQ ID NO: 11820) |
| 71 | GRMAWAR + RG + CYAT + AG (SEQ ID NO: 11821) |
| 71 | GRMAWAR + RG + CYATAGG (SEQ ID NO: 11822) |
| 71 | GRMAWAR + RG + CYA + TAG (SEQ ID NO: 11823) |
| 71 | CATAAAGCHATAGGT (SEQ ID NO: 11824) |
| 71 | GGRMAWARRGCYATAGGKWC (SEQ ID NO: 11825) |
| 71 | GGRMAWARRGCYATAGGKW (SEQ ID NO: 11826) |
| 71 | GRMAWARRGCYATAGGK (SEQ ID NO: 11827) |
| 71 | GRMAWARRGCYATAG (SEQ ID NO: 11828) |
| 71 | GRMAWARRGCYATAGG (SEQ ID NO: 11829) |
| 73 | RRG + CYATAGGKWCAGTRYTR (SEQ ID NO: 11830) |
| 73 | R + RGCYATAGGKWCAGTRYTR (SEQ ID NO: 11831) |
| 73 | RRGC + YATAGGKWCAGTRYTR (SEQ ID NO: 11832) |
| 73 | RRGCYAT + AGGKWCAGTRYTR (SEQ ID NO: 11833) |
| 73 | RRGCYATAGGKWCAGTRY + TR (SEQ ID NO: 11834) |
| 73 | RRGCYATAGG + KWCAGTRYTR (SEQ ID NO: 11835) |
| 73 | RRGCYATAGGKWC + AGTRYTR (SEQ ID NO: 11836) |

TABLE 10 -continued

| | |
|---|---|
| 73 | RRGCYATAGGK + WCAGTRYTR (SEQ ID NO: 11837) |
| 73 | RRGCYAT + A + GG + KWCAGTRYTR (SEQ ID NO: 11838) |
| 73 | RRGCY + ATA + GG + KWCAGTRYTR (SEQ ID NO: 11839) |
| 73 | RR + GCYATA + GG + KWCAGTRYTR (SEQ ID NO: 11840) |
| 73 | RRG + CYATA + GG + KWCAGTRYTR (SEQ ID NO: 11841) |
| 73 | RRGCYATA + GG + KWC + AGTRYTR (SEQ ID NO: 11842) |
| 73 | RRGCYATA + GG + K + WCAGTRYTR (SEQ ID NO: 11843) |
| 73 | RRGCYATA + GG + KWCAGTR + YTR (SEQ ID NO: 11844) |
| 73 | RRGCYATA + GG + KW + CAGTRYTR (SEQ ID NO: 11845) |
| 73 | ARRGCYA + TAGGKWCAGTRYT (SEQ ID NO: 11846) |
| 73 | A + RRGCYATAGGKWCAGTRYT (SEQ ID NO: 11847) |
| 73 | AR + RGCYATAGGKWCAGTRYT (SEQ ID NO: 11848) |
| 73 | ARRG + CYATAGGKWCAGTRYT (SEQ ID NO: 11849) |
| 73 | ARRGCYATAGGKWC + AGTRYT (SEQ ID NO: 11850) |
| 73 | ARRGCYATAGGK + WCAGTRYT (SEQ ID NO: 11851) |
| 73 | ARRGCYATAGG + KWCAGTRYT (SEQ ID NO: 11852) |
| 73 | ARRGCYATAGGKWCAGTR + YT (SEQ ID NO: 11853) |
| 73 | ARRGCYA + T + AG + GKWCAGTRYT (SEQ ID NO: 11854) |
| 73 | ARRG + CYAT + AG + GKWCAGTRYT (SEQ ID NO: 11855) |
| 73 | A + RRGCYAT + AG + GKWCAGTRYT (SEQ ID NO: 11856) |
| 73 | ARRGCY + AT + AG + GKWCAGTRYT (SEQ ID NO: 11857) |
| 73 | ARRGCYAT + AG + GKWC + AGTRYT (SEQ ID NO: 11858) |
| 73 | ARRGCYAT + AG + GKWCAGTR + YT (SEQ ID NO: 11859) |
| 73 | ARRGCYAT + AG + GKW + CAGTRYT (SEQ ID NO: 11860) |
| 73 | ARRGCYAT + AG + GK + WCAGTRYT (SEQ ID NO: 11861) |
| 73 | RRG + CYATAGGKWCAGTRYT (SEQ ID NO: 11862) |
| 73 | R + RGCYATAGGKWCAGTRYT (SEQ ID NO: 11863) |
| 73 | RRGC + YATAGGKWCAGTRYT (SEQ ID NO: 11864) |
| 73 | RRGCYAT + AGGKWCAGTRYT (SEQ ID NO: 11865) |
| 73 | RRGCYATAGGKWCAGTRY + T (SEQ ID NO: 11866) |
| 73 | RRGCYATAGG + KWCAGTRYT (SEQ ID NO: 11867) |
| 73 | RRGCYATAGGKWC + AGTRYT (SEQ ID NO: 11868) |
| 73 | RRGCYATAGGK + WCAGTRYT (SEQ ID NO: 11869) |
| 73 | RRGCYAT + A + GG + KWCAGTRYT (SEQ ID NO: 11870) |
| 73 | RRGCY + ATA + GG + KWCAGTRYT (SEQ ID NO: 11871) |
| 73 | RR + GCYATA + GG + KWCAGTRYT (SEQ ID NO: 11872) |
| 73 | RRG + CYATA + GG + KWCAGTRYT (SEQ ID NO: 11873) |
| 73 | RRGCYATA + GG + KWC + AGTRYT (SEQ ID NO: 11874) |
| 73 | RRGCYATA + GG + K + WCAGTRYT (SEQ ID NO: 11875) |
| 73 | RRGCYATA + GG + KWCAGTR + YT (SEQ ID NO: 11876) |

TABLE 10 -continued

| | |
|---|---|
| 73 | RRGCYATA + GG + KW + CAGTRYT (SEQ ID NO: 11877) |
| 73 | ARRGCYA + TAGGKWCAGTRY (SEQ ID NO: 11878) |
| 73 | A + RRGCYATAGGKWCAGTRY (SEQ ID NO: 11879) |
| 73 | AR + RGCYATAGGKWCAGTRY (SEQ ID NO: 11880) |
| 73 | ARRG + CYATAGGKWCAGTRY (SEQ ID NO: 11881) |
| 73 | ARRGCYATAGGKWC + AGTRY (SEQ ID NO: 11882) |
| 73 | ARRGCYATAGGK + WCAGTRY (SEQ ID NO: 11883) |
| 73 | ARRGCYATAGG + KWCAGTRY (SEQ ID NO: 11884) |
| 73 | ARRGCYATAGGKWCAGTR + Y (SEQ ID NO: 11885) |
| 73 | ARRGCYA + T + AG + GKWCAGTRY (SEQ ID NO: 11886) |
| 73 | ARRG + CYAT + AG + GKWCAGTRY (SEQ ID NO: 11887) |
| 73 | A + RRGCYAT + AG + GKWCAGTRY (SEQ ID NO: 11888) |
| 73 | ARRGCY + AT + AG + GKWCAGTRY (SEQ ID NO: 11889) |
| 73 | ARRGCYAT + AG + GKWC + AGTRY (SEQ ID NO: 11890) |
| 73 | ARRGCYAT + AG + GKWCAGTR + Y (SEQ ID NO: 11891) |
| 73 | ARRGCYAT + AG + GKW + CAGTRY (SEQ ID NO: 11892) |
| 73 | ARRGCYAT + AG + GK + WCAGTRY (SEQ ID NO: 11893) |
| 73 | RG + CYATAGGKWCAGTRY (SEQ ID NO: 11894) |
| 73 | + RGCYATAGGKWCAGTRY (SEQ ID NO: 11895) |
| 73 | RGC + YATAGGKWCAGTRY (SEQ ID NO: 11896) |
| 73 | RGCYAT + AGGKWCAGTRY (SEQ ID NO: 11897) |
| 73 | RGCYATAGGKWCAGTRY (SEQ ID NO: 11898) |
| 73 | RGCYATAGG + KWCAGTRY (SEQ ID NO: 11899) |
| 73 | RGCYATAGGKWC + AGTRY (SEQ ID NO: 11900) |
| 73 | RGCYATAGGK + WCAGTRY (SEQ ID NO: 11901) |
| 73 | RGCYAT + A + GG + KWCAGTRY (SEQ ID NO: 11902) |
| 73 | RGCY + ATA + GG + KWCAGTRY (SEQ ID NO: 11903) |
| 73 | R + GCYATA + GG + KWCAGTRY (SEQ ID NO: 11904) |
| 73 | RG + CYATA + GG + KWCAGTRY (SEQ ID NO: 11905) |
| 73 | RGCYATA + GG + KWC + AGTRY (SEQ ID NO: 11906) |
| 73 | RGCYATA + GG + K + WCAGTRY (SEQ ID NO: 11907) |
| 73 | RGCYATA + GG + KWCAGTR + Y (SEQ ID NO: 11908) |
| 73 | RGCYATA + GG + KW + CAGTRY (SEQ ID NO: 11909) |
| 73 | RRGCYA + TAGGKWCAGTR (SEQ ID NO: 11910) |
| 73 | +RRGCYATAGGKWCAGTR (SEQ ID NO: 11911) |
| 73 | R + RGCYATAGGKWCAGTR (SEQ ID NO: 11912) |
| 73 | RRG + CYATAGGKWCAGTR (SEQ ID NO: 11913) |
| 73 | RRGCYATAGGKWC + AGTR (SEQ ID NO: 11914) |
| 73 | RRGCYATAGGK + WCAGTR (SEQ ID NO: 11915) |
| 73 | RRGCYATAGG + KWCAGTR (SEQ ID NO: 11916) |

TABLE 10 -continued

| | |
|---|---|
| 73 | RRGCYATAGGKWCAGTR (SEQ ID NO: 11917) |
| 73 | RRGCYA + T + AG + GKWCAGTR (SEQ ID NO: 11918) |
| 73 | RRG + CYAT + AG + GKWCAGTR (SEQ ID NO: 11919) |
| 73 | +RRGCYAT + AG + GKWCAGTR (SEQ ID NO: 11920) |
| 73 | RRGCY + AT + AG + GKWCAGTR (SEQ ID NO: 11921) |
| 73 | RRGCYAT + AG + GKWC + AGTR (SEQ ID NO: 11922) |
| 73 | RRGCYAT + AG + GKWCAGTR (SEQ ID NO: 11923) |
| 73 | RRGCYAT + AG + GKW + CAGTR (SEQ ID NO: 11924) |
| 73 | RRGCYAT + AG + GK + WCAGTR (SEQ ID NO: 11925) |
| 73 | RG + CYATAGGKWCAGT (SEQ ID NO: 11926) |
| 73 | +RGCYATAGGKWCAGT (SEQ ID NO: 11927) |
| 73 | RGC + YATAGGKWCAGT (SEQ ID NO: 11928) |
| 73 | RGCYAT + AGGKWCAGT (SEQ ID NO: 11929) |
| 73 | RGCYATAGGKWCAGTR (SEQ ID NO: 11930) |
| 73 | RGCYATAGG + KWCAGT (SEQ ID NO: 11931) |
| 73 | RGCYATAGGKWC + AGT (SEQ ID NO: 11932) |
| 73 | RGCYATAGGK + WCAGT (SEQ ID NO: 11933) |
| 73 | RGCYAT + A + GG + KWCAGT (SEQ ID NO: 11934) |
| 73 | RGCY + ATA + GG + KWCAGT (SEQ ID NO: 11935) |
| 73 | R + GCYATA + GG + KWCAGT (SEQ ID NO: 11936) |
| 73 | RG + CYATA + GG + KWCAGT (SEQ ID NO: 11937) |
| 73 | RGCYATA + GG + KWC + AGT (SEQ ID NO: 11938) |
| 73 | RGCYATA + GG + K + WCAGT (SEQ ID NO: 11939) |
| 73 | RGCYATA + GG + KWCAGTR (SEQ ID NO: 11940) |
| 73 | RGCYATA + GG + KW + CAGT (SEQ ID NO: 11941) |
| 73 | RRGCYA + TAGGKWCAG (SEQ ID NO: 11942) |
| 73 | +RRGCYATAGGKWCAG (SEQ ID NO: 11943) |
| 73 | R + RGCYATAGGKWCAG (SEQ ID NO: 11944) |
| 73 | RRG + CYATAGGKWCAG (SEQ ID NO: 11945) |
| 73 | RRGCYATAGGKWC + AG (SEQ ID NO: 11946) |
| 73 | RRGCYATAGGK + WCAG (SEQ ID NO: 11947) |
| 73 | RRGCYATAGG + KWCAG (SEQ ID NO: 11948) |
| 73 | RRGCYATAGGKWCAGT (SEQ ID NO: 11949) |
| 73 | RRGCYA + T + AG + GKWCAG (SEQ ID NO: 11950) |
| 73 | RRG + CYAT + AG + GKWCAG (SEQ ID NO: 11951) |
| 73 | +RRGCYAT + AG + GKWCAG (SEQ ID NO: 11952) |
| 73 | RRGCY + AT + AG + GKWCAG (SEQ ID NO: 11953) |
| 73 | RRGCYAT + AG + GKWC + AG (SEQ ID NO: 11954) |
| 73 | RRGCYAT + AG + GKWCAGT (SEQ ID NO: 11955) |
| 73 | RRGCYAT + AG + GKW + CAG (SEQ ID NO: 11956) |

TABLE 10 -continued

| | |
|---|---|
| 73 | RRGCYAT + AG + GK + WCAG (SEQ ID NO: 11957) |
| 73 | TACTGTNCCTATAGC (SEQ ID NO: 11958) |
| 73 | RRGCYATAGGKWCAGTRYTR (SEQ ID NO: 11959) |
| 73 | ARRGCYATAGGKWCAGTRYT (SEQ ID NO: 11960) |
| 73 | RRGCYATAGGKWCAGTRYT (SEQ ID NO: 11961) |
| 73 | ARRGCYATAGGKWCAGTRY (SEQ ID NO: 11962) |
| 73 | RGCYATAGGKWCAGTRY (SEQ ID NO: 11963) |
| 73 | RRGCYATAGGKWCAGTR (SEQ ID NO: 11964) |
| 73 | RGCYATAGGKWCAGT (SEQ ID NO: 11965) |
| 73 | RRGCYATAGGKWCAG (SEQ ID NO: 11966) |
| 74 | GCYATAG + GKACAGTRYTRRT (SEQ ID NO: 11967) |
| 74 | GCY + ATAGGKACAGTRYTRRT (SEQ ID NO: 11968) |
| 74 | GC + YATAGGKACAGTRYTRRT (SEQ ID NO: 11969) |
| 74 | GCYATAGG + KACAGTRYTRRT (SEQ ID NO: 11970) |
| 74 | GCYATAGGKACA + GTRYTRRT (SEQ ID NO: 11971) |
| 74 | GCYATAGGKACAGTRYTR + RT (SEQ ID NO: 11972) |
| 74 | GCYATAGGKA + CAGTRYTRRT (SEQ ID NO: 11973) |
| 74 | GCYATAGGKACAGTRYT + RRT (SEQ ID NO: 11974) |
| 74 | GC + YATAGG + KA + CAGTRYTRRT (SEQ ID NO: 11975) |
| 74 | GCYATA + GG + KA + CAGTRYTRRT (SEQ ID NO: 11976) |
| 74 | GCY + ATAGG + KA + CAGTRYTRRT (SEQ ID NO: 11977) |
| 74 | GCYA + TAGG + KA + CAGTRYTRRT (SEQ ID NO: 11978) |
| 74 | GCYATAGG + KA + CAGTRYTR + RT (SEQ ID NO: 11979) |
| 74 | GCYATAGG + KA + CAG + TRYTRRT (SEQ ID NO: 11980) |
| 74 | GCYATAGG + KA + CAGT + RYTRRT (SEQ ID NO: 11981) |
| 74 | GCYATAGG + KA + C + AGTRYTRRT (SEQ ID NO: 11982) |
| 74 | GCYATAG + GKACAGTRYTRR (SEQ ID NO: 11983) |
| 74 | GCY + ATAGGKACAGTRYTRR (SEQ ID NO: 11984) |
| 74 | GC + YATAGGKACAGTRYTRR (SEQ ID NO: 11985) |
| 74 | GCYATAGG + KACAGTRYTRR (SEQ ID NO: 11986) |
| 74 | GCYATAGGKACA + GTRYTRR (SEQ ID NO: 11987) |
| 74 | GCYATAGGKACAGTRYTR + R (SEQ ID NO: 11988) |
| 74 | GCYATAGGKA + CAGTRYTRR (SEQ ID NO: 11989) |
| 74 | GCYATAGGKACAGTRYT + RR (SEQ ID NO: 11990) |
| 74 | GC + YATAGG + KA + CAGTRYTRR (SEQ ID NO: 11991) |
| 74 | GCYATA + GG + KA + CAGTRYTRR (SEQ ID NO: 11992) |
| 74 | GCY + ATAGG + KA + CAGTRYTRR (SEQ ID NO: 11993) |
| 74 | GCYA + TAGG + KA + CAGTRYTRR (SEQ ID NO: 11994) |
| 74 | GCYATAGG + KA + CAGTRYTR + R (SEQ ID NO: 11995) |
| 74 | GCYATAGG + KA + CAG + TRYTRR (SEQ ID NO: 11996) |

TABLE 10 -continued

| | | |
|---|---|---|
| 74 | GCYATAGG + KA + CAGT + RYTRR | (SEQ ID NO: 11997) |
| 74 | GCYATAGG + KA + C + AGTRYTRR | (SEQ ID NO: 11998) |
| 74 | CYATAG + GKACAGTRYTR | (SEQ ID NO: 11999) |
| 74 | CY + ATAGGKACAGTRYTR | (SEQ ID NO: 12000) |
| 74 | C + YATAGGKACAGTRYTR | (SEQ ID NO: 12001) |
| 74 | CYATAGG + KACAGTRYTR | (SEQ ID NO: 12002) |
| 74 | CYATAGGKACA + GTRYTR | (SEQ ID NO: 12003) |
| 74 | CYATAGGKACAGTRYTR | (SEQ ID NO: 12004) |
| 74 | CYATAGGKA + CAGTRYTR | (SEQ ID NO: 12005) |
| 74 | CYATAGGKACAGTRYT + R | (SEQ ID NO: 12006) |
| 74 | C + YATAGG + KA + CAGTRYTR | (SEQ ID NO: 12007) |
| 74 | CYATA + GG + KA + CAGTRYTR | (SEQ ID NO: 12008) |
| 74 | CY + ATAGG + KA + CAGTRYTR | (SEQ ID NO: 12009) |
| 74 | CYA + TAGG + KA + CAGTRYTR | (SEQ ID NO: 12010) |
| 74 | CYATAGG + KA + CAGTRYTR | (SEQ ID NO: 12011) |
| 74 | CYATAGG + KA + CAG + TRYTR | (SEQ ID NO: 12012) |
| 74 | CYATAGG + KA + CAGT + RYTR | (SEQ ID NO: 12013) |
| 74 | CYATAGG + KA + C + AGTRYTR | (SEQ ID NO: 12014) |
| 74 | CYATAG + GKACAGTRY | (SEQ ID NO: 12015) |
| 74 | CY + ATAGGKACAGTRY | (SEQ ID NO: 12016) |
| 74 | C + YATAGGKACAGTRY | (SEQ ID NO: 12017) |
| 74 | CYATAGG + KACAGTRY | (SEQ ID NO: 12018) |
| 74 | CYATAGGKACA + GTRY | (SEQ ID NO: 12019) |
| 74 | CYATAGGKACAGTRYT | (SEQ ID NO: 12020) |
| 74 | CYATAGGKA + CAGTRY | (SEQ ID NO: 12021) |
| 74 | C + YATAGG + KA + CAGTRY | (SEQ ID NO: 12022) |
| 74 | CYATA + GG + KA + CAGTRY | (SEQ ID NO: 12023) |
| 74 | CY + ATAGG + KA + CAGTRY | (SEQ ID NO: 12024) |
| 74 | CYA + TAGG + KA + CAGTRY | (SEQ ID NO: 12025) |
| 74 | CYATAGG + KA + CAGTRYT | (SEQ ID NO: 12026) |
| 74 | CYATAGG + KA + CAG + TRY | (SEQ ID NO: 12027) |
| 74 | CYATAGG + KA + CAGT + RY | (SEQ ID NO: 12028) |
| 74 | CYATAGG + KA + C + AGTRY | (SEQ ID NO: 12029) |
| 74 | ATAGGTACRGTATTA | (SEQ ID NO: 12030) |
| 74 | GCYATAGGKACAGTRYTRRT | (SEQ ID NO: 12031) |
| 74 | GCYATAGGKACAGTRYTRR | (SEQ ID NO: 12032) |
| 74 | CYATAGGKACAGTRYTR | (SEQ ID NO: 12033) |
| 74 | CYATAGGKACAGTRY | (SEQ ID NO: 12034) |
| 76 | GGKWCA + GTRYTRRTRGGRCC | (SEQ ID NO: 12035) |
| 76 | GGK + WCAGTRYTRRTRGGRCC | (SEQ ID NO: 12036) |

TABLE 10 -continued

| 76 | GGKWCAGT + RYTRRTRGGRCC (SEQ ID NO: 12037) |
| 76 | G + GKWCAGTRYTRRTRGGRCC (SEQ ID NO: 12038) |
| 76 | GGKWCAGTRYTRRTRGGR + CC (SEQ ID NO: 12039) |
| 76 | GGKWCAGTRYTRRT + RGGRCC (SEQ ID NO: 12040) |
| 76 | GGKWCAGTRYTR + RTGGRCC (SEQ ID NO: 12041) |
| 76 | GGKWCAGTRY + TRRTRGGRCC (SEQ ID NO: 12042) |
| 76 | GGKW + CAGT + RY + TRRTRGGRCC (SEQ ID NO: 12043) |
| 76 | GG + KWCAGT + RY + TRRTRGGRCC (SEQ ID NO: 12044) |
| 76 | GGKWC + AGT + RY + TRRTRGGRCC (SEQ ID NO: 12045) |
| 76 | G + GKWCAGT + RY + TRRTRGGRCC (SEQ ID NO: 12046) |
| 76 | GGKWCAGT + RY + T + RRTRGGRCC (SEQ ID NO: 12047) |
| 76 | GGKWCAGT + RY + TRR + TRGGRCC (SEQ ID NO: 12048) |
| 76 | GGKWCAGT + RY + TRRT + RGGRCC (SEQ ID NO: 12049) |
| 76 | GGKWCAGT + RY + TRRTR + GGRCC (SEQ ID NO: 12050) |
| 76 | GGKWCA + GTRYTRRTRGGRC (SEQ ID NO: 12051) |
| 76 | GGK + WCAGTRYTRRTRGGRC (SEQ ID NO: 12052) |
| 76 | GGKWCAGT + RYTRRTRGGRC (SEQ ID NO: 12053) |
| 76 | G + GKWCAGTRYTRRTRGGRC (SEQ ID NO: 12054) |
| 76 | GGKWCAGTRYTRRTRGGR + C (SEQ ID NO: 12055) |
| 76 | GGKWCAGTRYTRRT + RGGRC (SEQ ID NO: 12056) |
| 76 | GGKWCAGTRYTR + RTGGRC (SEQ ID NO: 12057) |
| 76 | GGKWCAGTRY + TRRTRGGRC (SEQ ID NO: 12058) |
| 76 | GGKW + CAGT + RY + TRRTRGGRC (SEQ ID NO: 12059) |
| 76 | GG + KWCAGT + RY + TRRTRGGRC (SEQ ID NO: 12060) |
| 76 | GGKWC + AGT + RY + TRRTRGGRC (SEQ ID NO: 12061) |
| 76 | G + GKWCAGT + RY + TRRTRGGRC (SEQ ID NO: 12062) |
| 76 | GGKWCAGT + RY + T + RRTRGGRC (SEQ ID NO: 12063) |
| 76 | GGKWCAGT + RY + TRR + TRGGRC (SEQ ID NO: 12064) |
| 76 | GGKWCAGT + RY + TRRT + RGGRC (SEQ ID NO: 12065) |
| 76 | GGKWCAGT + RY + TRRTR + GGRC (SEQ ID NO: 12066) |
| 76 | GKWCA + GTRYTRRTRGGR (SEQ ID NO: 12067) |
| 76 | GK + WCAGTRYTRRTRGGR (SEQ ID NO: 12068) |
| 76 | GKWCAGT + RYTRRTRGGR (SEQ ID NO: 12069) |
| 76 | +GKWCAGTRYTRRTRGGR (SEQ ID NO: 12070) |
| 76 | GKWCAGTRYTRRTRGGR (SEQ ID NO: 12071) |
| 76 | GKWCAGTRYTRRT + RGGR (SEQ ID NO: 12072) |
| 76 | GKWCAGTRYTR + RTGGR (SEQ ID NO: 12073) |
| 76 | GKWCAGTRY + TRRTRGGR (SEQ ID NO: 12074) |
| 76 | GKW + CAGT + RY + TRRTRGGR (SEQ ID NO: 12075) |
| 76 | G + KWCAGT + RY + TRRTRGGR (SEQ ID NO: 12076) |

TABLE 10 -continued

| | |
|---|---|
| 76 | GKWC + AGT + RY + TRRTRGGR (SEQ ID NO: 12077) |
| 76 | +GKWCAGT + RY + TRRTRGGR (SEQ ID NO: 12078) |
| 76 | GKWCAGT + RY + T + RRTRGGR (SEQ ID NO: 12079) |
| 76 | GKWCAGT + RY + TRR + TRGGR (SEQ ID NO: 12080) |
| 76 | GKWCAGT + RY + TRRT + RGGR (SEQ ID NO: 12081) |
| 76 | GKWCAGT + RY + TRRTR + GGR (SEQ ID NO: 12082) |
| 76 | GKWCA + GTRYTRRTRG (SEQ ID NO: 12083) |
| 76 | GK + WCAGTRYTRRTRG (SEQ ID NO: 12084) |
| 76 | GKWCAGT + RYTRRTRG (SEQ ID NO: 12085) |
| 76 | +GKWCAGTRYTRRTRG (SEQ ID NO: 12086) |
| 76 | GKWCAGTRYTRRTRGG (SEQ ID NO: 12087) |
| 76 | GKWCAGTRYTRRT + RG (SEQ ID NO: 12088) |
| 76 | GKWCAGTRYTR + RTRG (SEQ ID NO: 12089) |
| 76 | GKWCAGTRY + TRRTRG (SEQ ID NO: 12090) |
| 76 | GKW + CAGT + RY + TRRTRG (SEQ ID NO: 12091) |
| 76 | G + KWCAGT + RY + TRRTRG (SEQ ID NO: 12092) |
| 76 | GKWC + AGT + RY + TRRTRG (SEQ ID NO: 12093) |
| 76 | +GKWCAGT + RY + TRRTRG (SEQ ID NO: 12094) |
| 76 | GKWCAGT + RY + T + RRTRG (SEQ ID NO: 12095) |
| 76 | GKWCAGT + RY + TRR + TRG (SEQ ID NO: 12096) |
| 76 | GKWCAGT + RY + TRRT + RG (SEQ ID NO: 12097) |
| 76 | GKWCAGT + RY + TRRTR + G (SEQ ID NO: 12098) |
| 76 | ACAGTAYTRGTAGGA (SEQ ID NO: 12099) |
| 76 | GGKWCAGTRYTRRTRGGRCC (SEQ ID NO: 12100) |
| 76 | GGKWCAGTRYTRRTRGGRC (SEQ ID NO: 12101) |
| 76 | GKWCAGTRYTRRTRGGR (SEQ ID NO: 12102) |
| 76 | GKWCAGTRYTRRTRG (SEQ ID NO: 12103) |
| 82 | CYACA + CCTRTCAACATAATT (SEQ ID NO: 12104) |
| 82 | CYA + CACCTRTCAACATAATT (SEQ ID NO: 12105) |
| 82 | CYACAC + CTRTCAACATAATT (SEQ ID NO: 12106) |
| 82 | CYACACCT + RTCAACATAATT (SEQ ID NO: 12107) |
| 82 | CYACACCTRTCAACAT + AATT (SEQ ID NO: 12108) |
| 82 | CYACACCTRTCAACA + TAATT (SEQ ID NO: 12109) |
| 82 | CYACACCTRTCAACATAA + TT (SEQ ID NO: 12110) |
| 82 | CYACACCTRTCA + ACATAATT (SEQ ID NO: 12111) |
| 82 | CYAC + ACCT + RT + CAACATAATT (SEQ ID NO: 12112) |
| 82 | CYA + CACCT + RT + CAACATAATT (SEQ ID NO: 12113) |
| 82 | CYACACC + T + RT + CAACATAATT (SEQ ID NO: 12114) |
| 82 | C + YACACCT + RT + CAACATAATT (SEQ ID NO: 12115) |
| 82 | CYACACCT + RT + CAAC + ATAATT (SEQ ID NO: 12116) |

TABLE 10 -continued

| | | |
|---|---|---|
| 82 | CYACACCT + RT + CAACATAA + TT | (SEQ ID NO: 12117) |
| 82 | CYACACCT + RT + CAACA + TAATT | (SEQ ID NO: 12118) |
| 82 | CYACACCT + RT + CAA + CATAATT | (SEQ ID NO: 12119) |
| 82 | CCYA + CACCTGTCAACATAAT | (SEQ ID NO: 12120) |
| 82 | CCYACACC + TGTCAACATAAT | (SEQ ID NO: 12121) |
| 82 | CC + YACACCTGTCAACATAAT | (SEQ ID NO: 12122) |
| 82 | CCYACAC + CTGTCAACATAAT | (SEQ ID NO: 12123) |
| 82 | CCYACACCTGTCAA + CATAAT | (SEQ ID NO: 12124) |
| 82 | CCYACACCTGTCAAC + ATAAT | (SEQ ID NO: 12125) |
| 82 | CCYACACCTGTCAACA + TAAT | (SEQ ID NO: 12126) |
| 82 | CCYACACCTGTC + AACATAAT | (SEQ ID NO: 12127) |
| 82 | CCY + ACACC + TG + TCAACATAAT | (SEQ ID NO: 12128) |
| 82 | CC + YACACC + TG + TCAACATAAT | (SEQ ID NO: 12129) |
| 82 | C + CYACACC + TG + TCAACATAAT | (SEQ ID NO: 12130) |
| 82 | CCYACAC + C + TG + TCAACATAAT | (SEQ ID NO: 12131) |
| 82 | CCYACACC + TG + TC + AACATAAT | (SEQ ID NO: 12132) |
| 82 | CCYACACC + TG + TCAAC + ATAAT | (SEQ ID NO: 12133) |
| 82 | CCYACACC + TG + TCA + ACATAAT | (SEQ ID NO: 12134) |
| 82 | CCYACACC + TG + TCAACAT + AAT | (SEQ ID NO: 12135) |
| 82 | CYACA + CCTRTCAACATAAT | (SEQ ID NO: 12136) |
| 82 | CYA + CACCTRTCAACATAAT | (SEQ ID NO: 12137) |
| 82 | CYACAC + CTRTCAACATAAT | (SEQ ID NO: 12138) |
| 82 | CYACACCT + RTCAACATAAT | (SEQ ID NO: 12139) |
| 82 | CYACACCTRTCAACAT + AAT | (SEQ ID NO: 12140) |
| 82 | CYACACCTRTCAACA + TAAT | (SEQ ID NO: 12141) |
| 82 | CYACACCTRTCAACATAA + T | (SEQ ID NO: 12142) |
| 82 | CYACACCTRTCA + ACATAAT | (SEQ ID NO: 12143) |
| 82 | CYAC + ACCT + RT + CAACATAAT | (SEQ ID NO: 12144) |
| 82 | CYA + CACCT + RT + CAACATAAT | (SEQ ID NO: 12145) |
| 82 | CYACACC + T + RT + CAACATAAT | (SEQ ID NO: 12146) |
| 82 | C + YACACCT + RT + CAACATAAT | (SEQ ID NO: 12147) |
| 82 | CYACACCT + RT + CAAC + ATAAT | (SEQ ID NO: 12148) |
| 82 | CYACACCT + RT + CAACATAA + T | (SEQ ID NO: 12149) |
| 82 | CYACACCT + RT + CAACA + TAAT | (SEQ ID NO: 12150) |
| 82 | CYACACCT + RT + CAA + CATAAT | (SEQ ID NO: 12151) |
| 82 | CCYA + CACCTGTCAACATAA | (SEQ ID NO: 12152) |
| 82 | CCYACACC + TGTCAACATAA | (SEQ ID NO: 12153) |
| 82 | CC + YACACCTGTCAACATAA | (SEQ ID NO: 12154) |
| 82 | CCYACAC + CTGTCAACATAA | (SEQ ID NO: 12155) |
| 82 | CCYACACCTGTCAA + CATAA | (SEQ ID NO: 12156) |

| | | |
|---|---|---|
| 82 | CCYACACCTGTCAAC + ATAA | (SEQ ID NO: 12157) |
| 82 | CCYACACCTGTCAACA + TAA | (SEQ ID NO: 12158) |
| 82 | CCYACACCTGTC + AACATAA | (SEQ ID NO: 12159) |
| 82 | CCY + ACACC + TG + TCAACATAA | (SEQ ID NO: 12160) |
| 82 | CC + YACACC + TG + TCAACATAA | (SEQ ID NO: 12161) |
| 82 | C + CYACACC + TG + TCAACATAA | (SEQ ID NO: 12162) |
| 82 | CCYACAC + C + TG + TCAACATAA | (SEQ ID NO: 12163) |
| 82 | CCYACACC + TG + TC + AACATAA | (SEQ ID NO: 12164) |
| 82 | CCYACACC + TG + TCAAC + ATAA | (SEQ ID NO: 12165) |
| 82 | CCYACACC + TG + TCA + ACATAA | (SEQ ID NO: 12166) |
| 82 | CCYACACC + TG + TCAACAT + AA | (SEQ ID NO: 12167) |
| 82 | YACA + CCTRTCAACATAA | (SEQ ID NO: 12168) |
| 82 | YA + CACCTRTCAACATAA | (SEQ ID NO: 12169) |
| 82 | YACAC + CTRTCAACATAA | (SEQ ID NO: 12170) |
| 82 | YACACCT + RTCAACATAA | (SEQ ID NO: 12171) |
| 82 | YACACCTRTCAACAT + AA | (SEQ ID NO: 12172) |
| 82 | YACACCTRTCAACA + TAA | (SEQ ID NO: 12173) |
| 82 | YACACCTRTCAACATAA | (SEQ ID NO: 12174) |
| 82 | YACACCTRTCA + ACATAA | (SEQ ID NO: 12175) |
| 82 | YAC + ACCT + RT + CAACATAA | (SEQ ID NO: 12176) |
| 82 | YA + CACCT + RT + CAACATAA | (SEQ ID NO: 12177) |
| 82 | YACACC + T + RT + CAACATAA | (SEQ ID NO: 12178) |
| 82 | +YACACCT + RT + CAACATAA | (SEQ ID NO: 12179) |
| 82 | YACACCT + RT + CAAC + ATAA | (SEQ ID NO: 12180) |
| 82 | YACACCT + RT + CAACATAA | (SEQ ID NO: 12181) |
| 82 | YACACCT + RT + CAACA + TAA | (SEQ ID NO: 12182) |
| 82 | YACACCT + RT + CAA + CATAA | (SEQ ID NO: 12183) |
| 82 | CYA + CACCTGTCAACATA | (SEQ ID NO: 12184) |
| 82 | CYACACC + TGTCAACATA | (SEQ ID NO: 12185) |
| 82 | C + YACACCTGTCAACATA | (SEQ ID NO: 12186) |
| 82 | CYACAC + CTGTCAACATA | (SEQ ID NO: 12187) |
| 82 | CYACACCTGTCAA + CATA | (SEQ ID NO: 12188) |
| 82 | CYACACCTGTCAAC + ATA | (SEQ ID NO: 12189) |
| 82 | CYACACCTGTCAACA + TA | (SEQ ID NO: 12190) |
| 82 | CYACACCTGTC + AACATA | (SEQ ID NO: 12191) |
| 82 | CY + ACACC + TG + TCAACATA | (SEQ ID NO: 12192) |
| 82 | C + YACACC + TG + TCAACATA | (SEQ ID NO: 12193) |
| 82 | +CYACACC + TG + TCAACATA | (SEQ ID NO: 12194) |
| 82 | CYACAC + C + TG + TCAACATA | (SEQ ID NO: 12195) |
| 82 | CYACACC + TG + TC + AACATA | (SEQ ID NO: 12196) |

TABLE 10 -continued

| | |
|---|---|
| 82 | CYACACC + TG + TCAAC + ATA (SEQ ID NO: 12197) |
| 82 | CYACACC + TG + TCA + ACATA (SEQ ID NO: 12198) |
| 82 | CYACACC + TG + TCAACAT + A (SEQ ID NO: 12199) |
| 82 | YACA + CCTRTCAACAT (SEQ ID NO: 12200) |
| 82 | YA + CACCTRTCAACAT (SEQ ID NO: 12201) |
| 82 | YACAC + CTRTCAACAT (SEQ ID NO: 12202) |
| 82 | YACACCT + RTCAACAT (SEQ ID NO: 12203) |
| 82 | YACACCTRTCAACAT (SEQ ID NO: 12204) |
| 82 | YACACCTRTCAACA + T (SEQ ID NO: 12205) |
| 82 | YACACCTRTCAACATA (SEQ ID NO: 12206) |
| 82 | YACACCTRTCA + ACAT (SEQ ID NO: 12207) |
| 82 | YAC + ACCT + RT + CAACAT (SEQ ID NO: 12208) |
| 82 | YA + CACCT + RT + CAACAT (SEQ ID NO: 12209) |
| 82 | YACACC + T + RT + CAACAT (SEQ ID NO: 12210) |
| 82 | +YACACCT + RT + CAACAT (SEQ ID NO: 12211) |
| 82 | YACACCT + RT + CAAC + AT (SEQ ID NO: 12212) |
| 82 | YACACCT + RT + CAACATA (SEQ ID NO: 12213) |
| 82 | YACACCT + RT + CAACA + T (SEQ ID NO: 12214) |
| 82 | YACACCT + RT + CAA + CAT (SEQ ID NO: 12215) |
| 82 | CYA + CACCTGTCAACA (SEQ ID NO: 12216) |
| 82 | CYACACC + TGTCAACA (SEQ ID NO: 12217) |
| 82 | C + YACACCTGTCAACA (SEQ ID NO: 12218) |
| 82 | CYACAC + CTGTCAACA (SEQ ID NO: 12219) |
| 82 | CYACACCTGTCAA + CA (SEQ ID NO: 12220) |
| 82 | CYACACCTGTCAAC + A (SEQ ID NO: 12221) |
| 82 | CYACACCTGTCAACA (SEQ ID NO: 12222) |
| 82 | CYACACCTGTC + AACA (SEQ ID NO: 12223) |
| 82 | CY + ACACC + TG + TCAACA (SEQ ID NO: 12224) |
| 82 | C + YACACC + TG + TCAACA (SEQ ID NO: 12225) |
| 82 | +CYACACC + TG + TCAACA (SEQ ID NO: 12226) |
| 82 | CYACAC + C + TG + TCAACA (SEQ ID NO: 12227) |
| 82 | CYACACC + TG + TC + AACA (SEQ ID NO: 12228) |
| 82 | CYACACC + TG + TCAAC + A (SEQ ID NO: 12229) |
| 82 | CYACACC + TG + TCA + ACA (SEQ ID NO: 12230) |
| 82 | CYACACC + TG + TCAACAT (SEQ ID NO: 12231) |
| 82 | ACACCTGTYAACATA (SEQ ID NO: 12232) |
| 82 | CYACACCTRTCAACATAATT (SEQ ID NO: 12233) |
| 82 | CCYACACCTGTCAACATAAT (SEQ ID NO: 12234) |
| 82 | CYACACCTRTCAACATAAT (SEQ ID NO: 12235) |
| 82 | CCYACACCTGTCAACATAA (SEQ ID NO: 12236) |

TABLE 10 -continued

| | |
|---|---|
| 82 | YACACCTRTCAACATAA (SEQ ID NO: 12237) |
| 82 | CYACACCTGTCAACATA (SEQ ID NO: 12238) |
| 82 | YACACCTRTCAACAT (SEQ ID NO: 12239) |
| 82 | CYACACCTGTCAACA (SEQ ID NO: 12240) |
| 82 | CYACACCTGTCAACAT (SEQ ID NO: 12241) |
| 83 | ACAC + CTRTCAACATAATTGG (SEQ ID NO: 12242) |
| 83 | AC + ACCTRTCAACATAATTGG (SEQ ID NO: 12243) |
| 83 | ACACC + TRTCAACATAATTGG (SEQ ID NO: 12244) |
| 83 | ACACCTRT + CAACATAATTGG (SEQ ID NO: 12245) |
| 83 | ACACCTRTCAACATA + ATTGG (SEQ ID NO: 12246) |
| 83 | ACACCTRTCAACATAA + TTGG (SEQ ID NO: 12247) |
| 83 | ACACCTRTCAA + CATAATTGG (SEQ ID NO: 12248) |
| 83 | ACACCTRTCAACAT + AATTGG (SEQ ID NO: 12249) |
| 83 | AC + ACCTRT + CA + ACATAATTGG (SEQ ID NO: 12250) |
| 83 | ACACCT + RT + CA + ACATAATTGG (SEQ ID NO: 12251) |
| 83 | A + CACCTRT + CA + ACATAATTGG (SEQ ID NO: 12252) |
| 83 | ACACC + TRT + CA + ACATAATTGG (SEQ ID NO: 12253) |
| 83 | ACACCTRT + CA + ACATAAT + TGG (SEQ ID NO: 12254) |
| 83 | ACACCTRT + CA + ACA + TAATTGG (SEQ ID NO: 12255) |
| 83 | ACACCTRT + CA + ACATAATT + GG (SEQ ID NO: 12256) |
| 83 | ACACCTRT + CA + A + CATAATTGG (SEQ ID NO: 12257) |
| 83 | ACAC + CTRTCAACATAATTG (SEQ ID NO: 12258) |
| 83 | AC + ACCTRTCAACATAATTG (SEQ ID NO: 12259) |
| 83 | ACACC + TRTCAACATAATTG (SEQ ID NO: 12260) |
| 83 | ACACCTRT + CAACATAATTG (SEQ ID NO: 12261) |
| 83 | ACACCTRTCAACATA + ATTG (SEQ ID NO: 12262) |
| 83 | ACACCTRTCAACATAA + TTG (SEQ ID NO: 12263) |
| 83 | ACACCTRTCAA + CATAATTG (SEQ ID NO: 12264) |
| 83 | ACACCTRTCAACAT + AATTG (SEQ ID NO: 12265) |
| 83 | AC + ACCTRT + CA + ACATAATTG (SEQ ID NO: 12266) |
| 83 | ACACCT + RT + CA + ACATAATTG (SEQ ID NO: 12267) |
| 83 | A + CACCTRT + CA + ACATAATTG (SEQ ID NO: 12268) |
| 83 | ACACC + TRT + CA + ACATAATTG (SEQ ID NO: 12269) |
| 83 | ACACCTRT + CA + ACATAAT + TG (SEQ ID NO: 12270) |
| 83 | ACACCTRT + CA + ACA + TAATTG (SEQ ID NO: 12271) |
| 83 | ACACCTRT + CA + ACATAATT + G (SEQ ID NO: 12272) |
| 83 | ACACCTRT + CA + A + CATAATTG (SEQ ID NO: 12273) |
| 83 | CAC + CTRTCAACATAATT (SEQ ID NO: 12274) |
| 83 | C + ACCTRTCAACATAATT (SEQ ID NO: 12275) |
| 83 | CACC + TRTCAACATAATT (SEQ ID NO: 12276) |

| | TABLE 10 -continued | |
|---|---|---|
| 83 | CACCTRT + CAACATAATT (SEQ ID NO: 12277) | |
| 83 | CACCTRTCAACATA + ATT (SEQ ID NO: 12278) | |
| 83 | CACCTRTCAACATAA + TT (SEQ ID NO: 12279) | |
| 83 | CACCTRTCAA + CATAATT (SEQ ID NO: 12280) | |
| 83 | CACCTRTCAACAT + AATT (SEQ ID NO: 12281) | |
| 83 | C + ACCTRT + CA + ACATAATT (SEQ ID NO: 12282) | |
| 83 | CACCT + RT + CA + ACATAATT (SEQ ID NO: 12283) | |
| 83 | +CACCTRT + CA + ACATAATT (SEQ ID NO: 12284) | |
| 83 | CACC + TRT + CA + ACATAATT (SEQ ID NO: 12285) | |
| 83 | CACCTRT + CA + ACATAAT + T (SEQ ID NO: 12286) | |
| 83 | CACCTRT + CA + ACA + TAATT (SEQ ID NO: 12287) | |
| 83 | CACCTRT + CA + ACATAATT (SEQ ID NO: 12288) | |
| 83 | CACCTRT + CA + A + CATAATT (SEQ ID NO: 12289) | |
| 83 | CAC + CTRTCAACATAA (SEQ ID NO: 12290) | |
| 83 | C + ACCTRTCAACATAA (SEQ ID NO: 12291) | |
| 83 | CACC + TRTCAACATAA (SEQ ID NO: 12292) | |
| 83 | CACCTRT + CAACATAA (SEQ ID NO: 12293) | |
| 83 | CACCTRTCAACATA + A (SEQ ID NO: 12294) | |
| 83 | CACCTRTCAACATAA (SEQ ID NO: 12295) | |
| 83 | CACCTRTCAA + CATAA (SEQ ID NO: 12296) | |
| 83 | CACCTRTCAACAT + AA (SEQ ID NO: 12297) | |
| 83 | C + ACCTRT + CA + ACATAA (SEQ ID NO: 12298) | |
| 83 | CACCT + RT + CA + ACATAA (SEQ ID NO: 12299) | |
| 83 | +CACCTRT + CA + ACATAA (SEQ ID NO: 12300) | |
| 83 | CACC + TRT + CA + ACATAA (SEQ ID NO: 12301) | |
| 83 | CACCTRT + CA + ACATAAT (SEQ ID NO: 12302) | |
| 83 | CACCTRT + CA + ACA + TAA (SEQ ID NO: 12303) | |
| 83 | CACCTRT + CA + A + CATAA (SEQ ID NO: 12304) | |
| 83 | ACCTGTCAAYATAAT (SEQ ID NO: 12305) | |
| 83 | ACACCTRTCAACATAATTGG (SEQ ID NO: 12306) | |
| 83 | ACACCTRTCAACATAATTG (SEQ ID NO: 12307) | |
| 83 | CACCTRTCAACATAATT (SEQ ID NO: 12308) | |
| 83 | CACCTRTCAACATAA (SEQ ID NO: 12309) | |
| 83 | CACCTRTCAACATAAT (SEQ ID NO: 12310) | |
| 84 | C + CTRTCAACATAATTGGRMG (SEQ ID NO: 12311) | |
| 84 | CC + TRTCAACATAATTGGRMG (SEQ ID NO: 12312) | |
| 84 | CCTRTCAA + CATAATTGGRMG (SEQ ID NO: 12313) | |
| 84 | CCTR + TCAACATAATTGGRMG (SEQ ID NO: 12314) | |
| 84 | CCTRTCAACATAAT + TGGRMG (SEQ ID NO: 12315) | |
| 84 | CCTRTCAACATAATTGGR + MG (SEQ ID NO: 12316) | |

TABLE 10 -continued

| 84 | CCTRTCAACAT + AATTGGRMG (SEQ ID NO: 12317) |
| 84 | CCTRTCAACATA + ATTGGRMG (SEQ ID NO: 12318) |
| 84 | CCTRTC + AA + CA + TAATTGGRMG (SEQ ID NO: 12319) |
| 84 | CCTRT + CAA + CA + TAATTGGRMG (SEQ ID NO: 12320) |
| 84 | CC + TRTCAA + CA + TAATTGGRMG (SEQ ID NO: 12321) |
| 84 | CCTR + TCAA + CA + TAATTGGRMG (SEQ ID NO: 12322) |
| 84 | CCTRTCAA + CA + TAATTG + GRMG (SEQ ID NO: 12323) |
| 84 | CCTRTCAA + CA + T + AATTGGRMG (SEQ ID NO: 12324) |
| 84 | CCTRTCAA + CA + TAAT + TGGRMG (SEQ ID NO: 12325) |
| 84 | CCTRTCAA + CA + TAATTGGR + MG (SEQ ID NO: 12326) |
| 84 | C + CTRTCAACATAATTGGRM (SEQ ID NO: 12327) |
| 84 | CC + TRTCAACATAATTGGRM (SEQ ID NO: 12328) |
| 84 | CCTRTCAA + CATAATTGGRM (SEQ ID NO: 12329) |
| 84 | CCTR + TCAACATAATTGGRM (SEQ ID NO: 12330) |
| 84 | CCTRTCAACATAAT + TGGRM (SEQ ID NO: 12331) |
| 84 | CCTRTCAACATAATTGGR + M (SEQ ID NO: 12332) |
| 84 | CCTRTCAACAT + AATTGGRM (SEQ ID NO: 12333) |
| 84 | CCTRTCAACATA + ATTGGRM (SEQ ID NO: 12334) |
| 84 | CCTRTC + AA + CA + TAATTGGRM (SEQ ID NO: 12335) |
| 84 | CCTRT + CAA + CA + TAATTGGRM (SEQ ID NO: 12336) |
| 84 | CC + TRTCAA + CA + TAATTGGRM (SEQ ID NO: 12337) |
| 84 | CCTR + TCAA + CA + TAATTGGRM (SEQ ID NO: 12338) |
| 84 | CCTRTCAA + CA + TAATTG + GRM (SEQ ID NO: 12339) |
| 84 | CCTRTCAA + CA + T + AATTGGRM (SEQ ID NO: 12340) |
| 84 | CCTRTCAA + CA + TAAT + TGGRM (SEQ ID NO: 12341) |
| 84 | CCTRTCAA + CA + TAATTGGR + M (SEQ ID NO: 12342) |
| 84 | +CTRTCAACATAATTGGR (SEQ ID NO: 12343) |
| 84 | C + TRTCAACATAATTGGR (SEQ ID NO: 12344) |
| 84 | CTRTCAA + CATAATTGGR (SEQ ID NO: 12345) |
| 84 | CTR + TCAACATAATTGGR (SEQ ID NO: 12346) |
| 84 | CTRTCAACATAAT + TGGR (SEQ ID NO: 12347) |
| 84 | CTRTCAACATAATTGGR (SEQ ID NO: 12348) |
| 84 | CTRTCAACAT + AATTGGR (SEQ ID NO: 12349) |
| 84 | CTRTCAACATA + ATTGGR (SEQ ID NO: 12350) |
| 84 | CTRTC + AA + CA + TAATTGGR (SEQ ID NO: 12351) |
| 84 | CTRT + CAA + CA + TAATTGGR (SEQ ID NO: 12352) |
| 84 | C + TRTCAA + CA + TAATTGGR (SEQ ID NO: 12353) |
| 84 | CTR + TCAA + CA + TAATTGGR (SEQ ID NO: 12354) |
| 84 | CTRTCAA + CA + TAATTG + GR (SEQ ID NO: 12355) |
| 84 | CTRTCAA + CA + T + AATTGGR (SEQ ID NO: 12356) |

TABLE 10 -continued

| | | |
|---|---|---|
| 84 | CTRTCAA + CA + TAAT + TGGR (SEQ ID NO:1 2357) | |
| 84 | CTRTCAA + CA + TAATTGGR (SEQ ID NO: 12358) | |
| 84 | +CTRTCAACATAATTG (SEQ ID NO: 12359) | |
| 84 | C + TRTCAACATAATTG (SEQ ID NO: 12360) | |
| 84 | CTRTCAA + CATAATTG (SEQ ID NO: 12361) | |
| 84 | CTR + TCAACATAATTG (SEQ ID NO: 12362) | |
| 84 | CTRTCAACATAAT + TG (SEQ ID NO: 12363) | |
| 84 | CTRTCAACATAATTGG (SEQ ID NO: 12364) | |
| 84 | CTRTCAACAT + AATTG (SEQ ID NO: 12365) | |
| 84 | CTRTCAACATA + ATTG (SEQ ID NO: 12366) | |
| 84 | CTRTC + AA + CA + TAATTG (SEQ ID NO: 12367) | |
| 84 | CTRT + CAA + CA + TAATTG (SEQ ID NO: 12368) | |
| 84 | C + TRTCAA + CA + TAATTG (SEQ ID NO: 12369) | |
| 84 | CTR + TCAA + CA + TAATTG (SEQ ID NO: 12370) | |
| 84 | CTRTCAA + CA + TAATTG (SEQ ID NO: 12371) | |
| 84 | CTRTCAA + CA + T + AATTG (SEQ ID NO: 12372) | |
| 84 | CTRTCAA + CA + TAAT + TG (SEQ ID NO: 12373) | |
| 84 | CTRTCAA + CA + TAATTGG (SEQ ID NO: 12374) | |
| 84 | TCCAATTATGTTGAC (SEQ ID NO: 12375) | |
| 84 | CCTRTCAACATAATTGGRMG (SEQ ID NO: 12376) | |
| 84 | CCTRTCAACATAATTGGRM (SEQ ID NO: 12377) | |
| 84 | CTRTCAACATAATTGGR (SEQ ID NO: 12378) | |
| 84 | CTRTCAACATAATTG (SEQ ID NO: 12379) | |
| 88 | T + TGGRMGRAAYHTGTTGACY (SEQ ID NO: 12380) | |
| 88 | TTGG + RMGRAAYHTGTTGACY (SEQ ID NO: 12381) | |
| 88 | TTG + GRMGRAAYHTGTTGACY (SEQ ID NO: 12382) | |
| 88 | TT + GGRMGRAAYHTGTTGACY (SEQ ID NO: 12383) | |
| 88 | TTGGRMGRAAYHTGTTGA + CY (SEQ ID NO: 12384) | |
| 88 | TTGGRMGRAAYHTGTT + GACY (SEQ ID NO: 12385) | |
| 88 | TTGGRMGRAAYHTG + TTGACY (SEQ ID NO: 12386) | |
| 88 | TTGGRMGRAAYH + TGTTGACY (SEQ ID NO: 12387) | |
| 88 | TTGGRM + GR + AA + YHTGTTGACY (SEQ ID NO: 12388) | |
| 88 | TT + GGRMGR + AA + YHTGTTGACY (SEQ ID NO: 12389) | |
| 88 | TTGGRMG + R + AA + YHTGTTGACY (SEQ ID NO: 12390) | |
| 88 | TTGGR + MGR + AA + YHTGTTGACY (SEQ ID NO: 12391) | |
| 88 | TTGGRMGR + AA + YHTGTTGA + CY (SEQ ID NO: 12392) | |
| 88 | TTGGRMGR + AA + Y + HTGTTGACY (SEQ ID NO: 12393) | |
| 88 | TTGGRMGR + AA + YHTG + TTGACY (SEQ ID NO: 12394) | |
| 88 | TTGGRMGR + AA + YH + TGTTGACY (SEQ ID NO: 12395) | |
| 88 | T + TGGRMGRAAYHTGTTGAC (SEQ ID NO: 12396) | |

TABLE 10 -continued

| 88 | TTGG + RMGRAAYHTGTTGAC (SEQ ID NO: 12397) |
| 88 | TTG + GRMGRAAYHTGTTGAC (SEQ ID NO: 12398) |
| 88 | TT + GGRMGRAAYHTGTTGAC (SEQ ID NO: 12399) |
| 88 | TTGGRMGRAAYHTGTTGA + C (SEQ ID NO: 12400) |
| 88 | TTGGRMGRAAYHTGTT + GAC (SEQ ID NO: 12401) |
| 88 | TTGGRMGRAAYHTG + TTGAC (SEQ ID NO: 12402) |
| 88 | TTGGRMGRAAYH + TGTTGAC (SEQ ID NO: 12403) |
| 88 | TTGGRM + GR + AA + YHTGTTGAC (SEQ ID NO: 12404) |
| 88 | TT + GGRMGR + AA + YHTGTTGAC (SEQ ID NO: 12405) |
| 88 | TTGGRMG + R + AA + YHTGTTGAC (SEQ ID NO: 12406) |
| 88 | TTGGR + MGR + AA + YHTGTTGAC (SEQ ID NO: 12407) |
| 88 | TTGGRMGR + AA + YHTGTTGA + C (SEQ ID NO: 12408) |
| 88 | TTGGRMGR + AA + Y + HTGTTGAC (SEQ ID NO: 12409) |
| 88 | TTGGRMGR + AA + YHTG + TTGAC (SEQ ID NO: 12410) |
| 88 | TTGGRMGR + AA + YH + TGTTGAC (SEQ ID NO: 12411) |
| 88 | +TGGRMGRAAYHTGTTGA (SEQ ID NO: 12412) |
| 88 | TGG + RMGRAAYHTGTTGA (SEQ ID NO: 12413) |
| 88 | TG + GRMGRAAYHTGTTGA (SEQ ID NO: 12414) |
| 88 | T + GGRMGRAAYHTGTTGA (SEQ ID NO: 12415) |
| 88 | TGGRMGRAAYHTGTTGA (SEQ ID NO: 12416) |
| 88 | TGGRMGRAAYHTGTT + GA (SEQ ID NO: 12417) |
| 88 | TGGRMGRAAYHTG + TTGA (SEQ ID NO: 12418) |
| 88 | TGGRMGRAAYH + TGTTGA (SEQ ID NO: 12419) |
| 88 | TGGRM + GR + AA + YHTGTTGA (SEQ ID NO: 12420) |
| 88 | T + GGRMGR + AA + YHTGTTGA (SEQ ID NO: 12421) |
| 88 | TGGRMG + R + AA + YHTGTTGA (SEQ ID NO: 12422) |
| 88 | TGGR + MGR + AA + YHTGTTGA (SEQ ID NO: 12423) |
| 88 | TGGRMGR + AA + YHTGTTGA (SEQ ID NO: 12424) |
| 88 | TGGRMGR + AA + Y + HTGTTGA (SEQ ID NO: 12425) |
| 88 | TGGRMGR + AA + YHTG + TTGA (SEQ ID NO: 12426) |
| 88 | TGGRMGR + AA + YH + TGTTGA (SEQ ID NO: 12427) |
| 88 | +TGGRMGRAAYHTGTT (SEQ ID NO: 12428) |
| 88 | TGG + RMGRAAYHTGTT (SEQ ID NO: 12429) |
| 88 | TG + GRMGRAAYHTGTT (SEQ ID NO: 12430) |
| 88 | T + GGRMGRAAYHTGTT (SEQ ID NO: 12431) |
| 88 | TGGRMGRAAYHTGTTG (SEQ ID NO: 12432) |
| 88 | TGGRMGRAAYHTGTT (SEQ ID NO: 12433) |
| 88 | TGGRMGRAAYHTG + TT (SEQ ID NO: 12434) |
| 88 | TGGRMGRAAYH + TGTT (SEQ ID NO: 12435) |
| 88 | TGGRM + GR + AA + YHTGTT (SEQ ID NO: 12436) |

TABLE 10 -continued

| | | |
|---|---|---|
| 88 | T + GGRMGR + AA + YHTGTT | (SEQ ID NO: 12437) |
| 88 | TGGRMG + R + AA + YHTGTT | (SEQ ID NO: 12438) |
| 88 | TGGR + MGR + AA + YHTGTT | (SEQ ID NO: 12439) |
| 88 | TGGRMGR + AA + YHTGTTG | (SEQ ID NO: 12440) |
| 88 | TGGRMGR + AA + Y + HTGTT | (SEQ ID NO: 12441) |
| 88 | TGGRMGR + AA + YHTG + TT | (SEQ ID NO: 12442) |
| 88 | TGGRMGR + AA + YH + TGTT | (SEQ ID NO: 12443) |
| 88 | TGGAAGAAAYCTGTT | (SEQ ID NO: 12444) |
| 88 | TTGGRMGRAAYHTGTTGACY | (SEQ ID NO: 12445) |
| 88 | TTGGRMGRAAYHTGTTGAC | (SEQ ID NO: 12446) |
| 88 | TGGRMGRAAYHTGTTGA | (SEQ ID NO: 12447) |
| 88 | TGGRMGRAAYHTGTT | (SEQ ID NO: 12448) |
| 89 | G + GRMGRAAYYTGTTGACYCA | (SEQ ID NO: 12449) |
| 89 | GG + RMGRAAYYTGTTGACYCA | (SEQ ID NO: 12450) |
| 89 | GGRMGRAA + YYTGTTGACYCA | (SEQ ID NO: 12451) |
| 89 | GGR + MGRAAYYTGTTGACYCA | (SEQ ID NO: 12452) |
| 89 | GGRMGRAAYYTGTTGACY + CA | (SEQ ID NO: 12453) |
| 89 | GGRMGRAAYYTGTT + GACYCA | (SEQ ID NO: 12454) |
| 89 | GGRMGRAAYYTGT + TGACYCA | (SEQ ID NO: 12455) |
| 89 | GGRMGRAAYYTGTTG + ACYCA | (SEQ ID NO: 12456) |
| 89 | GG + RMGRAA + YY + TGTTGACYCA | (SEQ ID NO: 12457) |
| 89 | GGR + MGRAA + YY + TGTTGACYCA | (SEQ ID NO: 12458) |
| 89 | GGRMGRA + A + YY + TGTTGACYCA | (SEQ ID NO: 12459) |
| 89 | GGRMG + RAA + YY + TGTTGACYCA | (SEQ ID NO: 12460) |
| 89 | GGRMGRAA + YY + TGTTG + ACYCA | (SEQ ID NO: 12461) |
| 89 | GGRMGRAA + YY + T + GTTGACYCA | (SEQ ID NO: 12462) |
| 89 | GGRMGRAA + YY + TGTT + GACYCA | (SEQ ID NO: 12463) |
| 89 | GGRMGRAA + YY + TGTTGACY + CA | (SEQ ID NO: 12464) |
| 89 | G + GRMGRAAYYTGTTGACYC | (SEQ ID NO: 12465) |
| 89 | GG + RMGRAAYYTGTTGACYC | (SEQ ID NO: 12466) |
| 89 | GGRMGRAA + YYTGTTGACYC | (SEQ ID NO: 12467) |
| 89 | GGR + MGRAAYYTGTTGACYC | (SEQ ID NO: 12468) |
| 89 | GGRMGRAAYYTGTTGACY + C | (SEQ ID NO: 12469) |
| 89 | GGRMGRAAYYTGTT + GACYC | (SEQ ID NO: 12470) |
| 89 | GGRMGRAAYYTGT + TGACYC | (SEQ ID NO: 12471) |
| 89 | GGRMGRAAYYTGTTG + ACYC | (SEQ ID NO: 12472) |
| 89 | GG + RMGRAA + YY + TGTTGACYC | (SEQ ID NO: 12473) |
| 89 | GGR + MGRAA + YY + TGTTGACYC | (SEQ ID NO: 12474) |
| 89 | GGRMGRA + A + YY + TGTTGACYC | (SEQ ID NO: 12475) |
| 89 | GGRMG + RAA + YY + TGTTGACYC | (SEQ ID NO: 12476) |

TABLE 10 -continued

| 89 | GGRMGRAA + YY + TGTTG + ACYC (SEQ ID NO: 12477) |
| 89 | GGRMGRAA + YY + T + GTTGACYC (SEQ ID NO: 12478) |
| 89 | GGRMGRAA + YY + TGTT + GACYC (SEQ ID NO: 12479) |
| 89 | GGRMGRAA + YY + TGTTGACY + C (SEQ ID NO: 12480) |
| 89 | +GRMGRAAYYTGTTGACY (SEQ ID NO: 12481) |
| 89 | G + RMGRAAYYTGTTGACY (SEQ ID NO: 12482) |
| 89 | GRMGRAA + YYTGTTGACY (SEQ ID NO: 12483) |
| 89 | GR + MGRAAYYTGTTGACY (SEQ ID NO: 12484) |
| 89 | GRMGRAAYYTGTTGACY (SEQ ID NO: 12485) |
| 89 | GRMGRAAYYTGTT + GACY (SEQ ID NO: 12486) |
| 89 | GRMGRAAYYTGT + TGACY (SEQ ID NO: 12487) |
| 89 | GRMGRAAYYTGTTG + ACY (SEQ ID NO: 12488) |
| 89 | G + RMGRAA + YY + TGTTGACY (SEQ ID NO: 12489) |
| 89 | GR + MGRAA + YY + TGTTGACY (SEQ ID NO: 12490) |
| 89 | GRMGRA + A + YY + TGTTGACY (SEQ ID NO: 12491) |
| 89 | GRMG + RAA + YY + TGTTGACY (SEQ ID NO: 12492) |
| 89 | GRMGRAA + YY + TGTTG + ACY (SEQ ID NO: 12493) |
| 89 | GRMGRAA + YY + T + GTTGACY (SEQ ID NO: 12494) |
| 89 | GRMGRAA + YY + TGTT + GACY (SEQ ID NO: 12495) |
| 89 | GRMGRAA + YY + TGTTGACY (SEQ ID NO: 12496) |
| 89 | +GRMGRAAYYTGTTGA (SEQ ID NO: 12497) |
| 89 | G + RMGRAAYYTGTTGA (SEQ ID NO: 12498) |
| 89 | GRMGRAA + YYTGTTGA (SEQ ID NO: 12499) |
| 89 | GR + MGRAAYYTGTTGA (SEQ ID NO: 12500) |
| 89 | GRMGRAAYYTGTTGAC (SEQ ID NO: 12501) |
| 89 | GRMGRAAYYTGTT + GA (SEQ ID NO: 12502) |
| 89 | GRMGRAAYYTGT + TGA (SEQ ID NO: 12503) |
| 89 | GRMGRAAYYTGTTG + A (SEQ ID NO: 12504) |
| 89 | G + RMGRAA + YY + TGTTGA (SEQ ID NO: 12505) |
| 89 | GR + MGRAA + YY + TGTTGA (SEQ ID NO: 12506) |
| 89 | GRMGRA + A + YY + TGTTGA (SEQ ID NO: 12507) |
| 89 | GRMG + RAA + YY + TGTTGA (SEQ ID NO: 12508) |
| 89 | GRMGRAA + YY + TGTTG + A (SEQ ID NO: 12509) |
| 89 | GRMGRAA + YY + T + GTTGA (SEQ ID NO: 12510) |
| 89 | GRMGRAA + YY + TGTT + GA (SEQ ID NO: 12511) |
| 89 | GRMGRAA + YY + TGTTGAC (SEQ ID NO: 12512) |
| 89 | AAGAAATYTRTTGAC (SEQ ID NO: 12513) |
| 89 | GGRMGRAAYYTGTTGACYCA (SEQ ID NO: 12514) |
| 89 | GGRMGRAAYYTGTTGACYC (SEQ ID NO: 12515) |
| 89 | GRMGRAAYYTGTTGACY (SEQ ID NO: 12516) |

TABLE 10 -continued

| | |
|---|---|
| 89 | GRMGRAAYYTGTTGA (SEQ ID NO: 12517) |
| 90 | MGRAA + YHTGYTGACYCARMT (SEQ ID NO: 12518) |
| 90 | MGRAAYH + TGYTGACYCARMT (SEQ ID NO: 12519) |
| 90 | MGRA + AYHTGYTGACYCARMT (SEQ ID NO: 12520) |
| 90 | MGR + AAYHTGYTGACYCARMT (SEQ ID NO: 12521) |
| 90 | MGRAAYHTGYTGACYC + ARMT (SEQ ID NO: 12522) |
| 90 | MGRAAYHTGY + TGACYCARMT (SEQ ID NO: 12523) |
| 90 | MGRAAYHTGYTGACY + CARMT (SEQ ID NO: 12524) |
| 90 | MGRAAYHTGYTGAC + YCARMT (SEQ ID NO: 12525) |
| 90 | MGRA + AYHT + GY + TGACYCARMT (SEQ ID NO: 12526) |
| 90 | M + GRAAYHT + GY + TGACYCARMT (SEQ ID NO: 12527) |
| 90 | MG + RAAYHT + GY + TGACYCARMT (SEQ ID NO: 12528) |
| 90 | MGRAA + YHT + GY + TGACYCARMT (SEQ ID NO: 12529) |
| 90 | MGRAAYHT + GY + TGACYCA + RMT (SEQ ID NO: 12530) |
| 90 | MGRAAYHT + GY + T + GACYCARMT (SEQ ID NO: 12531) |
| 90 | MGRAAYHT + GY + TGAC + YCARMT (SEQ ID NO: 12532) |
| 90 | MGRAAYHT + GY + TGACYC + ARMT (SEQ ID NO: 12533) |
| 90 | MGRAA + YHTGYTGACYCARM (SEQ ID NO: 12534) |
| 90 | MGRAAYH + TGYTGACYCARM (SEQ ID NO: 12535) |
| 90 | MGRA + AYHTGYTGACYCARM (SEQ ID NO: 12536) |
| 90 | MGR + AAYHTGYTGACYCARM (SEQ ID NO: 12537) |
| 90 | MGRAAYHTGYTGACYC + ARM (SEQ ID NO: 12538) |
| 90 | MGRAAYHTGY + TGACYCARM (SEQ ID NO: 12539) |
| 90 | MGRAAYHTGYTGACY + CARM (SEQ ID NO: 12540) |
| 90 | MGRAAYHTGYTGAC + YCARM (SEQ ID NO: 12541) |
| 90 | MGRA + AYHT + GY + TGACYCARM (SEQ ID NO: 12542) |
| 90 | M + GRAAYHT + GY + TGACYCARM (SEQ ID NO: 12543) |
| 90 | MG + RAAYHT + GY + TGACYCARM (SEQ ID NO: 12544) |
| 90 | MGRAA + YHT + GY + TGACYCARM (SEQ ID NO: 12545) |
| 90 | MGRAAYHT + GY + TGACYCA + RM (SEQ ID NO: 12546) |
| 90 | MGRAAYHT + GY + T + GACYCARM (SEQ ID NO: 12547) |
| 90 | MGRAAYHT + GY + TGAC + YCARM (SEQ ID NO: 12548) |
| 90 | MGRAAYHT + GY + TGACYC + ARM (SEQ ID NO: 12549) |
| 90 | GRAA + YHTGYTGACYCAR (SEQ ID NO: 12550) |
| 90 | GRAAYH + TGYTGACYCAR (SEQ ID NO: 12551) |
| 90 | GRA + AYHTGYTGACYCAR (SEQ ID NO: 12552) |
| 90 | GR + AAYHTGYTGACYCAR (SEQ ID NO: 12553) |
| 90 | GRAAYHTGYTGACYC + AR (SEQ ID NO: 12554) |
| 90 | GRAAYHTGY + TGACYCAR (SEQ ID NO: 12555) |
| 90 | GRAAYHTGYTGACY + CAR (SEQ ID NO: 12556) |

TABLE 10 -continued

| | |
|---|---|
| 90 | GRAAYHTGYTGAC + YCAR (SEQ ID NO: 12557) |
| 90 | GRA + AYHT + GY + TGACYCAR (SEQ ID NO: 12558) |
| 90 | +GRAAYHT + GY + TGACYCAR (SEQ ID NO: 12559) |
| 90 | G + RAAYHT + GY + TGACYCAR (SEQ ID NO: 12560) |
| 90 | GRAA + YHT + GY + TGACYCAR (SEQ ID NO: 12561) |
| 90 | GRAAYHT + GY + TGACYCA + R (SEQ ID NO: 12562) |
| 90 | GRAAYHT + GY + T + GACYCAR (SEQ ID NO: 12563) |
| 90 | GRAAYHT + GY + TGAC + YCAR (SEQ ID NO: 12564) |
| 90 | GRAAYHT + GY + TGACYC + AR (SEQ ID NO: 12565) |
| 90 | GRAA + YHTGYTGACYC (SEQ ID NO: 12566) |
| 90 | GRAAYH + TGYTGACYC (SEQ ID NO: 12567) |
| 90 | GRA + AYHTGYTGACYC (SEQ ID NO: 12568) |
| 90 | GR + AAYHTGYTGACYC (SEQ ID NO: 12569) |
| 90 | GRAAYHTGYTGACYC (SEQ ID NO: 12570) |
| 90 | GRAAYHTGY + TGACYC (SEQ ID NO: 12571) |
| 90 | GRAAYHTGYTGACY + C (SEQ ID NO: 12572) |
| 90 | GRAAYHTGYTGAC + YC (SEQ ID NO: 12573) |
| 90 | GRA + AYHT + GY + TGACYC (SEQ ID NO: 12574) |
| 90 | +GRAAYHT + GY + TGACYC (SEQ ID NO: 12575) |
| 90 | G + RAAYHT + GY + TGACYC (SEQ ID NO: 12576) |
| 90 | GRAA + YHT + GY + TGACYC (SEQ ID NO: 12577) |
| 90 | GRAAYHT + GY + TGACYCA (SEQ ID NO: 12578) |
| 90 | GRAAYHT + GY + T + GACYC (SEQ ID NO: 12579) |
| 90 | GRAAYHT + GY + TGAC + YC (SEQ ID NO: 12580) |
| 90 | GRAAYHT + GY + TGACYC (SEQ ID NO: 12581) |
| 90 | AAATCTGYTRACTCA (SEQ ID NO: 12582) |
| 90 | MGRAAYHTGYTGACYCARMT (SEQ ID NO: 12583) |
| 90 | MGRAAYHTGYTGACYCARM (SEQ ID NO: 12584) |
| 90 | GRAAYHTGYTGACYCAR (SEQ ID NO: 12585) |
| 90 | GRAAYHTGYTGACYC (SEQ ID NO: 12586) |
| 90 | GRAAYHTGYTGACYCA (SEQ ID NO: 12587) |
| Codon | Mutant Probe (5' to 3') |
| 10 | CGACCCTTYGTCACA (SEQ ID NO: 12588) |
| 10 | CGACCCCGHGTCACA (SEQ ID NO: 12589) |
| 10 | CGACCCAGAGTCACA (SEQ ID NO: 12590) |
| 10 | CGACCCTAYGTCACA (SEQ ID NO: 12591) |
| 11 | CCCCTCATYACAATA (SEQ ID NO: 12592) |
| 11 | CCCCTCCTYACAATA (SEQ ID NO: 12593) |
| 20 | CAACTAACRGAAGCT (SEQ ID NO: 12594) |
| 20 | CAACTAGTRGAAGCT (SEQ ID NO: 12595) |

TABLE 10 -continued

| | |
|---|---|
| 23 | TATCTADATGAGCTT (SEQ ID NO: 12596) |
| 24 | TGTATCTATTAGAGC (SEQ ID NO: 12597) |
| 24 | TGTATCTAATAGAGC (SEQ ID NO: 12598) |
| 30 | TACTGTRTTATCTGC (SEQ ID NO: 12599) |
| 32 | TTCTAATATTGTATC (SEQ ID NO: 12600) |
| 33 | ACAGTATTYGAAGAA (SEQ ID NO: 12601) |
| 43 | AAATGGACRCCAAAA (SEQ ID NO: 12602) |
| 46 | CCAAAAATHATAGGG (SEQ ID NO: 12603) |
| 46 | CCAAAAYTGATAGGG (SEQ ID NO: 12604) |
| 46 | CCAAAAGTGATAGGG (SEQ ID NO: 12605) |
| 47 | CCAARAAT + G + TAGGRGGAAT (SEQ ID NO: 12606) |
| 47 | CCAA + RAATGTAGGRGGAAT (SEQ ID NO: 12607) |
| 47 | CCAARAAT + GTAGGRGGAAT (SEQ ID NO: 12608) |
| 47 | CC + AARAATGTAGGRGGAAT (SEQ ID NO: 12609) |
| 47 | CCAARAA + TGTAGGRGGAAT (SEQ ID NO: 12610) |
| 47 | CCAARAATGTAGG + RGGAAT (SEQ ID NO: 12611) |
| 47 | CCAARAATGTAGGR + GGAAT (SEQ ID NO: 12612) |
| 47 | CCAARAATGTAGGRG + GAAT (SEQ ID NO: 12613) |
| 47 | CCAARAATGTA + GGRGGAAT (SEQ ID NO: 12614) |
| 47 | CCA + ARAAT + G + TAGGRGGAAT (SEQ ID NO: 12615) |
| 47 | CC + AARAAT + G + TAGGRGGAAT (SEQ ID NO: 12616) |
| 47 | C + CAARAAT + G + TAGGRGGAAT (SEQ ID NO: 12617) |
| 47 | CCAARAA + T + G + TAGGRGGAAT (SEQ ID NO: 12618) |
| 47 | CCAARAAT + G + TA + GGRGGAAT (SEQ ID NO: 12619) |
| 47 | CCAARAAT + G + TAGGR + GGAAT (SEQ ID NO: 12620) |
| 47 | CCAARAAT + G + TAG + GRGGAAT (SEQ ID NO: 12621) |
| 47 | CCAARAAT + G + TAGGRGG + AAT (SEQ ID NO: 12622) |
| 47 | CCAARAAT + G + TAGGRGGAA (SEQ ID NO: 12623) |
| 47 | CCAA + RAATGTAGGRGGAA (SEQ ID NO: 12624) |
| 47 | CCAARAAT + GTAGGRGGAA (SEQ ID NO: 12625) |
| 47 | CC + AARAATGTAGGRGGAA (SEQ ID NO: 12626) |
| 47 | CCAARAA + TGTAGGRGGAA (SEQ ID NO: 12627) |
| 47 | CCAARAATGTAGG + RGGAA (SEQ ID NO: 12628) |
| 47 | CCAARAATGTAGGR + GGAA (SEQ ID NO: 12629) |
| 47 | CCAARAATGTAGGRG + GAA (SEQ ID NO: 12630) |
| 47 | CCAARAATGTA + GGRGGAA (SEQ ID NO: 12631) |
| 47 | CCA + ARAAT + G + TAGGRGGAA (SEQ ID NO: 12632) |
| 47 | CC + AARAAT + G + TAGGRGGAA (SEQ ID NO: 12633) |
| 47 | C + CAARAAT + G + TAGGRGGAA (SEQ ID NO: 12634) |
| 47 | CCAARAA + T + G + TAGGRGGAA (SEQ ID NO: 12635) |

TABLE 10 -continued

| | |
|---|---|
| 47 | CCAARAAT + G + TA + GGRGGAA (SEQ ID NO: 12636) |
| 47 | CCAARAAT + G + TAGGR + GGAA (SEQ ID NO: 12637) |
| 47 | CCAARAAT + G + TAG + GRGGAA (SEQ ID NO: 12638) |
| 47 | CCAARAAT + G + TAGGRGG + AA (SEQ ID NO: 12639) |
| 47 | CAARAAT + G + TAGGRGGAA (SEQ ID NO: 12640) |
| 47 | CAA + RAATGTAGGRGGAA (SEQ ID NO: 12641) |
| 47 | CAARAAT + GTAGGRGGAA (SEQ ID NO: 12642) |
| 47 | C + AARAATGTAGGRGGAA (SEQ ID NO: 12643) |
| 47 | CAARAA + TGTAGGRGGAA (SEQ ID NO: 12644) |
| 47 | CAARAATGTAGG + RGGAA (SEQ ID NO: 12645) |
| 47 | CAARAATGTAGGR + GGAA (SEQ ID NO: 12646) |
| 47 | CAARAATGTAGGRG + GAA (SEQ ID NO: 12647) |
| 47 | CAARAATGTA + GGRGGAA (SEQ ID NO: 12648) |
| 47 | CA + ARAAT + G + TAGGRGGAA (SEQ ID NO: 12649) |
| 47 | C + AARAAT + G + TAGGRGGAA (SEQ ID NO: 12650) |
| 47 | +CAARAAT + G + TAGGRGGAA (SEQ ID NO: 12651) |
| 47 | CAARAA + T + G + TAGGRGGAA (SEQ ID NO: 12652) |
| 47 | CAARAAT + G + TA + GGRGGAA (SEQ ID NO: 12653) |
| 47 | CAARAAT + G + TAGGR + GGAA (SEQ ID NO: 12654) |
| 47 | CAARAAT + G + TAG + GRGGAA (SEQ ID NO: 12655) |
| 47 | CAARAAT + G + TAGGRGG + AA (SEQ ID NO: 12656) |
| 47 | CAARAAT + G + TAGGRGG (SEQ ID NO: 12657) |
| 47 | CAA + RAATGTAGGRGG (SEQ ID NO: 12658) |
| 47 | CAARAAT + GTAGGRGG (SEQ ID NO: 12659) |
| 47 | C + AARAATGTAGGRGG (SEQ ID NO: 12660) |
| 47 | CAARAA + TGTAGGRGG (SEQ ID NO: 12661) |
| 47 | CAARAATGTAGG + RGG (SEQ ID NO: 12662) |
| 47 | CAARAATGTAGGR + GG (SEQ ID NO: 12663) |
| 47 | CAARAATGTAGGRG + G (SEQ ID NO: 12664) |
| 47 | CAARAATGTA + GGRGG (SEQ ID NO: 12665) |
| 47 | CA + ARAAT + G + TAGGRGG (SEQ ID NO: 12666) |
| 47 | C + AARAAT + G + TAGGRGG (SEQ ID NO: 12667) |
| 47 | +CAARAAT + G + TAGGRGG (SEQ ID NO: 12668) |
| 47 | CAARAA + T + G + TAGGRGG (SEQ ID NO: 12669) |
| 47 | CAARAAT + G + TA + GGRGG (SEQ ID NO: 12670) |
| 47 | CAARAAT + G + TAGGR + GG (SEQ ID NO: 12671) |
| 47 | CAARAAT + G + TAG + GRGG (SEQ ID NO: 12672) |
| 47 | CAARAAT + G + TAGGRGG (SEQ ID NO: 12673) |
| 47 | AAAATGGTAGGGGGA (SEQ ID NO: 12674) |
| 47 | AAAATGCTAGGGGGA (SEQ ID NO: 12675) |

TABLE 10 -continued

| | |
|---|---|
| 47 | CCAARAATGTAGGRGGAAT (SEQ ID NO: 12676) |
| 47 | CCAARAATGTAGGRGGAA (SEQ ID NO: 12677) |
| 47 | CAARAATGTAGGRGGAA (SEQ ID NO: 12678) |
| 47 | CAARAATGTAGGRGG (SEQ ID NO: 12679) |
| 48 | ATGATAGTRGGAATT (SEQ ID NO: 12680) |
| 48 | ATGATAATGGGAATT (SEQ ID NO: 12681) |
| 48 | ATGATAGCRGGAATT (SEQ ID NO: 12682) |
| 48 | ATGATAAGYGGAATT (SEQ ID NO: 12683) |
| 48 | ATGATAACRGGAATT (SEQ ID NO: 12684) |
| 48 | ATGATAYTRGGAATT (SEQ ID NO: 12685) |
| 48 | ATGATACARGGAATT (SEQ ID NO: 12686) |
| 50 | ATAGGRGG + A + TTGGAGGYTT (SEQ ID NO: 12687) |
| 50 | ATAGGR + GGATTGGAGGYTT (SEQ ID NO: 12688) |
| 50 | ATAG + GRGGATTGGAGGYTT (SEQ ID NO: 12689) |
| 50 | ATAGGRG + GATTGGAGGYTT (SEQ ID NO: 12690) |
| 50 | AT + AGGRGGATTGGAGGYTT (SEQ ID NO: 12691) |
| 50 | ATAGGRGGATT + GGAGGYTT (SEQ ID NO: 12692) |
| 50 | ATAGGRGGATTGGAG + GYTT (SEQ ID NO: 12693) |
| 50 | ATAGGRGGA + TTGGAGGYTT (SEQ ID NO: 12694) |
| 50 | ATAGGRGGATTGG + AGGYTT (SEQ ID NO: 12695) |
| 50 | ATAGGR + GG + A + TTGGAGGYTT (SEQ ID NO: 12696) |
| 50 | ATAGG + RGG + A + TTGGAGGYTT (SEQ ID NO: 12697) |
| 50 | A + TAGGRGG + A + TTGGAGGYTT (SEQ ID NO: 12698) |
| 50 | AT + AGGRGG + A + TTGGAGGYTT (SEQ ID NO: 12699) |
| 50 | ATAGGRGG + A + TTGGAGG + YTT (SEQ ID NO: 12700) |
| 50 | ATAGGRGG + A + TTGGAG + GYTT (SEQ ID NO: 12701) |
| 50 | ATAGGRGG + A + TTG + GAGGYTT (SEQ ID NO: 12702) |
| 50 | ATAGGRGG + A + TTGGA + GGYTT (SEQ ID NO: 12703) |
| 50 | ATAGGRGG + A + TTGGAGGYT (SEQ ID NO: 12704) |
| 50 | ATAGGR + GGATTGGAGGYT (SEQ ID NO: 12705) |
| 50 | ATAG + GRGGATTGGAGGYT (SEQ ID NO: 12706) |
| 50 | ATAGGRG + GATTGGAGGYT (SEQ ID NO: 12707) |
| 50 | AT + AGGRGGATTGGAGGYT (SEQ ID NO: 12708) |
| 50 | ATAGGRGGATT + GGAGGYT (SEQ ID NO: 12709) |
| 50 | ATAGGRGGATTGGAG + GYT (SEQ ID NO: 12710) |
| 50 | ATAGGRGGA + TTGGAGGYT (SEQ ID NO: 12711) |
| 50 | ATAGGRGGATTGG + AGGYT (SEQ ID NO: 12712) |
| 50 | ATAGGR + GG + A + TTGGAGGYT (SEQ ID NO: 12713) |
| 50 | ATAGG + RGG + A + TTGGAGGYT (SEQ ID NO: 12714) |
| 50 | A + TAGGRGG + A + TTGGAGGYT (SEQ ID NO: 12715) |

TABLE 10 -continued

| | |
|---|---|
| 50 | AT + AGGRGG + A + TTGGAGGYT (SEQ ID NO: 12716) |
| 50 | ATAGGRGG + A + TTGGAGG + YT (SEQ ID NO: 12717) |
| 50 | ATAGGRGG + A + TTGGAG + GYT (SEQ ID NO: 12718) |
| 50 | ATAGGRGG + A + TTG + GAGGYT (SEQ ID NO: 12719) |
| 50 | ATAGGRGG + A + TTGGA + GGYT (SEQ ID NO: 12720) |
| 50 | TAGGRGG + A + TTGGAGGYT (SEQ ID NO: 12721) |
| 50 | TAGGR + GGATTGGAGGYT (SEQ ID NO: 12722) |
| 50 | TAG + GRGGATTGGAGGYT (SEQ ID NO: 12723) |
| 50 | TAGGRG + GATTGGAGGYT (SEQ ID NO: 12724) |
| 50 | T + AGGRGGATTGGAGGYT (SEQ ID NO: 12725) |
| 50 | TAGGRGGATT + GGAGGYT (SEQ ID NO: 12726) |
| 50 | TAGGRGGATTGGAG + GYT (SEQ ID NO: 12727) |
| 50 | TAGGRGGA + TTGGAGGYT (SEQ ID NO: 12728) |
| 50 | TAGGRGGATTGG + AGGYT (SEQ ID NO: 12729) |
| 50 | TAGGR + GG + A + TTGGAGGYT (SEQ ID NO: 12730) |
| 50 | TAGG + RGG + A + TTGGAGGYT (SEQ ID NO: 12731) |
| 50 | (SEQ ID NO: 12732) |
| 50 | T + AGGRGG + A + TTGGAGGYT (SEQ ID NO: 12733) |
| 50 | TAGGRGG + A + TTGGAGG + YT (SEQ ID NO: 12734) |
| 50 | TAGGRGG + A + TTGGAG + GYT (SEQ ID NO: 12735) |
| 50 | TAGGRGG + A + TTG + GAGGYT (SEQ ID NO: 12736) |
| 50 | TAGGRGG + A + TTGGA + GGYT (SEQ ID NO: 12737) |
| 50 | TAGGRGG + A + TTGGAGG (SEQ ID NO: 12738) |
| 50 | TAGGR + GGATTGGAGG (SEQ ID NO: 12739) |
| 50 | TAG + GRGGATTGGAGG (SEQ ID NO: 12740) |
| 50 | TAGGRG + GATTGGAGG (SEQ ID NO: 12741) |
| 50 | T + AGGRGGATTGGAGG (SEQ ID NO: 12742) |
| 50 | TAGGRGGATT + GGAGG (SEQ ID NO: 12743) |
| 50 | TAGGRGGATTGGAG + G (SEQ ID NO: 12744) |
| 50 | TAGGRGGA + TTGGAGG (SEQ ID NO: 12745) |
| 50 | TAGGRGGATTGG + AGG (SEQ ID NO: 12746) |
| 50 | TAGGR + GG + A + TTGGAGG (SEQ ID NO: 12747) |
| 50 | TAGG + RGG + A + TTGGAGG (SEQ ID NO: 12748) |
| 50 | (SEQ ID NO: 12749) |
| 50 | T + AGGRGG + A + TTGGAGG (SEQ ID NO: 12750) |
| 50 | TAGGRGG + A + TTGGAGG (SEQ ID NO: 12751) |
| 50 | TAGGRGG + A + TTGGAG + G (SEQ ID NO: 12752) |
| 50 | TAGGRGG + A + TTG + GAGG (SEQ ID NO: 12753) |
| 50 | TAGGRGG + A + TTGGA + GG (SEQ ID NO: 12754) |
| 50 | ACCTCCAACTCCCCC (SEQ ID NO: 12755) |

TABLE 10 -continued

| | |
|---|---|
| 50 | ACCTCCAAGTCCCCC (SEQ ID NO: 12756) |
| 50 | ATAGGRGGATTGGAGGYTT (SEQ ID NO: 12757) |
| 50 | ATAGGRGGATTGGAGGYT (SEQ ID NO: 12758) |
| 50 | TAGGRGGATTGGAGGYT (SEQ ID NO: 12759) |
| 50 | TAGGRGGATTGGAGG (SEQ ID NO: 12760) |
| 53 | TGGAGGYT + T + ATYAARGTAA (SEQ ID NO: 12761) |
| 53 | TGGAGGY + TTATYAARGTAA (SEQ ID NO: 12762) |
| 53 | T + GGAGGYTTATYAARGTAA (SEQ ID NO: 12763) |
| 53 | TGGAGG + YTTATYAARGTAA (SEQ ID NO: 12764) |
| 53 | TG + GAGGYTTATYAARGTAA (SEQ ID NO: 12765) |
| 53 | TGGAGGYTTATYA + ARGTAA (SEQ ID NO: 12766) |
| 53 | TGGAGGYTTATYAAR + GTAA (SEQ ID NO: 12767) |
| 53 | TGGAGGYTT + ATYAARGTAA (SEQ ID NO: 12768) |
| 53 | TGGAGGYTTATY + AARGTAA (SEQ ID NO: 12769) |
| 53 | TGGA + GGYT + T + ATYAARGTAA (SEQ ID NO: 12770) |
| 53 | TG + GAGGYT + T + ATYAARGTAA (SEQ ID NO: 12771) |
| 53 | TGGAGGY + T + T + ATYAARGTAA (SEQ ID NO: 12772) |
| 53 | TGG + AGGYT + T + ATYAARGTAA (SEQ ID NO: 12773) |
| 53 | TGGAGGYT + T + ATY + AARGTAA (SEQ ID NO: 12774) |
| 53 | TGGAGGYT + T + AT + YAARGTAA (SEQ ID NO: 12775) |
| 53 | TGGAGGYT + T + ATYAA + RGTAA (SEQ ID NO: 12776) |
| 53 | TGGAGGYT + T + ATYAAR + GTAA (SEQ ID NO: 12777) |
| 53 | TTGGAGGY + T + TATYAARGTA (SEQ ID NO: 12778) |
| 53 | TTGGA + GGYTTATYAARGTA (SEQ ID NO: 12779) |
| 53 | TTGGAGG + YTTATYAARGTA (SEQ ID NO: 12780) |
| 53 | TTGGAG + GYTTATYAARGTA (SEQ ID NO: 12781) |
| 53 | TT + GGAGGYTTATYAARGTA (SEQ ID NO: 12782) |
| 53 | TTGGAGGYTTATYAA + RGTA (SEQ ID NO: 12783) |
| 53 | TTGGAGGYTTATYAAR + GTA (SEQ ID NO: 12784) |
| 53 | TTGGAGGYTT + ATYAARGTA (SEQ ID NO: 12785) |
| 53 | TTGGAGGYTTAT + YAARGTA (SEQ ID NO: 12786) |
| 53 | T + TGGAGGY + T + TATYAARGTA (SEQ ID NO: 12787) |
| 53 | TTGGAG + GY + T + TATYAARGTA (SEQ ID NO: 12788) |
| 53 | TTGG + AGGY + T + TATYAARGTA (SEQ ID NO: 12789) |
| 53 | TTGGAGG + Y + T + TATYAARGTA (SEQ ID NO: 12790) |
| 53 | TTGGAGGY + T + TATYA + ARGTA (SEQ ID NO: 12791) |
| 53 | TTGGAGGY + T + T + ATYAARGTA (SEQ ID NO: 12792) |
| 53 | TTGGAGGY + T + TATYAAR + GTA (SEQ ID NO: 12793) |
| 53 | TTGGAGGY + T + TATY + AARGTA (SEQ ID NO: 12794) |
| 53 | TGGAGGYT + T + ATYAARGTA (SEQ ID NO: 12795) |

TABLE 10 -continued

| | |
|---|---|
| 53 | TGGAGGY + TTATYAARGTA (SEQ ID NO: 12796) |
| 53 | T + GGAGGYTTATYAARGTA (SEQ ID NO: 12797) |
| 53 | TGGAGG + YTTATYAARGTA (SEQ ID NO: 12798) |
| 53 | TG + GAGGYTTATYAARGTA (SEQ ID NO: 12799) |
| 53 | TGGAGGYTTATYA + ARGTA (SEQ ID NO: 12800) |
| 53 | TGGAGGYTTATYAAR + GTA (SEQ ID NO: 12801) |
| 53 | TGGAGGYTT + ATYAARGTA (SEQ ID NO: 12802) |
| 53 | TGGAGGYTTATY + AARGTA (SEQ ID NO: 12803) |
| 53 | TGGA + GGYT + T + ATYAARGTA (SEQ ID NO: 12804) |
| 53 | TG + GAGGYT + T + ATYAARGTA (SEQ ID NO: 12805) |
| 53 | TGGAGGY + T + T + ATYAARGTA (SEQ ID NO: 12806) |
| 53 | TGG + AGGYT + T + ATYAARGTA (SEQ ID NO: 12807) |
| 53 | TGGAGGYT + T + ATY + AARGTA (SEQ ID NO: 12808) |
| 53 | TGGAGGYT + T + AT + YAARGTA (SEQ ID NO: 12809) |
| 53 | TGGAGGYT + T + ATYAA + RGTA (SEQ ID NO: 12810) |
| 53 | TGGAGGYT + T + ATYAAR + GTA (SEQ ID NO: 12811) |
| 53 | TTGGAGGY + T + TATYAARGT (SEQ ID NO: 12812) |
| 53 | TTGGA + GGYTTATYAARGT (SEQ ID NO: 12813) |
| 53 | TTGGAGG + YTTATYAARGT (SEQ ID NO: 12814) |
| 53 | TTGGAG + GYTTATYAARGT (SEQ ID NO: 12815) |
| 53 | TT + GGAGGYTTATYAARGT (SEQ ID NO: 12816) |
| 53 | TTGGAGGYTTATYAA + RGT (SEQ ID NO: 12817) |
| 53 | TTGGAGGYTTATYAAR + GT (SEQ ID NO: 12818) |
| 53 | TTGGAGGYTT + ATYAARGT (SEQ ID NO: 12819) |
| 53 | TTGGAGGYTTAT + YAARGT (SEQ ID NO: 12820) |
| 53 | T + TGGAGGY + T + TATYAARGT (SEQ ID NO: 12821) |
| 53 | TTGGAG + GY + T + TATYAARGT (SEQ ID NO: 12822) |
| 53 | TTGG + AGGY + T + TATYAARGT (SEQ ID NO: 12823) |
| 53 | TTGGAGG + Y + T + TATYAARGT (SEQ ID NO: 12824) |
| 53 | TTGGAGGY + T + TATYA + ARGT (SEQ ID NO: 12825) |
| 53 | TTGGAGGY + T + T + ATYAARGT (SEQ ID NO: 12826) |
| 53 | TTGGAGGY + T + TATYAAR + GT (SEQ ID NO: 12827) |
| 53 | TTGGAGGY + T + TATY + AARGT (SEQ ID NO: 12828) |
| 53 | GGAGGYT + T + ATYAARGTA (SEQ ID NO: 12829) |
| 53 | GGAGGY + TTATYAARGTA (SEQ ID NO: 12830) |
| 53 | +GGAGGYTTATYAARGTA (SEQ ID NO: 12831) |
| 53 | GGAGG + YTTATYAARGTA (SEQ ID NO: 12832) |
| 53 | G + GAGGYTTATYAARGTA (SEQ ID NO: 12833) |
| 53 | GGAGGYTTATYA + ARGTA (SEQ ID NO: 12834) |
| 53 | GGAGGYTTATYAAR + GTA (SEQ ID NO: 12835) |

TABLE 10 -continued

| | |
|---|---|
| 53 | GGAGGYTT + ATYAARGTA (SEQ ID NO: 12836) |
| 53 | GGAGGYTTATY + AARGTA (SEQ ID NO: 12837) |
| 53 | GGA + GGYT + T + ATYAARGTA (SEQ ID NO: 12838) |
| 53 | G + GAGGYT + T + ATYAARGTA (SEQ ID NO: 12839) |
| 53 | GGAGGY + T + T + ATYAARGTA (SEQ ID NO: 12840) |
| 53 | GG + AGGYT + T + ATYAARGTA (SEQ ID NO: 12841) |
| 53 | GGAGGYT + T + ATY + AARGTA (SEQ ID NO: 12842) |
| 53 | GGAGGYT + T + AT + YAARGTA (SEQ ID NO: 12843) |
| 53 | GGAGGYT + T + ATYAA + RGTA (SEQ ID NO: 12844) |
| 53 | GGAGGYT + T + ATYAAR + GTA (SEQ ID NO: 12845) |
| 53 | TGGAGGY + T + TATYAARGT (SEQ ID NO: 12846) |
| 53 | TGGA + GGYTTATYAARGT (SEQ ID NO: 12847) |
| 53 | TGGAGG + YTTATYAARGT (SEQ ID NO: 12848) |
| 53 | TGGAG + GYTTATYAARGT (SEQ ID NO: 12849) |
| 53 | T + GGAGGYTTATYAARGT (SEQ ID NO: 12850) |
| 53 | TGGAGGYTTATYAA + RGT (SEQ ID NO: 12851) |
| 53 | TGGAGGYTTATYAAR + GT (SEQ ID NO: 12852) |
| 53 | TGGAGGYTT + ATYAARGT (SEQ ID NO: 12853) |
| 53 | TGGAGGYTTAT + YAARGT (SEQ ID NO: 12854) |
| 53 | +TGGAGGY + T + TATYAARGT (SEQ ID NO: 12855) |
| 53 | TGGAG + GY + T + TATYAARGT (SEQ ID NO: 12856) |
| 53 | TGG + AGGY + T + TATYAARGT (SEQ ID NO: 12857) |
| 53 | TGGAGG + Y + T + TATYAARGT (SEQ ID NO: 12858) |
| 53 | TGGAGGY + T + TATYA + ARGT (SEQ ID NO: 12859) |
| 53 | TGGAGGY + T + T + ATYAARGT (SEQ ID NO: 12860) |
| 53 | TGGAGGY + T + TATYAAR + GT (SEQ ID NO: 12861) |
| 53 | TGGAGGY + T + TATY + AARGT (SEQ ID NO: 12862) |
| 53 | GGAGGYT + T + ATYAARG (SEQ ID NO: 12863) |
| 53 | GGAGGY + TTATYAARG (SEQ ID NO: 12864) |
| 53 | +GGAGGYTTATYAARG (SEQ ID NO: 12865) |
| 53 | GGAGG + YTTATYAARG (SEQ ID NO: 12866) |
| 53 | G + GAGGYTTATYAARG (SEQ ID NO: 12867) |
| 53 | GGAGGYTTATYA + ARG (SEQ ID NO: 12868) |
| 53 | GGAGGYTTATYAAR + G (SEQ ID NO: 12869) |
| 53 | GGAGGYTT + ATYAARG (SEQ ID NO: 12870) |
| 53 | GGAGGYTTATY + AARG (SEQ ID NO: 12871) |
| 53 | GGA + GGYT + T + ATYAARG (SEQ ID NO: 12872) |
| 53 | G + GAGGYT + T + ATYAARG (SEQ ID NO: 12873) |
| 53 | GGAGGY + T + T + ATYAARG (SEQ ID NO: 12874) |
| 53 | GG + AGGYT + T + ATYAARG (SEQ ID NO: 12875) |

TABLE 10 -continued

| | |
|---|---|
| 53 | GGAGGYT + T + ATY + AARG (SEQ ID NO: 12876) |
| 53 | GGAGGYT + T + AT + YAARG (SEQ ID NO: 12877) |
| 53 | GGAGGYT + T + ATYAA + RG (SEQ ID NO: 12878) |
| 53 | GGAGGYT + T + ATYAAR + G (SEQ ID NO: 12879) |
| 53 | TGGAGGY + T + TATYAAR (SEQ ID NO: 12880) |
| 53 | TGGA + GGYTTATYAAR (SEQ ID NO: 12881) |
| 53 | TGGAGG + YTTATYAAR (SEQ ID NO: 12882) |
| 53 | TGGAG + GYTTATYAAR (SEQ ID NO: 12883) |
| 53 | T + GGAGGYTTATYAAR (SEQ ID NO: 12884) |
| 53 | TGGAGGYTTATYAA + R (SEQ ID NO: 12885) |
| 53 | TGGAGGYTTATYAAR (SEQ ID NO: 12886) |
| 53 | TGGAGGYTT + ATYAAR (SEQ ID NO: 12887) |
| 53 | TGGAGGYTTAT + YAAR (SEQ ID NO: 12888) |
| 53 | +TGGAGGY + T + TATYAAR (SEQ ID NO: 12889) |
| 53 | TGGAG + GY + T + TATYAAR (SEQ ID NO: 12890) |
| 53 | TGG + AGGY + T + TATYAAR (SEQ ID NO: 12891) |
| 53 | TGGAGG + Y + T + TATYAAR (SEQ ID NO: 12892) |
| 53 | TGGAGGY + T + TATYA + AR (SEQ ID NO: 12893) |
| 53 | TGGAGGY + T + T + ATYAAR (SEQ ID NO: 12894) |
| 53 | TGGAGGY + T + TATYAAR (SEQ ID NO: 12895) |
| 53 | TGGAGGY + T + TATY + AAR (SEQ ID NO: 12896) |
| 53 | TTTGATRAGACCTCC (SEQ ID NO: 12897) |
| 53 | TTTGATYAAACCTCC (SEQ ID NO: 12898) |
| 53 | TTTGATRTAACCTCC (SEQ ID NO: 12899) |
| 53 | TGGAGGYTTATYAARGTAA (SEQ ID NO: 12900) |
| 53 | TTGGAGGYTTATYAARGTA (SEQ ID NO: 12901) |
| 53 | TGGAGGYTTATYAARGTA (SEQ ID NO: 12902) |
| 53 | TTGGAGGYTTATYAARGT (SEQ ID NO: 12903) |
| 53 | GGAGGYTTATYAARGTA (SEQ ID NO: 12904) |
| 53 | TGGAGGYTTATYAARGT (SEQ ID NO: 12905) |
| 53 | GGAGGYTTATYAARG (SEQ ID NO: 12906) |
| 53 | TGGAGGYTTATYAAR (SEQ ID NO: 12907) |
| 54 | AGGYTTTA + T + AARGTAARRC (SEQ ID NO: 12908) |
| 54 | AGGYT + TTATAARGTAARRC (SEQ ID NO: 12909) |
| 54 | AGGYTTTA + TAARGTAARRC (SEQ ID NO: 12910) |
| 54 | AGGYTT + TATAARGTAARRC (SEQ ID NO: 12911) |
| 54 | AGGYTTT + ATAARGTAARRC (SEQ ID NO: 12912) |
| 54 | AGGYTTTAT + AARGTAARRC (SEQ ID NO: 12913) |
| 54 | AGGYTTTATAARG + TAARRC (SEQ ID NO: 12914) |
| 54 | AGGYTTTATAARGTA + ARRC (SEQ ID NO: 12915) |

TABLE 10 -continued

| | | |
|---|---|---|
| 54 | AGGYTTTATAA + RGTAARRC | (SEQ ID NO: 12916) |
| 54 | AGGYT + TTA + T + AARGTAARRC | (SEQ ID NO: 12917) |
| 54 | AGGY + TTTA + T + AARGTAARRC | (SEQ ID NO: 12918) |
| 54 | AGG + YTTTA + T + AARGTAARRC | (SEQ ID NO: 12919) |
| 54 | AG + GYTTTA + T + AARGTAARRC | (SEQ ID NO: 12920) |
| 54 | AGGYTTTA + T + AAR + GTAARRC | (SEQ ID NO: 12921) |
| 54 | AGGYTTTA + T + AARGTAAR + RC | (SEQ ID NO: 12922) |
| 54 | AGGYTTTA + T + AA + RGTAARRC | (SEQ ID NO: 12923) |
| 54 | AGGYTTTA + T + A + ARGTAARRC | (SEQ ID NO: 12924) |
| 54 | GAGGYTTT + A + YAARGTAARR | (SEQ ID NO: 12925) |
| 54 | GAGGYT + TTAYAARGTAARR | (SEQ ID NO: 12926) |
| 54 | GA + GGYTTTAYAARGTAARR | (SEQ ID NO: 12927) |
| 54 | GAGGYTT + TAYAARGTAARR | (SEQ ID NO: 12928) |
| 54 | GAG + GYTTTAYAARGTAARR | (SEQ ID NO: 12929) |
| 54 | GAGGYTTTA + YAARGTAARR | (SEQ ID NO: 12930) |
| 54 | GAGGYTTTAYAA + RGTAARR | (SEQ ID NO: 12931) |
| 54 | GAGGYTTTAYAARGT + AARR | (SEQ ID NO: 12932) |
| 54 | GAGGYTTTAY + AARGTAARR | (SEQ ID NO: 12933) |
| 54 | GAGGYT + TT + A + YAARGTAARR | (SEQ ID NO: 12934) |
| 54 | GAG + GYTTT + A + YAARGTAARR | (SEQ ID NO: 12935) |
| 54 | GA + GGYTTT + A + YAARGTAARR | (SEQ ID NO: 12936) |
| 54 | GAGG + YTTT + A + YAARGTAARR | (SEQ ID NO: 12937) |
| 54 | GAGGYTTT + A + YAARGT + AARR | (SEQ ID NO: 12938) |
| 54 | GAGGYTTT + A + YAARG + TAARR | (SEQ ID NO: 12939) |
| 54 | GAGGYTTT + A + YAA + RGTAARR | (SEQ ID NO: 12940) |
| 54 | GAGGYTTT + A + Y + AARGTAARR | (SEQ ID NO: 12941) |
| 54 | GGAGGYTT + T + TYAARGTAAR | (SEQ ID NO: 12942) |
| 54 | GGA + GGYTTTTYAARGTAAR | (SEQ ID NO: 12943) |
| 54 | G + GAGGYTTTTYAARGTAAR | (SEQ ID NO: 12944) |
| 54 | GG + AGGYTTTTYAARGTAAR | (SEQ ID NO: 12945) |
| 54 | GGAGGY + TTTTYAARGTAAR | (SEQ ID NO: 12946) |
| 54 | GGAGGYTTTTY + AARGTAAR | (SEQ ID NO: 12947) |
| 54 | GGAGGYTTTTYAARGT + AAR | (SEQ ID NO: 12948) |
| 54 | GGAGGYTTTTYAARG + TAAR | (SEQ ID NO: 12949) |
| 54 | GGAGGYTTTTYAARGTA + AR | (SEQ ID NO: 12950) |
| 54 | GG + AGGYTT + T + TYAARGTAAR | (SEQ ID NO: 12951) |
| 54 | G + GAGGYTT + T + TYAARGTAAR | (SEQ ID NO: 12952) |
| 54 | GGAGGY + TT + T + TYAARGTAAR | (SEQ ID NO: 12953) |
| 54 | GGA + GGYTT + T + TYAARGTAAR | (SEQ ID NO: 12954) |
| 54 | GGAGGYTT + T + TYAA + RGTAAR | (SEQ ID NO: 12955) |

TABLE 10 -continued

| | |
|---|---|
| 54 | GGAGGYTT + T + TYA + ARGTAAR (SEQ ID NO: 12956) |
| 54 | GGAGGYTT + T + TYAAR + GTAAR (SEQ ID NO: 12957) |
| 54 | GGAGGYTT + T + TY + AARGTAAR (SEQ ID NO: 12958) |
| 54 | AGGYTTTA + T + AARGTAARR (SEQ ID NO: 12959) |
| 54 | AGGYT + TTATAARGTAARR (SEQ ID NO: 12960) |
| 54 | AGGYTTTA + TAARGTAARR (SEQ ID NO: 12961) |
| 54 | AGGYTT + TATAARGTAARR (SEQ ID NO: 12962) |
| 54 | AGGYTTT + ATAARGTAARR (SEQ ID NO: 12963) |
| 54 | AGGYTTTAT + AARGTAARR (SEQ ID NO: 12964) |
| 54 | AGGYTTTATAARG + TAARR (SEQ ID NO: 12965) |
| 54 | AGGYTTTATAARGTA + ARR (SEQ ID NO: 12966) |
| 54 | AGGYTTTATAA + RGTAARR (SEQ ID NO: 12967) |
| 54 | AGGYT + TTA + T + AARGTAARR (SEQ ID NO: 12968) |
| 54 | AGGY + TTTA + T + AARGTAARR (SEQ ID NO: 12969) |
| 54 | AGG + YTTTA + T + AARGTAARR (SEQ ID NO: 12970) |
| 54 | AG + GYTTTA + T + AARGTAARR (SEQ ID NO: 12971) |
| 54 | AGGYTTTA + T + AAR + GTAARR (SEQ ID NO: 12972) |
| 54 | AGGYTTTA + T + AARGTAAR + R (SEQ ID NO: 12973) |
| 54 | AGGYTTTA + T + AA + RGTAARR (SEQ ID NO: 12974) |
| 54 | AGGYTTTA + T + A + ARGTAARR (SEQ ID NO: 12975) |
| 54 | GAGGYTTT + A + YAARGTAAR (SEQ ID NO: 12976) |
| 54 | GAGGYT + TTAYAARGTAAR (SEQ ID NO: 12977) |
| 54 | GA + GGYTTTAYAARGTAAR (SEQ ID NO: 12978) |
| 54 | GAGGYTT + TAYAARGTAAR (SEQ ID NO: 12979) |
| 54 | GAG + GYTTTAYAARGTAAR (SEQ ID NO: 12980) |
| 54 | GAGGYTTTA + YAARGTAAR (SEQ ID NO: 12981) |
| 54 | GAGGYTTTAYAA + RGTAAR (SEQ ID NO: 12982) |
| 54 | GAGGYTTTAYAARGT + AAR (SEQ ID NO: 12983) |
| 54 | GAGGYTTTAY + AARGTAAR (SEQ ID NO: 12984) |
| 54 | GAGGYT + TT + A + YAARGTAAR (SEQ ID NO: 12985) |
| 54 | GAG + GYTTT + A + YAARGTAAR (SEQ ID NO: 12986) |
| 54 | GA + GGYTTT + A + YAARGTAAR (SEQ ID NO: 12987) |
| 54 | GAGG + YTTT + A + YAARGTAAR (SEQ ID NO: 12988) |
| 54 | GAGGYTTT + A + YAARGT + AAR (SEQ ID NO: 12989) |
| 54 | GAGGYTTT + A + YAARG + TAAR (SEQ ID NO: 12990) |
| 54 | GAGGYTTT + A + YAA + RGTAAR (SEQ ID NO: 12991) |
| 54 | GAGGYTTT + A + Y + AARGTAAR (SEQ ID NO: 12992) |
| 54 | GGAGGYTT + T + TYAARGTAA (SEQ ID NO: 12993) |
| 54 | GGA + GGYTTTTYAARGTAA (SEQ ID NO: 12994) |
| 54 | G + GAGGYTTTTYAARGTAA (SEQ ID NO: 12995) |

| | | |
|---|---|---|
| 54 | GG + AGGYTTTTYAARGTAA | (SEQ ID NO: 12996) |
| 54 | GGAGGY + TTTTYAARGTAA | (SEQ ID NO: 12997) |
| 54 | GGAGGYTTTTY + AARGTAA | (SEQ ID NO: 12998) |
| 54 | GGAGGYTTTTYAARGT + AA | (SEQ ID NO: 12999) |
| 54 | GGAGGYTTTTYAARG + TAA | (SEQ ID NO: 13000) |
| 54 | GGAGGYTTTTYAARGTA + A | (SEQ ID NO: 13001) |
| 54 | GG + AGGYTT + T + TYAARGTAA | (SEQ ID NO: 13002) |
| 54 | G + GAGGYTT + T + TYAARGTAA | (SEQ ID NO: 13003) |
| 54 | GGAGGY + TT + T + TYAARGTAA | (SEQ ID NO: 13004) |
| 54 | GGA + GGYTT + T + TYAARGTAA | (SEQ ID NO: 13005) |
| 54 | GGAGGYTT + T + TYAA + RGTAA | (SEQ ID NO: 13006) |
| 54 | GGAGGYTT + T + TYA + ARGTAA | (SEQ ID NO: 13007) |
| 54 | GGAGGYTT + T + TYAAR + GTAA | (SEQ ID NO: 13008) |
| 54 | GGAGGYTT + T + TY + AARGTAA | (SEQ ID NO: 13009) |
| 54 | GGYTTTA + T + AARGTAARR | (SEQ ID NO: 13010) |
| 54 | GGYT + TTATAARGTAARR | (SEQ ID NO: 13011) |
| 54 | GGYTTTA + TAARGTAARR | (SEQ ID NO: 13012) |
| 54 | GGYTT + TATAARGTAARR | (SEQ ID NO: 13013) |
| 54 | GGYTTT + ATAARGTAARR | (SEQ ID NO: 13014) |
| 54 | GGYTTTAT + AARGTAARR | (SEQ ID NO: 13015) |
| 54 | GGYTTTATAARG + TAARR | (SEQ ID NO: 13016) |
| 54 | GGYTTTATAARGTA + ARR | (SEQ ID NO: 13017) |
| 54 | GGYTTTATAA + RGTAARR | (SEQ ID NO: 13018) |
| 54 | GGYT + TTA + T + AARGTAARR | (SEQ ID NO: 13019) |
| 54 | GGY + TTTA + T + AARGTAARR | (SEQ ID NO: 13020) |
| 54 | GG + YTTTA + T + AARGTAARR | (SEQ ID NO: 13021) |
| 54 | G + GYTTTA + T + AARGTAARR | (SEQ ID NO: 13022) |
| 54 | GGYTTTA + T + AAR + GTAARR | (SEQ ID NO: 13023) |
| 54 | GGYTTTA + T + AARGTAAR + R | (SEQ ID NO: 13024) |
| 54 | GGYTTTA + T + AA + RGTAARR | (SEQ ID NO: 13025) |
| 54 | GGYTTTA + T + A + ARGTAARR | (SEQ ID NO: 13026) |
| 54 | AGGYTTT + A + YAARGTAAR | (SEQ ID NO: 13027) |
| 54 | AGGYT + TTAYAARGTAAR | (SEQ ID NO: 13028) |
| 54 | A + GGYTTTAYAARGTAAR | (SEQ ID NO: 13029) |
| 54 | AGGYTT + TAYAARGTAAR | (SEQ ID NO: 13030) |
| 54 | AG + GYTTTAYAARGTAAR | (SEQ ID NO: 13031) |
| 54 | AGGYTTTA + YAARGTAAR | (SEQ ID NO: 13032) |
| 54 | AGGYTTTAYAA + RGTAAR | (SEQ ID NO: 13033) |
| 54 | AGGYTTTAYAARGT + AAR | (SEQ ID NO: 13034) |
| 54 | AGGYTTTAY + AARGTAAR | (SEQ ID NO: 13035) |

TABLE 10 -continued

| | |
|---|---|
| 54 | AGGYT + TT + A + YAARGTAAR (SEQ ID NO: 13036) |
| 54 | AG + GYTTT + A + YAARGTAAR (SEQ ID NO: 13037) |
| 54 | A + GGYTTT + A + YAARGTAAR (SEQ ID NO: 13038) |
| 54 | AGG + YTTT + A + YAARGTAAR (SEQ ID NO: 13039) |
| 54 | AGGYTTT + A + YAARGT + AAR (SEQ ID NO: 13040) |
| 54 | AGGYTTT + A + YAARG + TAAR (SEQ ID NO: 13041) |
| 54 | AGGYTTT + A + YAA + RGTAAR (SEQ ID NO: 13042) |
| 54 | AGGYTTT + A + Y + AARGTAAR (SEQ ID NO: 13043) |
| 54 | GAGGYTT + T + TYAARGTAA (SEQ ID NO: 13044) |
| 54 | GA + GGYTTTTYAARGTAA (SEQ ID NO: 13045) |
| 54 | +GAGGYTTTTYAARGTAA (SEQ ID NO: 13046) |
| 54 | G + AGGYTTTTYAARGTAA (SEQ ID NO: 13047) |
| 54 | GAGGY + TTTTYAARGTAA (SEQ ID NO: 13048) |
| 54 | GAGGYTTTTY + AARGTAA (SEQ ID NO: 13049) |
| 54 | GAGGYTTTTYAARGT + AA (SEQ ID NO: 13050) |
| 54 | GAGGYTTTTYAARG + TAA (SEQ ID NO: 13051) |
| 54 | GAGGYTTTTYAARGTA + A (SEQ ID NO: 13052) |
| 54 | G + AGGYTT + T + TYAARGTAA (SEQ ID NO: 13053) |
| 54 | +GAGGYTT + T + TYAARGTAA (SEQ ID NO: 13054) |
| 54 | GAGGY + TT + T + TYAARGTAA (SEQ ID NO: 13055) |
| 54 | GA + GGYTT + T + TYAARGTAA (SEQ ID NO: 13056) |
| 54 | GAGGYTT + T + TYAA + RGTAA (SEQ ID NO: 13057) |
| 54 | GAGGYTT + T + TYA + ARGTAA (SEQ ID NO: 13058) |
| 54 | GAGGYTT + T + TYAAR + GTAA (SEQ ID NO: 13059) |
| 54 | GAGGYTT + T + TY + AARGTAA (SEQ ID NO: 13060) |
| 54 | GGYTTTA + T + AARGTAA (SEQ ID NO: 13061) |
| 54 | GGYT + TTATAARGTAA (SEQ ID NO: 13062) |
| 54 | GGYTTTA + TAARGTAA (SEQ ID NO: 13063) |
| 54 | GGYTT + TATAARGTAA (SEQ ID NO: 13064) |
| 54 | GGYTTT + ATAARGTAA (SEQ ID NO: 13065) |
| 54 | GGYTTTAT + AARGTAA (SEQ ID NO: 13066) |
| 54 | GGYTTTATAARG + TAA (SEQ ID NO: 13067) |
| 54 | GGYTTTATAARGTA + A (SEQ ID NO: 13068) |
| 54 | GGYTTTATAA + RGTAA (SEQ ID NO: 13069) |
| 54 | GGYT + TTA + T + AARGTAA (SEQ ID NO: 13070) |
| 54 | GGY + TTTA + T + AARGTAA (SEQ ID NO: 13071) |
| 54 | GG + YTTTA + T + AARGTAA (SEQ ID NO: 13072) |
| 54 | G + GYTTTA + T + AARGTAA (SEQ ID NO: 13073) |
| 54 | GGYTTTA + T + AAR + GTAA (SEQ ID NO: 13074) |
| 54 | GGYTTTA + T + AARGTAAR (SEQ ID NO: 13075) |

TABLE 10 -continued

| | |
|---|---|
| 54 | GGYTTTA + T + AA + RGTAA (SEQ ID NO: 13076) |
| 54 | GGYTTTA + T + A + ARGTAA (SEQ ID NO: 13077) |
| 54 | AGGYTTT + A + YAARGTA (SEQ ID NO:13078) |
| 54 | AGGYT + TTAYAARGTA (SEQ ID NO: 13079) |
| 54 | A + GGYTTTAYAARGTA (SEQ ID NO: 13080) |
| 54 | AGGYTT + TAYAARGTA (SEQ ID NO: 13081) |
| 54 | AG + GYTTTAYAARGTA (SEQ ID NO: 13082) |
| 54 | AGGYTTTA + YAARGTA (SEQ ID NO: 13083) |
| 54 | AGGYTTTAYAA + RGTA (SEQ ID NO: 13084) |
| 54 | AGGYTTTAYAARGT + A (SEQ ID NO: 13085) |
| 54 | AGGYTTTAY + AARGTA (SEQ ID NO: 13086) |
| 54 | AGGYT + TT + A + YAARGTA (SEQ ID NO: 13087) |
| 54 | AG + GYTTT + A + YAARGTA (SEQ ID NO: 13088) |
| 54 | A + GGYTTT + A + YAARGTA (SEQ ID NO: 13089) |
| 54 | AGG + YTTT + A + YAARGTA (SEQ ID NO: 13090) |
| 54 | AGGYTTT + A + YAARGT + A (SEQ ID NO: 13091) |
| 54 | AGGYTTT + A + YAARG + TA (SEQ ID NO: 13092) |
| 54 | AGGYTTT + A + YAA + RGTA (SEQ ID NO: 13093) |
| 54 | AGGYTTT + A + Y + AARGTA (SEQ ID NO: 13094) |
| 54 | GAGGYTT + T + TYAARGT (SEQ ID NO: 13095) |
| 54 | GA + GGYTTTTYAARGT (SEQ ID NO: 13096) |
| 54 | +GAGGYTTTTYAARGT (SEQ ID NO: 13097) |
| 54 | G + AGGYTTTTYAARGT (SEQ ID NO: 13098) |
| 54 | GAGGY + TTTTYAARGT (SEQ ID NO: 13099) |
| 54 | GAGGYTTTTY + AARGT (SEQ ID NO: 13100) |
| 54 | GAGGYTTTTYAARGT (SEQ ID NO: 13101) |
| 54 | GAGGYTTTTYAARG + T (SEQ ID NO: 13102) |
| 54 | GAGGYTTTTYAARGTA (SEQ ID NO: 13103) |
| 54 | G + AGGYTT + T + TYAARGT (SEQ ID NO: 13104) |
| 54 | +GAGGYTT + T + TYAARGT (SEQ ID NO: 13105) |
| 54 | GAGGY + TT + T + TYAARGT (SEQ ID NO: 13106) |
| 54 | GA + GGYTT + T + TYAARGT (SEQ ID NO: 13107) |
| 54 | GAGGYTT + T + TYAA + RGT (SEQ ID NO: 13108) |
| 54 | GAGGYTT + T + TYA + ARGT (SEQ ID NO: 13109) |
| 54 | GAGGYTT + T + TYAAR + GT (SEQ ID NO: 13110) |
| 54 | GAGGYTT + T + TY + AARGT (SEQ ID NO: 13111) |
| 54 | TACTTTRACAAAACC (SEQ ID NO: 13112) |
| 54 | TACTTTRGTAAAACC (SEQ ID NO: 13113) |
| 54 | TACTTTRGCAAAACC (SEQ ID NO: 13114) |
| 54 | TACTTTRAGAAAACC (SEQ ID NO: 13115) |

TABLE 10 -continued

| | |
|---|---|
| 54 | TACTTTRCTAAAACC (SEQ ID NO: 13116) |
| 54 | TACTTTCATAAAACC (SEQ ID NO: 13117) |
| 54 | AGGYTTTATAARGTAARRC (SEQ ID NO: 13118) |
| 54 | GAGGYTTTAYAARGTAARR (SEQ ID NO: 13119) |
| 54 | GGAGGYTTTTYAARGTAAR (SEQ ID NO: 13120) |
| 54 | AGGYTTTATAARGTAARR (SEQ ID NO: 13121) |
| 54 | GAGGYTTTAYAARGTAAR (SEQ ID NO: 13122) |
| 54 | GGAGGYTTTTYAARGTAA (SEQ ID NO: 13123) |
| 54 | GGYTTTATAARGTAARR (SEQ ID NO: 13124) |
| 54 | AGGYTTTAYAARGTAAR (SEQ ID NO: 13125) |
| 54 | GAGGYTTTTYAARGTAA (SEQ ID NO: 13126) |
| 54 | GGYTTTATAARGTAA (SEQ ID NO: 13127) |
| 54 | GGYTTTATAARGTAAR (SEQ ID NO: 13128) |
| 54 | AGGYTTTAYAARGTA (SEQ ID NO: 13129) |
| 54 | GAGGYTTTTYAARGT (SEQ ID NO: 13130) |
| 58 | AARGTAAR + R + ARTATGAKSA (SEQ ID NO: 13131) |
| 58 | AA + RGTAARRARTATGAKSA (SEQ ID NO: 13132) |
| 58 | AARGTAA + RRARTATGAKSA (SEQ ID NO: 13133) |
| 58 | A + ARGTAARRARTATGAKSA (SEQ ID NO: 13134) |
| 58 | AARGTAAR + RARTATGAKSA (SEQ ID NO: 13135) |
| 58 | AARGTAARRART + ATGAKSA (SEQ ID NO: 13136) |
| 58 | AARGTAARRARTATGAK + SA (SEQ ID NO: 13137) |
| 58 | AARGTAARRA + RTATGAKSA (SEQ ID NO: 13138) |
| 58 | AARGTAARRAR + TATGAKSA (SEQ ID NO: 13139) |
| 58 | AA + RGTAAR + R + ARTATGAKSA (SEQ ID NO: 13140) |
| 58 | AARG + TAAR + R + ARTATGAKSA (SEQ ID NO: 13141) |
| 58 | AAR + GTAAR + R + ARTATGAKSA (SEQ ID NO: 13142) |
| 58 | A + ARGTAAR + R + ARTATGAKSA (SEQ ID NO: 13143) |
| 58 | AARGTAAR + R + ARTATGAK + SA (SEQ ID NO: 13144) |
| 58 | AARGTAAR + R + ARTAT + GAKSA (SEQ ID NO: 13145) |
| 58 | AARGTAAR + R + ARTA + TGAKSA (SEQ ID NO: 13146) |
| 58 | AARGTAAR + R + AR + TATGAKSA (SEQ ID NO: 13147) |
| 58 | AARGTAAR + R + ARTATGAKS (SEQ ID NO: 13148) |
| 58 | AA + RGTAARRARTATGAKS (SEQ ID NO: 13149) |
| 58 | AARGTAA + RRARTATGAKS (SEQ ID NO: 13150) |
| 58 | A + ARGTAARRARTATGAKS (SEQ ID NO: 13151) |
| 58 | AARGTAAR + RARTATGAKS (SEQ ID NO: 13152) |
| 58 | AARGTAARRART + ATGAKS (SEQ ID NO: 13153) |
| 58 | AARGTAARRARTATGAK + S (SEQ ID NO: 13154) |
| 58 | AARGTAARRA + RTATGAKS (SEQ ID NO: 13155) |

TABLE 10 -continued

| 58 | AARGTAARRAR + TATGAKS (SEQ ID NO: 13156) |
| 58 | AA + RGTAAR + R + ARTATGAKS (SEQ ID NO: 13157) |
| 58 | AARG + TAAR + R + ARTATGAKS (SEQ ID NO: 13158) |
| 58 | AAR + GTAAR + R + ARTATGAKS (SEQ ID NO: 13159) |
| 58 | A + ARGTAAR + R + ARTATGAKS (SEQ ID NO: 13160) |
| 58 | AARGTAAR + R + ARTATGAK + S (SEQ ID NO: 13161) |
| 58 | AARGTAAR + R + ARTAT + GAKS (SEQ ID NO: 13162) |
| 58 | AARGTAAR + R + ARTA + TGAKS (SEQ ID NO: 13163) |
| 58 | AARGTAAR + R + AR + TATGAKS (SEQ ID NO: 13164) |
| 58 | ARGTAAR + R + ARTATGAKS (SEQ ID NO: 13165) |
| 58 | A + RGTAARRARTATGAKS (SEQ ID NO: 13166) |
| 58 | ARGTAA + RRARTATGAKS (SEQ ID NO: 13167) |
| 58 | +ARGTAARRARTATGAKS (SEQ ID NO: 13168) |
| 58 | ARGTAAR + RARTATGAKS (SEQ ID NO: 13169) |
| 58 | ARGTAARRART + ATGAKS (SEQ ID NO: 13170) |
| 58 | ARGTAARRARTATGAK + S (SEQ ID NO: 13171) |
| 58 | ARGTAARRA + RTATGAKS (SEQ ID NO: 13172) |
| 58 | ARGTAARRAR + TATGAKS (SEQ ID NO: 13173) |
| 58 | A + RGTAAR + R + ARTATGAKS (SEQ ID NO: 13174) |
| 58 | ARG + TAAR + R + ARTATGAKS (SEQ ID NO: 13175) |
| 58 | AR + GTAAR + R + ARTATGAKS (SEQ ID NO: 13176) |
| 58 | +ARGTAAR + R + ARTATGAKS (SEQ ID NO: 13177) |
| 58 | ARGTAAR + R + ARTATGAK + S (SEQ ID NO: 13178) |
| 58 | ARGTAAR + R + ARTAT + GAKS (SEQ ID NO: 13179) |
| 58 | ARGTAAR + R + ARTA + TGAKS (SEQ ID NO: 13180) |
| 58 | ARGTAAR + R + AR + TATGAKS (SEQ ID NO: 13181) |
| 58 | ARGTAAR + R + ARTATGA (SEQ ID NO: 13182) |
| 58 | A + RGTAARRARTATGA (SEQ ID NO: 13183) |
| 58 | ARGTAA + RRARTATGA (SEQ ID NO: 13184) |
| 58 | +ARGTAARRARTATGA (SEQ ID NO: 13185) |
| 58 | ARGTAAR + RARTATGA (SEQ ID NO: 13186) |
| 58 | ARGTAARRART + ATGA (SEQ ID NO: 13187) |
| 58 | ARGTAARRARTATGAK (SEQ ID NO: 13188) |
| 58 | ARGTAARRA + RTATGA (SEQ ID NO: 13189) |
| 58 | ARGTAARRAR + TATGA (SEQ ID NO: 13190) |
| 58 | A + RGTAAR + R + ARTATGA (SEQ ID NO: 13191) |
| 58 | ARG + TAAR + R + ARTATGA (SEQ ID NO: 13192) |
| 58 | AR + GTAAR + R + ARTATGA (SEQ ID NO: 13193) |
| 58 | +ARGTAAR + R + ARTATGA (SEQ ID NO: 13194) |
| 58 | ARGTAAR + R + ARTATGAK (SEQ ID NO: 13195) |

TABLE 10 -continued

| | |
|---|---|
| 58 | ARGTAAR + R + ARTAT + GA (SEQ ID NO: 13196) |
| 58 | ARGTAAR + R + ARTA + TGA (SEQ ID NO: 13197) |
| 58 | ARGTAAR + R + AR + TATGA (SEQ ID NO: 13198) |
| 58 | AGTAAGAGARTATGA (SEQ ID NO: 13199) |
| 58 | AARGTAARRARTATGAKSA (SEQ ID NO: 13200) |
| 58 | AARGTAARRARTATGAKS (SEQ ID NO: 13201) |
| 58 | ARGTAARRARTATGAKS (SEQ ID NO: 13202) |
| 58 | ARGTAARRARTATGA (SEQ ID NO: 13203) |
| 71 | GGRMAWAR + R + CYATAGGKWC (SEQ ID NO: 13204) |
| 71 | G + GRMAWARRCYATAGGKWC (SEQ ID NO: 13205) |
| 71 | GGRMAW + ARRCYATAGGKWC (SEQ ID NO: 13206) |
| 71 | GGR + MAWARRCYATAGGKWC (SEQ ID NO: 13207) |
| 71 | GGRM + AWARRCYATAGGKWC (SEQ ID NO: 13208) |
| 71 | GGRMAWARRCYATA + GGKWC (SEQ ID NO: 13209) |
| 71 | GGRMAWARRCYATAG + GKWC (SEQ ID NO: 13210) |
| 71 | GGRMAWARR + CYATAGGKWC (SEQ ID NO: 13211) |
| 71 | GGRMAWARRC + YATAGGKWC (SEQ ID NO: 13212) |
| 71 | G + GRMAWAR + R + CYATAGGKWC (SEQ ID NO: 13213) |
| 71 | GGRMAWA + R + R + CYATAGGKWC (SEQ ID NO: 13214) |
| 71 | GG + RMAWAR + R + CYATAGGKWC (SEQ ID NO: 13215) |
| 71 | GGRMAW + AR + R + CYATAGGKWC (SEQ ID NO: 13216) |
| 71 | GGRMAWAR + R + C + YATAGGKWC (SEQ ID NO: 13217) |
| 71 | GGRMAWAR + R + CYAT + AGGKWC (SEQ ID NO: 13218) |
| 71 | GGRMAWAR + R + CYATAGG + KWC (SEQ ID NO: 13219) |
| 71 | GGRMAWAR + R + CYA + TAGGKWC (SEQ ID NO: 13220) |
| 71 | GGRMAWAR + R + CYATAGGKW (SEQ ID NO: 13221) |
| 71 | G + GRMAWARRCYATAGGKW (SEQ ID NO: 13222) |
| 71 | GGRMAW + ARRCYATAGGKW (SEQ ID NO: 13223) |
| 71 | GGR + MAWARRCYATAGGKW (SEQ ID NO: 13224) |
| 71 | GGRM + AWARRCYATAGGKW (SEQ ID NO: 13225) |
| 71 | GGRMAWARRCYATA + GGKW (SEQ ID NO: 13226) |
| 71 | GGRMAWARRCYATAG + GKW (SEQ ID NO: 13227) |
| 71 | GGRMAWARR + CYATAGGKW (SEQ ID NO: 13228) |
| 71 | GGRMAWARRC + YATAGGKW (SEQ ID NO: 13229) |
| 71 | G + GRMAWAR + R + CYATAGGKW (SEQ ID NO: 13230) |
| 71 | GGRMAWA + R + R + CYATAGGKW (SEQ ID NO: 13231) |
| 71 | GG + RMAWAR + R + CYATAGGKW (SEQ ID NO: 13232) |
| 71 | GGRMAW + AR + R + CYATAGGKW (SEQ ID NO: 13233) |
| 71 | GGRMAWAR + R + C + YATAGGKW (SEQ ID NO: 13234) |
| 71 | GGRMAWAR + R + CYAT + AGGKW (SEQ ID NO: 13235) |

TABLE 10 -continued

| | |
|---|---|
| 71 | GGRMAWAR + R + CYATAGG + KW (SEQ ID NO: 13236) |
| 71 | GGRMAWAR + R + CYA + TAGGKW (SEQ ID NO: 13237) |
| 71 | GRMAWAR + R + CYATAGGKW (SEQ ID NO: 13238) |
| 71 | +GRMAWARRCYATAGGKW (SEQ ID NO: 13239) |
| 71 | GRMAW + ARRCYATAGGKW (SEQ ID NO: 13240) |
| 71 | GR + MAWARRCYATAGGKW (SEQ ID NO: 13241) |
| 71 | GRM + AWARRCYATAGGKW (SEQ ID NO: 13242) |
| 71 | GRMAWARRCYATA + GGKW (SEQ ID NO: 13243) |
| 71 | GRMAWARRCYATAG + GKW (SEQ ID NO: 13244) |
| 71 | GRMAWARR + CYATAGGKW (SEQ ID NO: 13245) |
| 71 | GRMAWARRC + YATAGGKW (SEQ ID NO: 13246) |
| 71 | +GRMAWAR + R + CYATAGGKW (SEQ ID NO: 13247) |
| 71 | GRMAWA + R + R + CYATAGGKW (SEQ ID NO: 13248) |
| 71 | G + RMAWAR + R + CYATAGGKW (SEQ ID NO: 13249) |
| 71 | GRMAW + AR + R + CYATAGGKW (SEQ ID NO: 13250) |
| 71 | GRMAWAR + R + C + YATAGGKW (SEQ ID NO: 13251) |
| 71 | GRMAWAR + R + CYAT + AGGKW (SEQ ID NO: 13252) |
| 71 | GRMAWAR + R + CYATAGG + KW (SEQ ID NO: 13253) |
| 71 | GRMAWAR + R + CYA + TAGGKW (SEQ ID NO: 13254) |
| 71 | GRMAWAR + R + CYATAGG (SEQ ID NO: 13255) |
| 71 | +GRMAWARRCYATAGG (SEQ ID NO: 13256) |
| 71 | GRMAW + ARRCYATAGG (SEQ ID NO: 13257) |
| 71 | GR + MAWARRCYATAGG (SEQ ID NO: 13258) |
| 71 | GRM + AWARRCYATAGG (SEQ ID NO: 13259) |
| 71 | GRMAWARRCYATA + GG (SEQ ID NO: 13260) |
| 71 | GRMAWARRCYATAG + G (SEQ ID NO: 13261) |
| 71 | GRMAWARR + CYATAGG (SEQ ID NO: 13262) |
| 71 | GRMAWARRC + YATAGG (SEQ ID NO: 13263) |
| 71 | +GRMAWAR + R + CYATAGG (SEQ ID NO: 13264) |
| 71 | GRMAWA + R + R + CYATAGG (SEQ ID NO: 13265) |
| 71 | G + RMAWAR + R + CYATAGG (SEQ ID NO: 13266) |
| 71 | GRMAW + AR + R + CYATAGG (SEQ ID NO: 13267) |
| 71 | GRMAWAR + R + C + YATAGG (SEQ ID NO: 13268) |
| 71 | GRMAWAR + R + CYAT + AGG (SEQ ID NO: 13269) |
| 71 | GRMAWAR + R + CYATAGG (SEQ ID NO: 13270) |
| 71 | GRMAWAR + R + CYA + TAGG (SEQ ID NO: 13271) |
| 71 | CATAAAATHATAGGT (SEQ ID NO: 13272) |
| 71 | CATAAACTHATAGGT (SEQ ID NO: 13273) |
| 71 | CATAAATTAATAGGT (SEQ ID NO: 13274) |
| 71 | GGRMAWARRCYATAGGKWC (SEQ ID NO: 13275) |

TABLE 10 -continued

| | |
|---|---|
| 71 | GGRMAWARRCYATAGGKW (SEQ ID NO: 13276) |
| 71 | GRMAWARRCYATAGGKW (SEQ ID NO: 13277) |
| 71 | GRMAWARRCYATAGG (SEQ ID NO: 13278) |
| 73 | RRGCYATA + G + KWCAGTRYTR (SEQ ID NO: 13279) |
| 73 | RRG + CYATAGKWCAGTRYTR (SEQ ID NO: 13280) |
| 73 | R + RGCYATAGKWCAGTRYTR (SEQ ID NO: 13281) |
| 73 | RRGC + YATAGKWCAGTRYTR (SEQ ID NO: 13282) |
| 73 | RRGCYAT + AGKWCAGTRYTR (SEQ ID NO: 13283) |
| 73 | RRGCYATAGKWCAGTRY + TR (SEQ ID NO: 13284) |
| 73 | RRGCYATAG + KWCAGTRYTR (SEQ ID NO: 13285) |
| 73 | RRGCYATAGKWC + AGTRYTR (SEQ ID NO: 13286) |
| 73 | RRGCYATAGK + WCAGTRYTR (SEQ ID NO: 13287) |
| 73 | RRGCYAT + A + G + KWCAGTRYTR (SEQ ID NO: 13288) |
| 73 | RRGCY + ATA + G + KWCAGTRYTR (SEQ ID NO: 13289) |
| 73 | RR + GCYATA + G + KWCAGTRYTR (SEQ ID NO: 13290) |
| 73 | RRG + CYATA + G + KWCAGTRYTR (SEQ ID NO: 13291) |
| 73 | RRGCYATA + G + KWC + AGTRYTR (SEQ ID NO: 13292) |
| 73 | RRGCYATA + G + K + WCAGTRYTR (SEQ ID NO: 13293) |
| 73 | RRGCYATA + G + KWCAGTR + YTR (SEQ ID NO: 13294) |
| 73 | RRGCYATA + G + KW + CAGTRYTR (SEQ ID NO: 13295) |
| 73 | ARRGCYAT + A + GKWCAGTRYT (SEQ ID NO: 13296) |
| 73 | ARRGCYA + TAGKWCAGTRYT (SEQ ID NO: 13297) |
| 73 | A + RRGCYATAGKWCAGTRYT (SEQ ID NO: 13298) |
| 73 | AR + RGCYATAGKWCAGTRYT (SEQ ID NO: 13299) |
| 73 | ARRG + CYATAGKWCAGTRYT (SEQ ID NO: 13300) |
| 73 | ARRGCYATAGKWC + AGTRYT (SEQ ID NO: 13301) |
| 73 | ARRGCYATAGK + WCAGTRYT (SEQ ID NO: 13302) |
| 73 | ARRGCYATAG + KWCAGTRYT (SEQ ID NO: 13303) |
| 73 | ARRGCYATAGKWCAGTR + YT (SEQ ID NO: 13304) |
| 73 | ARRGCYA + T + A + GKWCAGTRYT (SEQ ID NO: 13305) |
| 73 | ARRG + CYAT + A + GKWCAGTRYT (SEQ ID NO: 13306) |
| 73 | A + RRGCYAT + A + GKWCAGTRYT (SEQ ID NO: 13307) |
| 73 | ARRGCY + AT + A + GKWCAGTRYT (SEQ ID NO: 13308) |
| 73 | ARRGCYAT + A + GKWC + AGTRYT (SEQ ID NO: 13309) |
| 73 | ARRGCYAT + A + GKWCAGTR + YT (SEQ ID NO: 13310) |
| 73 | ARRGCYAT + A + GKW + CAGTRYT (SEQ ID NO: 13311) |
| 73 | ARRGCYAT + A + GK + WCAGTRYT (SEQ ID NO: 13312) |
| 73 | RRGCYATA + G + KWCAGTRYT (SEQ ID NO: 13313) |
| 73 | RRG + CYATAGKWCAGTRYT (SEQ ID NO: 13314) |
| 73 | R + RGCYATAGKWCAGTRYT (SEQ ID NO: 13315) |

TABLE 10 -continued

| 73 | RRGC + YATAGKWCAGTRYT (SEQ ID NO: 13316) |
| 73 | RRGCYAT + AGKWCAGTRYT (SEQ ID NO: 13317) |
| 73 | RRGCYATAGKWCAGTRY + T (SEQ ID NO: 13318) |
| 73 | RRGCYATAG + KWCAGTRYT (SEQ ID NO: 13319) |
| 73 | RRGCYATAGKWC + AGTRYT (SEQ ID NO: 13320) |
| 73 | RRGCYATAGK + WCAGTRYT (SEQ ID NO: 13321) |
| 73 | RRGCYAT + A + G + KWCAGTRYT (SEQ ID NO: 13322) |
| 73 | RRGCY + ATA + G + KWCAGTRYT (SEQ ID NO: 13323) |
| 73 | RR + GCYATA + G + KWCAGTRYT (SEQ ID NO: 13324) |
| 73 | RRG + CYATA + G + KWCAGTRYT (SEQ ID NO: 13325) |
| 73 | RRGCYATA + G + KWC + AGTRYT (SEQ ID NO: 13326) |
| 73 | RRGCYATA + G + K + WCAGTRYT (SEQ ID NO: 13327) |
| 73 | RRGCYATA + G + KWCAGTR + YT (SEQ ID NO: 13328) |
| 73 | RRGCYATA + G + KW + CAGTRYT (SEQ ID NO: 13329) |
| 73 | ARRGCYAT + A + GKWCAGTRY (SEQ ID NO: 13330) |
| 73 | ARRGCYA + TAGKWCAGTRY (SEQ ID NO: 13331) |
| 73 | A + RRGCYATAGKWCAGTRY (SEQ ID NO: 13332) |
| 73 | AR + RGCYATAGKWCAGTRY (SEQ ID NO: 13333) |
| 73 | ARRG + CYATAGKWCAGTRY (SEQ ID NO: 13334) |
| 73 | ARRGCYATAGKWC + AGTRY (SEQ ID NO: 13335) |
| 73 | ARRGCYATAGK + WCAGTRY (SEQ ID NO: 13336) |
| 73 | ARRGCYATAG + KWCAGTRY (SEQ ID NO: 13337) |
| 73 | ARRGCYATAGKWCAGTR + Y (SEQ ID NO: 13338) |
| 73 | ARRGCYA + T + A + GKWCAGTRY (SEQ ID NO: 13339) |
| 73 | ARRG + CYAT + A + GKWCAGTRY (SEQ ID NO: 13340) |
| 73 | A + RRGCYAT + A + GKWCAGTRY (SEQ ID NO: 13341) |
| 73 | ARRGCY + AT + A + GKWCAGTRY (SEQ ID NO: 13342) |
| 73 | ARRGCYAT + A + GKWC + AGTRY (SEQ ID NO: 13343) |
| 73 | ARRGCYAT + A + GKWCAGTR + Y (SEQ ID NO: 13344) |
| 73 | ARRGCYAT + A + GKW + CAGTRY (SEQ ID NO: 13345) |
| 73 | ARRGCYAT + A + GK + WCAGTRY (SEQ ID NO: 13346) |
| 73 | RGCYATA + G + KWCAGTRYT (SEQ ID NO: 13347) |
| 73 | RG + CYATAGKWCAGTRYT (SEQ ID NO: 13348) |
| 73 | +RGCYATAGKWCAGTRYT (SEQ ID NO: 13349) |
| 73 | RGC + YATAGKWCAGTRYT (SEQ ID NO: 13350) |
| 73 | RGCYAT + AGKWCAGTRYT (SEQ ID NO: 13351) |
| 73 | RGCYATAGKWCAGTRY + T (SEQ ID NO: 13352) |
| 73 | RGCYATAG + KWCAGTRYT (SEQ ID NO: 13353) |
| 73 | RGCYATAGKWC + AGTRYT (SEQ ID NO: 13354) |
| 73 | RGCYATAGK + WCAGTRYT (SEQ ID NO: 13355) |

TABLE 10 -continued

| 73 | RGCYAT + A + G + KWCAGTRYT (SEQ ID NO: 13356) |
| 73 | RGCY + ATA + G + KWCAGTRYT (SEQ ID NO: 13357) |
| 73 | R + GCYATA + G + KWCAGTRYT (SEQ ID NO: 13358) |
| 73 | RG + CYATA + G + KWCAGTRYT (SEQ ID NO: 13359) |
| 73 | RGCYATA + G + KWC + AGTRYT (SEQ ID NO: 13360) |
| 73 | RGCYATA + G + K + WCAGTRYT (SEQ ID NO: 13361) |
| 73 | RGCYATA + G + KWCAGTR + YT (SEQ ID NO: 13362) |
| 73 | RGCYATA + G + KW + CAGTRYT (SEQ ID NO: 13363) |
| 73 | RRGCYAT + A + GKWCAGTRY (SEQ ID NO: 13364) |
| 73 | RRGCYA + TAGKWCAGTRY (SEQ ID NO: 13365) |
| 73 | +RRGCYATAGKWCAGTRY (SEQ ID NO: 13366) |
| 73 | R + RGCYATAGKWCAGTRY (SEQ ID NO: 13367) |
| 73 | RRG + CYATAGKWCAGTRY (SEQ ID NO: 13368) |
| 73 | RRGCYATAGKWC + AGTRY (SEQ ID NO: 13369) |
| 73 | RRGCYATAGK + WCAGTRY (SEQ ID NO: 13370) |
| 73 | RRGCYATAG + KWCAGTRY (SEQ ID NO: 13371) |
| 73 | RRGCYATAGKWCAGTR + Y (SEQ ID NO: 13372) |
| 73 | RRGCYA + T + A + GKWCAGTRY (SEQ ID NO: 13373) |
| 73 | RRG + CYAT + A + GKWCAGTRY (SEQ ID NO: 13374) |
| 73 | +RRGCYAT + A + GKWCAGTRY (SEQ ID NO: 13375) |
| 73 | RRGCY + AT + A + GKWCAGTRY (SEQ ID NO: 13376) |
| 73 | RRGCYAT + A + GKWC + AGTRY (SEQ ID NO: 13377) |
| 73 | RRGCYAT + A + GKWCAGTR + Y (SEQ ID NO: 13378) |
| 73 | RRGCYAT + A + GKW + CAGTRY (SEQ ID NO: 13379) |
| 73 | RRGCYAT + A + GK + WCAGTRY (SEQ ID NO: 13380) |
| 73 | RGCYATA + G + KWCAGTR (SEQ ID NO: 13381) |
| 73 | RG + CYATAGKWCAGTR (SEQ ID NO: 13382) |
| 73 | +RGCYATAGKWCAGTR (SEQ ID NO: 13383) |
| 73 | RGC + YATAGKWCAGTR (SEQ ID NO: 13384) |
| 73 | RGCYAT + AGKWCAGTR (SEQ ID NO: 13385) |
| 73 | RGCYATAGKWCAGTRY (SEQ ID NO: 13386) |
| 73 | RGCYATAG + KWCAGTR (SEQ ID NO: 13387) |
| 73 | RGCYATAGKWC + AGTR (SEQ ID NO: 13388) |
| 73 | RGCYATAGK + WCAGTR (SEQ ID NO: 13389) |
| 73 | RGCYAT + A + G + KWCAGTR (SEQ ID NO: 13390) |
| 73 | RGCY + ATA + G + KWCAGTR (SEQ ID NO: 13391) |
| 73 | R + GCYATA + G + KWCAGTR (SEQ ID NO: 13392) |
| 73 | RG + CYATA + G + KWCAGTR (SEQ ID NO: 13393) |
| 73 | RGCYATA + G + KWC + AGTR (SEQ ID NO: 13394) |
| 73 | RGCYATA + G + K + WCAGTR (SEQ ID NO: 13395) |

TABLE 10 -continued

| | |
|---|---|
| 73 | RGCYATA + G + KWCAGTR (SEQ ID NO: 13396) |
| 73 | RGCYATA + G + KW + CAGTR (SEQ ID NO: 13397) |
| 73 | RRGCYAT + A + GKWCAGT (SEQ ID NO: 13398) |
| 73 | RRGCYA + TAGKWCAGT (SEQ ID NO: 13399) |
| 73 | +RRGCYATAGKWCAGT (SEQ ID NO: 13400) |
| 73 | R + RGCYATAGKWCAGT (SEQ ID NO: 13401) |
| 73 | RRG + CYATAGKWCAGT (SEQ ID NO: 13402) |
| 73 | RRGCYATAGKWC + AGT (SEQ ID NO: 13403) |
| 73 | RRGCYATAGK + WCAGT (SEQ ID NO: 13404) |
| 73 | RRGCYATAG + KWCAGT (SEQ ID NO: 13405) |
| 73 | RRGCYATAGKWCAGTR (SEQ ID NO: 13406) |
| 73 | RRGCYA + T + A + GKWCAGT (SEQ ID NO: 13407) |
| 73 | RRG + CYAT + A + GKWCAGT (SEQ ID NO: 13408) |
| 73 | +RRGCYAT + A + GKWCAGT (SEQ ID NO: 13409) |
| 73 | RRGCY + AT + A + GKWCAGT (SEQ ID NO: 13410) |
| 73 | RRGCYAT + A + GKWC + AGT (SEQ ID NO: 13411) |
| 73 | RRGCYAT + A + GKWCAGTR (SEQ ID NO: 13412) |
| 73 | RRGCYAT + A + GKW + CAGT (SEQ ID NO: 13413) |
| 73 | RRGCYAT + A + GK + WCAGT (SEQ ID NO: 13414) |
| 73 | TACTGTRCTTATAGC (SEQ ID NO: 13415) |
| 73 | TACTGTNGTTATAGC (SEQ ID NO: 13416) |
| 73 | TACTGTRCATATAGC (SEQ ID NO: 13417) |
| 73 | TACTGTNGCTATAGC (SEQ ID NO: 13418) |
| 73 | RRGCYATAGKWCAGTRYTR (SEQ ID NO: 13419) |
| 73 | ARRGCYATAGKWCAGTRYT (SEQ ID NO: 13420) |
| 73 | RRGCYATAGKWCAGTRYT (SEQ ID NO: 13421) |
| 73 | ARRGCYATAGKWCAGTRY (SEQ ID NO: 13422) |
| 73 | RGCYATAGKWCAGTRYT (SEQ ID NO: 13423) |
| 73 | RRGCYATAGKWCAGTRY (SEQ ID NO: 13424) |
| 73 | RGCYATAGKWCAGTR (SEQ ID NO: 13425) |
| 73 | RRGCYATAGKWCAGT (SEQ ID NO: 13426) |
| 74 | GCYATAGG + K + CAGTRYTRRT (SEQ ID NO: 13427) |
| 74 | GCYATAG + GKCAGTRYTRRT (SEQ ID NO: 13428) |
| 74 | GCY + ATAGGKCAGTRYTRRT (SEQ ID NO: 13429) |
| 74 | GC + YATAGGKCAGTRYTRRT (SEQ ID NO: 13430) |
| 74 | GCYATAGG + KCAGTRYTRRT (SEQ ID NO: 13431) |
| 74 | GCYATAGGKCA + GTRYTRRT (SEQ ID NO: 13432) |
| 74 | GCYATAGGKCAGTRYTR + RT (SEQ ID NO: 13433) |
| 74 | GCYATAGGK + CAGTRYTRRT (SEQ ID NO: 13434) |
| 74 | GCYATAGGKCAGTRYT + RRT (SEQ ID NO: 13435) |

TABLE 10 -continued

| | |
|---|---|
| 74 | GC + YATAGG + K + CAGTRYTRRT (SEQ ID NO: 13436) |
| 74 | GCYATA + GG + K + CAGTRYTRRT (SEQ ID NO: 13437) |
| 74 | GCY + ATAGG + K + CAGTRYTRRT (SEQ ID NO: 13438) |
| 74 | GCYA + TAGG + K + CAGTRYTRRT (SEQ ID NO: 13439) |
| 74 | GCYATAGG + K + CAGTRYTR + RT (SEQ ID NO: 13440) |
| 74 | GCYATAGG + K + CAG + TRYTRRT (SEQ ID NO: 13441) |
| 74 | GCYATAGG + K + CAGT + RYTRRT (SEQ ID NO: 13442) |
| 74 | GCYATAGG + K + C + AGTRYTRRT (SEQ ID NO: 13443) |
| 74 | GCYATAGG + K + CAGTRYTRR (SEQ ID NO: 13444) |
| 74 | GCYATAG + GKCAGTRYTRR (SEQ ID NO: 13445) |
| 74 | GCY + ATAGGKCAGTRYTRR (SEQ ID NO: 13446) |
| 74 | GC + YATAGGKCAGTRYTRR (SEQ ID NO: 13447) |
| 74 | GCYATAGG + KCAGTRYTRR (SEQ ID NO: 13448) |
| 74 | GCYATAGGKCA + GTRYTRR (SEQ ID NO: 13449) |
| 74 | GCYATAGGKCAGTRYTR + R (SEQ ID NO: 13450) |
| 74 | GCYATAGGK + CAGTRYTRR (SEQ ID NO: 13451) |
| 74 | GCYATAGGKCAGTRYT + RR (SEQ ID NO: 13452) |
| 74 | GC + YATAGG + K + CAGTRYTRR (SEQ ID NO: 13453) |
| 74 | GCYATA + GG + K + CAGTRYTRR (SEQ ID NO: 13454) |
| 74 | GCY + ATAGG + K + CAGTRYTRR (SEQ ID NO: 13455) |
| 74 | GCYA + TAGG + K + CAGTRYTRR (SEQ ID NO: 13456) |
| 74 | GCYATAGG + K + CAGTRYTR + R (SEQ ID NO: 13457) |
| 74 | GCYATAGG + K + CAG + TRYTRR (SEQ ID NO: 13458) |
| 74 | GCYATAGG + K + CAGT + RYTRR (SEQ ID NO: 13459) |
| 74 | GCYATAGG + K + C + AGTRYTRR (SEQ ID NO: 13460) |
| 74 | CYATAGG + K + CAGTRYTRR (SEQ ID NO: 13461) |
| 74 | CYATAG + GKCAGTRYTRR (SEQ ID NO: 13462) |
| 74 | CY + ATAGGKCAGTRYTRR (SEQ ID NO: 13463) |
| 74 | C + YATAGGKCAGTRYTRR (SEQ ID NO: 13464) |
| 74 | CYATAGG + KCAGTRYTRR (SEQ ID NO: 13465) |
| 74 | CYATAGGKCA + GTRYTRR (SEQ ID NO: 13466) |
| 74 | CYATAGGKCAGTRYTR + R (SEQ ID NO: 13467) |
| 74 | CYATAGGK + CAGTRYTRR (SEQ ID NO: 13468) |
| 74 | CYATAGGKCAGTRYT + RR (SEQ ID NO: 13469) |
| 74 | C + YATAGG + K + CAGTRYTRR (SEQ ID NO: 13470) |
| 74 | CYATA + GG + K + CAGTRYTRR (SEQ ID NO: 13471) |
| 74 | CY + ATAGG + K + CAGTRYTRR (SEQ ID NO: 13472) |
| 74 | CYA + TAGG + K + CAGTRYTRR (SEQ ID NO: 13473) |
| 74 | CYATAGG + K + CAGTRYTR + R (SEQ ID NO: 13474) |
| 74 | CYATAGG + K + CAG + TRYTRR (SEQ ID NO: 13475) |

TABLE 10 -continued

| | |
|---|---|
| 74 | CYATAGG + K + CAGT + RYTRR (SEQ ID NO: 13476) |
| 74 | CYATAGG + K + C + AGTRYTRR (SEQ ID NO: 13477) |
| 74 | CYATAGG + K + CAGTRYT (SEQ ID NO: 13478) |
| 74 | CYATAG + GKCAGTRYT (SEQ ID NO: 13479) |
| 74 | CY + ATAGGKCAGTRYT (SEQ ID NO: 13480) |
| 74 | C + YATAGGKCAGTRYT (SEQ ID NO: 13481) |
| 74 | CYATAGG + KCAGTRYT (SEQ ID NO: 13482) |
| 74 | CYATAGGKCA + GTRYT (SEQ ID NO: 13483) |
| 74 | CYATAGGKCAGTRYTR (SEQ ID NO: 13484) |
| 74 | CYATAGGK + CAGTRYT (SEQ ID NO: 13485) |
| 74 | CYATAGGKCAGTRYT (SEQ ID NO: 13486) |
| 74 | C + YATAGG + K + CAGTRYT (SEQ ID NO: 13487) |
| 74 | CYATA + GG + K + CAGTRYT (SEQ ID NO: 13488) |
| 74 | CY + ATAGG + K + CAGTRYT (SEQ ID NO: 13489) |
| 74 | CYA + TAGG + K + CAGTRYT (SEQ ID NO: 13490) |
| 74 | CYATAGG + K + CAGTRYTR (SEQ ID NO: 13491) |
| 74 | CYATAGG + K + CAG + TRYT (SEQ ID NO: 13492) |
| 74 | CYATAGG + K + CAGT + RYT (SEQ ID NO: 13493) |
| 74 | CYATAGG + K + C + AGTRYT (SEQ ID NO: 13494) |
| 74 | ATAGGTCCRGTATTA (SEQ ID NO: 13495) |
| 74 | GCYATAGGKCAGTRYTRRT (SEQ ID NO: 13496) |
| 74 | GCYATAGGKCAGTRYTRR (SEQ ID NO: 13497) |
| 74 | CYATAGGKCAGTRYTRR (SEQ ID NO: 13498) |
| 74 | CYATAGGKCAGTRYT (SEQ ID NO: 13499) |
| 76 | GGKWCAGT + R + TRRTRGGRCC (SEQ ID NO: 13500) |
| 76 | GGKWCA + GTRTRRTRGGRCC (SEQ ID NO: 13501) |
| 76 | GGK + WCAGTRTRRTRGGRCC (SEQ ID NO: 13502) |
| 76 | GGKWCAGT + RTRRTRGGRCC (SEQ ID NO: 13503) |
| 76 | G + GKWCAGTRTRRTRGGRCC (SEQ ID NO: 13504) |
| 76 | GGKWCAGTRTRRTRGGR + CC (SEQ ID NO: 13505) |
| 76 | GGKWCAGTRTRRT + RGGRCC (SEQ ID NO: 13506) |
| 76 | GGKWCAGTRTR + RTRGGRCC (SEQ ID NO: 13507) |
| 76 | GGKWCAGTR + TRRTRGGRCC (SEQ ID NO: 13508) |
| 76 | GGKW + CAGT + R + TRRTRGGRCC (SEQ ID NO: 13509) |
| 76 | GG + KWCAGT + R + TRRTRGGRCC (SEQ ID NO: 13510) |
| 76 | GGKWC + AGT + R + TRRTRGGRCC (SEQ ID NO: 13511) |
| 76 | G + GKWCAGT + R + TRRTRGGRCC (SEQ ID NO: 13512) |
| 76 | GGKWCAGT + R + T + RRTRGGRCC (SEQ ID NO: 13513) |
| 76 | GGKWCAGT + R + TRR + TRGGRCC (SEQ ID NO: 13514) |
| 76 | GGKWCAGT + R + TRRT + RGGRCC (SEQ ID NO: 13515) |

TABLE 10 -continued

| | |
|---|---|
| 76 | GGKWCAGT + R + TRRTR + GGRCC (SEQ ID NO: 13516) |
| 76 | GGKWCAGT + R + TRRTRGGRC (SEQ ID NO: 13517) |
| 76 | GGKWCA + GTRTRRTRGGRC (SEQ ID NO: 13518) |
| 76 | GGK + WCAGTRTRRTRGGRC (SEQ ID NO: 13519) |
| 76 | GGKWCAGT + RTRRTRGGRC (SEQ ID NO: 13520) |
| 76 | G + GKWCAGTRTRRTRGGRC (SEQ ID NO: 13521) |
| 76 | GGKWCAGTRTRRTRGGR + C (SEQ ID NO: 13522) |
| 76 | GGKWCAGTRTRRT + RGGRC (SEQ ID NO: 13523) |
| 76 | GGKWCAGTRTR + RTGGRC (SEQ ID NO: 13524) |
| 76 | GGKWCAGTR + TRRTRGGRC (SEQ ID NO: 13525) |
| 76 | GGKW + CAGT + R + TRRTRGGRC (SEQ ID NO: 13526) |
| 76 | GG + KWCAGT + R + TRRTRGGRC (SEQ ID NO: 13527) |
| 76 | GGKWC + AGT + R + TRRTRGGRC (SEQ ID NO: 13528) |
| 76 | G + GKWCAGT + R + TRRTRGGRC (SEQ ID NO: 13529) |
| 76 | GGKWCAGT + R + T + RRTRGGRC (SEQ ID NO: 13530) |
| 76 | GGKWCAGT + R + TRR + TRGGRC (SEQ ID NO: 13531) |
| 76 | GGKWCAGT + R + TRRT + RGGRC (SEQ ID NO: 13532) |
| 76 | GGKWCAGT + R + TRRTR + GGRC (SEQ ID NO: 13533) |
| 76 | GKWCAGT + R + TRRTRGGRC (SEQ ID NO: 13534) |
| 76 | GKWCA + GTRTRRTRGGRC (SEQ ID NO: 13535) |
| 76 | GK + WCAGTRTRRTRGGRC (SEQ ID NO: 13536) |
| 76 | GKWCAGT + RTRRTRGGRC (SEQ ID NO: 13537) |
| 76 | +GKWCAGTRTRRTRGGRC (SEQ ID NO: 13538) |
| 76 | GKWCAGTRTRRTRGGR + C (SEQ ID NO: 13539) |
| 76 | GKWCAGTRTRRT + RGGRC (SEQ ID NO: 13540) |
| 76 | GKWCAGTRTR + RTGGRC (SEQ ID NO: 13541) |
| 76 | GKWCAGTR + TRRTRGGRC (SEQ ID NO: 13542) |
| 76 | GKW + CAGT + R + TRRTRGGRC (SEQ ID NO: 13543) |
| 76 | G + KWCAGT + R + TRRTRGGRC (SEQ ID NO: 13544) |
| 76 | GKWC + AGT + R + TRRTRGGRC (SEQ ID NO: 13545) |
| 76 | +GKWCAGT + R + TRRTRGGRC (SEQ ID NO: 13546) |
| 76 | GKWCAGT + R + T + RRTRGGRC (SEQ ID NO: 13547) |
| 76 | GKWCAGT + R + TRR + TRGGRC (SEQ ID NO: 13548) |
| 76 | GKWCAGT + R + TRRT + RGGRC (SEQ ID NO: 13549) |
| 76 | GKWCAGT + R + TRRTR + GGRC (SEQ ID NO: 13550) |
| 76 | GKWCAGT + R + TRRTRGG (SEQ ID NO: 13551) |
| 76 | GKWCA + GTRTRRTRGG (SEQ ID NO: 13552) |
| 76 | GK + WCAGTRTRRTRGG (SEQ ID NO: 13553) |
| 76 | GKWCAGT + RTRRTRGG (SEQ ID NO: 13554) |
| 76 | +GKWCAGTRTRRTRGG (SEQ ID NO: 13555) |

TABLE 10 -continued

| | |
|---|---|
| 76 | GKWCAGTRTRRTRGGR (SEQ ID NO: 13556) |
| 76 | GKWCAGTRTRRT + RGG (SEQ ID NO: 13557) |
| 76 | GKWCAGTRTR + RTRGG (SEQ ID NO: 13558) |
| 76 | GKWCAGTR + TRRTRGG (SEQ ID NO: 13559) |
| 76 | GKW + CAGT + R + TRRTRGG (SEQ ID NO: 13560) |
| 76 | G + KWCAGT + R + TRRTRGG (SEQ ID NO: 13561) |
| 76 | GKWC + AGT + R + TRRTRGG (SEQ ID NO: 13562) |
| 76 | +GKWCAGT + R + TRRTRGG (SEQ ID NO: 13563) |
| 76 | GKWCAGT + R + T + RRTRGG (SEQ ID NO: 13564) |
| 76 | GKWCAGT + R + TRR + TRGG (SEQ ID NO: 13565) |
| 76 | GKWCAGT + R + TRRT + RGG (SEQ ID NO: 13566) |
| 76 | GKWCAGT + R + TRRTR + GG (SEQ ID NO: 13567) |
| 76 | ACAGTAGTRGTAGGA (SEQ ID NO: 13568) |
| 76 | GGKWCAGTRTRRTRGGRCC (SEQ ID NO: 13569) |
| 76 | GGKWCAGTRTRRTRGGRC (SEQ ID NO: 13570) |
| 76 | GKWCAGTRTRRTRGGRC (SEQ ID NO: 13571) |
| 76 | GKWCAGTRTRRTRGG (SEQ ID NO: 13572) |
| 82 | CYACACCT + R + CAACATAATT (SEQ ID NO: 13573) |
| 82 | CYACA + CCTRCAACATAATT (SEQ ID NO: 13574) |
| 82 | CYA + CACCTRCAACATAATT (SEQ ID NO: 13575) |
| 82 | CYACAC + CTRCAACATAATT (SEQ ID NO: 13576) |
| 82 | CYACACCT + RCAACATAATT (SEQ ID NO: 13577) |
| 82 | CYACACCTRCAACAT + AATT (SEQ ID NO: 13578) |
| 82 | CYACACCTRCAACA + TAATT (SEQ ID NO: 13579) |
| 82 | CYACACCTRCAACATAA + TT (SEQ ID NO: 13580) |
| 82 | CYACACCTRCA + ACATAATT (SEQ ID NO: 13581) |
| 82 | CYAC + ACCT + R + CAACATAATT (SEQ ID NO: 13582) |
| 82 | CYA + CACCT + R + CAACATAATT (SEQ ID NO: 13583) |
| 82 | CYACACC + T + R + CAACATAATT (SEQ ID NO: 13584) |
| 82 | C + YACACCT + R + CAACATAATT (SEQ ID NO: 13585) |
| 82 | CYACACCT + R + CAAC + ATAATT (SEQ ID NO: 13586) |
| 82 | CYACACCT + R + CAACATAA + TT (SEQ ID NO: 13587) |
| 82 | CYACACCT + R + CAACA + TAATT (SEQ ID NO: 13588) |
| 82 | CYACACCT + R + CAA + CATAATT (SEQ ID NO: 13589) |
| 82 | CCYACACC + T + TCAACATAAT (SEQ ID NO: 13590) |
| 82 | CCYA + CACCTTCAACATAAT (SEQ ID NO: 13591) |
| 82 | CCYACACC + TTCAACATAAT (SEQ ID NO: 13592) |
| 82 | CC + YACACCTTCAACATAAT (SEQ ID NO: 13593) |
| 82 | CCYACAC + CTTCAACATAAT (SEQ ID NO: 13594) |
| 82 | CCYACACCTTCAA + CATAAT (SEQ ID NO: 13595) |

TABLE 10 -continued

| | |
|---|---|
| 82 | CCYACACCTTCAAC + ATAAT (SEQ ID NO: 13596) |
| 82 | CCYACACCTTCAACA + TAAT (SEQ ID NO: 13597) |
| 82 | CCYACACCTTC + AACATAAT (SEQ ID NO: 13598) |
| 82 | CCY + ACACC + T + TCAACATAAT (SEQ ID NO: 13599) |
| 82 | CC + YACACC + T + TCAACATAAT (SEQ ID NO: 13600) |
| 82 | C + CYACACC + T + TCAACATAAT (SEQ ID NO: 13601) |
| 82 | CCYACAC + C + T + TCAACATAAT (SEQ ID NO: 13602) |
| 82 | CCYACACC + T + TC + AACATAAT (SEQ ID NO: 13603) |
| 82 | CCYACACC + T + TCAAC + ATAAT (SEQ ID NO: 13604) |
| 82 | CCYACACC + T + TCA + ACATAAT (SEQ ID NO: 13605) |
| 82 | CCYACACC + T + TCAACAT + AAT (SEQ ID NO: 13606) |
| 82 | CYACACCT + R + CAACATAAT (SEQ ID NO: 13607) |
| 82 | CYACA + CCTRCAACATAAT (SEQ ID NO: 13608) |
| 82 | CYA + CACCTRCAACATAAT (SEQ ID NO: 13609) |
| 82 | CYACAC + CTRCAACATAAT (SEQ ID NO: 13610) |
| 82 | CYACACCT + RCAACATAAT (SEQ ID NO: 13611) |
| 82 | CYACACCTRCAACAT + AAT (SEQ ID NO: 13612) |
| 82 | CYACACCTRCAACA + TAAT (SEQ ID NO: 13613) |
| 82 | CYACACCTRCAACATAA + T (SEQ ID NO: 13614) |
| 82 | CYACACCTRCA + ACATAAT (SEQ ID NO: 13615) |
| 82 | CYAC + ACCT + R + CAACATAAT (SEQ ID NO: 13616) |
| 82 | CYA + CACCT + R + CAACATAAT (SEQ ID NO: 13617) |
| 82 | CYACACC + T + R + CAACATAAT (SEQ ID NO: 13618) |
| 82 | C + YACACCT + R + CAACATAAT (SEQ ID NO: 13619) |
| 82 | CYACACCT + R + CAAC + ATAAT (SEQ ID NO: 13620) |
| 82 | CYACACCT + R + CAACATAA + T (SEQ ID NO: 13621) |
| 82 | CYACACCT + R + CAACA + TAAT (SEQ ID NO: 13622) |
| 82 | CYACACCT + R + CAA + CATAT (SEQ ID NO: 13623) |
| 82 | CCYACACC + T + TCAACATAA (SEQ ID NO: 13624) |
| 82 | CCYA + CACCTTCAACATAA (SEQ ID NO: 13625) |
| 82 | CCYACACC + TTCAACATAA (SEQ ID NO: 13626) |
| 82 | CC + YACACCTTCAACATAA (SEQ ID NO: 13627) |
| 82 | CCYACAC + CTTCAACATAA (SEQ ID NO: 13628) |
| 82 | CCYACACCTTCAA + CATAA (SEQ ID NO: 13629) |
| 82 | CCYACACCTTCAAC + ATAA (SEQ ID NO: 13630) |
| 82 | CCYACACCTTCAACA + TAA (SEQ ID NO: 13631) |
| 82 | CCYACACCTTC + AACATAA (SEQ ID NO: 13632) |
| 82 | CCY + ACACC + T + TCAACATAA (SEQ ID NO: 13633) |
| 82 | CC + YACACC + T + TCAACATAA (SEQ ID NO: 13634) |
| 82 | C + CYACACC + T + TCAACATAA (SEQ ID NO: 13635) |

TABLE 10 -continued

| | |
|---|---|
| 82 | CCYACAC + C + T + TCAACATAA (SEQ ID NO: 13636) |
| 82 | CCYACACC + T + TC + AACATAA (SEQ ID NO: 13637) |
| 82 | CCYACACC + T + TCAAC + ATAA (SEQ ID NO: 13638) |
| 82 | CCYACACC + T + TCA + ACATAA (SEQ ID NO: 13639) |
| 82 | CCYACACC + T + TCAACAT + AA (SEQ ID NO: 13640) |
| 82 | YACACCT + R + CAACATAAT (SEQ ID NO: 13641) |
| 82 | YACA + CCTRCAACATAAT (SEQ ID NO: 13642) |
| 82 | YA + CACCTRCAACATAAT (SEQ ID NO: 13643) |
| 82 | YACAC + CTRCAACATAAT (SEQ ID NO: 13644) |
| 82 | YACACCT + RCAACATAAT (SEQ ID NO: 13645) |
| 82 | YACACCTRCAACAT + AAT (SEQ ID NO: 13646) |
| 82 | YACACCTRCAACA + TAAT (SEQ ID NO: 13647) |
| 82 | YACACCTRCAACATAA + T (SEQ ID NO: 13648) |
| 82 | YACACCTRCA + ACATAAT (SEQ ID NO: 13649) |
| 82 | YAC + ACCT + R + CAACATAAT (SEQ ID NO: 13650) |
| 82 | YA + CACCT + R + CAACATAAT (SEQ ID NO: 13651) |
| 82 | YACACC + T + R + CAACATAAT (SEQ ID NO: 13652) |
| 82 | +YACACCT + R + CAACATAAT (SEQ ID NO: 13653) |
| 82 | YACACCT + R + CAAC + ATAAT (SEQ ID NO: 13654) |
| 82 | YACACCT + R + CAACATAA + T (SEQ ID NO: 13655) |
| 82 | YACACCT + R + CAACA + TAAT (SEQ ID NO: 13656) |
| 82 | YACACCT + R + CAA + CATAAT (SEQ ID NO: 13657) |
| 82 | CYACACC + T + TCAACATAA (SEQ ID NO: 13658) |
| 82 | CYA + CACCTTCAACATAA (SEQ ID NO: 13659) |
| 82 | CYACACC + TTCAACATAA (SEQ ID NO: 13660) |
| 82 | C + YACACCTTCAACATAA (SEQ ID NO: 13661) |
| 82 | CYACAC + CTTCAACATAA (SEQ ID NO: 13662) |
| 82 | CYACACCTTCAA + CATAA (SEQ ID NO: 13663) |
| 82 | CYACACCTTCAAC + ATAA (SEQ ID NO: 13664) |
| 82 | CYACACCTTCAACA + TAA (SEQ ID NO: 13665) |
| 82 | CYACACCTTC + AACATAA (SEQ ID NO: 13666) |
| 82 | CY + ACACC + T + TCAACATAA (SEQ ID NO: 13667) |
| 82 | C + YACACC + T + TCAACATAA (SEQ ID NO: 13668) |
| 82 | +CYACACC + T + TCAACATAA (SEQ ID NO: 13669) |
| 82 | CYACAC + C + T + TCAACATAA (SEQ ID NO: 13670) |
| 82 | CYACACC + T + TC + AACATAA (SEQ ID NO: 13671) |
| 82 | CYACACC + T + TCAAC + ATAA (SEQ ID NO: 13672) |
| 82 | CYACACC + T + TCA + ACATAA (SEQ ID NO: 13673) |
| 82 | CYACACC + T + TCAACAT + AA (SEQ ID NO: 13674) |
| 82 | YACACCT + R + CAACATA (SEQ ID NO: 13675) |

TABLE 10 -continued

| | |
|---|---|
| 82 | YACA + CCTRCAACATA (SEQ ID NO: 13676) |
| 82 | YA + CACCTRCAACATA (SEQ ID NO: 13677) |
| 82 | YACAC + CTRCAACATA (SEQ ID NO: 13678) |
| 82 | YACACCT + RCAACATA (SEQ ID NO: 13679) |
| 82 | YACACCTRCAACAT + A (SEQ ID NO: 13680) |
| 82 | YACACCTRCAACA + TA (SEQ ID NO: 13681) |
| 82 | YACACCTRCAACATAA (SEQ ID NO: 13682) |
| 82 | YACACCTRCA + ACATA (SEQ ID NO: 13683) |
| 82 | YAC + ACCT + R + CAACATA (SEQ ID NO: 13684) |
| 82 | YA + CACCT + R + CAACATA (SEQ ID NO: 13685) |
| 82 | YACACC + T + R + CAACATA (SEQ ID NO: 13686) |
| 82 | +YACACCT + R + CAACATA (SEQ ID NO: 13687) |
| 82 | YACACCT + R + CAAC + ATA (SEQ ID NO: 13688) |
| 82 | YACACCT + R + CAACATAA (SEQ ID NO: 13689) |
| 82 | YACACCT + R + CAACA + TA (SEQ ID NO: 13690) |
| 82 | YACACCT + R + CAA + CATA (SEQ ID NO: 13691) |
| 82 | CYACACC + T + TCAACAT (SEQ ID NO: 13692) |
| 82 | CYA + CACCTTCAACAT (SEQ ID NO: 13693) |
| 82 | CYACACC + TTCAACAT (SEQ ID NO: 13694) |
| 82 | C + YACACCTTCAACAT (SEQ ID NO: 13695) |
| 82 | CYACAC + CTTCAACAT (SEQ ID NO: 13696) |
| 82 | CYACACCTTCAA + CAT (SEQ ID NO: 13697) |
| 82 | CYACACCTTCAAC + AT (SEQ ID NO: 13698) |
| 82 | CYACACCTTCAACA + T (SEQ ID NO: 13699) |
| 82 | CYACACCTTC + AACAT (SEQ ID NO: 13700) |
| 82 | CY + ACACC + T + TCAACAT (SEQ ID NO: 13701) |
| 82 | C + YACACC + T + TCAACAT (SEQ ID NO: 13702) |
| 82 | +CYACACC + T + TCAACAT (SEQ ID NO: 13703) |
| 82 | CYACAC + C + T + TCAACAT (SEQ ID NO: 13704) |
| 82 | CYACACC + T + TC + AACAT (SEQ ID NO: 13705) |
| 82 | CYACACC + T + TCAAC + AT (SEQ ID NO: 13706) |
| 82 | CYACACC + T + TCA + ACAT (SEQ ID NO: 13707) |
| 82 | CYACACC + T + TCAACAT (SEQ ID NO: 13708) |
| 82 | ACACCTGCYAACATA (SEQ ID NO: 13709) |
| 82 | ACACCTACYAACATA (SEQ ID NO: 13710) |
| 82 | ACACCTAGYAACATA (SEQ ID NO: 13711) |
| 82 | ACACCTTTYAACATA (SEQ ID NO: 13712) |
| 82 | ACACCTCTYAACATA (SEQ ID NO: 13713) |
| 82 | ACACCTTGYAACATA (SEQ ID NO: 13714) |
| 82 | ACACCTATGAACATA (SEQ ID NO: 13715) |

TABLE 10 -continued

| | | |
|---|---|---|
| 82 | CYACACCTRCAACATAATT | (SEQ ID NO: 13716) |
| 82 | CCYACACCTTCAACATAAT | (SEQ ID NO: 13717) |
| 82 | CYACACCTRCAACATAAT | (SEQ ID NO: 13718) |
| 82 | CCYACACCTTCAACATAA | (SEQ ID NO: 13719) |
| 82 | YACACCTRCAACATAAT | (SEQ ID NO: 13720) |
| 82 | CYACACCTTCAACATAA | (SEQ ID NO: 13721) |
| 82 | YACACCTRCAACATA | (SEQ ID NO: 13722) |
| 82 | CYACACCTTCAACAT | (SEQ ID NO: 13723) |
| 83 | ACACCTRT + C + ACATAATTGG | (SEQ ID NO: 13724) |
| 83 | ACAC + CTRTCACATAATTGG | (SEQ ID NO: 13725) |
| 83 | AC + ACCTRTCACATAATTGG | (SEQ ID NO: 13726) |
| 83 | ACACC + TRTCACATAATTGG | (SEQ ID NO: 13727) |
| 83 | ACACCTRT + CACATAATTGG | (SEQ ID NO: 13728) |
| 83 | ACACCTRTCACATA + ATTGG | (SEQ ID NO: 13729) |
| 83 | ACACCTRTCACATAA + TTGG | (SEQ ID NO: 13730) |
| 83 | ACACCTRTCA + CATAATTGG | (SEQ ID NO: 13731) |
| 83 | ACACCTRTCACAT + AATTGG | (SEQ ID NO: 13732) |
| 83 | AC + ACCTRT + C + ACATAATTGG | (SEQ ID NO: 13733) |
| 83 | ACACCT + RT + C + ACATAATTGG | (SEQ ID NO: 13734) |
| 83 | A + CACCTRT + C + ACATAATTGG | (SEQ ID NO: 13735) |
| 83 | ACACC + TRT + C + ACATAATTGG | (SEQ ID NO: 13736) |
| 83 | ACACCTRT + C + ACATAAT + TGG | (SEQ ID NO: 13737) |
| 83 | ACACCTRT + C + ACA + TAATTGG | (SEQ ID NO: 13738) |
| 83 | ACACCTRT + C + ACATAATT + GG | (SEQ ID NO: 13739) |
| 83 | ACACCTRT + C + A + CATAATTGG | (SEQ ID NO: 13740) |
| 83 | ACACCTRT + C + ACATAATTG | (SEQ ID NO: 13741) |
| 83 | ACAC + CTRTCACATAATTG | (SEQ ID NO: 13742) |
| 83 | AC + ACCTRTCACATAATTG | (SEQ ID NO: 13743) |
| 83 | ACACC + TRTCACATAATTG | (SEQ ID NO: 13744) |
| 83 | ACACCTRT + CACATAATTG | (SEQ ID NO: 13745) |
| 83 | ACACCTRTCACATA + ATTG | (SEQ ID NO: 13746) |
| 83 | ACACCTRTCACATAA + TTG | (SEQ ID NO: 13747) |
| 83 | ACACCTRTCA + CATAATTG | (SEQ ID NO: 13748) |
| 83 | ACACCTRTCACAT + AATTG | (SEQ ID NO: 13749) |
| 83 | AC + ACCTRT + C + ACATAATTG | (SEQ ID NO: 13750) |
| 83 | ACACCT + RT + C + ACATAATTG | (SEQ ID NO: 13751) |
| 83 | A + CACCTRT + C + ACATAATTG | (SEQ ID NO: 13752) |
| 83 | ACACC + TRT + C + ACATAATTG | (SEQ ID NO: 13753) |
| 83 | ACACCTRT + C + ACATAAT + TG | (SEQ ID NO: 13754) |
| 83 | ACACCTRT + C + ACA + TAATTG | (SEQ ID NO: 13755) |

TABLE 10 -continued

| 83 | ACACCTRT + C + ACATAATT + G (SEQ ID NO: 13756) |
| 83 | ACACCTRT + C + A + CATAATTG (SEQ ID NO: 13757) |
| 83 | CACCTRT + C + ACATAATTG (SEQ ID NO: 13758) |
| 83 | CAC + CTRTCACATAATTG (SEQ ID NO: 13759) |
| 83 | C + ACCTRTCACATAATTG (SEQ ID NO: 13760) |
| 83 | CACC + TRTCACATAATTG (SEQ ID NO: 13761) |
| 83 | CACCTRT + CACATAATTG (SEQ ID NO: 13762) |
| 83 | CACCTRTCACATA + ATTG (SEQ ID NO: 13763) |
| 83 | CACCTRTCACATAA + TTG (SEQ ID NO: 13764) |
| 83 | CACCTRTCA + CATAATTG (SEQ ID NO: 13765) |
| 83 | CACCTRTCACAT + AATTG (SEQ ID NO: 13766) |
| 83 | C + ACCTRT + C + ACATAATTG (SEQ ID NO: 13767) |
| 83 | CACCT + RT + C + ACATAATTG (SEQ ID NO: 13768) |
| 83 | +CACCTRT + C + ACATAATTG (SEQ ID NO: 13769) |
| 83 | CACC + TRT + C + ACATAATTG (SEQ ID NO: 13770) |
| 83 | CACCTRT + C + ACATAAT + TG (SEQ ID NO: 13771) |
| 83 | CACCTRT + C + ACA + TAATTG (SEQ ID NO: 13772) |
| 83 | CACCTRT + C + ACATAATT + G (SEQ ID NO: 13773) |
| 83 | CACCTRT + C + A + CATAATTG (SEQ ID NO: 13774) |
| 83 | CACCTRT + C + ACATAAT (SEQ ID NO: 13775) |
| 83 | CAC + CTRTCACATAAT (SEQ ID NO: 13776) |
| 83 | C + ACCTRTCACATAAT (SEQ ID NO: 13777) |
| 83 | CACC + TRTCACATAAT (SEQ ID NO: 13778) |
| 83 | CACCTRT + CACATAAT (SEQ ID NO: 13779) |
| 83 | CACCTRTCACATA + AT (SEQ ID NO: 13780) |
| 83 | CACCTRTCACATAA + T (SEQ ID NO: 13781) |
| 83 | CACCTRTCA + CATAAT (SEQ ID NO: 13782) |
| 83 | CACCTRTCACAT + AAT (SEQ ID NO: 13783) |
| 83 | C + ACCTRT + C + ACATAAT (SEQ ID NO: 13784) |
| 83 | CACCT + RT + C + ACATAAT (SEQ ID NO: 13785) |
| 83 | +CACCTRT + C + ACATAAT (SEQ ID NO: 13786) |
| 83 | CACC + TRT + C + ACATAAT (SEQ ID NO: 13787) |
| 83 | CACCTRT + C + ACATAAT (SEQ ID NO: 13788) |
| 83 | CACCTRT + C + ACA + TAAT (SEQ ID NO: 13789) |
| 83 | CACCTRT + C + ACATAATT (SEQ ID NO: 13790) |
| 83 | CACCTRT + C + A + CATAAT (SEQ ID NO: 13791) |
| 83 | ACCTGTCGAYATAAT (SEQ ID NO: 13792) |
| 83 | ACACCTRTCACATAATTGG (SEQ ID NO: 13793) |
| 83 | ACACCTRTCACATAATTG (SEQ ID NO: 13794) |
| 83 | CACCTRTCACATAATTG (SEQ ID NO: 13795) |

TABLE 10 -continued

| | |
|---|---|
| 83 | CACCTRTCACATAAT (SEQ ID NO: 13796) |
| 83 | CACCTRTCACATAATT (SEQ ID NO: 13797) |
| 84 | CCTRTCAA + C + TAATTGGRMG (SEQ ID NO: 13798) |
| 84 | C + CTRTCAACTAATTGGRMG (SEQ ID NO: 13799) |
| 84 | CC + TRTCAACTAATTGGRMG (SEQ ID NO: 13800) |
| 84 | CCTRTCAA + CTAATTGGRMG (SEQ ID NO: 13801) |
| 84 | CCTR + TCAACTAATTGGRMG (SEQ ID NO: 13802) |
| 84 | CCTRTCAACTAAT + TGGRMG (SEQ ID NO: 13803) |
| 84 | CCTRTCAACTAATTGGR + MG (SEQ ID NO: 13804) |
| 84 | CCTRTCAACT + AATTGGRMG (SEQ ID NO: 13805) |
| 84 | CCTRTCAACTA + ATTGGRMG (SEQ ID NO: 13806) |
| 84 | CCTRTC + AA + C + TAATTGGRMG (SEQ ID NO: 13807) |
| 84 | CCTRT + CAA + C + TAATTGGRMG (SEQ ID NO: 13808) |
| 84 | CC + TRTCAA + C + TAATTGGRMG (SEQ ID NO: 13809) |
| 84 | CCTR + TCAA + C + TAATTGGRMG (SEQ ID NO: 13810) |
| 84 | CCTRTCAA + C + TAATTG + GRMG (SEQ ID NO: 13811) |
| 84 | CCTRTCAA + C + T + AATTGGRMG (SEQ ID NO: 13812) |
| 84 | CCTRTCAA + C + TAAT + TGGRMG (SEQ ID NO: 13813) |
| 84 | CCTRTCAA + C + TAATTGGR + MG (SEQ ID NO: 13814) |
| 84 | CCTRTCAA + C + TAATTGGRM (SEQ ID NO: 13815) |
| 84 | C + CTRTCAACTAATTGGRM (SEQ ID NO: 13816) |
| 84 | CC + TRTCAACTAATTGGRM (SEQ ID NO: 13817) |
| 84 | CCTRTCAA + CTAATTGGRM (SEQ ID NO: 13818) |
| 84 | CCTR + TCAACTAATTGGRM (SEQ ID NO: 13819) |
| 84 | CCTRTCAACTAAT + TGGRM (SEQ ID NO: 13820) |
| 84 | CCTRTCAACTAATTGGR + M (SEQ ID NO: 13821) |
| 84 | CCTRTCAACT + AATTGGRM (SEQ ID NO: 13822) |
| 84 | CCTRTCAACTA + ATTGGRM (SEQ ID NO: 13823) |
| 84 | CCTRTC + AA + C + TAATTGGRM (SEQ ID NO: 13824) |
| 84 | CCTRT + CAA + C + TAATTGGRM (SEQ ID NO: 13825) |
| 84 | CC + TRTCAA + C + TAATTGGRM (SEQ ID NO: 13826) |
| 84 | CCTR + TCAA + C + TAATTGGRM (SEQ ID NO: 13827) |
| 84 | CCTRTCAA + C + TAATTG + GRM (SEQ ID NO: 13828) |
| 84 | CCTRTCAA + C + T + AATTGGRM (SEQ ID NO: 13829) |
| 84 | CCTRTCAA + C + TAAT + TGGRM (SEQ ID NO: 13830) |
| 84 | CCTRTCAA + C + TAATTGGR + M (SEQ ID NO: 13831) |
| 84 | CTRTCAA + C + TAATTGGRM (SEQ ID NO: 13832) |
| 84 | +CTRTCAACTAATTGGRM (SEQ ID NO: 13833) |
| 84 | C + TRTCAACTAATTGGRM (SEQ ID NO: 13834) |
| 84 | CTRTCAA + CTAATTGGRM (SEQ ID NO: 13835) |

TABLE 10 -continued

| | |
|---|---|
| 84 | CTR + TCAACTAATTGGRM (SEQ ID NO: 13836) |
| 84 | CTRTCAACTAAT + TGGRM (SEQ ID NO: 13837) |
| 84 | CTRTCAACTAATTGGR + M (SEQ ID NO: 13838) |
| 84 | CTRTCAACT + AATTGGRM (SEQ ID NO: 13839) |
| 84 | CTRTCAACTA + ATTGGRM (SEQ ID NO: 13840) |
| 84 | CTRTC + AA + C + TAATTGGRM (SEQ ID NO: 13841) |
| 84 | CTRT + CAA + C + TAATTGGRM (SEQ ID NO: 13842) |
| 84 | C + TRTCAA + C + TAATTGGRM (SEQ ID NO: 13843) |
| 84 | CTR + TCAA + C + TAATTGGRM (SEQ ID NO: 13844) |
| 84 | CTRTCAA + C + TAATTG + GRM (SEQ ID NO: 13845) |
| 84 | CTRTCAA + C + T + AATTGGRM (SEQ ID NO: 13846) |
| 84 | CTRTCAA + C + TAAT + TGGRM (SEQ ID NO: 13847) |
| 84 | CTRTCAA + C + TAATTGGR + M (SEQ ID NO: 13848) |
| 84 | CTRTCAA + C + TAATTGG (SEQ ID NO: 13849) |
| 84 | +CTRTCAACTAATTGG (SEQ ID NO: 13850) |
| 84 | C + TRTCAACTAATTGG (SEQ ID NO: 13851) |
| 84 | CTRTCAA + CTAATTGG (SEQ ID NO: 13852) |
| 84 | CTR + TCAACTAATTGG (SEQ ID NO: 13853) |
| 84 | CTRTCAACTAAT + TGG (SEQ ID NO: 13854) |
| 84 | CTRTCAACTAATTGGR (SEQ ID NO: 13855) |
| 84 | CTRTCAACT + AATTGG (SEQ ID NO: 13856) |
| 84 | CTRTCAACTA + ATTGG (SEQ ID NO: 13857) |
| 84 | CTRTC + AA + C + TAATTGG (SEQ ID NO: 13858) |
| 84 | CTRT + CAA + C + TAATTGG (SEQ ID NO: 13859) |
| 84 | C + TRTCAA + C + TAATTGG (SEQ ID NO: 13860) |
| 84 | CTR + TCAA + C + TAATTGG (SEQ ID NO: 13861) |
| 84 | CTRTCAA + C + TAATTG + G (SEQ ID NO: 13862) |
| 84 | CTRTCAA + C + T + AATTGG (SEQ ID NO: 13863) |
| 84 | CTRTCAA + C + TAAT + TGG (SEQ ID NO: 13864) |
| 84 | CTRTCAA + C + TAATTGGR (SEQ ID NO: 13865) |
| 84 | TCCAATTACGTTGAC (SEQ ID NO: 13866) |
| 84 | TCCAATTGCGTTGAC (SEQ ID NO: 13867) |
| 84 | TCCAATRCAGTTGAC (SEQ ID NO: 13868) |
| 84 | CCTRTCAACTAATTGGRMG (SEQ ID NO: 13869) |
| 84 | CCTRTCAACTAATTGGRM (SEQ ID NO: 13870) |
| 84 | CTRTCAACTAATTGGRM (SEQ ID NO: 13871) |
| 84 | CTRTCAACTAATTGG (SEQ ID NO: 13872) |
| 88 | TTGGRMGR + A + YHTGTTGACY (SEQ ID NO: 13873) |
| 88 | T + TGGRMGRAYHTGTTGACY (SEQ ID NO: 13874) |
| 88 | TTGG + RMGRAYHTGTTGACY (SEQ ID NO: 13875) |

TABLE 10 -continued

| | | |
|---|---|---|
| 88 | TTG + GRMGRAYHTGTTGACY | (SEQ ID NO: 13876) |
| 88 | TT + GGRMGRAYHTGTTGACY | (SEQ ID NO: 13877) |
| 88 | TTGGRMGRAYHTGTTGA + CY | (SEQ ID NO: 13878) |
| 88 | TTGGRMGRAYHTGTT + GACY | (SEQ ID NO: 13879) |
| 88 | TTGGRMGRAYHTG + TTGACY | (SEQ ID NO: 13880) |
| 88 | TTGGRMGRAYH + TGTTGACY | (SEQ ID NO: 13881) |
| 88 | TTGGRM + GR + A + YHTGTTGACY | (SEQ ID NO: 13882) |
| 88 | TT + GGRMGR + A + YHTGTTGACY | (SEQ ID NO: 13883) |
| 88 | TTGGRMG + R + A + YHTGTTGACY | (SEQ ID NO: 13884) |
| 88 | TTGGR + MGR + A + YHTGTTGACY | (SEQ ID NO: 13885) |
| 88 | TTGGRMGR + A + YHTGTTGA + CY | (SEQ ID NO: 13886) |
| 88 | TTGGRMGR + A + Y + HTGTTGACY | (SEQ ID NO: 13887) |
| 88 | TTGGRMGR + A + YHTG + TTGACY | (SEQ ID NO: 13888) |
| 88 | TTGGRMGR + A + YH + TGTTGACY | (SEQ ID NO: 13889) |
| 88 | TTGGRMGR + A + YHTGTTGAC | (SEQ ID NO: 13890) |
| 88 | T + TGGRMGRAYHTGTTGAC | (SEQ ID NO: 13891) |
| 88 | TTGG + RMGRAYHTGTTGAC | (SEQ ID NO: 13892) |
| 88 | TTG + GRMGRAYHTGTTGAC | (SEQ ID NO: 13893) |
| 88 | TT + GGRMGRAYHTGTTGAC | (SEQ ID NO: 13894) |
| 88 | TTGGRMGRAYHTGTTGA + C | (SEQ ID NO: 13895) |
| 88 | TTGGRMGRAYHTGTT + GAC | (SEQ ID NO: 13896) |
| 88 | TTGGRMGRAYHTG + TTGAC | (SEQ ID NO: 13897) |
| 88 | TTGGRMGRAYH + TGTTGAC | (SEQ ID NO: 13898) |
| 88 | TTGGRM + GR + A + YHTGTTGAC | (SEQ ID NO: 13899) |
| 88 | TT + GGRMGR + A + YHTGTTGAC | (SEQ ID NO: 13900) |
| 88 | TTGGRMG + R + A + YHTGTTGAC | (SEQ ID NO: 13901) |
| 88 | TTGGR + MGR + A + YHTGTTGAC | (SEQ ID NO: 13902) |
| 88 | TTGGRMGR + A + YHTGTTGA + C | (SEQ ID NO: 13903) |
| 88 | TTGGRMGR + A + Y + HTGTTGAC | (SEQ ID NO: 13904) |
| 88 | TTGGRMGR + A + YHTG + TTGAC | (SEQ ID NO: 13905) |
| 88 | TTGGRMGR + A + YH + TGTTGAC | (SEQ ID NO: 13906) |
| 88 | TGGRMGR + A + YHTGTTGAC | (SEQ ID NO: 13907) |
| 88 | +TGGRMGRAYHTGTTGAC | (SEQ ID NO: 13908) |
| 88 | TGG + RMGRAYHTGTTGAC | (SEQ ID NO: 13909) |
| 88 | TG + GRMGRAYHTGTTGAC | (SEQ ID NO: 13910) |
| 88 | T + GGRMGRAYHTGTTGAC | (SEQ ID NO: 13911) |
| 88 | TGGRMGRAYHTGTTGA + C | (SEQ ID NO: 13912) |
| 88 | TGGRMGRAYHTGTT + GAC | (SEQ ID NO: 13913) |
| 88 | TGGRMGRAYHTG + TTGAC | (SEQ ID NO: 13914) |
| 88 | TGGRMGRAYH + TGTTGAC | (SEQ ID NO: 13915) |

TABLE 10 -continued

| | |
|---|---|
| 88 | TGGRM + GR + A + YHTGTTGAC (SEQ ID NO: 13916) |
| 88 | T + GGRMGR + A + YHTGTTGAC (SEQ ID NO: 13917) |
| 88 | TGGRMG + R + A + YHTGTTGAC (SEQ ID NO: 13918) |
| 88 | TGGR + MGR + A + YHTGTTGAC (SEQ ID NO: 13919) |
| 88 | TGGRMGR + A + YHTGTTGA + C (SEQ ID NO: 13920) |
| 88 | TGGRMGR + A + Y + HTGTTGAC (SEQ ID NO: 13921) |
| 88 | TGGRMGR + A + YHTG + TTGAC (SEQ ID NO: 13922) |
| 88 | TGGRMGR + A + YH + TGTTGAC (SEQ ID NO: 13923) |
| 88 | TGGRMGR + A + YHTGTTG (SEQ ID NO: 13924) |
| 88 | +TGGRMGRAYHTGTTG (SEQ ID NO: 13925) |
| 88 | TGG + RMGRAYHTGTTG (SEQ ID NO: 13926) |
| 88 | TG + GRMGRAYHTGTTG (SEQ ID NO: 13927) |
| 88 | T + GGRMGRAYHTGTTG (SEQ ID NO: 13928) |
| 88 | TGGRMGRAYHTGTTGA (SEQ ID NO: 13929) |
| 88 | TGGRMGRAYHTGTT + G (SEQ ID NO: 13930) |
| 88 | TGGRMGRAYHTG + TTG (SEQ ID NO: 13931) |
| 88 | TGGRMGRAYH + TGTTG (SEQ ID NO: 13932) |
| 88 | TGGRM + GR + A + YHTGTTG (SEQ ID NO: 13933) |
| 88 | T + GGRMGR + A + YHTGTTG (SEQ ID NO: 13934) |
| 88 | TGGRMG + R + A + YHTGTTG (SEQ ID NO: 13935) |
| 88 | TGGR + MGR + A + YHTGTTG (SEQ ID NO: 13936) |
| 88 | TGGRMGR + A + YHTGTTGA (SEQ ID NO: 13937) |
| 88 | TGGRMGR + A + Y + HTGTTG (SEQ ID NO: 13938) |
| 88 | TGGRMGR + A + YHTG + TTG (SEQ ID NO: 13939) |
| 88 | TGGRMGR + A + YH + TGTTG (SEQ ID NO: 13940) |
| 88 | TGGAAGAGAYCTGTT (SEQ ID NO: 13941) |
| 88 | TGGAAGAAGYCTGTT (SEQ ID NO: 13942) |
| 88 | TGGAAGAACYCTGTT (SEQ ID NO: 13943) |
| 88 | TGGAAGAGGYCTGTT (SEQ ID NO: 13944) |
| 88 | TTGGRMGRAYHTGTTGACY (SEQ ID NO: 13945) |
| 88 | TTGGRMGRAYHTGTTGAC (SEQ ID NO: 13946) |
| 88 | TGGRMGRAYHTGTTGAC (SEQ ID NO: 13947) |
| 88 | TGGRMGRAYHTGTTG (SEQ ID NO: 13948) |
| 89 | GGRMGRAA + Y + TGTTGACYCA (SEQ ID NO: 13949) |
| 89 | G + GRMGRAAYTGTTGACYCA (SEQ ID NO: 13950) |
| 89 | GG + RMGRAAYTGTTGACYCA (SEQ ID NO: 13951) |
| 89 | GGRMGRAA + YTGTTGACYCA (SEQ ID NO: 13952) |
| 89 | GGR + MGRAAYTGTTGACYCA (SEQ ID NO: 13953) |
| 89 | GGRMGRAAYTGTTGACY + CA (SEQ ID NO: 13954) |
| 89 | GGRMGRAAYTGTT + GACYCA (SEQ ID NO: 13955) |

TABLE 10 -continued

| | |
|---|---|
| 89 | GGRMGRAAYTGT + TGACYCA (SEQ ID NO: 13956) |
| 89 | GGRMGRAAYTGTTG + ACYCA (SEQ ID NO: 13957) |
| 89 | GG + RMGRAA + Y + TGTTGACYCA (SEQ ID NO: 13958) |
| 89 | GGR + MGRAA + Y + TGTTGACYCA (SEQ ID NO: 13959) |
| 89 | GGRMGRA + A + Y + TGTTGACYCA (SEQ ID NO: 13960) |
| 89 | GGRMG + RAA + Y + TGTTGACYCA (SEQ ID NO: 13961) |
| 89 | GGRMGRAA + Y + TGTTG + ACYCA (SEQ ID NO: 13962) |
| 89 | GGRMGRAA + Y + T + GTTGACYCA (SEQ ID NO: 13963) |
| 89 | GGRMGRAA + Y + TGTT + GACYCA (SEQ ID NO: 13964) |
| 89 | GGRMGRAA + Y + TGTTGACY + CA (SEQ ID NO: 13965) |
| 89 | GGRMGRAA + Y + TGTTGACYC (SEQ ID NO: 13966) |
| 89 | G + GRMGRAAYTGTTGACYC (SEQ ID NO: 13967) |
| 89 | GG + RMGRAAYTGTTGACYC (SEQ ID NO: 13968) |
| 89 | GGRMGRAA + YTGTTGACYC (SEQ ID NO: 13969) |
| 89 | GGR + MGRAAYTGTTGACYC (SEQ ID NO: 13970) |
| 89 | GGRMGRAAYTGTTGACY + C (SEQ ID NO: 13971) |
| 89 | GGRMGRAAYTGTT + GACYC (SEQ ID NO: 13972) |
| 89 | GGRMGRAAYTGT + TGACYC (SEQ ID NO: 13973) |
| 89 | GGRMGRAAYTGTTG + ACYC (SEQ ID NO: 13974) |
| 89 | GG + RMGRAA + Y + TGTTGACYC (SEQ ID NO: 13975) |
| 89 | GGR + MGRAA + Y + TGTTGACYC (SEQ ID NO: 13976) |
| 89 | GGRMGRA + A + Y + TGTTGACYC (SEQ ID NO: 13977) |
| 89 | GGRMG + RAA + Y + TGTTGACYC (SEQ ID NO: 13978) |
| 89 | GGRMGRAA + Y + TGTTG + ACYC (SEQ ID NO: 13979) |
| 89 | GGRMGRAA + Y + T + GTTGACYC (SEQ ID NO: 13980) |
| 89 | GGRMGRAA + Y + TGTT + GACYC (SEQ ID NO: 13981) |
| 89 | GGRMGRAA + Y + TGTTGACY + C (SEQ ID NO: 13982) |
| 89 | GRMGRAA + Y + TGTTGACYC (SEQ ID NO: 13983) |
| 89 | +GRMGRAAYTGTTGACYC (SEQ ID NO: 13984) |
| 89 | G + RMGRAAYTGTTGACYC (SEQ ID NO: 13985) |
| 89 | GRMGRAA + YTGTTGACYC (SEQ ID NO: 13986) |
| 89 | GR + MGRAAYTGTTGACYC (SEQ ID NO: 13987) |
| 89 | GRMGRAAYTGTTGACY + C (SEQ ID NO: 13988) |
| 89 | GRMGRAAYTGTT + GACYC (SEQ ID NO: 13989) |
| 89 | GRMGRAAYTGT + TGACYC (SEQ ID NO: 13990) |
| 89 | GRMGRAAYTGTTG + ACYC (SEQ ID NO: 13991) |
| 89 | G + RMGRAA + Y + TGTTGACYC (SEQ ID NO: 13992) |
| 89 | GR + MGRAA + Y + TGTTGACYC (SEQ ID NO: 13993) |
| 89 | GRMGRA + A + Y + TGTTGACYC (SEQ ID NO: 13994) |
| 89 | GRMG + RAA + Y + TGTTGACYC (SEQ ID NO: 13995) |

TABLE 10 -continued

| | |
|---|---|
| 89 | GRMGRAA + Y + TGTTG + ACYC (SEQ ID NO: 13996) |
| 89 | GRMGRAA + Y + T + GTTGACYC (SEQ ID NO: 13997) |
| 89 | GRMGRAA + Y + TGTT + GACYC (SEQ ID NO: 13998) |
| 89 | GRMGRAA + Y + TGTTGACY + C (SEQ ID NO: 13999) |
| 89 | GRMGRAA + Y + TGTTGAC (SEQ ID NO: 14000) |
| 89 | +GRMGRAAYTGTTGAC (SEQ ID NO: 14001) |
| 89 | G + RMGRAAYTGTTGAC (SEQ ID NO: 14002) |
| 89 | GRMGRAA + YTGTTGAC (SEQ ID NO: 14003) |
| 89 | GR + MGRAAYTGTTGAC (SEQ ID NO: 14004) |
| 89 | GRMGRAAYTGTTGACY (SEQ ID NO: 14005) |
| 89 | GRMGRAAYTGTT + GAC (SEQ ID NO: 14006) |
| 89 | GRMGRAAYTGT + TGAC (SEQ ID NO: 14007) |
| 89 | GRMGRAAYTGTTG + AC (SEQ ID NO: 14008) |
| 89 | G + RMGRAA + Y + TGTTGAC (SEQ ID NO: 14009) |
| 89 | GR + MGRAA + Y + TGTTGAC (SEQ ID NO: 14010) |
| 89 | GRMGRA + A + Y + TGTTGAC (SEQ ID NO: 14011) |
| 89 | GRMG + RAA + Y + TGTTGAC (SEQ ID NO: 14012) |
| 89 | GRMGRAA + Y + TGTTG + AC (SEQ ID NO: 14013) |
| 89 | GRMGRAA + Y + T + GTTGAC (SEQ ID NO: 14014) |
| 89 | GRMGRAA + Y + TGTT + GAC (SEQ ID NO: 14015) |
| 89 | GRMGRAA + Y + TGTTGACY (SEQ ID NO: 14016) |
| 89 | AAGAAATGTRTTGAC (SEQ ID NO: 14017) |
| 89 | GGRMGRAAYTGTTGACYCA (SEQ ID NO: 14018) |
| 89 | GGRMGRAAYTGTTGACYC (SEQ ID NO: 14019) |
| 89 | GRMGRAAYTGTTGACYC (SEQ ID NO: 14020) |
| 89 | GRMGRAAYTGTTGAC (SEQ ID NO: 14021) |
| 90 | MGRAAYHT + G + TGACYCARMT (SEQ ID NO: 14022) |
| 90 | MGRAA + YHTGTGACYCARMT (SEQ ID NO: 14023) |
| 90 | MGRAAYH + TGTGACYCARMT (SEQ ID NO: 14024) |
| 90 | MGRA + AYHTGTGACYCARMT (SEQ ID NO: 14025) |
| 90 | MGR + AAYHTGTGACYCARMT (SEQ ID NO: 14026) |
| 90 | MGRAAYHTGTGACYC + ARMT (SEQ ID NO: 14027) |
| 90 | MGRAAYHTG + TGACYCARMT (SEQ ID NO: 14028) |
| 90 | MGRAAYHTGTGACY + CARMT (SEQ ID NO: 14029) |
| 90 | MGRAAYHTGTGAC + YCARMT (SEQ ID NO: 14030) |
| 90 | MGRA + AYHT + G + TGACYCARMT (SEQ ID NO: 14031) |
| 90 | M + GRAAYHT + G + TGACYCARMT (SEQ ID NO: 14032) |
| 90 | MG + RAAYHT + G + TGACYCARMT (SEQ ID NO: 14033) |
| 90 | MGRAA + YHT + G + TGACYCARMT (SEQ ID NO: 14034) |
| 90 | MGRAAYHT + G + TGACYCA + RMT (SEQ ID NO: 14035) |

TABLE 10 -continued

| | |
|---|---|
| 90 | MGRAAYHT + G + T + GACYCARMT (SEQ ID NO: 14036) |
| 90 | MGRAAYHT + G + TGAC + YCARMT (SEQ ID NO: 14037) |
| 90 | MGRAAYHT + G + TGACYC + ARMT (SEQ ID NO: 14038) |
| 90 | MGRAAYHT + G + TGACYCARM (SEQ ID NO: 14039) |
| 90 | MGRAA + YHTGTGACYCARM (SEQ ID NO: 14040) |
| 90 | MGRAAYH + TGTGACYCARM (SEQ ID NO: 14041) |
| 90 | MGRA + AYHTGTGACYCARM (SEQ ID NO: 14042) |
| 90 | MGR + AAYHTGTGACYCARM (SEQ ID NO: 14043) |
| 90 | MGRAAYHTGTGACYC + ARM (SEQ ID NO: 14044) |
| 90 | MGRAAYHTG + TGACYCARM (SEQ ID NO: 14045) |
| 90 | MGRAAYHTGTGACY + CARM (SEQ ID NO: 14046) |
| 90 | MGRAAYHTGTGAC + YCARM (SEQ ID NO: 14047) |
| 90 | MGRA + AYHT + G + TGACYCARM (SEQ ID NO: 14048) |
| 90 | M + GRAAYHT + G + TGACYCARM (SEQ ID NO: 14049) |
| 90 | MG + RAAYHT + G + TGACYCARM (SEQ ID NO: 14050) |
| 90 | MGRAA + YHT + G + TGACYCARM (SEQ ID NO: 14051) |
| 90 | MGRAAYHT + G + TGACYCA + RM (SEQ ID NO: 14052) |
| 90 | MGRAAYHT + G + T + GACYCARM (SEQ ID NO: 14053) |
| 90 | MGRAAYHT + G + TGAC + YCARM (SEQ ID NO: 14054) |
| 90 | MGRAAYHT + G + TGACYC + ARM (SEQ ID NO: 14055) |
| 90 | GRAAYHT + G + TGACYCARM (SEQ ID NO: 14056) |
| 90 | GRAA + YHTGTGACYCARM (SEQ ID NO: 14057) |
| 90 | GRAAYH + TGTGACYCARM (SEQ ID NO: 14058) |
| 90 | GRA + AYHTGTGACYCARM (SEQ ID NO: 14059) |
| 90 | GR + AAYHTGTGACYCARM (SEQ ID NO: 14060) |
| 90 | GRAAYHTGTGACYC + ARM (SEQ ID NO: 14061) |
| 90 | GRAAYHTG + TGACYCARM (SEQ ID NO: 14062) |
| 90 | GRAAYHTGTGACY + CARM (SEQ ID NO: 14063) |
| 90 | GRAAYHTGTGAC + YCARM (SEQ ID NO: 14064) |
| 90 | GRA + AYHT + G + TGACYCARM (SEQ ID NO: 14065) |
| 90 | +GRAAYHT + G + TGACYCARM (SEQ ID NO: 14066) |
| 90 | G + RAAYHT + G + TGACYCARM (SEQ ID NO: 14067) |
| 90 | GRAA + YHT + G + TGACYCARM (SEQ ID NO: 14068) |
| 90 | GRAAYHT + G + TGACYCA + RM (SEQ ID NO: 14069) |
| 90 | GRAAYHT + G + T + GACYCARM (SEQ ID NO: 14070) |
| 90 | GRAAYHT + G + TGAC + YCARM (SEQ ID NO: 14071) |
| 90 | GRAAYHT + G + TGACYC + ARM (SEQ ID NO: 14072) |
| 90 | GRAAYHT + G + TGACYCA (SEQ ID NO: 14073) |
| 90 | GRAA + YHTGTGACYCA (SEQ ID NO: 14074) |
| 90 | GRAAYH + TGTGACYCA (SEQ ID NO: 14075) |

TABLE 10 -continued

| 90 | GRA + AYHTGTGACYCA (SEQ ID NO: 14076) |
| 90 | GR + AAYHTGTGACYCA (SEQ ID NO: 14077) |
| 90 | GRAAYHTGTGACYC + A (SEQ ID NO: 14078) |
| 90 | GRAAYHTG + TGACYCA (SEQ ID NO: 14079) |
| 90 | GRAAYHTGTGACY + CA (SEQ ID NO: 14080) |
| 90 | GRAAYHTGTGAC + YCA (SEQ ID NO: 14081) |
| 90 | GRA + AYHT + G + TGACYCA (SEQ ID NO: 14082) |
| 90 | +GRAAYHT + G + TGACYCA (SEQ ID NO: 14083) |
| 90 | G + RAAYHT + G + TGACYCA (SEQ ID NO: 14084) |
| 90 | GRAA + YHT + G + TGACYCA (SEQ ID NO: 14085) |
| 90 | GRAAYHT + G + TGACYCA (SEQ ID NO: 14086) |
| 90 | GRAAYHT + G + T + GACYCA (SEQ ID NO: 14087) |
| 90 | GRAAYHT + G + TGAC + YCA (SEQ ID NO: 14088) |
| 90 | GRAAYHT + G + TGACYC + A (SEQ ID NO: 14089) |
| 90 | AAATCTGATGACTCA (SEQ ID NO: 14090) |
| 90 | MGRAAYHTGTGACYCARMT (SEQ ID NO: 14091) |
| 90 | MGRAAYHTGTGACYCARM (SEQ ID NO: 14092) |
| 90 | GRAAYHTGTGACYCARM (SEQ ID NO: 14093) |
| 90 | GRAAYHTGTGACYCA (SEQ ID NO: 14094) |

Table 11 depicts forward and reverse primers for the HIV-1 integrase gene. A "+" symbol preceding a nucleotide denotes that the nucleotide is an LNA.

TABLE 11

| Codon | Forward Primer (5' to 3') |
|---|---|
| 51 | ATAGTRGCYWRYTGTGAYAARTGYCARBTAAAAGGRGAAGCCATG (SEQ ID NO: 14095) |
| 51 | ATAGTRGCYWRYTGTGAYAARTGYCARBTAAAAGGRGAAGCCATG + N (SEQ ID NO: 14096) |
| 66 | A + C + ARG + TRGAYTGYAGYCCAGGRATATGGCARYTAGAYTGY (SEQ ID NO: 14097) |
| 66 | A + CARG + TRG + AYTGYAGYCCAGGRATATGGCARYTAGAYTGY (SEQ ID NO: 14098) |
| 66 | A + C + ARGTRG + AYTGYAGYCCAGGRATATGGCARYTAGAYTGY (SEQ ID NO:14099) |
| 66 | +ARG + TRG + AYTGYAGYCCAGGRATATGGCARYTAGAYTGY (SEQ ID NO: 14100) |
| 66 | +ARGTRG + AYT + GYAGYCCAGGRATATGGCARYTAGAYTGY (SEQ ID NO: 14101) |
| 66 | +ARG + TRGAYT + GYAGYCCAGGRATATGGCARYTAGAYTGY (SEQ ID NO: 14102) |
| 66 | +TRG + AYT + GYAGYCCAGGRATATGGCARYTAGAYTGY (SEQ ID NO: 14103) |
| 66 | +TRGAYT + GYAGY + CCAGGRATATGGCARYTAGAYTGY (SEQ ID NO: 14104) |
| 66 | +TRG + AYTGYAGY + CCAGGRATATGGCARYTAGAYTGY (SEQ ID NO: 14105) |
| 66 | +AYT + GYAGY + CCAGGRATATGGCARYTAGAYTGY (SEQ ID NO: 14106) |
| 66 | +AYTGYAGY + C + CAGGRATATGGCARYTAGAYTGY (SEQ ID NO: 14107) |
| 66 | +AYT + GYAGYC + CAGGRATATGGCARYTAGAYTGY (SEQ ID NO: 14108) |

TABLE 11-continued

| | |
|---|---|
| 66 | +GYAGY + C + CAGGRATATGGCARYTAGAYTGY (SEQ ID NO: 14109) |
| 66 | +GYAGYC + CA + GGRATATGGCARYTAGAYTGY (SEQ ID NO: 14110) |
| 66 | +GYAGY + CCA + GGRATATGGCARYTAGAYTGY (SEQ ID NO: 14111) |
| 66 | +C + CA + GGRATATGGCARYTAGAYTGY (SEQ ID NO: 14112) |
| 66 | +CCA + GGRATA + TGGCARYTAGAYTGY (SEQ ID NO: 14113) |
| 66 | +C + CAGGRATA + TGGCARYTAGAYTGY (SEQ ID NO: 14114) |
| 66 | +C + ARG + TRGAYTGYAGYCCAGGRATATGGCARYTAGAYTGYA (SEQ ID NO: 14115) |
| 66 | +CARG + TRG + AYTGYAGYCCAGGRATATGGCARYTAGAYTGYA (SEQ ID NO: 14116) |
| 66 | +C + ARGTRG + AYTGYAGYCCAGGRATATGGCARYTAGAYTGYA (SEQ ID NO: 14117) |
| 66 | +ARG + TRG + AYTGYAGYCCAGGRATATGGCARYTAGAYTGYA (SEQ ID NO: 14118) |
| 66 | +ARGTRG + AYT + GYAGYCCAGGRATATGGCARYTAGAYTGYA (SEQ ID NO: 14119) |
| 66 | +ARG + TRGAYT + GYAGYCCAGGRATATGGCARYTAGAYTGYA (SEQ ID NO: 14120) |
| 66 | +TRG + AYT + GYAGYCCAGGRATATGGCARYTAGAYTGYA (SEQ ID NO: 14121) |
| 66 | +TRGAYT + GYAGY + CCAGGRATATGGCARYTAGAYTGYA (SEQ ID NO: 14122) |
| 66 | +TRG + AYTGYAGY + CCAGGRATATGGCARYTAGAYTGYA (SEQ ID NO: 14123) |
| 66 | +AYT + GYAGY + CCAGGRATATGGCARYTAGAYTGYA (SEQ ID NO: 14124) |
| 66 | +AYTGYAGY + C + CAGGRATATGGCARYTAGAYTGYA (SEQ ID NO: 14125) |
| 66 | +AYT + GYAGYC + CAGGRATATGGCARYTAGAYTGYA (SEQ ID NO: 14126) |
| 66 | +GYAGY + C + CAGGRATATGGCARYTAGAYTGYA (SEQ ID NO: 14127) |
| 66 | +GYAGYC + CA + GGRATATGGCARYTAGAYTGYA (SEQ ID NO: 14128) |
| 66 | +GYAGY + CCA + GGRATATGGCARYTAGAYTGYA (SEQ ID NO: 14129) |
| 66 | +C + CA + GGRATATGGCARYTAGAYTGYA (SEQ ID NO: 14130) |
| 66 | +CCA + GGRATA + TGGCARYTAGAYTGYA (SEQ ID NO: 14131) |
| 66 | +C + CAGGRATA + TGGCARYTAGAYTGYA (SEQ ID NO: 14132) |
| 66 | ACARGTRGAYTGYAGYCCAGGRATATGGCARYTAGAYTGY (SEQ ID NO: 14133) |
| 66 | ARGTRGAYTGYAGYCCAGGRATATGGCARYTAGAYTGY (SEQ ID NO: 14134) |
| 66 | TRGAYTGYAGYCCAGGRATATGGCARYTAGAYTGY (SEQ ID NO: 14135) |
| 66 | AYTGYAGYCCAGGRATATGGCARYTAGAYTGY (SEQ ID NO: 14136) |
| 66 | GYAGYCCAGGRATATGGCARYTAGAYTGY (SEQ ID NO: 14137) |
| 66 | CCAGGRATATGGCARYTAGAYTGY (SEQ ID NO: 14138) |
| 66 | CARGTRGAYTGYAGYCCAGGRATATGGCARYTAGAYTGYA (SEQ ID NO: 14139) |
| 66 | ARGTRGAYTGYAGYCCAGGRATATGGCARYTAGAYTGYA (SEQ ID NO: 14140) |
| 66 | TRGAYTGYAGYCCAGGRATATGGCARYTAGAYTGYA (SEQ ID NO: 14141) |
| 66 | AYTGYAGYCCAGGRATATGGCARYTAGAYTGYA (SEQ ID NO: 14142) |
| 66 | GYAGYCCAGGRATATGGCARYTAGAYTGYA (SEQ ID NO: 14143) |
| 66 | CCAGGRATATGGCARYTAGAYTGYA (SEQ ID NO:14144) |
| 66 | CATGGACARGTRGAYTGYAGYCCAGGRATATGGCARYTAGATTGT (SEQ ID NO: 14145) |
| 66 | ACARGTRGAYTGYAGYCCAGGRATATGGCARYTAGAYTGY + N (SEQ ID NO: 14146) |

TABLE 11-continued

| | |
|---|---|
| 66 | ARGTRGAYTGYAGYCCAGGRATATGGCARYTAGAYTGY + N (SEQ ID NO: 14147) |
| 66 | TRGAYTGYAGYCCAGGRATATGGCARYTAGAYTGY + N (SEQ ID NO: 14148) |
| 66 | AYTGYAGYCCAGGRATATGGCARYTAGAYTGY + N (SEQ ID NO: 14149) |
| 66 | GYAGYCCAGGRATATGGCARYTAGAYTGY + N (SEQ ID NO: 14150) |
| 66 | CCAGGRATATGGCARYTAGAYTGY + N (SEQ ID NO: 14151) |
| 66 | CARGTRGAYTGYAGYCCAGGRATATGGCARYTAGAYTGYA + N (SEQ ID NO: 14152) |
| 66 | ARGTRGAYTGYAGYCCAGGRATATGGCARYTAGAYTGYA + N (SEQ ID NO: 14153) |
| 66 | TRGAYTGYAGYCCAGGRATATGGCARYTAGAYTGYA + N (SEQ ID NO: 14154) |
| 66 | AYTGYAGYCCAGGRATATGGCARYTAGAYTGYA + N (SEQ ID NO: 14155) |
| 66 | GYAGYCCAGGRATATGGCARYTAGAYTGYA + N (SEQ ID NO: 14156) |
| 66 | CCAGGRATATGGCARYTAGAYTGYA + N (SEQ ID NO: 14157) |
| 66 | CATGGACARGTRGAYTGYAGYCCAGGRATATGGCARYTAGATTGT + N (SEQ ID NO: 14158) |
| 74 | A + T + G + GCARYTAGAYTGYACACAYYTAGAAGGRAAARTHATY (SEQ ID NO: 14159) |
| 74 | A + TG + G + CARYTAGAYTGYACACAYYTAGAAGGRAAARTHATY (SEQ ID NO: 14160) |
| 74 | A + T + GG + CARYTAGAYTGYACACAYYTAGAAGGRAAARTHATY (SEQ ID NO: 14161) |
| 74 | +G + G + CARYTAGAYTGYACACAYYTAGAAGGRAAARTHATY (SEQ ID NO: 14162) |
| 74 | +GG + C + ARYTAGAYTGYACACAYYTAGAAGGRAAARTHATY (SEQ ID NO: 14163) |
| 74 | +G + GC + ARYTAGAYTGYACACAYYTAGAAGGRAAARTHATY (SEQ ID NO: 14164) |
| 74 | +G + C + ARYTAGAYTGYACACAYYTAGAAGGRAAARTHATY (SEQ ID NO: 14165) |
| 74 | +GC + ARY + TAGAYTGYACACAYYTAGAAGGRAAARTHATY (SEQ ID NO: 14166) |
| 74 | +G + CARY + TAGAYTGYACACAYYTAGAAGGRAAARTHATY (SEQ ID NO: 14167) |
| 74 | +C + ARY + TAGAYTGYACACAYYTAGAAGGRAAARTHATY (SEQ ID NO: 14168) |
| 74 | +CARY + TA + GAYTGYACACAYYTAGAAGGRAAARTHATY (SEQ ID NO: 14169) |
| 74 | +C + ARYTA + GAYTGYACACAYYTAGAAGGRAAARTHATY (SEQ ID NO: 14170) |
| 74 | +ARY + TA + GAYTGYACACAYYTAGAAGGRAAARTHATY (SEQ ID NO: 14171) |
| 74 | +ARYTA + G + AYTGYACACAYYTAGAAGGRAAARTHATY (SEQ ID NO: 14172) |
| 74 | +ARY + TAG + AYTGYACACAYYTAGAAGGRAAARTHATY (SEQ ID NO: 14173) |
| 74 | +TA + G + AYTGYACACAYYTAGAAGGRAAARTHATY (SEQ ID NO: 14174) |
| 74 | +TAG + AY + TGYACACAYYTAGAAGGRAAARTHATY (SEQ ID NO: 14175) |
| 74 | +TA + GAY + TGYACACAYYTAGAAGGRAAARTHATY (SEQ ID NO: 14176) |
| 74 | ATGGCARYTAGAYTGYACACAYYTAGAAGGRAAARTHATY (SEQ ID NO: 14177) |
| 74 | GGCARYTAGAYTGYACACAYYTAGAAGGRAAARTHATY (SEQ ID NO: 14178) |
| 74 | GCARYTAGAYTGYACACAYYTAGAAGGRAAARTHATY (SEQ ID NO: 14179) |
| 74 | CARYTAGAYTGYACACAYYTAGAAGGRAAARTHATY (SEQ ID NO: 14180) |
| 74 | ARYTAGAYTGYACACAYYTAGAAGGRAAARTHATY (SEQ ID NO: 14181) |
| 74 | TAGAYTGYACACAYYTAGAAGGRAAARTHATY (SEQ ID NO: 14182) |
| 74 | GGRATATGGCARYTAGAYTGYACACAYYTAGAAGGRAAAATTATC (SEQ ID NO: 14183) |
| 74 | ATGGCARYTAGAYTGYACACAYYTAGAAGGRAAARTHATY + N (SEQ ID NO: 14184) |
| 74 | GGCARYTAGAYTGYACACAYYTAGAAGGRAAARTHATY + N (SEQ ID NO: 14185) |

TABLE 11-continued

| | |
|---|---|
| 74 | GCARYTAGAYTGYACACAYYTAGAAGGRAAARTHATY + N (SEQ ID NO: 14186) |
| 74 | CARYTAGAYTGYACACAYYTAGAAGGRAAARTHATY + N (SEQ ID NO: 14187) |
| 74 | ARYTAGAYTGYACACAYYTAGAAGGRAAARTHATY + N (SEQ ID NO: 14188) |
| 74 | TAGAYTGYACACAYYTAGAAGGRAAARTHATY + N (SEQ ID NO: 14189) |
| 74 | GGRATATGGCARYTAGAYTGYACACAYYTAGAAGGRAAAATTATC + N (SEQ ID NO: 14190) |
| 92 | +G + TR + GCYAGTGGMTAYATRGAAGCAGARGTYATYCCAGCAG (SEQ ID NO: 14191) |
| 92 | +GTR + G + CYAGTGGMTAYATRGAAGCAGARGTYATYCCAGCAG (SEQ ID NO: 14192) |
| 92 | +G + TRG + CYAGTGGMTAYATRGAAGCAGARGTYATYCCAGCAG (SEQ ID NO: 14193) |
| 92 | +TR + G + CYAGTGGMTAYATRGAAGCAGARGTYATYCCAGCAG (SEQ ID NO: 14194) |
| 92 | +TRG + CY + AGTGGMTAYATRGAAGCAGARGTYATYCCAGCAG (SEQ ID NO: 14195) |
| 92 | +TR + GCY + AGTGGMTAYATRGAAGCAGARGTYATYCCAGCAG (SEQ IDNO:14196) |
| 92 | +G + CY + AGTGGMTAYATRGAAGCAGARGTYATYCCAGCAG (SEQ IDNO:14197) |
| 92 | +GCY + A + GTGGMTAYATRGAAGCAGARGTYATYCCAGCAG (SEQ IDNO:14198) |
| 92 | +G + CYA + GTGGMTAYATRGAAGCAGARGTYATYCCAGCAG (SEQ IDNO:14199) |
| 92 | +CY + A + GTGGMTAYATRGAAGCAGARGTYATYCCAGCAG (SEQ IDNO:14200) |
| 92 | +CYA + GT + GGMTAYATRGAAGCAGARGTYATYCCAGCAG (SEQ ID NO: 14201) |
| 92 | +CY + AGT + GGMTAYATRGAAGCAGARGTYATYCCAGCAG (SEQ ID NO: 14202) |
| 92 | +A + GT + GGMTAYATRGAAGCAGARGTYATYCCAGCAG (SEQ ID NO: 14203) |
| 92 | +AGT + G + GMTAYATRGAAGCAGARGTYATYCCAGCAG (SEQ ID NO: 14204) |
| 92 | +A + GTG + GMTAYATRGAAGCAGARGTYATYCCAGCAG (SEQ ID NO: 14205) |
| 92 | +GT + G + GMTAYATRGAAGCAGARGTYATYCCAGCAG (SEQ ID NO: 14206) |
| 92 | +GTG + GM + TAYATRGAAGCAGARGTYATYCCAGCAG (SEQ ID NO: 14207) |
| 92 | +GT + GGM + TAYATRGAAGCAGARGTYATYCCAGCAG (SEQ ID NO: 14208) |
| 92 | Y + G + TR + GCYAGTGGMTAYATRGAAGCAGARGTYATYCCAGCA (SEQ ID NO: 14209) |
| 92 | Y + GTR + G + CYAGTGGMTAYATRGAAGCAGARGTYATYCCAGCA (SEQ ID NO: 14210) |
| 92 | Y + G + TRG + CYAGTGGMTAYATRGAAGCAGARGTYATYCCAGCA (SEQ ID NO: 14211) |
| 92 | +TR + G + CYAGTGGMTAYATRGAAGCAGARGTYATYCCAGCA (SEQ ID NO: 14212) |
| 92 | +TRG + CY + AGTGGMTAYATRGAAGCAGARGTYATYCCAGCA (SEQ ID NO: 14213) |
| 92 | +TR + GCY + AGTGGMTAYATRGAAGCAGARGTYATYCCAGCA (SEQ ID NO: 14214) |
| 92 | +G + CY + AGTGGMTAYATRGAAGCAGARGTYATYCCAGCA (SEQ ID NO: 14215) |
| 92 | +GCY + A + GTGGMTAYATRGAAGCAGARGTYATYCCAGCA (SEQ ID NO: 14216) |
| 92 | +G + CYA + GTGGMTAYATRGAAGCAGARGTYATYCCAGCA (SEQ ID NO: 14217) |
| 92 | +CY + A + GTGGMTAYATRGAAGCAGARGTYATYCCAGCA (SEQ ID NO: 14218) |
| 92 | +CYA + GT + GGMTAYATRGAAGCAGARGTYATYCCAGCA (SEQ ID NO: 14219) |
| 92 | +CY + AGT + GGMTAYATRGAAGCAGARGTYATYCCAGCA (SEQ ID NO: 14220) |
| 92 | +A + GT + GGMTAYATRGAAGCAGARGTYATYCCAGCA (SEQ ID NO: 14221) |
| 92 | +AGT + G + GMTAYATRGAAGCAGARGTYATYCCAGCA (SEQ ID NO: 14222) |
| 92 | +A + GTG + GMTAYATRGAAGCAGARGTYATYCCAGCA (SEQ ID NO: 14223) |

TABLE 11-continued

| | |
|---|---|
| 92 | +GT + G + GMTAYATRGAAGCAGARGTYATYCCAGCA (SEQ ID NO: 14224) |
| 92 | +GTG + GM + TAYATRGAAGCAGARGTYATYCCAGCA (SEQ ID NO: 14225) |
| 92 | +GT + GGM + TAYATRGAAGCAGARGTYATYCCAGCA (SEQ ID NO: 14226) |
| 92 | GTRGCYAGTGGMTAYATRGAAGCAGARGTYATYCCAGCAG (SEQ ID NO: 14227) |
| 92 | TRGCYAGTGGMTAYATRGAAGCAGARGTYATYCCAGCAG (SEQ ID NO: 14228) |
| 92 | GCYAGTGGMTAYATRGAAGCAGARGTYATYCCAGCAG (SEQ ID NO: 14229) |
| 92 | CYAGTGGMTAYATRGAAGCAGARGTYATYCCAGCAG (SEQ ID NO: 14230) |
| 92 | AGTGGMTAYATRGAAGCAGARGTYATYCCAGCAG (SEQ ID NO: 14231) |
| 92 | GTGGMTAYATRGAAGCAGARGTYATYCCAGCAG (SEQ ID NO: 14232) |
| 92 | YGTRGCYAGTGGMTAYATRGAAGCAGARGTYATYCCAGCA (SEQ ID NO: 14233) |
| 92 | TRGCYAGTGGMTAYATRGAAGCAGARGTYATYCCAGCA (SEQ ID NO: 14234) |
| 92 | GCYAGTGGMTAYATRGAAGCAGARGTYATYCCAGCA (SEQ ID NO: 14235) |
| 92 | CYAGTGGMTAYATRGAAGCAGARGTYATYCCAGCA (SEQ ID NO: 14236) |
| 92 | AGTGGMTAYATRGAAGCAGARGTYATYCCAGCA (SEQ ID NO: 14237) |
| 92 | GTGGMTAYATRGAAGCAGARGTYATYCCAGCA (SEQ ID NO: 14238) |
| 92 | GTYCAYGTRGCYAGTGGVTAYATRGAAGCAGARGTYATCCCAGCA (SEQ ID NO: 14239) |
| 92 | GTRGCYAGTGGMTAYATRGAAGCAGARGTYATYCCAGCAG + N (SEQ ID NO: 14240) |
| 92 | TRGCYAGTGGMTAYATRGAAGCAGARGTYATYCCAGCAG + N (SEQ ID NO: 14241) |
| 92 | GCYAGTGGMTAYATRGAAGCAGARGTYATYCCAGCAG + N (SEQ ID NO: 14242) |
| 92 | CYAGTGGMTAYATRGAAGCAGARGTYATYCCAGCAG + N (SEQ ID NO: 14243) |
| 92 | AGTGGMTAYATRGAAGCAGARGTYATYCCAGCAG + N (SEQ ID NO: 14244) |
| 92 | GTGGMTAYATRGAAGCAGARGTYATYCCAGCAG + N (SEQ ID NO: 14245) |
| 92 | YGTRGCYAGTGGMTAYATRGAAGCAGARGTYATYCCAGCA + N (SEQ ID NO: 14246) |
| 92 | TRGCYAGTGGMTAYATRGAAGCAGARGTYATYCCAGCA + N (SEQ ID NO: 14247) |
| 92 | GCYAGTGGMTAYATRGAAGCAGARGTYATYCCAGCA + N (SEQ ID NO: 14248) |
| 92 | CYAGTGGMTAYATRGAAGCAGARGTYATYCCAGCA + N (SEQ ID NO: 14249) |
| 92 | AGTGGMTAYATRGAAGCAGARGTYATYCCAGCA + N (SEQ ID NO: 14250) |
| 92 | GTGGMTAYATRGAAGCAGARGTYATYCCAGCA + N (SEQ ID NO: 14251) |
| 92 | GTYCAYGTRGCYAGTGGVTAYATRGAAGCAGARGTYATCCCAGCA + N (SEQ ID NO: 14252) |
| 97 | YA + TR + G + AAGCAGARGTYATYCCAGCAGARACAGGRCARGAR (SEQ ID NO: 14253) |
| 97 | YA + TRG + AA + GCAGARGTYATYCCAGCAGARACAGGRCARGAR (SEQ ID NO: 14254) |
| 97 | YA + TR + GAA + GCAGARGTYATYCCAGCAGARACAGGRCARGAR (SEQ ID NO: 14255) |
| 97 | +G + AA + GCAGARGTYATYCCAGCAGARACAGGRCARGAR (SEQ ID NO: 14256) |
| 97 | +GAA + G + CAGARGTYATYCCAGCAGARACAGGRCARGAR (SEQ ID NO: 14257) |
| 97 | +G + AAG + CAGARGTYATYCCAGCAGARACAGGRCARGAR (SEQ ID NO: 14258) |

TABLE 11-continued

| | |
|---|---|
| 97 | +AA + G + CAGARGTYATYCCAGCAGARACAGGRCARGAR (SEQ ID NO: 14259) |
| 97 | +AAG + CAG + ARGTYATYCCAGCAGARACAGGRCARGAR (SEQ ID NO: 14260) |
| 97 | +AA + GCAG + ARGTYATYCCAGCAGARACAGGRCARGAR (SEQ ID NO: 14261) |
| 97 | +G + CAG + ARGTYATYCCAGCAGARACAGGRCARGAR (SEQ ID NO: 14262) |
| 97 | +GCAG + ARG + TYATYCCAGCAGARACAGGRCARGAR (SEQ ID NO: 14263) |
| 97 | +G + CAGARG + TYATYCCAGCAGARACAGGRCARGAR (SEQ ID NO: 14264) |
| 97 | +CAG + ARG + TYATYCCAGCAGARACAGGRCARGAR (SEQ ID NO: 14265) |
| 97 | +CAGARG + TYA + TYCCAGCAGARACAGGRCARGAR (SEQ ID NO: 14266) |
| 97 | +CAG + ARGTYA + TYCCAGCAGARACAGGRCARGAR (SEQ ID NO: 14267) |
| 97 | +ARG + TYA + TYCCAGCAGARACAGGRCARGAR (SEQ ID NO: 14268) |
| 97 | +ARGTYA + TYCCAGCAGARACAGGRCARGAR (SEQ ID NO: 14269) |
| 97 | +ARG + TYATYCCAGCAGARACAGGRCARGAR (SEQ ID NO: 14270) |
| 97 | YATRGAAGCAGARGTYATYCCAGCAGARACAGGRCARGAR (SEQ ID NO: 14271) |
| 97 | GAAGCAGARGTYATYCCAGCAGARACAGGRCARGAR (SEQ ID NO: 14272) |
| 97 | AAGCAGARGTYATYCCAGCAGARACAGGRCARGAR (SEQ ID NO: 14273) |
| 97 | GCAGARGTYATYCCAGCAGARACAGGRCARGAR (SEQ ID NO: 14274) |
| 97 | CAGARGTYATYCCAGCAGARACAGGRCARGAR (SEQ ID NO: 14275) |
| 97 | ARGTYATYCCAGCAGARACAGGRCARGAR (SEQ ID NO: 14276) |
| 97 | TGGVTAYATRGAAGCAGARGTYATYCCAGCAGARACAGGACAGGAA (SEQ ID NO: 14277) |
| 97 | YATRGAAGCAGARGTYATYCCAGCAGARACAGGRCARGAR + N (SEQ ID NO: 14278) |
| 97 | GAAGCAGARGTYATYCCAGCAGARACAGGRCARGAR + N (SEQ ID NO: 14279) |
| 97 | AAGCAGARGTYATYCCAGCAGARACAGGRCARGAR + N (SEQ ID NO: 14280) |
| 97 | GCAGARGTYATYCCAGCAGARACAGGRCARGAR + N (SEQ ID NO: 14281) |
| 97 | CAGARGTYATYCCAGCAGARACAGGRCARGAR + N (SEQ ID NO: 14282) |
| 97 | ARGTYATYCCAGCAGARACAGGRCARGAR + N (SEQ ID NO: 14283) |
| 97 | TGGVTAYATRGAAGCAGARGTYATYCCAGCAGARACAGGACAGGAA + N (SEQ ID NO: 14284) |
| 118 | AG + CA + GGAAGR + TGGCCAGTVAARRYARTACAYACAGAYAAT (SEQ ID NO: 14285) |
| 118 | AG + CAGGAAGR + T + GGCCAGTVAARRYARTACAYACAGAYAAT (SEQ ID NO: 14286) |
| 118 | AG + CA + GGAAGRT + GGCCAGTVAARRYARTACAYACAGAYAAT (SEQ ID NO: 14287) |
| 118 | +GGAAGR + T + GGCCAGTVAARRYARTACAYACAGAYAAT (SEQ ID NO: 14288) |
| 118 | +GGAAGRT + G + GCCAGTVAARRYARTACAYACAGAYAAT (SEQ ID NO: 14289) |
| 118 | +GGAAGR + TG + GCCAGTVAARRYARTACAYACAGAYAAT (SEQ ID NO: 14290) |
| 118 | +T + G + GCCAGTVAARRYARTACAYACAGAYAAT (SEQ ID NO: 14291) |
| 118 | +TG + G + CCAGTVAARRYARTACAYACAGAYAAT (SEQ ID NO: 14292) |
| 118 | +T + GG + CCAGTVAARRYARTACAYACAGAYAAT (SEQ ID NO: 14293) |
| 118 | +G + G + CCAGTVAARRYARTACAYACAGAYAAT (SEQ ID NO: 14294) |
| 118 | +GG + C + CAGTVAARRYARTACAYACAGAYAAT (SEQ ID NO: 14295) |
| 118 | +G + GC + CAGTVAARRYARTACAYACAGAYAAT (SEQ ID NO: 14296) |
| 118 | +G + C + CAGTVAARRYARTACAYACAGAYAAT (SEQ ID NO: 14297) |

TABLE 11-continued

| | | |
|---|---|---|
| 118 | +GC + CAG + TVAARRYARTACAYACAGAYAAT | (SEQ ID NO: 14298) |
| 118 | +G + CCAG + TVAARRYARTACAYACAGAYAAT | (SEQ ID NO: 14299) |
| 118 | +C + CAG + TVAARRYARTACAYACAGAYAAT | (SEQ ID NO: 14300) |
| 118 | +CCAG + TVAARRYAR + TACAYACAGAYAAT | (SEQ ID NO: 14301) |
| 118 | +C + CAGTVAARRYAR + TACAYACAGAYAAT | (SEQ ID NO: 14302) |
| 118 | AGCAGGAAGRTGGCCAGTVAARRYARTACAYACAGAYAAT | (SEQ ID NO: 14303) |
| 118 | GGAAGRTGGCCAGTVAARRYARTACAYACAGAYAAT | (SEQ ID NO: 14304) |
| 118 | TGGCCAGTVAARRYARTACAYACAGAYAAT | (SEQ ID NO: 14305) |
| 118 | GGCCAGTVAARRYARTACAYACAGAYAAT | (SEQ ID NO: 14306) |
| 118 | GCCAGTVAARRYARTACAYACAGAYAAT | (SEQ ID NO: 14307) |
| 118 | CCAGTVAARRYARTACAYACAGAYAAT | (SEQ ID NO: 14308) |
| 118 | AAARYTAGCAGGRAGRTGGCCAGTVARARYARTACAYACAGACAAT | (SEQ ID NO: 14309) |
| 118 | AGCAGGAAGRTGGCCAGTVAARRYARTACAYACAGAYAAT + N | (SEQ ID NO: 14310) |
| 118 | GGAAGRTGGCCAGTVAARRYARTACAYACAGAYAAT + N | (SEQ ID NO: 14311) |
| 118 | TGGCCAGTVAARRYARTACAYACAGAYAAT + N | (SEQ ID NO: 14312) |
| 118 | GGCCAGTVAARRYARTACAYACAGAYAAT + N | (SEQ ID NO: 14313) |
| 118 | GCCAGTVAARRYARTACAYACAGAYAAT + N | (SEQ ID NO: 14314) |
| 118 | CCAGTVAARRYARTACAYACAGAYAAT + N | (SEQ ID NO: 14315) |
| 118 | AAARYTAGCAGGRAGRTGGCCAGTVARARYARTACAYACAGACAAT + N | (SEQ ID NO: 14316) |
| 121 | +T + G + GCCAGTVAARRYARTACAYACAGAYAATGGYMSYAAYT | (SEQ ID NO: 14317) |
| 121 | +TG + G + CCAGTVAARRYARTACAYACAGAYAATGGYMSYAAYT | (SEQ ID NO: 14318) |
| 121 | +T + GG + CCAGTVAARRYARTACAYACAGAYAATGGYMSYAAYT | (SEQ ID NO: 14319) |
| 121 | +G + G + CCAGTVAARRYARTACAYACAGAYAATGGYMSYAAYT | (SEQ ID NO: 14320) |
| 121 | +GG + C + CAGTVAARRYARTACAYACAGAYAATGGYMSYAAYT | (SEQ ID NO: 14321) |
| 121 | +G + GC + CAGTVAARRYARTACAYACAGAYAATGGYMSYAAYT | (SEQ ID NO: 14322) |
| 121 | +G + C + CAGTVAARRYARTACAYACAGAYAATGGYMSYAAYT | (SEQ ID NO: 14323) |
| 121 | +GC + CAG + TVAARRYARTACAYACAGAYAATGGYMSYAAYT | (SEQ ID NO: 14324) |
| 121 | +G + CCAG + TVAARRYARTACAYACAGAYAATGGYMSYAAYT | (SEQ ID NO: 14325) |
| 121 | +C + CAG + TVAARRYARTACAYACAGAYAATGGYMSYAAYT | (SEQ ID NO: 14326) |
| 121 | +CCAG + TVAARRYAR + TACAYACAGAYAATGGYMSYAAYT | (SEQ ID NO: 14327) |
| 121 | +C + CAGTVAARRYAR + TACAYACAGAYAATGGYMSYAAYT | (SEQ ID NO: 14328) |
| 121 | +CAG + TVAARRYAR + TACAYACAGAYAATGGYMSYAAYT | (SEQ ID NO: 14329) |
| 121 | +CAGTVAARRYAR + TA + CAYACAGAYAATGGYMSYAAYT | (SEQ ID NO: 14330) |
| 121 | +CAG + TVAARRYARTA + CAYACAGAYAATGGYMSYAAYT | (SEQ ID NO: 14331) |
| 121 | +TVAARRYAR + TA + CAYACAGAYAATGGYM SYAAYT | (SEQ ID NO: 14332) |
| 121 | +TVAARRYARTA + C + AYACAGAYAATGGYM SYAAYT | (SEQ ID NO: 14333) |

TABLE 11-continued

| | |
|---|---|
| 121 | +TVAARRYAR + TAC + AYACAGAYAATGGYM SYAAYT (SEQ ID NO: 14334) |
| 121 | TGGCCAGTVAARRYARTACAYACAGAYAATGGYMSYAAYT (SEQ ID NO: 14335) |
| 121 | GGCCAGTVAARRYARTACAYACAGAYAATGGYMSYAAYT (SEQ ID NO: 14336) |
| 121 | GCCAGTVAARRYARTACAYACAGAYAATGGYMSYAAYT (SEQ ID NO: 14337) |
| 121 | CCAGTVAARRYARTACAYACAGAYAATGGYMSYAAYT (SEQ ID NO: 14338) |
| 121 | CAGTVAARRYARTACAYACAGAYAATGGYM SYAAYT (SEQ ID NO: 14339) |
| 121 | TVAARRYARTACAYACAGAYAATGGYMSYAAYT (SEQ ID NO: 14340) |
| 121 | GGRAGRTGGCCAGTVARARYARTACAYACAGAYAAYGGYAGCAAT (SEQ ID NO: 14341) |
| 121 | TGGCCAGTVAARRYARTACAYACAGAYAATGGYMSYAAYT + N (SEQ ID NO: 14342) |
| 121 | GGCCAGTVAARRYARTACAYACAGAYAATGGYMSYAAYT + N (SEQ ID NO: 14343) |
| 121 | GCCAGTVAARRYARTACAYACAGAYAATGGYMSYAAYT + N (SEQ ID NO: 14344) |
| 121 | CCAGTVAARRYARTACAYACAGAYAATGGYMSYAAYT + N (SEQ ID NO: 14345) |
| 121 | CAGTVAARRYARTACAYACAGAYAATGGYMSYAAYT + N (SEQ ID NO: 14346) |
| 121 | TVAARRYARTACAYACAGAYAATGGYMSYAAYT + N (SEQ ID NO: 14347) |
| 121 | GGRAGRTGGCCAGTVARARYARTACAYACAGAYAAYGGYAGCAAT + N (SEQ ID NO: 14348) |
| 138 | RCRGTHAAR + G + CH + GCMTGYTGGTGGGCVRRBRTCMMRCARG (SEQ ID NO: 14349) |
| 138 | RCRGTHAAR + GCH + G + CMTGYTGGTGGGCVRRBRTCMMRCARG (SEQ ID NO: 14350) |
| 138 | RCRGTHAAR + G + CHG + CMTGYTGGTGGGCVRRBRTCMMRCARG (SEQ ID NO: 14351) |
| 138 | +CH + G + CMTGYTGGTGGGCVRRBRTCMMRCARG (SEQ ID NO: 14352) |
| 138 | +CHG + CM + TGYTGGTGGGCVRRBRTCMMRCARG (SEQ ID NO: 14353) |
| 138 | +CH + GCM + TGYTGGTGGGCVRRBRTCMMRCARG (SEQ ID NO: 14354) |
| 138 | +G + CM + TGYTGGTGGGCVRRBRTCMMRCARG (SEQ ID NO: 14355) |
| 138 | +GCM + T + GYTGGTGGGCVRRBRTCMMRCARG (SEQ ID NO: 14356) |
| 138 | +G + CMT + GYTGGTGGGCVRRBRTCMMRCARG (SEQ ID NO: 14357) |
| 138 | +CM + T + GYTGGTGGGCVRRBRTCMMRCARG (SEQ ID NO: 14358) |
| 138 | +CMT + GY + TGGTGGGCVRRBRTCMMRCARG (SEQ ID NO: 14359) |
| 138 | +CM + TGY + TGGTGGGCVRRBRTCMMRCARG (SEQ ID NO: 14360) |
| 138 | +T + GY + TGGTGGGCVRRBRTCMMRCARG (SEQ ID NO: 14361) |
| 138 | +TGY + T + GGTGGGCVRRBRTCMMRCARG (SEQ ID NO: 14362) |
| 138 | +T + GYT + GGTGGGCVRRBRTCMMRCARG (SEQ ID NO: 14363) |
| 138 | +GY + T + GGTGGGCVRRBRTCMMRCARG (SEQ ID NO: 14364) |
| 138 | +GYT + G + GTGGGCVRRBRTCMMRCARG (SEQ ID NO: 14365) |
| 138 | +GY + TG + GTGGGCVRRBRTCMMRCARG (SEQ ID NO: 14366) |
| 138 | TRCRGTHAAR + G + CH + GCMTGYTGGTGGGCVRRBRTCMMRCAR (SEQ ID NO: 14367) |
| 138 | TRCRGTHAAR + GCH + G + CMTGYTGGTGGGCVRRBRTCMMRCAR (SEQ ID NO: 14368) |

TABLE 11-continued

| | | |
|---|---|---|
| 138 | TRCRGTHAAR + G + CHG + CMTGYTGGTGGGCVRRBRTCMMRCAR (SEQ ID NO: 14369) | |
| 138 | +CH + G + CMTGYTGGTGGGCVRRBRTCMMRCAR (SEQ ID NO: 14370) | |
| 138 | +CHG + CM + TGYTGGTGGGCVRRBRTCMMRCAR (SEQ ID NO: 14371) | |
| 138 | +CH + GCM + TGYTGGTGGGCVRRBRTCMMRCAR (SEQ ID NO: 14372) | |
| 138 | +G + CM + TGYTGGTGGGCVRRBRTCMMRCAR (SEQ ID NO: 14373) | |
| 138 | +GCM + T + GYTGGTGGGCVRRBRTCMMRCAR (SEQ ID NO: 14374) | |
| 138 | +G + CMT + GYTGGTGGGCVRRBRTCMMRCAR (SEQ ID NO: 14375) | |
| 138 | +CM + T + GYTGGTGGGCVRRBRTCMMRCAR (SEQ ID NO: 14376) | |
| 138 | +CMT + GY + TGGTGGGCVRRBRTCMMRCAR (SEQ ID NO: 14377) | |
| 138 | +CM + TGY + TGGTGGGCVRRBRTCMMRCAR (SEQ ID NO: 14378) | |
| 138 | +T + GY + TGGTGGGCVRRBRTCMMRCAR (SEQ ID NO: 14379) | |
| 138 | +TGY + T + GGTGGGCVRRBRTCMMRCAR (SEQ ID NO: 14380) | |
| 138 | +T + GYT + GGTGGGCVRRBRTCMMRCAR (SEQ ID NO: 14381) | |
| 138 | +GY + T + GGTGGGCVRRBRTCMMRCAR (SEQ ID NO: 14382) | |
| 138 | +GYT + G + GTGGGCVRRBRTCMMRCAR (SEQ ID NO: 14383) | |
| 138 | +GY + TG + GTGGGCVRRBRTCMMRCAR (SEQ ID NO: 14384) | |
| 138 | RCRGTHAARGCHGCMTGYTGGTGGGCVRRBRTCMMRCARG (SEQ ID NO: 14385) | |
| 138 | CHGCMTGYTGGTGGGCVRRBRTCMMRCARG (SEQ ID NO: 14386) | |
| 138 | GCMTGYTGGTGGGCVRRBRTCMMRCARG (SEQ ID NO: 14387) | |
| 138 | CMTGYTGGTGGGCVRRBRTCMMRCARG (SEQ ID NO: 14388) | |
| 138 | TGYTGGTGGGCVRRBRTCMMRCARG (SEQ ID NO: 14389) | |
| 138 | GYTGGTGGGCVRRBRTCMMRCARG (SEQ ID NO: 14390) | |
| 138 | TRCRGTHAARGCHGCMTGYTGGTGGGCVRRBRTCMMRCAR (SEQ ID NO: 14391) | |
| 138 | CHGCMTGYTGGTGGGCVRRBRTCMMRCAR (SEQ ID NO: 14392) | |
| 138 | GCMTGYTGGTGGGCVRRBRTCMMRCAR (SEQ ID NO: 14393) | |
| 138 | CMTGYTGGTGGGCVRRBRTCMMRCAR (SEQ ID NO: 14394) | |
| 138 | TGYTGGTGGGCVRRBRTCMMRCAR (SEQ ID NO: 14395) | |
| 138 | GYTGGTGGGCVRRBRTCMMRCAR (SEQ ID NO: 14396) | |
| 138 | AGYRMYRCRGTHAARGCHGCMTGYTGGTGGGCVRRDRTYAAACAG (SEQ ID NO: 14397) | |
| 138 | RCRGTHAARGCHGCMTGYTGGTGGGCVRRBRTCMMRCARG + N (SEQ ID NO: 14398) | |
| 138 | CHGCMTGYTGGTGGGCVRRBRTCMMRCARG + N (SEQ ID NO: 14399) | |
| 138 | GCMTGYTGGTGGGCVRRBRTCMMRCARG + N (SEQ ID NO: 14400) | |
| 138 | CMTGYTGGTGGGCVRRBRTCMMRCARG + N (SEQ ID NO: 14401) | |
| 138 | TGYTGGTGGGCVRRBRTCMMRCARG + N (SEQ ID NO: 14402) | |
| 138 | GYTGGTGGGCVRRBRTCMMRCARG + N (SEQ ID NO: 14403) | |
| 138 | TRCRGTHAARGCHGCMTGYTGGTGGGCVRRBRTCMMRCAR + N (SEQ ID NO: 14404) | |
| 138 | CHGCMTGYTGGTGGGCVRRBRTCMMRCAR + N (SEQ ID NO: 14405) | |
| 138 | GCMTGYTGGTGGGCVRRBRTCMMRCAR + N (SEQ ID NO: 14406) | |
| 138 | CMTGYTGGTGGGCVRRBRTCMMRCAR + N (SEQ ID NO: 14407) | |

TABLE 11-continued

| | |
|---|---|
| 138 | TGYTGGTGGGCVRRBRTCMMRCAR + N (SEQ ID NO: 14408) |
| 138 | GYTGGTGGGCVRRBRTCMMRCAR + N (SEQ ID NO: 14409) |
| 138 | AGYRMYRCRGTHAARGCHGCMTGYTGGTGGGCVRRDRTYAAACAG + N (SEQ ID NO: 14410) |
| 140 | AAR + G + CH + GCMTGYTGGTGGGCVRRBRTCMMRCARGAATTTG (SEQ ID NO: 14411) |
| 140 | AAR + GCH + G + CMTGYTGGTGGGCVRRBRTCMMRCARGAATTTG (SEQ ID NO: 14412) |
| 140 | AAR + G + CHG + CMTGYTGGTGGGCVRRBRTCMMRCARGAATTTG (SEQ ID NO: 14413) |
| 140 | +CH + G + CMTGYTGGTGGGCVRRBRTCMMRCARGAATTTG (SEQ ID NO: 14414) |
| 140 | +CHG + CM + TGYTGGTGGGCVRRBRTCMMRCARGAATTTG (SEQ ID NO: 14415) |
| 140 | +CH + GCM + TGYTGGTGGGCVRRBRTCMMRCARGAATTTG (SEQ ID NO: 14416) |
| 140 | +G + CM + TGYTGGTGGGCVRRBRTCMMRCARGAATTTG (SEQ ID NO: 14417) |
| 140 | +GCM + T + GYTGGTGGGCVRRBRTCMMRCARGAATTTG (SEQ ID NO: 14418) |
| 140 | +G + CMT + GYTGGTGGGCVRRBRTCMMRCARGAATTTG (SEQ ID NO: 14419) |
| 140 | +CM + T + GYTGGTGGGCVRRBRTCMMRCARGAATTTG (SEQ ID NO: 14420) |
| 140 | +CMT + GY + TGGTGGGCVRRBRTCMMRCARGAATTTG (SEQ ID NO: 14421) |
| 140 | +CM + TGY + TGGTGGGCVRRBRTCMMRCARGAATTTG (SEQ ID NO: 14422) |
| 140 | +T + GY + TGGTGGGCVRRBRTCMMRCARGAATTTG (SEQ ID NO: 14423) |
| 140 | +TGY + T + GGTGGGCVRRBRTCMMRCARGAATTTG (SEQ ID NO: 14424) |
| 140 | +T + GYT + GGTGGGCVRRBRTCMMRCARGAATTTG (SEQ ID NO: 14425) |
| 140 | +GY + T + GGTGGGCVRRBRTCMMRCARGAATTTG (SEQ ID NO: 14426) |
| 140 | +GYT + G + GTGGGCVRRBRTCMMRCARGAATTTG (SEQ ID NO: 14427) |
| 140 | +GY + TG + GTGGGCVRRBRTCMMRCARGAATTTG (SEQ ID NO: 14428) |
| 140 | HAAR + G + CH + GCMTGYTGGTGGGCVRRBRTCMMRCARGAATTT (SEQ ID NO: 14429) |
| 140 | HAAR + GCH + G + CMTGYTGGTGGGCVRRBRTCMMRCARGAATTT (SEQ ID NO: 14430) |
| 140 | HAAR + G + CHG + CMTGYTGGTGGGCVRRBRTCMMRCARGAATTT (SEQ ID NO: 14431) |
| 140 | +CH + G + CMTGYTGGTGGGCVRRBRTCMMRCARGAATTT (SEQ ID NO: 14432) |
| 140 | +CHG + CM + TGYTGGTGGGCVRRBRTCMMRCARGAATTT (SEQ ID NO: 14433) |
| 140 | +CH + GCM + TGYTGGTGGGCVRRBRTCMMRCARGAATTT (SEQ ID NO: 14434) |
| 140 | +G + CM + TGYTGGTGGGCVRRBRTCMMRCARGAATTT (SEQ ID NO: 14435) |
| 140 | +GCM + T + GYTGGTGGGCVRRBRTCMMRCARGAATTT (SEQ ID NO: 14436) |
| 140 | +G + CMT + GYTGGTGGGCVRRBRTCMMRCARGAATTT (SEQ ID NO: 14437) |
| 140 | +CM + T + GYTGGTGGGCVRRBRTCMMRCARGAATTT (SEQ ID NO: 14438) |
| 140 | +CMT + GY + TGGTGGGCVRRBRTCMMRCARGAATTT (SEQ ID NO: 14439) |
| 140 | +CM + TGY + TGGTGGGCVRRBRTCMMRCARGAATTT (SEQ ID NO: 14440) |
| 140 | +T + GY + TGGTGGGCVRRBRTCMMRCARGAATTT (SEQ ID NO: 14441) |
| 140 | +TGY + T + GGTGGGCVRRBRTCMMRCARGAATTT (SEQ ID NO: 14442) |
| 140 | +T + GYT + GGTGGGCVRRBRTCMMRCARGAATTT (SEQ ID NO: 14443) |
| 140 | +GY + T + GGTGGGCVRRBRTCMMRCARGAATTT (SEQ ID NO: 14444) |
| 140 | +GYT + G + GTGGGCVRRBRTCMMRCARGAATTT (SEQ ID NO: 14445) |
| 140 | +GY + TG + GTGGGCVRRBRTCMMRCARGAATTT (SEQ ID NO: 14446) |

TABLE 11-continued

| 140 | AARGCHGCMTGYTGGTGGGCVRRBRTCMMRCARGAATTTG (SEQ ID NO: 14447) |
| 140 | CHGCMTGYTGGTGGGCVRRBRTCMMRCARGAATTTG (SEQ ID NO: 14448) |
| 140 | GCMTGYTGGTGGGCVRRBRTCMMRCARGAATTTG (SEQ ID NO: 14449) |
| 140 | CMTGYTGGTGGGCVRRBRTCMMRCARGAATTTG (SEQ ID NO: 14450) |
| 140 | TGYTGGTGGGCVRRBRTCMMRCARGAATTTG (SEQ ID NO: 14451) |
| 140 | GYTGGTGGGCVRRBRTCMMRCARGAATTTG (SEQ ID NO: 14452) |
| 140 | HAARGCHGCMTGYTGGTGGGCVRRBRTCMMRCARGAATTT (SEQ ID NO: 14453) |
| 140 | CHGCMTGYTGGTGGGCVRRBRTCMMRCARGAATTT (SEQ ID NO: 14454) |
| 140 | GCMTGYTGGTGGGCVRRBRTCMMRCARGAATTT (SEQ ID NO: 14455) |
| 140 | CMTGYTGGTGGGCVRRBRTCMMRCARGAATTT (SEQ ID NO: 14456) |
| 140 | TGYTGGTGGGCVRRBRTCMMRCARGAATTT (SEQ ID NO: 14457) |
| 140 | GYTGGTGGGCVRRBRTCMMRCARGAATTT (SEQ ID NO: 14458) |
| 140 | RCRGTHAARGCHGCMTGYTGGTGGGCVRRDRTYMVRCARGAATTT (SEQ ID NO: 14459) |
| 140 | AARGCHGCMTGYTGGTGGGCVRRBRTCMMRCARGAATTTG + N (SEQ ID NO: 14460) |
| 140 | CHGCMTGYTGGTGGGCVRRBRTCMMRCARGAATTTG + N (SEQ ID NO: 14461) |
| 140 | GCMTGYTGGTGGGCVRRBRTCMMRCARGAATTTG + N (SEQ ID NO: 14462) |
| 140 | CMTGYTGGTGGGCVRRBRTCMMRCARGAATTTG + N (SEQ ID NO:14463) |
| 140 | TGYTGGTGGGCVRRBRTCMMRCARGAATTTG + N (SEQ ID NO: 14464) |
| 140 | GYTGGTGGGCVRRBRTCMMRCARGAATTTG + N (SEQ ID NO: 14465) |
| 140 | HAARGCHGCMTGYTGGTGGGCVRRBRTCMMRCARGAATTT + N (SEQ ID NO: 14466) |
| 140 | CHGCMTGYTGGTGGGCVRRBRTCMMRCARGAATTT + N (SEQ ID NO: 14467) |
| 140 | GCMTGYTGGTGGGCVRRBRTCMMRCARGAATTT + N (SEQ ID NO: 14468) |
| 140 | CMTGYTGGTGGGCVRRBRTCMMRCARGAATTT + N (SEQ ID NO: 14469) |
| 140 | TGYTGGTGGGCVRRBRTCMMRCARGAATTT + N (SEQ ID NO: 14470) |
| 140 | GYTGGTGGGCVRRBRTCMMRCARGAATTT + N (SEQ ID NO: 14471) |
| 140 | RCRGTHAARGCHGCMTGYTGGTGGGCVRRDRTYMVRCARGAATTT + N (SEQ ID NO: 14472) |
| 143 | +T + GY + TGGTGGGCVRRBRTCMMRCARGAATTTGGVATYCCCT (SEQ ID NO: 14473) |
| 143 | +TGY + T + GGTGGGCVRRBRTCMMRCARGAATTTGGVATYCCCT (SEQ ID NO: 14474) |
| 143 | +T + GYT + GGTGGGCVRRBRTCMMRCARGAATTTGGVATYCCCT (SEQ ID NO: 14475) |
| 143 | +GY + T + GGTGGGCVRRBRTCMMRCARGAATTTGGVATYCCCT (SEQ ID NO: 14476) |
| 143 | +GYT + G + GTGGGCVRRBRTCMMRCARGAATTTGGVATYCCCT (SEQ ID NO: 14477) |
| 143 | +GY + TG + GTGGGCVRRBRTCMMRCARGAATTTGGVATYCCCT (SEQ ID NO: 14478) |
| 143 | +T + G + GTGGGCVRRBRTCMMRCARGAATTTGGVATYCCCT (SEQ ID NO: 14479) |
| 143 | +TG + GTG + GGCVRRBRTCMMRCARGAATTTGGVATYCCCT (SEQ ID NO: 14480) |
| 143 | +T + GGTG + GGCVRRBRTCMMRCARGAATTTGGVATYCCCT (SEQ ID NO: 14481) |
| 143 | +G + GTG + GGCVRRBRTCMMRCARGAATTTGGVATYCCCT (SEQ ID NO: 14482) |
| 143 | +GGTG + G + GCVRRBRTCMMRCARGAATTTGGVATYCCCT (SEQ ID NO: 14483) |
| 143 | +G + GTGG + GCVRRBRTCMMRCARGAATTTGGVATYCCCT (SEQ ID NO: 14484) |
| 143 | +GTG + G + GCVRRBRTCMMRCARGAATTTGGVATYCCCT (SEQ ID NO: 14485) |

TABLE 11-continued

| | |
|---|---|
| 143 | +GTGG + G + CVRRBRTCMMRCARGAATTTGGVATYCCCT (SEQ ID NO: 14486) |
| 143 | +GTG + GG + CVRRBRTCMMRCARGAATTTGGVATYCCCT (SEQ ID NO: 14487) |
| 143 | +G + G + CVRRBRTCMMRCARGAATTTGGVATYCCCT (SEQ ID NO: 14488) |
| 143 | +GG + CVRRBR + TCMMRCARGAATTTGGVATYCCCT (SEQ ID NO: 14489) |
| 143 | +G + GCVRRBR + TCMMRCARGAATTTGGVATYCCCT (SEQ ID NO: 14490) |
| 143 | M + T + GY + TGGTGGGCVRRBRTCMMRCARGAATTTGGVATYCCC (SEQ ID NO: 14491) |
| 143 | M + TGY + T + GGTGGGCVRRBRTCMMRCARGAATTTGGVATYCCC (SEQ ID NO: 14492) |
| 143 | M + T + GYT + GGTGGGCVRRBRTCMMRCARGAATTTGGVATYCCC (SEQ ID NO: 14493) |
| 143 | +GY + T + GGTGGGCVRRBRTCMMRCARGAATTTGGVATYCCC (SEQ ID NO: 14494) |
| 143 | +GYT + G + GTGGGCVRRBRTCMMRCARGAATTTGGVATYCCC (SEQ ID NO: 14495) |
| 143 | +GY + TG + GTGGGCVRRBRTCMMRCARGAATTTGGVATYCCC (SEQ ID NO: 14496) |
| 143 | +T + G + GTGGGCVRRBRTCMMRCARGAATTTGGVATYCCC (SEQ ID NO: 14497) |
| 143 | +TG + GTG + GGCVRRBRTCMMRCARGAATTTGGVATYCCC (SEQ ID NO: 14498) |
| 143 | +T + GGTG + GGCVRRBRTCMMRCARGAATTTGGVATYCCC (SEQ ID NO: 14499) |
| 143 | +G + GTG + GGCVRRBRTCMMRCARGAATTTGGVATYCCC (SEQ ID NO: 14500) |
| 143 | +GGTG + G + GCVRRBRTCMMRCARGAATTTGGVATYCCC (SEQ ID NO: 14501) |
| 143 | +G + GTGG + GCVRRBRTCMMRCARGAATTTGGVATYCCC (SEQ ID NO: 14502) |
| 143 | +GTG + G + GCVRRBRTCMMRCARGAATTTGGVATYCCC (SEQ ID NO: 14503) |
| 143 | +GTGG + G + CVRRBRTCMMRCARGAATTTGGVATYCCC (SEQ ID NO: 14504) |
| 143 | +GTG + GG + CVRRBRTCMMRCARGAATTTGGVATYCCC (SEQ ID NO: 14505) |
| 143 | +G + G + CVRRBRTCMMRCARGAATTTGGVATYCCC (SEQ ID NO: 14506) |
| 143 | +GG + CVRRBR + TCMMRCARGAATTTGGVATYCCC (SEQ ID NO: 14507) |
| 143 | +G + GCVRRBR + TCMMRCARGAATTTGGVATYCCC (SEQ ID NO: 14508) |
| 143 | TGYTGGTGGGCVRRBRTCMMRCARGAATTTGGVATYCCCT (SEQ ID NO: 14509) |
| 143 | GYTGGTGGGCVRRBRTCMMRCARGAATTTGGVATYCCCT (SEQ ID NO: 14510) |
| 143 | TGGTGGGCVRRBRTCMMRCARGAATTTGGVATYCCCT (SEQ ID NO: 14511) |
| 143 | GGTGGGCVRRBRTCMMRCARGAATTTGGVATYCCCT (SEQ ID NO: 14512) |
| 143 | GTGGGCVRRBRTCMMRCARGAATTTGGVATYCCCT (SEQ ID NO: 14513) |
| 143 | GGCVRRBRTCMMRCARGAATTTGGVATYCCCT (SEQ ID NO: 14514) |
| 143 | MTGYTGGTGGGCVRRBRTCMMRCARGAATTTGGVATYCCC (SEQ ID NO: 14515) |
| 143 | GYTGGTGGGCVRRBRTCMMRCARGAATTTGGVATYCCC (SEQ ID NO: 14516) |
| 143 | TGGTGGGCVRRBRTCMMRCARGAATTTGGVATYCCC (SEQ ID NO: 14517) |
| 143 | GGTGGGCVRRBRTCMMRCARGAATTTGGVATYCCC (SEQ ID NO: 14518) |
| 143 | GTGGGCVRRBRTCMMRCARGAATTTGGVATYCCC (SEQ ID NO: 14519) |
| 143 | GGCVRRBRTCMMRCARGAATTTGGVATYCCC (SEQ ID NO: 14520) |
| 143 | GCHGCMTGYTGGTGGGCVRRDRTYMVRCARGARTTTGGVATTCCC (SEQ ID NO: 14521) |
| 143 | TGYTGGTGGGCVRRBRTCMMRCARGAATTTGGVATYCCCT + N (SEQ ID NO: 14522) |
| 143 | GYTGGTGGGCVRRBRTCMMRCARGAATTTGGVATYCCCT + N (SEQ ID NO: 14523) |
| 143 | TGGTGGGCVRRBRTCMMRCARGAATTTGGVATYCCCT + N (SEQ ID NO: 14524) |

TABLE 11-continued

| | |
|---|---|
| 143 | GGTGGGCVRRBRTCMMRCARGAATTTGGVATYCCCT + N (SEQ ID NO: 14525) |
| 143 | GTGGGCVRRBRTCMMRCARGAATTTGGVATYCCCT + N (SEQ ID NO: 14526) |
| 143 | GGCVRRBRTCMMRCARGAATTTGGVATYCCCT + N (SEQ ID NO: 14527) |
| 143 | MTGYTGGTGGGCVRRBRTCMMRCARGAATTTGGVATYCCC + N (SEQ ID NO: 14528) |
| 143 | GYTGGTGGGCVRRBRTCMMRCARGAATTTGGVATYCCC + N (SEQ ID NO: 14529) |
| 143 | TGGTGGGCVRRBRTCMMRCARGAATTTGGVATYCCC + N (SEQ ID NO: 14530) |
| 143 | GGTGGGCVRRBRTCMMRCARGAATTTGGVATYCCC + N (SEQ ID NO: 14531) |
| 143 | GTGGGCVRRBRTCMMRCARGAATTTGGVATYCCC + N (SEQ ID NO: 14532) |
| 143 | GGCVRRBRTCMMRCARGAATTTGGVATYCCC + N (SEQ ID NO: 14533) |
| 143 | GCHGCMTGYTGGTGGGCVRRDRTYMVRCARGARTTTGGVATTCCC + N (SEQ ID NO: 14534) |
| 145 | +GTG + G + GCVRRBRTCMMRCARGAATTTGGVATYCCCTACAAT (SEQ ID NO: 14535) |
| 145 | +GTGG + G + CVRRBRTCMMRCARGAATTTGGVATYCCCTACAAT (SEQ ID NO: 14536) |
| 145 | +GTG + GG + CVRRBRTCMMRCARGAATTTGGVATYCCCTACAAT (SEQ ID NO: 14537) |
| 145 | +G + G + CVRRBRTCMMRCARGAATTTGGVATYCCCTACAAT (SEQ ID NO: 14538) |
| 145 | +GG + CVRRBR + TCMMRCARGAATTTGGVATYCCCTACAAT (SEQ ID NO: 14539) |
| 145 | +G + GCVRRBR + TCMMRCARGAATTTGGVATYCCCTACAAT (SEQ ID NO: 14540) |
| 145 | +G + CVRRBR + TCMMRCARGAATTTGGVATYCCCTACAAT (SEQ ID NO: 14541) |
| 145 | +GCVRRBR + TCMMR + CARGAATTTGGVATYCCCTACAAT (SEQ ID NO: 14542) |
| 145 | +G + CVRRBRTCMMR + CARGAATTTGGVATYCCCTACAAT (SEQ ID NO: 14543) |
| 145 | +CVRRBR + TCMMR + CARGAATTTGGVATYCCCTACAAT (SEQ ID NO: 14544) |
| 145 | +CVRRBRTCMMR + C + ARGAATTTGGVATYCCCTACAAT (SEQ ID NO: 14545) |
| 145 | +CVRRBR + TCMMRC + ARGAATTTGGVATYCCCTACAAT (SEQ ID NO: 14546) |
| 145 | +TCMMR + C + ARGAATTTGGVATYCCCTACAAT (SEQ ID NO: 14547) |
| 145 | +TCMMRC + AR + GAATTTGGVATYCCCTACAAT (SEQ ID NO: 14548) |
| 145 | +TCMMR + CAR + GAATTTGGVATYCCCTACAAT (SEQ ID NO: 14549) |
| 145 | +C + AR + GAATTTGGVATYCCCTACAAT (SEQ ID NO: 14550) |
| 145 | +CAR + GAA + TTTGGVATYCCCTACAAT (SEQ ID NO: 14551) |
| 145 | +C + ARGAA + TTTGGVATYCCCTACAAT (SEQ ID NO: 14552) |
| 145 | GTGGGCVRRBRTCMMRCARGAATTTGGVATYCCCTACAAT (SEQ ID NO: 14553) |
| 145 | GGCVRRBRTCMMRCARGAATTTGGVATYCCCTACAAT (SEQ ID NO: 14554) |
| 145 | GCVRRBRTCMMRCARGAATTTGGVATYCCCTACAAT (SEQ ID NO: 14555) |
| 145 | CVRRBRTCMMRCARGAATTTGGVATYCCCTACAAT (SEQ ID NO: 14556) |
| 145 | TCMMRCARGAATTTGGVATYCCCTACAAT (SEQ ID NO: 14557) |
| 145 | CARGAATTTGGVATYCCCTACAAT (SEQ ID NO: 14558) |
| 145 | TGYTGGTGGGCVRRDRTYMVRCARGARTTTGGVATYCCCTACAAT (SEQ ID NO: 14559) |
| 145 | GTGGGCVRRBRTCMMRCARGAATTTGGVATYCCCTACAAT + N (SEQ ID NO: 14560) |

TABLE 11-continued

| | |
|---|---|
| 145 | GGCVRRBRTCMMRCARGAATTTGGVATYCCCTACAAT + N (SEQ ID NO: 14561) |
| 145 | GCVRRBRTCMMRCARGAATTTGGVATYCCCTACAAT + N (SEQ ID NO: 14562) |
| 145 | CVRRBRTCMMRCARGAATTTGGVATYCCCTACAAT + N (SEQ ID NO: 14563) |
| 145 | TCMMRCARGAATTTGGVATYCCCTACAAT + N (SEQ ID NO: 14564) |
| 145 | CARGAATTTGGVATYCCCTACAAT + N (SEQ ID NO: 14565) |
| 145 | TGYTGGTGGGCVRRDRTYMVRCARGARTTTGGVATYCCCTACAAT + N (SEQ ID NO: 14566) |
| 146 | +G + CVRRBR + TCMMRCARGAATTTGGVATYCCCTACAATCCCC (SEQ ID NO: 14567) |
| 146 | +GCVRRBR + TCMMR + CARGAATTTGGVATYCCCTACAATCCCC (SEQ ID NO: 14568) |
| 146 | +G + CVRRBRTCMMR + CARGAATTTGGVATYCCCTACAATCCCC (SEQ ID NO: 14569) |
| 146 | +CVRRBR + TCMMR + CARGAATTTGGVATYCCCTACAATCCCC (SEQ ID NO: 14570) |
| 146 | +CVRRBRTCMMR + C + ARGAATTTGGVATYCCCTACAATCCCC (SEQ ID NO: 14571) |
| 146 | +CVRRBR + TCMMRC + ARGAATTTGGVATYCCCTACAATCCCC (SEQ ID NO: 14572) |
| 146 | +TCMMR + C + ARGAATTTGGVATYCCCTACAATCCCC (SEQ ID NO: 14573) |
| 146 | +TCMMRC + AR + GAATTTGGVATYCCCTACAATCCCC (SEQ ID NO: 14574) |
| 146 | +TCMMR + CAR + GAATTTGGVATYCCCTACAATCCCC (SEQ ID NO: 14575) |
| 146 | +C + AR + GAATTTGGVATYCCCTACAATCCCC (SEQ ID NO: 14576) |
| 146 | +CAR + GAA + TTTGGVATYCCCTACAATCCCC (SEQ ID NO: 14577) |
| 146 | +C + ARGAA + TTTGGVATYCCCTACAATCCCC (SEQ ID NO: 14578) |
| 146 | +AR + GAA + TTTGGVATYCCCTACAATCCCC (SEQ ID NO: 14579) |
| 146 | +ARGAA + TTTG + GVATYCCCTACAATCCCC (SEQ ID NO: 14580) |
| 146 | +AR + GAATTTG + GVATYCCCTACAATCCCC (SEQ ID NO: 14581) |
| 146 | +GAA + TTTG + GVATYCCCTACAATCCCC (SEQ ID NO: 14582) |
| 146 | +GAATTTG + GVA + TYCCCTACAATCCCC (SEQ ID NO: 14583) |
| 146 | +GAA + TTTGGVA + TYCCCTACAATCCCC (SEQ ID NO: 14584) |
| 146 | GCVRRBRTCMMRCARGAATTTGGVATYCCCTACAATCCCC (SEQ ID NO: 14585) |
| 146 | CVRRBRTCMMRCARGAATTTGGVATYCCCTACAATCCCC (SEQ ID NO: 14586) |
| 146 | TCMMRCARGAATTTGGVATYCCCTACAATCCCC (SEQ ID NO: 14587) |
| 146 | CARGAATTTGGVATYCCCTACAATCCCC (SEQ ID NO: 14588) |
| 146 | ARGAATTTGGVATYCCCTACAATCCCC (SEQ ID NO: 14589) |
| 146 | GAATTTGGVATYCCCTACAATCCCC (SEQ ID NO: 14590) |
| 146 | TGGTGGGCVRRDRTYMVRCARGARTTTGGVATYCCCTACAATCCC (SEQ ID NO: 14591) |
| 146 | GCVRRBRTCMMRCARGAATTTGGVATYCCCTACAATCCCC + N (SEQ ID NO: 14592) |
| 146 | CVRRBRTCMMRCARGAATTTGGVATYCCCTACAATCCCC + N (SEQ ID NO: 14593) |
| 146 | TCMMRCARGAATTTGGVATYCCCTACAATCCCC + N (SEQ ID NO: 14594) |
| 146 | CARGAATTTGGVATYCCCTACAATCCCC + N (SEQ ID NO: 14595) |
| 146 | ARGAATTTGGVATYCCCTACAATCCCC + N (SEQ ID NO: 14596) |
| 146 | GAATTTGGVATYCCCTACAATCCCC + N (SEQ ID NO: 14597) |

| | | |
|---|---|---|
| 146 | TGGTGGGCVRRDRTYMVRCARGARTTTGGVATYCCCTACAATCCC + N | (SEQ ID NO: 14598) |
| 147 | VRRBR + TCMMR + C + ARGAATTTGGVATYCCCTACAATCCCCAA | (SEQ ID NO: 14599) |
| 147 | VRRBR + TCMMRC + AR + GAATTTGGVATYCCCTACAATCCCCAA | (SEQ ID NO: 14600) |
| 147 | VRRBR + TCMMR + CAR + GAATTTGGVATYCCCTACAATCCCCAA | (SEQ ID NO: 14601) |
| 147 | +C + AR + GAATTTGGVATYCCCTACAATCCCCAA | (SEQ ID NO: 14602) |
| 147 | +CAR + GAA + TTTGGVATYCCCTACAATCCCCAA | (SEQ ID NO: 14603) |
| 147 | +C + ARGAA + TTTGGVATYCCCTACAATCCCCAA | (SEQ ID NO: 14604) |
| 147 | +AR + GAA + TTTGGVATYCCCTACAATCCCCAA | (SEQ ID NO: 14605) |
| 147 | +ARGAA + TTTG + GVATYCCCTACAATCCCCAA | (SEQ ID NO: 14606) |
| 147 | +AR + GAATTTG + GVATYCCCTACAATCCCCAA | (SEQ ID NO: 14607) |
| 147 | +GAA + TTTG + GVATYCCCTACAATCCCCAA | (SEQ ID NO: 14608) |
| 147 | +GAATTTG + GVA + TYCCCTACAATCCCCAA | (SEQ ID NO: 14609) |
| 147 | +GAA + TTTGGVA + TYCCCTACAATCCCCAA | (SEQ ID NO: 14610) |
| 147 | +TTTG + GVA + TYCCCTACAATCCCCAA | (SEQ ID NO: 14611) |
| 147 | +TTTGGVA + TY + CCCTACAATCCCCAA | (SEQ ID NO: 14612) |
| 147 | +TTTG + GVATY + CCCTACAATCCCCAA | (SEQ ID NO: 14613) |
| 147 | VRRBRTCMMRCARGAATTTGGVATYCCCTACAATCCCCAA | (SEQ ID NO: 14614) |
| 147 | CARGAATTTGGVATYCCCTACAATCCCCAA | (SEQ ID NO: 14615) |
| 147 | ARGAATTTGGVATYCCCTACAATCCCCAA | (SEQ ID NO: 14616) |
| 147 | GAATTTGGVATYCCCTACAATCCCCAA | (SEQ ID NO: 14617) |
| 147 | TTTGGVATYCCCTACAATCCCCAA | (SEQ ID NO: 14618) |
| 147 | TGGGCVRRDRTYMVRCARGARTTTGGVATYCCCTACAATCCCCAA | (SEQ ID NO: 14619) |
| 147 | VRRBRTCMMRCARGAATTTGGVATYCCCTACAATCCCCAA + N | (SEQ ID NO: 14620) |
| 147 | CARGAATTTGGVATYCCCTACAATCCCCAA + N | (SEQ ID NO: 14621) |
| 147 | ARGAATTTGGVATYCCCTACAATCCCCAA + N | (SEQ ID NO: 14622) |
| 147 | GAATTTGGVATYCCCTACAATCCCCAA + N | (SEQ ID NO: 14623) |
| 147 | TTTGGVATYCCCTACAATCCCCAA + N | (SEQ ID NO: 14624) |
| 147 | TGGGCVRRDRTYMVRCARGARTTTGGVATYCCCTACAATCCCCAA + N | (SEQ ID NO: 14625) |
| 148 | +TCMMR + C + ARGAATTTGGVATYCCCTACAATCCCCAAAGYCA | (SEQ ID NO: 14626) |
| 148 | +TCMMRC + AR + GAATTTGGVATYCCCTACAATCCCCAAAGYCA | (SEQ ID NO: 14627) |
| 148 | +TCMMR + CAR + GAATTTGGVATYCCCTACAATCCCCAAAGYCA | (SEQ ID NO: 14628) |
| 148 | +C + AR + GAATTTGGVATYCCCTACAATCCCCAAAGYCA | (SEQ ID NO: 14629) |
| 148 | +CAR + GAA + TTTGGVATYCCCTACAATCCCCAAAGYCA | (SEQ ID NO: 14630) |
| 148 | +C + ARGAA + TTTGGVATYCCCTACAATCCCCAAAGYCA | (SEQ ID NO: 14631) |
| 148 | +AR + GAA + TTTGGVATYCCCTACAATCCCCAAAGYCA | (SEQ ID NO: 14632) |
| 148 | +ARGAA + TTTG + GVATYCCCTACAATCCCCAAAGYCA | (SEQ ID NO: 14633) |
| 148 | +AR + GAATTTG + GVATYCCCTACAATCCCCAAAGYCA | (SEQ ID NO: 14634) |

TABLE 11-continued

| | | |
|---|---|---|
| 148 | +GAA + TTTG + GVATYCCCTACAATCCCCAAAGYCA | (SEQ ID NO: 14635) |
| 148 | +GAATTTG + GVA + TYCCCTACAATCCCCAAAGYCA | (SEQ ID NO: 14636) |
| 148 | +GAA + TTTGGVA + TYCCCTACAATCCCCAAAGYCA | (SEQ ID NO: 14637) |
| 148 | +TTTG + GVA + TYCCCTACAATCCCCAAAGYCA | (SEQ ID NO: 14638) |
| 148 | +TTTGGVA + TY + CCCTACAATCCCCAAAGYCA | (SEQ ID NO: 14639) |
| 148 | +TTTG + GVATY + CCCTACAATCCCCAAAGYCA | (SEQ ID NO: 14640) |
| 148 | +GVA + TY + CCCTACAATCCCCAAAGYCA | (SEQ ID NO: 14641) |
| 148 | +GVATY + C + CCTACAATCCCCAAAGYCA | (SEQ ID NO: 14642) |
| 148 | +GVA + TYC + CCTACAATCCCCAAAGYCA | (SEQ ID NO: 14643) |
| 148 | BR + TCMMR + C + ARGAATTTGGVATYCCCTACAATCCCCAAAGY | (SEQ ID NO: 14644) |
| 148 | BR + TCMMRC + AR + GAATTTGGVATYCCCTACAATCCCCAAAGY | (SEQ ID NO: 14645) |
| 148 | BR + TCMMR + CAR + GAATTTGGVATYCCCTACAATCCCCAAAGY | (SEQ ID NO: 14646) |
| 148 | +C + AR + GAATTTGGVATYCCCTACAATCCCCAAAGY | (SEQ ID NO: 14647) |
| 148 | +CAR + GAA + TTTGGVATYCCCTACAATCCCCAAAGY | (SEQ ID NO: 14648) |
| 148 | +C + ARGAA + TTTGGVATYCCCTACAATCCCCAAAGY | (SEQ ID NO: 14649) |
| 148 | +AR + GAA + TTTGGVATYCCCTACAATCCCCAAAGY | (SEQ ID NO: 14650) |
| 148 | +ARGAA + TTTG + GVATYCCCTACAATCCCCAAAGY | (SEQ ID NO: 14651) |
| 148 | +AR + GAATTTG + GVATYCCCTACAATCCCCAAAGY | (SEQ ID NO: 14652) |
| 148 | +GAA + TTTG + GVATYCCCTACAATCCCCAAAGY | (SEQ ID NO: 14653) |
| 148 | +GAATTTG + GVA + TYCCCTACAATCCCCAAAGY | (SEQ ID NO: 14654) |
| 148 | +GAA + TTTGGVA + TYCCCTACAATCCCCAAAGY | (SEQ ID NO: 14655) |
| 148 | +TTTG + GVA + TYCCCTACAATCCCCAAAGY | (SEQ ID NO: 14656) |
| 148 | +TTTGGVA + TY + CCCTACAATCCCCAAAGY | (SEQ ID NO: 14657) |
| 148 | +TTTG + GVATY + CCCTACAATCCCCAAAGY | (SEQ ID NO: 14658) |
| 148 | +GVA + TY + CCCTACAATCCCCAAAGY | (SEQ ID NO: 14659) |
| 148 | +GVATY + C + CCTACAATCCCCAAAGY | (SEQ ID NO: 14660) |
| 148 | +GVA + TYC + CCTACAATCCCCAAAGY | (SEQ ID NO: 14661) |
| 148 | R + TCMMR + C + ARGAATTTGGVATYCCCTACAATCCCCAAAGYC | (SEQ ID NO: 14662) |
| 148 | R + TCMMRC + AR + GAATTTGGVATYCCCTACAATCCCCAAAGYC | (SEQ ID NO: 14663) |
| 148 | R + TCMMR + CAR + GAATTTGGVATYCCCTACAATCCCCAAAGYC | (SEQ ID NO: 14664) |
| 148 | +C + AR + GAATTTGGVATYCCCTACAATCCCCAAAGYC | (SEQ ID NO: 14665) |
| 148 | +CAR + GAA + TTTGGVATYCCCTACAATCCCCAAAGYC | (SEQ ID NO: 14666) |
| 148 | +C + ARGAA + TTTGGVATYCCCTACAATCCCCAAAGYC | (SEQ ID NO: 14667) |
| 148 | +AR + GAA + TTTGGVATYCCCTACAATCCCCAAAGYC | (SEQ ID NO: 14668) |
| 148 | +ARGAA + TTTG + GVATYCCCTACAATCCCCAAAGYC | (SEQ ID NO: 14669) |
| 148 | +AR + GAATTTG + GVATYCCCTACAATCCCCAAAGYC | (SEQ ID NO: 14670) |
| 148 | +GAA + TTTG + GVATYCCCTACAATCCCCAAAGYC | (SEQ ID NO: 14671) |

TABLE 11-continued

| | |
|---|---|
| 148 | +GAATTTG + GVA + TYCCCTACAATCCCCAAAGYC (SEQ ID NO: 14672) |
| 148 | +GAA + TTTGGVA + TYCCCTACAATCCCCAAAGYC (SEQ ID NO: 14673) |
| 148 | +TTTG + GVA + TYCCCTACAATCCCCAAAGYC (SEQ ID NO: 14674) |
| 148 | +TTTGGVA + TY + CCCTACAATCCCCAAAGYC (SEQ ID NO: 14675) |
| 148 | +TTTG + GVATY + CCCTACAATCCCCAAAGYC (SEQ ID NO: 14676) |
| 148 | +GVA + TY + CCCTACAATCCCCAAAGYC (SEQ ID NO: 14677) |
| 148 | +GVATY + C + CCTACAATCCCCAAAGYC (SEQ ID NO: 14678) |
| 148 | +GVA + TYC + CCTACAATCCCCAAAGYC (SEQ ID NO: 14679) |
| 148 | TCMMRCARGAATTTGGVATYCCCTACAATCCCCAAAGYCA (SEQ ID NO: 14680) |
| 148 | CARGAATTTGGVATYCCCTACAATCCCCAAAGYCA (SEQ ID NO: 14681) |
| 148 | ARGAATTTGGVATYCCCTACAATCCCCAAAGYCA (SEQ ID NO: 14682) |
| 148 | GAATTTGGVATYCCCTACAATCCCCAAAGYCA (SEQ ID NO: 14683) |
| 148 | TTTGGVATYCCCTACAATCCCCAAAGYCA (SEQ ID NO: 14684) |
| 148 | GVATYCCCTACAATCCCCAAAGYCA (SEQ ID NO: 14685) |
| 148 | BRTCMMRCARGAATTTGGVATYCCCTACAATCCCCAAAGY (SEQ ID NO: 14686) |
| 148 | CARGAATTTGGVATYCCCTACAATCCCCAAAGY (SEQ ID NO: 14687) |
| 148 | ARGAATTTGGVATYCCCTACAATCCCCAAAGY (SEQ ID NO: 14688) |
| 148 | GAATTTGGVATYCCCTACAATCCCCAAAGY (SEQ ID NO: 14689) |
| 148 | TTTGGVATYCCCTACAATCCCCAAAGY (SEQ ID NO: 14690) |
| 148 | GVATYCCCTACAATCCCCAAAGY (SEQ ID NO: 14691) |
| 148 | RTCMMRCARGAATTTGGVATYCCCTACAATCCCCAAAGYC (SEQ ID NO: 14692) |
| 148 | CARGAATTTGGVATYCCCTACAATCCCCAAAGYC (SEQ ID NO: 14693) |
| 148 | ARGAATTTGGVATYCCCTACAATCCCCAAAGYC (SEQ ID NO: 14694) |
| 148 | GAATTTGGVATYCCCTACAATCCCCAAAGYC (SEQ ID NO: 14695) |
| 148 | TTTGGVATYCCCTACAATCCCCAAAGYC (SEQ ID NO: 14696) |
| 148 | GVATYCCCTACAATCCCCAAAGYC (SEQ ID NO: 14697) |
| 148 | GCVRRDRTYMVRCARGARTTTGGVATYCCCTACAATCCYCAAAGT (SEQ ID NO: 14698) |
| 148 | TCMMRCARGAATTTGGVATYCCCTACAATCCCCAAAGYCA + N (SEQ ID NO: 14699) |
| 148 | CARGAATTTGGVATYCCCTACAATCCCCAAAGYCA + N (SEQ ID NO: 14700) |
| 148 | ARGAATTTGGVATYCCCTACAATCCCCAAAGYCA + N (SEQ ID NO: 14701) |
| 148 | GAATTTGGVATYCCCTACAATCCCCAAAGYCA + N (SEQ ID NO: 14702) |
| 148 | TTTGGVATYCCCTACAATCCCCAAAGYCA + N (SEQ ID NO: 14703) |
| 148 | GVATYCCCTACAATCCCCAAAGYCA + N (SEQ ID NO: 14704) |
| 148 | BRTCMMRCARGAATTTGGVATYCCCTACAATCCCCAAAGY + N (SEQ ID NO: 14705) |
| 148 | CARGAATTTGGVATYCCCTACAATCCCCAAAGY + N (SEQ ID NO: 14706) |
| 148 | ARGAATTTGGVATYCCCTACAATCCCCAAAGY + N (SEQ ID NO: 14707) |
| 148 | GAATTTGGVATYCCCTACAATCCCCAAAGY + N (SEQ ID NO: 14708) |
| 148 | TTTGGVATYCCCTACAATCCCCAAAGY + N (SEQ ID NO: 14709) |

TABLE 11-continued

| | |
|---|---|
| 148 | GVATYCCCTACAATCCCCAAAGY + N (SEQ ID NO: 14710) |
| 148 | RTCMMRCARGAATTTGGVATYCCCTACAATCCCCAAAGYC + N (SEQ ID NO: 14711) |
| 148 | CARGAATTTGGVATYCCCTACAATCCCCAAAGYC + N (SEQ ID NO: 14712) |
| 148 | ARGAATTTGGVATYCCCTACAATCCCCAAAGYC + N (SEQ ID NO: 14713) |
| 148 | GAATTTGGVATYCCCTACAATCCCCAAAGYC + N (SEQ ID NO: 14714) |
| 148 | TTTGGVATYCCCTACAATCCCCAAAGYC + N (SEQ ID NO: 14715) |
| 148 | GVATYCCCTACAATCCCCAAAGYC + N (SEQ ID NO: 14716) |
| 148 | GCVRRDRTYMVRCARGARTTTGGVATYCCCTACAATCCYCAAAGT + N (SEQ ID NO: 14717) |
| 153 | GARTTTGGVATYCCCTACAATCCYCAAAGYCARGGAGTAGTAGAA (SEQ ID NO: 14718) |
| 153 | GARTTTGGVATYCCCTACAATCCYCAAAGYCARGGAGTAGTAGAA + N (SEQ ID NO: 14719) |
| 155 | Y + C + CC + TACAATCCCCAAAGYCARGGAGTAGTRGARTCYATG (SEQ ID NO: 14720) |
| 155 | Y + CCC + T + ACAATCCCCAAAGYCARGGAGTAGTRGARTCYATG (SEQ ID NO: 14721) |
| 155 | Y + C + CCT + ACAATCCCCAAAGYCARGGAGTAGTRGARTCYATG (SEQ ID NO: 14722) |
| 155 | +CC + T + ACAATCCCCAAAGYCARGGAGTAGTRGARTCYATG (SEQ ID NO: 14723) |
| 155 | +CCT + AC + AATCCCCAAAGYCARGGAGTAGTRGARTCYATG (SEQ ID NO: 14724) |
| 155 | +CC + TAC + AATCCCCAAAGYCARGGAGTAGTRGARTCYATG (SEQ ID NO: 14725) |
| 155 | +T + AC + AATCCCCAAAGYCARGGAGTAGTRGARTCYATG (SEQ ID NO: 14726) |
| 155 | +TAC + A + ATCCCCAAAGYCARGGAGTAGTRGARTCYATG (SEQ ID NO: 14727) |
| 155 | +T + ACA + ATCCCCAAAGYCARGGAGTAGTRGARTCYATG (SEQ ID NO: 14728) |
| 155 | +AC + A + ATCCCCAAAGYCARGGAGTAGTRGARTCYATG (SEQ ID NO: 14729) |
| 155 | +ACA + AT + CCCCAAAGYCARGGAGTAGTRGARTCYATG (SEQ ID NO: 14730) |
| 155 | +AC + AAT + CCCCAAAGYCARGGAGTAGTRGARTCYATG (SEQ ID NO: 14731) |
| 155 | +A + AT + CCCCAAAGYCARGGAGTAGTRGARTCYATG (SEQ ID NO: 14732) |
| 155 | +AAT + C + CCCAAAGYCARGGAGTAGTRGARTCYATG (SEQ ID NO: 14733) |
| 155 | +A + ATC + CCCAAAGYCARGGAGTAGTRGARTCYATG (SEQ ID NO: 14734) |
| 155 | +AT + C + CCCAAAGYCARGGAGTAGTRGARTCYATG (SEQ ID NO: 14735) |
| 155 | +ATC + CC + CAAAGYCARGGAGTAGTRGARTCYATG (SEQ ID NO: 14736) |
| 155 | +AT + CCC + CAAAGYCARGGAGTAGTRGARTCYATG (SEQ ID NO: 14737) |
| 155 | +C + CC + TACAATCCCCAAAGYCARGGAGTAGTRGARTCYATGA (SEQ ID NO: 14738) |
| 155 | +CCC + T + ACAATCCCCAAAGYCARGGAGTAGTRGARTCYATGA (SEQ ID NO: 14739) |
| 155 | +C + CCT + ACAATCCCCAAAGYCARGGAGTAGTRGARTCYATGA (SEQ ID NO: 14740) |
| 155 | +CC + T + ACAATCCCCAAAGYCARGGAGTAGTRGARTCYATGA (SEQ ID NO:14741) |
| 155 | +CCT + AC + AATCCCCAAAGYCARGGAGTAGTRGARTCYATGA (SEQ ID NO: 14742) |
| 155 | +CC + TAC + AATCCCCAAAGYCARGGAGTAGTRGARTCYATGA (SEQ ID NO: 14743) |

TABLE 11-continued

| | |
|---|---|
| 155 | +T + AC + AATCCCCAAAGYCARGGAGTAGTRGARTCYATGA (SEQ ID NO: 14744) |
| 155 | +TAC + A + ATCCCCAAAGYCARGGAGTAGTRGARTCYATGA (SEQ ID NO: 14745) |
| 155 | +T + ACA + ATCCCCAAAGYCARGGAGTAGTRGARTCYATGA (SEQ ID NO: 14746) |
| 155 | +AC + A + ATCCCCAAAGYCARGGAGTAGTRGARTCYATGA (SEQ ID NO: 14747) |
| 155 | +ACA + AT + CCCCAAAGYCARGGAGTAGTRGARTCYATGA (SEQ ID NO: 14748) |
| 155 | +AC + AAT + CCCCAAAGYCARGGAGTAGTRGARTCYATGA (SEQ ID NO: 14749) |
| 155 | +A + AT + CCCCAAAGYCARGGAGTAGTRGARTCYATGA (SEQ ID NO: 14750) |
| 155 | +AAT + C + CCCAAAGYCARGGAGTAGTRGARTCYATGA (SEQ ID NO: 14751) |
| 155 | +A + ATC + CCCAAAGYCARGGAGTAGTRGARTCYATGA (SEQ ID NO: 14752) |
| 155 | +AT + C + CCCAAAGYCARGGAGTAGTRGARTCYATGA (SEQ ID NO: 14753) |
| 155 | +ATC + CC + CAAAGYCARGGAGTAGTRGARTCYATGA (SEQ ID NO: 14754) |
| 155 | +AT + CCC + CAAAGYCARGGAGTAGTRGARTCYATGA (SEQ ID NO: 14755) |
| 155 | YCCCTACAATCCCCAAAGYCARGGAGTAGTRGARTCYATG (SEQ ID NO: 14756) |
| 155 | CCTACAATCCCCAAAGYCARGGAGTAGTRGARTCYATG (SEQ ID NO: 14757) |
| 155 | TACAATCCCCAAAGYCARGGAGTAGTRGARTCYATG (SEQ ID NO: 14758) |
| 155 | ACAATCCCCAAAGYCARGGAGTAGTRGARTCYATG (SEQ ID NO: 14759) |
| 155 | AATCCCCAAAGYCARGGAGTAGTRGARTCYATG (SEQ ID NO: 14760) |
| 155 | ATCCCCAAAGYCARGGAGTAGTRGARTCYATG (SEQ ID NO: 14761) |
| 155 | CCCTACAATCCCCAAAGYCARGGAGTAGTRGARTCYATGA (SEQ ID NO: 14762) |
| 155 | CCTACAATCCCCAAAGYCARGGAGTAGTRGARTCYATGA (SEQ ID NO: 14763) |
| 155 | TACAATCCCCAAAGYCARGGAGTAGTRGARTCYATGA (SEQ ID NO: 14764) |
| 155 | ACAATCCCCAAAGYCARGGAGTAGTRGARTCYATGA (SEQ ID NO: 14765) |
| 155 | AATCCCCAAAGYCARGGAGTAGTRGARTCYATGA (SEQ ID NO: 14766) |
| 155 | ATCCCCAAAGYCARGGAGTAGTRGARTCYATGA (SEQ ID NO: 14767) |
| 155 | GGVATYCCCTACAATCCYCAAAGYCARGGAGTAGTRGARTCTATG (SEQ ID NO: 14768) |
| 155 | YCCCTACAATCCCCAAAGYCARGGAGTAGTRGARTCYATG + N (SEQ ID NO: 14769) |
| 155 | CCTACAATCCCCAAAGYCARGGAGTAGTRGARTCYATG + N (SEQ ID NO: 14770) |
| 155 | TACAATCCCCAAAGYCARGGAGTAGTRGARTCYATG + N (SEQ ID NO: 14771) |
| 155 | ACAATCCCCAAAGYCARGGAGTAGTRGARTCYATG + N (SEQ ID NO: 14772) |
| 155 | AATCCCCAAAGYCARGGAGTAGTRGARTCYATG + N (SEQ ID NO: 14773) |
| 155 | ATCCCCAAAGYCARGGAGTAGTRGARTCYATG + N (SEQ ID NO: 14774) |
| 155 | CCCTACAATCCCCAAAGYCARGGAGTAGTRGARTCYATGA + N (SEQ ID NO: 14775) |
| 155 | CCTACAATCCCCAAAGYCARGGAGTAGTRGARTCYATGA + N (SEQ ID NO: 14776) |
| 155 | TACAATCCCCAAAGYCARGGAGTAGTRGARTCYATGA + N (SEQ ID NO: 14777) |
| 155 | ACAATCCCCAAAGYCARGGAGTAGTRGARTCYATGA + N (SEQ ID NO: 14778) |

TABLE 11-continued

| | |
|---|---|
| 155 | AATCCCCAAAGYCARGGAGTAGTRGARTCYATGA + N (SEQ ID NO: 14779) |
| 155 | ATCCCCAAAGYCARGGAGTAGTRGARTCYATGA + N (SEQ ID NO: 14780) |
| 155 | GGVATYCCCTACAATCCYCAAAGYCARGGAGTAGTRGARTCTATG + N (SEQ ID NO: 14781) |
| 163 | A + GTAGTRG + ARTCYATGA + ATAARGAATTAAAGAAAATYATA (SEQ ID NO: 14782) |
| 163 | A + GTAGTRGARTCYATGA + ATAARGAAT + TAAAGAAAATYATA (SEQ ID NO: 14783) |
| 163 | A + GTAGTRG + ARTCYATGAATAARGAAT + TAAAGAAAATYATA (SEQ ID NO: 14784) |
| 163 | +ARTCYATGA + ATAARGAAT + TAAAGAAAATYATA (SEQ ID NO: 14785) |
| 163 | +ARTCYATGAATAARGAAT + TA + AGAAAATYATA (SEQ ID NO: 14786) |
| 163 | +ARTCYATGA + ATAARGAATTA + AGAAAATYATA (SEQ ID NO: 14787) |
| 163 | +ATAARGAAT + TA + AGAAAATYATA (SEQ ID NO: 14788) |
| 163 | +ATAARGAATTA + AAGAAAA + TYATA (SEQ ID NO: 14789) |
| 163 | +ATAARGAAT + TAAAGAAAA + TYATA (SEQ ID NO: 14790) |
| 163 | AGTAGTRGARTCYATGAATAARGAATTAAAGAAAATYATA (SEQ ID NO: 14791) |
| 163 | ARTCYATGAATAARGAATTAAAGAAAATYATA (SEQ ID NO: 14792) |
| 163 | ATAARGAATTAAAGAAAATYATA (SEQ ID NO: 14793) |
| 163 | CARGGAGTAGTRGARTCYATGAATAADGARTTAAAGAARATTATA (SEQ ID NO: 14794) |
| 163 | AGTAGTRGARTCYATGAATAARGAATTAAAGAAAATYATA + N (SEQ ID NO: 14795) |
| 163 | ARTCYATGAATAARGAATTAAAGAAAATYATA + N (SEQ ID NO: 14796) |
| 163 | ATAARGAATTAAAGAAAATYATA + N (SEQ ID NO: 14797) |
| 163 | CARGGAGTAGTRGARTCYATGAATAADGARTTAAAGAARATTATA + N (SEQ ID NO: 14798) |
| 230 | AA + TTWYAAAAA + TTCAAAAT + TTTCGGGTTTATTACAGRGAC (SEQ ID NO: 14799) |
| 230 | AA + TTWYAAAAATTCAAAAT + T + TTCGGGTTTATTACAGRGAC (SEQ ID NO: 14800) |
| 230 | AA + TTWYAAAAA + TTCAAAATT + TTCGGGTTTATTACAGRGAC (SEQ ID NO :14801) |
| 230 | +TTCAAAAT + T + TTCGGGTTTATTACAGRGAC (SEQ ID NO: 14802) |
| 230 | +TTCAAAATT + TT + CGGGTTTATTACAGRGAC (SEQ ID NO: 14803) |
| 230 | +TTCAAAAT + TTT + CGGGTTTATTACAGRGAC (SEQ ID NO: 14804) |
| 230 | +T + TT + CGGGTTTATTACAGRGAC (SEQ ID NO: 14805) |
| 230 | +TTT + CG + GGTTTATTACAGRGAC (SEQ ID NO: 14806) |
| 230 | +T + TTCG + GGTTTATTACAGRGAC (SEQ ID NO: 14807) |
| 230 | AATTWYAAAAATTCAAAATTTTCGGGTTTATTACAGRGAC (SEQ ID NO: 14808) |
| 230 | TTCAAAATTTTCGGGTTTATTACAGRGAC (SEQ ID NO: 14809) |
| 230 | TTTCGGGTTTATTACAGRGAC (SEQ ID NO: 14810) |
| 230 | AAMCARATTWYAAAAATTCAAAATTTTCGGGTTTATTACAGGGAC (SEQ ID NO: 14811) |
| 230 | AATTWYAAAAATTCAAAATTTTCGGGTTTATTACAGRGAC + N (SEQ ID NO: 14812) |
| 230 | TTCAAAATTTTCGGGTTTATTACAGRGAC + N (SEQ ID NO: 14813) |

TABLE 11-continued

| | |
|---|---|
| 230 | TTTCGGGTTTATTACAGRGAC + N (SEQ ID NO: 14814) |
| 230 | AAMCARATTWYAAAAATTCAAAATTTTCGGGTTTATTACAGGGAC + N (SEQ ID NO: 14815) |
| 263 | GTRM + TA + C + ARGAYAAYARYGAHATAAARGTAGTRCCAAGRA (SEQ ID NO: 14816) |
| 263 | GTRM + TAC + ARG + AYAAYARYGAHATAAARGTAGTRCCAAGRA (SEQ ID NO: 14817) |
| 263 | GTRM + TA + CARG + AYAAYARYGAHATAAARGTAGTRCCAAGRA (SEQ ID NO: 14818) |
| 263 | +C + ARG + AYAAYARYGAHATAAARGTAGTRCCAAGRA (SEQ ID NO: 14819) |
| 263 | +CARG + AYAAYARY + GAHATAAARGTAGTRCCAAGRA (SEQ ID NO: 14820) |
| 263 | +C + ARGAYAAYARY + GAHATAAARGTAGTRCCAAGRA (SEQ ID NO: 14821) |
| 263 | +ARG + AYAAYARY + GAHATAAARGTAGTRCCAAGRA (SEQ ID NO: 14822) |
| 263 | +ARGAYAAYARY + GAHA + TAAARGTAGTRCCAAGRA (SEQ ID NO: 14823) |
| 263 | +ARG + AYAAYARYGAHA + TAAARGTAGTRCCAAGRA (SEQ ID NO: 14824) |
| 263 | +AYAAYARY + GAHA + TAAARGTAGTRCCAAGRA (SEQ ID NO: 14825) |
| 263 | +AYAAYARYGAHA + TA + AARGTAGTRCCAAGRA (SEQ ID NO: 14826) |
| 263 | +AYAAYARY + GAHATA + AARGTAGTRCCAAGRA (SEQ ID NO: 14827) |
| 263 | +GAHA + TA + AARGTAGTRCCAAGRA (SEQ ID NO: 14828) |
| 263 | +GAHATA + A + ARGTAGTRCCAAGRA (SEQ ID NO: 14829) |
| 263 | +GAHA + TAA + ARGTAGTRCCAAGRA (SEQ ID NO: 14830) |
| 263 | GTRMTACARGAYAAYARYGAHATAAARGTAGTRCCAAGRA (SEQ ID NO: 14831) |
| 263 | CARGAYAAYARYGAHATAAARGTAGTRCCAAGRA (SEQ ID NO: 14832) |
| 263 | ARGAYAAYARYGAHATAAARGTAGTRCCAAGRA (SEQ ID NO: 14833) |
| 263 | AYAAYARYGAHATAAARGTAGTRCCAAGRA (SEQ ID NO: 14834) |
| 263 | GAHATAAARGTAGTRCCAAGRA (SEQ ID NO: 14835) |
| 263 | GCAGTAGTVATACARGAYAAYARTGAHATAAARGTAGTRCCAAGA (SEQ ID NO: 14836) |
| 263 | GTRMTACARGAYAAYARYGAHATAAARGTAGTRCCAAGRA + N (SEQ ID NO: 14837) |
| 263 | CARGAYAAYARYGAHATAAARGTAGTRCCAAGRA + N (SEQ ID NO: 14838) |
| 263 | ARGAYAAYARYGAHATAAARGTAGTRCCAAGRA + N (SEQ ID NO: 14839) |
| 263 | AYAAYARYGAHATAAARGTAGTRCCAAGRA + N (SEQ ID NO: 14840) |
| 263 | GAHATAAARGTAGTRCCAAGRA + N (SEQ ID NO: 14841) |
| 263 | GCAGTAGTVATACARGAYAAYARTGAHATAAARGTAGTRCCAAGA + N (SEQ ID NO: 14842) |

| Codon | Reverse Primer (5' to ') |
|---|---|
| 51 | ARRTGTGTRCARTCTARYTGCCATATYCCTGGRCTRCARTCYACYTGTCC (SEQ ID NO:14843) |
| 51 | ARRTGTGTRCARTCTARYTGCCATATYCCTGGRCTRCARTCYACYTGTCC (SEQ ID NO:14844) |
| 51 | ARRTGTGTRCARTCTARYTGCCATATYCCTGGRCTRCARTCYACYTGTCC + N (SEQ ID NO: 14845) |
| 66 | +AC + R + TGRACTGCTACYADRATDAYTTTYCCTTCTARRTGTG (SEQ ID NO: 14846) |
| 66 | +ACR + TGR + ACTGCTACYADRATDAYTTTYCCTTCTARRTGTG (SEQ ID NO: 14847) |
| 66 | +AC + RTGR + ACTGCTACYADRATDAYTTTYCCTTCTARRTGTG (SEQ ID NO: 14848) |

TABLE 11-continued

| | | |
|---|---|---|
| 66 | +R + TGR + ACTGCTACYADRATDAYTTTYCCTTCTARRTGTG | (SEQ ID NO: 14849) |
| 66 | +RTGR + AC + TGCTACYADRATDAYTTTYCCTTCTARRTGTG | (SEQ ID NO: 14850) |
| 66 | +R + TGRAC + TGCTACYADRATDAYTTTYCCTTCTARRTGTG | (SEQ ID NO: 14851) |
| 66 | +TGR + AC + TGCTACYADRATDAYTTTYCCTTCTARRTGTG | (SEQ ID NO: 14852) |
| 66 | +TGRAC + T + GCTACYADRATDAYTTTYCCTTCTARRTGTG | (SEQ ID NO: 14853) |
| 66 | +TGR + ACT + GCTACYADRATDAYTTTYCCTTCTARRTGTG | (SEQ ID NO: 14854) |
| 66 | +AC + T + GCTACYADRATDAYTTTYCCTTCTARRTGTG | (SEQ ID NO: 14855) |
| 66 | +ACT + GC + TACYADRATDAYTTTYCCTTCTARRTGTG | (SEQ ID NO: 14856) |
| 66 | +AC + TGC + TACYADRATDAYTTTYCCTTCTARRTGTG | (SEQ ID NO: 14857) |
| 66 | +T + GC + TACYADRATDAYTTTYCCTTCTARRTGTG | (SEQ ID NO: 14858) |
| 66 | +TGC + TACYADRATD + AYTTTYCCTTCTARRTGTG | (SEQ ID NO: 14859) |
| 66 | +T + GCTACYADRATD + AYTTTYCCTTCTARRTGTG | (SEQ ID NO: 14860) |
| 66 | +GC + TACYADRATD + AYTTTYCCTTCTARRTGTG | (SEQ ID NO: 14861) |
| 66 | +GCTACYADRATD + AYT + TTYCCTTCTARRTGTG | (SEQ ID NO: 14862) |
| 66 | +GC + TACYADRATDAYT + TTYCCTTCTARRTGTG | (SEQ ID NO: 14863) |
| 66 | Y + A + CRT + GRACTGCTACYADRATDAYTTTYCCTTCTARRTGT | (SEQ ID NO: 14864) |
| 66 | Y + ACRT + GR + ACTGCTACYADRATDAYTTTYCCTTCTARRTGTG | (SEQ ID NO: 14865) |
| 66 | Y + A + CRTGR + ACTGCTACYADRATDAYTTTYCCTTCTARRTGT | (SEQ ID NO: 14866) |
| 66 | +CRT + GR + ACTGCTACYADRATDAYTTTYCCTTCTARRTGT | (SEQ ID NO: 14867) |
| 66 | +CRTGR + A + CTGCTACYADRATDAYTTTYCCTTCTARRTGT | (SEQ ID NO: 14868) |
| 66 | +CRT + GRA + CTGCTACYADRATDAYTTTYCCTTCTARRTGT | (SEQ ID NO: 14869) |
| 66 | +GR + A + CTGCTACYADRATDAYTTTYCCTTCTARRTGT | (SEQ ID NO: 14870) |
| 66 | +GRA + CT + GCTACYADRATDAYTTTYCCTTCTARRTGT | (SEQ ID NO: 14871) |
| 66 | +GR + ACT + GCTACYADRATDAYTTTYCCTTCTARRTGT | (SEQ ID NO: 14872) |
| 66 | +A + CT + GCTACYADRATDAYTTTYCCTTCTARRTGT | (SEQ ID NO: 14873) |
| 66 | +ACT + GCTACYADRA + TDAYTTTYCCTTCTARRTGT | (SEQ ID NO: 14874) |
| 66 | +A + CTGCTACYADRA + TDAYTTTYCCTTCTARRTGT | (SEQ ID NO: 14875) |
| 66 | +CT + GCTACYADRA + TDAYTTTYCCTTCTARRTGT | (SEQ ID NO: 14876) |
| 66 | +CTGCTACYADRA + TDA + YTTTYCCTTCTARRTGT | (SEQ ID NO: 14877) |
| 66 | +CT + GCTACYADRATDA + YTTTYCCTTCTARRTGT | (SEQ ID NO: 14878) |
| 66 | +GCTACYADRA + TDA + YTTTYCCTTCTARRTGT | (SEQ ID NO: 14879) |
| 66 | +GCTACYADRATDA + YT + TTYCCTTCTARRTGT | (SEQ ID NO: 14880) |
| 66 | +GCTACYADRA + TDAYT + TTYCCTTCTARRTGT | (SEQ ID NO: 14881) |
| 66 | ACRTGRACTGCTACYADRATDAYTTTYCCTTCTARRTGTG | (SEQ ID NO: 14882) |
| 66 | RTGRACTGCTACYADRATDAYTTTYCCTTCTARRTGTG | (SEQ ID NO: 14883) |
| 66 | TGRACTGCTACYADRATDAYTTTYCCTTCTARRTGTG | (SEQ ID NO: 14884) |
| 66 | ACTGCTACYADRATDAYTTTYCCTTCTARRTGTG | (SEQ ID NO: 14885) |

| | TABLE 11-continued | |
|---|---|---|
| 66 | TGCTACYADRATDAYTTTYCCTTCTARRTGTG (SEQ ID NO: 14886) | |
| 66 | GCTACYADRATDAYTTTYCCTTCTARRTGTG (SEQ ID NO: 14887) | |
| 66 | YACRTGRACTGCTACYADRATDAYTTTYCCTTCTARRTGT (SEQ ID NO: 14888) | |
| 66 | CRTGRACTGCTACYADRATDAYTTTYCCTTCTARRTGT (SEQ ID NO: 14889) | |
| 66 | GRACTGCTACYADRATDAYTTTYCCTTCTARRTGT (SEQ ID NO: 14890) | |
| 66 | ACTGCTACYADRATDAYTTTYCCTTCTARRTGT (SEQ ID NO: 14891) | |
| 66 | CTGCTACYADRATDAYTTTYCCTTCTARRTGT (SEQ ID NO: 14892) | |
| 66 | GCTACYADRATDAYTTTYCCTTCTARRTGT (SEQ ID NO: 14893) | |
| 66 | RTABCCACTRGCYACRTGRACTGCTACYAKRATDAYTTTYCCTTCTAAATG (SEQ ID NO: 14894) | |
| 66 | ACRTGRACTGCTACYADRATDAYTTTYCCTTCTARRTGTG + N (SEQ ID NO: 14895) | |
| 66 | RTGRACTGCTACYADRATDAYTTTYCCTTCTARRTGTG + N (SEQ ID NO: 14896) | |
| 66 | TGRACTGCTACYADRATDAYTTTYCCTTCTARRTGTG + N (SEQ ID NO: 14897) | |
| 66 | ACTGCTACYADRATDAYTTTYCCTTCTARRTGTG + N (SEQ ID NO: 14898) | |
| 66 | TGCTACYADRATDAYTTTYCCTTCTARRTGTG + N (SEQ ID NO: 14899) | |
| 66 | GCTACYADRATDAYTTTYCCTTCTARRTGTG + N (SEQ ID NO: 14900) | |
| 66 | YACRTGRACTGCTACYADRATDAYTTTYCCTTCTARRTGT + N (SEQ ID NO: 14901) | |
| 66 | CRTGRACTGCTACYADRATDAYTTTYCCTTCTARRTGT + N (SEQ ID NO: 14902) | |
| 66 | GRACTGCTACYADRATDAYTTTYCCTTCTARRTGT + N (SEQ ID NO: 14903) | |
| 66 | ACTGCTACYADRATDAYTTTYCCTTCTARRTGT + N (SEQ ID NO: 14904) | |
| 66 | CTGCTACYADRATDAYTTTYCCTTCTARRTGT + N (SEQ ID NO: 14905) | |
| 66 | GCTACYADRATDAYTTTYCCTTCTARRTGT + N (SEQ ID NO: 14906) | |
| 66 | RTABCCACTRGCYACRTGRACTGCTACYAKRATDAYTTTYCCTTCTAAATG + N (SEQ ID NO: 14907) | |
| 74 | +TC + T + GCTTCYATRTADCCACTRGCYACRTGRACTGCTACYA (SEQ ID NO: 14908) | |
| 74 | +TCT + GC + TTCYATRTADCCACTRGCYACRTGRACTGCTACYA (SEQ ID NO: 14909) | |
| 74 | +TC + TGC + TTCYATRTADCCACTRGCYACRTGRACTGCTACYA (SEQ ID NO: 14910) | |
| 74 | +T + GC + TTCYATRTADCCACTRGCYACRTGRACTGCTACYA (SEQ ID NO: 14911) | |
| 74 | +TGC + T + TCYATRTADCCACTRGCYACRTGRACTGCTACYA (SEQ ID NO: 14912) | |
| 74 | +T + GCT + TCYATRTADCCACTRGCYACRTGRACTGCTACYA (SEQ ID NO: 14913) | |
| 74 | +GC + T + TCYATRTADCCACTRGCYACRTGRACTGCTACYA (SEQ ID NO: 14914) | |
| 74 | +GCT + TCYAT + RTADCCACTRGCYACRTGRACTGCTACYA (SEQ ID NO:14915) | |
| 74 | +GC + TTCYAT + RTADCCACTRGCYACRTGRACTGCTACYA (SEQ ID NO:14916) | |
| 74 | +T + TCYAT + RTADCCACTRGCYACRTGRACTGCTACYA (SEQ ID NO: 14917) | |
| 74 | +TTCYAT + R + TADCCACTRGCYACRTGRACTGCTACYA (SEQ ID NO: 14918) | |

TABLE 11-continued

| | |
|---|---|
| 74 | +T + TCYATR + TADCCACTRGCYACRTGRACTGCTACYA (SEQ ID NO: 14919) |
| 74 | +TCYAT + R + TADCCACTRGCYACRTGRACTGCTACYA (SEQ ID NO: 14920) |
| 74 | +TCYATR + TA + DCCACTRGCYACRTGRACTGCTACYA (SEQ ID NO: 14921) |
| 74 | +TCYAT + RTA + DCCACTRGCYACRTGRACTGCTACYA (SEQ ID NO: 14922) |
| 74 | +R + TA + DCCACTRGCYACRTGRACTGCTACYA (SEQ ID NO: 14923) |
| 74 | +RTA + D + CCACTRGCYACRTGRACTGCTACYA (SEQ ID NO: 14924) |
| 74 | +R + TAD + CCACTRGCYACRTGRACTGCTACYA (SEQ ID NO: 14925) |
| 74 | TCTGCTTCYATRTADCCACTRGCYACRTGRACTGCTACYA (SEQ ID NO: 14926) |
| 74 | TGCTTCYATRTADCCACTRGCYACRTGRACTGCTACYA (SEQ ID NO: 14927) |
| 74 | GCTTCYATRTADCCACTRGCYACRTGRACTGCTACYA (SEQ ID NO: 14928) |
| 74 | TTCYATRTADCCACTRGCYACRTGRACTGCTACYA (SEQ ID NO: 14929) |
| 74 | TCYATRTADCCACTRGCYACRTGRACTGCTACYA (SEQ ID NO: 14930) |
| 74 | RTADCCACTRGCYACRTGRACTGCTACYA (SEQ ID NO :14931) |
| 74 | GCTGGRATRACYTCTGCTTCYATRTABCCACTRGCYACRTGRACTGCTAC (SEQ ID NO: 14932) |
| 74 | TCTGCTTCYATRTADCCACTRGCYACRTGRACTGCTACYA + N (SEQ ID NO: 14933) |
| 74 | TGCTTCYATRTADCCACTRGCYACRTGRACTGCTACYA + N (SEQ ID NO: 14934) |
| 74 | GCTTCYATRTADCCACTRGCYACRTGRACTGCTACYA + N (SEQ ID NO: 14935) |
| 74 | TTCYATRTADCCACTRGCYACRTGRACTGCTACYA + N (SEQ ID NO: 14936) |
| 74 | TCYATRTADCCACTRGCYACRTGRACTGCTACYA + N (SEQ ID NO: 14937) |
| 74 | RTADCCACTRGCYACRTGRACTGCTACYA + N (SEQ ID NO: 14938) |
| 74 | GCTGGRATRACYTCTGCTTCYATRTABCCACTRGCYACRTGRACTGCTAC + N (SEQ ID NO: 14939) |
| 92 | TGCTARYTTTARBAKRWARTATGCTG + TYTCYTGYC + CT + GTY (SEQ ID NO: 14940) |
| 92 | TGCTARYTTTARBAKRWARTATGCTG + TYTCYTGYCCT + G + TY (SEQ ID NO: 14941) |
| 92 | TGCTARYTTTARBAKRWARTATGCTG + TYTCYTGYC + CTG + TY (SEQ ID NO: 14942) |
| 92 | GCTARYTTTARBAKRWARTATGCTGTY + TCYTGYCCT + GT + YT (SEQ ID NO: 14943) |
| 92 | +GCTARYTTTARBAKRWARTATGCTGTY + TCYTGYCCTGT + YT (SEQ ID NO: 14944) |
| 92 | TGCTARYTTTARBAKRWARTATGCTGTYTCYTGYCCTGTY (SEQ ID NO: 14945) |
| 92 | GCTARYTTTARBAKRWARTATGCTGTYTCYTGYCCTGTYT (SEQ ID NO: 14946) |
| 92 | GGCCAYCTYCCTGCTARYTTTARNAKRWARTAKGCTGTYTCYTGYCCTGT (SEQ ID NO: 14947) |
| 92 | TGCTARYTTTARBAKRWARTATGCTGTYTCYTGYCCTGTY + N (SEQ ID NO: 14948) |
| 92 | GCTARYTTTARBAKRWARTATGCTGTYTCYTGYCCTGTYT + N (SEQ ID NO: 14949) |
| 92 | GGCCAYCTYCCTGCTARYTTTARNAKRWARTAKGCTGTYTCYTGYCCTGT + N (SEQ ID NO: 14950) |
| 97 | ACTGGCCAYCTT + CCTGCTARY + TT + TARBAKRWARTATGCTG (SEQ ID NO: 14951) |
| 97 | +ACTGGCCAYCTT + CCTGCTARYTT + TARBAKRWARTATGCTG (SEQ ID NO: 14952) |

TABLE 11-continued

| | |
|---|---|
| 97 | +TT + T + ARBAKRWARTATGCTG (SEQ ID NO: 14953) |
| 97 | +TTT + AR + BAKRWARTATGCTG (SEQ ID NO: 14954) |
| 97 | +TT + TAR + BAKRWARTATGCTG (SEQ ID NO: 14955) |
| 97 | +T + AR + BAKRWARTATGCTG (SEQ ID NO: 14956) |
| 97 | +TAR + BAKRWA + RTATGCTG (SEQ ID NO: 14957) |
| 97 | +T + ARBAKRWA + RTATGCTG (SEQ ID NO: 14958) |
| 97 | +AR + BAKRWA + RTATGCTG (SEQ ID NO: 14959) |
| 97 | +ARBAKRWA + R + TATGCTG (SEQ ID NO: 14960) |
| 97 | +AR + BAKRWAR + TATGCTG (SEQ ID NO: 14961) |
| 97 | +BAKRWA + R + TATGCTG (SEQ ID NO: 14962) |
| 97 | +BAKRWAR + T + ATGCTG (SEQ ID NO: 14963) |
| 97 | +BAKRWA + RT + ATGCTG (SEQ ID NO: 14964) |
| 97 | ACTGGCCAYCTTCCTGCTARYTTTARBAKRWARTATGCTG (SEQ ID NO: 14965) |
| 97 | TTTARBAKRWARTATGCTG (SEQ ID NO: 14966) |
| 97 | TARBAKRWARTATGCTG (SEQ ID NO: 14967) |
| 97 | ARBAKRWARTATGCTG (SEQ ID NO: 14968) |
| 97 | BAKRWARTATGCTG (SEQ ID NO: 14969) |
| 97 | TGTAYTRYTYTBACTGGCCAYCTYCCTGCTARYTTTARNAKRWARTATGC (SEQ ID NO: 14970) |
| 97 | ACTGGCCAYCTTCCTGCTARYTTTARBAKRWARTATGCTG + N (SEQ ID NO: 14971) |
| 97 | TTTARBAKRWARTATGCTG + N (SEQ ID NO: 14972) |
| 97 | TARBAKRWARTATGCTG + N (SEQ ID NO: 14973) |
| 97 | ARBAKRWARTATGCTG + N (SEQ ID NO: 14974) |
| 97 | BAKRWARTATGCTG + N (SEQ ID NO: 14975) |
| 97 | TGTAYTRYTYTBACTGGCCAYCTYCCTGCTARYTTTARNAKRWARTATGC + N (SEQ ID NO: 14976) |
| 118 | +CARCA + K + GCDGCYTTDACYGYABYRCTRGTRAARTTRSKRC (SEQ ID NO: 14977) |
| 118 | +CARCAK + GC + DGCYTTDACYGYABYRCTRGTRAARTTRSKRC (SEQ ID NO: 14978) |
| 118 | +CARCA + KGC + DGCYTTDACYGYABYRCTRGTRAARTTRSKRC (SEQ ID NO: 14979) |
| 118 | +K + GC + DGCYTTDACYGYABYRCTRGTRAARTTRSKRC (SEQ ID NO: 14980) |
| 118 | +KGC + D + GCYTTDACYGYABYRCTRGTRAARTTRSKRC (SEQ ID NO: 14981) |
| 118 | +K + GCD + GCYTTDACYGYABYRCTRGTRAARTTRSKRC (SEQ ID NO: 14982) |
| 118 | + GC + D + GCYTTDACYGYABYRCTRGTRAARTTRSKRC (SEQ ID NO: 14983) |
| 118 | +GCD + GC + YTTDACYGYABYRCTRGTRAARTTRSKRC (SEQ ID NO: 14984) |
| 118 | +GC + DGC + YTTDACYGYABYRCTRGTRAARTTRSKRC (SEQ ID NO: 14985) |
| 118 | +D + GC + YTTDACYGYABYRCTRGTRAARTTRSKRC (SEQ ID NO: 14986) |
| 118 | +DGC + YTTD + ACYGYABYRCTRGTRAARTTRSKRC (SEQ ID NO: 14987) |
| 118 | +D + GCYTTD + ACYGYABYRCTRGTRAARTTRSKRC (SEQ ID NO: 14988) |
| 118 | +GC + YTTD + ACYGYABYRCTRGTRAARTTRSKRC (SEQ ID NO: 14989) |
| 118 | +GCYTTD + ACYGYABYRCTRGT + RAARTTRSKRC (SEQ ID NO: 14990) |
| 118 | +GC + YTTDACYGYABYRCTRGT + RAARTTRSKRC (SEQ ID NO: 14991) |

| | |
|---|---|
| 118 | +YTTD + ACYGYABYRCTRGT + RAARTTRSKRC (SEQ ID NO: 14992) |
| 118 | +YTTDACYGYABYRCTRGT + R + AARTTRSKRC (SEQ ID NO: 14993) |
| 118 | +YTTD + ACYGYABYRCTRGTR + AARTTRSKRC (SEQ ID NO: 14994) |
| 118 | CARCAKGCDGCYTTDACYGYABYRCTRGTRAARTTRSKRC (SEQ ID NO: 14995) |
| 118 | KGCDGCYTTDACYGYABYRCTRGTRAARTTRSKRC (SEQ ID NO: 14996) |
| 118 | GCDGCYTTDACYGYABYRCTRGTRAARTTRSKRC (SEQ ID NO: 14997) |
| 118 | DGCYTTDACYGYABYRCTRGTRAARTTRSKRC (SEQ ID NO: 14998) |
| 118 | GCYTTDACYGYABYRCTRGTRAARTTRSKRC (SEQ ID NO: 14999) |
| 118 | YTTDACYGYABYRCTRGTRAARTTRSKRC (SEQ ID NO: 15000) |
| 118 | AYHYYBGCCCACCARCAKGCDGCYTTDACYGYRKYRCTRRTRAARTTGCT (SEQ ID NO: 15001) |
| 118 | CARCAKGCDGCYTTDACYGYABYRCTRGTRAARTTRSKRC + N (SEQ ID NO: 15002) |
| 118 | KGCDGCYTTDACYGYABYRCTRGTRAARTTRSKRC + N (SEQ ID NO: 15003) |
| 118 | GCDGCYTTDACYGYABYRCTRGTRAARTTRSKRC + N (SEQ ID NO: 15004) |
| 118 | DGCYTTDACYGYABYRCTRGTRAARTTRSKRC + N (SEQ ID NO: 15005) |
| 118 | GCYTTDACYGYABYRCTRGTRAARTTRSKRC + N (SEQ ID NO: 15006) |
| 118 | YTTDACYGYABYRCTRGTRAARTTRSKRC + N (SEQ ID NO: 15007) |
| 118 | AYHYYBGCCCACCARCAKGCDGCYTTDACYGYRKYRCTRRTRAARTTGCT + N (SEQ ID NO: 15008) |
| 121 | V + YYBG + CCCACCARCAKGCD + GCYTTDACYGYABYRCTRGTR (SEQ ID NO: 15009) |
| 121 | V + YYBGCCCACCARCAKGCD + G + CYTTDACYGYABYRCTRGTR (SEQ ID NO: 15010) |
| 121 | V + YYBG + CCCACCARCAKGCDG + CYTTDACYGYABYRCTRGTR (SEQ ID NO: 15011) |
| 121 | +CCCACCARCAKGCD + G + CYTTDACYGYABYRCTRGTR (SEQ ID NO: 15012) |
| 121 | +CCCACCARCAKGCDG + CY + TTDACYGYABYRCTRGTR (SEQ ID NO: 15013) |
| 121 | +CCCACCARCAKGCD + GCY + TTDACYGYABYRCTRGTR (SEQ ID NO: 15014) |
| 121 | +G + CY + TTDACYGYABYRCTRGTR (SEQ ID NO: 15015) |
| 121 | +GCY + T + TDACYGYABYRCTRGTR (SEQ ID NO: 15016) |
| 121 | +G + CYT + TDACYGYABYRCTRGTR (SEQ ID NO: 15017) |
| 121 | +CY + T + TDACYGYABYRCTRGTR (SEQ ID NO: 15018) |
| 121 | +CYT + TD + ACYGYABYRCTRGTR (SEQ ID NO: 15019) |
| 121 | +CY + TTD + ACYGYABYRCTRGTR (SEQ ID NO: 15020) |
| 121 | +T + TD + ACYGYABYRCTRGTR (SEQ ID NO: 15021) |
| 121 | +TTD + A + CYGYABYRCTRGTR (SEQ ID NO: 15022) |
| 121 | +T + TDA + CYGYABYRCTRGTR (SEQ ID NO: 15023) |
| 121 | +TD + A + CYGYABYRCTRGTR (SEQ ID NO: 15024) |
| 121 | +TDA + CY + GYABYRCTRGTR (SEQ ID NO: 15025) |
| 121 | +TD + ACY + GYABYRCTRGTR (SEQ ID NO: 15026) |
| 121 | VYYBGCCCACCARCAKGCDGCYTTDACYGYABYRCTRGTR (SEQ ID NO: 15027) |
| 121 | CCCACCARCAKGCDGCYTTDACYGYABYRCTRGTR (SEQ ID NO: 15028) |
| 121 | GCYTTDACYGYABYRCTRGTR (SEQ ID NO: 15029) |

TABLE 11-continued

| | |
|---|---|
| 121 | CYTTDACYGYABYRCTRGTR (SEQ ID NO: 15030) |
| 121 | TTDACYGYABYRCTRGTR (SEQ ID NO: 15031) |
| 121 | TDACYGYABYRCTRGTR (SEQ ID NO: 15032) |
| 121 | YTCYTGYBKRAYHYYBGCCCACCARCAKGCDGCYTTDACYGYRKYACTGGT (SEQ ID NO: 15033) |
| 121 | VYYBGCCCACCARCAKGCDGCYTTDACYGYABYRCTRGTR + N (SEQ ID NO: 15034) |
| 121 | CCCACCARCAKGCDGCYTTDACYGYABYRCTRGTR + N (SEQ ID NO: 15035) |
| 121 | GCYTTDACYGYABYRCTRGTR + N (SEQ ID NO: 15036) |
| 121 | CYTTDACYGYABYRCTRGTR + N (SEQ ID NO: 15037) |
| 121 | TTDACYGYABYRCTRGTR + N (SEQ ID NO: 15038) |
| 121 | TDACYGYABYRCTRGTR + N (SEQ ID NO: 15039) |
| 121 | YTCYTGYBKRAYHYYBGCCCACCARCAKGCDGCYTTDACYGYRKYACTGGT + N (SEQ ID NO: 15040) |
| 138 | Y + ACTA + CTC + CYTGRCTTTGGGGATTGTAGGGRATBCCAAAT (SEQ ID NO: 15041) |
| 138 | Y + ACTACTC + CY + TGRCTTTGGGGATTGTAGGGRATBCCAAAT (SEQ ID NO: 15042) |
| 138 | Y + ACTA + CTCCY + TGRCTTTGGGGATTGTAGGGRATBCCAAAT (SEQ ID NO: 15043) |
| 138 | +CTC + CY + TGRCTTTGGGGATTGTAGGGRATBCCAAAT (SEQ ID NO: 15044) |
| 138 | +CTCCY + T + GRCTTTGGGGATTGTAGGGRATBCCAAAT (SEQ ID NO: 15045) |
| 138 | +CTC + CYT + GRCTTTGGGGATTGTAGGGRATBCCAAAT (SEQ ID NO: 15046) |
| 138 | +CY + T + GRCTTTGGGGATTGTAGGGRATBCCAAAT (SEQ ID NO: 15047) |
| 138 | +CYT + GR + CTTTGGGGATTGTAGGGRATBCCAAAT (SEQ ID NO: 15048) |
| 138 | +CY + TGR + CTTTGGGGATTGTAGGGRATBCCAAAT (SEQ ID NO: 15049) |
| 138 | +T + GR + CTTTGGGGATTGTAGGGRATBCCAAAT (SEQ ID NO: 15050) |
| 138 | +TGR + C + TTTGGGGATTGTAGGGRATBCCAAAT (SEQ ID NO: 15051) |
| 138 | +T + GRC + TTTGGGGATTGTAGGGRATBCCAAAT (SEQ ID NO: 15052) |
| 138 | +GR + C + TTTGGGGATTGTAGGGRATBCCAAAT (SEQ ID NO: 15053) |
| 138 | +GRC + TT + TGGGGATTGTAGGGRATBCCAAAT (SEQ ID NO: 15054) |
| 138 | +GR + CTT + TGGGGATTGTAGGGRATBCCAAAT (SEQ ID NO: 15055) |
| 138 | +C + TT + TGGGGATTGTAGGGRATBCCAAAT (SEQ ID NO: 15056) |
| 138 | +CTT + T + GGGGATTGTAGGGRATBCCAAAT (SEQ ID NO: 15057) |
| 138 | +C + TTT + GGGGATTGTAGGGRATBCCAAAT (SEQ ID NO: 15058) |
| 138 | AC + TACT + CCY + TGRCTTTGGGGATTGTAGGGRATBCCAAATT (SEQ ID NO: 15059) |
| 138 | AC + TACTCCY + TG + RCTTTGGGGATTGTAGGGRATBCCAAATT (SEQ ID NO: 15060) |
| 138 | AC + TACT + CCYTG + RCTTTGGGGATTGTAGGGRATBCCAAATT (SEQ ID NO: 15061) |
| 138 | +CCY + TG + RCTTTGGGGATTGTAGGGRATBCCAAATT (SEQ ID NO: 15062) |
| 138 | +CCYTG + R + CTTTGGGGATTGTAGGGRATBCCAAATT (SEQ ID NO: 15063) |
| 138 | +CCY + TGR + CTTTGGGGATTGTAGGGRATBCCAAATT (SEQ ID NO: 15064) |
| 138 | +TG + R + CTTTGGGGATTGTAGGGRATBCCAAATT (SEQ ID NO: 15065) |
| 138 | +TGR + CT + TTGGGGATTGTAGGGRATBCCAAATT (SEQ ID NO: 15066) |

TABLE 11-continued

| | | |
|---|---|---|
| 138 | +TG + RCT + TTGGGGATTGTAGGGRATBCCAAATT (SEQ ID NO: 15067) | |
| 138 | +R + CT + TTGGGGATTGTAGGGRATBCCAAATT (SEQ ID NO: 15068) | |
| 138 | +RCT + T + TGGGGATTGTAGGGRATBCCAAATT (SEQ ID NO: 15069) | |
| 138 | +R + CTT + TGGGGATTGTAGGGRATBCCAAATT (SEQ ID NO: 15070) | |
| 138 | +CT + T + TGGGGATTGTAGGGRATBCCAAATT (SEQ ID NO: 15071) | |
| 138 | +CTT + TG + GGGATTGTAGGGRATBCCAAATT (SEQ ID NO: 15072) | |
| 138 | +CT + TTG + GGGATTGTAGGGRATBCCAAATT (SEQ ID NO: 15073) | |
| 138 | +T + TG + GGGGATTGTAGGGRATBCCAAATT (SEQ ID NO: 15074) | |
| 138 | +TTG + G + GGATTGTAGGGRATBCCAAATT (SEQ ID NO: 15075) | |
| 138 | +T + TGG + GGATTGTAGGGRATBCCAAATT (SEQ ID NO: 15076) | |
| 138 | YACTACTCCYTGRCTTTGGGGATTGTAGGGRATBCCAAAT (SEQ ID NO: 15077) | |
| 138 | CTCCYTGRCTTTGGGGATTGTAGGGRATBCCAAAT (SEQ ID NO: 15078) | |
| 138 | CYTGRCTTTGGGGATTGTAGGGRATBCCAAAT (SEQ ID NO: 15079) | |
| 138 | TGRCTTTGGGGATTGTAGGGRATBCCAAAT (SEQ ID NO: 15080) | |
| 138 | GRCTTTGGGGATTGTAGGGRATBCCAAAT (SEQ ID NO: 15081) | |
| 138 | CTTTGGGGATTGTAGGGRATBCCAAAT (SEQ ID NO: 15082) | |
| 138 | ACTACTCCYTGRCTTTGGGGATTGTAGGGRATBCCAAATT (SEQ ID NO: 15083) | |
| 138 | CCYTGRCTTTGGGGATTGTAGGGRATBCCAAATT (SEQ ID NO: 15084) | |
| 138 | TGRCTTTGGGGATTGTAGGGRATBCCAAATT (SEQ ID NO: 15085) | |
| 138 | RCTTTGGGGATTGTAGGGRATBCCAAATT (SEQ ID NO: 15086) | |
| 138 | CTTTGGGGATTGTAGGGRATBCCAAATT (SEQ ID NO: 15087) | |
| 138 | TTGGGGATTGTAGGGRATBCCAAATT (SEQ ID NO: 15088) | |
| 138 | ATTCATRGAYTCYACTACTCCYTGRCTTTGRGGATTGTAGGGRATTCCAAA (SEQ ID NO: 15089) | |
| 138 | YACTACTCCYTGRCTTTGGGGATTGTAGGGRATBCCAAAT + N (SEQ ID NO: 15090) | |
| 138 | CTCCYTGRCTTTGGGGATTGTAGGGRATBCCAAAT + N (SEQ ID NO: 15091) | |
| 138 | CYTGRCTTTGGGGATTGTAGGGRATBCCAAAT + N (SEQ ID NO: 15092) | |
| 138 | TGRCTTTGGGGATTGTAGGGRATBCCAAAT + N (SEQ ID NO: 15093) | |
| 138 | GRCTTTGGGGATTGTAGGGRATBCCAAAT + N (SEQ ID NO: 15094) | |
| 138 | CTTTGGGGATTGTAGGGRATBCCAAAT + N (SEQ ID NO: 15095) | |
| 138 | ACTACTCCYTGRCTTTGGGGATTGTAGGGRATBCCAAATT + N (SEQ ID NO: 15096) | |
| 138 | CCYTGRCTTTGGGGATTGTAGGGRATBCCAAATT + N (SEQ ID NO: 15097) | |
| 138 | TGRCTTTGGGGATTGTAGGGRATBCCAAATT + N (SEQ ID NO: 15098) | |
| 138 | RCTTTGGGGATTGTAGGGRATBCCAAATT + N (SEQ ID NO: 15099) | |
| 138 | CTTTGGGGATTGTAGGGRATBCCAAATT + N (SEQ ID NO: 15100) | |
| 138 | TTGGGGATTGTAGGGRATBCCAAATT + N (SEQ ID NO: 15101) | |
| 138 | ATTCATRGAYTCYACTACTCCYTGRCTTTGRGGATTGTAGGGRATTCCAAA + N (SEQ ID NO: 15102) | |
| 140 | RG + AY + T + CYACTACTCCYTGRCTTTGGGGATTGTAGGGRATB (SEQ ID NO: 15103) | |

TABLE 11-continued

140 RG + AYT + CY + ACTACTCCYTGRCTTTGGGGATTGTAGGGRATB (SEQ ID NO: 15104)

140 RG + AY + TCY + ACTACTCCYTGRCTTTGGGGATTGTAGGGRATB (SEQ ID NO: 15105)

140 +T + CY + ACTACTCCYTGRCTTTGGGGATTGTAGGGRATB (SEQ ID NO: 15106)

140 +TCY + A + CTACTCCYTGRCTTTGGGGATTGTAGGGRATB (SEQ ID NO: 15107)

140 +T + CYA + CTACTCCYTGRCTTTGGGGATTGTAGGGRATB (SEQ ID NO: 15108)

140 +CY + A + CTACTCCYTGRCTTTGGGGATTGTAGGGRATB (SEQ ID NO: 15109)

140 +CYA + CT + ACTCCYTGRCTTTGGGGATTGTAGGGRATB (SEQ ID NO: 15110)

140 +CY + ACT + ACTCCYTGRCTTTGGGGATTGTAGGGRATB (SEQ ID NO: 15111)

140 +A + CT + ACTCCYTGRCTTTGGGGATTGTAGGGRATB (SEQ ID NO: 15112)

140 +ACT + A + CTCCYTGRCTTTGGGGATTGTAGGGRATB (SEQ ID NO: 15113)

140 +A + CTA + CTCCYTGRCTTTGGGGATTGTAGGGRATB (SEQ ID NO: 15114)

140 +CT + A + CTCCYTGRCTTTGGGGATTGTAGGGRATB (SEQ ID NO: 15115)

140 +CTA + CT + CCYTGRCTTTGGGGATTGTAGGGRATB (SEQ ID NO: 15116)

140 +CT + ACT + CCYTGRCTTTGGGGATTGTAGGGRATB (SEQ ID NO: 15117)

140 +A + CT + CCYTGRCTTTGGGGATTGTAGGGRATB (SEQ ID NO: 15118)

140 +ACT + C + CYTGRCTTTGGGGATTGTAGGGRATB (SEQ ID NO: 15119)

140 +A + CTC + CYTGRCTTTGGGGATTGTAGGGRATB (SEQ ID NO: 15120)

140 +GAY + TC + YACTACTCCYTGRCTTTGGGGATTGTAGGGRATBC (SEQ ID NO: 15121)

140 GAYTC + Y + AC + TACTCCYTGRCTTTGGGGATTGTAGGGRATBC (SEQ ID NO: 15122)

140 GAY + TC + YAC + TACTCCYTGRCTTTGGGGATTGTAGGGRATBC (SEQ ID NO: 15123)

140 +TC + Y + ACTACTCCYTGRCTTTGGGGATTGTAGGGRATBC (SEQ ID NO: 15124)

140 +TCY + AC + TACTCCYTGRCTTTGGGGATTGTAGGGRATBC (SEQ ID NO: 15125)

140 +TC + YAC + TACTCCYTGRCTTTGGGGATTGTAGGGRATBC (SEQ ID NO: 15126)

140 +Y + AC + TACTCCYTGRCTTTGGGGATTGTAGGGRATBC (SEQ ID NO: 15127)

140 +YAC + T + ACTCCYTGRCTTTGGGGATTGTAGGGRATBC (SEQ ID NO: 15128)

140 +Y + ACT + ACTCCYTGRCTTTGGGGATTGTAGGGRATBC (SEQ ID NO: 15129)

140 +AC + T + ACTCCYTGRCTTTGGGGATTGTAGGGRATBC (SEQ ID NO: 15130)

140 +ACT + AC + TCCYTGRCTTTGGGGATTGTAGGGRATBC (SEQ ID NO: 15131)

140 +AC + TAC + TCCYTGRCTTTGGGGATTGTAGGGRATBC (SEQ ID NO: 15132)

140 +T + AC + TCCYTGRCTTTGGGGATTGTAGGGRATBC (SEQ ID NO: 15133)

140 +TAC + T + CCYTGRCTTTGGGGATTGTAGGGRATBC (SEQ ID NO: 15134)

140 +T + ACT + CCYTGRCTTTGGGGATTGTAGGGRATBC (SEQ ID NO: 15135)

140 +AC + T + CCYTGRCTTTGGGGATTGTAGGGRATBC (SEQ ID NO: 15136)

140 +ACT + CC + YTGRCTTTGGGGATTGTAGGGRATBC (SEQ ID NO: 15137)

140 +AC + TCC + YTGRCTTTGGGGATTGTAGGGRATBC (SEQ ID NO: 15138)

TABLE 11-continued

140 RGAYTCYACTACTCCYTGRCTTTGGGGATTGTAGGGRATB (SEQ ID
    NO: 15139)

140 TCYACTACTCCYTGRCTTTGGGGATTGTAGGGRATB (SEQ ID NO: 15140)

140 CYACTACTCCYTGRCTTTGGGGATTGTAGGGRATB (SEQ ID NO: 15141)

140 ACTACTCCYTGRCTTTGGGGATTGTAGGGRATB (SEQ ID NO: 15142)

140 CTACTCCYTGRCTTTGGGGATTGTAGGGRATB (SEQ ID NO: 15143)

140 ACTCCYTGRCTTTGGGGATTGTAGGGRATB (SEQ ID NO: 15144)

140 GAYTCYACTACTCCYTGRCTTTGGGGATTGTAGGGRATBC (SEQ ID NO: 15145)

140 TCYACTACTCCYTGRCTTTGGGGATTGTAGGGRATBC (SEQ ID NO: 15146)

140 YACTACTCCYTGRCTTTGGGGATTGTAGGGRATBC (SEQ ID NO: 15147)

140 ACTACTCCYTGRCTTTGGGGATTGTAGGGRATBC (SEQ ID NO: 15148)

140 TACTCCYTGRCTTTGGGGATTGTAGGGRATBC (SEQ ID NO: 15149)

140 ACTCCYTGRCTTTGGGGATTGTAGGGRATBC (SEQ ID NO: 15150)

140 AYTCHTTATTCATRGAYTCYACTACTCCYTGRCTTTGRGGATTGTAGGGAAT
    (SEQ ID NO: 15151)

140 RGAYTCYACTACTCCYTGRCTTTGGGGATTGTAGGGRATB + N (SEQ ID NO: 15152)

140 TCYACTACTCCYTGRCTTTGGGGATTGTAGGGRATB + N (SEQ ID NO: 15153)

140 CYACTACTCCYTGRCTTTGGGGATTGTAGGGRATB + N (SEQ ID NO: 15154)

140 ACTACTCCYTGRCTTTGGGGATTGTAGGGRATB + N (SEQ ID NO: 15155)

140 CTACTCCYTGRCTTTGGGGATTGTAGGGRATB + N (SEQ ID NO: 15156)

140 ACTCCYTGRCTTTGGGGATTGTAGGGRATB + N (SEQ ID NO: 15157)

140 GAYTCYACTACTCCYTGRCTTTGGGGATTGTAGGGRATBC + N (SEQ ID NO: 15158)

140 TCYACTACTCCYTGRCTTTGGGGATTGTAGGGRATBC + N (SEQ ID NO: 15159)

140 YACTACTCCYTGRCTTTGGGGATTGTAGGGRATBC + N (SEQ ID NO: 15160)

140 ACTACTCCYTGRCTTTGGGGATTGTAGGGRATBC + N (SEQ ID NO: 15161)

140 TACTCCYTGRCTTTGGGGATTGTAGGGRATBC + N (SEQ ID NO: 15162)

140 ACTCCYTGRCTTTGGGGATTGTAGGGRATBC + N (SEQ ID NO: 15163)

140 AYTCHTTATTCATRGAYTCYACTACTCCYTGRCTTTGRGGATTGTAGGGAAT + N
    (SEQ ID NO: 15164)

143 Y + T + TA + TTCATRGAYTCYACTACTCCYTGRCTTTGGGGATTG (SEQ ID NO: 15165)

143 Y + TTA + T + TCATRGAYTCYACTACTCCYTGRCTTTGGGGATTG (SEQ ID NO: 15166)

143 Y + T + TAT + TCATRGAYTCYACTACTCCYTGRCTTTGGGGATTG (SEQ ID
    NO: 15167)

143 +TA + T + TCATRGAYTCYACTACTCCYTGRCTTTGGGGATTG (SEQ ID
    NO: 15168)

143 +TAT + TC + ATRGAYTCYACTACTCCYTGRCTTTGGGGATTG (SEQ ID
    NO: 15169)

143 + A + TTC + ATRGAYTCYACTACTCCYTGRCTTTGGGGATTG (SEQ ID
    NO: 15170)

143 +T + TC + ATRGAYTCYACTACTCCYTGRCTTTGGGGATTG (SEQ ID NO: 15171)

143 +TTC + A + TRGAYTCYACTACTCCYTGRCTTTGGGGATTG (SEQ ID NO: 15172)

143 +T + TCA + TRGAYTCYACTACTCCYTGRCTTTGGGGATTG (SEQ ID NO: 15173)

143 +TC + A + TRGAYTCYACTACTCCYTGRCTTTGGGGATTG (SEQ ID NO: 15174)

| | | |
|---|---|---|
| 143 | +TCA + TR + | GAYTCYACTACTCCYTGRCTTTGGGGATTG (SEQ ID NO: 15175) |
| 143 | +TC + ATR + | GAYTCYACTACTCCYTGRCTTTGGGGATTG (SEQ ID NO: 15176) |
| 143 | +A + TR + | GAYTCYACTACTCCYTGRCTTTGGGGATTG (SEQ ID NO: 15177) |
| 143 | +ATR + G + | AYTCYACTACTCCYTGRCTTTGGGGATTG (SEQ ID NO: 15178) |
| 143 | +A + TRG + | AYTCYACTACTCCYTGRCTTTGGGGATTG (SEQ ID NO: 15179) |
| 143 | +TR + G + | AYTCYACTACTCCYTGRCTTTGGGGATTG (SEQ ID NO: 15180) |
| 143 | +TRG + AY + | TCYACTACTCCYTGRCTTTGGGGATTG (SEQ ID NO: 15181) |
| 143 | +TR + GAY + | TCYACTACTCCYTGRCTTTGGGGATTG (SEQ ID NO: 15182) |
| 143 | +TT + A + | TTCATRGAYTCYACTACTCCYTGRCTTTGGGGATTGT (SEQ ID NO: 15183) |
| 143 | TTA + TT + C + | ATRGAYTCYACTACTCCYTGRCTTTGGGGATTGT (SEQ ID NO: 15184) |
| 143 | TT + A + TTC + | ATRGAYTCYACTACTCCYTGRCTTTGGGGATTGT (SEQ ID NO: 15185) |
| 143 | +A + TT + | CATRGAYTCYACTACTCCYTGRCTTTGGGGATTGT (SEQ ID NO: 15186) |
| 143 | +ATT + C + | ATRGAYTCYACTACTCCYTGRCTTTGGGGATTGT (SEQ ID NO: 15187) |
| 143 | +A + TTC + | ATRGAYTCYACTACTCCYTGRCTTTGGGGATTGT (SEQ ID NO: 15188) |
| 143 | +TT + C + | ATRGAYTCYACTACTCCYTGRCTTTGGGGATTGT (SEQ ID NO: 15189) |
| 143 | +TTC + AT + | RGAYTCYACTACTCCYTGRCTTTGGGGATTGT (SEQ ID NO: 15190) |
| 143 | +TT + CAT + | RGAYTCYACTACTCCYTGRCTTTGGGGATTGT (SEQ ID NO: 15191) |
| 143 | +C + AT + | RGAYTCYACTACTCCYTGRCTTTGGGGATTGT (SEQ ID NO: 15192) |
| 143 | +CAT + R + | GAYTCYACTACTCCYTGRCTTTGGGGATTGT (SEQ ID NO: 15193) |
| 143 | +C + ATR + | GAYTCYACTACTCCYTGRCTTTGGGGATTGT (SEQ ID NO: 15194) |
| 143 | +AT + R + | GAYTCYACTACTCCYTGRCTTTGGGGATTGT (SEQ ID NO: 15195) |
| 143 | +ATR + GA + | YTCYACTACTCCYTGRCTTTGGGGATTGT (SEQ ID NO: 15196) |
| 143 | +AT + RGA + | YTCYACTACTCCYTGRCTTTGGGGATTGT (SEQ ID NO: 15197) |
| 143 | +R + GA + | YTCYACTACTCCYTGRCTTTGGGGATTGT (SEQ ID NO: 15198) |
| 143 | +RGA + Y + | TCYACTACTCCYTGRCTTTGGGGATTGT (SEQ ID NO: 15199) |
| 143 | +R + GAY + | TCYACTACTCCYTGRCTTTGGGGATTGT (SEQ ID NO: 15200) |
| 143 | YTTATTCATRGAYTCYACTACTCCYTGRCTTTGGGGATTG (SEQ ID NO: 15201) | |
| 143 | TATTCATRGAYTCYACTACTCCYTGRCTTTGGGGATTG (SEQ ID NO: 15202) | |
| 143 | TTCATRGAYTCYACTACTCCYTGRCTTTGGGGATTG (SEQ ID NO: 15203) | |
| 143 | TCATRGAYTCYACTACTCCYTGRCTTTGGGGATTG (SEQ ID NO: 15204) | |
| 143 | ATRGAYTCYACTACTCCYTGRCTTTGGGGATTG (SEQ ID NO: 15205) | |
| 143 | TRGAYTCYACTACTCCYTGRCTTTGGGGATTG (SEQ ID NO: 15206) | |
| 143 | TTATTCATRGAYTCYACTACTCCYTGRCTTTGGGGATTGT (SEQ ID NO: 15207) | |
| 143 | ATTCATRGAYTCYACTACTCCYTGRCTTTGGGGATTGT (SEQ ID NO: 15208) | |
| 143 | TTCATRGAYTCYACTACTCCYTGRCTTTGGGGATTGT (SEQ ID NO: 15209) | |
| 143 | CATRGAYTCYACTACTCCYTGRCTTTGGGGATTGT (SEQ ID NO: 15210) | |

TABLE 11-continued

| | |
|---|---|
| 143 | ATRGAYTCYACTACTCCYTGRCTTTGGGGATTGT (SEQ ID NO: 15211) |
| 143 | RGAYTCYACTACTCCYTGRCTTTGGGGATTGT (SEQ ID NO: 15212) |
| 143 | YTTCTTTAAYTCHTTATTCATRGAYTCYACTACTCCYTGRCTTTGGGGATT (SEQ ID NO: 15213) |
| 143 | YTTATTCATRGAYTCYACTACTCCYTGRCTTTGGGGATTG + N (SEQ ID NO: 15214) |
| 143 | TATTCATRGAYTCYACTACTCCYTGRCTTTGGGGATTG + N (SEQ ID NO: 15215) |
| 143 | TTCATRGAYTCYACTACTCCYTGRCTTTGGGGATTG + N (SEQ ID NO: 15216) |
| 143 | TCATRGAYTCYACTACTCCYTGRCTTTGGGGATTG + N (SEQ ID NO: 15217) |
| 143 | ATRGAYTCYACTACTCCYTGRCTTTGGGGATTG + N (SEQ ID NO: 15218) |
| 143 | TRGAYTCYACTACTCCYTGRCTTTGGGGATTG + N (SEQ ID NO: 15219) |
| 143 | TTATTCATRGAYTCYACTACTCCYTGRCTTTGGGGATTGT + N (SEQ ID NO: 15220) |
| 143 | ATTCATRGAYTCYACTACTCCYTGRCTTTGGGGATTGT + N (SEQ ID NO: 15221) |
| 143 | TTCATRGAYTCYACTACTCCYTGRCTTTGGGGATTGT + N (SEQ ID NO: 15222) |
| 143 | CATRGAYTCYACTACTCCYTGRCTTTGGGGATTGT + N (SEQ ID NO: 15223) |
| 143 | ATRGAYTCYACTACTCCYTGRCTTTGGGGATTGT + N (SEQ ID NO: 15224) |
| 143 | RGAYTCYACTACTCCYTGRCTTTGGGGATTGT + N (SEQ ID NO: 15225) |
| 143 | YTTCTTTAAYTCHTTATTCATRGAYTCYACTACTCCYTGRCTTTGGGGATT + N (SEQ ID NO: 15226) |
| 145 | +AA + Y + TCYTTATTCATRGAYTCYACTACTCCYTGRCTTTGGG (SEQ ID NO: 15227) |
| 145 | +AAY + TC + YTTATTCATRGAYTCYACTACTCCYTGRCTTTGGG (SEQ ID NO: 15228) |
| 145 | +AA + YTC + YTTATTCATRGAYTCYACTACTCCYTGRCTTTGGG (SEQ ID NO: 15229) |
| 145 | +Y + TC + YTTATTCATRGAYTCYACTACTCCYTGRCTTTGGG (SEQ ID NO: 15230) |
| 145 | +YTC + Y + TTATTCATRGAYTCYACTACTCCYTGRCTTTGGG (SEQ ID NO: 15231) |
| 145 | +Y + TCY + TTATTCATRGAYTCYACTACTCCYTGRCTTTGGG (SEQ ID NO: 15232) |
| 145 | +TC + Y + TTATTCATRGAYTCYACTACTCCYTGRCTTTGGG (SEQ ID NO: 15233) |
| 145 | +TCY + TT + ATTCATRGAYTCYACTACTCCYTGRCTTTGGG (SEQ ID NO: 15234) |
| 145 | +TC + YTT + ATTCATRGAYTCYACTACTCCYTGRCTTTGGG (SEQ ID NO: 15235) |
| 145 | +Y + TT + ATTCATRGAYTCYACTACTCCYTGRCTTTGGG (SEQ ID NO: 15236) |
| 145 | +YTT + A + TTCATRGAYTCYACTACTCCYTGRCTTTGGG (SEQ ID NO: 15237) |
| 145 | +Y + TTA + TTCATRGAYTCYACTACTCCYTGRCTTTGGG (SEQ ID NO: 15238) |
| 145 | +TT + A + TTCATRGAYTCYACTACTCCYTGRCTTTGGG (SEQ ID NO: 15239) |
| 145 | +TTA + TT + CATRGAYTCYACTACTCCYTGRCTTTGGG (SEQ ID NO: 15240) |
| 145 | +TT + ATT + CATRGAYTCYACTACTCCYTGRCTTTGGG (SEQ ID NO: 15241) |
| 145 | +A + TT + CATRGAYTCYACTACTCCYTGRCTTTGGG (SEQ ID NO: 15242) |
| 145 | +ATT + C + ATRGAYTCYACTACTCCYTGRCTTTGGG (SEQ ID NO: 15243) |
| 145 | +A + TTC + ATRGAYTCYACTACTCCYTGRCTTTGGG (SEQ ID NO: 15244) |

TABLE 11-continued

| | |
|---|---|
| 145 | AAYTCYTTATTCATRGAYTCYACTACTCCYTGRCTTTGGG (SEQ ID NO: 15245) |
| 145 | YTCYTTATTCATRGAYTCYACTACTCCYTGRCTTTGGG (SEQ ID NO: 15246) |
| 145 | TCYTTATTCATRGAYTCYACTACTCCYTGRCTTTGGG (SEQ ID NO: 15247) |
| 145 | YTTATTCATRGAYTCYACTACTCCYTGRCTTTGGG (SEQ ID NO: 15248) |
| 145 | TTATTCATRGAYTCYACTACTCCYTGRCTTTGGG (SEQ ID NO: 15249) |
| 145 | ATTCATRGAYTCYACTACTCCYTGRCTTTGGG (SEQ ID NO: 15250) |
| 145 | TATRATYTTCTTTAAYTCHTTATTCATRGAYTCYACTACTCCYTGACTTTG (SEQ ID NO: 15251) |
| 145 | AAYTCYTTATTCATRGAYTCYACTACTCCYTGRCTTTGGG + N (SEQ ID NO: 15252) |
| 145 | YTCYTTATTCATRGAYTCYACTACTCCYTGRCTTTGGG + N (SEQ ID NO: 15253) |
| 145 | TCYTTATTCATRGAYTCYACTACTCCYTGRCTTTGGG + N (SEQ ID NO: 15254) |
| 145 | YTTATTCATRGAYTCYACTACTCCYTGRCTTTGGG + N (SEQ ID NO: 15255) |
| 145 | TTATTCATRGAYTCYACTACTCCYTGRCTTTGGG + N (SEQ ID NO: 15256) |
| 145 | ATTCATRGAYTCYACTACTCCYTGRCTTTGGG + N (SEQ ID NO: 15257) |
| 145 | TATRATYTTCTTTAAYTCHTTATTCATRGAYTCYACTACTCCYTGACTTTG + N (SEQ ID NO: 15258) |
| 146 | C + T + TT + AAYTCYTTATTCATRGAYTCYACTACTCCYTGRCTT (SEQ ID NO: 15259) |
| 146 | C + TTT + A + AYTCYTTATTCATRGAYTCYACTACTCCYTGRCTT (SEQ ID NO: 15260) |
| 146 | C + T + TTA + AYTCYTTATTCATRGAYTCYACTACTCCYTGRCTT (SEQ ID NO: 15261) |
| 146 | +TT + A + AYTCYTTATTCATRGAYTCYACTACTCCYTGRCTT (SEQ ID NO: 1562) |
| 146 | +TTA + AY + TCYTTATTCATRGAYTCYACTACTCCYTGRCTT (SEQ ID NO: 15262) |
| 146 | +TT + AAY + TCYTTATTCATRGAYTCYACTACTCCYTGRCTT (SEQ ID NO: 15263) NO: 15264) |
| 146 | +A + AY + TCYTTATTCATRGAYTCYACTACTCCYTGRCTT (SEQ ID NO: 15265) |
| 146 | +AAY + T + CYTTATTCATRGAYTCYACTACTCCYTGRCTT (SEQ ID NO: 15266) |
| 146 | +A + AYT + CYTTATTCATRGAYTCYACTACTCCYTGRCTT (SEQ ID NO: 15267) |
| 146 | +AY + T + CYTTATTCATRGAYTCYACTACTCCYTGRCTT (SEQ ID NO: 15268) |
| 146 | +AYT + CY + TTATTCATRGAYTCYACTACTCCYTGRCTT (SEQ ID NO: 15269) |
| 146 | +AY + TCY + TTATTCATRGAYTCYACTACTCCYTGRCTT (SEQ ID NO: 15270) |
| 146 | +T + CY + TTATTCATRGAYTCYACTACTCCYTGRCTT (SEQ ID NO: 15271) |
| 146 | +TCY + TTATTCA + TRGAYTCYACTACTCCYTGRCTT (SEQ ID NO: 15272) |
| 146 | +T + CYTTATTCA + TRGAYTCYACTACTCCYTGRCTT (SEQ ID NO: 15273) |
| 146 | +CY + TTATTCA + TRGAYTCYACTACTCCYTGRCTT (SEQ ID NO: 15274) |
| 146 | +CYTTATTCA + TRGAYTCYA + CTACTCCYTGRCTT (SEQ ID NO: 15275) |
| 146 | +CY + TTATTCATRGAYTCYA + CTACTCCYTGRCTT (SEQ ID NO: 15276) |
| 146 | CTTTAAYTCYTTATTCATRGAYTCYACTACTCCYTGRCTT (SEQ ID NO: 15277) |
| 146 | TTAAYTCYTTATTCATRGAYTCYACTACTCCYTGRCTT (SEQ ID NO: 15278) |
| 146 | AAYTCYTTATTCATRGAYTCYACTACTCCYTGRCTT (SEQ ID NO: 15279) |

TABLE 11-continued

| | |
|---|---|
| 146 | AYTCYTTATTCATRGAYTCYACTACTCCYTGRCTT (SEQ ID NO: 15280) |
| 146 | TCYTTATTCATRGAYTCYACTACTCCYTGRCTT (SEQ ID NO: 15281) |
| 146 | CYTTATTCATRGAYTCYACTACTCCYTGRCTT (SEQ ID NO: 15282) |
| 146 | YYCTATRATYTTCTTTAAYTCHTTATTCATRGAYTCYACTACTCCTTGACT (SEQ ID NO: 15283) |
| 146 | CTTTAAYTCYTTATTCATRGAYTCYACTACTCCYTGRCTT + N (SEQ ID NO: 15284) |
| 146 | TTAAYTCYTTATTCATRGAYTCYACTACTCCYTGRCTT + N (SEQ ID NO: 15285) |
| 146 | AAYTCYTTATTCATRGAYTCYACTACTCCYTGRCTT + N (SEQ ID NO: 15286) |
| 146 | AYTCYTTATTCATRGAYTCYACTACTCCYTGRCTT + N (SEQ ID NO: 15287) |
| 146 | TCYTTATTCATRGAYTCYACTACTCCYTGRCTT + N (SEQ ID NO: 15288) |
| 146 | CYTTATTCATRGAYTCYACTACTCCYTGRCTT + N (SEQ ID NO: 15289) |
| 146 | YYCTATRATYTTCTTTAAYTCHTTATTCATRGAYTCYACTACTCCTTGACT + N (SEQ ID NO: 15290) |
| 147 | + TT + C + TTTAAYTCYTTATTCATRGAYTCYACTACTCCYTGRC (SEQ ID NO: 15291) |
| 147 | TTC + TT + T + AAYTCYTTATTCATRGAYTCYACTACTCCYTGRC (SEQ ID NO: 15292) |
| 147 | TT + C + TTT + AAYTCYTTATTCATRGAYTCYACTACTCCYTGRC (SEQ ID NO: 15293) |
| 147 | +C + TT + TAAYTCYTTATTCATRGAYTCYACTACTCCYTGRC (SEQ ID NO: 15294) |
| 147 | +CTT + T + AAYTCYTTATTCATRGAYTCYACTACTCCYTGRC (SEQ ID NO: 15295) |
| 147 | +C + TTT + AAYTCYTTATTCATRGAYTCYACTACTCCYTGRC (SEQ ID NO: 15296) |
| 147 | +TT + T + AAYTCYTTATTCATRGAYTCYACTACTCCYTGRC (SEQ ID NO: 15297) |
| 147 | +TTT + AA + YTCYTTATTCATRGAYTCYACTACTCCYTGRC (SEQ ID NO: 15298) |
| 147 | +TT + TAA + YTCYTTATTCATRGAYTCYACTACTCCYTGRC (SEQ ID NO: 15299) |
| 147 | +T + AA + YTCYTTATTCATRGAYTCYACTACTCCYTGRC (SEQ ID NO: 15300) |
| 147 | +TAA + YTCYTTA + TTCATRGAYTCYACTACTCCYTGRC (SEQ ID NO: 15301) |
| 147 | +T + AAYTCYTTA + TTCATRGAYTCYACTACTCCYTGRC (SEQ ID NO: 15302) |
| 147 | +AA + YTCYTTA + TTCATRGAYTCYACTACTCCYTGRC (SEQ ID NO: 15303) |
| 147 | +AAYTCYTTA + TTCATRGAY + TCYACTACTCCYTGRC (SEQ ID NO: 15304) |
| 147 | +AA + YTCYTTATTCATRGAY + TCYACTACTCCYTGRC (SEQ ID NO: 15305) |
| 147 | +YTCYTTA + TTCATRGAY + TCYACTACTCCYTGRC (SEQ ID NO: 15306) |
| 147 | +YTCYTTATTCATRGAY + TCYACTACT + CCYTGRC (SEQ ID NO: 15307) |
| 147 | +YTCYTTA + TTCATRGAYTCYACTACT + CCYTGRC (SEQ ID NO: 15308) |
| 147 | TTCTTTAAYTCYTTATTCATRGAYTCYACTACTCCYTGRC (SEQ ID NO: 15309) |
| 147 | CTTTAAYTCYTTATTCATRGAYTCYACTACTCCYTGRC (SEQ ID NO: 15310) |
| 147 | TTTAAYTCYTTATTCATRGAYTCYACTACTCCYTGRC (SEQ ID NO: 15311) |
| 147 | TAAYTCYTTATTCATRGAYTCYACTACTCCYTGRC (SEQ ID NO: 15312) |
| 147 | AAYTCYTTATTCATRGAYTCYACTACTCCYTGRC (SEQ ID NO: 15313) |
| 147 | YTCYTTATTCATRGAYTCYACTACTCCYTGRC (SEQ ID NO: 15314) |
| 147 | TGYYCTATRATYTTCTTTAAYTCHTTATTCATRGAYTCYACTACTCCTTG (SEQ ID NO: 15315) |
| 147 | TTCTTTAAYTCYTTATTCATRGAYTCYACTACTCCYTGRC + N (SEQ ID NO: 15316) |

TABLE 11-continued

| | |
|---|---|
| 147 | CTTTAAYTCYTTATTCATRGAYTCYACTACTCCYTGRC + N (SEQ ID NO: 15317) |
| 147 | TTTAAYTCYTTATTCATRGAYTCYACTACTCCYTGRC + N (SEQ ID NO: 15318) |
| 147 | TAAYTCYTTATTCATRGAYTCYACTACTCCYTGRC + N (SEQ ID NO: 15319) |
| 147 | AAYTCYTTATTCATRGAYTCYACTACTCCYTGRC + N (SEQ ID NO: 15320) |
| 147 | YTCYTTATTCATRGAYTCYACTACTCCYTGRC + N (SEQ ID NO: 15321) |
| 147 | TGYYCTATRATYTTCTTTAAYTCHTTATTCATRGAYTCYACTACTCCTTG + N (SEQ ID NO: 15322) |
| 148 | +T + RA + TTTTCTTTAAYTCYTTATTCATRGAYTCYACTACTCC (SEQ ID NO: 15323) |
| 148 | TRA + TTTTCTT + TAAYTCYTT + ATTCATRGAYTCYACTACTCC (SEQ ID NO: 15324) |
| 148 | T + RA + TTTTCTTTAAYTCYTT + ATTCATRGAYTCYACTACTCC (SEQ ID NO: 15325) |
| 148 | +RA + TTTTCTT + TAAYTCYTTATTCATRGAYTCYACTACTCC (SEQ ID NO: 15326) |
| 148 | +RATTTTCTT + TAAYTCYTT + ATTCATRGAYTCYACTACTCC (SEQ ID NO: 15327) |
| 148 | +RA + TTTTCTTTAAYTCYTT + ATTCATRGAYTCYACTACTCC (SEQ ID NO: 15328) |
| 148 | +TTTTCTT + TAAYTCYTT + ATTCATRGAYTCYACTACTCC (SEQ ID NO: 15329) |
| 148 | +TTTTCTTTAAYTCYTT + ATTCATRGA + YTCYACTACTCC (SEQ ID NO: 15330) |
| 148 | +TTTTCTT + TAAYTCYTTATTCATRGA + YTCYACTACTCC (SEQ ID NO: 15331) |
| 148 | +TAAYTCYTT + ATTCATRGA + YTCYACTACTCC (SEQ ID NO: 15332) |
| 148 | +TAAYTCYTTATTCATRGA + YT + CYACTACTCC (SEQ ID NO: 15333) |
| 148 | +TAAYTCYTT + ATTCATRGAYT + CYACTACTCC (SEQ ID NO: 15334) |
| 148 | +ATTCATRGA + YT + CYACTACTCC (SEQ ID NO: 15335) |
| 148 | +ATTCATRGAYT + CYACTAC + TCC (SEQ ID NO: 15336) |
| 148 | +ATTCATRGA + YTCYACTAC + TCC (SEQ ID NO: 15337) |
| 148 | +AT + T + TTCTTTAAYTCYTTATTCATRGAYTCYACTACTCCYT (SEQ ID NO: 15338) |
| 148 | +ATT + TT + CTTTAAYTCYTTATTCATRGAYTCYACTACTCCYT (SEQ ID NO: 15339) |
| 148 | +AT + TTT + CTTTAAYTCYTTATTCATRGAYTCYACTACTCCYT (SEQ ID NO: 15340) |
| 148 | +T + TT + CTTTAAYTCYTTATTCATRGAYTCYACTACTCCYT (SEQ ID NO: 15341) |
| 148 | +TTT + CTTTAAY + TCYTTATTCATRGAYTCYACTACTCCYT (SEQ ID NO: 15342) |
| 148 | +T + TTCTTTAAY + TCYTTATTCATRGAYTCYACTACTCCYT (SEQ ID NO: 15343) |
| 148 | +TT + CTTTAAY + TCYTTATTCATRGAYTCYACTACTCCYT (SEQ ID NO: 15344) |
| 148 | +TTCTTTAAY + TCYTTATTC + ATRGAYTCYACTACTCCYT (SEQ ID NO: 15345) |
| 148 | +TT + CTTTAAYTCYTTATTC + ATRGAYTCYACTACTCCYT (SEQ ID NO: 15346) |
| 148 | +CTTTAAY + TCYTTATTC + ATRGAYTCYACTACTCCYT (SEQ ID NO: 15347) |
| 148 | +CTTTAAYTCYTTATTC + ATRGAYTCY + ACTACTCCYT (SEQ ID NO: 15348) |
| 148 | +CTTTAAY + TCYTTATTCATRGAYTCY + ACTACTCCYT (SEQ ID NO: 15349) |

TABLE 11-continued

| | |
|---|---|
| 148 | +TCYTTATTC + ATRGAYTCY + ACTACTCCYT (SEQ ID NO: 15350) |
| 148 | +TCYTTATTCATRGAYTCY + AC + TACTCCYT (SEQ ID NO: 15351) |
| 148 | +TCYTTATTC + ATRGAYTCYAC + TACTCCYT (SEQ ID NO: 15352) |
| 148 | +ATRGAYTCY + AC + TACTCCYT (SEQ ID NO: 15353) |
| 148 | +ATRGAYTCYAC + TACTCCY + T (SEQ ID NO: 15354) |
| 148 | +ATRGAYTCY + ACTACTCCY + T (SEQ ID NO: 15355) |
| 148 | R + A + TT + TTCTTTAAYTCYTTATTCATRGAYTCYACTACTCCY (SEQ ID NO: 15356) |
| 148 | R + ATT + TTCTTTA + AYTCYTTATTCATRGAYTCYACTACTCCY (SEQ ID NO: 15357) |
| 148 | R + A + TTTTCTTTA + AYTCYTTATTCATRGAYTCYACTACTCCY (SEQ ID NO: 15358) |
| 148 | +TT + TTCTTTA + AYTCYTTATTCATRGAYTCYACTACTCCY (SEQ ID NO: 15359) |
| 148 | +TTTTCTTTA + AYTCYTTAT + TCATRGAYTCYACTACTCCY (SEQ ID NO: 15360) |
| 148 | +TT + TTCTTTAAYTCYTTAT + TCATRGAYTCYACTACTCCY (SEQ ID NO: 15361) |
| 148 | +TTCTTTA + AYTCYTTAT + TCATRGAYTCYACTACTCCY (SEQ ID NO: 15362) |
| 148 | +TTCTTTAAYTCYTTAT + TCATRGAYT + CYACTACTCCY (SEQ ID NO: 15363) |
| 148 | +TTCTTTA + AYTCYTTATTCATRGAYT + CYACTACTCCY (SEQ ID NO: 15364) |
| 148 | +AYTCYTTAT + TCATRGAYT + CYACTACTCCY (SEQ ID NO: 15365) |
| 148 | +AYTCYTTATTCATRGAYT + CY + ACTACTCCY (SEQ ID NO: 15366) |
| 148 | +AYTCYTTAT + TCATRGAYTCY + ACTACTCCY (SEQ ID NO: 15367) |
| 148 | +TCATRGAYT + CY + ACTACTCCY (SEQ ID NO: 15368) |
| 148 | +TCATRGAYTCY + ACTACTC + CY (SEQ ID NO: 15369) |
| 148 | +TCATRGAYT + CYACTACTC + CY (SEQ ID NO: 15370) |
| 148 | TRATTTTCTTTAAYTCYTTATTCATRGAYTCYACTACTCC (SEQ ID NO: 15371) |
| 148 | RATTTTCTTTAAYTCYTTATTCATRGAYTCYACTACTCC (SEQ ID NO: 15372) |
| 148 | TTTTCTTTAAYTCYTTATTCATRGAYTCYACTACTCC (SEQ ID NO: 15373) |
| 148 | TAAYTCYTTATTCATRGAYTCYACTACTCC (SEQ ID NO: 15374) |
| 148 | ATTCATRGAYTCYACTACTCC (SEQ ID NO: 15375) |
| 148 | ATTTTCTTTAAYTCYTTATTCATRGAYTCYACTACTCCYT (SEQ ID NO: 15376) |
| 148 | TTTCTTTAAYTCYTTATTCATRGAYTCYACTACTCCYT (SEQ ID NO: 15377) |
| 148 | TTCTTTAAYTCYTTATTCATRGAYTCYACTACTCCYT (SEQ ID NO: 15378) |
| 148 | CTTTAAYTCYTTATTCATRGAYTCYACTACTCCYT (SEQ ID NO: 15379) |
| 148 | TCYTTATTCATRGAYTCYACTACTCCYT (SEQ ID NO: 15380) |
| 148 | ATRGAYTCYACTACTCCYT (SEQ ID NO: 15381) |
| 148 | RATTTTCTTTAAYTCYTTATTCATRGAYTCYACTACTCCY (SEQ ID NO: 15382) |
| 148 | TTTTCTTTAAYTCYTTATTCATRGAYTCYACTACTCCY (SEQ ID NO: 15383) |
| 148 | TTCTTTAAYTCYTTATTCATRGAYTCYACTACTCCY (SEQ ID NO: 15384) |
| 148 | AYTCYTTATTCATRGAYTCYACTACTCCY (SEQ ID NO: 15385) |

TABLE 11-continued

| | |
|---|---|
| 148 | TCATRGAYTCYACTACTCCY (SEQ ID NO: 15386) |
| 148 | KAYYTGYYCTATRATYTTCTTTAAYTCHTTATTCATRGAYTCYACTACTCC (SEQ ID NO: 15387) |
| 148 | TRATTTTCTTTAAYTCYTTATTCATRGAYTCYACTACTCC + N (SEQ ID NO: 15388) |
| 148 | RATTTTCTTTAAYTCYTTATTCATRGAYTCYACTACTCC + N (SEQ ID NO: 15389) |
| 148 | TTTTCTTTAAYTCYTTATTCATRGAYTCYACTACTCC + N (SEQ ID NO: 15390) |
| 148 | TAAYTCYTTATTCATRGAYTCYACTACTC C + N (SEQ ID NO: 15391) |
| 148 | ATTCATRGAYTCYACTACTCC + N (SEQ ID NO: 15392) |
| 148 | ATTTTCTTTAAYTCYTTATTCATRGAYTCYACTACTCCYT + N (SEQ ID NO: 15393) |
| 148 | TTTCTTTAAYTCYTTATTCATRGAYTCYACTACTCCYT + N (SEQ ID NO: 15394) |
| 148 | TTCTTTAAYTCYTTATTCATRGAYTCYACTACTCCYT + N (SEQ ID NO: 15395) |
| 148 | CTTTAAYTCYTTATTCATRGAYTCYACTACTCCYT + N (SEQ ID NO: 15396) |
| 148 | TCYTTATTCATRGAYTCYACTACTCCYT + N (SEQ ID NO: 15397) |
| 148 | ATRGAYTCYACTACTCCYT + N (SEQ ID NO: 15398) |
| 148 | RATTTTCTTTAAYTCYTTATTCATRGAYTCYACTACTCCY + N (SEQ ID NO: 15399) |
| 148 | TTTTCTTTAAYTCYTTATTCATRGAYTCYACTACTCCY + N (SEQ ID NO: 15400) |
| 148 | TTCTTTAAYTCYTTATTCATRGAYTCYACTACTCCY + N (SEQ ID NO: 15401) |
| 148 | AYTCYTTATTCATRGAYTCYACTACTCCY + N (SEQ ID NO: 15402) |
| 148 | TCATRGAYTCYACTACTCCY + N (SEQ ID NO: 15403) |
| 148 | KAYYTGYYCTATRATYTTCTTTAAYTCHTTATTCATRGAYTCYACTACTCC + N (SEQ ID NO: 15404) |
| 153 | YTCAGCYTGVTCYCTKAYYTGYYCTATRATYTTCTTTAAYTCHTTATTCAT (SEQ ID NO: 15405) |
| 153 | YTCAGCYTGVTCYCTKAYYTGYYCTATRATYTTCTTTAAYTCHTTATTCAT + N (SEQ ID NO: 15406) |
| 155 | +TGNTCYCTK + AC + YTGYCCTATRATTTTCTTTAAYTCYTTAT (SEQ ID NO: 15407) |
| 155 | +TGNTCYCTKAC + YTGYCCT + ATRATTTTCTTTAAYTCYTTAT (SEQ ID NO: 15408) |
| 155 | +TGNTCYCTK + ACYTGYCCT + ATRATTTTCTTTAAYTCYTTAT (SEQ ID NO: 15409) |
| 155 | +AC + YTGYCCT + ATRATTTTCTTTAAYTCYTTAT (SEQ ID NO: 15410) |
| 155 | +ACYTGYCCT + ATR + ATTTTCTTTAAYTCYTTAT (SEQ ID NO: 15411) |
| 155 | +AC + YTGYCCTATR + ATTTTCTTTAAYTCYTTAT (SEQ ID NO: 15412) |
| 155 | +YTGYCCT + ATR + ATTTTCTTTAAYTCYTTAT (SEQ ID NO: 15413) |
| 155 | +YTGYCCTATR + ATTTTC + TTTAAYTCYTTAT (SEQ ID NO: 15414) |
| 155 | +YTGYCCT + ATRATTTTC + TTTAAYTCYTTAT (SEQ ID NO: 15415) |
| 155 | +ATR + ATTTTC + TTTAAYTCYTTAT (SEQ ID NO: 15416) |
| 155 | +ATRATTTTC + TTTAAYTCY + TTAT (SEQ ID NO: 15417) |
| 155 | +ATR + ATTTTCTTTAAYTCY + TTAT (SEQ ID NO: 15418) |
| 155 | +ATTTTC + TTTAAYTCY + TTAT (SEQ ID NO: 15419) |
| 155 | +ATTTTCTTTAAYTCY + TT + AT (SEQ ID NO: 15420) |
| 155 | +ATTTTC + TTTAAYTCYTT + AT (SEQ ID NO: 15421) |

TABLE 11-continued

| | |
|---|---|
| 155 | +TTTAAYTCY + TT + AT (SEQ ID NO: 15422) |
| 155 | +TTTAAYTCYTT + A + T (SEQ ID NO: 15423) |
| 155 | +TTTAAYTCY + TTA + T (SEQ ID NO: 15424) |
| 155 | YTGNTCYC + TK + ACYTGYC + CTATRATTTTCTTTAAYTCYTTA (SEQ ID NO: 15425) |
| 155 | YTGNTCYC + TKACYTGYC + CTA + TRATTTTCTTTAAYTCYTTA (SEQ ID NO: 15426) |
| 155 | YTGNTCYC + TK + ACYTGYCCTA + TRATTTTCTTTAAYTCYTTA (SEQ ID NO: 15427) |
| 155 | +ACYTGYC + CTA + TRATTTTCTTTAAYTCYTTA (SEQ ID NO: 15428) |
| 155 | +ACYTGYCCTA + TRATTT + TCTTTAAYTCYTTA (SEQ ID NO: 15429) |
| 155 | +ACYTGYC + CTATRATTT + TCTTTAAYTCYTTA (SEQ ID NO: 15430) |
| 155 | +CTA + TRATTT + TCTTTAAYTCYTTA (SEQ ID NO: 15431) |
| 155 | +CTATRATTT + TCTTTAAYT + CYTTA (SEQ ID NO: 15432) |
| 155 | +CTA + TRATTTTCTTTAAYT + CYTTA (SEQ ID NO: 15433) |
| 155 | +TRATTT + TCTTTAAYT + CYTTA (SEQ ID NO: 15434) |
| 155 | +TRATTTTCTTTAAYT + CY + TTA (SEQ ID NO: 15435) |
| 155 | +TRATTT + TCTTTAAYTCY + TTA (SEQ ID NO: 15436) |
| 155 | +TCTTTAAYT + CY + TTA (SEQ ID NO: 15437) |
| 155 | +TCTTTAAYTCY + T + TA (SEQ ID NO: 15438) |
| 155 | +TCTTTAAYT + CYT + TA (SEQ ID NO: 15439) |
| 155 | TGNTCYCTKACYTGYCCTATRATTTTCTTTAAYTCYTTAT (SEQ ID NO: 15440) |
| 155 | ACYTGYCCTATRATTTTCTTTAAYTCYTTAT (SEQ ID NO: 15441) |
| 155 | YTGYCCTATRATTTTCTTTAAYTCYTTAT (SEQ ID NO: 15442) |
| 155 | ATRATTTTCTTTAAYTCYTTAT (SEQ ID NO: 15443) |
| 155 | ATTTTCTTTAAYTCYTTAT (SEQ ID NO: 15444) |
| 155 | TTTAAYTCYTTAT (SEQ ID NO: 15445) |
| 155 | YTGNTCYCTKACYTGYCCTATRATTTTCTTTAAYTCYTTA (SEQ ID NO: 15446) |
| 155 | ACYTGYCCTATRATTTTCTTTAAYTCYTTA (SEQ ID NO: 15447) |
| 155 | CTATRATTTTCTTTAAYTCYTTA (SEQ ID NO: 15448) |
| 155 | TRATTTTCTTTAAYTCYTTA (SEQ ID NO: 15449) |
| 155 | TCTTTAAYTCYTTA (SEQ ID NO: 15450) |
| 155 | AAGRTGYTCAGCYTGVTCYCTKAYYTGYYCTATRATYTTCTTTAATTCTTT (SEQ ID NO: 15451) |
| 155 | TGNTCYCTKACYTGYCCTATRATTTTCTTTAAYTCYTTAT + N (SEQ ID NO: 15452) |
| 155 | ACYTGYCCTATRATTTTCTTTAAYTCYTTAT + N (SEQ ID NO: 15453) |
| 155 | YTGYCCTATRATTTTCTTTAAYTCYTTAT + N (SEQ ID NO: 15454) |
| 155 | ATRATTTTCTTTAAYTCYTTAT + N (SEQ ID NO: 15455) |
| 155 | ATTTTCTTTAAYTCYTTAT + N (SEQ ID NO: 15456) |
| 155 | TTTAAYTCYTTAT + N (SEQ ID NO: 15457) |
| 155 | YTGNTCYCTKACYTGYCCTATRATTTTCTTTAAYTCYTTA + N (SEQ ID NO: 15458) |

TABLE 11-continued

| | |
|---|---|
| 155 | ACYTGYCCTATRATTTTCTTTAAYTCYTTA + N (SEQ ID NO: 15459) |
| 155 | CTATRATTTTCTTTAAYTCYTTA + N (SEQ ID NO: 15460) |
| 155 | TRATTTTCTTTAAYTCYTTA + N (SEQ ID NO: 15461) |
| 155 | TCTTTAAYTCYTTA + N (SEQ ID NO: 15462) |
| 155 | AAGRTGYTCAGCYTGVTCYCTKAYYTGYYCTATRATYTTCTTTAATTCTTT + N (SEQ ID NO: 15463) |
| 163 | ACT + GCTGTYTTA + AG + RTGYTCAGCYTGNTCYCTKACYTGYC (SEQ ID NO: 15464) |
| 163 | +ACT + GCTGTYTTAAG + RTGYTCAGCYTGNTCYCTKACYTGYC (SEQ ID NO: 15465) |
| 163 | +AG + R + TGYTCAGCYTGNTCYCTKACYTGYC (SEQ ID NO: 15466) |
| 163 | +AGR + TGYTCAGCYTGNTCYCT + KACYTGYC (SEQ ID NO: 15467) |
| 163 | +AG + RTGYTCAGCYTGNTCYCT + KACYTGYC (SEQ ID NO: 15468) |
| 163 | +R + TGYTCAGCYTGNTCYCT + KACYTGYC (SEQ ID NO: 15469) |
| 163 | +RTGYTCAGCYTGNTCYCT + K + ACYTGYC (SEQ ID NO: 15470) |
| 163 | +R + TGYTCAGCYTGNTCYCTK + ACYTGYC (SEQ ID NO: 15471) |
| 163 | +TGYTCAGCYTGNTCYCT + K + ACYTGYC (SEQ ID NO: 15472) |
| 163 | +TGYTCAGCYTGNTCYCTK + AC + YTGYC (SEQ ID NO: 15473) |
| 163 | +TGYTCAGCYTGNTCYCT + KAC + YTGYC (SEQ ID NO: 15474) |
| 163 | ACTGCTGTYTTAAGRTGYTCAGCYTGNTCYCTKACYTGYC (SEQ ID NO: 15475) |
| 163 | AGRTGYTCAGCYTGNTCYCTKACYTGYC (SEQ ID NO: 15476) |
| 163 | RTGYTCAGCYTGNTCYCTKACYTGYC (SEQ ID NO: 15477) |
| 163 | TGYTCAGCYTGNTCYCTKACYTGYC (SEQ ID NO: 15478) |
| 163 | TACTGCCATYTGTACTGCTGTYTTAAGRTGYTCAGCYTGVTCYCTTACCTG (SEQ ID NO: 15479) |
| 163 | ACTGCTGTYTTAAGRTGYTCAGCYTGNTCYCTKACYTGYC + N (SEQ ID NO: 15480) |
| 163 | AGRTGYTCAGCYTGNTCYCTKACYTGYC + N (SEQ ID NO: 15481) |
| 163 | RTGYTCAGCYTGNTCYCTKACYTGYC + N (SEQ ID NO: 15482) |
| 163 | TGYTCAGCYTGNTCYCTKACYTGYC + N (SEQ ID NO: 15483) |
| 163 | TACTGCCATYTGTACTGCTGTYTTAAGRTGYTCAGCYTGVTCYCTTACCTG + N (SEQ ID NO: 15484) |
| 230 | C + ARA + GN + AGYTTKGCTGGTCCTTTCCAAAKDGGRTCTCTGC (SEQ ID NO: 15485) |
| 230 | +C + ARAGN + AGYTTKGCTGGTCCTTTCCAAAKDGGRTCTCTGC (SEQ ID NO: 15486) |
| 230 | +GN + AG + YTTKGCTGGTCCTTTCCAAAKDGGRTCTCTGC (SEQ ID NO: 15487) |
| 230 | +GNAG + Y + TTKGCTGGTCCTTTCCAAAKDGGRTCTCTGC (SEQ ID NO: 15488) |
| 230 | +GN + AGY + TTKGCTGGTCCTTTCCAAAKDGGRTCTCTGC (SEQ ID NO: 15489) |
| 230 | +AG + Y + TTKGCTGGTCCTTTCCAAAKDGGRTCTCTGC (SEQ ID NO: 15490) |
| 230 | +AGY + TTKGC + TGGTCCTTTCCAAAKDGGRTCTCTGC (SEQ ID NO: 15491) |
| 230 | +AG + YTTKGC + TGGTCCTTTCCAAAKDGGRTCTCTGC (SEQ ID NO: 15492) |
| 230 | +Y + TTKGC + TGGTCCTTTCCAAAKDGGRTCTCTGC (SEQ ID NO: 15493) |
| 230 | +YTTKGC + T + GGTCCTTTCCAAAKDGGRTCTCTGC (SEQ ID NO: 15494) |

TABLE 11-continued

230 +Y + TTKGCT + GGTCCTTTCCAAAKDGGRTCTCTGC (SEQ ID NO: 15495)

230 +TTKGC + T + GGTCCTTTCCAAAKDGGRTCTCTGC (SEQ ID NO: 15496)

230 +TTKGCT + G + GTCCTTTCCAAAKDGGRTCTCTGC (SEQ ID NO: 15497)

230 +TTKGC + TG + GTCCTTTCCAAAKDGGRTCTCTGC (SEQ ID NO: 15498)

230 +T + G + GTCCTTTCCAAAKDGGRTCTCTGC (SEQ ID NO: 15499)

230 +TG + G + TCCTTTCCAAAKDGGRTCTCTGC (SEQ ID NO: 15500)

230 +T + GG + TCCTTTCCAAAKDGGRTCTCTGC (SEQ ID NO: 15501)

230 CARAGNAGYTTKGCTGGTCCTTTCCAAAKDGGRTCTCTGC (SEQ ID NO: 15502)

230 GNAGYTTKGCTGGTCCTTTCCAAAKDGGRTCTCTGC (SEQ ID NO: 15503)

230 AGYTTKGCTGGTCCTTTCCAAAKDGGRTCTCTGC (SEQ ID NO: 15504)

230 YTTKGCTGGTCCTTTCCAAAKDGGRTCTCTGC (SEQ ID NO: 15505)

230 TTKGCTGGTCCTTTCCAAAKDGGRTCTCTGC (SEQ ID NO: 15506)

230 TGGTCCTTTCCAAAKDGGRTCTCTGC (SEQ ID NO: 15507)

230 CCCTTCACCTTTCCARAGDAGYTTKGCTGGTCCTTTCCAAABDGGGTCTCT (SEQ ID NO: 15508)

230 CARAGNAGYTTKGCTGGTCCTTTCCAAAKDGGRTCTCTGC + N (SEQ ID NO: 15509)

230 GNAGYTTKGCTGGTCCTTTCCAAAKDGGRTCTCTGC + N (SEQ ID NO: 15510)

230 AGYTTKGCTGGTCCTTTCCAAAKDGGRTCTCTGC + N (SEQ ID NO: 15511)

230 YTTKGCTGGTCCTTTCCAAAKDGGRTCTCTGC + N (SEQ ID NO: 15512)

230 TTKGCTGGTCCTTTCCAAAKDGGRTCTCTGC + N (SEQ ID NO: 15513)

230 TGGTCCTTTCCAAAKDGGRTCTCTGC + N (SEQ ID NO: 15514)

230 CCCTTCACCTTTCCARAGDAGYTTKGCTGGTCCTTTCCAAABDGGGTCTCT + N (SEQ ID NO: 15515)

263 T + GCCATC + T + GTTTTCCATARTCYYTAATRATYTTTRCTTTY (SEQ ID NO: 15516)

263 +T + GCCATCT + GTTTTCCATARTCYYTAATRATYTTTRCTTTY (SEQ ID NO: 15517)

263 +T + GT + TTTCCATARTCYYTAATRATYTTTRCTTTY (SEQ ID NO: 15518)

263 +TGT + T + TTCCATARTCYYTAATRATYTTTRCTTTY (SEQ ID NO: 15519)

263 +T + GTT + TTCCATARTCYYTAATRATYTTTRCTTTY (SEQ ID NO: 15520)

263 +GT + T + TTCCATARTCYYTAATRATYTTTRCTTTY (SEQ ID NO: 15521)

263 +GTT + TTC + CATARTCYYTAATRATYTTTRCTTTY (SEQ ID NO: 15522)

263 +GT + TTTC + CATARTCYYTAATRATYTTTRCTTTY (SEQ ID NO: 15523)

263 +T + TTC + CATARTCYYTAATRATYTTTRCTTTY (SEQ ID NO: 15524)

263 +TTTC + CATARTCYYTA + ATRATYTTTRCTTTY (SEQ ID NO: 15525)

263 +T + TTCCATARTCYYTA + ATRATYTTTRCTTTY (SEQ ID NO: 15526)

263 +TTC + CATARTCYYTA + ATRATYTTTRCTTTY (SEQ ID NO: 15527)

263 +TTCCATARTCYYTA + A + TRATYTTTRCTTTY (SEQ ID NO: 15528)

263 +TTC + CATARTCYYTAA + TRATYTTTRCTTTY (SEQ ID NO: 15529)

263 +CATARTCYYTA + A + TRATYTTTRCTTTY (SEQ ID NO: 15530)

263 +CATARTCYYTAA + TRATY + TTTRCTTTY (SEQ ID NO: 15531)

TABLE 11-continued

| 263 | +CATARTCYYTA + ATRATY + TTTRCTTTY (SEQ ID NO: 15532) |
| --- | --- |
| 263 | TGCCATCTGTTTTCCATARTCYYTAATRATYTTTRCTTTY (SEQ ID NO: 15533) |
| 263 | TGTTTTCCATARTCYYTAATRATYTTTRCTTTY (SEQ ID NO: 15534) |
| 263 | GTTTTCCATARTCYYTAATRATYTTTRCTTTY (SEQ ID NO: 15535) |
| 263 | TTTCCATARTCYYTAATRATYTTTRCTTTY (SEQ ID NO: 15536) |
| 263 | TTCCATARTCYYTAATRATYTTTRCTTTY (SEQ ID NO: 15537) |
| 263 | CATARTCYYTAATRATYTTTRCTTTY (SEQ ID NO: 15538) |
| 263 | ACAATCAKCACCTGCCATCTGTTTTCCATARTCYYTRATRATYTTTGCTTT (SEQ ID NO: 15539) |
| 263 | TGCCATCTGTTTTCCATARTCYYTAATRATYTTTRCTTTY + N (SEQ ID NO: 15540) |
| 263 | TGTTTTCCATARTCYYTAATRATYTTTRCTTTY + N (SEQ ID NO: 15541) |
| 263 | GTTTTCCATARTCYYTAATRATYTTTRCTTTY + N (SEQ ID NO: 15542) |
| 263 | TTTCCATARTCYYTAATRATYTTTRCTTTY + N (SEQ ID NO: 15543) |
| 263 | TTCCATARTCYYTAATRATYTTTRCTTTY + N (SEQ ID NO: 15544) |
| 263 | CATARTCYYTAATRATYTTTRCTTTY + N (SEQ ID NO: 15545) |

Table 12 depicts amino acid substitutions in HIV-1 integrase protein

TABLE 12

| Codon | Single Letter Amino Acid Code | Amino Acid |
| --- | --- | --- |
| 51 | Y | Tyrosine |
| 66 | I | Isoleucine |
| 66 | A | Alanine |
| 66 | K | Lysine |
| 74 | M | Methionine |
| 92 | Q | Glutamine |
| 92 | G | Glycine |
| 92 | V | Valine |
| 97 | A | Alanine |
| 118 | R | Arginine |
| 121 | Y | Tyrosine |
| 138 | K | Lysine |
| 138 | A | Alanine |
| 140 | S | Serine |
| 140 | A | Alanine |
| 140 | C | Cysteine |
| 143 | C | Cysteine |
| 143 | R | Arginine |
| 143 | H | Histidine |
| 143 | K | Lysine |
| 143 | S | Serine |
| 143 | G | Glycine |
| 143 | A | Alanine |
| 145 | S | Serine |
| 146 | P | Proline |
| 147 | G | Glycine |
| 148 | H | Histidine |
| 148 | R | Arginine |
| 148 | K | Lysine |
| 153 | Y | Tyrosine |
| 153 | F | Phenylalanine |
| 155 | H | Histidine |
| 155 | S | Serine |
| 155 | T | Threonine |
| 163 | R | Arginine |
| 163 | K | Lysine |

TABLE 12-continued

| Codon | Single Letter Amino Acid Code | Amino Acid |
| --- | --- | --- |
| 230 | R | Arginine |
| 263 | K | Lysine |

Table 13 depicts wild-type and mutant probes for the HIV-1 integrase protein. A "+" symbol preceding a nucleotide denotes that the nucleotide is an LNA.

TABLE 13

| Codon | Wild-Type Probe (5' to 3') |
| --- | --- |
| 51 | AGCCATGCATGGACA (SEQ ID NO: 15546) |
| 66 | YTAGAYT + GYACACAYYTAG (SEQ ID NO: 15547) |
| 66 | Y + TAGAYTGYACACAYYTAG (SEQ ID NO: 15548) |
| 66 | YTAGAY + TGYACACAYYTAG (SEQ ID NO: 15549) |
| 66 | YT + AGAYTGYACACAYYTAG (SEQ ID NO: 15550) |
| 66 | YTAGAYTGYACACA + YYTAG (SEQ ID NO: 15551) |
| 66 | YTAGAYTGYACACAYY + TAG (SEQ ID NO: 15552) |
| 66 | YTAGAYTGYA + CACAYYTAG (SEQ ID NO: 15553) |
| 66 | YTAGAYTGYACAC + AYYTAG (SEQ ID NO: 15554) |
| 66 | YTAG + AYTG + YA + CACAYYTAG (SEQ ID NO: 15555) |
| 66 | YT + AGAYTG + YA + CACAYYTAG (SEQ ID NO: 15556) |
| 66 | YTAGAYT + G + YA + CACAYYTAG (SEQ ID NO: 15557) |
| 66 | YTA + GAYTG + YA + CACAYYTAG (SEQ ID NO: 15558) |

TABLE 13-continued

| | |
|---|---|
| 66 | YTAGAYTG + YA + CAC + AYYTAG (SEQ ID NO: 15559) |
| 66 | YTAGAYTG + YA + CA + CAYYTAG (SEQ ID NO: 15560) |
| 66 | YTAGAYTG + YA + CACAY + YTAG (SEQ ID NO: 15561) |
| 66 | YTAGAYTG + YA + CACAYY + TAG (SEQ ID NO: 15562) |
| 66 | TAGAYT + GYACACAYYTAGA (SEQ ID NO: 15563) |
| 66 | TAGA + YTGYACACAYYTAGA (SEQ ID NO: 15564) |
| 66 | TAGAYTG + YACACAYYTAGA (SEQ ID NO: 15565) |
| 66 | TA + GAYTGYACACAYYTAGA (SEQ ID NO: 15566) |
| 66 | TAGAYTGYACAC + AYYTAGA (SEQ ID NO: 15567) |
| 66 | TAGAYTGYACACAYYT + AGA (SEQ ID NO: 15568) |
| 66 | TAGAYTGYAC + ACAYYTAGA (SEQ ID NO: 15569) |
| 66 | TAGAYTGYACACAY + YTAGA (SEQ ID NO: 15570) |
| 66 | TAGAYT + GY + AC + ACAYYTAGA (SEQ ID NO: 15571) |
| 66 | TAGAY + TGY + AC + ACAYYTAGA (SEQ ID NO: 15572) |
| 66 | T + AGAYTGY + AC + ACAYYTAGA (SEQ ID NO: 15573) |
| 66 | TA + GAYTGY + AC + ACAYYTAGA (SEQ ID NO: 15574) |
| 66 | TAGAYTGY + AC + ACAYYTA + GA (SEQ ID NO: 15575) |
| 66 | TAGAYTGY + AC + ACAYYT + AGA (SEQ ID NO: 15576) |
| 66 | TAGAYTGY + AC + ACA + YYTAGA (SEQ ID NO: 15577) |
| 66 | TAGAYTGY + AC + ACAYY + TAGA (SEQ ID NO: 15578) |
| 66 | TAGAY + TGYACACAYYTAGA (SEQ ID NO: 15579) |
| 66 | TAGAYTGYACACAYYTA + GA (SEQ ID NO: 15580) |
| 66 | TAGAYTGYACA + CAYYTAGA (SEQ ID NO: 15581) |
| 66 | TAGAYTGYACACA + YYTAGA (SEQ ID NO: 15582) |
| 66 | TAGA + YTGY + AC + ACAYYTAGA (SEQ ID NO: 15583) |
| 66 | TAGAYTG + Y + AC + ACAYYTAGA (SEQ ID NO: 15584) |
| 66 | TAGAYTGY + AC + A + CAYYTAGA (SEQ ID NO: 15585) |
| 66 | TAGAYTGY + AC + ACAY + YTAGA (SEQ ID NO: 15586) |
| 66 | TAGAYT + GYACACAYYTA (SEQ ID NO: 15587) |
| 66 | +TAGAYTGYACACAYYTA (SEQ ID NO: 15588) |
| 66 | TAGAY + TGYACACAYYTA (SEQ ID NO: 15589) |
| 66 | T + AGAYTGYACACAYYTA (SEQ ID NO: 15590) |
| 66 | TAGAYTGYACACA + YYTA (SEQ ID NO: 15591) |
| 66 | TAGAYTGYACACAYY + TA (SEQ ID NO: 15592) |
| 66 | TAGAYTGYA + CACAYYTA (SEQ ID NO: 15593) |
| 66 | TAGAYTGYACAC + AYYTA (SEQ ID NO: 15594) |
| 66 | TAG + AYTG + YA + CACAYYTA (SEQ ID NO: 15595) |
| 66 | T + AGAYTG + YA + CACAYYTA (SEQ ID NO: 15596) |
| 66 | TAGAYT + G + YA + CACAYYTA (SEQ ID NO: 15597) |
| 66 | TA + GAYTG + YA + CACAYYTA (SEQ ID NO: 15598) |
| 66 | TAGAYTG + YA + CAC + AYYTA (SEQ ID NO: 15599) |
| 66 | TAGAYTG + YA + CA + CAYYTA (SEQ ID NO: 15600) |
| 66 | TAGAYTG + YA + CACAY + YTA (SEQ ID NO: 15601) |
| 66 | TAGAYTG + YA + CACAYY + TA (SEQ ID NO: 15602) |
| 66 | AGAYT + GYACACAYYTAG (SEQ ID NO: 15603) |
| 66 | AGA + YTGYACACAYYTAG (SEQ ID NO: 15604) |
| 66 | AGAYTG + YACACAYYTAG (SEQ ID NO: 15605) |
| 66 | A + GAYTGYACACAYYTAG (SEQ ID NO: 15606) |
| 66 | AGAYTGYACAC + AYYTAG (SEQ ID NO: 15607) |
| 66 | AGAYTGYACACAYYT + AG (SEQ ID NO: 15608) |
| 66 | AGAYTGYAC + ACAYYTAG (SEQ ID NO: 15609) |
| 66 | AGAYTGYACACAY + YTAG (SEQ ID NO: 15610) |
| 66 | AGAYT + GY + AC + ACAYYTAG (SEQ ID NO: 15611) |
| 66 | AGAY + TGY + AC + ACAYYTAG (SEQ ID NO: 15612) |
| 66 | +AGAYTGY + AC + ACAYYTAG (SEQ ID NO: 15613) |
| 66 | A + GAYTGY + AC + ACAYYTAG (SEQ ID NO: 15614) |
| 66 | AGAYTGY + AC + ACAYYTA + G (SEQ ID NO: 15615) |
| 66 | AGAYTGY + AC + ACAYYT + AG (SEQ ID NO: 15616) |
| 66 | AGAYTGY + AC + ACA + YYTAG (SEQ ID NO: 15617) |
| 66 | AGAYTGY + AC + ACAYY + TAG (SEQ ID NO: 15618) |
| 66 | AGAY + TGYACACAYYTAG (SEQ ID NO: 15619) |
| 66 | AGAYTGYACACAYYTA + G (SEQ ID NO: 15620) |
| 66 | AGAYTGYACA + CAYYTAG (SEQ ID NO: 15621) |
| 66 | AGAYTGYACACA + YYTAG (SEQ ID NO: 15622) |

TABLE 13-continued

| | | |
|---|---|---|
| 66 | AGA + YTGY + AC + ACAYYTAG (SEQ ID NO: 15623) | |
| 66 | AGAYTG + Y + AC + ACAYYTAG (SEQ ID NO: 15624) | |
| 66 | AGAYTGY + AC + A + CAYYTAG (SEQ ID NO: 15625) | |
| 66 | AGAYTGY + AC + ACAY + YTAG (SEQ ID NO: 15626) | |
| 66 | TAGAYT + GYACACAYY (SEQ ID NO: 15627) | |
| 66 | +TAGAYTGYACACAYY (SEQ ID NO: 15628) | |
| 66 | TAGAY + TGYACACAYY (SEQ ID NO: 15629) | |
| 66 | T + AGAYTGYACACAYY (SEQ ID NO: 15630) | |
| 66 | TAGAYTGYACACA + YY (SEQ ID NO: 15631) | |
| 66 | TAGAYTGYACACAYY (SEQ ID NO: 15632) | |
| 66 | TAGAYTGYA + CACAYY (SEQ ID NO: 15633) | |
| 66 | TAGAYTGYACAC + AYY (SEQ ID NO: 15634) | |
| 66 | TAG + AYTG + YA + CACAYY (SEQ ID NO: 15635) | |
| 66 | T + AGAYTG + YA + CACAYY (SEQ ID NO: 15636) | |
| 66 | TAGAYT + G + YA + CACAYY (SEQ ID NO: 15637) | |
| 66 | TA + GAYTG + YA + CACAYY (SEQ ID NO: 15638) | |
| 66 | TAGAYTG + YA + CAC + AYY (SEQ ID NO: 15639) | |
| 66 | TAGAYTG + YA + CA + CAYY (SEQ ID NO: 15640) | |
| 66 | TAGAYTG + YA + CACAY + Y (SEQ ID NO: 15641) | |
| 66 | TAGAYTG + YA + CACAYY (SEQ ID NO: 15642) | |
| 66 | AGAYT + GYACACAYYT (SEQ ID NO: 15643) | |
| 66 | AGA + YTGYACACAYYT (SEQ ID NO: 15644) | |
| 66 | AGAYTG + YACACAYYT (SEQ ID NO: 15645) | |
| 66 | A + GAYTGYACACAYYT (SEQ ID NO: 15646) | |
| 66 | AGAYTGYACAC + AYYT (SEQ ID NO: 15647) | |
| 66 | AGAYTGYACACAYYT (SEQ ID NO: 15648) | |
| 66 | AGAYTGYAC + ACAYYT (SEQ ID NO: 15649) | |
| 66 | AGAYTGYACACAY + YT (SEQ ID NO: 15650) | |
| 66 | AGAYT + GY + AC + ACAYYT (SEQ ID NO: 15651) | |
| 66 | AGAY + TGY + AC + ACAYYT (SEQ ID NO: 15652) | |
| 66 | +AGAYTGY + AC + ACAYYT (SEQ ID NO: 15653) | |
| 66 | A + GAYTGY + AC + ACAYYT (SEQ ID NO: 15654) | |
| 66 | AGAYTGY + AC + ACAYYTA (SEQ ID NO: 15655) | |
| 66 | AGAYTGY + AC + ACAYYT (SEQ ID NO: 15656) | |
| 66 | AGAYTGY + AC + ACA + YYT (SEQ ID NO: 15657) | |
| 66 | AGAYTGY + AC + ACAYY + T (SEQ ID NO: 15658) | |
| 66 | AGAY + TGYACACAYYT (SEQ ID NO: 15659) | |
| 66 | AGAYTGYACACAYYTA (SEQ ID NO: 15660) | |
| 66 | AGAYTGYACA + CAYYT (SEQ ID NO: 15661) | |
| 66 | AGAYTGYACACA + YYT (SEQ ID NO: 15662) | |
| 66 | AGA + YTGY + AC + ACAYYT (SEQ ID NO: 15663) | |
| 66 | AGAYTG + Y + AC + ACAYYT (SEQ ID NO: 15664) | |
| 66 | AGAYTGY + AC + A + CAYYT (SEQ ID NO: 15665) | |
| 66 | AGAYTGY + AC + ACAY + YT (SEQ ID NO: 15666) | |
| 66 | TAGAYT + GYACACA (SEQ ID NO: 15667) | |
| 66 | +TAGAYTGYACACA (SEQ ID NO: 15668) | |
| 66 | TAGAY + TGYACACA (SEQ ID NO: 15669) | |
| 66 | T + AGAYTGYACACA (SEQ ID NO: 15670) | |
| 66 | TAGAYTGYACACA (SEQ ID NO: 15671) | |
| 66 | TAGAYTGYACACAY (SEQ ID NO: 15672) | |
| 66 | TAGAYTGYA + CACA (SEQ ID NO: 15673) | |
| 66 | TAGAYTGYACAC + A (SEQ ID NO: 15674) | |
| 66 | TAG + AYTG + YA + CACA (SEQ ID NO: 15675) | |
| 66 | T + AGAYTG + YA + CACA (SEQ ID NO: 15676) | |
| 66 | TAGAYT + G + YA + CACA (SEQ ID NO: 15677) | |
| 66 | TA + GAYTG + YA + CACA (SEQ ID NO: 15678) | |
| 66 | TAGAYTG + YA + CAC + A (SEQ ID NO: 15679) | |
| 66 | TAGAYTG + YA + CA + CA (SEQ ID NO: 15680) | |
| 66 | TAGAYTG + YA + CACAY (SEQ ID NO: 15681) | |
| 66 | AGAYT + GYACACAY (SEQ ID NO: 15682) | |
| 66 | AGA + YTGYACACAY (SEQ ID NO: 15683) | |
| 66 | AGAYTG + YACACAY (SEQ ID NO: 15684) | |
| 66 | A + GAYTGYACACAY (SEQ ID NO: 15685) | |
| 66 | AGAYTGYACAC + AY (SEQ ID NO: 15686) | |
| 66 | AGAYTGYACACAYY (SEQ ID NO: 15687) | |
| 66 | AGAYTGYAC + ACAY (SEQ ID NO: 15688) | |
| 66 | AGAYTGYACACAY (SEQ ID NO: 15689) | |
| 66 | AGAYT + GY + AC + ACAY (SEQ ID NO: 15690) | |
| 66 | AGAY + TGY + AC + ACAY (SEQ ID NO: 15691) | |
| 66 | +AGAYTGY + AC + ACAY (SEQ ID NO: 15692) | |

TABLE 13-continued

| | | |
|---|---|---|
| 66 | A + GAYTGY + AC + ACAY | (SEQ ID NO: 15693) |
| 66 | AGAYTGY + AC + ACAYY | (SEQ ID NO: 15694) |
| 66 | AGAYTGY + AC + ACA + Y | (SEQ ID NO: 15695) |
| 66 | AGAY + TGYACACAY | (SEQ ID NO: 15696) |
| 66 | AGAYTGYACA + CAY | (SEQ ID NO: 15697) |
| 66 | AGAYTGYACACA + Y | (SEQ ID NO: 15698) |
| 66 | AGA + YTGY + AC + ACAY | (SEQ ID NO: 15699) |
| 66 | AGAYTG + Y + AC + ACAY | (SEQ ID NO: 15700) |
| 66 | AGAYTGY + AC + A + CAY | (SEQ ID NO: 15701) |
| 66 | AGAYTGY + AC + ACAY | (SEQ ID NO: 15702) |
| 66 | YTAGAYTGYACACAYYTAG | (SEQ ID NO: 15703) |
| 66 | TAGAYTGYACACAYYTAGA | (SEQ ID NO: 15704) |
| 66 | TAGAYTGYACACAYYTA | (SEQ ID NO: 15705) |
| 66 | AGAYTGYACACAYYTAG | (SEQ ID NO: 15706) |
| 66 | TAGAYTGYACACAYY | (SEQ ID NO: 15707) |
| 66 | AGAYTGYACACAYYT | (SEQ ID NO: 15708) |
| 66 | TAGAYTGYACACA | (SEQ ID NO: 15709) |
| 66 | AGAYTGYACACAY | (SEQ ID NO: 15710) |
| 66 | TAAATGKGTACAATC | (SEQ ID NO: 15711) |
| 74 | AAA + RTHATYYTRGTAGCAG | (SEQ ID NO: 15712) |
| 74 | A + AARTHATYYTRGTAGCAG | (SEQ ID NO: 15713) |
| 74 | AA + ARTHATYYTRGTAGCAG | (SEQ ID NO: 15714) |
| 74 | AAARTH + ATYYTRGTAGCAG | (SEQ ID NO: 15715) |
| 74 | AAARTHATYYTR + GTAGCAG | (SEQ ID NO: 15716) |
| 74 | AAARTHATYYTRGTAGC + AG | (SEQ ID NO: 15717) |
| 74 | AAARTHATYYTRGTAG + CAG | (SEQ ID NO: 15718) |
| 74 | AAARTHATYYTRGTAGCA + G | (SEQ ID NO: 15719) |
| 74 | AA + ARTHAT + YY + TRGTAGCAG (SEQ ID NO: 15720) | |
| 74 | A + AARTHAT + YY + TRGTAGCAG (SEQ ID NO: 15721) | |
| 74 | AAARTH + AT + YY + TRGTAGCAG (SEQ ID NO: 15722) | |
| 74 | AAA + RTHAT + YY + TRGTAGCAG (SEQ ID NO: 15723) | |
| 74 | AAARTHAT + YY + TRGT + AGCAG (SEQ ID NO: 15724) | |
| 74 | AAARTHAT + YY + TRG + TAGCAG (SEQ ID NO: 15725) | |
| 74 | AAARTHAT + YY + TRGTA + GCAG (SEQ ID NO: 15726) | |
| 74 | AAARTHAT + YY + TR + GTAGCAG (SEQ ID NO: 15727) | |
| 74 | AA + RTHATYYTRGTAGCA | (SEQ ID NO: 15728) |
| 74 | +AARTHATYYTRGTAGCA | (SEQ ID NO: 15729) |
| 74 | A + ARTHATYYTRGTAGCA | (SEQ ID NO: 15730) |
| 74 | AARTH + ATYYTRGTAGCA | (SEQ ID NO: 15731) |
| 74 | AARTHATYYTR + GTAGCA | (SEQ ID NO: 15732) |
| 74 | AARTHATYYTRGTAGC + A | (SEQ ID NO: 15733) |
| 74 | AARTHATYYTRGTAG + CA | (SEQ ID NO: 15734) |
| 74 | AARTHATYYTRGTAGCA | (SEQ ID NO: 15735) |
| 74 | A + ARTHAT + YY + TRGTAGCA (SEQ ID NO: 15736) | |
| 74 | +AARTHAT + YY + TRGTAGCA (SEQ ID NO: 15737) | |
| 74 | AARTH + AT + YY + TRGTAGCA (SEQ ID NO: 15738) | |
| 74 | AA + RTHAT + YY + TRGTAGCA (SEQ ID NO: 15739) | |
| 74 | AARTHAT + YY + TRGT + AGCA (SEQ ID NO: 15740) | |
| 74 | AARTHAT + YY + TRG + TAGCA (SEQ ID NO: 15741) | |
| 74 | AARTHAT + YY + TRGTA + GCA (SEQ ID NO: 15742) | |
| 74 | AARTHAT + YY + TR + GTAGCA (SEQ ID NO: 15743) | |
| 74 | AA + RTHATYYTRGTAG | (SEQ ID NO: 15744) |
| 74 | +AARTHATYYTRGTAG | (SEQ ID NO: 15745) |
| 74 | A + ARTHATYYTRGTAG | (SEQ ID NO: 15746) |
| 74 | AARTH + ATYYTRGTAG | (SEQ ID NO: 15747) |
| 74 | AARTHATYYTR + GTAG | (SEQ ID NO: 15748) |
| 74 | AARTHATYYTRGTAGC | (SEQ ID NO: 15749) |
| 74 | AARTHATYYTRGTAG | (SEQ ID NO: 15750) |
| 74 | A + ARTHAT + YY + TRGTAG (SEQ ID NO: 15751) | |
| 74 | +AARTHAT + YY + TRGTAG | (SEQ ID NO: 15752) |
| 74 | AARTH + AT + YY + TRGTAG (SEQ ID NO: 15753) | |
| 74 | AA + RTHAT + YY + TRGTAG (SEQ ID NO: 15754) | |
| 74 | AARTHAT + YY + TRGT + AG (SEQ ID NO: 15755) | |
| 74 | AARTHAT + YY + TRG + TAG (SEQ ID NO: 15756) | |
| 74 | AARTHAT + YY + TRGTA + G (SEQ ID NO: 15757) | |
| 74 | AARTHAT + YY + TR + GTAG (SEQ ID NO: 15758) | |
| 74 | AA + RTHATYYTRGT | (SEQ ID NO: 15759) |
| 74 | +AARTHATYYTRGT | (SEQ ID NO: 15760) |

TABLE 13-continued

| | |
|---|---|
| 74 | A + ARTHATYYTRGT (SEQ ID NO: 15761) |
| 74 | AARTH + ATYYTRGT (SEQ ID NO: 15762) |
| 74 | AARTHATYYTR + GT (SEQ ID NO: 15763) |
| 74 | AARTHATYYTRGTA (SEQ ID NO: 15764) |
| 74 | A + ARTHAT + YY + TRGT (SEQ ID NO: 15765) |
| 74 | +AARTHAT + YY + TRGT (SEQ ID NO: 15766) |
| 74 | AARTH + AT + YY + TRGT (SEQ ID NO: 15767) |
| 74 | AA + RTHAT + YY + TRGT (SEQ ID NO: 15768) |
| 74 | AARTHAT + YY + TRGT (SEQ ID NO: 15769) |
| 74 | AARTHAT + YY + TRG + T (SEQ ID NO: 15770) |
| 74 | AARTHAT + YY + TRGTA (SEQ ID NO: 15771) |
| 74 | AARTHAT + YY + TR + GT (SEQ ID NO: 15772) |
| 74 | AAARTHATYYTRGTAGCAG (SEQ ID NO: 15773) |
| 74 | AARTHATYYTRGTAGCA (SEQ ID NO: 15774) |
| 74 | AARTHATYYTRGTAG (SEQ ID NO: 15775) |
| 74 | AARTHATYYTRGT (SEQ ID NO: 15776) |
| 74 | AATTATCYTRGTAGC (SEQ ID NO: 15777) |
| 92 | TYCCA + GCAGARACAGGRCA (SEQ ID NO: 15778) |
| 92 | TYCCAGCA + GARACAGGRCA (SEQ ID NO: 15779) |
| 92 | TYCCAG + CAGARACAGGRCA (SEQ ID NO: 15780) |
| 92 | TYCCAGC + AGARACAGGRCA (SEQ ID NO: 15781) |
| 92 | TYCCAGCAGA + RACAGGRCA (SEQ ID NO: 15782) |
| 92 | TYCCAGCAGARACA + GGRCA (SEQ ID NO: 15783) |
| 92 | TYCCAGCAGARACAGG + RCA (SEQ ID NO: 15784) |
| 92 | TYCCAGCAGARA + CAGGRCA (SEQ ID NO: 15785) |
| 92 | TYCCA + GCA + GA + RACAGGRCA (SEQ ID NO: 15786) |
| 92 | TYCC + AGCA + GA + RACAGGRCA (SEQ ID NO: 15787) |
| 92 | TYC + CAGCA + GA + RACAGGRCA (SEQ ID NO: 15788) |
| 92 | TY + CCAGCA + GA + RACAGGRCA (SEQ ID NO: 15789) |
| 92 | TYCCAGCA + GA + RAC + AGGRCA (SEQ ID NO: 15790) |
| 92 | TYCCAGCA + GA + RACAGGRC + A (SEQ ID NO: 15791) |
| 92 | TYCCAGCA + GA + RA + CAGGRCA (SEQ ID NO: 15792) |
| 92 | TYCCAGCA + GA + R + ACAGGRCA (SEQ ID NO: 15793) |
| 92 | ATYCCA + GCAGARACAGGRC (SEQ ID NO: 15794) |
| 92 | AT + YCCAGCAGARACAGGRC (SEQ ID NO: 15795) |
| 92 | ATYCCAG + CAGARACAGGRC (SEQ ID NO: 15796) |
| 92 | ATY + CCAGCAGARACAGGRC (SEQ ID NO: 15797) |
| 92 | ATYCCAGCAG + ARACAGGRC (SEQ ID NO: 15798) |
| 92 | ATYCCAGCAGARA + CAGGRC (SEQ ID NO: 15799) |
| 92 | ATYCCAGCAGARACAG + GRC (SEQ ID NO: 15800) |
| 92 | ATYCCAGCAGA + RACAGGRC (SEQ ID NO: 15801) |
| 92 | ATYCCA + GC + AG + ARACAGGRC (SEQ ID NO: 15802) |
| 92 | ATY + CCAGC + AG + ARACAGGRC (SEQ ID NO: 15803) |
| 92 | AT + YCCAGC + AG + ARACAGGRC (SEQ ID NO: 15804) |
| 92 | ATYC + CAGC + AG + ARACAGGRC (SEQ ID NO: 15805) |
| 92 | ATYCCAGC + AG + ARACAG + GRC (SEQ ID NO: 15806) |
| 92 | ATYCCAGC + AG + ARACA + GGRC (SEQ ID NO: 15807) |
| 92 | ATYCCAGC + AG + ARA + CAGGRC (SEQ ID NO: 15808) |
| 92 | ATYCCAGC + AG + A + RACAGGRC (SEQ ID NO: 15809) |
| 92 | YCCA + GCAGARACAGGRC (SEQ ID NO: 15810) |
| 92 | YCCAGCA + GARACAGGRC (SEQ ID NO: 15811) |
| 92 | YCCAG + CAGARACAGGRC (SEQ ID NO: 15812) |
| 92 | YCCAGC + AGARACAGGRC (SEQ ID NO: 15813) |
| 92 | YCCAGCAGA + RACAGGRC (SEQ ID NO: 15814) |
| 92 | YCCAGCAGARACA + GGRC (SEQ ID NO: 15815) |
| 92 | YCCAGCAGARACAGG + RC (SEQ ID NO: 15816) |
| 92 | YCCAGCAGARA + CAGGRC (SEQ ID NO: 15817) |
| 92 | YCCA + GCA + GA + RACAGGRC (SEQ ID NO: 15818) |
| 92 | YCC + AGCA + GA + RACAGGRC (SEQ ID NO: 15819) |
| 92 | YC + CAGCA + GA + RACAGGRC (SEQ ID NO: 15820) |
| 92 | Y + CCAGCA + GA + RACAGGRC (SEQ ID NO: 15821) |
| 92 | YCCAGCA + GA + RAC + AGGRC (SEQ ID NO: 15822) |
| 92 | YCCAGCA + GA + RACAGGRC (SEQ ID NO: 15823) |
| 92 | YCCAGCA + GA + RA + CAGGRC (SEQ ID NO: 15824) |
| 92 | YCCAGCA + GA + R + ACAGGRC (SEQ ID NO: 15825) |
| 92 | TYCCA + GCAGARACAGGR (SEQ ID NO: 15826) |
| 92 | T + YCCAGCAGARACAGGR (SEQ ID NO: 15827) |
| 92 | TYCCAG + CAGARACAGGR (SEQ ID NO: 15828) |
| 92 | TY + CCAGCAGARACAGGR (SEQ ID NO: 15829) |

TABLE 13-continued

| | |
|---|---|
| 92 | TYCCAGCAG + ARACAGGR (SEQ ID NO: 15830) |
| 92 | TYCCAGCAGARA + CAGGR (SEQ ID NO: 15831) |
| 92 | TYCCAGCAGARACAG + GR (SEQ ID NO: 15832) |
| 92 | TYCCAGCAGA + RACAGGR (SEQ ID NO: 15833) |
| 92 | TYCCA + GC + AG + ARACAGGR (SEQ ID NO: 15834) |
| 92 | TY + CCAGC + AG + ARACAGGR (SEQ ID NO: 15835) |
| 92 | T + YCCAGC + AG + ARACAGGR (SEQ ID NO: 15836) |
| 92 | TYC + CAGC + AG + ARACAGGR (SEQ ID NO: 15837) |
| 92 | TYCCAGC + AG + ARACAG + GR (SEQ ID NO: 15838) |
| 92 | TYCCAGC + AG + ARACA + GGR (SEQ ID NO: 15839) |
| 92 | TYCCAGC + AG + ARA + CAGGR (SEQ ID NO: 15840) |
| 92 | TYCCAGC + AG + A + RACAGGR (SEQ ID NO: 15841) |
| 92 | YCCA + GCAGARACAGG (SEQ ID NO: 15842) |
| 92 | YCCAGCA + GARACAGG (SEQ ID NO: 15843) |
| 92 | YCCAG + CAGARACAGG (SEQ ID NO: 15844) |
| 92 | YCCAGC + AGARACAGG (SEQ ID NO: 15845) |
| 92 | YCCAGCAGA + RACAGG (SEQ ID NO: 15846) |
| 92 | YCCAGCAGARACA + GG (SEQ ID NO: 15847) |
| 92 | YCCAGCAGARACAGG (SEQ ID NO: 15848) |
| 92 | YCCAGCAGARA + CAGG (SEQ ID NO: 15849) |
| 92 | YCCA + GCA + GA + RACAGG (SEQ ID NO: 15850) |
| 92 | YCC + AGCA + GA + RACAGG (SEQ ID NO: 15851) |
| 92 | YC + CAGCA + GA + RACAGG (SEQ ID NO: 15852) |
| 92 | Y + CCAGCA + GA + RACAGG (SEQ ID NO: 15853) |
| 92 | YCCAGCA + GA + RAC + AGG (SEQ ID NO: 15854) |
| 92 | YCCAGCA + GA + RACAGGR (SEQ ID NO: 15855) |
| 92 | YCCAGCA + GA + RA + CAGG (SEQ ID NO: 15856) |
| 92 | YCCAGCA + GA + R + ACAGG (SEQ ID NO: 15857) |
| 92 | TYCCA + GCAGARACAG (SEQ ID NO: 15858) |
| 92 | T + YCCAGCAGARACAG (SEQ ID NO: 15859) |
| 92 | TYCCAG + CAGARACAG (SEQ ID NO: 15860) |
| 92 | TY + CCAGCAGARACAG (SEQ ID NO: 15861) |
| 92 | TYCCAGCAG + ARACAG (SEQ ID NO: 15862) |
| 92 | TYCCAGCAGARA + CAG (SEQ ID NO: 15863) |
| 92 | TYCCAGCAGARACAG (SEQ ID NO: 15864) |
| 92 | TYCCAGCAGA + RACAG (SEQ ID NO: 15865) |
| 92 | TYCCA + GC + AG + ARACAG (SEQ ID NO: 15866) |
| 92 | TY + CCAGC + AG + ARACAG (SEQ ID NO: 15867) |
| 92 | T + YCCAGC + AG + ARACAG (SEQ ID NO: 15868) |
| 92 | TYC + CAGC + AG + ARACAG (SEQ ID NO: 15869) |
| 92 | TYCCAGC + AG + ARACAG (SEQ ID NO: 15870) |
| 92 | TYCCAGC + AG + ARACA + G (SEQ ID NO: 15871) |
| 92 | TYCCAGC + AG + ARA + CAG (SEQ ID NO: 15872) |
| 92 | TYCCAGC + AG + A + RACAG (SEQ ID NO: 15873) |
| 92 | YCCA + GCAGARACA (SEQ ID NO: 15874) |
| 92 | YCCAGCA + GARACA (SEQ ID NO: 15875) |
| 92 | YCCAG + CAGARACA (SEQ ID NO: 15876) |
| 92 | YCCAGC + AGARACA (SEQ ID NO: 15877) |
| 92 | YCCAGCAGA + RACA (SEQ ID NO: 15878) |
| 92 | YCCAGCAGARACA (SEQ ID NO: 15879) |
| 92 | YCCAGCAGARACAG (SEQ ID NO: 15880) |
| 92 | YCCAGCAGARA + CA (SEQ ID NO: 15881) |
| 92 | YCCA + GCA + GA + RACA (SEQ ID NO: 15882) |
| 92 | YCC + AGCA + GA + RACA (SEQ ID NO: 15883) |
| 92 | YC + CAGCA + GA + RACA (SEQ ID NO: 15884) |
| 92 | Y + CCAGCA + GA + RACA (SEQ ID NO: 15885) |
| 92 | YCCAGCA + GA + RAC + A (SEQ ID NO: 15886) |
| 92 | YCCAGCA + GA + RACAG (SEQ ID NO: 15887) |
| 92 | YCCAGCA + GA + RA + CA (SEQ ID NO: 15888) |
| 92 | YCCAGCA + GA + R + ACA (SEQ ID NO: 15889) |
| 92 | TYCCA + GCAGARAC (SEQ ID NO: 15890) |
| 92 | T + YCCAGCAGARAC (SEQ ID NO: 15891) |
| 92 | TYCCAG + CAGARAC (SEQ ID NO: 15892) |
| 92 | TY + CCAGCAGARAC (SEQ ID NO: 15893) |
| 92 | TYCCAGCAG + ARAC (SEQ ID NO: 15894) |
| 92 | TYCCAGCAGARA + C (SEQ ID NO: 15895) |
| 92 | TYCCAGCAGARACA (SEQ ID NO: 15896) |
| 92 | TYCCAGCAGA + RAC (SEQ ID NO: 15897) |
| 92 | TYCCA + GC + AG + ARAC (SEQ ID NO: 15898) |

TABLE 13-continued

| | | |
|---|---|---|
| 92 | TY + CCAGC + AG + ARAC (SEQ ID NO: 15899) | |
| 92 | T + YCCAGC + AG + ARAC (SEQ ID NO: 15900) | |
| 92 | TYC + CAGC + AG + ARAC (SEQ ID NO: 15901) | |
| 92 | TYCCAGC + AG + ARACA (SEQ ID NO: 15902) | |
| 92 | TYCCAGC + AG + ARA + C (SEQ ID NO: 15903) | |
| 92 | TYCCAGC + AG + A + RAC (SEQ ID NO: 15904) | |
| 92 | TYCCAGCAGARACAGGRCA (SEQ ID NO: 15905) | |
| 92 | ATYCCAGCAGARACAGGRC (SEQ ID NO: 15906) | |
| 92 | YCCAGCAGARACAGGRC (SEQ ID NO: 15907) | |
| 92 | TYCCAGCAGARACAGGR (SEQ ID NO: 15908) | |
| 92 | YCCAGCAGARACAGG (SEQ ID NO: 15909) | |
| 92 | YCCAGCAGARACAGGR (SEQ ID NO: 15910) | |
| 92 | TYCCAGCAGARACAG (SEQ ID NO: 15911) | |
| 92 | YCCAGCAGARACA (SEQ ID NO: 15912) | |
| 92 | TYCCAGCAGARAC (SEQ ID NO: 15913) | |
| 92 | CCCAGCAGARACAGG (SEQ ID NO: 15914) | |
| 97 | GG + RCARGARACAGCATAYT (SEQ ID NO: 15915) | |
| 97 | GGRCARG + ARACAGCATAYT (SEQ ID NO: 15916) | |
| 97 | G + GRCARGARACAGCATAYT (SEQ ID NO: 15917) | |
| 97 | GGRCARGA + RACAGCATAYT (SEQ ID NO: 15918) | |
| 97 | GGRCARGARACAG + CATAYT (SEQ ID NO: 15919) | |
| 97 | GGRCARGARACAGCATAY + T (SEQ ID NO: 15920) | |
| 97 | GGRCARGARAC + AGCATAYT (SEQ ID NO: 15921) | |
| 97 | GGRCARGARACA + GCATAYT (SEQ ID NO: 15922) | |
| 97 | GG + RCARGA + RA + CAGCATAYT (SEQ ID NO: 15923) | |
| 97 | GGRC + ARGA + RA + CAGCATAYT (SEQ ID NO: 15924) | |
| 97 | GGR + CARGA + RA + CAGCATAYT (SEQ ID NO: 15925) | |
| 97 | G + GRCARGA + RA + CAGCATAYT (SEQ ID NO: 15926) | |
| 97 | GGRCARGA + RA + CAGCATAY + T (SEQ ID NO: 15927) | |
| 97 | GGRCARGA + RA + CAGCA + TAYT (SEQ ID NO: 15928) | |
| 97 | GGRCARGA + RA + CAGC + ATAYT (SEQ ID NO: 15929) | |
| 97 | GGRCARGA + RA + CA + GCATAYT (SEQ ID NO: 15930) | |
| 97 | G + RCARGARACAGCATAY (SEQ ID NO: 15931) | |
| 97 | GRCARG + ARACAGCATAY (SEQ ID NO: 15932) | |
| 97 | +GRCARGARACAGCATAY (SEQ ID NO: 15933) | |
| 97 | GRCARGA + RACAGCATAY (SEQ ID NO: 15934) | |
| 97 | GRCARGARACAG + CATAY (SEQ ID NO: 15935) | |
| 97 | GRCARGARACAGCATAY (SEQ ID NO: 15936) | |
| 97 | GRCARGARAC + AGCATAY (SEQ ID NO: 15937) | |
| 97 | GRCARGARACA + GCATAY (SEQ ID NO: 15938) | |
| 97 | G + RCARGA + RA + CAGCATAY (SEQ ID NO: 15939) | |
| 97 | GRC + ARGA + RA + CAGCATAY (SEQ ID NO: 15940) | |
| 97 | GR + CARGA + RA + CAGCATAY (SEQ ID NO: 15941) | |
| 97 | +GRCARGA + RA + CAGCATAY (SEQ ID NO: 15942) | |
| 97 | GRCARGA + RA + CAGCATAY (SEQ ID NO: 15943) | |
| 97 | GRCARGA + RA + CAGCA + TAY (SEQ ID NO: 15944) | |
| 97 | GRCARGA + RA + CAGC + ATAY (SEQ ID NO: 15945) | |
| 97 | GRCARGA + RA + CA + GCATAY (SEQ ID NO: 15946) | |
| 97 | G + RCARGARACAGCAT (SEQ ID NO: 15947) | |
| 97 | GRCARG + ARACAGCAT (SEQ ID NO: 15948) | |
| 97 | +GRCARGARACAGCAT (SEQ ID NO: 15949) | |
| 97 | GRCARGA + RACAGCAT (SEQ ID NO: 15950) | |
| 97 | GRCARGARACAG + CAT (SEQ ID NO: 15951) | |
| 97 | GRCARGARACAGCATA (SEQ ID NO: 15952) | |
| 97 | GRCARGARAC + AGCAT (SEQ ID NO: 15953) | |
| 97 | GRCARGARACA + GCAT (SEQ ID NO: 15954) | |
| 97 | G + RCARGA + RA + CAGCAT (SEQ ID NO: 15955) | |
| 97 | GRC + ARGA + RA + CAGCAT (SEQ ID NO: 15956) | |
| 97 | GR + CARGA + RA + CAGCAT (SEQ ID NO: 15957) | |
| 97 | +GRCARGA + RA + CAGCAT (SEQ ID NO: 15958) | |
| 97 | GRCARGA + RA + CAGCATA (SEQ ID NO: 15959) | |
| 97 | GRCARGA + RA + CAGCA + T (SEQ ID NO: 15960) | |
| 97 | GRCARGA + RA + CAGC + AT (SEQ ID NO: 15961) | |
| 97 | GRCARGA + RA + CA + GCAT (SEQ ID NO: 15962) | |
| 97 | G + RCARGARACAGC (SEQ ID NO: 15963) | |
| 97 | GRCARG + ARACAGC (SEQ ID NO: 15964) | |
| 97 | +GRCARGARACAGC (SEQ ID NO: 15965) | |
| 97 | GRCARGA + RACAGC (SEQ ID NO: 15966) | |
| 97 | GRCARGARACAG + C (SEQ ID NO: 15967) | |

TABLE 13-continued

| | |
|---|---|
| 97 | GRCARGARACAGCA (SEQ ID NO: 15968) |
| 97 | GRCARGARAC + AGC (SEQ ID NO: 15969) |
| 97 | GRCARGARACA + GC (SEQ ID NO: 15970) |
| 97 | G + RCARGA + RA + CAGC (SEQ ID NO: 15971) |
| 97 | GRC + ARGA + RA + CAGC (SEQ ID NO: 15972) |
| 97 | GR + CARGA + RA + CAGC (SEQ ID NO: 15973) |
| 97 | +GRCARGA + RA + CAGC (SEQ ID NO: 15974) |
| 97 | GRCARGA + RA + CAGCA (SEQ ID NO: 15975) |
| 97 | GRCARGA + RA + CAGC (SEQ ID NO: 15976) |
| 97 | GRCARGA + RA + CA + GC (SEQ ID NO: 15977) |
| 97 | GGRCARGARACAGCATAYT (SEQ ID NO: 15978) |
| 97 | GRCARGARACAGCATAY (SEQ ID NO: 15979) |
| 97 | GRCARGARACAGCAT (SEQ ID NO: 15980) |
| 97 | GRCARGARACAGC (SEQ ID NO: 15981) |
| 97 | ACAGGAAACWGCATA (SEQ ID NO: 15982) |
| 118 | A + CAGAYAATGGYMSYAAYT (SEQ ID NO: 15983) |
| 118 | ACAGAY + AATGGYMSYAAYT (SEQ ID NO: 15984) |
| 118 | ACA + GAYAATGGYMSYAAYT (SEQ ID NO: 15985) |
| 118 | ACAG + AYAATGGYMSYAAYT (SEQ ID NO: 15986) |
| 118 | ACAGAYAATGGYMSY + AAYT (SEQ ID NO: 15987) |
| 118 | ACAGAYAATGGYMSYA + AYT (SEQ ID NO: 15988) |
| 118 | ACAGAYAATG + GYMSYAAYT (SEQ ID NO: 15989) |
| 118 | ACAGAYAATGG + YMSYAAYT (SEQ ID NO: 15990) |
| 118 | A + CAGAYAA + TG + GYMSYAAYT (SEQ ID NO: 15991) |
| 118 | ACAGAYA + A + TG + GYMSYAAYT (SEQ ID NO: 15992) |
| 118 | AC + AGAYAA + TG + GYMSYAAYT (SEQ ID NO: 15993) |
| 118 | ACAGAY + AA + TG + GYMSYAAYT (SEQ ID NO: 15994) |
| 118 | ACAGAYAA + TG + G + YMSYAAYT (SEQ ID NO: 15995) |
| 118 | ACAGAYAA + TG + GYMS + YAAYT (SEQ ID NO: 15996) |
| 118 | ACAGAYAA + TG + GYMSYAA + YT (SEQ ID NO: 15997) |
| 118 | ACAGAYAA + TG + GYM + SYAAYT (SEQ ID NO: 15998) |
| 118 | +CAGAYAATGGYMSYAAY (SEQ ID NO: 15999) |
| 118 | CAGAY + AATGGYMSYAAY (SEQ ID NO: 16000) |
| 118 | CA + GAYAATGGYMSYAAY (SEQ ID NO: 16001) |
| 118 | CAG + AYAATGGYMSYAAY (SEQ ID NO: 16002) |
| 118 | CAGAYAATGGYMSY + AAY (SEQ ID NO: 16003) |
| 118 | CAGAYAATGGYMSYA + AY (SEQ ID NO: 16004) |
| 118 | CAGAYAATG + GYMSYAAY (SEQ ID NO: 16005) |
| 118 | CAGAYAATGG + YMSYAAY (SEQ ID NO: 16006) |
| 118 | +CAGAYAA + TG + GYMSYAAY (SEQ ID NO: 16007) |
| 118 | CAGAYA + A + TG + GYMSYAAY (SEQ ID NO: 16008) |
| 118 | C + AGAYAA + TG + GYMSYAAY (SEQ ID NO: 16009) |
| 118 | CAGAY + AA + TG + GYMSYAAY (SEQ ID NO: 16010) |
| 118 | CAGAYAA + TG + G + YMSYAAY (SEQ ID NO: 16011) |
| 118 | CAGAYAA + TG + GYMS + YAAY (SEQ ID NO: 16012) |
| 118 | CAGAYAA + TG + GYMSYAA + Y (SEQ ID NO: 16013) |
| 118 | CAGAYAA + TG + GYM + SYAAY (SEQ ID NO: 16014) |
| 118 | +CAGAYAATGGYMSYA (SEQ ID NO: 16015) |
| 118 | CAGAY + AATGGYMSYA (SEQ ID NO: 16016) |
| 118 | CA + GAYAATGGYMSYA (SEQ ID NO: 16017) |
| 118 | CAG + AYAATGGYMSYA (SEQ ID NO: 16018) |
| 118 | CAGAYAATGGYMSY + A (SEQ ID NO: 16019) |
| 118 | CAGAYAATGGYMSYA (SEQ ID NO: 16020) |
| 118 | CAGAYAATG + GYMSYA (SEQ ID NO: 16021) |
| 118 | CAGAYAATGG + YMSYA (SEQ ID NO: 16022) |
| 118 | +CAGAYAA + TG + GYMSYA (SEQ ID NO: 16023) |
| 118 | CAGAYA + A + TG + GYMSYA (SEQ ID NO: 16024) |
| 118 | C + AGAYAA + TG + GYMSYA (SEQ ID NO: 16025) |
| 118 | CAGAY + AA + TG + GYMSYA (SEQ ID NO: 16026) |
| 118 | CAGAYAA + TG + G + YMSYA (SEQ ID NO: 16027) |
| 118 | CAGAYAA + TG + GYMS + YA (SEQ ID NO: 16028) |
| 118 | CAGAYAA + TG + GYMSYAA (SEQ ID NO: 16029) |
| 118 | CAGAYAA + TG + GYM + SYA (SEQ ID NO: 16030) |
| 118 | +CAGAYAATGGYMS (SEQ ID NO: 16031) |
| 118 | CAGAY + AATGGYMS (SEQ ID NO: 16032) |
| 118 | CA + GAYAATGGYMS (SEQ ID NO: 16033) |
| 118 | CAG + AYAATGGYMS (SEQ ID NO: 16034) |
| 118 | CAGAYAATGGYMSY (SEQ ID NO: 16035) |
| 118 | CAGAYAATG + GYMS (SEQ ID NO: 16036) |

TABLE 13-continued

| | |
|---|---|
| 118 | CAGAYAATGG + YMS (SEQ ID NO: 16037) |
| 118 | +CAGAYAA + TG + GYMS (SEQ ID NO: 16038) |
| 118 | CAGAYA + A + TG + GYMS (SEQ ID NO: 16039) |
| 118 | C + AGAYAA + TG + GYMS (SEQ ID NO: 16040) |
| 118 | CAGAY + AA + TG + GYMS (SEQ ID NO: 16041) |
| 118 | CAGAYAA + TG + G + YMS (SEQ ID NO: 16042) |
| 118 | CAGAYAA + TG + GYMS (SEQ ID NO: 16043) |
| 118 | CAGAYAA + TG + GYMSY (SEQ ID NO: 16044) |
| 118 | CAGAYAA + TG + GYM + S (SEQ ID NO: 16045) |
| 118 | ACAGAYAATGGYMSYAAYT (SEQ ID NO: 16046) |
| 118 | CAGAYAATGGYMSYAAY (SEQ ID NO: 16047) |
| 118 | CAGAYAATGGYMSYA (SEQ ID NO: 16048) |
| 118 | CAGAYAATGGYMSYAA (SEQ ID NO: 16049) |
| 118 | CAGAYAATGGYMS (SEQ ID NO: 16050) |
| 118 | AGACAATGGNAGCAA (SEQ ID NO: 16051) |
| 121 | GYMSYAA + YTTYACYAGYRV (SEQ ID NO: 16052) |
| 121 | G + YMSYAAYTTYACYAGYRV (SEQ ID NO: 16053) |
| 121 | GY + MSYAAYTTYACYAGYRV (SEQ ID NO: 16054) |
| 121 | GYMS + YAAYTTYACYAGYRV (SEQ ID NO: 16055) |
| 121 | GYMSYAAYTTYACY + AGYRV (SEQ ID NO: 16056) |
| 121 | GYMSYAAYTTYA + CYAGYRV (SEQ ID NO: 16057) |
| 121 | GYMSYAAYTTY + ACYAGYRV (SEQ ID NO: 16058) |
| 121 | GYMSYAAYTTYACYAGYR + V (SEQ ID NO: 16059) |
| 121 | GYMSYAA + Y + TT + YACYAGYRV (SEQ ID NO: 16060) |
| 121 | GYMS + YAAY + TT + YACYAGYRV (SEQ ID NO: 16061) |
| 121 | G + YMSYAAY + TT + YACYAGYRV (SEQ ID NO: 16062) |
| 121 | GYMSYA + AY + TT + YACYAGYRV (SEQ ID NO: 16063) |
| 121 | GYMSYAAY + TT + YACY + AGYRV (SEQ ID NO: 16064) |
| 121 | GYMSYAAY + TT + YACYAGYR + V (SEQ ID NO: 16065) |
| 121 | GYMSYAAY + TT + YAC + YAGYRV (SEQ ID NO: 16066) |
| 121 | GYMSYAAY + TT + YA + CYAGYRV (SEQ ID NO: 16067) |
| 121 | YMSYAA + YTTYACYAGYR (SEQ ID NO: 16068) |
| 121 | +YMSYAAYTTYACYAGYR (SEQ ID NO: 16069) |
| 121 | Y + MSYAAYTTYACYAGYR (SEQ ID NO: 16070) |
| 121 | YMS + YAAYTTYACYAGYR (SEQ ID NO: 16071) |
| 121 | YMSYAAYTTYACY + AGYR (SEQ ID NO: 16072) |
| 121 | YMSYAAYTTYA + CYAGYR (SEQ ID NO: 16073) |
| 121 | YMSYAAYTTY + ACYAGYR (SEQ ID NO: 16074) |
| 121 | YMSYAAYTTYACYAGYR (SEQ ID NO: 16075) |
| 121 | YMSYAA + Y + TT + YACYAGYR (SEQ ID NO: 16076) |
| 121 | YMS + YAAY + TT + YACYAGYR (SEQ ID NO: 16077) |
| 121 | +YMSYAAY + TT + YACYAGYR (SEQ ID NO: 16078) |
| 121 | YMSYA + AY + TT + YACYAGYR (SEQ ID NO: 16079) |
| 121 | YMSYAAY + TT + YACY + AGYR (SEQ ID NO: 16080) |
| 121 | YMSYAAY + TT + YACYAGYR (SEQ ID NO: 16081) |
| 121 | YMSYAAY + TT + YAC + YAGYR (SEQ ID NO: 16082) |
| 121 | YMSYAAY + TT + YA + CYAGYR (SEQ ID NO: 16083) |
| 121 | YMSYAA + YTTYACYAG (SEQ ID NO: 16084) |
| 121 | +YMSYAAYTTYACYAG (SEQ ID NO: 16085) |
| 121 | Y + MSYAAYTTYACYAG (SEQ ID NO: 16086) |
| 121 | YMS + YAAYTTYACYAG (SEQ ID NO: 16087) |
| 121 | YMSYAAYTTYACY + AG (SEQ ID NO: 16088) |
| 121 | YMSYAAYTTYA + CYAG (SEQ ID NO: 16089) |
| 121 | YMSYAAYTTY + ACYAG (SEQ ID NO: 16090) |
| 121 | YMSYAAYTTYACYAGY (SEQ ID NO: 16091) |
| 121 | YMSYAA + Y + TT + YACYAG (SEQ ID NO: 16092) |
| 121 | YMS + YAAY + TT + YACYAG (SEQ ID NO: 16093) |
| 121 | +YMSYAAY + TT + YACYAG (SEQ ID NO: 16094) |
| 121 | YMSYA + AY + TT + YACYAG (SEQ ID NO: 16095) |
| 121 | YMSYAAY + TT + YACY + AG (SEQ ID NO: 16096) |
| 121 | YMSYAAY + TT + YACYAGY (SEQ ID NO: 16097) |
| 121 | YMSYAAY + TT + YAC + YAG (SEQ ID NO: 16098) |
| 121 | YMSYAAY + TT + YA + CYAG (SEQ ID NO: 16099) |
| 121 | YMSYAA + YTTYACY (SEQ ID NO: 16100) |
| 121 | +YMSYAAYTTYACY (SEQ ID NO: 16101) |
| 121 | Y + MSYAAYTTYACY (SEQ ID NO: 16102) |
| 121 | YMS + YAAYTTYACY (SEQ ID NO: 16103) |
| 121 | YMSYAAYTTYACY (SEQ ID NO: 16104) |
| 121 | YMSYAAYTTYA + CY (SEQ ID NO: 16105) |
| 121 | YMSYAAYTTY + ACY (SEQ ID NO: 16106) |

TABLE 13-continued

| | |
|---|---|
| 121 | YMSYAAYTTYACYA (SEQ ID NO: 16107) |
| 121 | YMSYAA + Y + TT + YACY (SEQ ID NO: 16108) |
| 121 | YMS + YAAY + TT + YACY (SEQ ID NO: 16109) |
| 121 | +YMSYAAY + TT + YACY (SEQ ID NO: 16110) |
| 121 | YMSYA + AY + TT + YACY (SEQ ID NO: 16111) |
| 121 | YMSYAAY + TT + YACY (SEQ ID NO: 16112) |
| 121 | YMSYAAY + TT + YACYA (SEQ ID NO: 16113) |
| 121 | YMSYAAY + TT + YAC + Y (SEQ ID NO: 16114) |
| 121 | YMSYAAY + TT + YA + CY (SEQ ID NO: 16115) |
| 121 | GYMSYAAYTTYACYAGYRV (SEQ ID NO: 16116) |
| 121 | YMSYAAYTTYACYAGYR (SEQ ID NO: 16117) |
| 121 | YMSYAAYTTYACYAG (SEQ ID NO: 16118) |
| 121 | YMSYAAYTTYACY (SEQ ID NO: 16119) |
| 121 | AGCAATTTYACCAGT (SEQ ID NO: 16120) |
| 138 | TCMMRCA + RGAATTTGGVAT (SEQ ID NO: 16121) |
| 138 | TCM + MRCARGAATTTGGVAT (SEQ ID NO: 16122) |
| 138 | TC + MMRCARGAATTTGGVAT (SEQ ID NO: 16123) |
| 138 | TCMMRCAR + GAATTTGGVAT (SEQ ID NO: 16124) |
| 138 | TCMMRCARGAAT + TTGGVAT (SEQ ID NO: 16125) |
| 138 | TCMMRCARGAATTTGGVA + T (SEQ ID NO: 16126) |
| 138 | TCMMRCARGA + ATTGGVAT (SEQ ID NO: 16127) |
| 138 | TCMMRCARGAATTTGGV + AT (SEQ ID NO: 16128) |
| 138 | TC + MMRCAR + GA + ATTTGGVAT (SEQ ID NO: 16129) |
| 138 | TCMMRC + AR + GA + ATTTGGVAT (SEQ ID NO: 16130) |
| 138 | TCM + MRCAR + GA + ATTTGGVAT (SEQ ID NO: 16131) |
| 138 | TCMM + RCAR + GA + ATTTGGVAT (SEQ ID NO: 16132) |
| 138 | TCMMRCAR + GA + ATTTGGVA + T (SEQ ID NO: 16133) |
| 138 | TCMMRCAR + GA + ATT + TGGVAT (SEQ ID NO: 16134) |
| 138 | TCMMRCAR + GA + ATTT + GGVAT (SEQ ID NO: 16135) |
| 138 | TCMMRCAR + GA + A + TTTGGVAT (SEQ ID NO: 16136) |
| 138 | RTC + MMRCARGAATTTGGVA (SEQ ID NO: 16137) |
| 138 | R + TCMMRCARGAATTTGGVA (SEQ ID NO: 16138) |
| 138 | RTCM + MRCARGAATTTGGVA (SEQ ID NO: 16139) |
| 138 | RTCMMRC + ARGAATTTGGVA (SEQ ID NO: 16140) |
| 138 | RTCMMRCARGAATTTGGV + A (SEQ ID NO: 16141) |
| 138 | RTCMMRCARG + AATTTGGVA (SEQ ID NO: 16142) |
| 138 | RTCMMRCARGAAT + TTGGVA (SEQ ID NO: 16143) |
| 138 | RTCMMRCARGA + ATTTGGVA (SEQ ID NO: 16144) |
| 138 | RTCMMRC + A + RG + AATTTGGVA (SEQ ID NO: 16145) |
| 138 | RTCMM + RCA + RG + AATTTGGVA (SEQ ID NO: 16146) |
| 138 | RT + CMMRCA + RG + AATTTGGVA (SEQ ID NO: 16147) |
| 138 | RTC + MMRCA + RG + AATTTGGVA (SEQ ID NO: 16148) |
| 138 | RTCMMRCA + RG + AAT + TTGGVA (SEQ ID NO: 16149) |
| 138 | RTCMMRCA + RG + A + ATTTGGVA (SEQ ID NO: 16150) |
| 138 | RTCMMRCA + RG + AATTTGG + VA (SEQ ID NO: 16151) |
| 138 | RTCMMRCA + RG + AA + TTTGGVA (SEQ ID NO: 16152) |
| 138 | CMMRCA + RGAATTTGGVA (SEQ ID NO: 16153) |
| 138 | CM + MRCARGAATTTGGVA (SEQ ID NO: 16154) |
| 138 | C + MMRCARGAATTTGGVA (SEQ ID NO: 16155) |
| 138 | CMMRCAR + GAATTTGGVA (SEQ ID NO: 16156) |
| 138 | CMMRCARGAAT + TTGGVA (SEQ ID NO: 16157) |
| 138 | CMMRCARGAATTTGGVA (SEQ ID NO: 16158) |
| 138 | CMMRCARGA + ATTTGGVA (SEQ ID NO: 16159) |
| 138 | CMMRCARGAATTTGGV + A (SEQ ID NO: 16160) |
| 138 | C + MMRCAR + GA + ATTTGGVA (SEQ ID NO: 16161) |
| 138 | CMMRC + AR + GA + ATTTGGVA (SEQ ID NO: 16162) |
| 138 | CM + MRCAR + GA + ATTTGGVA (SEQ ID NO: 16163) |
| 138 | CMM + RCAR + GA + ATTTGGVA (SEQ ID NO: 16164) |
| 138 | CMMRCAR + GA + ATTTGGVA (SEQ ID NO: 16165) |
| 138 | CMMRCAR + GA + ATT + TGGVA (SEQ ID NO: 16166) |
| 138 | CMMRCAR + GA + ATTT + GGVA (SEQ ID NO: 16167) |
| 138 | CMMRCAR + GA + A + TTTGGVA (SEQ ID NO: 16168) |
| 138 | TC + MMRCARGAATTTGGV (SEQ ID NO: 16169) |
| 138 | +TCMMRCARGAATTTGGV (SEQ ID NO: 16170) |
| 138 | TCM + MRCARGAATTTGGV (SEQ ID NO: 16171) |
| 138 | TCMMRC + ARGAATTTGGV (SEQ ID NO: 16172) |
| 138 | TCMMRCARGAATTTGGV (SEQ ID NO: 16173) |
| 138 | TCMMRCARG + AATTTGGV (SEQ ID NO: 16174) |

TABLE 13-continued

| 138 | TCMMRCARGAAT + TTGGV (SEQ ID NO: 16175) |
| 138 | TCMMRCARGA + ATTGGV (SEQ ID NO: 16176) |
| 138 | TCMMRC + A + RG + AATTTGGV (SEQ ID NO: 16177) |
| 138 | TCMM + RCA + RG + AATTTGGV (SEQ ID NO: 16178) |
| 138 | T + CMMRCA + RG + AATTTGGV (SEQ ID NO: 16179) |
| 138 | TC + MMRCA + RG + AATTTGGV (SEQ ID NO: 16180) |
| 138 | TCMMRCA + RG + AAT + TTGGV (SEQ ID NO: 16181) |
| 138 | TCMMRCA + RG + A + ATTTGGV (SEQ ID NO: 16182) |
| 138 | TCMMRCA + RG + AATTTGG + V (SEQ ID NO: 16183) |
| 138 | TCMMRCA + RG + AA + TTTGGV (SEQ ID NO: 16184) |
| 138 | CMMRCA + RGAATTTGG (SEQ ID NO: 16185) |
| 138 | CM + MRCARGAATTTGG (SEQ ID NO: 16186) |
| 138 | C + MMRCARGAATTTGG (SEQ ID NO: 16187) |
| 138 | CMMRCAR + GAATTTGG (SEQ ID NO: 16188) |
| 138 | CMMRCARGAAT + TTGG (SEQ ID NO: 16189) |
| 138 | CMMRCARGAATTTGGV (SEQ ID NO: 16190) |
| 138 | CMMRCARGA + ATTTGG (SEQ ID NO: 16191) |
| 138 | C + MMRCAR + GA + ATTTGG (SEQ ID NO: 16192) |
| 138 | CMMRC + AR + GA + ATTTGG (SEQ ID NO: 16193) |
| 138 | CM + MRCAR + GA + ATTTGG (SEQ ID NO: 16194) |
| 138 | CMM + RCAR + GA + ATTTGG (SEQ ID NO: 16195) |
| 138 | CMMRCAR + GA + ATTTGGV (SEQ ID NO: 16196) |
| 138 | CMMRCAR + GA + ATT + TGG (SEQ ID NO: 16197) |
| 138 | CMMRCAR + GA + ATTT + GG (SEQ ID NO: 16198) |
| 138 | CMMRCAR + GA + A + TTTGG (SEQ ID NO: 16199) |
| 138 | TC + MMRCARGAATTTG (SEQ ID NO: 16200) |
| 138 | +TCMMRCARGAATTTG (SEQ ID NO: 16201) |
| 138 | TCM + MRCARGAATTTG (SEQ ID NO: 16202) |
| 138 | TCMMRC + ARGAATTTG (SEQ ID NO: 16203) |
| 138 | TCMMRCARGAATTTGG (SEQ ID NO: 16204) |
| 138 | TCMMRCARG + AATTTG (SEQ ID NO: 16205) |
| 138 | TCMMRCARGAAT + TTG (SEQ ID NO: 16206) |
| 138 | TCMMRCARGA + ATTTG (SEQ ID NO: 16207) |
| 138 | TCMMRC + A + RG + AATTTG (SEQ ID NO: 16208) |
| 138 | TCMM + RCA + RG + AATTTG (SEQ ID NO: 16209) |
| 138 | T + CMMRCA + RG + AATTTG (SEQ ID NO: 16210) |
| 138 | TC + MMRCA + RG + AATTTG (SEQ ID NO: 16211) |
| 138 | TCMMRCA + RG + AAT + TTG (SEQ ID NO: 16212) |
| 138 | TCMMRCA + RG + A + ATTTG (SEQ ID NO: 16213) |
| 138 | TCMMRCA + RG + AATTTGG (SEQ ID NO: 16214) |
| 138 | TCMMRCA + RG + AA + TTTG (SEQ ID NO: 16215) |
| 138 | CMMRCA + RGAATTT (SEQ ID NO: 16216) |
| 138 | CM + MRCARGAATT (SEQ ID NO: 16217) |
| 138 | C + MMRCARGAATT (SEQ ID NO: 16218) |
| 138 | CMMRCAR + GAATTT (SEQ ID NO: 16219) |
| 138 | CMMRCARGAAT + TT (SEQ ID NO: 16220) |
| 138 | CMMRCARGAATTTG (SEQ ID NO: 16221) |
| 138 | CMMRCARGA + ATTT (SEQ ID NO: 16222) |
| 138 | C + MMRCAR + GA + ATTT (SEQ ID NO: 16223) |
| 138 | CMMRC + AR + GA + ATTT (SEQ ID NO: 16224) |
| 138 | CM + MRCAR + GA + ATTT (SEQ ID NO: 16225) |
| 138 | CMM + RCAR + GA + ATTT (SEQ ID NO: 16226) |
| 138 | CMMRCAR + GA + ATTTG (SEQ ID NO: 16227) |
| 138 | CMMRCAR + GA + ATT + T (SEQ ID NO: 16228) |
| 138 | CMMRCAR + GA + ATTT (SEQ ID NO: 16229) |
| 138 | CMMRCAR + GA + A + TTT (SEQ ID NO: 16230) |
| 138 | TC + MMRCARGAATT (SEQ ID NO: 16231) |
| 138 | +TCMMRCARGAATT (SEQ ID NO: 16232) |
| 138 | TCM + MRCARGAATT (SEQ ID NO: 16233) |
| 138 | TCMMRC + ARGAATT (SEQ ID NO: 16234) |
| 138 | TCMMRCARGAATTT (SEQ ID NO: 16235) |
| 138 | TCMMRCARG + AATT (SEQ ID NO: 16236) |
| 138 | TCMMRCARGAAT + T (SEQ ID NO: 16237) |
| 138 | TCMMRCARGA + ATT (SEQ ID NO: 16238) |
| 138 | TCMMRC + A + RG + AATT (SEQ ID NO: 16239) |
| 138 | TCMM + RCA + RG + AATT (SEQ ID NO: 16240) |
| 138 | T + CMMRCA + RG + AATT (SEQ ID NO: 16241) |
| 138 | TC + MMRCA + RG + AATT (SEQ ID NO: 16242) |
| 138 | TCMMRCA + RG + AAT + T (SEQ ID NO: 16243) |

TABLE 13-continued

| | |
|---|---|
| 138 | TCMMRCA + RG + A + ATT (SEQ ID NO: 16244) |
| 138 | TCMMRCA + RG + AATTT (SEQ ID NO: 16245) |
| 138 | TCMMRCA + RG + AA + TT (SEQ ID NO: 16246) |
| 138 | TCMMRCARGAATTTGGVAT (SEQ ID NO: 16247) |
| 138 | RTCMMRCARGAATTTGGVA (SEQ ID NO: 16248) |
| 138 | CMMRCARGAATTTGGVA (SEQ ID NO: 16249) |
| 138 | TCMMRCARGAATTTGGV (SEQ ID NO: 16250) |
| 138 | CMMRCARGAATTTGG (SEQ ID NO: 16251) |
| 138 | TCMMRCARGAATTTG (SEQ ID NO: 16252) |
| 138 | CMMRCARGAATTT (SEQ ID NO: 16253) |
| 138 | TCMMRCARGAATT (SEQ ID NO: 16254) |
| 138 | AAACAGGARTTTGGA (SEQ ID NO: 16255) |
| 140 | ARGAA + TTTGGVATYCCCTA (SEQ ID NO: 16256) |
| 140 | ARG + AATTTGGVATYCCCTA (SEQ ID NO: 16257) |
| 140 | ARGAAT + TTGGVATYCCCTA (SEQ ID NO: 16258) |
| 140 | ARGAATTT + GGVATYCCCTA (SEQ ID NO: 16259) |
| 140 | ARGAATTTGGVATYCC + CTA (SEQ ID NO: 16260) |
| 140 | ARGAATTTGGVATYC + CCTA (SEQ ID NO: 16261) |
| 140 | ARGAATTTGGVATYCCCT + A (SEQ ID NO: 16262) |
| 140 | ARGAATTTGGVA + TYCCCTA (SEQ ID NO: 16263) |
| 140 | ARGA + ATTT + GG + VATYCCCTA (SEQ ID NO: 16264) |
| 140 | ARG + AATTT + GG + VATYCCCTA (SEQ ID NO: 16265) |
| 140 | ARGAATT + T + GG + VATYCCCTA (SEQ ID NO: 16266) |
| 140 | A + RGAATTT + GG + VATYCCCTA (SEQ ID NO: 16267) |
| 140 | ARGAATTT + GG + VATY + CCCTA (SEQ ID NO: 16268) |
| 140 | ARGAATTT + GG + VATYCCCT + A (SEQ ID NO: 16269) |
| 140 | ARGAATTT + GG + VATYC + CCTA (SEQ ID NO: 16270) |
| 140 | ARGAATTT + GG + VAT + YCCCTA (SEQ ID NO: 16271) |
| 140 | CARG + AATTTGGVATYCCCT (SEQ ID NO: 16272) |
| 140 | CARGAATT + TGGVATYCCCT (SEQ ID NO: 16273) |
| 140 | CA + RGAATTTGGVATYCCCT (SEQ ID NO: 16274) |
| 140 | CARGAAT + TTGGVATYCCCT (SEQ ID NO: 16275) |
| 140 | CARGAATTTGGVAT + YCCCT (SEQ ID NO: 16276) |
| 140 | CARGAATTTGGVATY + CCCT (SEQ ID NO: 16277) |
| 140 | CARGAATTTGGVATYC + CCT (SEQ ID NO: 16278) |
| 140 | CARGAATTTGGV + ATYCCCT (SEQ ID NO: 16279) |
| 140 | CAR + GAATT + TG + GVATYCCCT (SEQ ID NO: 16280) |
| 140 | CA + RGAATT + TG + GVATYCCCT (SEQ ID NO: 16281) |
| 140 | C + ARGAATT + TG + GVATYCCCT (SEQ ID NO: 16282) |
| 140 | CARGAAT + T + TG + GVATYCCCT (SEQ ID NO: 16283) |
| 140 | CARGAATT + TG + GV + ATYCCCT (SEQ ID NO: 16284) |
| 140 | CARGAATT + TG + GVATY + CCCT (SEQ ID NO: 16285) |
| 140 | CARGAATT + TG + GVA + TYCCCT (SEQ ID NO: 16286) |
| 140 | CARGAATT + TG + GVATYCC + CT (SEQ ID NO: 16287) |
| 140 | CARGAA + TTTGGVATYCCCT (SEQ ID NO: 16288) |
| 140 | CAR + GAATTTGGVATYCCCT (SEQ ID NO: 16289) |
| 140 | C + ARGAATTTGGVATYCCCT (SEQ ID NO: 16290) |
| 140 | CARGAATTTGGVATYCCC + T (SEQ ID NO: 16291) |
| 140 | CARGAATTTG + GVATYCCCT (SEQ ID NO: 16292) |
| 140 | CARG + AATT + TG + GVATYCCCT (SEQ ID NO: 16293) |
| 140 | CARGA + ATT + TG + GVATYCCCT (SEQ ID NO: 16294) |
| 140 | CARGAATT + TG + G + VATYCCCT (SEQ ID NO: 16295) |
| 140 | CARGAATT + TG + GVAT + YCCCT (SEQ ID NO: 16296) |
| 140 | RGAA + TTTGGVATYCCCT (SEQ ID NO: 16297) |
| 140 | RG + AATTTGGVATYCCCT (SEQ ID NO: 16298) |
| 140 | RGAAT + TTGGVATYCCCT (SEQ ID NO: 16299) |
| 140 | RGAATTT + GGVATYCCCT (SEQ ID NO: 16300) |
| 140 | RGAATTTGGVATYCC + CT (SEQ ID NO: 16301) |
| 140 | RGAATTTGGVATYC + CCT (SEQ ID NO: 16302) |
| 140 | RGAATTTGGVATYCCCT (SEQ ID NO: 16303) |
| 140 | RGAATTTGGVA + TYCCCT (SEQ ID NO: 16304) |
| 140 | RGA + ATTT + GG + VATYCCCT (SEQ ID NO: 16305) |
| 140 | RG + AATTT + GG + VATYCCCT (SEQ ID NO: 16306) |
| 140 | RGAATT + T + GG + VATYCCCT (SEQ ID NO: 16307) |
| 140 | +RGAATTT + GG + VATYCCCT (SEQ ID NO: 16308) |
| 140 | RGAATTT + GG + VATY + CCCT (SEQ ID NO: 16309) |
| 140 | RGAATTT + GG + VATYCCCT (SEQ ID NO: 16310) |

TABLE 13-continued

| | |
|---|---|
| 140 | RGAATTT + GG + VATYC + CCT (SEQ ID NO: 16311) |
| 140 | RGAATTT + GG + VAT + YCCCT (SEQ ID NO: 16312) |
| 140 | ARG + AATTTGGVATYCCC (SEQ ID NO: 16313) |
| 140 | ARGAATT + TGGVATYCCC (SEQ ID NO: 16314) |
| 140 | A + RGAATTTGGVATYCCC (SEQ ID NO: 16315) |
| 140 | ARGAAT + TTGGVATYCCC (SEQ ID NO: 16316) |
| 140 | ARGAATTTGGVAT + YCCC (SEQ ID NO: 16317) |
| 140 | ARGAATTTGGVATY + CCC (SEQ ID NO: 16318) |
| 140 | ARGAATTTGGVATYC + CC (SEQ ID NO: 16319) |
| 140 | ARGAATTTGGV + ATYCCC (SEQ ID NO: 16320) |
| 140 | AR + GAATT + TG + GVATYCCC (SEQ ID NO: 16321) |
| 140 | A + RGAATT + TG + GVATYCCC (SEQ ID NO: 16322) |
| 140 | +ARGAATT + TG + GVATYCCC (SEQ ID NO: 16323) |
| 140 | ARGAAT + T + TG + GVATYCCC (SEQ ID NO: 16324) |
| 140 | ARGAATT + TG + GV + ATYCCC (SEQ ID NO: 16325) |
| 140 | ARGAATT + TG + GVATY + CCC (SEQ ID NO: 16326) |
| 140 | ARGAATT + TG + GVA + TYCCC (SEQ ID NO: 16327) |
| 140 | ARGAATT + TG + GVATYCC + C (SEQ ID NO: 16328) |
| 140 | ARGAA + TTTGGVATYCCC (SEQ ID NO: 16329) |
| 140 | AR + GAATTTGGVATYCCC (SEQ ID NO: 16330) |
| 140 | +ARGAATTTGGVATYCCC (SEQ ID NO: 16331) |
| 140 | ARGAATTTGGVATYCCC (SEQ ID NO: 16332) |
| 140 | ARGAATTTG + GVATYCCC (SEQ ID NO: 16333) |
| 140 | ARG + AATT + TG + GVATYCCC (SEQ ID NO: 16334) |
| 140 | ARGA + ATT + TG + GVATYCCC (SEQ ID NO: 16335) |
| 140 | ARGAATT + TG + G + VATYCCC (SEQ ID NO: 16336) |
| 140 | ARGAATT + TG + GVAT + YCCC (SEQ ID NO: 16337) |
| 140 | RGAA + TTTGGVATYCC (SEQ ID NO: 16338) |
| 140 | RG + AATTTGGVATYCC (SEQ ID NO: 16339) |
| 140 | RGAAT + TTGGVATYCC (SEQ ID NO: 16340) |
| 140 | RGAATTT + GGVATYCC (SEQ ID NO: 16341) |
| 140 | RGAATTTGGVATYCC (SEQ ID NO: 16342) |
| 140 | RGAATTTGGVATYC + C (SEQ ID NO: 16343) |
| 140 | RGAATTTGGVATYCCC (SEQ ID NO: 16344) |
| 140 | RGAATTTGGVA + TYCC (SEQ ID NO: 16345) |
| 140 | RGA + ATTT + GG + VATYCC (SEQ ID NO: 16346) |
| 140 | RG + AATTT + GG + VATYCC (SEQ ID NO: 16347) |
| 140 | RGAATT + T + GG + VATYCC (SEQ ID NO: 16348) |
| 140 | +RGAATTT + GG + VATYCC (SEQ ID NO: 16349) |
| 140 | RGAATTT + GG + VATY + CC (SEQ ID NO: 16350) |
| 140 | RGAATTT + GG + VATYCCC (SEQ ID NO: 16351) |
| 140 | RGAATTT + GG + VATYC + C (SEQ ID NO: 16352) |
| 140 | RGAATTT + GG + VAT + YCC (SEQ ID NO: 16353) |
| 140 | ARG + AATTTGGVATYC (SEQ ID NO: 16354) |
| 140 | ARGAATT + TGGVATYC (SEQ ID NO: 16355) |
| 140 | A + RGAATTTGGVATYC (SEQ ID NO: 16356) |
| 140 | ARGAAT + TTGGVATYC (SEQ ID NO: 16357) |
| 140 | ARGAATTTGGVAT + YC (SEQ ID NO: 16358) |
| 140 | ARGAATTTGGVATY + C (SEQ ID NO: 16359) |
| 140 | ARGAATTTGGVATYC (SEQ ID NO: 16360) |
| 140 | ARGAATTTGGV + ATYC (SEQ ID NO: 16361) |
| 140 | AR + GAATT + TG + GVATYC (SEQ ID NO: 16362) |
| 140 | A + RGAATT + TG + GVATYC (SEQ ID NO: 16363) |
| 140 | +ARGAATT + TG + GVATYC (SEQ ID NO: 16364) |
| 140 | ARGAAT + T + TG + GVATYC (SEQ ID NO: 16365) |
| 140 | ARGAATT + TG + GV + ATYC (SEQ ID NO: 16366) |
| 140 | ARGAATT + TG + GVATY + C (SEQ ID NO: 16367) |
| 140 | ARGAATT + TG + GVA + TYC (SEQ ID NO: 16368) |
| 140 | ARGAATT + TG + GVATYCC (SEQ ID NO: 16369) |
| 140 | ARGAA + TTTGGVATYC (SEQ ID NO: 16370) |
| 140 | AR + GAATTTGGVATYC (SEQ ID NO: 16371) |
| 140 | +ARGAATTTGGVATYC (SEQ ID NO: 16372) |
| 140 | ARGAATTTGGVATYCC (SEQ ID NO: 16373) |
| 140 | ARGAATTTG + GVATYC (SEQ ID NO: 16374) |
| 140 | ARG + AATT + TG + GVATYC (SEQ ID NO: 16375) |
| 140 | ARGA + ATT + TG + GVATYC (SEQ ID NO: 16376) |

TABLE 13-continued

| | |
|---|---|
| 140 | ARGAATT + TG + G + VATYC (SEQ ID NO: 16377) |
| 140 | ARGAATT + TG + GVAT + YC (SEQ ID NO: 16378) |
| 140 | RGAA + TTTGGVATY (SEQ ID NO: 16379) |
| 140 | RG + AATTTGGVATY (SEQ ID NO: 16380) |
| 140 | RGAAT + TTGGVATY (SEQ ID NO: 16381) |
| 140 | RGAATTT + GGVATY (SEQ ID NO: 16382) |
| 140 | RGAATTTGGVATYC (SEQ ID NO: 16383) |
| 140 | RGAATTTGGVA + TY (SEQ ID NO: 16384) |
| 140 | RGA + ATTT + GG + VATY (SEQ ID NO: 16385) |
| 140 | RG + AATTT + GG + VATY (SEQ ID NO: 16386) |
| 140 | RGAATT + T + GG + VATY (SEQ ID NO: 16387) |
| 140 | +RGAATTT + GG + VATY (SEQ ID NO: 16388) |
| 140 | RGAATTT + GG + VATY (SEQ ID NO: 16389) |
| 140 | RGAATTT + GG + VATYC (SEQ ID NO: 16390) |
| 140 | RGAATTT + GG + VAT + Y (SEQ ID NO: 16391) |
| 140 | ARG + AATTTGGVAT (SEQ ID NO: 16392) |
| 140 | ARGAATT + TGGVAT (SEQ ID NO: 16393) |
| 140 | A + RGAATTTGGVAT (SEQ ID NO: 16394) |
| 140 | ARGAAT + TTGGVAT (SEQ ID NO: 16395) |
| 140 | ARGAATTTGGVAT (SEQ ID NO: 16396) |
| 140 | ARGAATTTGGVATY (SEQ ID NO: 16397) |
| 140 | ARGAATTTGGV + AT (SEQ ID NO: 16398) |
| 140 | AR + GAATT + TG + GVAT (SEQ ID NO: 16399) |
| 140 | A + RGAATT + TG + GVAT (SEQ ID NO: 16400) |
| 140 | +ARGAATT + TG + GVAT (SEQ ID NO: 16401) |
| 140 | ARGAAT + T + TG + GVAT (SEQ ID NO: 16402) |
| 140 | ARGAATT + TG + GV + AT (SEQ ID NO: 16403) |
| 140 | ARGAATT + TG + GVATY (SEQ ID NO: 16404) |
| 140 | ARGAATT + TG + GVA + T (SEQ ID NO: 16405) |
| 140 | ARGAA + TTTGGVAT (SEQ ID NO: 16406) |
| 140 | AR + GAATTTGGVAT (SEQ ID NO: 16407) |
| 140 | +ARGAATTTGGVAT (SEQ ID NO: 16408) |
| 140 | ARGAATTTG + GVAT (SEQ ID NO: 16409) |
| 140 | ARG + AATT + TG + GVAT (SEQ ID NO: 16410) |
| 140 | ARGA + ATT + TG + GVAT (SEQ ID NO: 16411) |
| 140 | ARGAATT + TG + G + VAT (SEQ ID NO: 16412) |
| 140 | ARGAATT + TG + GVAT (SEQ ID NO: 16413) |
| 140 | ARGAATTTGGVATYCCCTA (SEQ ID NO: 16414) |
| 140 | CARGAATTTGGVATYCCCT (SEQ ID NO: 16415) |
| 140 | RGAATTTGGVATYCCCT (SEQ ID NO: 16416) |
| 140 | ARGAATTTGGVATYCCC (SEQ ID NO: 16417) |
| 140 | RGAATTTGGVATYCC (SEQ ID NO: 16418) |
| 140 | ARGAATTTGGVATYC (SEQ ID NO: 16419) |
| 140 | RGAATTTGGVATY (SEQ ID NO: 16420) |
| 140 | ARGAATTTGGVAT (SEQ ID NO: 16421) |
| 140 | AATTTGGNATTCCCT (SEQ ID NO: 16422) |
| 143 | GVAT + YCCCTACAATCCCCA (SEQ ID NO: 16423) |
| 143 | GV + ATYCCCTACAATCCCCA (SEQ ID NO: 16424) |
| 143 | GVATY + CCCTACAATCCCCA (SEQ ID NO: 16425) |
| 143 | GVATYCCC + TACAATCCCCA (SEQ ID NO: 16426) |
| 143 | GVATYCCCTACAATC + CCCA (SEQ ID NO: 16427) |
| 143 | GVATYCCCTACAATCC + CCA (SEQ ID NO: 16428) |
| 143 | GVATYCCCTAC + AATCCCCA (SEQ ID NO: 16429) |
| 143 | GVATYCCCTACAAT + CCCCA (SEQ ID NO: 16430) |
| 143 | GV + ATYCCC + TA + CAATCCCCA (SEQ ID NO: 16431) |
| 143 | GVATYC + CC + TA + CAATCCCCA (SEQ ID NO: 16432) |
| 143 | G + VATYCCC + TA + CAATCCCCA (SEQ ID NO: 16433) |
| 143 | GVATY + CCC + TA + CAATCCCCA (SEQ ID NO: 16434) |
| 143 | GVATYCCC + TA + CAATCCC + CA (SEQ ID NO: 16435) |
| 143 | GVATYCCC + TA + CAA + TCCCCA (SEQ ID NO: 16436) |
| 143 | GVATYCCC + TA + CAATCCCC + A (SEQ ID NO: 16437) |
| 143 | GVATYCCC + TA + C + AATCCCCA (SEQ ID NO: 16438) |
| 143 | G + GVATYCCCTACAATCCCC (SEQ ID NO: 16439) |
| 143 | GG + VATYCCCTACAATCCCC (SEQ ID NO: 16440) |
| 143 | GGVATYCC + CTACAATCCCC (SEQ ID NO: 16441) |
| 143 | GGVA + TYCCCTACAATCCCC (SEQ ID NO: 16442) |
| 143 | GGVATYCCCTACAA + TCCCC (SEQ ID NO: 16443) |
| 143 | GGVATYCCCTACAATCCC + C (SEQ ID NO: 16444) |
| 143 | GGVATYCCCTA + CAATCCCC (SEQ ID NO: 16445) |
| 143 | GGVATYCCCTAC + AATCCCC (SEQ ID NO: 16446) |
| 143 | GGVATY + CC + CT + ACAATCCCC (SEQ ID NO: 16447) |
| 143 | GGVAT + YCC + CT + ACAATCCCC (SEQ ID NO: 16448) |
| 143 | GG + VATYCC + CT + ACAATCCCC (SEQ ID NO: 16449) |

TABLE 13-continued

| | |
|---|---|
| 143 | GGVA + TYCC + CT + ACAATCCCC (SEQ ID NO: 16450) |
| 143 | GGVATYCC + CT + ACAATC + CCC (SEQ ID NO: 16451) |
| 143 | GGVATYCC + CT + A + CAATCCCC (SEQ ID NO: 16452) |
| 143 | GGVATYCC + CT + ACAA + TCCCC (SEQ ID NO: 16453) |
| 143 | GGVATYCC + CT + ACAATCCC + C (SEQ ID NO: 16454) |
| 143 | G + VATYCCCTACAATCCCCA (SEQ ID NO: 16455) |
| 143 | GVA + TYCCCTACAATCCCCA (SEQ ID NO: 16456) |
| 143 | GVATYCCCTACAATCCCC + A (SEQ ID NO: 16457) |
| 143 | GVATYCCCTACA + ATCCCCA (SEQ ID NO: 16458) |
| 143 | GVATYCC + C + TA + CAATCCCCA (SEQ ID NO: 16459) |
| 143 | GVATYCCC + TA + CAAT + CCCCA (SEQ ID NO: 16460) |
| 143 | GVATYCCC + TA + CA + ATCCCCA (SEQ ID NO: 16461) |
| 143 | VAT + YCCCTACAATCCCC (SEQ ID NO: 16462) |
| 143 | V + ATYCCCTACAATCCCC (SEQ ID NO: 16463) |
| 143 | VATY + CCCTACAATCCCC (SEQ ID NO: 16464) |
| 143 | VATYCCC + TACAATCCCC (SEQ ID NO: 16465) |
| 143 | VATYCCCTACAAT + CCC (SEQ ID NO: 16466) |
| 143 | VATYCCCTACAATCC + CC (SEQ ID NO: 16467) |
| 143 | VATYCCCTAC + AATCCC (SEQ ID NO: 16468) |
| 143 | VATYCCCTACAAT + CCCC (SEQ ID NO: 16469) |
| 143 | V + ATYCCC + TA + CAATCCCC (SEQ ID NO: 16470) |
| 143 | VATYC + CC + TA + CAATCCCC (SEQ ID NO: 16471) |
| 143 | +VATYCCC + TA + CAATCCCC (SEQ ID NO: 16472) |
| 143 | VATY + CCC + TA + CAATCCCC (SEQ ID NO: 16473) |
| 143 | VATYCCC + TA + CAATCCC + C (SEQ ID NO: 16474) |
| 143 | VATYCCC + TA + CAA + TCCCC (SEQ ID NO: 16475) |
| 143 | VATYCCC + TA + CAATCCCC (SEQ ID NO: 16476) |
| 143 | VATYCCC + TA + C + AATCCC (SEQ ID NO: 16477) |
| 143 | +GVATYCCCTACAATCCC (SEQ ID NO: 16478) |
| 143 | G + VATYCCCTACAATCCC (SEQ ID NO: 16479) |
| 143 | GVATYCC + CTACAATCCC (SEQ ID NO: 16480) |
| 143 | GVA + TYCCCTACAATCCC (SEQ ID NO: 16481) |
| 143 | GVATYCCCTACAA + TCCC (SEQ ID NO: 16482) |
| 143 | GVATYCCCTACAATCCC (SEQ ID NO: 16483) |
| 143 | GVATYCCCTA + CAATCCC (SEQ ID NO: 16484) |
| 143 | GVATYCCCTAC + AATCCC (SEQ ID NO: 16485) |
| 143 | GVATY + CC + CT + ACAATCCC (SEQ ID NO: 16486) |
| 143 | GVAT + YCC + CT + ACAATCCC (SEQ ID NO: 16487) |
| 143 | G + VATYCC + CT + ACAATCCC (SEQ ID NO: 16488) |
| 143 | GVA + TYCC + CT + ACAATCCC (SEQ ID NO: 16489) |
| 143 | GVATYCC + CT + ACAATC + CC (SEQ ID NO: 16490) |
| 143 | GVATYCC + CT + A + CAATCCC (SEQ ID NO: 16491) |
| 143 | GVATYCC + CT + ACAA + TCCC (SEQ ID NO: 16492) |
| 143 | GVATYCC + CT + ACAATCCC (SEQ ID NO: 16493) |
| 143 | +VATYCCCTACAATCCC (SEQ ID NO: 16494) |
| 143 | VA + TYCCCTACAATCCCC (SEQ ID NO: 16495) |
| 143 | VATYCCCTACAATCCCC (SEQ ID NO: 16496) |
| 143 | VATYCCCTACA + ATCCCC (SEQ ID NO: 16497) |
| 143 | VATYCC + C + TA + CAATCCCC (SEQ ID NO: 16498) |
| 143 | VATYCCC + TA + CAAT + CCCC (SEQ ID NO: 16499) |
| 143 | VATYCCC + TA + CA + ATCCCC (SEQ ID NO: 16500) |
| 143 | VAT + YCCCTACAATCC (SEQ ID NO: 16501) |
| 143 | V + ATYCCCTACAATCC (SEQ ID NO: 16502) |
| 143 | VATY + CCCTACAATCC (SEQ ID NO: 16503) |
| 143 | VATYCCC + TACAATCC (SEQ ID NO: 16504) |
| 143 | VATYCCCTACAATC + C (SEQ ID NO: 16505) |
| 143 | VATYCCCTACAATCC (SEQ ID NO: 16506) |
| 143 | VATYCCCTAC + AATCC (SEQ ID NO: 16507) |
| 143 | VATYCCCTACAAT + CC (SEQ ID NO: 16508) |
| 143 | V + ATYCCC + TA + CAATCC (SEQ ID NO: 16509) |
| 143 | VATYC + CC + TA + CAATCC (SEQ ID NO: 16510) |
| 143 | +VATYCCC + TA + CAATCC (SEQ ID NO: 16511) |
| 143 | VATY + CCC + TA + CAATCC (SEQ ID NO: 16512) |
| 143 | VATYCCC + TA + CAATCCC (SEQ ID NO: 16513) |
| 143 | VATYCCC + TA + CAA + TCC (SEQ ID NO: 16514) |
| 143 | VATYCCC + TA + C + AATCC (SEQ ID NO: 16515) |
| 143 | +GVATYCCCTACAATC (SEQ ID NO: 16516) |
| 143 | G + VATYCCCTACAATC (SEQ ID NO: 16517) |

TABLE 13-continued

| | |
|---|---|
| 143 | GVATYCC + CTACAATC (SEQ ID NO: 16518) |
| 143 | GVA + TYCCCTACAATC (SEQ ID NO: 16519) |
| 143 | GVATYCCCTACAA + TC (SEQ ID NO: 16520) |
| 143 | GVATYCCCTACAATCC (SEQ ID NO: 16521) |
| 143 | GVATYCCCTA + CAATC (SEQ ID NO: 16522) |
| 143 | GVATYCCCTAC + AATC (SEQ ID NO: 16523) |
| 143 | GVATY + CC + CT + ACAATC (SEQ ID NO: 16524) |
| 143 | GVAT + YCC + CT + ACAATC (SEQ ID NO: 16525) |
| 143 | G + VATYCC + CT + ACAATC (SEQ ID NO: 16526) |
| 143 | GVA + TYCC + CT + ACAATC (SEQ ID NO: 16527) |
| 143 | GVATYCC + CT + ACAATC (SEQ ID NO: 16528) |
| 143 | GVATYCC + CT + A + CAATC (SEQ ID NO: 16529) |
| 143 | GVATYCC + CT + ACAA + TC (SEQ ID NO: 16530) |
| 143 | GVATYCC + CT + ACAATCC (SEQ ID NO: 16531) |
| 143 | +VATYCCCTACAATCC (SEQ ID NO: 16532) |
| 143 | VA + TYCCCTACAATCC (SEQ ID NO: 16533) |
| 143 | VATYCCCTACAATCCC (SEQ ID NO: 16534) |
| 143 | VATYCCCTACA + ATCC (SEQ ID NO: 16535) |
| 143 | VATYCC + C + TA + CAATCC (SEQ ID NO: 16536) |
| 143 | VATYCCC + TA + CAAT + CC (SEQ ID NO: 16537) |
| 143 | VATYCCC + TA + CA + ATCC (SEQ ID NO: 16538) |
| 143 | VAT + YCCCTACAAT (SEQ ID NO: 16539) |
| 143 | V + ATYCCCTACAAT (SEQ ID NO: 16540) |
| 143 | VATY + CCCTACAAT (SEQ ID NO: 16541) |
| 143 | VATYCCC + TACAAT (SEQ ID NO: 16542) |
| 143 | VATYCCCTACAATC (SEQ ID NO: 16543) |
| 143 | VATYCCCTAC + AAT (SEQ ID NO: 16544) |
| 143 | VATYCCCTACAAT (SEQ ID NO: 16545) |
| 143 | V + ATYCCC + TA + CAAT (SEQ ID NO: 16546) |
| 143 | VATYC + CC + TA + CAAT (SEQ ID NO: 16547) |
| 143 | +VATYCCC + TA + CAAT (SEQ ID NO: 16548) |
| 143 | VATY + CCC + TA + CAAT (SEQ ID NO: 16549) |
| 143 | VATYCCC + TA + CAATC (SEQ ID NO: 16550) |
| 143 | VATYCCC + TA + CAA + T (SEQ ID NO: 16551) |
| 143 | VATYCCC + TA + C + AAT (SEQ ID NO: 16552) |
| 143 | +GVATYCCCTACAA (SEQ ID NO: 16553) |
| 143 | G + VATYCCCTACAA (SEQ ID NO: 16554) |
| 143 | GVATYCC + CTACAA (SEQ ID NO: 16555) |
| 143 | GVA + TYCCCTACAA (SEQ ID NO: 16556) |
| 143 | GVATYCCCTACAA (SEQ ID NO: 16557) |
| 143 | GVATYCCCTACAAT (SEQ ID NO: 16558) |
| 143 | GVATYCCCTA + CAA (SEQ ID NO: 16559) |
| 143 | GVATYCCCTAC + AA (SEQ ID NO: 16560) |
| 143 | GVATY + CC + CT + ACAA (SEQ ID NO: 16561) |
| 143 | GVAT + YCC + CT + ACAA (SEQ ID NO: 16562) |
| 143 | G + VATYCC + CT + ACAA (SEQ ID NO: 16563) |
| 143 | GVA + TYCC + CT + ACAA (SEQ ID NO: 16564) |
| 143 | GVATYCC + CT + ACAAT (SEQ ID NO: 16565) |
| 143 | GVATYCC + CT + A + CAA (SEQ ID NO: 16566) |
| 143 | GVATYCC + CT + ACAA (SEQ ID NO: 16567) |
| 143 | +VATYCCCTACAAT (SEQ ID NO: 16568) |
| 143 | VA + TYCCCTACAAT (SEQ ID NO: 16569) |
| 143 | VATYCCCTACA + AT (SEQ ID NO: 16570) |
| 143 | VATYCC + C + TA + CAAT (SEQ ID NO: 16571) |
| 143 | VATYCCC + TA + CAAT (SEQ ID NO: 16572) |
| 143 | VATYCCC + TA + CA + AT (SEQ ID NO: 16573) |
| 143 | GVATYCCCTACAATCCCCA (SEQ ID NO: 16574) |
| 143 | GGVATYCCCTACAATCCCC (SEQ ID NO: 16575) |
| 143 | VATYCCCTACAATCCCC (SEQ ID NO: 16576) |
| 143 | GVATYCCCTACAATCCC (SEQ ID NO: 16577) |
| 143 | VATYCCCTACAATCC (SEQ ID NO: 16578) |
| 143 | GVATYCCCTACAATC (SEQ ID NO: 16579) |
| 143 | VATYCCCTACAAT (SEQ ID NO: 16580) |
| 143 | GVATYCCCTACAA (SEQ ID NO: 16581) |
| 143 | ATTCCCTAYAATCCC (SEQ ID NO: 16582) |
| 145 | C + CCTACAATCCCAAAGYC (SEQ ID NO: 16583) |
| 145 | CC + CTACAATCCCAAAGYC (SEQ ID NO: 16584) |
| 145 | CCCTACAA + TCCCAAAGYC (SEQ ID NO: 16585) |
| 145 | CCC + TACAATCCCAAAGYC (SEQ ID NO: 16586) |
| 145 | CCCTACAATCCCAAAGY + C (SEQ ID NO: 16587) |
| 145 | CCCTACAATCCCA + AAGYC (SEQ ID NO: 16588) |
| 145 | CCCTACAATCCCC + AAAGYC (SEQ ID NO: 16589) |
| 145 | CCCTACAATCCCAA + AGYC (SEQ ID NO: 16590) |
| 145 | CC + CTACAA + TC + CCCAAAGYC (SEQ ID NO: 16591) |
| 145 | CCC + TACAA + TC + CCCAAAGYC (SEQ ID NO: 16592) |
| 145 | CCCTACA + A + TC + CCCAAAGYC (SEQ ID NO: 16593) |
| 145 | CCCTA + CAA + TC + CCCAAAGYC (SEQ ID NO: 16594) |

TABLE 13-continued

| | |
|---|---|
| 145 | CCCTACAA + TC + CCCAA + AGYC (SEQ ID NO: 16595) |
| 145 | CCCTACAA + TC + C + CCAAAGYC (SEQ ID NO: 16596) |
| 145 | CCCTACAA + TC + CCCA + AAGYC (SEQ ID NO: 16597) |
| 145 | CCCTACAA + TC + CCCAAAGY + C (SEQ ID NO: 16598) |
| 145 | +CCTACAATCCCCAAAGY (SEQ ID NO: 16599) |
| 145 | C + CTACAATCCCCAAAGY (SEQ ID NO: 16600) |
| 145 | CCTACAA + TCCCCAAAGY (SEQ ID NO: 16601) |
| 145 | CC + TACAATCCCCAAAGY (SEQ ID NO: 16602) |
| 145 | CCTACAATCCCCAAAGY (SEQ ID NO: 16603) |
| 145 | CCTACAATCCCCA + AAGY (SEQ ID NO: 16604) |
| 145 | CCTACAATCCCC + AAAGY (SEQ ID NO: 16605) |
| 145 | CCTACAATCCCCAA + AGY (SEQ ID NO: 16606) |
| 145 | C + CTACAA + TC + CCCAAAGY (SEQ ID NO: 16607) |
| 145 | CC + TACAA + TC + CCCAAAGY (SEQ ID NO: 16608) |
| 145 | CCTACA + A + TC + CCCAAAGY (SEQ ID NO: 16609) |
| 145 | CCTA + CAA + TC + CCCAAAGY (SEQ ID NO: 16610) |
| 145 | CCTACAA + TC + CCCAA + AGY (SEQ ID NO: 16611) |
| 145 | CCTACAA + TC + C + CCAAAGY (SEQ ID NO: 16612) |
| 145 | CCTACAA + TC + CCCA + AAGY (SEQ ID NO: 16613) |
| 145 | CCTACAA + TC + CCCAAAGY (SEQ ID NO: 16614) |
| 145 | +CCTACAATCCCCAAA (SEQ ID NO: 16615) |
| 145 | C + CTACAATCCCCAAA (SEQ ID NO: 16616) |
| 145 | CCTACAA + TCCCCAAA (SEQ ID NO: 16617) |
| 145 | CC + TACAATCCCCAAA (SEQ ID NO: 16618) |
| 145 | CCTACAATCCCCAAAG (SEQ ID NO: 16619) |
| 145 | CCTACAATCCCCA + AA (SEQ ID NO: 16620) |
| 145 | CCTACAATCCCC + AAA (SEQ ID NO: 16621) |
| 145 | CCTACAATCCCCAA + A (SEQ ID NO: 16622) |
| 145 | C + CTACAA + TC + CCCAAA (SEQ ID NO: 16623) |
| 145 | CC + TACAA + TC + CCCAAA (SEQ ID NO: 16624) |
| 145 | CCTACA + A + TC + CCCAAA (SEQ ID NO: 16625) |
| 145 | CCTA + CAA + TC + CCCAAA (SEQ ID NO: 16626) |
| 145 | CCTACAA + TC + CCCAA + A (SEQ ID NO: 16627) |
| 145 | CCTACAA + TC + C + CCAAA (SEQ ID NO: 16628) |
| 145 | CCTACAA + TC + CCCA + AA (SEQ ID NO: 16629) |
| 145 | CCTACAA + TC + CCCAAAG (SEQ ID NO: 16630) |
| 145 | +CCTACAATCCCCA (SEQ ID NO: 16631) |
| 145 | C + CTACAATCCCCA (SEQ ID NO: 16632) |
| 145 | CCTACAA + TCCCCA (SEQ ID NO: 16633) |
| 145 | CC + TACAATCCCCA (SEQ ID NO: 16634) |
| 145 | CCTACAATCCCAA (SEQ ID NO: 16635) |
| 145 | CCTACAATCCCCA (SEQ ID NO: 16636) |
| 145 | CCTACAATCCCC + A (SEQ ID NO: 16637) |
| 145 | C + CTACAA + TC + CCCA (SEQ ID NO: 16638) |
| 145 | CC + TACAA + TC + CCCA (SEQ ID NO: 16639) |
| 145 | CCTACA + A + TC + CCCA (SEQ ID NO: 16640) |
| 145 | CCTA + CAA + TC + CCCA (SEQ ID NO: 16641) |
| 145 | CCTACAA + TC + CCCAA (SEQ ID NO: 16642) |
| 145 | CCTACAA + TC + C + CCA (SEQ ID NO: 16643) |
| 145 | CCTACAA + TC + CCCA (SEQ ID NO: 16644) |
| 145 | CCCTACAATCCCCAAAGYC (SEQ ID NO: 16645) |
| 145 | CCTACAATCCCCAAAGY (SEQ ID NO: 16646) |
| 145 | CCTACAATCCCCAAA (SEQ ID NO: 16647) |
| 145 | CCTACAATCCCCA (SEQ ID NO: 16648) |
| 145 | TACAATCCYCAAAGT (SEQ ID NO: 16649) |
| 146 | ACAAT + CCCCAAAGYCARGG (SEQ ID NO: 16650) |
| 146 | ACAATCC + CCAAAGYCARGG (SEQ ID NO: 16651) |
| 146 | ACAA + TCCCCAAAGYCARGG (SEQ ID NO: 16652) |
| 146 | ACA + ATCCCCAAAGYCARGG (SEQ ID NO: 16653) |
| 146 | ACAATCCCCAAAGYCA + RGG (SEQ ID NO: 16654) |
| 146 | ACAATCCCCA + AAGYCARGG (SEQ ID NO: 16655) |
| 146 | ACAATCCCCAAAGYC + ARGG (SEQ ID NO: 16656) |
| 146 | ACAATCCCCAAAGY + CARGG (SEQ ID NO: 16657) |
| 146 | ACAA + TCCC + CA + AAGYCARGG (SEQ ID NO: 16658) |
| 146 | A + CAATCCC + CA + AAGYCARGG (SEQ ID NO: 16659) |
| 146 | AC + AATCCC + CA + AAGYCARGG (SEQ ID NO: 16660) |
| 146 | ACAAT + CCC + CA + AAGYCARGG (SEQ ID NO: 16661) |
| 146 | ACAATCCC + CA + AAGYCAR + GG (SEQ ID NO: 16662) |
| 146 | ACAATCCC + CA + A + AGYCARGG (SEQ ID NO: 16663) |
| 146 | ACAATCCC + CA + AAGY + CARGG (SEQ ID NO: 16664) |

TABLE 13-continued

| | | |
|---|---|---|
| 146 | ACAATCCC + CA + AAGYCA + RGG (SEQ ID NO: 16665) | |
| 146 | CAAT + CCCCAAAGYCARG (SEQ ID NO: 16666) | |
| 146 | CAATCC + CCAAAGYCARG (SEQ ID NO: 16667) | |
| 146 | CAA + TCCCCAAAGYCARG (SEQ ID NO: 16668) | |
| 146 | CA + ATCCCCAAAGYCARG (SEQ ID NO: 16669) | |
| 146 | CAATCCCCAAAGYCA + RG (SEQ ID NO: 16670) | |
| 146 | CAATCCCCA + AAGYCARG (SEQ ID NO: 16671) | |
| 146 | CAATCCCCAAAGYC + ARG (SEQ ID NO: 16672) | |
| 146 | CAATCCCCAAAGY + CARG (SEQ ID NO: 16673) | |
| 146 | CAA + TCCC + CA + AAGYCARG (SEQ ID NO: 16674) | |
| 146 | +CAATCCC + CA + AAGYCARG (SEQ ID NO: 16675) | |
| 146 | C + AATCCC + CA + AAGYCARG (SEQ ID NO: 16676) | |
| 146 | CAAT + CCC + CA + AAGYCARG (SEQ ID NO: 16677) | |
| 146 | CAATCCC + CA + AAGYCAR + G (SEQ ID NO: 16678) | |
| 146 | CAATCCC + CA + A + AGYCARG (SEQ ID NO: 16679) | |
| 146 | CAATCCC + CA + AAGY + CARG (SEQ ID NO: 16680) | |
| 146 | CAATCCC + CA + AAGYCA + RG (SEQ ID NO: 16681) | |
| 146 | CAAT + CCCCAAAGYCA (SEQ ID NO: 16682) | |
| 146 | CAATCC + CCAAAGYCA (SEQ ID NO: 16683) | |
| 146 | CAA + TCCCCAAAGYCA (SEQ ID NO: 16684) | |
| 146 | CA + ATCCCCAAAGYCA (SEQ ID NO: 16685) | |
| 146 | CAATCCCCAAAGYCA (SEQ ID NO: 16686) | |
| 146 | CAATCCCCA + AAGYCA (SEQ ID NO: 16687) | |
| 146 | CAATCCCCAAAGYC + A (SEQ ID NO: 16688) | |
| 146 | CAATCCCCAAAGY + CA (SEQ ID NO: 16689) | |
| 146 | CAA + TCCC + CA + AAGYCA (SEQ ID NO: 16690) | |
| 146 | +CAATCCC + CA + AAGYCA (SEQ ID NO: 16691) | |
| 146 | C + AATCCC + CA + AAGYCA (SEQ ID NO: 16692) | |
| 146 | CAAT + CCC + CA + AAGYCA (SEQ ID NO: 16693) | |
| 146 | CAATCCC + CA + AAGYCAR (SEQ ID NO: 16694) | |
| 146 | CAATCCC + CA + A + AGYCA (SEQ ID NO: 16695) | |
| 146 | CAATCCC + CA + AAGY + CA (SEQ ID NO: 16696) | |
| 146 | CAATCCC + CA + AAGYCA (SEQ ID NO: 16697) | |
| 146 | CAAT + CCCCAAAGY (SEQ ID NO: 16698) | |
| 146 | CAATCC + CCAAAGY (SEQ ID NO: 16699) | |
| 146 | CAA + TCCCCAAAGY (SEQ ID NO: 16700) | |
| 146 | CA + ATCCCCAAAGY (SEQ ID NO: 16701) | |
| 146 | CAATCCCCAAAGYC (SEQ ID NO: 16702) | |
| 146 | CAATCCCCA + AAGY (SEQ ID NO: 16703) | |
| 146 | CAATCCCCAAAGY (SEQ ID NO: 16704) | |
| 146 | CAA + TCCC + CA + AAGY (SEQ ID NO: 16705) | |
| 146 | +CAATCCC + CA + AAGY (SEQ ID NO: 16706) | |
| 146 | C + AATCCC + CA + AAGY (SEQ ID NO: 16707) | |
| 146 | CAAT + CCC + CA + AAGY (SEQ ID NO: 16708) | |
| 146 | CAATCCC + CA + AAGYC (SEQ ID NO: 16709) | |
| 146 | CAATCCC + CA + A + AGY (SEQ ID NO: 16710) | |
| 146 | CAATCCC + CA + AAGY (SEQ ID NO: 16711) | |
| 146 | ACAATCCCCAAAGYCARGG (SEQ ID NO: 16712) | |
| 146 | CAATCCCCAAAGYCARG (SEQ ID NO: 16713) | |
| 146 | CAATCCCCAAAGYCA (SEQ ID NO: 16714) | |
| 146 | CAATCCCCAAAGYCAR (SEQ ID NO: 16715) | |
| 146 | CAATCCCCAAAGY (SEQ ID NO: 16716) | |
| 146 | AATCCCCARAGTCAA (SEQ ID NO: 16717) | |
| 147 | AATCCCC + AAAGYCARGGAG (SEQ ID NO: 16718) | |
| 147 | AAT + CCCCAAAGYCARGGAG (SEQ ID NO: 16719) | |
| 147 | AATCCC + CAAAGYCARGGAG (SEQ ID NO: 16720) | |
| 147 | AATCC + CCAAAGYCARGGAG (SEQ ID NO: 16721) | |
| 147 | AATCCCCAAAGYCARG + GAG (SEQ ID NO: 16722) | |
| 147 | AATCCCCAAAGYCARGG + AG (SEQ ID NO: 16723) | |
| 147 | AATCCCCAAAGYCARGGA + G (SEQ ID NO: 16724) | |
| 147 | AATCCCCAAAGY + CARGGAG (SEQ ID NO: 16725) | |
| 147 | A + ATCCCCA + AA + GYCARGGAG (SEQ ID NO: 16726) | |
| 147 | AATCCC + CA + AA + GYCARGGAG (SEQ ID NO: 16727) | |
| 147 | AATC + CCCA + AA + GYCARGGAG (SEQ ID NO: 16728) | |
| 147 | AAT + CCCCA + AA + GYCARGGAG (SEQ ID NO: 16729) | |
| 147 | AATCCCCA + AA + GYCA + RGGAG (SEQ ID NO: 16730) | |
| 147 | AATCCCCA + AA + G + YCARGGAG (SEQ ID NO: 16731) | |
| 147 | AATCCCCA + AA + GY + CARGGAG (SEQ ID NO: 16732) | |
| 147 | AATCCCCA + AA + GYCARGG + AG (SEQ ID NO: 16733) | |
| 147 | ATCCCC + AAAGYCARGGA (SEQ ID NO: 16734) | |
| 147 | AT + CCCCAAAGYCARGGA (SEQ ID NO: 16735) | |
| 147 | ATCCC + CAAAGYCARGGA (SEQ ID NO: 16736) | |

TABLE 13-continued

| | | |
|---|---|---|
| 147 | ATCC + CCAAAGYCARGGA | (SEQ ID NO: 16737) |
| 147 | ATCCCCAAAGYCARG + GA | (SEQ ID NO: 16738) |
| 147 | ATCCCCAAAGYCARGG + A | (SEQ ID NO: 16739) |
| 147 | ATCCCCAAAGYCARGGA | (SEQ ID NO: 16740) |
| 147 | ATCCCCAAAGY + CARGGA | (SEQ ID NO: 16741) |
| 147 | +ATCCCCA + AA + GYCARGGA | (SEQ ID NO: 16742) |
| 147 | ATCCC + CA + AA + GYCARGGA | (SEQ ID NO: 16743) |
| 147 | ATC + CCCA + AA + GYCARGGA | (SEQ ID NO: 16744) |
| 147 | AT + CCCCA + AA + GYCARGGA | (SEQ ID NO: 16745) |
| 147 | ATCCCCA + AA + GYCA + RGGA | (SEQ ID NO: 16746) |
| 147 | ATCCCCA + AA + G + YCARGGA | (SEQ ID NO: 16747) |
| 147 | ATCCCCA + AA + GY + CARGGA | (SEQ ID NO: 16748) |
| 147 | ATCCCCA + AA + GYCARGG + A | (SEQ ID NO: 16749) |
| 147 | ATCCCC + AAAGYCARG | (SEQ ID NO: 16750) |
| 147 | AT + CCCCAAAGYCARG | (SEQ ID NO: 16751) |
| 147 | ATCCC + CAAAGYCARG | (SEQ ID NO: 16752) |
| 147 | ATCC + CCAAAGYCARG | (SEQ ID NO: 16753) |
| 147 | ATCCCCAAAGYCARG | (SEQ ID NO: 16754) |
| 147 | ATCCCCAAAGYCARGG | (SEQ ID NO: 16755) |
| 147 | ATCCCCAAAGY + CARG | (SEQ ID NO: 16756) |
| 147 | +ATCCCCA + AA + GYCARG | (SEQ ID NO: 16757) |
| 147 | ATCCC + CA + AA + GYCARG | (SEQ ID NO: 16758) |
| 147 | ATC + CCCA + AA + GYCARG | (SEQ ID NO: 16759) |
| 147 | AT + CCCCA + AA + GYCARG | (SEQ ID NO: 16760) |
| 147 | ATCCCCA + AA + GYCA + RG | (SEQ ID NO: 16761) |
| 147 | ATCCCCA + AA + G + YCARG | (SEQ ID NO: 16762) |
| 147 | ATCCCCA + AA + GY + CARG | (SEQ ID NO: 16763) |
| 147 | ATCCCCA + AA + GYCARGG | (SEQ ID NO: 16764) |
| 147 | ATCCCC + AAAGYCA | (SEQ ID NO: 16765) |
| 147 | AT + CCCCAAAGYCA | (SEQ ID NO: 16766) |
| 147 | ATCCC + CAAAGYCA | (SEQ ID NO: 16767) |
| 147 | ATCC + CCAAAGYCA | (SEQ ID NO: 16768) |
| 147 | ATCCCCAAAGYCAR | (SEQ ID NO: 16769) |
| 147 | ATCCCCAAAGY + CA | (SEQ ID NO: 16770) |
| 147 | +ATCCCCA + AA + GYCA | (SEQ ID NO: 16771) |
| 147 | ATCCC + CA + AA + GYCA | (SEQ ID NO: 16772) |
| 147 | ATC + CCCA + AA + GYCA | (SEQ ID NO: 16773) |
| 147 | AT + CCCCA + AA + GYCA | (SEQ ID NO: 16774) |
| 147 | ATCCCCA + AA + GYCA | (SEQ ID NO: 16775) |
| 147 | ATCCCCA + AA + G + YCA | (SEQ ID NO: 16776) |
| 147 | ATCCCCA + AA + GY + CA | (SEQ ID NO: 16777) |
| 147 | ATCCCCA + AA + GYCAR | (SEQ ID NO: 16778) |
| 147 | AATCCCCAAAGYCARGGAG | (SEQ ID NO: 16779) |
| 147 | ATCCCCAAAGYCARGGA | (SEQ ID NO: 16780) |
| 147 | ATCCCCAAAGYCARG | (SEQ ID NO: 16781) |
| 147 | ATCCCCAAAGYCA | (SEQ ID NO: 16782) |
| 147 | TCCCCAAAGYCAAGG | (SEQ ID NO: 16783) |
| 148 | CCAAA + GYCARGGAGTAGTR | (SEQ ID NO: 16784) |
| 148 | CCA + AAGYCARGGAGTAGTR | (SEQ ID NO: 16785) |
| 148 | C + CAAAGYCARGGAGTAGTR | (SEQ ID NO: 16786) |
| 148 | CC + AAAGYCARGGAGTAGTR | (SEQ ID NO: 16787) |
| 148 | CCAAAGYCARGGAGT + AGTR | (SEQ ID NO: 16788) |
| 148 | CCAAAGYCARGGAGTA + GTR | (SEQ ID NO: 16789) |
| 148 | CCAAAGYCARGGA + GTAGTR | (SEQ ID NO: 16790) |
| 148 | CCAAAGYCARG + GAGTAGTR | (SEQ ID NO: 16791) |
| 148 | CCAAAGY + C + AR + GGAGTAGTR | (SEQ ID NO: 16792) |
| 148 | CCA + AAGYC + AR + GGAGTAGTR | (SEQ ID NO: 16793) |
| 148 | CC + AAAGYC + AR + GGAGTAGTR | (SEQ ID NO: 16794) |
| 148 | CCAA + AGYC + AR + GGAGTAGTR | (SEQ ID NO: 16795) |
| 148 | CCAAAGYC + AR + GG + AGTAGTR | (SEQ ID NO: 16796) |
| 148 | CCAAAGYC + AR + GGAG + TAGTR | (SEQ ID NO: 16797) |
| 148 | CCAAAGYC + AR + GGAGTAGT + R | (SEQ ID NO: 16798) |
| 148 | CCAAAGYC + AR + GGAGT + AGTR | (SEQ ID NO: 16799) |
| 148 | CCC + CAAAGYCARGGAGTAG | (SEQ ID NO: 16800) |
| 148 | CCCCA + AAGYCARGGAGTAG | (SEQ ID NO: 16801) |
| 148 | CCCCAAAG + YCARGGAGTAG | (SEQ ID NO: 16802) |
| 148 | CCCCAAA + GYCARGGAGTAG | (SEQ ID NO: 16803) |
| 148 | CCCCAAAGYCARGGAG + TAG | (SEQ ID NO: 16804) |
| 148 | CCCCAAAGYCARG + GAGTAG | (SEQ ID NO: 16805) |
| 148 | CCCCAAAGYC + ARGGAGTAG | (SEQ ID NO: 16806) |
| 148 | CCCCAAAGYCAR + GGAGTAG | (SEQ ID NO: 16807) |
| 148 | CCC + CAAAG + YC + ARGGAGTAG | (SEQ ID NO: 16808) |

| | | |
|---|---|---|
| 148 | CCCCA + AAG + YC + ARGGAGTAG (SEQ ID NO: 16809) | |
| 148 | CC + CCAAAG + YC + ARGGAGTAG (SEQ ID NO: 16810) | |
| 148 | CCCC + AAAG + YC + ARGGAGTAG (SEQ ID NO: 16811) | |
| 148 | CCCCAAAG + YC + AR + GGAGTAG (SEQ ID NO: 16812) | |
| 148 | CCCCAAAG + YC + ARGGA + GTAG (SEQ ID NO: 16813) | |
| 148 | CCCCAAAG + YC + ARGGAG + TAG (SEQ ID NO: 16814) | |
| 148 | CCCCAAAG + YC + ARGGAGTA + G (SEQ ID NO: 16815) | |
| 148 | CCCAA + AGYCARGGAGTAGT (SEQ ID NO: 16816) | |
| 148 | CCC + AAAGYCARGGAGTAGT (SEQ ID NO: 16817) | |
| 148 | CCCAAAG + YCARGGAGTAGT (SEQ ID NO: 16818) | |
| 148 | CCCAAAGY + CARGGAGTAGT (SEQ ID NO: 16819) | |
| 148 | CCCAAAGYCARGGAG + TAGT (SEQ ID NO: 16820) | |
| 148 | CCCAAAGYCARGGAGTA + GT (SEQ ID NO: 16821) | |
| 148 | CCCAAAGYCARGG + AGTAGT (SEQ ID NO: 16822) | |
| 148 | CCCAAAGYCAR + GGAGTAGT (SEQ ID NO: 16823) | |
| 148 | CCCAAAG + Y + CA + RGGAGTAGT (SEQ ID NO: 16824) | |
| 148 | CC + CAAAGY + CA + RGGAGTAGT (SEQ ID NO: 16825) | |
| 148 | CCCAAA + GY + CA + RGGAGTAGT (SEQ ID NO: 16826) | |
| 148 | C + CCAAAGY + CA + RGGAGTAGT (SEQ ID NO: 16827) | |
| 148 | CCCAAAGY + CA + RGG + AGTAGT (SEQ ID NO: 16828) | |
| 148 | CCCAAAGY + CA + R + GGAGTAGT (SEQ ID NO: 16829) | |
| 148 | CCCAAAGY + CA + RGGAG + TAGT (SEQ ID NO: 16830) | |
| 148 | CCCAAAGY + CA + RGGAGT + AGT (SEQ ID NO: 16831) | |
| 148 | CAAA + GYCARGGAGTAGT (SEQ ID NO: 16832) | |
| 148 | CA + AAGYCARGGAGTAGT (SEQ ID NO: 16833) | |
| 148 | +CAAAGYCARGGAGTAGT (SEQ ID NO: 16834) | |
| 148 | C + AAAGYCARGGAGTAGT (SEQ ID NO: 16835) | |
| 148 | CAAAGYCARGGAGT + AGT (SEQ ID NO: 16836) | |
| 148 | CAAAGYCARGGAGTA + GT (SEQ ID NO: 16837) | |
| 148 | CAAAGYCARGGA + GTAGT (SEQ ID NO: 16838) | |
| 148 | CAAAGYCARG + GAGTAGT (SEQ ID NO: 16839) | |
| 148 | CAAAGY + C + AR + GGAGTAGT (SEQ ID NO: 16840) | |
| 148 | CA + AAGYC + AR + GGAGTAGT (SEQ ID NO: 16841) | |
| 148 | C + AAAGYC + AR + GGAGTAGT (SEQ ID NO: 16842) | |
| 148 | CAA + AGYC + AR + GGAGTAGT (SEQ ID NO: 16843) | |
| 148 | CAAAGYC + AR + GG + AGTAGT (SEQ ID NO: 16844) | |
| 148 | CAAAGYC + AR + GGAG + TAGT (SEQ ID NO: 16845) | |
| 148 | CAAAGYC + AR + GGAGTAGT (SEQ ID NO: 16846) | |
| 148 | CAAAGYC + AR + GGAGT + AGT (SEQ ID NO: 16847) | |
| 148 | CC + CAAAGYCARGGAGTA (SEQ ID NO: 16848) | |
| 148 | CCCA + AAGYCARGGAGTA (SEQ ID NO: 16849) | |
| 148 | CCCAAAG + YCARGGAGTA (SEQ ID NO: 16850) | |
| 148 | CCCAAA + GYCARGGAGTA (SEQ ID NO: 16851) | |
| 148 | CCCAAAGYCARGGAG + TA (SEQ ID NO: 16852) | |
| 148 | CCCAAAGYCARG + GAGTA (SEQ ID NO: 16853) | |
| 148 | CCCAAAGYC + ARGGAGTA (SEQ ID NO: 16854) | |
| 148 | CCCAAAGYCAR + GGAGTA (SEQ ID NO: 16855) | |
| 148 | CC + CAAAG + YC + ARGGAGTA (SEQ ID NO: 16856) | |
| 148 | CCCA + AAG + YC + ARGGAGTA (SEQ ID NO: 16857) | |
| 148 | C + CCAAAG + YC + ARGGAGTA (SEQ ID NO: 16858) | |
| 148 | CCC + AAAG + YC + ARGGAGTA (SEQ ID NO: 16859) | |
| 148 | CCCAAAG + YC + AR + GGAGTA (SEQ ID NO: 16860) | |
| 148 | CCCAAAG + YC + ARGGA + GTA (SEQ ID NO: 16861) | |
| 148 | CCCAAAG + YC + ARGGAG + TA (SEQ ID NO: 16862) | |
| 148 | CCCAAAG + YC + ARGGAGTA (SEQ ID NO: 16863) | |
| 148 | CCAA + AGYCARGGAGTAG (SEQ ID NO: 16864) | |
| 148 | CC + AAAGYCARGGAGTAG (SEQ ID NO: 16865) | |
| 148 | CCAAAG + YCARGGAGTAG (SEQ ID NO: 16866) | |
| 148 | CCAAAGY + CARGGAGTAG (SEQ ID NO: 16867) | |
| 148 | CCAAAGYCARGGAG + TAG (SEQ ID NO: 16868) | |
| 148 | CCAAAGYCARGGAGTA + G (SEQ ID NO: 16869) | |
| 148 | CCAAAGYCARGG + AGTAG (SEQ ID NO: 16870) | |
| 148 | CCAAAGYCAR + GGAGTAG (SEQ ID NO: 16871) | |
| 148 | CCAAAG + Y + CA + RGGAGTAG (SEQ ID NO: 16872) | |

TABLE 13-continued

| | |
|---|---|
| 148 | C + CAAAGY + CA + RGGAGTAG (SEQ ID NO: 16873) |
| 148 | CCAAA + GY + CA + RGGAGTAG (SEQ ID NO: 16874) |
| 148 | +CCAAAGY + CA + RGGAGTAG (SEQ ID NO: 16875) |
| 148 | CCAAAGY + CA + RGG + AGTAG (SEQ ID NO: 16876) |
| 148 | CCAAAGY + CA + R + GGAGTAG (SEQ ID NO: 16877) |
| 148 | CCAAAGY + CA + RGGAG + TAG (SEQ ID NO: 16878) |
| 148 | CCAAAGY + CA + RGGAGT + AG (SEQ ID NO: 16879) |
| 148 | CAAA + GYCARGGAGTA (SEQ ID NO: 16880) |
| 148 | CA + AAGYCARGGAGTA (SEQ ID NO: 16881) |
| 148 | +CAAAGYCARGGAGTA (SEQ ID NO: 16882) |
| 148 | C + AAAGYCARGGAGTA (SEQ ID NO: 16883) |
| 148 | CAAAGYCARGGAGT + A (SEQ ID NO: 16884) |
| 148 | CAAAGYCARGGAGTA (SEQ ID NO: 16885) |
| 148 | CAAAGYCARGGA + GTA (SEQ ID NO: 16886) |
| 148 | CAAAGYCARG + GAGTA (SEQ ID NO: 16887) |
| 148 | CAAAGY + C + AR + GGAGTA (SEQ ID NO: 16888) |
| 148 | CA + AAGYC + AR + GGAGTA (SEQ ID NO: 16889) |
| 148 | C + AAAGYC + AR + GGAGTA (SEQ ID NO: 16890) |
| 148 | CAA + AGYC + AR + GGAGTA (SEQ ID NO: 16891) |
| 148 | CAAAGYC + AR + GG + AGTA (SEQ ID NO: 16892) |
| 148 | CAAAGYC + AR + GGAG + TA (SEQ ID NO: 16893) |
| 148 | CAAAGYC + AR + GGAGTAG (SEQ ID NO: 16894) |
| 148 | CAAAGYC + AR + GGAGT + A (SEQ ID NO: 16895) |
| 148 | CC + CAAAGYCARGGAG (SEQ ID NO: 16896) |
| 148 | CCCA + AAGYCARGGAG (SEQ ID NO: 16897) |
| 148 | CCCAAAG + YCARGGAG (SEQ ID NO: 16898) |
| 148 | CCCAAA + GYCARGGAG (SEQ ID NO: 16899) |
| 148 | CCCAAAGYCARGGAG (SEQ ID NO: 16900) |
| 148 | CCCAAAGYCARG + GAG (SEQ ID NO: 16901) |
| 148 | CCCAAAGYC + ARGGAG (SEQ ID NO: 16902) |
| 148 | CCCAAAGYCAR + GGAG (SEQ ID NO: 16903) |
| 148 | CC + CAAAG + YC + ARGGAG (SEQ ID NO: 16904) |
| 148 | CCCA + AAG + YC + ARGGAG (SEQ ID NO: 16905) |
| 148 | C + CCAAAG + YC + ARGGAG (SEQ ID NO: 16906) |
| 148 | CCC + AAAG + YC + ARGGAG (SEQ ID NO: 16907) |
| 148 | CCCAAAG + YC + AR + GGAG (SEQ ID NO: 16908) |
| 148 | CCCAAAG + YC + ARGGA + G (SEQ ID NO: 16909) |
| 148 | CCCAAAG + YC + ARGGAG (SEQ ID NO: 16910) |
| 148 | CCCAAAG + YC + ARGGAGT (SEQ ID NO: 16911) |
| 148 | CCAA + AGYCARGGAGT (SEQ ID NO: 16912) |
| 148 | CC + AAAGYCARGGAGT (SEQ ID NO: 16913) |
| 148 | CCAAAG + YCARGGAGT (SEQ ID NO: 16914) |
| 148 | CCAAAGY + CARGGAGT (SEQ ID NO: 16915) |
| 148 | CCAAAGYCARGGAG + T (SEQ ID NO: 16916) |
| 148 | CCAAAGYCARGGAGTA (SEQ ID NO: 16917) |
| 148 | CCAAAGYCARGG + AGT (SEQ ID NO: 16918) |
| 148 | CCAAAGYCAR + GGAGT (SEQ ID NO: 16919) |
| 148 | CCAAAG + Y + CA + RGGAGT (SEQ ID NO: 16920) |
| 148 | C + CAAAGY + CA + RGGAGT (SEQ ID NO: 16921) |
| 148 | CCAAA + GY + CA + RGGAGT (SEQ ID NO: 16922) |
| 148 | +CCAAAGY + CA + RGGAGT (SEQ ID NO: 16923) |
| 148 | CCAAAGY + CA + RGG + AGT (SEQ ID NO: 16924) |
| 148 | CCAAAGY + CA + R + GGAGT (SEQ ID NO: 16925) |
| 148 | CCAAAGY + CA + RGGAG + T (SEQ ID NO: 16926) |
| 148 | CCAAAGY + CA + RGGAGT (SEQ ID NO: 16927) |
| 148 | CAAA + GYCARGGAG (SEQ ID NO: 16928) |
| 148 | CA + AAGYCARGGAG (SEQ ID NO: 16929) |
| 148 | +CAAAGYCARGGAG (SEQ ID NO: 16930) |
| 148 | C + AAAGYCARGGAG (SEQ ID NO: 16931) |
| 148 | CAAAGYCARGGAGT (SEQ ID NO: 16932) |
| 148 | CAAAGYCARGGA + G (SEQ ID NO: 16933) |
| 148 | CAAAGYCARG + GAG (SEQ ID NO: 16934) |
| 148 | CAAAGY + C + AR + GGAG (SEQ ID NO: 16935) |
| 148 | CA + AAGYC + AR + GGAG (SEQ ID NO: 16936) |
| 148 | C + AAAGYC + AR + GGAG (SEQ ID NO: 16937) |
| 148 | CAA + AGYC + AR + GGAG (SEQ ID NO: 16938) |
| 148 | CAAAGYC + AR + GG + AG (SEQ ID NO: 16939) |
| 148 | CAAAGYC + AR + GGAG (SEQ ID NO: 16940) |
| 148 | CAAAGYC + AR + GGAGT (SEQ ID NO: 16941) |
| 148 | CC + CAAAGYCARGG (SEQ ID NO: 16942) |
| 148 | CCCA + AAGYCARGG (SEQ ID NO: 16943) |
| 148 | CCCAAAG + YCARGG (SEQ ID NO: 16944) |
| 148 | CCCAAA + GYCARGG (SEQ ID NO: 16945) |
| 148 | CCCAAAGYCARGGA (SEQ ID NO: 16946) |
| 148 | CCCAAAGYCARG + G (SEQ ID NO: 16947) |
| 148 | CCCAAAGYC + ARGG (SEQ ID NO: 16948) |
| 148 | CCCAAAGYCAR + GG (SEQ ID NO: 16949) |

TABLE 13-continued

| | | |
|---|---|---|
| 148 | CC + CAAAG + YC + ARGG | (SEQ ID NO: 16950) |
| 148 | CCCA + AAG + YC + ARGG | (SEQ ID NO: 16951) |
| 148 | C + CCAAAG + YC + ARGG | (SEQ ID NO: 16952) |
| 148 | CCC + AAAG + YC + ARGG | (SEQ ID NO: 16953) |
| 148 | CCCAAAG + YC + AR + GG | (SEQ ID NO: 16954) |
| 148 | CCCAAAG + YC + ARGGA | (SEQ ID NO: 16955) |
| 148 | CCAA + AGYCARGGA | (SEQ ID NO: 16956) |
| 148 | CC + AAAGYCARGGA | (SEQ ID NO: 16957) |
| 148 | CCAAAG + YCARGGA | (SEQ ID NO: 16958) |
| 148 | CCAAAGY + CARGGA | (SEQ ID NO: 16959) |
| 148 | CCAAAGYCARGGAG | (SEQ ID NO: 16960) |
| 148 | CCAAAGYCARGG + A | (SEQ ID NO: 16961) |
| 148 | CCAAAGYCAR + GGA | (SEQ ID NO: 16962) |
| 148 | CCAAAG + Y + CA + RGGA | (SEQ ID NO: 16963) |
| 148 | C + CAAAGY + CA + RGGA | (SEQ ID NO: 16964) |
| 148 | CCAAA + GY + CA + RGGA | (SEQ ID NO: 16965) |
| 148 | +CCAAAGY + CA + RGGA | (SEQ ID NO: 16966) |
| 148 | CCAAAGY + CA + RGG + A | (SEQ ID NO: 16967) |
| 148 | CCAAAGY + CA + R + GGA | (SEQ ID NO: 16968) |
| 148 | CCAAAGY + CA + RGGAG | (SEQ ID NO: 16969) |
| 148 | CCAAAGYCARGGAGTAGTR | (SEQ ID NO: 16970) |
| 148 | CCCCAAAGYCARGGAGTAG | (SEQ ID NO: 16971) |
| 148 | CCCAAAGYCARGGAGTAGT | (SEQ ID NO: 16972) |
| 148 | CAAAGYCARGGAGTAGT | (SEQ ID NO: 16973) |
| 148 | CCCAAAGYCARGGAGTA | (SEQ ID NO: 16974) |
| 148 | CCAAAGYCARGGAGTAG | (SEQ ID NO: 16975) |
| 148 | CAAAGYCARGGAGTA | (SEQ ID NO: 16976) |
| 148 | CAAAGYCARGGAGTAG | (SEQ ID NO: 16977) |
| 148 | CCCAAAGYCARGGAG | (SEQ ID NO: 16978) |
| 148 | CCCAAAGYCARGGAGT | (SEQ ID NO: 16979) |
| 148 | CCAAAGYCARGGAGT | (SEQ ID NO: 16980) |
| 148 | CAAAGYCARGGAG | (SEQ ID NO: 16981) |
| 148 | CCCAAAGYCARGG | (SEQ ID NO: 16982) |
| 148 | CCAAAGYCARGGA | (SEQ ID NO: 16983) |
| 148 | CAAAGTCARGGAGTA | (SEQ ID NO: 16984) |
| 153 | ATTCATRCTTTCTAC | (SEQ ID NO: 16985) |
| 155 | GARTCYAT + GAATAARGAAT | (SEQ ID NO: 16986) |
| 155 | G + ARTCYATGAATAARGAAT | (SEQ ID NO: 16987) |
| 155 | GARTCY + ATGAATAARGAAT | (SEQ ID NO: 16988) |
| 155 | GART + CYATGAATAARGAAT | (SEQ ID NO: 16989) |
| 155 | GARTCYATGAATAAR + GAAT | (SEQ ID NO: 16990) |
| 155 | GARTCYATGAATAARGA + AT | (SEQ ID NO: 16991) |
| 155 | GARTCYATGAATAA + RGAAT | (SEQ ID NO: 16992) |
| 155 | GARTCYATGAA + TAARGAAT | (SEQ ID NO: 16993) |
| 155 | GARTCYA + T + GA + ATAARGAAT | (SEQ ID NO: 16994) |
| 155 | G + ARTCYAT + GA + ATAARGAAT | (SEQ ID NO: 16995) |
| 155 | GAR + TCYAT + GA + ATAARGAAT | (SEQ ID NO: 16996) |
| 155 | GART + CYAT + GA + ATAARGAAT | (SEQ ID NO: 16997) |
| 155 | GARTCYAT + GA + AT + AARGAAT | (SEQ ID NO: 16998) |
| 155 | GARTCYAT + GA + ATA + ARGAAT | (SEQ ID NO: 16999) |
| 155 | GARTCYAT + GA + ATAARGA + AT | (SEQ ID NO: 17000) |
| 155 | GARTCYAT + GA + ATAARG + AAT | (SEQ ID NO: 17001) |
| 155 | ART + CYATGAATAARGAATT | (SEQ ID NO: 17002) |
| 155 | ARTCY + ATGAATAARGAATT | (SEQ ID NO: 17003) |
| 155 | AR + TCYATGAATAARGAATT | (SEQ ID NO: 17004) |
| 155 | A + RTCYATGAATAARGAATT | (SEQ ID NO: 17005) |
| 155 | ARTCYATGAATAARGAAT + T | (SEQ ID NO: 17006) |
| 155 | ARTCYATGAA + TAARGAATT | (SEQ ID NO: 17007) |
| 155 | ARTCYATGAATAAR + GAATT | (SEQ ID NO: 17008) |
| 155 | ARTCYATGAATAARG + AATT | (SEQ ID NO: 17009) |
| 155 | AR + TCYATG + AA + TAARGAATT | (SEQ ID NO: 17010) |
| 155 | ARTCYA + TG + AA + TAARGAATT | (SEQ ID NO: 17011) |
| 155 | ARTCY + ATG + AA + TAARGAATT | (SEQ ID NO: 17012) |
| 155 | ARTCYAT + G + AA + TAARGAATT | (SEQ ID NO: 17013) |
| 155 | ARTCYATG + AA + TAAR + GAATT | (SEQ ID NO: 17014) |
| 155 | ARTCYATG + AA + TAARGA + ATT | (SEQ ID NO: 17015) |
| 155 | ARTCYATG + AA + TAARGAA + TT | (SEQ ID NO: 17016) |
| 155 | ARTCYATG + AA + TA + ARGAATT | (SEQ ID NO: 17017) |
| 155 | ARTCYAT + GAATAARGAA | (SEQ ID NO: 17018) |
| 155 | +ARTCYATGAATAARGAA | (SEQ ID NO: 17019) |
| 155 | ARTCY + ATGAATAARGAA | (SEQ ID NO: 17020) |
| 155 | ART + CYATGAATAARGAA | (SEQ ID NO: 17021) |

TABLE 13-continued

| | | |
|---|---|---|
| 155 | ARTCYATGAATAAR + GAA | (SEQ ID NO: 17022) |
| 155 | ARTCYATGAATAARGA + A | (SEQ ID NO: 17023) |
| 155 | ARTCYATGAATAA + RGAA | (SEQ ID NO: 17024) |
| 155 | ARTCYATGAA + TAARGAA | (SEQ ID NO: 17025) |
| 155 | ARTCYA + T + GA + ATAARGAA | (SEQ ID NO: 17026) |
| 155 | +ARTCYAT + GA + ATAARGAA | (SEQ ID NO: 17027) |
| 155 | AR + TCYAT + GA + ATAARGAA | (SEQ ID NO: 17028) |
| 155 | ART + CYAT + GA + ATAARGAA | (SEQ ID NO: 17029) |
| 155 | ARTCYAT + GA + AT + AARGAA | (SEQ ID NO: 17030) |
| 155 | ARTCYAT + GA + ATA + ARGAA | (SEQ ID NO: 17031) |
| 155 | ARTCYAT + GA + ATAARGA + A | (SEQ ID NO: 17032) |
| 155 | ARTCYAT + GA + ATAARG + AA | (SEQ ID NO: 17033) |
| 155 | RT + CYATGAATAARGAAT | (SEQ ID NO: 17034) |
| 155 | RTCY + ATGAATAARGAAT | (SEQ ID NO: 17035) |
| 155 | R + TCYATGAATAARGAAT | (SEQ ID NO: 17036) |
| 155 | +RTCYATGAATAARGAAT | (SEQ ID NO: 17037) |
| 155 | RTCYATGAATAARGAAT | (SEQ ID NO: 17038) |
| 155 | RTCYATGAA + TAARGAAT | (SEQ ID NO: 17039) |
| 155 | RTCYATGAATAAR + GAAT | (SEQ ID NO: 17040) |
| 155 | RTCYATGAATAARG + AAT | (SEQ ID NO: 17041) |
| 155 | R + TCYATG + AA + TAARGAAT | (SEQ ID NO: 17042) |
| 155 | RTCYA + TG + AA + TAARGAAT | (SEQ ID NO: 17043) |
| 155 | RTCY + ATG + AA + TAARGAAT | (SEQ ID NO: 17044) |
| 155 | RTCYAT + G + AA + TAARGAAT | (SEQ ID NO: 17045) |
| 155 | RTCYATG + AA + TAAR + GAAT | (SEQ ID NO: 17046) |
| 155 | RTCYATG + AA + TAARGA + AT | (SEQ ID NO: 17047) |
| 155 | RTCYATG + AA + TAARGAA + T | (SEQ ID NO: 17048) |
| 155 | RTCYATG + AA + TA + ARGAAT | (SEQ ID NO: 17049) |
| 155 | ARTCYAT + GAATAARG | (SEQ ID NO: 17050) |
| 155 | +ARTCYATGAATAARG | (SEQ ID NO: 17051) |
| 155 | ARTCY + ATGAATAARG | (SEQ ID NO: 17052) |
| 155 | ART + CYATGAATAARG | (SEQ ID NO: 17053) |
| 155 | ARTCYATGAATAAR + G | (SEQ ID NO: 17054) |
| 155 | ARTCYATGAATAARGA | (SEQ ID NO: 17055) |
| 155 | ARTCYATGAATAA + RG | (SEQ ID NO: 17056) |
| 155 | ARTCYATGAA + TAARG | (SEQ ID NO: 17057) |
| 155 | ARTCYA + T + GA + ATAARG | (SEQ ID NO: 17058) |
| 155 | +ARTCYAT + GA + ATAARG | (SEQ ID NO: 17059) |
| 155 | AR + TCYAT + GA + ATAARG | (SEQ ID NO: 17060) |
| 155 | ART + CYAT + GA + ATAARG | (SEQ ID NO: 17061) |
| 155 | ARTCYAT + GA + AT + AARG | (SEQ ID NO: 17062) |
| 155 | ARTCYAT + GA + ATA + ARG | (SEQ ID NO: 17063) |
| 155 | ARTCYAT + GA + ATAARGA | (SEQ ID NO: 17064) |
| 155 | ARTCYAT + GA + ATAARG | (SEQ ID NO: 17065) |
| 155 | RT + CYATGAATAARGA | (SEQ ID NO: 17066) |
| 155 | RTCY + ATGAATAARGA | (SEQ ID NO: 17067) |
| 155 | R + TCYATGAATAARGA | (SEQ ID NO: 17068) |
| 155 | +RTCYATGAATAARGA | (SEQ ID NO: 17069) |
| 155 | RTCYATGAATAARGAA | (SEQ ID NO: 17070) |
| 155 | RTCYATGAA + TAARGA | (SEQ ID NO: 17071) |
| 155 | RTCYATGAATAAR + GA | (SEQ ID NO: 17072) |
| 155 | RTCYATGAATAARG + A | (SEQ ID NO: 17073) |
| 155 | R + TCYATG + AA + TAARGA | (SEQ ID NO: 17074) |
| 155 | RTCYA + TG + AA + TAARGA | (SEQ ID NO: 17075) |
| 155 | RTCY + ATG + AA + TAARGA | (SEQ ID NO: 17076) |
| 155 | RTCYAT + G + AA + TAARGA | (SEQ ID NO: 17077) |
| 155 | RTCYATG + AA + TAAR + GA | (SEQ ID NO: 17078) |
| 155 | RTCYATG + AA + TAARGA | (SEQ ID NO: 17079) |
| 155 | RTCYATG + AA + TAARGAA | (SEQ ID NO: 17080) |
| 155 | RTCYATG + AA + TA + ARGA | (SEQ ID NO: 17081) |
| 155 | ARTCYAT + GAATAA | (SEQ ID NO: 17082) |
| 155 | +ARTCYATGAATAA | (SEQ ID NO: 17083) |
| 155 | ARTCY + ATGAATAA | (SEQ ID NO: 17084) |
| 155 | ART + CYATGAATAA | (SEQ ID NO: 17085) |
| 155 | ARTCYATGAATAAR | (SEQ ID NO: 17086) |
| 155 | ARTCYATGAATAA | (SEQ ID NO: 17087) |
| 155 | ARTCYATGAA + TAA | (SEQ ID NO: 17088) |
| 155 | ARTCYA + T + GA + ATAA | (SEQ ID NO: 17089) |
| 155 | +ARTCYAT + GA + ATAA | (SEQ ID NO: 17090) |
| 155 | AR + TCYAT + GA + ATAA | (SEQ ID NO: 17091) |
| 155 | ART + CYAT + GA + ATAA | (SEQ ID NO: 17092) |
| 155 | ARTCYAT + GA + AT + AA | (SEQ ID NO: 17093) |

TABLE 13-continued

| | | |
|---|---|---|
| 155 | ARTCYAT + GA + ATA + A (SEQ ID NO: 17094) | |
| 155 | ARTCYAT + GA + ATAAR (SEQ ID NO: 17095) | |
| 155 | RT + CYATGAATAAR (SEQ ID NO: 17096) | |
| 155 | RTCY + ATGAATAAR (SEQ ID NO: 17097) | |
| 155 | R + TCYATGAATAAR (SEQ ID NO: 17098) | |
| 155 | +RTCYATGAATAAR (SEQ ID NO: 17099) | |
| 155 | RTCYATGAATAARG (SEQ ID NO: 17100) | |
| 155 | RTCYATGAA + TAAR (SEQ ID NO: 17101) | |
| 155 | RTCYATGAATAAR (SEQ ID NO: 17102) | |
| 155 | R + TCYATG + AA + TAAR (SEQ ID NO: 17103) | |
| 155 | RTCYA + TG + AA + TAAR (SEQ ID NO: 17104) | |
| 155 | RTCY + ATG + AA + TAAR (SEQ ID NO: 17105) | |
| 155 | RTCYAT + G + AA + TAAR (SEQ ID NO: 17106) | |
| 155 | RTCYATG + AA + TAAR (SEQ ID NO: 17107) | |
| 155 | RTCYATG + AA + TAARG (SEQ ID NO: 17108) | |
| 155 | RTCYATG + AA + TA + AR (SEQ ID NO: 17109) | |
| 155 | GARTCYATGAATAARGAAT (SEQ ID NO: 17110) | |
| 155 | ARTCYATGAATAARGAATT (SEQ ID NO: 17111) | |
| 155 | ARTCYATGAATAARGAA (SEQ ID NO: 17112) | |
| 155 | RTCYATGAATAARGAAT (SEQ ID NO: 17113) | |
| 155 | ARTCYATGAATAARG (SEQ ID NO: 17114) | |
| 155 | RTCYATGAATAARGA (SEQ ID NO: 17115) | |
| 155 | ARTCYATGAATAA (SEQ ID NO: 17116) | |
| 155 | RTCYATGAATAAR (SEQ ID NO: 17117) | |
| 155 | TCTATGAAYAAAGAA (SEQ ID NO: 17118) | |
| 163 | AA + AATYATAGGRCARGTMA (SEQ ID NO: 17119) | |
| 163 | AAA + ATYATAGGRCARGTMA (SEQ ID NO: 17120) | |
| 163 | AAAATYA + TAGGRCARGTMA (SEQ ID NO: 17121) | |
| 163 | A + AAATYATAGGRCARGTMA (SEQ ID NO: 17122) | |
| 163 | AAAATYATAGGRCAR + GTMA (SEQ ID NO: 17123) | |
| 163 | AAAATYATAG + GRCARGTMA (SEQ ID NO: 17124) | |
| 163 | AAAATYATAGG + RCARGTMA (SEQ ID NO: 17125) | |
| 163 | AAAATYATAGGRCA + RGTMA (SEQ ID NO: 17126) | |
| 163 | AAAA + TYAT + AG + GRCARGTMA (SEQ ID NO: 17127) | |
| 163 | AA + AATYAT + AG + GRCARGTMA (SEQ ID NO: 17128) | |
| 163 | AAAAT + YAT + AG + GRCARGTMA (SEQ ID NO: 17129) | |
| 163 | AAAATY + AT + AG + GRCARGTMA (SEQ ID NO: 17130) | |
| 163 | AAAATYAT + AG + G + RCARGTMA (SEQ ID NO: 17131) | |
| 163 | AAAATYAT + AG + GRC + ARGTMA (SEQ ID NO: 17132) | |
| 163 | AAAATYAT + AG + GR + CARGTMA (SEQ ID NO: 17133) | |
| 163 | AAAATYAT + AG + GRCA + RGTMA (SEQ ID NO: 17134) | |
| 163 | A + AATYATAGGRCARGTM (SEQ ID NO: 17135) | |
| 163 | AA + ATYATAGGRCARGTM (SEQ ID NO: 17136) | |
| 163 | AAATYA + TAGGRCARGTM (SEQ ID NO: 17137) | |
| 163 | +AAATYATAGGRCARGTM (SEQ ID NO: 17138) | |
| 163 | AAATYATAGGRCAR + GTM (SEQ ID NO: 17139) | |
| 163 | AAATYATAG + GRCARGTM (SEQ ID NO: 17140) | |
| 163 | AAATYATAGG + RCARGTM (SEQ ID NO: 17141) | |
| 163 | AAATYATAGGRCA + RGTM (SEQ ID NO: 17142) | |
| 163 | AAA + TYAT + AG + GRCARGTM (SEQ ID NO: 17143) | |
| 163 | A + AATYAT + AG + GRCARGTM (SEQ ID NO: 17144) | |
| 163 | AAAT + YAT + AG + GRCARGTM (SEQ ID NO: 17145) | |
| 163 | AAATY + AT + AG + GRCARGTM (SEQ ID NO: 17146) | |
| 163 | AAATYAT + AG + G + RCARGTM (SEQ ID NO: 17147) | |
| 163 | AAATYAT + AG + GRC + ARGTM (SEQ ID NO: 17148) | |
| 163 | AAATYAT + AG + GR + CARGTM (SEQ ID NO: 17149) | |
| 163 | AAATYAT + AG + GRCA + RGTM (SEQ ID NO: 17150) | |
| 163 | A + AATYATAGGRCARG (SEQ ID NO: 17151) | |
| 163 | AA + ATYATAGGRCARG (SEQ ID NO: 17152) | |
| 163 | AAATYA + TAGGRCARG (SEQ ID NO: 17153) | |
| 163 | +AAATYATAGGRCARG (SEQ ID NO: 17154) | |
| 163 | AAATYATAGGRCAR + G (SEQ ID NO: 17155) | |
| 163 | AAATYATAG + GRCARG (SEQ ID NO: 17156) | |
| 163 | AAATYATAGG + RCARG (SEQ ID NO: 17157) | |
| 163 | AAATYATAGGRCA + RG (SEQ ID NO: 17158) | |
| 163 | AAA + TYAT + AG + GRCARG (SEQ ID NO: 17159) | |
| 163 | A + AATYAT + AG + GRCARG (SEQ ID NO: 17160) | |
| 163 | AAAT + YAT + AG + GRCARG (SEQ ID NO: 17161) | |
| 163 | AAATY + AT + AG + GRCARG (SEQ ID NO: 17162) | |
| 163 | AAATYAT + AG + G + RCARG (SEQ ID NO: 17163) | |
| 163 | AAATYAT + AG + GRC + ARG (SEQ ID NO: 17164) | |
| 163 | AAATYAT + AG + GR + CARG (SEQ ID NO: 17165) | |

TABLE 13-continued

| 163 | AAATYAT + AG + GRCA + RG (SEQ ID NO: 17166) |
| 163 | A + AATYATAGGRCA (SEQ ID NO: 17167) |
| 163 | AA + ATYATAGGRCA (SEQ ID NO: 17168) |
| 163 | AAATYA + TAGGRCA (SEQ ID NO: 17169) |
| 163 | +AAATYATAGGRCA (SEQ ID NO: 17170) |
| 163 | AAATYATAGGRCAR (SEQ ID NO: 17171) |
| 163 | AAATYATAG + GRCA (SEQ ID NO: 17172) |
| 163 | AAATYATAGG + RCA (SEQ ID NO: 17173) |
| 163 | AAATYATAGGRCA (SEQ ID NO: 17174) |
| 163 | AAA + TYAT + AG + GRCA (SEQ ID NO: 17175) |
| 163 | A + AATYAT + AG + GRCA (SEQ ID NO: 17176) |
| 163 | AAAT + YAT + AG + GRCA (SEQ ID NO: 17177) |
| 163 | AAATY + AT + AG + GRCA (SEQ ID NO: 17178) |
| 163 | AAATYAT + AG + G + RCA (SEQ ID NO: 17179) |
| 163 | AAATYAT + AG + GRC + A (SEQ ID NO: 17180) |
| 163 | AAATYAT + AG + GR + CA (SEQ ID NO: 17181) |
| 163 | AAATYAT + AG + GRCA (SEQ ID NO: 17182) |
| 163 | AAAATYATAGGRCARGTMA (SEQ ID NO: 17183) |
| 163 | AAATYATAGGRCARGTM (SEQ ID NO: 17184) |
| 163 | AAATYATAGGRCARG (SEQ ID NO: 17185) |
| 163 | AAATYATAGGRCA (SEQ ID NO: 17186) |
| 163 | ATTATAGGRCAGGTA (SEQ ID NO: 17187) |
| 230 | TACAGRGA + CAGCAGAGAYC (SEQ ID NO: 17188) |
| 230 | TACAGR + GACAGCAGAGAYC (SEQ ID NO: 17189) |
| 230 | TA + CAGRGACAGCAGAGAYC (SEQ ID NO: 17190) |
| 230 | T + ACAGRGACAGCAGAGAYC (SEQ ID NO: 17191) |
| 230 | TACAGRGACA + GCAGAGAYC (SEQ ID NO: 17192) |
| 230 | TACAGRGACAG + CAGAGAYC (SEQ ID NO: 17193) |
| 230 | TACAGRGACAGC + AGAGAYC (SEQ ID NO: 17194) |
| 230 | TACAGRGACAGCAGAGA + YC (SEQ ID NO: 17195) |
| 230 | TACAGRG + A + CA + GCAGAGAYC (SEQ ID NO: 17196) |
| 230 | TACAGR + GA + CA + GCAGAGAYC (SEQ ID NO: 17197) |
| 230 | TAC + AGRGA + CA + GCAGAGAYC (SEQ ID NO: 17198) |
| 230 | TACAG + RGA + CA + GCAGAGAYC (SEQ ID NO: 17199) |
| 230 | TACAGRGA + CA + GC + AGAGAYC (SEQ ID NO: 17200) |
| 230 | TACAGRGA + CA + GCAGAGAY + C (SEQ ID NO: 17201) |
| 230 | TACAGRGA + CA + G + CAGAGAYC (SEQ ID NO: 17202) |
| 230 | TACAGRGA + CA + GCAGA + GAYC (SEQ ID NO: 17203) |
| 230 | ACAGRGA + CAGCAGAGAY (SEQ ID NO: 17204) |
| 230 | ACAGR + GACAGCAGAGAY (SEQ ID NO: 17205) |
| 230 | A + CAGRGACAGCAGAGAY (SEQ ID NO: 17206) |
| 230 | +ACAGRGACAGCAGAGAY (SEQ ID NO: 17207) |
| 230 | ACAGRGACA + GCAGAGAY (SEQ ID NO: 17208) |
| 230 | ACAGRGACAG + CAGAGAY (SEQ ID NO: 17209) |
| 230 | ACAGRGACAGC + AGAGAY (SEQ ID NO: 17210) |
| 230 | ACAGRGACAGCAGAGA + Y (SEQ ID NO: 17211) |
| 230 | ACAGRG + A + CA + GCAGAGAY (SEQ ID NO: 17212) |
| 230 | ACAGR + GA + CA + GCAGAGAY (SEQ ID NO: 17213) |
| 230 | AC + AGRGA + CA + GCAGAGAY (SEQ ID NO: 17214) |
| 230 | ACAG + RGA + CA + GCAGAGAY (SEQ ID NO: 17215) |
| 230 | ACAGRGA + CA + GC + AGAGAY (SEQ ID NO: 17216) |
| 230 | ACAGRGA + CA + GCAGAGAY (SEQ ID NO: 17217) |
| 230 | ACAGRGA + CA + G + CAGAGAY (SEQ ID NO: 17218) |
| 230 | ACAGRGA + CA + GCAGA + GAY (SEQ ID NO: 17219) |
| 230 | ACAGRGA + CAGCAGAG (SEQ ID NO: 17220) |
| 230 | ACAGR + GACAGCAGAG (SEQ ID NO: 17221) |
| 230 | A + CAGRGACAGCAGAG (SEQ ID NO: 17222) |
| 230 | +ACAGRGACAGCAGAG (SEQ ID NO: 17223) |
| 230 | ACAGRGACA + GCAGAG (SEQ ID NO: 17224) |
| 230 | ACAGRGACAG + CAGAG (SEQ ID NO: 17225) |
| 230 | ACAGRGACAGC + AGAG (SEQ ID NO: 17226) |
| 230 | ACAGRGACAGCAGAGA (SEQ ID NO: 17227) |
| 230 | ACAGRG + A + CA + GCAGAG (SEQ ID NO: 17228) |
| 230 | ACAGR + GA + CA + GCAGAG (SEQ ID NO: 17229) |
| 230 | AC + AGRGA + CA + GCAGAG (SEQ ID NO: 17230) |
| 230 | ACAG + RGA + CA + GCAGAG (SEQ ID NO: 17231) |
| 230 | ACAGRGA + CA + GC + AGAG (SEQ ID NO: 17232) |
| 230 | ACAGRGA + CA + GCAGAGA (SEQ ID NO: 17233) |
| 230 | ACAGRGA + CA + G + CAGAG (SEQ ID NO: 17234) |
| 230 | ACAGRGA + CA + GCAGA + G (SEQ ID NO: 17235) |
| 230 | ACAGRGA + CAGCAG (SEQ ID NO: 17236) |
| 230 | ACAGR + GACAGCAG (SEQ ID NO: 17237) |
| 230 | A + CAGRGACAGCAG (SEQ ID NO: 17238) |

TABLE 13-continued

| | |
|---|---|
| 230 | +ACAGRGACAGCAG (SEQ ID NO: 17239) |
| 230 | ACAGRGACA + GCAG (SEQ ID NO: 17240) |
| 230 | ACAGRGACAG + CAG (SEQ ID NO: 17241) |
| 230 | ACAGRGACAGC + AG (SEQ ID NO: 17242) |
| 230 | ACAGRGACAGCAGA (SEQ ID NO: 17243) |
| 230 | ACAGRG + A + CA + GCAG (SEQ ID NO: 17244) |
| 230 | ACAGR + GA + CA + GCAG (SEQ ID NO: 17245) |
| 230 | AC + AGRGA + CA + GCAG (SEQ ID NO: 17246) |
| 230 | ACAG + RGA + CA + GCAG (SEQ ID NO: 17247) |
| 230 | ACAGRGA + CA + GC + AG (SEQ ID NO: 17248) |
| 230 | ACAGRGA + CA + GCAGA (SEQ ID NO: 17249) |
| 230 | ACAGRGA + CA + G + CAG (SEQ ID NO: 17250) |
| 230 | TACAGRGACAGCAGAGAYC (SEQ ID NO: 17251) |
| 230 | ACAGRGACAGCAGAGAY (SEQ ID NO: 17252) |
| 230 | ACAGRGACAGCAGAG (SEQ ID NO: 17253) |
| 230 | ACAGRGACAGCAG (SEQ ID NO: 17254) |
| 230 | AGGGACAGCAGAGAC (SEQ ID NO: 17255) |
| 263 | TRCCAAG + RAGRAAAGYAAA (SEQ ID NO: 17256) |
| 263 | TRCCAA + GRAGRAAAGYAAA (SEQ ID NO: 17257) |
| 263 | TR + CCAAGRAGRAAAGYAAA (SEQ ID NO: 17258) |
| 263 | TRC + CAAGRAGRAAAGYAAA (SEQ ID NO: 17259) |
| 263 | TRCCAAGRAGRAAA + GYAAA (SEQ ID NO: 17260) |
| 263 | TRCCAAGRAGRAAAGY + AAA (SEQ ID NO: 17261) |
| 263 | TRCCAAGRAGRAA + AGYAAA (SEQ ID NO: 17262) |
| 263 | TRCCAAGRAGR + AAAGYAAA (SEQ ID NO: 17263) |
| 263 | TR + CCAAGR + AG + RAAAGYAAA (SEQ ID NO: 17264) |
| 263 | TRC + CAAGR + AG + RAAAGYAAA (SEQ ID NO: 17265) |
| 263 | TRCCAA + GR + AG + RAAAGYAAA (SEQ ID NO: 17266) |
| 263 | TRCCAAG + R + AG + RAAAGYAAA (SEQ ID NO: 17267) |
| 263 | TRCCAAGR + AG + RAAAG + YAAA (SEQ ID NO: 17268) |
| 263 | TRCCAAGR + AG + RAA + AGYAAA (SEQ ID NO: 17269) |
| 263 | TRCCAAGR + AG + RAAA + GYAAA (SEQ ID NO: 17270) |
| 263 | TRCCAAGR + AG + R + AAAGYAAA (SEQ ID NO: 17271) |
| 263 | RCCAAG + RAGRAAAGYAA (SEQ ID NO: 17272) |
| 263 | RCCAA + GRAGRAAAGYAA (SEQ ID NO: 17273) |
| 263 | R + CCAAGRAGRAAAGYAA (SEQ ID NO: 17274) |
| 263 | RC + CAAGRAGRAAAGYAA (SEQ ID NO: 17275) |
| 263 | RCCAAGRAGRAAA + GYAA (SEQ ID NO: 17276) |
| 263 | RCCAAGRAGRAAAGY + AA (SEQ ID NO: 17277) |
| 263 | RCCAAGRAGRAA + AGYAA (SEQ ID NO: 17278) |
| 263 | RCCAAGRAGR + AAAGYAA (SEQ ID NO: 17279) |
| 263 | R + CCAAGR + AG + RAAAGYAA (SEQ ID NO: 17280) |
| 263 | RC + CAAGR + AG + RAAAGYAA (SEQ ID NO: 17281) |
| 263 | RCCAA + GR + AG + RAAAGYAA (SEQ ID NO: 17282) |
| 263 | RCCAAG + R + AG + RAAAGYAA (SEQ ID NO: 17283) |
| 263 | RCCAAGR + AG + RAAAG + YAA (SEQ ID NO: 17284) |
| 263 | RCCAAGR + AG + RAA + AGYAA (SEQ ID NO: 17285) |
| 263 | RCCAAGR + AG + RAAA + GYAA (SEQ ID NO: 17286) |
| 263 | RCCAAGR + AG + R + AAAGYAA (SEQ ID NO: 17287) |
| 263 | RCCAAG + RAGRAAAGY (SEQ ID NO: 17288) |
| 263 | RCCAA + GRAGRAAAGY (SEQ ID NO: 17289) |
| 263 | R + CCAAGRAGRAAAGY (SEQ ID NO: 17290) |
| 263 | RC + CAAGRAGRAAAGY (SEQ ID NO: 17291) |
| 263 | RCCAAGRAGRAAA + GY (SEQ ID NO: 17292) |
| 263 | RCCAAGRAGRAAAGY (SEQ ID NO: 17293) |
| 263 | RCCAAGRAGRAA + AGY (SEQ ID NO: 17294) |
| 263 | RCCAAGRAGR + AAAGY (SEQ ID NO: 17295) |
| 263 | R + CCAAGR + AG + RAAAGY (SEQ ID NO: 17296) |
| 263 | RC + CAAGR + AG + RAAAGY (SEQ ID NO: 17297) |
| 263 | RCCAA + GR + AG + RAAAGY (SEQ ID NO: 17298) |
| 263 | RCCAAG + R + AG + RAAAGY (SEQ ID NO: 17299) |
| 263 | RCCAAGR + AG + RAAAG + Y (SEQ ID NO: 17300) |
| 263 | RCCAAGR + AG + RAA + AGY (SEQ ID NO: 17301) |
| 263 | RCCAAGR + AG + RAAA + GY (SEQ ID NO: 17302) |
| 263 | RCCAAGR + AG + R + AAAGY (SEQ ID NO: 17303) |
| 263 | RCCAAG + RAGRAAA (SEQ ID NO: 17304) |
| 263 | RCCAA + GRAGRAAA (SEQ ID NO: 17305) |
| 263 | R + CCAAGRAGRAAA (SEQ ID NO: 17306) |
| 263 | RC + CAAGRAGRAAA (SEQ ID NO: 17307) |
| 263 | RCCAAGRAGRAAA (SEQ ID NO: 17308) |
| 263 | RCCAAGRAGRAAAG (SEQ ID NO: 17309) |
| 263 | RCCAAGRAGRAA + A (SEQ ID NO: 17310) |

TABLE 13-continued

| Codon | Mutant Probe (5' to 3') |
|---|---|
| 263 | RCCAAGRAGR + AAA (SEQ ID NO: 17311) |
| 263 | R + CCAAGR + AG + RAAA (SEQ ID NO: 17312) |
| 263 | RC + CAAGR + AG + RAAA (SEQ ID NO: 17313) |
| 263 | RCCAA + GR + AG + RAAA (SEQ ID NO: 17314) |
| 263 | RCCAAG + R + AG + RAAA (SEQ ID NO: 17315) |
| 263 | RCCAAGR + AG + RAAAG (SEQ ID NO: 17316) |
| 263 | RCCAAGR + AG + RAA + A (SEQ ID NO: 17317) |
| 263 | RCCAAGR + AG + RAAA (SEQ ID NO: 17318) |
| 263 | RCCAAGR + AG + R + AAA (SEQ ID NO: 17319) |
| 263 | TRCCAAGRAGRAAAGYAAA (SEQ ID NO: 17320) |
| 263 | RCCAAGRAGRAAAGYAA (SEQ ID NO: 17321) |
| 263 | RCCAAGRAGRAAAGY (SEQ ID NO: 17322) |
| 263 | RCCAAGRAGRAAA (SEQ ID NO: 17323) |
| 263 | CCAAGAAGRAAAGCA (SEQ ID NO: 17324) |

| Codon | Mutant Probe (5' to 3') |
|---|---|
| 51 | AGCCATGTATGGACA (SEQ ID NO: 17325) |
| 66 | YTAGAYTG + Y + CACAYYTAG (SEQ ID NO: 17326) |
| 66 | YTAGAYT + GYCACAYYTAG (SEQ ID NO: 17327) |
| 66 | Y + TAGAYTGYCACAYYTAG (SEQ ID NO: 17328) |
| 66 | YTAGAY + TGYCACAYYTAG (SEQ ID NO: 17329) |
| 66 | YT + AGAYTGYCACAYYTAG (SEQ ID NO: 17330) |
| 66 | YTAGAYTGYCACA + YYTAG (SEQ ID NO: 17331) |
| 66 | YTAGAYTGYCACAYY + TAG (SEQ ID NO: 17332) |
| 66 | YTAGAYTGY + CACAYYTAG (SEQ ID NO: 17333) |
| 66 | YTAGAYTGYCAC + AYYTAG (SEQ ID NO: 17334) |
| 66 | YTAG + AYTG + Y + CACAYYTAG (SEQ ID NO: 17335) |
| 66 | YT + AGAYTG + Y + CACAYYTAG (SEQ ID NO: 17336) |
| 66 | YTAGAYT + G + Y + CACAYYTAG (SEQ ID NO: 17337) |
| 66 | YTA + GAYTG + Y + CACAYYTAG (SEQ ID NO: 17338) |
| 66 | YTAGAYTG + Y + CAC + AYYTAG (SEQ ID NO: 17339) |
| 66 | YTAGAYTG + Y + CA + CAYYTAG (SEQ ID NO: 17340) |
| 66 | YTAGAYTG + Y + CACAY + YTAG (SEQ ID NO: 17341) |
| 66 | YTAGAYTG + Y + CACAYY + TAG (SEQ ID NO: 17342) |
| 66 | TAGAYTGY + A + ACAYYTAGA (SEQ ID NO: 17343) |
| 66 | TAGAYT + GYAACAYYTAGA (SEQ ID NO: 17344) |
| 66 | TAGA + YTGYAACAYYTAGA (SEQ ID NO: 17345) |
| 66 | TAGAYTG + YAACAYYTAGA (SEQ ID NO: 17346) |
| 66 | TA + GAYTGYAACAYYTAGA (SEQ ID NO: 17347) |
| 66 | TAGAYTGYAAC + AYYTAGA (SEQ ID NO: 17348) |
| 66 | TAGAYTGYAACAYYT + AGA (SEQ ID NO: 17349) |
| 66 | TAGAYTGYA + ACAYYTAGA (SEQ ID NO: 17350) |
| 66 | TAGAYTGYAACAY + YTAGA (SEQ ID NO: 17351) |
| 66 | TAGAYT + GY + A + ACAYYTAGA (SEQ ID NO: 17352) |
| 66 | TAGAY + TGY + A + ACAYYTAGA (SEQ ID NO: 17353) |
| 66 | T + AGAYTGY + A + ACAYYTAGA (SEQ ID NO: 17354) |
| 66 | TA + GAYTGY + A + ACAYYTAGA (SEQ ID NO: 17355) |
| 66 | TAGAYTGY + A + ACAYYTA + GA (SEQ ID NO: 17356) |
| 66 | TAGAYTGY + A + ACAYYT + AGA (SEQ ID NO: 17357) |
| 66 | TAGAYTGY + A + ACA + YYTAGA (SEQ ID NO: 17358) |
| 66 | TAGAYTGY + A + ACAYY + TAGA (SEQ ID NO: 17359) |
| 66 | TAGAY + TGYAACAYYTAGA (SEQ ID NO: 17360) |
| 66 | TAGAYTGYAACAYYTA + GA (SEQ ID NO: 17361) |
| 66 | TAGAYTGYAA + CAYYTAGA (SEQ ID NO: 17362) |
| 66 | TAGAYTGYAACA + YYTAGA (SEQ ID NO: 17363) |
| 66 | TAGA + YTGY + A + ACAYYTAGA (SEQ ID NO: 17364) |
| 66 | TAGAYTG + Y + A + ACAYYTAGA (SEQ ID NO: 17365) |
| 66 | TAGAYTGY + A + A + CAYYTAGA (SEQ ID NO: 17366) |
| 66 | TAGAYTGY + A + ACAY + YTAGA (SEQ ID NO: 17367) |
| 66 | TAGAYTG + Y + CACAYYTAG (SEQ ID NO: 17368) |
| 66 | TAGAYT + GYCACAYYTAG (SEQ ID NO: 17369) |
| 66 | +TAGAYTGYCACAYYTAG (SEQ ID NO: 17370) |
| 66 | TAGAY + TGYCACAYYTAG (SEQ ID NO: 17371) |
| 66 | T + AGAYTGYCACAYYTAG (SEQ ID NO: 17372) |
| 66 | TAGAYTGYCACA + YYTAG (SEQ ID NO: 17373) |
| 66 | TAGAYTGYCACAYY + TAG (SEQ ID NO: 17374) |
| 66 | TAGAYTGY + CACAYYTAG (SEQ ID NO: 17375) |
| 66 | TAGAYTGYCAC + AYYTAG (SEQ ID NO: 17376) |
| 66 | TAG + AYTG + Y + CACAYYTAG (SEQ ID NO: 17377) |
| 66 | T + AGAYTG + Y + CACAYYTAG (SEQ ID NO: 17378) |

TABLE 13-continued

| | |
|---|---|
| 66 | TAGAYT + G + Y + CACAYYTAG (SEQ ID NO: 17379) |
| 66 | TA + GAYTG + Y + CACAYYTAG (SEQ ID NO: 17380) |
| 66 | TAGAYTG + Y + CAC + AYYTAG (SEQ ID NO: 17381) |
| 66 | TAGAYTG + Y + CA + CAYYTAG (SEQ ID NO: 17382) |
| 66 | TAGAYTG + Y + CACAY + YTAG (SEQ ID NO: 17383) |
| 66 | TAGAYTG + Y + CACAYY + TAG (SEQ ID NO: 17384) |
| 66 | AGAYTGY + A + ACAYYTAGA (SEQ ID NO: 17385) |
| 66 | AGAYT + GYAACAYYTAGA (SEQ ID NO: 17386) |
| 66 | AGA + YTGYAACAYYTAGA (SEQ ID NO: 17387) |
| 66 | AGAYTG + YAACAYYTAGA (SEQ ID NO: 17388) |
| 66 | A + GAYTGYAACAYYTAGA (SEQ ID NO: 17389) |
| 66 | AGAYTGYAAC + AYYTAGA (SEQ ID NO: 17390) |
| 66 | AGAYTGYAACAYYT + AGA (SEQ ID NO: 17391) |
| 66 | AGAYTGYA + ACAYYTAGA (SEQ ID NO: 17392) |
| 66 | AGAYTGYAACAY + YTAGA (SEQ ID NO: 17393) |
| 66 | AGAYT + GY + A + ACAYYTAGA (SEQ ID NO: 17394) |
| 66 | AGAY + TGY + A + ACAYYTAGA (SEQ ID NO: 17395) |
| 66 | +AGAYTGY + A + ACAYYTAGA (SEQ ID NO: 17396) |
| 66 | A + GAYTGY + A + ACAYYTAGA (SEQ ID NO: 17397) |
| 66 | AGAYTGY + A + ACAYYTA + GA (SEQ ID NO: 17398) |
| 66 | AGAYTGY + A + ACAYYT + AGA (SEQ ID NO: 17399) |
| 66 | AGAYTGY + A + ACA + YYTAGA (SEQ ID NO: 17400) |
| 66 | AGAYTGY + A + ACAYY + TAGA (SEQ ID NO: 17401) |
| 66 | AGAY + TGYAACAYYTAGA (SEQ ID NO: 17402) |
| 66 | AGAYTGYAACAYYTA + GA (SEQ ID NO: 17403) |
| 66 | AGAYTGYAA + CAYYTAGA (SEQ ID NO: 17404) |
| 66 | AGAYTGYAACA + YYTAGA (SEQ ID NO: 17405) |
| 66 | AGA + YTGY + A + ACAYYTAGA (SEQ ID NO: 17406) |
| 66 | AGAYTG + Y + A + ACAYYTAGA (SEQ ID NO: 17407) |
| 66 | AGAYTGY + A + A + CAYYTAGA (SEQ ID NO: 17408) |
| 66 | AGAYTGY + A + ACAY + YTAGA (SEQ ID NO: 17409) |
| 66 | TAGAYTG + Y + CACAYYT (SEQ ID NO: 17410) |
| 66 | TAGAYT + GYCACAYYT (SEQ ID NO: 17411) |
| 66 | +TAGAYTGYCACAYYT (SEQ ID NO: 17412) |
| 66 | TAGAY + TGYCACAYYT (SEQ ID NO: 17413) |
| 66 | T + AGAYTGYCACAYYT (SEQ ID NO: 17414) |
| 66 | TAGAYTGYCACA + YYT (SEQ ID NO: 17415) |
| 66 | TAGAYTGYCACAYY + T (SEQ ID NO: 17416) |
| 66 | TAGAYTGY + CACAYYT (SEQ ID NO: 17417) |
| 66 | TAGAYTGYCAC + AYYT (SEQ ID NO: 17418) |
| 66 | TAG + AYTG + Y + CACAYYT (SEQ ID NO: 17419) |
| 66 | T + AGAYTG + Y + CACAYYT (SEQ ID NO: 17420) |
| 66 | TAGAYT + G + Y + CACAYYT (SEQ ID NO: 17421) |
| 66 | TA + GAYTG + Y + CACAYYT (SEQ ID NO: 17422) |
| 66 | TAGAYTG + Y + CAC + AYYT (SEQ ID NO: 17423) |
| 66 | TAGAYTG + Y + CA + CAYYT (SEQ ID NO: 17424) |
| 66 | TAGAYTG + Y + CACAY + YT (SEQ ID NO: 17425) |
| 66 | TAGAYTG + Y + CACAYY + T (SEQ ID NO: 17426) |
| 66 | AGAYTGY + A + ACAYYTA (SEQ ID NO: 17427) |
| 66 | AGAYT + GYAACAYYTA (SEQ ID NO: 17428) |
| 66 | AGA + YTGYAACAYYTA (SEQ ID NO: 17429) |
| 66 | AGAYTG + YAACAYYTA (SEQ ID NO: 17430) |
| 66 | A + GAYTGYAACAYYTA (SEQ ID NO: 17431) |
| 66 | AGAYTGYAAC + AYYTA (SEQ ID NO: 17432) |
| 66 | AGAYTGYAACAYYT + A (SEQ ID NO: 17433) |
| 66 | AGAYTGYA + ACAYYTA (SEQ ID NO: 17434) |
| 66 | AGAYTGYAACAY + YTA (SEQ ID NO: 17435) |
| 66 | AGAYT + GY + A + ACAYYTA (SEQ ID NO: 17436) |
| 66 | AGAY + TGY + A + ACAYYTA (SEQ ID NO: 17437) |
| 66 | +AGAYTGY + A + ACAYYTA (SEQ ID NO: 17438) |
| 66 | A + GAYTGY + A + ACAYYTA (SEQ ID NO: 17439) |
| 66 | AGAYTGY + A + ACAYYTA (SEQ ID NO: 17440) |
| 66 | AGAYTGY + A + ACAYYT + A (SEQ ID NO: 17441) |
| 66 | AGAYTGY + A + ACA + YYTA (SEQ ID NO: 17442) |
| 66 | AGAYTGY + A + ACAYY + TA (SEQ ID NO: 17443) |
| 66 | AGAY + TGYAACAYYTA (SEQ ID NO: 17444) |
| 66 | AGAYTGYAACAYYTA (SEQ ID NO: 17445) |
| 66 | AGAYTGYAA + CAYYTA (SEQ ID NO: 17446) |
| 66 | AGAYTGYAACA + YYTA (SEQ ID NO: 17447) |
| 66 | AGA + YTGY + A + ACAYYTA (SEQ ID NO: 17448) |
| 66 | AGAYTG + Y + A + ACAYYTA (SEQ ID NO: 17449) |

TABLE 13-continued

| | |
|---|---|
| 66 | AGAYTGY + A + A + CAYYTA (SEQ ID NO: 17450) |
| 66 | AGAYTGY + A + ACAY + YTA (SEQ ID NO: 17451) |
| 66 | TAGAYTG + Y + CACAY (SEQ ID NO: 17452) |
| 66 | TAGAYT + GYCACAY (SEQ ID NO: 17453) |
| 66 | +TAGAYTGYCACAY (SEQ ID NO: 17454) |
| 66 | TAGAY + TGYCACAY (SEQ ID NO: 17455) |
| 66 | T + AGAYTGYCACAY (SEQ ID NO: 17456) |
| 66 | TAGAYTGYCACA + Y (SEQ ID NO: 17457) |
| 66 | TAGAYTGYCACAYY (SEQ ID NO: 17458) |
| 66 | TAGAYTGY + CACAY (SEQ ID NO: 17459) |
| 66 | TAGAYTGYCAC + AY (SEQ ID NO: 17460) |
| 66 | TAG + AYTG + Y + CACAY (SEQ ID NO: 17461) |
| 66 | T + AGAYTG + Y + CACAY (SEQ ID NO: 17462) |
| 66 | TAGAYT + G + Y + CACAY (SEQ ID NO: 17463) |
| 66 | TA + GAYTG + Y + CACAY (SEQ ID NO: 17464) |
| 66 | TAGAYTG + Y + CAC + AY (SEQ ID NO: 17465) |
| 66 | TAGAYTG + Y + CA + CAY (SEQ ID NO: 17466) |
| 66 | TAGAYTG + Y + CACAY (SEQ ID NO: 17467) |
| 66 | TAGAYTG + Y + CACAYY (SEQ ID NO: 17468) |
| 66 | AGAYTGY + A + ACAYY (SEQ ID NO: 17469) |
| 66 | AGAYT + GYAACAYY (SEQ ID NO: 17470) |
| 66 | AGA + YTGYAACAYY (SEQ ID NO: 17471) |
| 66 | AGAYTG + YAACAYY (SEQ ID NO: 17472) |
| 66 | A + GAYTGYAACAYY (SEQ ID NO: 17473) |
| 66 | AGAYTGYAAC + AYY (SEQ ID NO: 17474) |
| 66 | AGAYTGYAACAYYT (SEQ ID NO: 17475) |
| 66 | AGAYTGYA + ACAYY (SEQ ID NO: 17476) |
| 66 | AGAYTGYAACAY + Y (SEQ ID NO: 17477) |
| 66 | AGAYT + GY + A + ACAYY (SEQ ID NO: 17478) |
| 66 | AGAY + TGY + A + ACAYY (SEQ ID NO: 17479) |
| 66 | +AGAYTGY + A + ACAYY (SEQ ID NO: 17480) |
| 66 | A + GAYTGY + A + ACAYY (SEQ ID NO: 17481) |
| 66 | AGAYTGY + A + ACAYYT (SEQ ID NO: 17482) |
| 66 | AGAYTGY + A + ACA + YY (SEQ ID NO: 17483) |
| 66 | AGAYTGY + A + ACAYY (SEQ ID NO: 17484) |
| 66 | AGAY + TGYAACAYY (SEQ ID NO: 17485) |
| 66 | AGAYTGYAA + CAYY (SEQ ID NO: 17486) |
| 66 | AGAYTGYAACA + YY (SEQ ID NO: 17487) |
| 66 | AGA + YTGY + A + ACAYY (SEQ ID NO: 17488) |
| 66 | AGAYTG + Y + A + ACAYY (SEQ ID NO: 17489) |
| 66 | AGAYTGY + A + A + CAYY (SEQ ID NO: 17490) |
| 66 | AGAYTGY + A + ACAY + Y (SEQ ID NO: 17491) |
| 66 | YTAGAYTGYCACAYYTAG (SEQ ID NO: 17492) |
| 66 | TAGAYTGYAACAYYTAGA (SEQ ID NO: 17493) |
| 66 | TAGAYTGYCACAYYTAG (SEQ ID NO: 17494) |
| 66 | AGAYTGYAACAYYTAGA (SEQ ID NO: 17495) |
| 66 | TAGAYTGYCACAYYT (SEQ ID NO: 17496) |
| 66 | AGAYTGYAACAYYTA (SEQ ID NO: 17497) |
| 66 | TAGAYTGYCACAY (SEQ ID NO: 17498) |
| 66 | AGAYTGYAACAYY (SEQ ID NO: 17499) |
| 66 | TAAATGKATACAATC (SEQ ID NO: 17500) |
| 66 | TAAATGKGCACAATC (SEQ ID NO: 17501) |
| 66 | TAAATGTTTACAATC (SEQ ID NO: 17502) |
| 74 | AAARTHAT + Y + TRGTAGCAG (SEQ ID NO: 17503) |
| 74 | AAA + RTHATYTRGTAGCAG (SEQ ID NO: 17504) |
| 74 | A + AARTHATYTRGTAGCAG (SEQ ID NO: 17505) |
| 74 | AA + ARTHATYTRGTAGCAG (SEQ ID NO: 17506) |
| 74 | AAARTH + ATYTRGTAGCAG (SEQ ID NO: 17507) |
| 74 | AAARTHATYTR + GTAGCAG (SEQ ID NO: 17508) |
| 74 | AAARTHATYTRGTAGC + AG (SEQ ID NO: 17509) |
| 74 | AAARTHATYTRGTAG + CAG (SEQ ID NO: 17510) |
| 74 | AAARTHATYTRGTAGCA + G (SEQ ID NO: 17511) |
| 74 | AA + ARTHAT + Y + TRGTAGCAG (SEQ ID NO: 17512) |
| 74 | A + AARTHAT + Y + TRGTAGCAG (SEQ ID NO: 17513) |
| 74 | AAARTH + AT + Y + TRGTAGCAG (SEQ ID NO: 17514) |
| 74 | AAA + RTHAT + Y + TRGTAGCAG (SEQ ID NO: 17515) |
| 74 | AAARTHAT + Y + TRGT + AGCAG (SEQ ID NO: 17516) |
| 74 | AAARTHAT + Y + TRG + TAGCAG (SEQ ID NO: 17517) |
| 74 | AAARTHAT + Y + TRGTA + GCAG (SEQ ID NO: 17518) |
| 74 | AAARTHAT + Y + TR + GTAGCAG (SEQ ID NO: 17519) |
| 74 | AARTHAT + Y + TRGTAGCAG (SEQ ID NO: 17520) |
| 74 | AA + RTHATYTRGTAGCAG (SEQ ID NO: 17521) |
| 74 | +AARTHATYTRGTAGCAG (SEQ ID NO: 17522) |
| 74 | A + ARTHATYTRGTAGCAG (SEQ ID NO: 17523) |
| 74 | AARTH + ATYTRGTAGCAG (SEQ ID NO: 17524) |
| 74 | AARTHATYTR + GTAGCAG (SEQ ID NO: 17525) |

TABLE 13-continued

| | |
|---|---|
| 74 | AARTHATYTRGTAGC + AG (SEQ ID NO: 17526) |
| 74 | AARTHATYTRGTAG + CAG (SEQ ID NO: 17527) |
| 74 | AARTHATYTRGTAGCA + G (SEQ ID NO: 17528) |
| 74 | A + ARTHAT + Y + TRGTAGCAG (SEQ ID NO: 17529) |
| 74 | +AARTHAT + Y + TRGTAGCAG (SEQ ID NO: 17530) |
| 74 | AARTH + AT + Y + TRGTAGCAG (SEQ ID NO: 17531) |
| 74 | AA + RTHAT + Y + TRGTAGCAG (SEQ ID NO: 17532) |
| 74 | AARTHAT + Y + TRGT + AGCAG (SEQ ID NO: 17533) |
| 74 | AARTHAT + Y + TRG + TAGCAG (SEQ ID NO: 17534) |
| 74 | AARTHAT + Y + TRGTA + GCAG (SEQ ID NO: 17535) |
| 74 | AARTHAT + Y + TR + GTAGCAG (SEQ ID NO: 17536) |
| 74 | AARTHAT + Y + TRGTAGC (SEQ ID NO: 17537) |
| 74 | AA + RTHATYTRGTAGC (SEQ ID NO: 17538) |
| 74 | +AARTHATYTRGTAGC (SEQ ID NO: 17539) |
| 74 | A + ARTHATYTRGTAGC (SEQ ID NO: 17540) |
| 74 | AARTH + ATYTRGTAGC (SEQ ID NO: 17541) |
| 74 | AARTHATYTR + GTAGC (SEQ ID NO: 17542) |
| 74 | AARTHATYTRGTAGC (SEQ ID NO: 17543) |
| 74 | AARTHATYTRGTAG + C (SEQ ID NO: 17544) |
| 74 | AARTHATYTRGTAGCA (SEQ ID NO: 17545) |
| 74 | A + ARTHAT + Y + TRGTAGC (SEQ ID NO: 17546) |
| 74 | +AARTHAT + Y + TRGTAGC (SEQ ID NO: 17547) |
| 74 | AARTH + AT + Y + TRGTAGC (SEQ ID NO: 17548) |
| 74 | AA + RTHAT + Y + TRGTAGC (SEQ ID NO: 17549) |
| 74 | AARTHAT + Y + TRGT + AGC (SEQ ID NO: 17550) |
| 74 | AARTHAT + Y + TRG + TAGC (SEQ ID NO: 17551) |
| 74 | AARTHAT + Y + TRGTA + GC (SEQ ID NO: 17552) |
| 74 | AARTHAT + Y + TR + GTAGC (SEQ ID NO: 17553) |
| 74 | AARTHAT + Y + TRGTA (SEQ ID NO: 17554) |
| 74 | AA + RTHATYTRGTA (SEQ ID NO: 17555) |
| 74 | +AARTHATYTRGTA (SEQ ID NO: 17556) |
| 74 | A + ARTHATYTRGTA (SEQ ID NO: 17557) |
| 74 | AARTH + ATYTRGTA (SEQ ID NO: 17558) |
| 74 | AARTHATYTR + GTA (SEQ ID NO: 17559) |
| 74 | AARTHATYTRGTAG (SEQ ID NO: 17560) |
| 74 | A + ARTHAT + Y + TRGTA (SEQ ID NO: 17561) |
| 74 | +AARTHAT + Y + TRGTA (SEQ ID NO: 17562) |
| 74 | AARTH + AT + Y + TRGTA (SEQ ID NO: 17563) |
| 74 | AA + RTHAT + Y + TRGTA (SEQ ID NO: 17564) |
| 74 | AARTHAT + Y + TRGT + A (SEQ ID NO: 17565) |
| 74 | AARTHAT + Y + TRG + TA (SEQ ID NO: 17566) |
| 74 | AARTHAT + Y + TRGTA (SEQ ID NO: 17567) |
| 74 | AARTHAT + Y + TR + GTA (SEQ ID NO: 17568) |
| 74 | AAARTHATYTRGTAGCAG (SEQ ID NO: 17569) |
| 74 | AARTHATYTRGTAGCAG (SEQ ID NO: 17570) |
| 74 | AARTHATYTRGTAGC (SEQ ID NO: 17571) |
| 74 | AARTHATYTRGTA (SEQ ID NO: 17572) |
| 74 | AATTATCATGGTAGC (SEQ ID NO: 17573) |
| 92 | TYCCAGCA + G + RACAGGRCA (SEQ ID NO: 17574) |
| 92 | TYCCA + GCAGRACAGGRCA (SEQ ID NO: 17575) |
| 92 | TYCCAGCA + GRACAGGRCA (SEQ ID NO: 17576) |
| 92 | TYCCAG + CAGRACAGGRCA (SEQ ID NO: 17577) |
| 92 | TYCCAGC + AGRACAGGRCA (SEQ ID NO: 17578) |
| 92 | TYCCAGCAG + RACAGGRCA (SEQ ID NO: 17579) |
| 92 | TYCCAGCAGRACA + GGRCA (SEQ ID NO: 17580) |
| 92 | TYCCAGCAGRACAGG + RCA (SEQ ID NO: 17581) |
| 92 | TYCCAGCAGRA + CAGGRCA (SEQ ID NO: 17582) |
| 92 | TYCCA + GCA + G + RACAGGRCA (SEQ ID NO: 17583) |
| 92 | TYCC + AGCA + G + RACAGGRCA (SEQ ID NO: 17584) |
| 92 | TYC + CAGCA + G + RACAGGRCA (SEQ ID NO: 17585) |
| 92 | TY + CCAGCA + G + RACAGGRCA (SEQ ID NO: 17586) |
| 92 | TYCCAGCA + G + RAC + AGGRCA (SEQ ID NO: 17587) |
| 92 | TYCCAGCA + G + RACAGGRC + A (SEQ ID NO: 17588) |
| 92 | TYCCAGCA + G + RA + CAGGRCA (SEQ ID NO: 17589) |
| 92 | TYCCAGCA + G + R + ACAGGRCA (SEQ ID NO: 17590) |
| 92 | ATYCCAGC + A + ARACAGGRC (SEQ ID NO: 17591) |
| 92 | ATYCCA + GCAARACAGGRC (SEQ ID NO: 17592) |
| 92 | AT + YCCAGCAARACAGGRC (SEQ ID NO: 17593) |
| 92 | ATYCCAG + CAARACAGGRC (SEQ ID NO: 17594) |
| 92 | ATY + CCAGCAARACAGGRC (SEQ ID NO: 17595) |
| 92 | ATYCCAGCA + ARACAGGRC (SEQ ID NO: 17596) |
| 92 | ATYCCAGCAARA + CAGGRC (SEQ ID NO: 17597) |
| 92 | ATYCCAGCAARACAG + GRC (SEQ ID NO: 17598) |

TABLE 13-continued

| 92 | ATYCCAGCAA + RACAGGRC (SEQ ID NO: 17599) |
| 92 | ATYCCA + GC + A + ARACAGGRC (SEQ ID NO: 17600) |
| 92 | ATY + CCAGC + A + ARACAGGRC (SEQ ID NO: 17601) |
| 92 | AT + YCCAGC + A + ARACAGGRC (SEQ ID NO: 17602) |
| 92 | ATYC + CAGC + A + ARACAGGRC (SEQ ID NO: 17603) |
| 92 | ATYCCAGC + A + ARACAG + GRC (SEQ ID NO: 17604) |
| 92 | ATYCCAGC + A + ARACA + GGRC (SEQ ID NO: 17605) |
| 92 | ATYCCAGC + A + ARA + CAGGRC (SEQ ID NO: 17606) |
| 92 | ATYCCAGC + A + A + RACAGGRC (SEQ ID NO: 17607) |
| 92 | YCCAGCA + G + RACAGGRCA (SEQ ID NO: 17608) |
| 92 | YCCA + GCAGRACAGGRCA (SEQ ID NO: 17609) |
| 92 | YCCAGCA + GRACAGGRCA (SEQ ID NO: 17610) |
| 92 | YCCAG + CAGRACAGGRCA (SEQ ID NO: 17611) |
| 92 | YCCAGC + AGRACAGGRCA (SEQ ID NO: 17612) |
| 92 | YCCAGCAG + RACAGGRCA (SEQ ID NO: 17613) |
| 92 | YCCAGCAGRACA + GGRCA (SEQ ID NO: 17614) |
| 92 | YCCAGCAGRACAGG + RCA (SEQ ID NO: 17615) |
| 92 | YCCAGCAGRA + CAGGRCA (SEQ ID NO: 17616) |
| 92 | YCCA + GCA + G + RACAGGRCA (SEQ ID NO: 17617) |
| 92 | YCC + AGCA + G + RACAGGRCA (SEQ ID NO: 17618) |
| 92 | YC + CAGCA + G + RACAGGRCA (SEQ ID NO: 17619) |
| 92 | Y + CCAGCA + G + RACAGGRCA (SEQ ID NO: 17620) |
| 92 | YCCAGCA + G + RAC + AGGRCA (SEQ ID NO: 17621) |
| 92 | YCCAGCA + G + RACAGGRC + A (SEQ ID NO: 17622) |
| 92 | YCCAGCA + G + RA + CAGGRCA (SEQ ID NO: 17623) |
| 92 | YCCAGCA + G + R + ACAGGRCA (SEQ ID NO: 17624) |
| 92 | TYCCAGC + A + ARACAGGRC (SEQ ID NO: 17625) |
| 92 | TYCCA + GCAARACAGGRC (SEQ ID NO: 17626) |
| 92 | T + YCCAGCAARACAGGRC (SEQ ID NO: 17627) |
| 92 | TYCCAG + CAARACAGGRC (SEQ ID NO: 17628) |
| 92 | TY + CCAGCAARACAGGRC (SEQ ID NO: 17629) |
| 92 | TYCCAGCA + ARACAGGRC (SEQ ID NO: 17630) |
| 92 | TYCCAGCAARA + CAGGRC (SEQ ID NO: 17631) |
| 92 | TYCCAGCAARACAG + GRC (SEQ ID NO: 17632) |
| 92 | TYCCAGCAA + RACAGGRC (SEQ ID NO: 17633) |
| 92 | TYCCA + GC + A + ARACAGGRC (SEQ ID NO: 17634) |
| 92 | TY + CCAGC + A + ARACAGGRC (SEQ ID NO: 17635) |
| 92 | T + YCCAGC + A + ARACAGGRC (SEQ ID NO: 17636) |
| 92 | TYC + CAGC + A + ARACAGGRC (SEQ ID NO: 17637) |
| 92 | TYCCAGC + A + ARACAG + GRC (SEQ ID NO: 17638) |
| 92 | TYCCAGC + A + ARACA + GGRC (SEQ ID NO: 17639) |
| 92 | TYCCAGC + A + ARA + CAGGRC (SEQ ID NO: 17640) |
| 92 | TYCCAGC + A + A + RACAGGRC (SEQ ID NO: 17641) |
| 92 | YCCAGCA + G + RACAGGR (SEQ ID NO: 17642) |
| 92 | YCCA + GCAGRACAGGR (SEQ ID NO: 17643) |
| 92 | YCCAGCA + GRACAGGR (SEQ ID NO: 17644) |
| 92 | YCCAG + CAGRACAGGR (SEQ ID NO: 17645) |
| 92 | YCCAGC + AGRACAGGR (SEQ ID NO: 17646) |
| 92 | YCCAGCAG + RACAGGR (SEQ ID NO: 17647) |
| 92 | YCCAGCAGRACA + GGR (SEQ ID NO: 17648) |
| 92 | YCCAGCAGRACAGG + R (SEQ ID NO: 17649) |
| 92 | YCCAGCAGRA + CAGGR (SEQ ID NO: 17650) |
| 92 | YCCA + GCA + G + RACAGGR (SEQ ID NO: 17651) |
| 92 | YCC + AGCA + G + RACAGGR (SEQ ID NO: 17652) |
| 92 | YC + CAGCA + G + RACAGGR (SEQ ID NO: 17653) |
| 92 | Y + CCAGCA + G + RACAGGR (SEQ ID NO: 17654) |
| 92 | YCCAGCA + G + RAC + AGGR (SEQ ID NO: 17655) |
| 92 | YCCAGCA + G + RACAGGRC (SEQ ID NO: 17656) |
| 92 | YCCAGCA + G + RA + CAGGR (SEQ ID NO: 17657) |
| 92 | YCCAGCA + G + R + ACAGGR (SEQ ID NO: 17658) |
| 92 | TYCCAGC + A + ARACAGG (SEQ ID NO: 17659) |
| 92 | TYCCA + GCAARACAGG (SEQ ID NO: 17660) |
| 92 | T + YCCAGCAARACAGG (SEQ ID NO: 17661) |
| 92 | TYCCAG + CAARACAGG (SEQ ID NO: 17662) |
| 92 | TY + CCAGCAARACAGG (SEQ ID NO: 17663) |
| 92 | TYCCAGCA + ARACAGG (SEQ ID NO: 17664) |
| 92 | TYCCAGCAARA + CAGG (SEQ ID NO: 17665) |
| 92 | TYCCAGCAARACAG + G (SEQ ID NO: 17666) |

TABLE 13-continued

| | |
|---|---|
| 92 | TYCCAGCAA + RACAGG (SEQ ID NO: 17667) |
| 92 | TYCCA + GC + A + ARACAGG (SEQ ID NO: 17668) |
| 92 | TY + CCAGC + A + ARACAGG (SEQ ID NO: 17669) |
| 92 | T + YCCAGC + A + ARACAGG (SEQ ID NO: 17670) |
| 92 | TYC + CAGC + A + ARACAGG (SEQ ID NO: 17671) |
| 92 | TYCCAGC + A + ARACAG + G (SEQ ID NO: 17672) |
| 92 | TYCCAGC + A + ARACA + GG (SEQ ID NO: 17673) |
| 92 | TYCCAGC + A + ARA + CAGG (SEQ ID NO: 17674) |
| 92 | TYCCAGC + A + A + RACAGG (SEQ ID NO: 17675) |
| 92 | YCCAGCA + G + RACAG (SEQ ID NO: 17676) |
| 92 | YCCA + GCAGRACAG (SEQ ID NO: 17677) |
| 92 | YCCAGCA + GRACAG (SEQ ID NO: 17678) |
| 92 | YCCAG + CAGRACAG (SEQ ID NO: 17679) |
| 92 | YCCAGC + AGRACAG (SEQ ID NO: 17680) |
| 92 | YCCAGCAG + RACAG (SEQ ID NO: 17681) |
| 92 | YCCAGCAGRACA + G (SEQ ID NO: 17682) |
| 92 | YCCAGCAGRACAGG (SEQ ID NO: 17683) |
| 92 | YCCAGCAGRA + CAG (SEQ ID NO: 17684) |
| 92 | YCCA + GCA + G + RACAG (SEQ ID NO: 17685) |
| 92 | YCC + AGCA + G + RACAG (SEQ ID NO: 17686) |
| 92 | YC + CAGCA + G + RACAG (SEQ ID NO: 17687) |
| 92 | Y + CCAGCA + G + RACAG (SEQ ID NO: 17688) |
| 92 | YCCAGCA + G + RAC + AG (SEQ ID NO: 17689) |
| 92 | YCCAGCA + G + RACAGG (SEQ ID NO: 17690) |
| 92 | YCCAGCA + G + RA + CAG (SEQ ID NO: 17691) |
| 92 | YCCAGCA + G + R + ACAG (SEQ ID NO: 17692) |
| 92 | TYCCAGC + A + ARACA (SEQ ID NO: 17693) |
| 92 | TYCCA + GCAARACA (SEQ ID NO: 17694) |
| 92 | T + YCCAGCAARACA (SEQ ID NO: 17695) |
| 92 | TYCCAG + CAARACA (SEQ ID NO: 17696) |
| 92 | TY + CCAGCAARACA (SEQ ID NO: 17697) |
| 92 | TYCCAGCA + ARACA (SEQ ID NO: 17698) |
| 92 | TYCCAGCAARA + CA (SEQ ID NO: 17699) |
| 92 | TYCCAGCAARACAG (SEQ ID NO: 17700) |
| 92 | TYCCAGCAA + RACA (SEQ ID NO: 17701) |
| 92 | TYCCA + GC + A + ARACA (SEQ ID NO: 17702) |
| 92 | TY + CCAGC + A + ARACA (SEQ ID NO: 17703) |
| 92 | T + YCCAGC + A + ARACA (SEQ ID NO: 17704) |
| 92 | TYC + CAGC + A + ARACA (SEQ ID NO: 17705) |
| 92 | TYCCAGC + A + ARACAG (SEQ ID NO: 17706) |
| 92 | TYCCAGC + A + ARACA (SEQ ID NO: 17707) |
| 92 | TYCCAGC + A + ARA + CA (SEQ ID NO: 17708) |
| 92 | TYCCAGC + A + A + RACA (SEQ ID NO: 17709) |
| 92 | TYCCAGCAGRACAGGRCA (SEQ ID NO: 17710) |
| 92 | ATYCCAGCAARACAGGRC (SEQ ID NO: 17711) |
| 92 | YCCAGCAGRACAGGRCA (SEQ ID NO: 17712) |
| 92 | TYCCAGCAARACAGGRC (SEQ ID NO: 17713) |
| 92 | YCCAGCAGRACAGGR (SEQ ID NO: 17714) |
| 92 | YCCAGCAGRACAGGRC (SEQ ID NO: 17715) |
| 92 | TYCCAGCAARACAGG (SEQ ID NO: 17716) |
| 92 | YCCAGCAGRACAG (SEQ ID NO: 17717) |
| 92 | TYCCAGCAARACA (SEQ ID NO: 17718) |
| 92 | CCCAGCACARACAGG (SEQ ID NO: 17719) |
| 92 | CCCAGCAGGRACAGG (SEQ ID NO: 17720) |
| 92 | CCCAGCAGTRACAGG (SEQ ID NO: 17721) |
| 97 | GGRCARGA + R + CAGCATAYT (SEQ ID NO: 17722) |
| 97 | GG + RCARGARCAGCATAYT (SEQ ID NO: 17723) |
| 97 | GGRCARG + ARCAGCATAYT (SEQ ID NO: 17724) |
| 97 | G + GRCARGARCAGCATAYT (SEQ ID NO: 17725) |
| 97 | GGRCARGA + RCAGCATAYT (SEQ ID NO: 17726) |
| 97 | GGRCARGARCAG + CATAYT (SEQ ID NO: 17727) |
| 97 | GGRCARGARCAGCATAY + T (SEQ ID NO: 17728) |
| 97 | GGRCARGARC + AGCATAYT (SEQ ID NO: 17729) |
| 97 | GGRCARGARCA + GCATAYT (SEQ ID NO: 17730) |
| 97 | GG + RCARGA + R + CAGCATAYT (SEQ ID NO: 17731) |
| 97 | GGRC + ARGA + R + CAGCATAYT (SEQ ID NO: 17732) |
| 97 | GGR + CARGA + R + CAGCATAYT (SEQ ID NO: 17733) |
| 97 | G + GRCARGA + R + CAGCATAYT (SEQ ID NO: 17734) |
| 97 | GGRCARGA + R + CAGCATAY + T (SEQ ID NO: 17735) |
| 97 | GGRCARGA + R + CAGCA + TAYT (SEQ ID NO: 17736) |
| 97 | GGRCARGA + R + CAGC + ATAYT (SEQ ID NO: 17737) |
| 97 | GGRCARGA + R + CA + GCATAYT (SEQ ID NO: 17738) |
| 97 | GRCARGA + R + CAGCATAYT (SEQ ID NO: 17739) |
| 97 | G + RCARGARCAGCATAYT (SEQ ID NO: 17740) |
| 97 | GRCARG + ARCAGCATAYT (SEQ ID NO: 17741) |
| 97 | +GRCARGARCAGCATAYT (SEQ ID NO: 17742) |

TABLE 13-continued

| | |
|---|---|
| 97 | GRCARGA + RCAGCATAYT (SEQ ID NO: 17743) |
| 97 | GRCARGARCAG + CATAYT (SEQ ID NO: 17744) |
| 97 | GRCARGARCAGCATAY + T (SEQ ID NO: 17745) |
| 97 | GRCARGARC + AGCATAYT (SEQ ID NO: 17746) |
| 97 | GRCARGARCA + GCATAYT (SEQ ID NO: 17747) |
| 97 | G + RCARGA + R + CAGCATAYT (SEQ ID NO: 17748) |
| 97 | GRC + ARGA + R + CAGCATAYT (SEQ ID NO: 17749) |
| 97 | GR + CARGA + R + CAGCATAYT (SEQ ID NO: 17750) |
| 97 | +GRCARGA + R + CAGCATAYT (SEQ ID NO: 17751) |
| 97 | GRCARGA + R + CAGCATAY + T (SEQ ID NO: 17752) |
| 97 | GRCARGA + R + CAGCA + TAYT (SEQ ID NO: 17753) |
| 97 | GRCARGA + R + CAGC + ATAYT (SEQ ID NO: 17754) |
| 97 | GRCARGA + R + CA + GCATAYT (SEQ ID NO: 17755) |
| 97 | GRCARGA + R + CAGCATA (SEQ ID NO: 17756) |
| 97 | G + RCARGARCAGCATA (SEQ ID NO: 17757) |
| 97 | GRCARG + ARCAGCATA (SEQ ID NO: 17758) |
| 97 | +GRCARGARCAGCATA (SEQ ID NO: 17759) |
| 97 | GRCARGA + RCAGCATA (SEQ ID NO: 17760) |
| 97 | GRCARGARCAG + CATA (SEQ ID NO: 17761) |
| 97 | GRCARGARCAGCATAY (SEQ ID NO: 17762) |
| 97 | GRCARGARC + AGCATA (SEQ ID NO: 17763) |
| 97 | GRCARGARCA + GCATA (SEQ ID NO: 17764) |
| 97 | G + RCARGA + R + CAGCATA (SEQ ID NO: 17765) |
| 97 | GRC + ARGA + R + CAGCATA (SEQ ID NO: 17766) |
| 97 | GR + CARGA + R + CAGCATA (SEQ ID NO: 17767) |
| 97 | +GRCARGA + R + CAGCATA (SEQ ID NO: 17768) |
| 97 | GRCARGA + R + CAGCATAY (SEQ ID NO: 17769) |
| 97 | GRCARGA + R + CAGCA + TA (SEQ ID NO: 17770) |
| 97 | GRCARGA + R + CAGC + ATA (SEQ ID NO: 17771) |
| 97 | GRCARGA + R + CA + GCATA (SEQ ID NO: 17772) |
| 97 | GRCARGA + R + CAGCA (SEQ ID NO: 17773) |
| 97 | G + RCARGARCAGCA (SEQ ID NO: 17774) |
| 97 | GRCARG + ARCAGCA (SEQ ID NO: 17775) |
| 97 | +GRCARGARCAGCA (SEQ ID NO: 17776) |
| 97 | GRCARGA + RCAGCA (SEQ ID NO: 17777) |
| 97 | GRCARGARCAG + CA (SEQ ID NO: 17778) |
| 97 | GRCARGARCAGCAT (SEQ ID NO: 17779) |
| 97 | GRCARGARC + AGCA (SEQ ID NO: 17780) |
| 97 | GRCARGARCA + GCA (SEQ ID NO: 17781) |
| 97 | G + RCARGA + R + CAGCA (SEQ ID NO: 17782) |
| 97 | GRC + ARGA + R + CAGCA (SEQ ID NO: 17783) |
| 97 | GR + CARGA + R + CAGCA (SEQ ID NO: 17784) |
| 97 | +GRCARGA + R + CAGCA (SEQ ID NO: 17785) |
| 97 | GRCARGA + R + CAGCAT (SEQ ID NO: 17786) |
| 97 | GRCARGA + R + CAGCA (SEQ ID NO: 17787) |
| 97 | GRCARGA + R + CAGC + A (SEQ ID NO: 17788) |
| 97 | GRCARGA + R + CA + GCA (SEQ ID NO: 17789) |
| 97 | GGRCARGARCAGCATAYT (SEQ ID NO: 17790) |
| 97 | GRCARGARCAGCATAYT (SEQ ID NO: 17791) |
| 97 | GRCARGARCAGCATA (SEQ ID NO: 17792) |
| 97 | GRCARGARCAGCA (SEQ ID NO: 17793) |
| 97 | ACAGGAAGCWGCATA (SEQ ID NO: 17794) |
| 118 | ACAGAYAA + T + GYMSYAAYT (SEQ ID NO: 17795) |
| 118 | A + CAGAYAATGYMSYAAYT (SEQ ID NO: 17796) |
| 118 | ACAGAY + AATGYMSYAAYT (SEQ ID NO: 17797) |
| 118 | ACA + GAYAATGYMSYAAYT (SEQ ID NO: 17798) |
| 118 | ACAG + AYAATGYMSYAAYT (SEQ ID NO: 17799) |
| 118 | ACAGAYAATGYMSY + AAYT (SEQ ID NO: 17800) |
| 118 | ACAGAYAATGYMSYA + AYT (SEQ ID NO: 17801) |
| 118 | ACAGAYAAT + GYMSYAAYT (SEQ ID NO: 17802) |
| 118 | ACAGAYAATG + YMSYAAYT (SEQ ID NO: 17803) |
| 118 | A + CAGAYAA + T + GYMSYAAYT (SEQ ID NO: 17804) |
| 118 | ACAGAYA + A + T + GYMSYAAYT (SEQ ID NO: 17805) |
| 118 | AC + AGAYAA + T + GYMSYAAYT (SEQ ID NO: 17806) |
| 118 | ACAGAY + AA + T + GYMSYAAYT (SEQ ID NO: 17807) |
| 118 | ACAGAYAA + T + G + YMSYAAYT (SEQ ID NO: 17808) |
| 118 | ACAGAYAA + T + GYMS + YAAYT (SEQ ID NO: 17809) |
| 118 | ACAGAYAA + T + GYMSYAA + YT (SEQ ID NO: 17810) |
| 118 | ACAGAYAA + T + GYM + SYAAYT (SEQ ID NO: 17811) |
| 118 | CAGAYAA + T + GYMSYAAYT (SEQ ID NO: 17812) |
| 118 | +CAGAYAATGYMSYAAYT (SEQ ID NO: 17813) |
| 118 | CAGAY + AATGYMSYAAYT (SEQ ID NO: 17814) |

TABLE 13-continued

| | |
|---|---|
| 118 | CA + GAYAATGYMSYAAYT (SEQ ID NO: 17815) |
| 118 | CAG + AYAATGYMSYAAYT (SEQ ID NO: 17816) |
| 118 | CAGAYAATGYMSY + AAYT (SEQ ID NO: 17817) |
| 118 | CAGAYAATGYMSYA + AYT (SEQ ID NO: 17818) |
| 118 | CAGAYAAT + GYMSYAAYT (SEQ ID NO: 17819) |
| 118 | CAGAYAATG + YMSYAAYT (SEQ ID NO: 17820) |
| 118 | +CAGAYAA + T + GYMSYAAYT (SEQ ID NO: 17821) |
| 118 | CAGAYA + A + T + GYMSYAAYT (SEQ ID NO: 17822) |
| 118 | C + AGAYAA + T + GYMSYAAYT (SEQ ID NO: 17823) |
| 118 | CAGAY + AA + T + GYMSYAAYT (SEQ ID NO: 17824) |
| 118 | CAGAYAA + T + G + YMSYAAYT (SEQ ID NO: 17825) |
| 118 | CAGAYAA + T + GYMS + YAAYT (SEQ ID NO: 17826) |
| 118 | CAGAYAA + T + GYMSYAA + YT (SEQ ID NO: 17827) |
| 118 | CAGAYAA + T + GYM + SYAAYT (SEQ ID NO: 17828) |
| 118 | CAGAYAA + T + GYMSYAA (SEQ ID NO: 17829) |
| 118 | +CAGAYAATGYMSYAA (SEQ ID NO: 17830) |
| 118 | CAGAY + AATGYMSYAA (SEQ ID NO: 17831) |
| 118 | CA + GAYAATGYMSYAA (SEQ ID NO: 17832) |
| 118 | CAG + AYAATGYMSYAA (SEQ ID NO: 17833) |
| 118 | CAGAYAATGYMSY + AA (SEQ ID NO: 17834) |
| 118 | CAGAYAATGYMSYA + A (SEQ ID NO: 17835) |
| 118 | CAGAYAAT + GYMSYAA (SEQ ID NO: 17836) |
| 118 | CAGAYAATG + YMSYAA (SEQ ID NO: 17837) |
| 118 | +CAGAYAA + T + GYMSYAA (SEQ ID NO: 17838) |
| 118 | CAGAYA + A + T + GYMSYAA (SEQ ID NO: 17839) |
| 118 | C + AGAYAA + T + GYMSYAA (SEQ ID NO: 17840) |
| 118 | CAGAY + AA + T + GYMSYAA (SEQ ID NO: 17841) |
| 118 | CAGAYAA + T + G + YMSYAA (SEQ ID NO: 17842) |
| 118 | CAGAYAA + T + GYMS + YAA (SEQ ID NO: 17843) |
| 118 | CAGAYAA + T + GYMSYAA (SEQ ID NO: 17844) |
| 118 | CAGAYAA + T + GYM + SYAA (SEQ ID NO: 17845) |
| 118 | CAGAYAA + T + GYMSY (SEQ ID NO: 17846) |
| 118 | +CAGAYAATGYMSY (SEQ ID NO: 17847) |
| 118 | CAGAY + AATGYMSY (SEQ ID NO: 17848) |
| 118 | CA + GAYAATGYMSY (SEQ ID NO: 17849) |
| 118 | CAG + AYAATGYMSY (SEQ ID NO: 17850) |
| 118 | CAGAYAATGYMSY (SEQ ID NO: 17851) |
| 118 | CAGAYAATGYMSYA (SEQ ID NO: 17852) |
| 118 | CAGAYAAT + GYMSY (SEQ ID NO: 17853) |
| 118 | CAGAYAATG + YMSY (SEQ ID NO: 17854) |
| 118 | +CAGAYAA + T + GYMSY (SEQ ID NO: 17855) |
| 118 | CAGAYA + A + T + GYMSY (SEQ ID NO: 17856) |
| 118 | C + AGAYAA + T + GYMSY (SEQ ID NO: 17857) |
| 118 | CAGAY + AA + T + GYMSY (SEQ ID NO: 17858) |
| 118 | CAGAYAA + T + G + YMSY (SEQ ID NO: 17859) |
| 118 | CAGAYAA + T + GYMS + Y (SEQ ID NO: 17860) |
| 118 | CAGAYAA + T + GYMSYA (SEQ ID NO: 17861) |
| 118 | CAGAYAA + T + GYM + SY (SEQ ID NO: 17862) |
| 118 | ACAGAYAATGYMSYAAYT (SEQ ID NO: 17863) |
| 118 | CAGAYAATGYMSYAAYT (SEQ ID NO: 17864) |
| 118 | CAGAYAATGYMSYAA (SEQ ID NO: 17865) |
| 118 | CAGAYAATGYMSY (SEQ ID NO: 17866) |
| 118 | AGACAATCGNAGCAA (SEQ ID NO: 17867) |
| 118 | AGACAATAGRAGCAA (SEQ ID NO: 17868) |
| 121 | GYMSYAAY + T + YACYAGYRV (SEQ ID NO: 17869) |
| 121 | GYMSYAA + YTYACYAGYRV (SEQ ID NO: 17870) |
| 121 | G + YMSYAAYTYACYAGYRV (SEQ ID NO: 17871) |
| 121 | GY + MSYAAYTYACYAGYRV (SEQ ID NO: 17872) |
| 121 | GYMS + YAAYTYACYAGYRV (SEQ ID NO: 17873) |
| 121 | GYMSYAAYTYACY + AGYRV (SEQ ID NO: 17874) |
| 121 | GYMSYAAYTYA + CYAGYRV (SEQ ID NO: 17875) |
| 121 | GYMSYAAYTY + ACYAGYRV (SEQ ID NO: 17876) |
| 121 | GYMSYAAYTYACYAGYR + V (SEQ ID NO: 17877) |
| 121 | GYMSYAA + Y + T + YACYAGYRV (SEQ ID NO: 17878) |
| 121 | GYMS + YAAY + T + YACYAGYRV (SEQ ID NO: 17879) |
| 121 | G + YMSYAAY + T + YACYAGYRV (SEQ ID NO: 17880) |
| 121 | GYMSYA + AY + T + YACYAGYRV (SEQ ID NO: 17881) |
| 121 | GYMSYAAY + T + YACY + AGYRV (SEQ ID NO: 17882) |
| 121 | GYMSYAAY + T + YACYAGYR + V (SEQ ID NO: 17883) |
| 121 | GYMSYAAY + T + YAC + YAGYRV (SEQ ID NO: 17884) |
| 121 | GYMSYAAY + T + YA + CYAGYRV (SEQ ID NO: 17885) |
| 121 | YMSYAAY + T + YACYAGYRV (SEQ ID NO: 17886) |
| 121 | YMSYAA + YTYACYAGYRV (SEQ ID NO: 17887) |

TABLE 13-continued

| | |
|---|---|
| 121 | +YMSYAAYTYACYAGYRV (SEQ ID NO: 17888) |
| 121 | Y + MSYAAYTYACYAGYRV (SEQ ID NO: 17889) |
| 121 | YMS + YAAYTYACYAGYRV (SEQ ID NO: 17890) |
| 121 | YMSYAAYTYACY + AGYRV (SEQ ID NO: 17891) |
| 121 | YMSYAAYTYA + CYAGYRV (SEQ ID NO: 17892) |
| 121 | YMSYAAYTY + ACYAGYRV (SEQ ID NO: 17893) |
| 121 | YMSYAAYTYACYAGYR + V (SEQ ID NO: 17894) |
| 121 | YMSYAA + Y + T + YACYAGYRV (SEQ ID NO: 17895) |
| 121 | YMS + YAAY + T + YACYAGYRV (SEQ ID NO: 17896) |
| 121 | +YMSYAAY + T + YACYAGYRV (SEQ ID NO: 17897) |
| 121 | YMSYA + AY + T + YACYAGYRV (SEQ ID NO: 17898) |
| 121 | YMSYAAY + T + YACY + AGYRV (SEQ ID NO: 17899) |
| 121 | YMSYAAY + T + YACYAGYR + V (SEQ ID NO: 17900) |
| 121 | YMSYAAY + T + YAC + YAGYRV (SEQ ID NO: 17901) |
| 121 | YMSYAAY + T + YA + CYAGYRV (SEQ ID NO: 17902) |
| 121 | YMSYAAY + T + YACYAGY (SEQ ID NO: 17903) |
| 121 | YMSYAA + YTYACYAGY (SEQ ID NO: 17904) |
| 121 | +YMSYAAYTYACYAGY (SEQ ID NO: 17905) |
| 121 | Y + MSYAAYTYACYAGY (SEQ ID NO: 17906) |
| 121 | YMS + YAAYTYACYAGY (SEQ ID NO: 17907) |
| 121 | YMSYAAYTYACY + AGY (SEQ ID NO: 17908) |
| 121 | YMSYAAYTYA + CYAGY (SEQ ID NO: 17909) |
| 121 | YMSYAAYTY + ACYAGY (SEQ ID NO: 17910) |
| 121 | YMSYAAYTYACYAGYR (SEQ ID NO: 17911) |
| 121 | YMSYAA + Y + T + YACYAGY (SEQ ID NO: 17912) |
| 121 | YMS + YAAY + T + YACYAGY (SEQ ID NO: 17913) |
| 121 | +YMSYAAY + T + YACYAGY (SEQ ID NO: 17914) |
| 121 | YMSYA + AY + T + YACYAGY (SEQ ID NO: 17915) |
| 121 | YMSYAAY + T + YACY + AGY (SEQ ID NO: 17916) |
| 121 | YMSYAAY + T + YACYAGYR (SEQ ID NO: 17917) |
| 121 | YMSYAAY + T + YAC + YAGY (SEQ ID NO: 17918) |
| 121 | YMSYAAY + T + YA + CYAGY (SEQ ID NO: 17919) |
| 121 | YMSYAAY + T + YACYA (SEQ ID NO: 17920) |
| 121 | YMSYAA + YTYACYA (SEQ ID NO: 17921) |
| 121 | +YMSYAAYTYACYA (SEQ ID NO: 17922) |
| 121 | Y + MSYAAYTYACYA (SEQ ID NO: 17923) |
| 121 | YMS + YAAYTYACYA (SEQ ID NO: 17924) |
| 121 | YMSYAAYTYACY + A (SEQ ID NO: 17925) |
| 121 | YMSYAAYTYA + CYA (SEQ ID NO: 17926) |
| 121 | YMSYAAYTY + ACYA (SEQ ID NO: 17927) |
| 121 | YMSYAAYTYACYAG (SEQ ID NO: 17928) |
| 121 | YMSYAA + Y + T + YACYA (SEQ ID NO: 17929) |
| 121 | YMS + YAAY + T + YACYA (SEQ ID NO: 17930) |
| 121 | +YMSYAAY + T + YACYA (SEQ ID NO: 17931) |
| 121 | YMSYA + AY + T + YACYA (SEQ ID NO: 17932) |
| 121 | YMSYAAY + T + YACY + A (SEQ ID NO: 17933) |
| 121 | YMSYAAY + T + YACYAG (SEQ ID NO: 17934) |
| 121 | YMSYAAY + T + YAC + YA (SEQ ID NO: 17935) |
| 121 | YMSYAAY + T + YA + CYA (SEQ ID NO: 17936) |
| 121 | GYMSYAAYTYACYAGYRV (SEQ ID NO: 17937) |
| 121 | YMSYAAYTYACYAGYRV (SEQ ID NO: 17938) |
| 121 | YMSYAAYTYACYAGY (SEQ ID NO: 17939) |
| 121 | YMSYAAYTYACYA (SEQ ID NO: 17940) |
| 121 | AGCAATTAYACCAGT (SEQ ID NO: 17941) |
| 138 | TCMMRCAR + G + ATTTGGVAT (SEQ ID NO: 17942) |
| 138 | TCMMRCA + RGATTTGGVAT (SEQ ID NO: 17943) |
| 138 | TCM + MRCARGATTTGGVAT (SEQ ID NO: 17944) |
| 138 | TC + MMRCARGATTTGGVAT (SEQ ID NO: 17945) |
| 138 | TCMMRCAR + GATTTGGVAT (SEQ ID NO: 17946) |
| 138 | TCMMRCARGAT + TTGGVAT (SEQ ID NO: 17947) |
| 138 | TCMMRCARGATTTGGVA + T (SEQ ID NO: 17948) |
| 138 | TCMMRCARG + ATTTGGVAT (SEQ ID NO: 17949) |
| 138 | TCMMRCARGATTTGGV + AT (SEQ ID NO: 17950) |
| 138 | TC + MMRCAR + G + ATTTGGVAT (SEQ ID NO: 17951) |
| 138 | TCMMRC + AR + G + ATTTGGVAT (SEQ ID NO: 17952) |
| 138 | TCM + MRCAR + G + ATTTGGVAT (SEQ ID NO: 17953) |
| 138 | TCMM + RCAR + G + ATTTGGVAT (SEQ ID NO: 17954) |
| 138 | TCMMRCAR + G + ATTTGGVA + T (SEQ ID NO: 17955) |
| 138 | TCMMRCAR + G + ATT + TGGVAT (SEQ ID NO: 17956) |
| 138 | TCMMRCAR + G + ATTT + GGVAT (SEQ ID NO: 17957) |
| 138 | TCMMRCAR + G + A + TTTGGVAT (SEQ ID NO: 17958) |
| 138 | RTCMMRCA + R + AATTTGGVA (SEQ ID NO: 17959) |

TABLE 13-continued

| | |
|---|---|
| 138 | RTC + MMRCARAATTTGGVA (SEQ ID NO: 17960) |
| 138 | R + TCMMRCARAATTTGGVA (SEQ ID NO: 17961) |
| 138 | RTCM + MRCARAATTTGGVA (SEQ ID NO: 17962) |
| 138 | RTCMMRC + ARAATTTGGVA (SEQ ID NO: 17963) |
| 138 | RTCMMRCARAATTTGGV + A (SEQ ID NO: 17964) |
| 138 | RTCMMRCAR + AATTTGGVA (SEQ ID NO: 17965) |
| 138 | RTCMMRCARAAT + TTGGVA (SEQ ID NO: 17966) |
| 138 | RTCMMRCARA + ATTTGGVA (SEQ ID NO: 17967) |
| 138 | RTCMMRC + A + R + AATTTGGVA (SEQ ID NO: 17968) |
| 138 | RTCMM + RCA + R + AATTTGGVA (SEQ ID NO: 17969) |
| 138 | RT + CMMRCA + R + AATTTGGVA (SEQ ID NO: 17970) |
| 138 | RTC + MMRCA + R + AATTTGGVA (SEQ ID NO: 17971) |
| 138 | RTCMMRCA + R + AAT + TTGGVA (SEQ ID NO: 17972) |
| 138 | RTCMMRCA + R + A + ATTTGGVA (SEQ ID NO: 17973) |
| 138 | RTCMMRCA + R + AATTTGG + VA (SEQ ID NO: 17974) |
| 138 | RTCMMRCA + R + AA + TTTGGVA (SEQ ID NO: 17975) |
| 138 | CMMRCAR + G + ATTTGGVAT (SEQ ID NO: 17976) |
| 138 | CMMRCA + RGATTTGGVAT (SEQ ID NO: 17977) |
| 138 | CM + MRCARGATTTGGVAT (SEQ ID NO: 17978) |
| 138 | C + MMRCARGATTTGGVAT (SEQ ID NO: 17979) |
| 138 | CMMRCAR + GATTTGGVAT (SEQ ID NO: 17980) |
| 138 | CMMRCARGAT + TTGGVAT (SEQ ID NO: 17981) |
| 138 | CMMRCARGATTTGGVA + T (SEQ ID NO: 17982) |
| 138 | CMMRCARG + ATTTGGVAT (SEQ ID NO: 17983) |
| 138 | CMMRCARGATTTGGV + AT (SEQ ID NO: 17984) |
| 138 | C + MMRCAR + G + ATTTGGVAT (SEQ ID NO: 17985) |
| 138 | CMMRC + AR + G + ATTTGGVAT (SEQ ID NO: 17986) |
| 138 | CM + MRCAR + G + ATTTGGVAT (SEQ ID NO: 17987) |
| 138 | CMM + RCAR + G + ATTTGGVAT (SEQ ID NO: 17988) |
| 138 | CMMRCAR + G + ATTTGGVA + T (SEQ ID NO: 17989) |
| 138 | CMMRCAR + G + ATT + TGGVAT (SEQ ID NO: 17990) |
| 138 | CMMRCAR + G + ATTT + GGVAT (SEQ ID NO: 17991) |

TABLE 13-continued

| | |
|---|---|
| 138 | CMMRCAR + G + A + TTTGGVAT (SEQ ID NO: 17992) |
| 138 | TCMMRCA + R + AATTTGGVA (SEQ ID NO: 17993) |
| 138 | TC + MMRCARAATTTGGVA (SEQ ID NO: 17994) |
| 138 | +TCMMRCARAATTTGGVA (SEQ ID NO: 17995) |
| 138 | TCM + MRCARAATTTGGVA (SEQ ID NO: 17996) |
| 138 | TCMMRC + ARAATTTGGVA (SEQ ID NO: 17997) |
| 138 | TCMMRCARAATTTGGV + A (SEQ ID NO: 17998) |
| 138 | TCMMRCAR + AATTTGGVA (SEQ ID NO: 17999) |
| 138 | TCMMRCARAAT + TTGGVA (SEQ ID NO: 18000) |
| 138 | TCMMRCARA + ATTTGGVA (SEQ ID NO: 18001) |
| 138 | TCMMRC + A + R + AATTTGGVA (SEQ ID NO: 18002) |
| 138 | TCMM + RCA + R + AATTTGGVA (SEQ ID NO: 18003) |
| 138 | T + CMMRCA + R + AATTTGGVA (SEQ ID NO: 18004) |
| 138 | TC + MMRCA + R + AATTTGGVA (SEQ ID NO: 18005) |
| 138 | TCMMRCA + R + AAT + TTGGVA (SEQ ID NO: 18006) |
| 138 | TCMMRCA + R + A + ATTTGGVA (SEQ ID NO: 18007) |
| 138 | TCMMRCA + R + AATTTGG + VA (SEQ ID NO: 18008) |
| 138 | TCMMRCA + R + AA + TTTGGVA (SEQ ID NO: 18009) |
| 138 | CMMRCAR + G + ATTTGGV (SEQ ID NO: 18010) |
| 138 | CMMRCA + RGATTTGGV (SEQ ID NO: 18011) |
| 138 | CM + MRCARGATTTGGV (SEQ ID NO: 18012) |
| 138 | C + MMRCARGATTTGGV (SEQ ID NO: 18013) |
| 138 | CMMRCAR + GATTTGGV (SEQ ID NO: 18014) |
| 138 | CMMRCARGAT + TTGGV (SEQ ID NO: 18015) |
| 138 | CMMRCARGATTTGGVA (SEQ ID NO: 18016) |
| 138 | CMMRCARG + ATTTGGV (SEQ ID NO: 18017) |
| 138 | CMMRCARGATTTGGV (SEQ ID NO: 18018) |
| 138 | C + MMRCAR + G + ATTTGGV (SEQ ID NO: 18019) |
| 138 | CMMRC + AR + G + ATTTGGV (SEQ ID NO: 18020) |
| 138 | CM + MRCAR + G + ATTTGGV (SEQ ID NO: 18021) |
| 138 | CMM + RCAR + G + ATTTGGV (SEQ ID NO: 18022) |
| 138 | CMMRCAR + G + ATTTGGVA (SEQ ID NO: 18023) |
| 138 | CMMRCAR + G + ATT + TGGV (SEQ ID NO: 18024) |
| 138 | CMMRCAR + G + ATTT + GGV (SEQ ID NO: 18025) |
| 138 | CMMRCAR + G + A + TTTGGV (SEQ ID NO: 18026) |

TABLE 13-continued

| | | |
|---|---|---|
| 138 | TCMMRCA + R + AATTTGG (SEQ ID NO: 18027) |
| 138 | TC + MMRCARAATTTGG (SEQ ID NO: 18028) |
| 138 | +TCMMRCARAATTTGG (SEQ ID NO: 18029) |
| 138 | TCM + MRCARAATTTGG (SEQ ID NO: 18030) |
| 138 | TCMMRC + ARAATTTGG (SEQ ID NO: 18031) |
| 138 | TCMMRCARAATTTGGV (SEQ ID NO: 18032) |
| 138 | TCMMRCAR + AATTTGG (SEQ ID NO: 18033) |
| 138 | TCMMRCARAAT + TTGG (SEQ ID NO: 18034) |
| 138 | TCMMRCARA + ATTTGG (SEQ ID NO: 18035) |
| 138 | TCMMRC + A + R + AATTTGG (SEQ ID NO: 18036) |
| 138 | TCMM + RCA + R + AATTTGG (SEQ ID NO: 18037) |
| 138 | T + CMMRCA + R + AATTTGG (SEQ ID NO: 18038) |
| 138 | TC + MMRCA + R + AATTTGG (SEQ ID NO: 18039) |
| 138 | TCMMRCA + R + AAT + TTGG (SEQ ID NO: 18040) |
| 138 | TCMMRCA + R + A + ATTTGG (SEQ ID NO: 18041) |
| 138 | TCMMRCA + R + AATTTGG (SEQ ID NO: 18042) |
| 138 | TCMMRCA + R + AA + TTTGG (SEQ ID NO: 18043) |
| 138 | CMMRCAR + G + ATTTG (SEQ ID NO: 18044) |
| 138 | CMMRCA + RGATTTG (SEQ ID NO: 18045) |
| 138 | CM + MRCARGATTTG (SEQ ID NO: 18046) |
| 138 | C + MMRCARGATTTG (SEQ ID NO: 18047) |
| 138 | CMMRCAR + GATTTG (SEQ ID NO: 18048) |
| 138 | CMMRCARGAT + TTG (SEQ ID NO: 18049) |
| 138 | CMMRCARGATTTGG (SEQ ID NO: 18050) |
| 138 | CMMRCARG + ATTTG (SEQ ID NO: 18051) |
| 138 | C + MMRCAR + G + ATTTG (SEQ ID NO: 18052) |
| 138 | CMMRC + AR + G + ATTTG (SEQ ID NO: 18053) |
| 138 | CM + MRCAR + G + ATTTG (SEQ ID NO: 18054) |
| 138 | CMM + RCAR + G + ATTTG (SEQ ID NO: 18055) |
| 138 | CMMRCAR + G + ATTTGG (SEQ ID NO: 18056) |
| 138 | CMMRCAR + G + ATT + TG (SEQ ID NO: 18057) |
| 138 | CMMRCAR + G + ATTT + G (SEQ ID NO: 18058) |
| 138 | CMMRCAR + G + A + TTTG (SEQ ID NO: 18059) |
| 138 | TCMMRCA + R + AATTT (SEQ ID NO: 18060) |
| 138 | TC + MMRCARAATTT (SEQ ID NO: 18061) |
| 138 | +TCMMRCARAATTT (SEQ ID NO: 18062) |
| 138 | TCM + MRCARAATTT (SEQ ID NO: 18063) |
| 138 | TCMMRC + ARAATTT (SEQ ID NO: 18064) |
| 138 | TCMMRCARAATTTG (SEQ ID NO: 18065) |
| 138 | TCMMRCAR + AATTT (SEQ ID NO: 18066) |
| 138 | TCMMRCARAAT + TT (SEQ ID NO: 18067) |
| 138 | TCMMRCARA + ATTT (SEQ ID NO: 18068) |
| 138 | TCMMRC + A + R + AATTT (SEQ ID NO: 18069) |
| 138 | TCMM + RCA + R + AATTT (SEQ ID NO: 18070) |
| 138 | T + CMMRCA + R + AATTT (SEQ ID NO: 18071) |
| 138 | TC + MMRCA + R + AATTT (SEQ ID NO: 18072) |
| 138 | TCMMRCA + R + AAT + TT (SEQ ID NO: 18073) |
| 138 | TCMMRCA + R + A + ATTT (SEQ ID NO: 18074) |
| 138 | TCMMRCA + R + AATTTG (SEQ ID NO: 18075) |
| 138 | TCMMRCA + R + AA + TTT (SEQ ID NO: 18076) |
| 138 | TCMMRCARGATTTGGVAT (SEQ ID NO: 18077) |
| 138 | RTCMMRCARAATTTGGVA (SEQ ID NO: 18078) |
| 138 | CMMRCARGATTTGGVAT (SEQ ID NO: 18079) |
| 138 | TCMMRCARAATTTGGVA (SEQ ID NO: 18080) |
| 138 | CMMRCARGATTTGGV (SEQ ID NO: 18081) |
| 138 | TCMMRCARAATTTGG (SEQ ID NO: 18082) |
| 138 | CMMRCARGATTTG (SEQ ID NO: 18083) |
| 138 | TCMMRCARAATTT (SEQ ID NO: 18084) |
| 138 | AAACAGAARTTTGGA (SEQ ID NO: 18085) |
| 138 | AAACAGGCRTTTGGA (SEQ ID NO: 18086) |
| 140 | ARGAATTT + G + VATYCCCTA (SEQ ID NO: 18087) |
| 140 | ARGAA + TTTGVATYCCCTA (SEQ ID NO: 18088) |
| 140 | ARG + AATTTGVATYCCCTA (SEQ ID NO: 18089) |
| 140 | ARGAAT + TTGVATYCCCTA (SEQ ID NO: 18090) |
| 140 | ARGAATTT + GVATYCCCTA (SEQ ID NO: 18091) |
| 140 | ARGAATTTGVATYCC + CTA (SEQ ID NO: 18092) |
| 140 | ARGAATTTGVATYC + CCTA (SEQ ID NO: 18093) |
| 140 | ARGAATTTGVATYCCCT + A (SEQ ID NO: 18094) |
| 140 | ARGAATTTGVA + TYCCCTA (SEQ ID NO: 18095) |
| 140 | ARGA + ATTT + G + VATYCCCTA (SEQ ID NO: 18096) |
| 140 | ARG + AATTT + G + VATYCCCTA (SEQ ID NO: 18097) |
| 140 | ARGAATT + T + G + VATYCCCTA (SEQ ID NO: 18098) |
| 140 | A + RGAATTT + G + VATYCCCTA (SEQ ID NO: 18099) |
| 140 | ARGAATTT + G + VATY + CCCTA (SEQ ID NO: 18100) |
| 140 | ARGAATTT + G + VATYCCCT + A (SEQ ID NO: 18101) |
| 140 | ARGAATTT + G + VATYC + CCTA (SEQ ID NO: 18102) |

TABLE 13-continued

| | | |
|---|---|---|
| 140 | ARGAATTT + G + VAT + YCCCTA (SEQ ID NO: 18103) | |
| 140 | CARGAATT + T + GVATYCCCT (SEQ ID NO: 18104) | |
| 140 | CARG + AATTTGVATYCCCT (SEQ ID NO: 18105) | |
| 140 | CARGAATT + TGVATYCCCT (SEQ ID NO: 18106) | |
| 140 | CA + RGAATTTGVATYCCCT (SEQ ID NO: 18107) | |
| 140 | CARGAAT + TTGVATYCCCT (SEQ ID NO: 18108) | |
| 140 | CARGAATTTGVAT + YCCCT (SEQ ID NO: 18109) | |
| 140 | CARGAATTTGVATY + CCCT (SEQ ID NO: 18110) | |
| 140 | CARGAATTTGVATYC + CCT (SEQ ID NO: 18111) | |
| 140 | CARGAATTTGV + ATYCCCT (SEQ ID NO: 18112) | |
| 140 | CAR + GAATT + T + GVATYCCCT (SEQ ID NO: 18113) | |
| 140 | CA + RGAATT + T + GVATYCCCT (SEQ ID NO: 18114) | |
| 140 | C + ARGAATT + T + GVATYCCCT (SEQ ID NO: 18115) | |
| 140 | CARGAAT + T + T + GVATYCCCT (SEQ ID NO: 18116) | |
| 140 | CARGAATT + T + GV + ATYCCCT (SEQ ID NO: 18117) | |
| 140 | CARGAATT + T + GVATY + CCCT (SEQ ID NO: 18118) | |
| 140 | CARGAATT + T + GVA + TYCCCT (SEQ ID NO: 18119) | |
| 140 | CARGAATT + T + GVATYCC + CT (SEQ ID NO: 18120) | |
| 140 | CARGAA + TTTGVATYCCCT (SEQ ID NO: 18121) | |
| 140 | CAR + GAATTTGVATYCCCT (SEQ ID NO: 18122) | |
| 140 | C + ARGAATTTGVATYCCCT (SEQ ID NO: 18123) | |
| 140 | CARGAATTTGVATYCCC + T (SEQ ID NO: 18124) | |
| 140 | CARGAATTT + GVATYCCCT (SEQ ID NO: 18125) | |
| 140 | CARG + AATT + T + GVATYCCCT (SEQ ID NO: 18126) | |
| 140 | CARGA + ATT + T + GVATYCCCT (SEQ ID NO: 18127) | |
| 140 | CARGAATT + T + G + VATYCCCT (SEQ ID NO: 18128) | |
| 140 | CARGAATT + T + GVAT + YCCCT (SEQ ID NO: 18129) | |
| 140 | RGAATTT + G + VATYCCCTA (SEQ ID NO: 18130) | |
| 140 | RGAA + TTTGVATYCCCTA (SEQ ID NO: 18131) | |
| 140 | RG + AATTTGVATYCCCTA (SEQ ID NO: 18132) | |
| 140 | RGAAT + TTGVATYCCCTA (SEQ ID NO: 18133) | |
| 140 | RGAATTT + GVATYCCCTA (SEQ ID NO: 18134) | |
| 140 | RGAATTTGVATYCC + CTA (SEQ ID NO: 18135) | |
| 140 | RGAATTTGVATYC + CCTA (SEQ ID NO: 18136) | |
| 140 | RGAATTTGVATYCCCT + A (SEQ ID NO: 18137) | |
| 140 | RGAATTTGVA + TYCCCTA (SEQ ID NO: 18138) | |
| 140 | RGA + ATTT + G + VATYCCCTA (SEQ ID NO: 18139) | |
| 140 | RG + AATTT + G + VATYCCCTA (SEQ ID NO: 18140) | |
| 140 | RGAATT + T + G + VATYCCCTA (SEQ ID NO: 18141) | |
| 140 | +RGAATTT + G + VATYCCCTA (SEQ ID NO: 18142) | |
| 140 | RGAATTT + G + VATY + CCCTA (SEQ ID NO: 18143) | |
| 140 | RGAATTT + G + VATYCCCT + A (SEQ ID NO: 18144) | |
| 140 | RGAATTT + G + VATYC + CCTA (SEQ ID NO: 18145) | |
| 140 | RGAATTT + G + VAT + YCCCTA (SEQ ID NO: 18146) | |
| 140 | ARGAATT + T + GVATYCCCT (SEQ ID NO: 18147) | |
| 140 | ARG + AATTTGVATYCCCT (SEQ ID NO: 18148) | |
| 140 | ARGAATT + TGVATYCCCT (SEQ ID NO: 18149) | |
| 140 | A + RGAATTTGVATYCCCT (SEQ ID NO: 18150) | |
| 140 | ARGAAT + TTGVATYCCCT (SEQ ID NO: 18151) | |
| 140 | ARGAATTTGVAT + YCCCT (SEQ ID NO: 18152) | |
| 140 | ARGAATTTGVATY + CCCT (SEQ ID NO: 18153) | |
| 140 | ARGAATTTGVATYC + CCT (SEQ ID NO: 18154) | |
| 140 | ARGAATTTGV + ATYCCCT (SEQ ID NO: 18155) | |
| 140 | AR + GAATT + T + GVATYCCCT (SEQ ID NO: 18156) | |
| 140 | A + RGAATT + T + GVATYCCCT (SEQ ID NO: 18157) | |
| 140 | +ARGAATT + T + GVATYCCCT (SEQ ID NO: 18158) | |
| 140 | ARGAAT + T + T + GVATYCCCT (SEQ ID NO: 18159) | |
| 140 | ARGAATT + T + GV + ATYCCCT (SEQ ID NO: 18160) | |
| 140 | ARGAATT + T + GVATY + CCCT (SEQ ID NO: 18161) | |
| 140 | ARGAATT + T + GVA + TYCCCT (SEQ ID NO: 18162) | |
| 140 | ARGAATT + T + GVATYCC + CT (SEQ ID NO: 18163) | |
| 140 | ARGAA + TTTGVATYCCCT (SEQ ID NO: 18164) | |
| 140 | AR + GAATTTGVATYCCCT (SEQ ID NO: 18165) | |
| 140 | +ARGAATTTGVATYCCCT (SEQ ID NO: 18166) | |
| 140 | ARGAATTTGVATYCCC + T (SEQ ID NO: 18167) | |
| 140 | ARGAATTT + GVATYCCCT (SEQ ID NO: 18168) | |

TABLE 13-continued

| | |
|---|---|
| 140 | ARG + AATT + T + GVATYCCCT (SEQ ID NO: 18169) |
| 140 | ARGA + ATT + T + GVATYCCCT (SEQ ID NO: 18170) |
| 140 | ARGAATT + T + G + VATYCCCT (SEQ ID NO: 18171) |
| 140 | ARGAATT + T + GVAT + YCCCT (SEQ ID NO: 18172) |
| 140 | RGAATTT + G + VATYCCC (SEQ ID NO: 18173) |
| 140 | RGAA + TTTGVATYCCC (SEQ ID NO: 18174) |
| 140 | RG + AATTTGVATYCCC (SEQ ID NO: 18175) |
| 140 | RGAAT + TTGVATYCCC (SEQ ID NO: 18176) |
| 140 | RGAATTT + GVATYCCC (SEQ ID NO: 18177) |
| 140 | RGAATTTGVATYCC + C (SEQ ID NO: 18178) |
| 140 | RGAATTTGVATYC + CC (SEQ ID NO: 18179) |
| 140 | RGAATTTGVATYCCCT (SEQ ID NO: 18180) |
| 140 | RGAATTTGVA + TYCCC (SEQ ID NO: 18181) |
| 140 | RGA + ATTT + G + VATYCCC (SEQ ID NO: 18182) |
| 140 | RG + AATTT + G + VATYCCC (SEQ ID NO: 18183) |
| 140 | RGAATT + T + G + VATYCCC (SEQ ID NO: 18184) |
| 140 | +RGAATTT + G + VATYCCC (SEQ ID NO: 18185) |
| 140 | RGAATTT + G + VATY + CCC (SEQ ID NO: 18186) |
| 140 | RGAATTT + G + VATYCCCT (SEQ ID NO: 18187) |
| 140 | RGAATTT + G + VATYC + CC (SEQ ID NO: 18188) |
| 140 | RGAATTT + G + VAT + YCCC (SEQ ID NO: 18189) |
| 140 | ARGAATT + T + GVATYCC (SEQ ID NO: 18190) |
| 140 | ARG + AATTTGVATYCC (SEQ ID NO: 18191) |
| 140 | ARGAATT + TGVATYCC (SEQ ID NO: 18192) |
| 140 | A + RGAATTTGVATYCC (SEQ ID NO: 18193) |
| 140 | ARGAAT + TTGVATYCC (SEQ ID NO: 18194) |
| 140 | ARGAATTTGVAT + YCC (SEQ ID NO: 18195) |
| 140 | ARGAATTTGVATY + CC (SEQ ID NO: 18196) |
| 140 | ARGAATTTGVATYC + C (SEQ ID NO: 18197) |
| 140 | ARGAATTTGV + ATYCC (SEQ ID NO: 18198) |
| 140 | AR + GAATT + T + GVATYCC (SEQ ID NO: 18199) |
| 140 | A + RGAATT + T + GVATYCC (SEQ ID NO: 18200) |
| 140 | +ARGAATT + T + GVATYCC (SEQ ID NO: 18201) |
| 140 | ARGAAT + T + T + GVATYCC (SEQ ID NO: 18202) |
| 140 | ARGAATT + T + GV + ATYCC (SEQ ID NO: 18203) |
| 140 | ARGAATT + T + GVATY + CC (SEQ ID NO: 18204) |
| 140 | ARGAATT + T + GVA + TYCC (SEQ ID NO: 18205) |
| 140 | ARGAATT + T + GVATYCC (SEQ ID NO: 18206) |
| 140 | ARGAA + TTTGVATYCC (SEQ ID NO: 18207) |
| 140 | AR + GAATTTGVATYCC (SEQ ID NO: 18208) |
| 140 | +ARGAATTTGVATYCC (SEQ ID NO: 18209) |
| 140 | ARGAATTTGVATYCC (SEQ ID NO: 18210) |
| 140 | ARGAATTT + GVATYCC (SEQ ID NO: 18211) |
| 140 | ARG + AATT + T + GVATYCC (SEQ ID NO: 18212) |
| 140 | ARGA + ATT + T + GVATYCC (SEQ ID NO: 18213) |
| 140 | ARGAATT + T + G + VATYCC (SEQ ID NO: 18214) |
| 140 | ARGAATT + T + GVAT + YCC (SEQ ID NO: 18215) |
| 140 | RGAATTT + G + VATYC (SEQ ID NO: 18216) |
| 140 | RGAA + TTTGVATYC (SEQ ID NO: 18217) |
| 140 | RG + AATTTGVATYC (SEQ ID NO: 18218) |
| 140 | RGAAT + TTGVATYC (SEQ ID NO: 18219) |
| 140 | RGAATTT + GVATYC (SEQ ID NO: 18220) |
| 140 | RGAATTTGVATYCC (SEQ ID NO: 18221) |
| 140 | RGAATTTGVATYC (SEQ ID NO: 18222) |
| 140 | RGAATTTGVA + TYC (SEQ ID NO: 18223) |
| 140 | RGA + ATTT + G + VATYC (SEQ ID NO: 18224) |
| 140 | RG + AATTT + G + VATYC (SEQ ID NO: 18225) |
| 140 | RGAATT + T + G + VATYC (SEQ ID NO: 18226) |
| 140 | +RGAATTT + G + VATYC (SEQ ID NO: 18227) |
| 140 | RGAATTT + G + VATY + C (SEQ ID NO: 18228) |
| 140 | RGAATTT + G + VATYCC (SEQ ID NO: 18229) |
| 140 | RGAATTT + G + VATYC (SEQ ID NO: 18230) |
| 140 | RGAATTT + G + VAT + YC (SEQ ID NO: 18231) |
| 140 | ARGAATT + T + GVATY (SEQ ID NO: 18232) |
| 140 | ARG + AATTTGVATY (SEQ ID NO: 18233) |
| 140 | ARGAATT + TGVATY (SEQ ID NO: 18234) |
| 140 | A + RGAATTTGVATY (SEQ ID NO: 18235) |
| 140 | ARGAAT + TTGVATY (SEQ ID NO: 18236) |
| 140 | ARGAATTTGVAT + Y (SEQ ID NO: 18237) |
| 140 | ARGAATTTGVATY (SEQ ID NO: 18238) |
| 140 | ARGAATTTGVATYC (SEQ ID NO: 18239) |
| 140 | ARGAATTTGV + ATY (SEQ ID NO: 18240) |
| 140 | AR + GAATT + T + GVATY (SEQ ID NO: 18241) |
| 140 | A + RGAATT + T + GVATY (SEQ ID NO: 18242) |
| 140 | +ARGAATT + T + GVATY (SEQ ID NO: 18243) |
| 140 | ARGAAT + T + T + GVATY (SEQ ID NO: 18244) |
| 140 | ARGAATT + T + GV + ATY (SEQ ID NO: 18245) |
| 140 | ARGAATT + T + GVATY (SEQ ID NO: 18246) |

TABLE 13-continued

| | |
|---|---|
| 140 | ARGAATT + T + GVA + TY (SEQ ID NO: 18247) |
| 140 | ARGAATT + T + GVATYC (SEQ ID NO: 18248) |
| 140 | ARGAA + TTTGVATY (SEQ ID NO: 18249) |
| 140 | AR + GAATTTGVATY (SEQ ID NO: 18250) |
| 140 | +ARGAATTTGVATY (SEQ ID NO: 18251) |
| 140 | ARGAATTT + GVATY (SEQ ID NO: 18252) |
| 140 | ARG + AATT + T + GVATY (SEQ ID NO: 18253) |
| 140 | ARGA + ATT + T + GVATY (SEQ ID NO: 18254) |
| 140 | ARGAATT + T + G + VATY (SEQ ID NO: 18255) |
| 140 | ARGAATT + T + GVAT + Y (SEQ ID NO: 18256) |
| 140 | ARGAATTTGVATYCCCTA (SEQ ID NO: 18257) |
| 140 | CARGAATTTGVATYCCCT (SEQ ID NO: 18258) |
| 140 | RGAATTTGVATYCCCTA (SEQ ID NO: 18259) |
| 140 | ARGAATTTGVATYCCCT (SEQ ID NO: 18260) |
| 140 | RGAATTTGVATYCCC (SEQ ID NO: 18261) |
| 140 | ARGAATTTGVATYCC (SEQ ID NO: 18262) |
| 140 | RGAATTTGVATYC (SEQ ID NO: 18263) |
| 140 | ARGAATTTGVATY (SEQ ID NO: 18264) |
| 140 | AATTTAGYATTCCCT (SEQ ID NO: 18265) |
| 140 | AATTTGCNATTCCCT (SEQ ID NO: 18266) |
| 140 | AATTTTGYATTCCCT (SEQ ID NO: 18267) |
| 143 | GVATYCCC + T + CAATCCCA (SEQ ID NO: 18268) |
| 143 | GVAT + YCCCTCAATCCCA (SEQ ID NO: 18269) |
| 143 | GV + ATYCCCTCAATCCCA (SEQ ID NO: 18270) |
| 143 | GVATY + CCCTCAATCCCA (SEQ ID NO: 18271) |
| 143 | GVATYCCC + TCAATCCCA (SEQ ID NO: 18272) |
| 143 | GVATYCCCTCAATC + CCA (SEQ ID NO: 18273) |
| 143 | GVATYCCCTCAATCC + CA (SEQ ID NO: 18274) |
| 143 | GVATYCCCTC + AATCCCA (SEQ ID NO: 18275) |
| 143 | GVATYCCCTCAAT + CCCA (SEQ ID NO: 18276) |
| 143 | GV + ATYCCC + T + CAATCCCA (SEQ ID NO: 18277) |
| 143 | GVATYC + CC + T + CAATCCCA (SEQ ID NO: 18278) |
| 143 | G + VATYCCC + T + CAATCCCA (SEQ ID NO: 18279) |
| 143 | GVATY + CCC + T + CAATCCCA (SEQ ID NO: 18280) |
| 143 | GVATYCCC + T + CAATCCC + CA (SEQ ID NO: 18281) |
| 143 | GVATYCCC + T + CAA + TCCCA (SEQ ID NO: 18282) |
| 143 | GVATYCCC + T + CAATCCCC + A (SEQ ID NO: 18283) |
| 143 | GVATYCCC + T + C + AATCCCCA (SEQ ID NO: 18284) |
| 143 | GGVATYCC + C + ACAATCCCC (SEQ ID NO: 18285) |
| 143 | G + GVATYCCCACAATCCCC (SEQ ID NO: 18286) |
| 143 | GG + VATYCCCACAATCCCC (SEQ ID NO: 18287) |
| 143 | GGVATYCC + CACAATCCCC (SEQ ID NO: 18288) |
| 143 | GGVA + TYCCCACAATCCCC (SEQ ID NO: 18289) |
| 143 | GGVATYCCCACAA + TCCCC (SEQ ID NO: 18290) |
| 143 | GGVATYCCCACAATCCC + C (SEQ ID NO: 18291) |
| 143 | GGVATYCCCA + CAATCCCC (SEQ ID NO: 18292) |
| 143 | GGVATYCCCAC + AATCCCC (SEQ ID NO: 18293) |
| 143 | GGVATY + CC + C + ACAATCCCC (SEQ ID NO: 18294) |
| 143 | GGVAT + YCC + C + ACAATCCCC (SEQ ID NO: 18295) |
| 143 | GG + VATYCC + C + ACAATCCCC (SEQ ID NO: 18296) |
| 143 | GGVA + TYCC + C + ACAATCCCC (SEQ ID NO: 18297) |
| 143 | GGVATYCC + C + ACAATC + CCC (SEQ ID NO: 18298) |
| 143 | GGVATYCC + C + A + CAATCCCC (SEQ ID NO: 18299) |
| 143 | GGVATYCC + C + ACAA + TCCCC (SEQ ID NO: 18300) |
| 143 | GGVATYCC + C + ACAATCCC + C (SEQ ID NO: 18301) |
| 143 | G + VATYCCCTCAATCCCA (SEQ ID NO: 18302) |
| 143 | GVA + TYCCCTCAATCCCA (SEQ ID NO: 18303) |
| 143 | GVATYCCCTCAATCCCC + A (SEQ ID NO: 18304) |
| 143 | GVATYCCCTCA + ATCCCCA (SEQ ID NO: 18305) |
| 143 | GVATYCC + C + T + CAATCCCCA (SEQ ID NO: 18306) |
| 143 | GVATYCCC + T + CAAT + CCCCA (SEQ ID NO: 18307) |
| 143 | GVATYCCC + T + CA + ATCCCCA (SEQ ID NO: 18308) |
| 143 | VATYCCC + T + CAATCCCCA (SEQ ID NO: 18309) |
| 143 | VAT + YCCCTCAATCCCCA (SEQ ID NO: 18310) |
| 143 | V + ATYCCCTCAATCCCCA (SEQ ID NO: 18311) |
| 143 | VATY + CCCTCAATCCCCA (SEQ ID NO: 18312) |
| 143 | VATYCCC + TCAATCCCCA (SEQ ID NO: 18313) |
| 143 | VATYCCCTCAATC + CCCA (SEQ ID NO: 18314) |
| 143 | VATYCCCTCAATCC + CCA (SEQ ID NO: 18315) |
| 143 | VATYCCCTC + AATCCCCA (SEQ ID NO: 18316) |
| 143 | VATYCCCTCAAT + CCCCA (SEQ ID NO: 18317) |

TABLE 13-continued

| 143 | V + ATYCCC + T + CAATCCCCA (SEQ ID NO: 18318) |
| --- | --- |
| 143 | VATYC + CC + T + CAATCCCCA (SEQ ID NO: 18319) |
| 143 | +VATYCCC + T + CAATCCCCA (SEQ ID NO: 18320) |
| 143 | VATY + CCC + T + CAATCCCCA (SEQ ID NO: 18321) |
| 143 | VATYCCC + T + CAATCCC + CA (SEQ ID NO: 18322) |
| 143 | VATYCCC + T + CAA + TCCCCA (SEQ ID NO: 18323) |
| 143 | VATYCCC + T + CAATCCCC + A (SEQ ID NO: 18324) |
| 143 | VATYCCC + T + C + AATCCCCA (SEQ ID NO: 18325) |
| 143 | GVATYCC + C + ACAATCCCC (SEQ ID NO: 18326) |
| 143 | +GVATYCCCACAATCCCC (SEQ ID NO: 18327) |
| 143 | G + VATYCCCACAATCCCC (SEQ ID NO: 18328) |
| 143 | GVATYCC + CACAATCCCC (SEQ ID NO: 18329) |
| 143 | GVA + TYCCCACAATCCCC (SEQ ID NO: 18330) |
| 143 | GVATYCCCACAA + TCCCC (SEQ ID NO: 18331) |
| 143 | GVATYCCCACAATCCC + C (SEQ ID NO: 18332) |
| 143 | GVATYCCCA + CAATCCCC (SEQ ID NO: 18333) |
| 143 | GVATYCCCAC + AATCCCC (SEQ ID NO: 18334) |
| 143 | GVATY + CC + C + ACAATCCCC (SEQ ID NO: 18335) |
| 143 | GVAT + YCC + C + ACAATCCCC (SEQ ID NO: 18336) |
| 143 | G + VATYCC + C + ACAATCCCC (SEQ ID NO: 18337) |
| 143 | GVA + TYCC + C + ACAATCCCC (SEQ ID NO: 18338) |
| 143 | GVATYCC + C + ACAATC + CCC (SEQ ID NO: 18339) |
| 143 | GVATYCC + C + A + CAATCCCC (SEQ ID NO: 18340) |
| 143 | GVATYCC + C + ACAA + TCCCC (SEQ ID NO: 18341) |
| 143 | GVATYCC + C + ACAATCCC + C (SEQ ID NO: 18342) |
| 143 | +VATYCCCTCAATCCCCA (SEQ ID NO: 18343) |
| 143 | VA + TYCCCTCAATCCCCA (SEQ ID NO: 18344) |
| 143 | VATYCCCTCAATCCCC + A (SEQ ID NO: 18345) |
| 143 | VATYCCCTCA + ATCCCCA (SEQ ID NO: 18346) |
| 143 | VATYCC + C + T + CAATCCCCA (SEQ ID NO: 18347) |
| 143 | VATYCCC + T + CAAT + CCCCA (SEQ ID NO: 18348) |
| 143 | VATYCCC + T + CA + ATCCCCA (SEQ ID NO: 18349) |
| 143 | VATYCCC + T + CAATCCC (SEQ ID NO: 18350) |
| 143 | VAT + YCCCTCAATCCC (SEQ ID NO: 18351) |
| 143 | V + ATYCCCTCAATCCC (SEQ ID NO: 18352) |
| 143 | VATY + CCCTCAATCCC (SEQ ID NO: 18353) |
| 143 | VATYCCC + TCAATCCC (SEQ ID NO: 18354) |
| 143 | VATYCCCTCAATC + CC (SEQ ID NO: 18355) |
| 143 | VATYCCCTCAATCC + C (SEQ ID NO: 18356) |
| 143 | VATYCCCTC + AATCCC (SEQ ID NO: 18357) |
| 143 | VATYCCCTCAAT + CCC (SEQ ID NO: 18358) |
| 143 | V + ATYCCC + T + CAATCCC (SEQ ID NO: 18359) |
| 143 | VATYC + CC + T + CAATCCC (SEQ ID NO: 18360) |
| 143 | +VATYCCC + T + CAATCCC (SEQ ID NO: 18361) |
| 143 | VATY + CCC + T + CAATCCC (SEQ ID NO: 18362) |
| 143 | VATYCCC + T + CAATCCC (SEQ ID NO: 18363) |
| 143 | VATYCCC + T + CAA + TCCC (SEQ ID NO: 18364) |
| 143 | VATYCCC + T + CAATCCCC (SEQ ID NO: 18365) |
| 143 | VATYCCC + T + C + AATCCC (SEQ ID NO: 18366) |
| 143 | GVATYCC + C + ACAATCC (SEQ ID NO: 18367) |
| 143 | +GVATYCCCACAATCC (SEQ ID NO: 18368) |
| 143 | G + VATYCCCACAATCC (SEQ ID NO: 18369) |
| 143 | GVATYCC + CACAATCC (SEQ ID NO: 18370) |
| 143 | GVA + TYCCCACAATCC (SEQ ID NO: 18371) |
| 143 | GVATYCCCACAA + TCC (SEQ ID NO: 18372) |
| 143 | GVATYCCCACAATCCC (SEQ ID NO: 18373) |
| 143 | GVATYCCCA + CAATCC (SEQ ID NO: 18374) |
| 143 | GVATYCCCAC + AATCC (SEQ ID NO: 18375) |
| 143 | GVATY + CC + C + ACAATCC (SEQ ID NO: 18376) |
| 143 | GVAT + YCC + C + ACAATCC (SEQ ID NO: 18377) |
| 143 | G + VATYCC + C + ACAATCC (SEQ ID NO: 18378) |
| 143 | GVA + TYCC + C + ACAATCC (SEQ ID NO: 18379) |
| 143 | GVATYCC + C + ACAATC + C (SEQ ID NO: 18380) |
| 143 | GVATYCC + C + A + CAATCC (SEQ ID NO: 18381) |
| 143 | GVATYCC + C + ACAA + TCC (SEQ ID NO: 18382) |
| 143 | GVATYCC + C + ACAATCCC (SEQ ID NO: 18383) |
| 143 | +VATYCCCTCAATCCC (SEQ ID NO: 18384) |
| 143 | VA + TYCCCTCAATCCC (SEQ ID NO: 18385) |
| 143 | VATYCCCTCAATCCCC (SEQ ID NO: 18386) |
| 143 | VATYCCCTCA + ATCCC (SEQ ID NO: 18387) |
| 143 | VATYCC + C + T + CAATCCC (SEQ ID NO: 18388) |

TABLE 13-continued

| | | |
|---|---|---|
| 143 | VATYCCC + T + CAAT + CCC (SEQ ID NO: 18389) | |
| 143 | VATYCCC + T + CA + ATCCC (SEQ ID NO: 18390) | |
| 143 | VATYCCC + T + CAATC (SEQ ID NO: 18391) | |
| 143 | VAT + YCCCTCAATC (SEQ ID NO: 18392) | |
| 143 | V + ATYCCCTCAATC (SEQ ID NO: 18393) | |
| 143 | VATY + CCCTCAATC (SEQ ID NO: 18394) | |
| 143 | VATYCCC + TCAATC (SEQ ID NO: 18395) | |
| 143 | VATYCCCTCAATC (SEQ ID NO: 18396) | |
| 143 | VATYCCCTCAATCC (SEQ ID NO: 18397) | |
| 143 | VATYCCCTC + AATC (SEQ ID NO: 18398) | |
| 143 | VATYCCCTCAAT + C (SEQ ID NO: 18399) | |
| 143 | V + ATYCCC + T + CAATC (SEQ ID NO: 18400) | |
| 143 | VATYC + CC + T + CAATC (SEQ ID NO: 18401) | |
| 143 | +VATYCCC + T + CAATC (SEQ ID NO: 18402) | |
| 143 | VATY + CCC + T + CAATC (SEQ ID NO: 18403) | |
| 143 | VATYCCC + T + CAATCC (SEQ ID NO: 18404) | |
| 143 | VATYCCC + T + CAA + TC (SEQ ID NO: 18405) | |
| 143 | VATYCCC + T + C + AATC (SEQ ID NO: 18406) | |
| 143 | GVATYCC + C + ACAAT (SEQ ID NO: 18407) | |
| 143 | +GVATYCCCACAAT (SEQ ID NO: 18408) | |
| 143 | G + VATYCCCACAAT (SEQ ID NO: 18409) | |
| 143 | GVATYCC + CACAAT (SEQ ID NO: 18410) | |
| 143 | GVA + TYCCCACAAT (SEQ ID NO: 18411) | |
| 143 | GVATYCCCACAA + T (SEQ ID NO: 18412) | |
| 143 | GVATYCCCACAATC (SEQ ID NO: 18413) | |
| 143 | GVATYCCCA + CAAT (SEQ ID NO: 18414) | |
| 143 | GVATYCCCAC + AAT (SEQ ID NO: 18415) | |
| 143 | GVATY + CC + C + ACAAT (SEQ ID NO: 18416) | |
| 143 | GVAT + YCC + C + ACAAT (SEQ ID NO: 18417) | |
| 143 | G + VATYCC + C + ACAAT (SEQ ID NO: 18418) | |
| 143 | GVA + TYCC + C + ACAAT (SEQ ID NO: 18419) | |
| 143 | GVATYCC + C + ACAATC (SEQ ID NO: 18420) | |
| 143 | GVATYCC + C + A + CAAT (SEQ ID NO: 18421) | |
| 143 | GVATYCC + C + ACAA + T (SEQ ID NO: 18422) | |
| 143 | +VATYCCCTCAATC (SEQ ID NO: 18423) | |
| 143 | VA + TYCCCTCAATC (SEQ ID NO: 18424) | |
| 143 | VATYCCCTCA + ATC (SEQ ID NO: 18425) | |
| 143 | VATYCC + C + T + CAATC (SEQ ID NO: 18426) | |
| 143 | VATYCCC + T + CAAT + C (SEQ ID NO: 18427) | |
| 143 | VATYCCC + T + CA + ATC (SEQ ID NO: 18428) | |
| 143 | GVATYCCCTCAATCCCCA (SEQ ID NO: 18429) | |
| 143 | GGVATYCCCACAATCCCC (SEQ ID NO: 18430) | |
| 143 | VATYCCCTCAATCCCCA (SEQ ID NO: 18431) | |
| 143 | GVATYCCCACAATCCCC (SEQ ID NO: 18432) | |
| 143 | VATYCCCTCAATCCC (SEQ ID NO: 18433) | |
| 143 | GVATYCCCACAATCC (SEQ ID NO: 18434) | |
| 143 | VATYCCCTCAATC (SEQ ID NO: 18435) | |
| 143 | GVATYCCCACAAT (SEQ ID NO: 18436) | |
| 143 | ATTCCCTGYAATCCC (SEQ ID NO: 18437) | |
| 143 | ATTCCCCGYAATCCC (SEQ ID NO: 18438) | |
| 143 | ATTCCCAGRAATCCC (SEQ ID NO: 18439) | |
| 143 | ATTCCCCAYAATCCC (SEQ ID NO: 18440) | |
| 143 | ATTCCCAARAATCCC (SEQ ID NO: 18441) | |
| 143 | ATTCCCAGYAATCCC (SEQ ID NO: 18442) | |
| 143 | ATTCCCGGYAATCCC (SEQ ID NO: 18443) | |
| 143 | ATTCCCGCYAATCCC (SEQ ID NO: 18444) | |
| 145 | CCCTACAA + T + CCCAAAGYC (SEQ ID NO: 18445) | |
| 145 | C + CCTACAATCCCAAAGYC (SEQ ID NO: 18446) | |
| 145 | CC + CTACAATCCCAAAGYC (SEQ ID NO: 18447) | |
| 145 | CCCTACAA + TCCCAAAGYC (SEQ ID NO: 18448) | |
| 145 | CCC + TACAATCCCAAAGYC (SEQ ID NO: 18449) | |
| 145 | CCCTACAATCCCAAAGY + C (SEQ ID NO: 18450) | |
| 145 | CCCTACAATCCCA + AAGYC (SEQ ID NO: 18451) | |
| 145 | CCCTACAATCCC + AAAGYC (SEQ ID NO: 18452) | |
| 145 | CCCTACAATCCCAA + AGYC (SEQ ID NO: 18453) | |
| 145 | CC + CTACAA + T + CCCAAAGYC (SEQ ID NO: 18454) | |
| 145 | CCC + TACAA + T + CCCAAAGYC (SEQ ID NO: 18455) | |
| 145 | CCCTACA + A + T + CCCAAAGYC (SEQ ID NO: 18456) | |
| 145 | CCCTA + CAA + T + CCCAAAGYC (SEQ ID NO: 18457) | |
| 145 | CCCTACAA + T + CCCAA + AGYC (SEQ ID NO: 18458) | |
| 145 | CCCTACAA + T + C + CCAAAGYC (SEQ ID NO: 18459) | |
| 145 | CCCTACAA + T + CCCA + AAGYC (SEQ ID NO: 18460) | |
| 145 | CCCTACAA + T + CCCAAAGY + C (SEQ ID NO: 18461) | |
| 145 | CCTACAA + T + CCCAAAGYC (SEQ ID NO: 18462) | |
| 145 | +CCTACAATCCCAAAGYC (SEQ ID NO: 18463) | |
| 145 | C + CTACAATCCCAAAGYC (SEQ ID NO: 18464) | |

TABLE 13-continued

| 145 | CCTACAA + TCCCAAAGYC (SEQ ID NO: 18465) |
| 145 | CC + TACAATCCCAAAGYC (SEQ ID NO: 18466) |
| 145 | CCTACAATCCCAAAGY + C (SEQ ID NO: 18467) |
| 145 | CCTACAATCCCA + AAGYC (SEQ ID NO: 18468) |
| 145 | CCTACAATCCC + AAAGYC (SEQ ID NO: 18469) |
| 145 | CCTACAATCCCAA + AGYC (SEQ ID NO: 18470) |
| 145 | C + CTACAA + T + CCCAAAGYC (SEQ ID NO: 18471) |
| 145 | CC + TACAA + T + CCCAAAGYC (SEQ ID NO: 18472) |
| 145 | CCTACA + A + T + CCCAAAGYC (SEQ ID NO: 18473) |
| 145 | CCTA + CAA + T + CCCAAAGYC (SEQ ID NO: 18474) |
| 145 | CCTACAA + T + CCCAA + AGYC (SEQ ID NO: 18475) |
| 145 | CCTACAA + T + C + CCAAAGYC (SEQ ID NO: 18476) |
| 145 | CCTACAA + T + CCCA + AAGYC (SEQ ID NO: 18477) |
| 145 | CCTACAA + T + CCCAAAGY + C (SEQ ID NO: 18478) |
| 145 | CCTACAA + T + CCCAAAG (SEQ ID NO: 18479) |
| 145 | +CCTACAATCCCAAAG (SEQ ID NO: 18480) |
| 145 | C + CTACAATCCCAAAG (SEQ ID NO: 18481) |
| 145 | CCTACAA + TCCCAAAG (SEQ ID NO: 18482) |
| 145 | CC + TACAATCCCAAAG (SEQ ID NO: 18483) |
| 145 | CCTACAATCCCAAAGY (SEQ ID NO: 18484) |
| 145 | CCTACAATCCCA + AAG (SEQ ID NO: 18485) |
| 145 | CCTACAATCCC + AAAG (SEQ ID NO: 18486) |
| 145 | CCTACAATCCCAA + AG (SEQ ID NO: 18487) |
| 145 | C + CTACAA + T + CCCAAAG (SEQ ID NO: 18488) |
| 145 | CC + TACAA + T + CCCAAAG (SEQ ID NO: 18489) |
| 145 | CCTACA + A + T + CCCAAAG (SEQ ID NO: 18490) |
| 145 | CCTA + CAA + T + CCCAAAG (SEQ ID NO: 18491) |
| 145 | CCTACAA + T + CCCAA + AG (SEQ ID NO: 18492) |
| 145 | CCTACAA + T + C + CCAAAG (SEQ ID NO: 18493) |
| 145 | CCTACAA + T + CCCA + AAG (SEQ ID NO: 18494) |
| 145 | CCTACAA + T + CCCAAAGY (SEQ ID NO: 18495) |
| 145 | CCTACAA + T + CCCAA (SEQ ID NO: 18496) |
| 145 | +CCTACAATCCCAA (SEQ ID NO: 18497) |
| 145 | C + CTACAATCCCAA (SEQ ID NO: 18498) |
| 145 | CCTACAA + TCCCAA (SEQ ID NO: 18499) |
| 145 | CC + TACAATCCCAA (SEQ ID NO: 18500) |
| 145 | CCTACAATCCCAAA (SEQ ID NO: 18501) |
| 145 | CCTACAATCCCA + A (SEQ ID NO: 18502) |
| 145 | CCTACAATCCC + AA (SEQ ID NO: 18503) |
| 145 | CCTACAATCCCAA (SEQ ID NO: 18504) |
| 145 | C + CTACAA + T + CCCAA (SEQ ID NO: 18505) |
| 145 | CC + TACAA + T + CCCAA (SEQ ID NO: 18506) |
| 145 | CCTACA + A + T + CCCAA (SEQ ID NO: 18507) |
| 145 | CCTA + CAA + T + CCCAA (SEQ ID NO: 18508) |
| 145 | CCTACAA + T + CCCAA (SEQ ID NO: 18509) |
| 145 | CCTACAA + T + C + CCAA (SEQ ID NO: 18510) |
| 145 | CCTACAA + T + CCCA + A (SEQ ID NO: 18511) |
| 145 | CCTACAA + T + CCCAAA (SEQ ID NO: 18512) |
| 145 | CCCTACAATCCCAAAGYC (SEQ ID NO: 18513) |
| 145 | CCTACAATCCCAAAGYC (SEQ ID NO: 18514) |
| 145 | CCTACAATCCCAAAG (SEQ ID NO: 18515) |
| 145 | CCTACAATCCCAA (SEQ ID NO: 18516) |
| 145 | TACAATAGYCAAAGT (SEQ ID NO: 18517) |
| 146 | ACAATCCC + C + AAGYCARGG (SEQ ID NO: 18518) |
| 146 | ACAAT + CCCCAAGYCARGG (SEQ ID NO: 18519) |
| 146 | ACAATCC + CCAAGYCARGG (SEQ ID NO: 18520) |
| 146 | ACAA + TCCCCAAGYCARGG (SEQ ID NO: 18521) |
| 146 | ACA + ATCCCCAAGYCARGG (SEQ ID NO: 18522) |
| 146 | ACAATCCCCAAGYCA + RGG (SEQ ID NO: 18523) |
| 146 | ACAATCCCC + AAGYCARGG (SEQ ID NO: 18524) |
| 146 | ACAATCCCCAAGYC + ARGG (SEQ ID NO: 18525) |
| 146 | ACAATCCCCAAGY + CARGG (SEQ ID NO: 18526) |
| 146 | ACAA + TCCC + C + AAGYCARGG (SEQ ID NO: 18527) |
| 146 | A + CAATCCC + C + AAGYCARGG (SEQ ID NO: 18528) |
| 146 | AC + AATCCC + C + AAGYCARGG (SEQ ID NO: 18529) |
| 146 | ACAAT + CCC + C + AAGYCARGG (SEQ ID NO: 18530) |
| 146 | ACAATCCC + C + AAGYCAR + GG (SEQ ID NO: 18531) |
| 146 | ACAATCCC + C + A + AGYCARGG (SEQ ID NO: 18532) |
| 146 | ACAATCCC + C + AAGY + CARGG (SEQ ID NO: 18533) |
| 146 | ACAATCCC + C + AAGYCA + RGG (SEQ ID NO: 18534) |
| 146 | CAATCCC + C + AAGYCARGG (SEQ ID NO: 18535) |
| 146 | CAAT + CCCCAAGYCARGG (SEQ ID NO: 18536) |

TABLE 13-continued

| | | |
|---|---|---|
| 146 | CAATCC + CCAAGYCARGG | (SEQ ID NO: 18537) |
| 146 | CAA + TCCCCAAGYCARGG | (SEQ ID NO: 18538) |
| 146 | CA + ATCCCCAAGYCARGG | (SEQ ID NO: 18539) |
| 146 | CAATCCCCAAGYCA + RGG | (SEQ ID NO: 18540) |
| 146 | CAATCCCC + AAGYCARGG | (SEQ ID NO: 18541) |
| 146 | CAATCCCCAAGYC + ARGG | (SEQ ID NO: 18542) |
| 146 | CAATCCCCAAGY + CARGG | (SEQ ID NO: 18543) |
| 146 | CAA + TCCC + C + AAGYCARGG | (SEQ ID NO: 18544) |
| 146 | +CAATCCC + C + AAGYCARGG | (SEQ ID NO: 18545) |
| 146 | C + AATCCC + C + AAGYCARGG | (SEQ ID NO: 18546) |
| 146 | CAAT + CCC + C + AAGYCARGG | (SEQ ID NO: 18547) |
| 146 | CAATCCC + C + AAGYCAR + GG | (SEQ ID NO: 18548) |
| 146 | CAATCCC + C + A + AGYCARGG | (SEQ ID NO: 18549) |
| 146 | CAATCCC + C + AAGY + CARGG | (SEQ ID NO: 18550) |
| 146 | CAATCCC + C + AAGYCA + RGG | (SEQ ID NO: 18551) |
| 146 | CAATCCC + C + AAGYCAR | (SEQ ID NO: 18552) |
| 146 | CAAT + CCCCAAGYCAR | (SEQ ID NO: 18553) |
| 146 | CAATCC + CCAAGYCAR | (SEQ ID NO: 18554) |
| 146 | CAA + TCCCCAAGYCAR | (SEQ ID NO: 18555) |
| 146 | CA + ATCCCCAAGYCAR | (SEQ ID NO: 18556) |
| 146 | CAATCCCCAAGYCA + R | (SEQ ID NO: 18557) |
| 146 | CAATCCCC + AAGYCAR | (SEQ ID NO: 18558) |
| 146 | CAATCCCCAAGYC + AR | (SEQ ID NO: 18559) |
| 146 | CAATCCCCAAGY + CAR | (SEQ ID NO: 18560) |
| 146 | CAA + TCCC + C + AAGYCAR | (SEQ ID NO: 18561) |
| 146 | +CAATCCC + C + AAGYCAR | (SEQ ID NO: 18562) |
| 146 | C + AATCCC + C + AAGYCAR | (SEQ ID NO: 18563) |
| 146 | CAAT + CCC + C + AAGYCAR | (SEQ ID NO: 18564) |
| 146 | CAATCCC + C + AAGYCAR | (SEQ ID NO: 18565) |
| 146 | CAATCCC + C + A + AGYCAR | (SEQ ID NO: 18566) |
| 146 | CAATCCC + C + AAGY + CAR | (SEQ ID NO: 18567) |
| 146 | CAATCCC + C + AAGYCA + R | (SEQ ID NO: 18568) |
| 146 | CAATCCC + C + AAGYC | (SEQ ID NO: 18569) |
| 146 | CAAT + CCCCAAGYC | (SEQ ID NO: 18570) |
| 146 | CAATCC + CCAAGYC | (SEQ ID NO: 18571) |
| 146 | CAA + TCCCCAAGYC | (SEQ ID NO: 18572) |
| 146 | CA + ATCCCCAAGYC | (SEQ ID NO: 18573) |
| 146 | CAATCCCCAAGYCA | (SEQ ID NO: 18574) |
| 146 | CAATCCCC + AAGYC | (SEQ ID NO: 18575) |
| 146 | CAATCCCCAAGYC | (SEQ ID NO: 18576) |
| 146 | CAATCCCCAAGY + C | (SEQ ID NO: 18577) |
| 146 | CAA + TCCC + C + AAGYC | (SEQ ID NO: 18578) |
| 146 | +CAATCCC + C + AAGYC | (SEQ ID NO: 18579) |
| 146 | C + AATCCC + C + AAGYC | (SEQ ID NO: 18580) |
| 146 | CAAT + CCC + C + AAGYC | (SEQ ID NO: 18581) |
| 146 | CAATCCC + C + AAGYCA | (SEQ ID NO: 18582) |
| 146 | CAATCCC + C + A + AGYC | (SEQ ID NO: 18583) |
| 146 | CAATCCC + C + AAGY + C | (SEQ ID NO: 18584) |
| 146 | ACAATCCCCAAGYCARGG | (SEQ ID NO: 18585) |
| 146 | CAATCCCCAAGYCARGG | (SEQ ID NO: 18586) |
| 146 | CAATCCCCAAGYCAR | (SEQ ID NO: 18587) |
| 146 | CAATCCCCAAGYC | (SEQ ID NO: 18588) |
| 146 | AATCCCCRAGTCAA | (SEQ ID NO: 18589) |
| 147 | AATCCCCA + A + GYCARGGAG | (SEQ ID NO: 18590) |
| 147 | AATCCCC + AAGYCARGGAG | (SEQ ID NO: 18591) |
| 147 | AAT + CCCCAAGYCARGGAG | (SEQ ID NO: 18592) |
| 147 | AATCCC + CAAGYCARGGAG | (SEQ ID NO: 18593) |
| 147 | AATCC + CCAAGYCARGGAG | (SEQ ID NO: 18594) |
| 147 | AATCCCCAAGYCARG + GAG | (SEQ ID NO: 18595) |
| 147 | AATCCCCAAGYCARGG + AG | (SEQ ID NO: 18596) |
| 147 | AATCCCCAAGYCARGGA + G | (SEQ ID NO: 18597) |
| 147 | AATCCCCAAGY + CARGGAG | (SEQ ID NO: 18598) |
| 147 | A + ATCCCCA + A + GYCARGGAG | (SEQ ID NO: 18599) |
| 147 | AATCCC + CA + A + GYCARGGAG | (SEQ ID NO: 18600) |
| 147 | AATC + CCCA + A + GYCARGGAG | (SEQ ID NO: 18601) |
| 147 | AAT + CCCCA + A + GYCARGGAG | (SEQ ID NO: 18602) |
| 147 | AATCCCCA + A + GYCA + RGGAG | (SEQ ID NO: 18603) |
| 147 | AATCCCCA + A + G + YCARGGAG | (SEQ ID NO: 18604) |
| 147 | AATCCCCA + A + GY + CARGGAG | (SEQ ID NO: 18605) |
| 147 | AATCCCCA + A + GYCARGG + AG | (SEQ ID NO: 18606) |
| 147 | ATCCCCA + A + GYCARGGAG | (SEQ ID NO: 18607) |
| 147 | ATCCCC + AAGYCARGGAG | (SEQ ID NO: 18608) |

TABLE 13-continued

| | |
|---|---|
| 147 | AT + CCCCAAGYCARGGAG (SEQ ID NO: 18609) |
| 147 | ATCCC + CAAGYCARGGAG (SEQ ID NO: 18610) |
| 147 | ATCC + CCAAGYCARGGAG (SEQ ID NO: 18611) |
| 147 | ATCCCCAAGYCARG + GAG (SEQ ID NO: 18612) |
| 147 | ATCCCCAAGYCARGG + AG (SEQ ID NO: 18613) |
| 147 | ATCCCCAAGYCARGGA + G (SEQ ID NO: 18614) |
| 147 | ATCCCCAAGY + CARGGAG (SEQ ID NO: 18615) |
| 147 | +ATCCCCA + A + GYCARGGAG (SEQ ID NO: 18616) |
| 147 | ATCCC + CA + A + GYCARGGAG (SEQ ID NO: 18617) |
| 147 | ATC + CCCA + A + GYCARGGAG (SEQ ID NO: 18618) |
| 147 | AT + CCCCA + A + GYCARGGAG (SEQ ID NO: 18619) |
| 147 | ATCCCCA + A + GYCA + RGGAG (SEQ ID NO: 18620) |
| 147 | ATCCCCA + A + G + YCARGGAG (SEQ ID NO: 18621) |
| 147 | ATCCCCA + A + GY + CARGGAG (SEQ ID NO: 18622) |
| 147 | ATCCCCA + A + GYCARGG + AG (SEQ ID NO: 18623) |
| 147 | ATCCCCA + A + GYCARGG (SEQ ID NO: 18624) |
| 147 | ATCCCC + AAGYCARGG (SEQ ID NO: 18625) |
| 147 | AT + CCCCAAGYCARGG (SEQ ID NO: 18626) |
| 147 | ATCCC + CAAGYCARGG (SEQ ID NO: 18627) |
| 147 | ATCC + CCAAGYCARGG (SEQ ID NO: 18628) |
| 147 | ATCCCCAAGYCARG + G (SEQ ID NO: 18629) |
| 147 | ATCCCCAAGYCARGG (SEQ ID NO: 18630) |
| 147 | ATCCCCAAGYCARGGA (SEQ ID NO: 18631) |
| 147 | ATCCCCAAGY + CARGG (SEQ ID NO: 18632) |
| 147 | +ATCCCCA + A + GYCARGG (SEQ ID NO: 18633) |
| 147 | ATCCC + CA + A + GYCARGG (SEQ ID NO: 18634) |
| 147 | ATC + CCCA + A + GYCARGG (SEQ ID NO: 18635) |
| 147 | AT + CCCCA + A + GYCARGG (SEQ ID NO: 18636) |
| 147 | ATCCCCA + A + GYCA + RGG (SEQ ID NO: 18637) |
| 147 | ATCCCCA + A + G + YCARGG (SEQ ID NO: 18638) |
| 147 | ATCCCCA + A + GY + CARGG (SEQ ID NO: 18639) |
| 147 | ATCCCCA + A + GYCARGG (SEQ ID NO: 18640) |
| 147 | ATCCCCA + A + GYCAR (SEQ ID NO: 18641) |
| 147 | ATCCCC + AAGYCAR (SEQ ID NO: 18642) |
| 147 | AT + CCCCAAGYCAR (SEQ ID NO: 18643) |
| 147 | ATCCC + CAAGYCAR (SEQ ID NO: 18644) |
| 147 | ATCC + CCAAGYCAR (SEQ ID NO: 18645) |
| 147 | ATCCCCAAGYCARG (SEQ ID NO: 18646) |
| 147 | ATCCCCAAGY + CAR (SEQ ID NO: 18647) |
| 147 | +ATCCCCA + A + GYCAR (SEQ ID NO: 18648) |
| 147 | ATCCC + CA + A + GYCAR (SEQ ID NO: 18649) |
| 147 | ATC + CCCA + A + GYCAR (SEQ ID NO: 18650) |
| 147 | AT + CCCCA + A + GYCAR (SEQ ID NO: 18651) |
| 147 | ATCCCCA + A + GYCA + R (SEQ ID NO: 18652) |
| 147 | ATCCCCA + A + G + YCAR (SEQ ID NO: 18653) |
| 147 | ATCCCCA + A + GY + CAR (SEQ ID NO: 18654) |
| 147 | ATCCCCA + A + GYCARG (SEQ ID NO: 18655) |
| 147 | AATCCCCAAGYCARGGAG (SEQ ID NO: 18656) |
| 147 | ATCCCCAAGYCARGGAG (SEQ ID NO: 18657) |
| 147 | ATCCCCAAGYCARGG (SEQ ID NO: 18658) |
| 147 | ATCCCCAAGYCAR (SEQ ID NO: 18659) |
| 147 | TCCCCAAGGYCAAGG (SEQ ID NO: 18660) |
| 148 | CCAAAGYC + A + GGAGTAGTR (SEQ ID NO: 18661) |
| 148 | CCAAA + GYCAGGAGTAGTR (SEQ ID NO: 18662) |
| 148 | CCA + AAGYCAGGAGTAGTR (SEQ ID NO: 18663) |
| 148 | C + CAAAGYCAGGAGTAGTR (SEQ ID NO: 18664) |
| 148 | CC + AAAGYCAGGAGTAGTR (SEQ ID NO: 18665) |
| 148 | CCAAAGYCAGGAGT + AGTR (SEQ ID NO: 18666) |
| 148 | CCAAAGYCAGGAGTA + GTR (SEQ ID NO: 18667) |
| 148 | CCAAAGYCAGGA + GTAGTR (SEQ ID NO: 18668) |
| 148 | CCAAAGYCAG + GAGTAGTR (SEQ ID NO: 18669) |
| 148 | CCAAAGY + C + A + GGAGTAGTR (SEQ ID NO: 18670) |
| 148 | CCA + AAGYC + A + GGAGTAGTR (SEQ ID NO: 18671) |
| 148 | CC + AAAGYC + A + GGAGTAGTR (SEQ ID NO: 18672) |
| 148 | CCAA + AGYC + A + GGAGTAGTR (SEQ ID NO: 18673) |
| 148 | CCAAAGYC + A + GG + AGTAGTR (SEQ ID NO: 18674) |
| 148 | CCAAAGYC + A + GGAG + TAGTR (SEQ ID NO: 18675) |
| 148 | CCAAAGYC + A + GGAGTAGT + R (SEQ ID NO: 18676) |
| 148 | CCAAAGYC + A + GGAGT + AGTR (SEQ ID NO: 18677) |
| 148 | CCCCAAAG + Y + ARGGAGTAG (SEQ ID NO: 18678) |
| 148 | CCC + CAAAGYARGGAGTAG (SEQ ID NO: 18679) |
| 148 | CCCCA + AAGYARGGAGTAG (SEQ ID NO: 18680) |
| 148 | CCCCAAAG + YARGGAGTAG (SEQ ID NO: 18681) |

TABLE 13-continued

| | | |
|---|---|---|
| 148 | CCCCAAA + GYARGGAGTAG (SEQ ID NO: 18682) | |
| 148 | CCCCAAAGYARGGAG + TAG (SEQ ID NO: 18683) | |
| 148 | CCCCAAAGYARG + GAGTAG (SEQ ID NO: 18684) | |
| 148 | CCCCAAAGY + ARGGAGTAG (SEQ ID NO: 18685) | |
| 148 | CCCCAAAGYAR + GGAGTAG (SEQ ID NO: 18686) | |
| 148 | CCC + CAAAG + Y + ARGGAGTAG (SEQ ID NO: 18687) | |
| 148 | CCCCA + AAG + Y + ARGGAGTAG (SEQ ID NO: 18688) | |
| 148 | CC + CCAAAG + Y + ARGGAGTAG (SEQ ID NO: 18689) | |
| 148 | CCCC + AAAG + Y + ARGGAGTAG (SEQ ID NO: 18690) | |
| 148 | CCCCAAAG + Y + AR + GGAGTAG (SEQ ID NO: 18691) | |
| 148 | CCCCAAAG + Y + ARGGA + GTAG (SEQ ID NO: 18692) | |
| 148 | CCCCAAAG + Y + ARGGAG + TAG (SEQ ID NO: 18693) | |
| 148 | CCCCAAAG + Y + ARGGAGTA + G (SEQ ID NO: 18694) | |
| 148 | CCCAAAGY + C + RGGAGTAGT (SEQ ID NO: 18695) | |
| 148 | CCCAA + AGYCRGGAGTAGT (SEQ ID NO: 18696) | |
| 148 | CCC + AAAGYCRGGAGTAGT (SEQ ID NO: 18697) | |
| 148 | CCCAAAG + YCRGGAGTAGT (SEQ ID NO: 18698) | |
| 148 | CCCAAAGY + CRGGAGTAGT (SEQ ID NO: 18699) | |
| 148 | CCCAAAGYCRGGAG + TAGT (SEQ ID NO: 18700) | |
| 148 | CCCAAAGYCRGGAGTA + GT (SEQ ID NO: 18701) | |
| 148 | CCCAAAGYCRGG + AGTAGT (SEQ ID NO: 18702) | |
| 148 | CCCAAAGYCR + GGAGTAGT (SEQ ID NO: 18703) | |
| 148 | CCCAAAG + Y + C + RGGAGTAGT (SEQ ID NO: 18704) | |
| 148 | CC + CAAAGY + C + RGGAGTAGT (SEQ ID NO: 18705) | |
| 148 | CCCAAA + GY + C + RGGAGTAGT (SEQ ID NO: 18706) | |
| 148 | C + CCAAAGY + C + RGGAGTAGT (SEQ ID NO: 18707) | |
| 148 | CCCAAAGY + C + RGG + AGTAGT (SEQ ID NO: 18708) | |
| 148 | CCCAAAGY + C + R + GGAGTAGT (SEQ ID NO: 18709) | |
| 148 | CCCAAAGY + C + RGGAG + TAGT (SEQ ID NO: 18710) | |
| 148 | CCCAAAGY + C + RGGAGT + AGT (SEQ ID NO: 18711) | |
| 148 | CAAAGYC + A + GGAGTAGTR (SEQ ID NO: 18712) | |
| 148 | CAAA + GYCAGGAGTAGTR (SEQ ID NO: 18713) | |
| 148 | CA + AAGYCAGGAGTAGTR (SEQ ID NO: 18714) | |
| 148 | +CAAAGYCAGGAGTAGTR (SEQ ID NO: 18715) | |
| 148 | C + AAAGYCAGGAGTAGTR (SEQ ID NO: 18716) | |
| 148 | CAAAGYCAGGAGT + AGTR (SEQ ID NO: 18717) | |
| 148 | CAAAGYCAGGAGTA + GTR (SEQ ID NO: 18718) | |
| 148 | CAAAGYCAGGA + GTAGTR (SEQ ID NO: 18719) | |
| 148 | CAAAGYCAG + GAGTAGTR (SEQ ID NO: 18720) | |
| 148 | CAAAGY + C + A + GGAGTAGTR (SEQ ID NO: 18721) | |
| 148 | CA + AAGYC + A + GGAGTAGTR (SEQ ID NO: 18722) | |
| 148 | C + AAAGYC + A + GGAGTAGTR (SEQ ID NO: 18723) | |
| 148 | CAA + AGYC + A + GGAGTAGTR (SEQ ID NO: 18724) | |
| 148 | CAAAGYC + A + GG + AGTAGTR (SEQ ID NO: 18725) | |
| 148 | CAAAGYC + A + GGAG + TAGTR (SEQ ID NO: 18726) | |
| 148 | CAAAGYC + A + GGAGTAGT + R (SEQ ID NO: 18727) | |
| 148 | CAAAGYC + A + GGAGT + AGTR (SEQ ID NO: 18728) | |
| 148 | CCCAAAG + Y + ARGGAGTAG (SEQ ID NO: 18729) | |
| 148 | CC + CAAAGYARGGAGTAG (SEQ ID NO: 18730) | |
| 148 | CCCA + AAGYARGGAGTAG (SEQ ID NO: 18731) | |
| 148 | CCCAAAG + YARGGAGTAG (SEQ ID NO: 18732) | |
| 148 | CCCAAA + GYARGGAGTAG (SEQ ID NO: 18733) | |
| 148 | CCCAAAGYARGGAG + TAG (SEQ ID NO: 18734) | |
| 148 | CCCAAAGYARG + GAGTAG (SEQ ID NO: 18735) | |
| 148 | CCCAAAGY + ARGGAGTAG (SEQ ID NO: 18736) | |
| 148 | CCCAAAGYAR + GGAGTAG (SEQ ID NO: 18737) | |
| 148 | CC + CAAAG + Y + ARGGAGTAG (SEQ ID NO: 18738) | |
| 148 | CCCA + AAG + Y + ARGGAGTAG (SEQ ID NO: 18739) | |
| 148 | C + CCAAAG + Y + ARGGAGTAG (SEQ ID NO: 18740) | |
| 148 | CC C + AAAG + Y + ARGGAGTAG (SEQ ID NO: 18741) | |
| 148 | CCCAAAG + Y + AR + GGAGTAG (SEQ ID NO: 18742) | |
| 148 | CCCAAAG + Y + ARGGA + GTAG (SEQ ID NO: 18743) | |
| 148 | CCCAAAG + Y + ARGGAG + TAG (SEQ ID NO: 18744) | |
| 148 | CCCAAAG + Y + ARGGAGTA + G (SEQ ID NO: 18745) | |

TABLE 13-continued

| 148 | CCAAAGY + C + RGGAGTAGT (SEQ ID NO: 18746) |
| --- | --- |
| 148 | CCAA + AGYCRGGAGTAGT (SEQ ID NO: 18747) |
| 148 | CC + AAAGYCRGGAGTAGT (SEQ ID NO: 18748) |
| 148 | CCAAAG + YCRGGAGTAGT (SEQ ID NO: 18749) |
| 148 | CCAAAGY + CRGGAGTAGT (SEQ ID NO: 18750) |
| 148 | CCAAAGYCRGGAG + TAGT (SEQ ID NO: 18751) |
| 148 | CCAAAGYCRGGAGTA + GT (SEQ ID NO: 18752) |
| 148 | CCAAAGYCRGG + AGTAGT (SEQ ID NO: 18753) |
| 148 | CCAAAGYCR + GGAGTAGT (SEQ ID NO: 18754) |
| 148 | CCAAAG + Y + C + RGGAGTAGT (SEQ ID NO: 18755) |
| 148 | C + CAAAGY + C + RGGAGTAGT (SEQ ID NO: 18756) |
| 148 | CCAAA + GY + C + RGGAGTAGT (SEQ ID NO: 18757) |
| 148 | +CCAAAGY + C + RGGAGTAGT (SEQ ID NO: 18758) |
| 148 | CCAAAGY + C + RGG + AGTAGT (SEQ ID NO: 18759) |
| 148 | CCAAAGY + C + R + GGAGTAGT (SEQ ID NO: 18760) |
| 148 | CCAAAGY + C + RGGAG + TAGT (SEQ ID NO: 18761) |
| 148 | CCAAAGY + C + RGGAGT + AGT (SEQ ID NO: 18762) |
| 148 | CAAAGYC + A + GGAGTAG (SEQ ID NO: 18763) |
| 148 | CAAA + GYCAGGAGTAG (SEQ ID NO: 18764) |
| 148 | CA + AAGYCAGGAGTAG (SEQ ID NO: 18765) |
| 148 | +CAAAGYCAGGAGTAG (SEQ ID NO: 18766) |
| 148 | C + AAAGYCAGGAGTAG (SEQ ID NO: 18767) |
| 148 | CAAAGYCAGGAGT + AG (SEQ ID NO: 18768) |
| 148 | CAAAGYCAGGAGTA + G (SEQ ID NO: 18769) |
| 148 | CAAAGYCAGGA + GTAG (SEQ ID NO: 18770) |
| 148 | CAAAGYCAG + GAGTAG (SEQ ID NO: 18771) |
| 148 | CAAAGY + C + A + GGAGTAG (SEQ ID NO: 18772) |
| 148 | CA + AAGYC + A + GGAGTAG (SEQ ID NO: 18773) |
| 148 | C + AAAGYC + A + GGAGTAG (SEQ ID NO: 18774) |
| 148 | CAA + AGYC + A + GGAGTAG (SEQ ID NO: 18775) |
| 148 | CAAAGYC + A + GG + AGTAG (SEQ ID NO: 18776) |
| 148 | CAAAGYC + A + GGAG + TAG (SEQ ID NO: 18777) |
| 148 | CAAAGYC + A + GGAGTAGT (SEQ ID NO: 18778) |
| 148 | CAAAGYC + A + GGAGT + AG (SEQ ID NO: 18779) |
| 148 | CCCAAAG + Y + ARGGAGT (SEQ ID NO: 18780) |
| 148 | CC + CAAAGYARGGAGT (SEQ ID NO: 18781) |
| 148 | CCCA + AAGYARGGAGT (SEQ ID NO: 18782) |
| 148 | CCCAAAG + YARGGAGT (SEQ ID NO: 18783) |
| 148 | CCCAAA + GYARGGAGT (SEQ ID NO: 18784) |
| 148 | CCCAAAGYARGGAG + T (SEQ ID NO: 18785) |
| 148 | CCCAAAGYARG + GAGT (SEQ ID NO: 18786) |
| 148 | CCCAAAGY + ARGGAGT (SEQ ID NO: 18787) |
| 148 | CCCAAAGYAR + GGAGT (SEQ ID NO: 18788) |
| 148 | CC + CAAAG + Y + ARGGAGT (SEQ ID NO: 18789) |
| 148 | CCCA + AAG + Y + ARGGAGT (SEQ ID NO: 18790) |
| 148 | C + CCAAAG + Y + ARGGAGT (SEQ ID NO: 18791) |
| 148 | CCC + AAAG + Y + ARGGAGT (SEQ ID NO: 18792) |
| 148 | CCCAAAG + Y + AR + GGAGT (SEQ ID NO: 18793) |
| 148 | CCCAAAG + Y + ARGGA + GT (SEQ ID NO: 18794) |
| 148 | CCCAAAG + Y + ARGGAG + T (SEQ ID NO: 18795) |
| 148 | CCCAAAG + Y + ARGGAGTA (SEQ ID NO: 18796) |
| 148 | CCAAAGY + C + RGGAGTA (SEQ ID NO: 18797) |
| 148 | CCAA + AGYCRGGAGTA (SEQ ID NO: 18798) |
| 148 | CC + AAAGYCRGGAGTA (SEQ ID NO: 18799) |
| 148 | CCAAAG + YCRGGAGTA (SEQ ID NO: 18800) |
| 148 | CCAAAGY + CRGGAGTA (SEQ ID NO: 18801) |
| 148 | CCAAAGYCRGGAG + TA (SEQ ID NO: 18802) |
| 148 | CCAAAGYCRGGAGTA (SEQ ID NO: 18803) |
| 148 | CCAAAGYCRGG + AGTA (SEQ ID NO: 18804) |
| 148 | CCAAAGYCR + GGAGTA (SEQ ID NO: 18805) |
| 148 | CCAAAG + Y + C + RGGAGTA (SEQ ID NO: 18806) |
| 148 | C + CAAAGY + C + RGGAGTA (SEQ ID NO: 18807) |
| 148 | CCAAA + GY + C + RGGAGTA (SEQ ID NO: 18808) |
| 148 | +CCAAAGY + C + RGGAGTA (SEQ ID NO: 18809) |
| 148 | CCAAAGY + C + RGG + AGTA (SEQ ID NO: 18810) |
| 148 | CCAAAGY + C + R + GGAGTA (SEQ ID NO: 18811) |
| 148 | CCAAAGY + C + RGGAG + TA (SEQ ID NO: 18812) |
| 148 | CCAAAGY + C + RGGAGT + A (SEQ ID NO: 18813) |
| 148 | CAAAGYC + A + GGAGT (SEQ ID NO: 18814) |
| 148 | CAAA + GYCAGGAGT (SEQ ID NO: 18815) |
| 148 | CA + AAGYCAGGAGT (SEQ ID NO: 18816) |
| 148 | +CAAAGYCAGGAGT (SEQ ID NO: 18817) |
| 148 | C + AAAGYCAGGAGT (SEQ ID NO: 18818) |
| 148 | CAAAGYCAGGAGT (SEQ ID NO: 18819) |
| 148 | CAAAGYCAGGAGTA (SEQ ID NO: 18820) |
| 148 | CAAAGYCAGGA + GT (SEQ ID NO: 18821) |

TABLE 13-continued

| | |
|---|---|
| 148 | CAAAGYCAG + GAGT (SEQ ID NO:1 8822) |
| 148 | CAAAGY + C + A + GGAGT (SEQ ID NO: 18823) |
| 148 | CA + AAGYC + A + GGAGT (SEQ ID NO: 18824) |
| 148 | C + AAAGYC + A + GGAGT (SEQ ID NO: 18825) |
| 148 | CAA + AGYC + A + GGAGT (SEQ ID NO: 18826) |
| 148 | CAAAGYC + A + GG + AGT (SEQ ID NO: 18827) |
| 148 | CAAAGYC + A + GGAG + T (SEQ ID NO: 18828) |
| 148 | CAAAGYC + A + GGAGTA (SEQ ID NO: 18829) |
| 148 | CAAAGYC + A + GGAGT (SEQ ID NO: 18830) |
| 148 | CCCAAAG + Y + ARGGA (SEQ ID NO: 18831) |
| 148 | CC + CAAAGYARGGA (SEQ ID NO: 18832) |
| 148 | CCCA + AAGYARGGA (SEQ ID NO: 18833) |
| 148 | CCCAAAG + YARGGA (SEQ ID NO: 18834) |
| 148 | CCCAAA + GYARGGA (SEQ ID NO: 18835) |
| 148 | CCCAAAGYARGGAG (SEQ ID NO: 18836) |
| 148 | CCCAAAGYARG + GA (SEQ ID NO: 18837) |
| 148 | CC CAAAGY + ARGGA (SEQ ID NO: 18838) |
| 148 | CCCAAAGYAR + GGA (SEQ ID NO: 18839) |
| 148 | CC + CAAAG + Y + ARGGA (SEQ ID NO: 18840) |
| 148 | CCCA + AAG + Y + ARGGA (SEQ ID NO: 18841) |
| 148 | C + CCAAAG + Y + ARGGA (SEQ ID NO: 18842) |
| 148 | CCC + AAAG + Y + ARGGA (SEQ ID NO: 18843) |
| 148 | CCCAAAG + Y + AR + GGA (SEQ ID NO: 18844) |
| 148 | CCCAAAG + Y + ARGGA (SEQ ID NO: 18845) |
| 148 | CCCAAAG + Y + ARGGAG (SEQ ID NO: 18846) |
| 148 | CCAAAGY + C + RGGAG (SEQ ID NO: 18847) |
| 148 | CCAA + AGYCRGGAG (SEQ ID NO: 18848) |
| 148 | CC + AAAGYCRGGAG (SEQ ID NO: 18849) |
| 148 | CCAAAG + YCRGGAG (SEQ ID NO: 18850) |
| 148 | CCAAAGY + CRGGAG (SEQ ID NO: 18851) |
| 148 | CCAAAGYCRGGAG (SEQ ID NO: 18852) |
| 148 | CCAAAGYCRGGAGT (SEQ ID NO: 18853) |
| 148 | CCAAAGYCRGG + AG (SEQ ID NO: 18854) |
| 148 | CCAAAGYCR + GGAG (SEQ ID NO: 18855) |
| 148 | CCAAAG + Y + C + RGGAG (SEQ ID NO: 18856) |
| 148 | C + CAAAGY + C + RGGAG (SEQ ID NO: 18857) |
| 148 | CCAAA + GY + C + RGGAG (SEQ ID NO: 18858) |
| 148 | +CCAAAGY + C + RGGAG (SEQ ID NO: 18859) |
| 148 | CCAAAGY + C + RGG + AG (SEQ ID NO: 18860) |
| 148 | CCAAAGY + C + R + GGAG (SEQ ID NO: 18861) |
| 148 | CCAAAGY + C + RGGAG (SEQ ID NO: 18862) |
| 148 | CCAAAGY + C + RGGAGT (SEQ ID NO: 18863) |
| 148 | CCAAAGYCAGGAGTAGTR (SEQ ID NO: 18864) |
| 148 | CCCCAAAGYARGGAGTAG (SEQ ID NO: 18865) |
| 148 | CCCAAAGYCRGGAGTAGT (SEQ ID NO: 18866) |
| 148 | CAAAGYCAGGAGTAGTR (SEQ ID NO: 18867) |
| 148 | CCCAAAGYARGGAGTAG (SEQ ID NO: 18868) |
| 148 | CCAAAGYCRGGAGTAGT (SEQ ID NO: 18869) |
| 148 | CAAAGYCAGGAGTAG (SEQ ID NO: 18870) |
| 148 | CAAAGYCAGGAGTAGT (SEQ ID NO: 18871) |
| 148 | CCCAAAGYARGGAGT (SEQ ID NO: 18872) |
| 148 | CCCAAAGYARGGAGTA (SEQ ID NO: 18873) |
| 148 | CCAAAGYCRGGAGTA (SEQ ID NO: 18874) |
| 148 | CAAAGYCAGGAGT (SEQ ID NO: 18875) |
| 148 | CCCAAAGYARGGA (SEQ ID NO: 18876) |
| 148 | CCAAAGYCRGGAG (SEQ ID NO: 18877) |
| 148 | CAAAGTCAYGGAGTA (SEQ ID NO: 18878) |
| 148 | CAAAGTMGRGGAGTA (SEQ ID NO: 18879) |
| 148 | CAAAGTAARGGAGTA (SEQ ID NO: 18880) |
| 153 | ATTCATRTATTCTAC (SEQ ID NO: 18881) |
| 153 | ATTCATRAATTCTAC (SEQ ID NO: 18882) |
| 155 | GARTCYAT + G + ATAARGAAT (SEQ ID NO: 18883) |
| 155 | GARTCYAT + GATAARGAAT (SEQ ID NO: 18884) |
| 155 | G + ARTCYATGATAARGAAT (SEQ ID NO: 18885) |
| 155 | GARTCY + ATGATAARGAAT (SEQ ID NO: 18886) |
| 155 | GART + CYATGATAARGAAT (SEQ ID NO: 18887) |
| 155 | GARTCYATGATAAR + GAAT (SEQ ID NO: 18888) |
| 155 | GARTCYATGATAARGA + AT (SEQ ID NO: 18889) |
| 155 | GARTCYATGATAA + RGAAT (SEQ ID NO: 18890) |
| 155 | GARTCYATGA + TAARGAAT (SEQ ID NO: 18891) |
| 155 | GARTCYA + T + G + ATAARGAAT (SEQ ID NO: 18892) |
| 155 | G + ARTCYAT + G + ATAARGAAT (SEQ ID NO: 18893) |
| 155 | GAR + TCYAT + G + ATAARGAAT (SEQ ID NO: 18894) |
| 155 | GART + CYAT + G + ATAARGAAT (SEQ ID NO: 18895) |
| 155 | GARTCYAT + G + AT + AARGAAT (SEQ ID NO: 18896) |
| 155 | GARTCYAT + G + ATA + ARGAAT (SEQ ID NO: 18897) |
| 155 | GARTCYAT + G + ATAARGA + AT (SEQ ID NO: 18898) |

TABLE 13-continued

| | |
|---|---|
| 155 | GARTCYAT + G + ATAARG + AAT (SEQ ID NO: 18899) |
| 155 | ARTCYATG + A + TAARGAATT (SEQ ID NO: 18900) |
| 155 | ART + CYATGATAARGAATT (SEQ ID NO: 18901) |
| 155 | ARTCY + ATGATAARGAATT (SEQ ID NO: 18902) |
| 155 | AR + TCYATGATAARGAATT (SEQ ID NO: 18903) |
| 155 | A + RTCYATGATAARGAATT (SEQ ID NO: 18904) |
| 155 | ARTCYATGATAARGAAT + T (SEQ ID NO: 18905) |
| 155 | ARTCYATGA + TAARGAATT (SEQ ID NO: 18906) |
| 155 | ARTCYATGATAAR + GAATT (SEQ ID NO: 18907) |
| 155 | ARTCYATGATAARG + AATT (SEQ ID NO: 18908) |
| 155 | AR + TCYATG + A + TAARGAATT (SEQ ID NO: 18909) |
| 155 | ARTCYA + TG + A + TAARGAATT (SEQ ID NO: 18910) |
| 155 | ARTCY + ATG + A + TAARGAATT (SEQ ID NO: 18911) |
| 155 | ARTCYAT + G + A + TAARGAATT (SEQ ID NO: 18912) |
| 155 | ARTCYATG + A + TAAR + GAATT (SEQ ID NO: 18913) |
| 155 | ARTCYATG + A + TAARGA + ATT (SEQ ID NO: 18914) |
| 155 | ARTCYATG + A + TAARGAA + TT (SEQ ID NO: 18915) |
| 155 | ARTCYATG + A + TA + ARGAATT (SEQ ID NO: 18916) |
| 155 | ARTCYAT + G + ATAARGAAT (SEQ ID NO: 18917) |
| 155 | ARTCYAT + GATAARGAAT (SEQ ID NO: 18918) |
| 155 | +ARTCYATGATAARGAAT (SEQ ID NO: 18919) |
| 155 | ARTCY + ATGATAARGAAT (SEQ ID NO: 18920) |
| 155 | ART + CYATGATAARGAAT (SEQ ID NO: 18921) |
| 155 | ARTCYATGATAAR + GAAT (SEQ ID NO: 18922) |
| 155 | ARTCYATGATAARGA + AT (SEQ ID NO: 18923) |
| 155 | ARTCYATGATAA + RGAAT (SEQ ID NO: 18924) |
| 155 | ARTCYATGA + TAARGAAT (SEQ ID NO: 18925) |
| 155 | ARTCYA + T + G + ATAARGAAT (SEQ ID NO: 18926) |
| 155 | +ARTCYAT + G + ATAARGAAT (SEQ ID NO: 18927) |
| 155 | AR + TCYAT + G + ATAARGAAT (SEQ ID NO: 18928) |
| 155 | ART + CYAT + G + ATAARGAAT (SEQ ID NO: 18929) |
| 155 | ARTCYAT + G + AT + AARGAAT (SEQ ID NO: 18930) |
| 155 | ARTCYAT + G + ATA + ARGAAT (SEQ ID NO: 18931) |
| 155 | ARTCYAT + G + ATAARGA + AT (SEQ ID NO: 18932) |
| 155 | ARTCYAT + G + ATAARG + AAT (SEQ ID NO: 18933) |
| 155 | RTCYATG + A + TAARGAATT (SEQ ID NO: 18934) |
| 155 | RT + CYATGATAARGAATT (SEQ ID NO: 18935) |
| 155 | RTCY + ATGATAARGAATT (SEQ ID NO: 18936) |
| 155 | R + TCYATGATAARGAATT (SEQ ID NO: 18937) |
| 155 | +RTCYATGATAARGAATT (SEQ ID NO: 18938) |
| 155 | RTCYATGATAARGAAT + T (SEQ ID NO: 18939) |
| 155 | RTCYATGA + TAARGAATT (SEQ ID NO: 18940) |
| 155 | RTCYATGATAAR + GAATT (SEQ ID NO: 18941) |
| 155 | RTCYATGATAARG + AATT (SEQ ID NO: 18942) |
| 155 | R + TCYATG + A + TAARGAATT (SEQ ID NO: 18943) |
| 155 | RTCYA + TG + A + TAARGAATT (SEQ ID NO: 18944) |
| 155 | RTCY + ATG + A + TAARGAATT (SEQ ID NO: 18945) |
| 155 | RTCYAT + G + A + TAARGAATT (SEQ ID NO: 18946) |
| 155 | RTCYATG + A + TAAR + GAATT (SEQ ID NO: 18947) |
| 155 | RTCYATG + A + TAARGA + ATT (SEQ ID NO: 18948) |
| 155 | RTCYATG + A + TAARGAA + TT (SEQ ID NO: 18949) |
| 155 | RTCYATG + A + TA + ARGAATT (SEQ ID NO: 18950) |
| 155 | ARTCYAT + G + ATAARGA (SEQ ID NO: 18951) |
| 155 | ARTCYAT + GATAARGA (SEQ ID NO: 18952) |
| 155 | +ARTCYATGATAARGA (SEQ ID NO: 18953) |
| 155 | ARTCY + ATGATAARGA (SEQ ID NO: 18954) |
| 155 | ART + CYATGATAARGA (SEQ ID NO: 18955) |
| 155 | ARTCYATGATAAR + GA (SEQ ID NO: 18956) |
| 155 | ARTCYATGATAARGA (SEQ ID NO: 18957) |
| 155 | ARTCYATGATAA + RGA (SEQ ID NO: 18958) |
| 155 | ARTCYATGA + TAARGA (SEQ ID NO: 18959) |
| 155 | ARTCYA + T + G + ATAARGA (SEQ ID NO: 18960) |
| 155 | +ARTCYAT + G + ATAARGA (SEQ ID NO: 18961) |
| 155 | AR + TCYAT + G + ATAARGA (SEQ ID NO: 18962) |
| 155 | ART + CYAT + G + ATAARGA (SEQ ID NO: 18963) |
| 155 | ARTCYAT + G + AT + AARGA (SEQ ID NO: 18964) |
| 155 | ARTCYAT + G + ATA + ARGA (SEQ ID NO: 18965) |
| 155 | ARTCYAT + G + ATAARGA (SEQ ID NO: 18966) |

TABLE 13-continued

| | |
|---|---|
| 155 | ARTCYAT + G + ATAARG + A (SEQ ID NO: 18967) |
| 155 | RTCYATG + A + TAARGAA (SEQ ID NO: 18968) |
| 155 | RT + CYATGATAARGAA (SEQ ID NO: 18969) |
| 155 | RTCY + ATGATAARGAA (SEQ ID NO: 18970) |
| 155 | R + TCYATGATAARGAA (SEQ ID NO: 18971) |
| 155 | +RTCYATGATAARGAA (SEQ ID NO: 18972) |
| 155 | RTCYATGATAARGAAT (SEQ ID NO: 18973) |
| 155 | RTCYATGA + TAARGAA (SEQ ID NO: 18974) |
| 155 | RTCYATGATAAR + GAA (SEQ ID NO: 18975) |
| 155 | RTCYATGATAARG + AA (SEQ ID NO: 18976) |
| 155 | R + TCYATG + A + TAARGAA (SEQ ID NO: 18977) |
| 155 | RTCYA + TG + A + TAARGAA (SEQ ID NO: 18978) |
| 155 | RTCY + ATG + A + TAARGAA (SEQ ID NO: 18979) |
| 155 | RTCYAT + G + A + TAARGAA (SEQ ID NO: 18980) |
| 155 | RTCYATG + A + TAAR + GAA (SEQ ID NO: 18981) |
| 155 | RTCYATG + A + TAARGA + A (SEQ ID NO: 18982) |
| 155 | RTCYATG + A + TAARGAA (SEQ ID NO: 18983) |
| 155 | RTCYATG + A + TA + ARGAA (SEQ ID NO: 18984) |
| 155 | ARTCYAT + G + ATAAR (SEQ ID NO: 18985) |
| 155 | ARTCYAT + GATAAR (SEQ ID NO: 18986) |
| 155 | +ARTCYATGATAAR (SEQ ID NO: 18987) |
| 155 | ARTCY + ATGATAAR (SEQ ID NO: 18988) |
| 155 | ART + CYATGATAAR (SEQ ID NO: 18989) |
| 155 | ARTCYATGATAAR (SEQ ID NO: 18990) |
| 155 | ARTCYATGATAARG (SEQ ID NO: 18991) |
| 155 | ARTCYATGATAA + R (SEQ ID NO: 18992) |
| 155 | ARTCYATGA + TAAR (SEQ ID NO: 18993) |
| 155 | ARTCYA + T + G + ATAAR (SEQ ID NO: 18994) |
| 155 | +ARTCYAT + G + ATAAR (SEQ ID NO: 18995) |
| 155 | AR + TCYAT + G + ATAAR (SEQ ID NO: 18996) |
| 155 | ART + CYAT + G + ATAAR (SEQ ID NO: 18997) |
| 155 | ARTCYAT + G + AT + AAR (SEQ ID NO: 18998) |
| 155 | ARTCYAT + G + ATA + AR (SEQ ID NO: 18999) |
| 155 | ARTCYAT + G + ATAARG (SEQ ID NO: 19000) |
| 155 | RTCYATG + A + TAARG (SEQ ID NO: 19001) |
| 155 | RT + CYATGATAARG (SEQ ID NO: 19002) |
| 155 | RTCY + ATGATAARG (SEQ ID NO: 19003) |
| 155 | R + TCYATGATAARG (SEQ ID NO: 19004) |
| 155 | +RTCYATGATAARG (SEQ ID NO: 19005) |
| 155 | RTCYATGATAARGA (SEQ ID NO: 19006) |
| 155 | RTCYATGA + TAARG (SEQ ID NO: 19007) |
| 155 | RTCYATGATAAR + G (SEQ ID NO: 19008) |
| 155 | RTCYATGATAARG (SEQ ID NO: 19009) |
| 155 | R + TCYATG + A + TAARG (SEQ ID NO: 19010) |
| 155 | RTCYA + TG + A + TAARG (SEQ ID NO: 19011) |
| 155 | RTCY + ATG + A + TAARG (SEQ ID NO: 19012) |
| 155 | RTCYAT + G + A + TAARG (SEQ ID NO: 19013) |
| 155 | RTCYATG + A + TAAR + G (SEQ ID NO: 19014) |
| 155 | RTCYATG + A + TAARGA (SEQ ID NO: 19015) |
| 155 | RTCYATG + A + TA + ARG (SEQ ID NO: 19016) |
| 155 | GARTCYATGATAARGAAT (SEQ ID NO: 19017) |
| 155 | ARTCYATGATAARGAATT (SEQ ID NO: 19018) |
| 155 | ARTCYATGATAARGAAT (SEQ ID NO: 19019) |
| 155 | RTCYATGATAARGAATT (SEQ ID NO: 19020) |
| 155 | ARTCYATGATAARGA (SEQ ID NO: 19021) |
| 155 | RTCYATGATAARGAA (SEQ ID NO: 19022) |
| 155 | ARTCYATGATAAR (SEQ ID NO: 19023) |
| 155 | RTCYATGATAARG (SEQ ID NO: 19024) |
| 155 | TCTATGCAYAAAGAA (SEQ ID NO: 19025) |
| 155 | TCTATGAGYAAAGAA (SEQ ID NO: 19026) |
| 155 | TCTATGACYAAAGAA (SEQ ID NO: 19027) |
| 163 | AAAATYAT + A + GRCARGTMA (SEQ ID NO: 19028) |
| 163 | AA + AATYATAGRCARGTMA (SEQ ID NO: 19029) |
| 163 | AAA + ATYATAGRCARGTMA (SEQ ID NO: 19030) |
| 163 | AAAATYA + TAGRCARGTMA (SEQ ID NO: 19031) |
| 163 | A + AAATYATAGRCARGTMA (SEQ ID NO: 19032) |
| 163 | AAAATYATAGRCAR + GTMA (SEQ ID NO: 19033) |
| 163 | AAAATYATA + GRCARGTMA (SEQ ID NO: 19034) |
| 163 | AAAATYATAG + RCARGTMA (SEQ ID NO: 19035) |
| 163 | AAAATYATAGRCA + RGTMA (SEQ ID NO: 19036) |
| 163 | AAAA + TYAT + A + GRCARGTMA (SEQ ID NO: 19037) |
| 163 | AA + AATYAT + A + GRCARGTMA (SEQ ID NO: 19038) |
| 163 | AAAAT + YAT + A + GRCARGTMA (SEQ ID NO: 19039) |
| 163 | AAAATY + AT + A + GRCARGTMA (SEQ ID NO: 19040) |
| 163 | AAAATYAT + A + G + RCARGTMA (SEQ ID NO: 19041) |
| 163 | AAAATYAT + A + GRC + ARGTMA (SEQ ID NO: 19042) |

TABLE 13-continued

| | |
|---|---|
| 163 | AAAATYAT + A + GR + CARGTMA (SEQ ID NO: 19043) |
| 163 | AAAATYAT + A + GRCA + RGTMA (SEQ ID NO: 19044) |
| 163 | AAATYAT + A + GRCARGTMA (SEQ ID NO: 19045) |
| 163 | A + AATYATAGRCARGTMA (SEQ ID NO: 19046) |
| 163 | AA + ATYATAGRCARGTMA (SEQ ID NO: 19047) |
| 163 | AAATYA + TAGRCARGTMA (SEQ ID NO: 19048) |
| 163 | +AAATYATAGRCARGTMA (SEQ ID NO: 19049) |
| 163 | AAATYATAGRCAR + GTMA (SEQ ID NO: 19050) |
| 163 | AAATYATA + GRCARGTMA (SEQ ID NO: 19051) |
| 163 | AAATYATAG + RCARGTMA (SEQ ID NO: 19052) |
| 163 | AAATYATAGRCA + RGTMA (SEQ ID NO: 19053) |
| 163 | AAA + TYAT + A + GRCARGTMA (SEQ ID NO: 19054) |
| 163 | A + AATYAT + A + GRCARGTMA (SEQ ID NO: 19055) |
| 163 | AAAT + YAT + A + GRCARGTMA (SEQ ID NO: 19056) |
| 163 | AAATY + AT + A + GRCARGTMA (SEQ ID NO: 19057) |
| 163 | AAATYAT + A + G + RCARGTMA (SEQ ID NO: 19058) |
| 163 | AAATYAT + A + GRC + ARGTMA (SEQ ID NO: 19059) |
| 163 | AAATYAT + A + GR + CARGTMA (SEQ ID NO: 19060) |
| 163 | AAATYAT + A + GRCA + RGTMA (SEQ ID NO: 19061) |
| 163 | AAATYAT + A + GRCARGT (SEQ ID NO: 19062) |
| 163 | A + AATYATAGRCARGT (SEQ ID NO: 19063) |
| 163 | AA + ATYATAGRCARGT (SEQ ID NO: 19064) |
| 163 | AAATYA + TAGRCARGT (SEQ ID NO: 19065) |
| 163 | +AAATYATAGRCARGT (SEQ ID NO: 19066) |
| 163 | AAATYATAGRCAR + GT (SEQ ID NO: 19067) |
| 163 | AAATYATA + GRCARGT (SEQ ID NO: 19068) |
| 163 | AAATYATAG + RCARGT (SEQ ID NO: 19069) |
| 163 | AAATYATAGRCA + RGT (SEQ ID NO: 19070) |
| 163 | AAA + TYAT + A + GRCARGT (SEQ ID NO: 19071) |
| 163 | A + AATYAT + A + GRCARGT (SEQ ID NO: 19072) |
| 163 | AAAT + YAT + A + GRCARGT (SEQ ID NO: 19073) |
| 163 | AAATY + AT + A + GRCARGT (SEQ ID NO: 19074) |
| 163 | AAATYAT + A + G + RCARGT (SEQ ID NO: 19075) |
| 163 | AAATYAT + A + GRC + ARGT (SEQ ID NO: 19076) |
| 163 | AAATYAT + A + GR + CARGT (SEQ ID NO: 19077) |
| 163 | AAATYAT + A + GRCA + RGT (SEQ ID NO: 19078) |
| 163 | AAATYAT + A + GRCAR (SEQ ID NO: 19079) |
| 163 | A + AATYATAGRCAR (SEQ ID NO: 19080) |
| 163 | AA + ATYATAGRCAR (SEQ ID NO: 19081) |
| 163 | AAATYA + TAGRCAR (SEQ ID NO: 19082) |
| 163 | +AAATYATAGRCAR (SEQ ID NO: 19083) |
| 163 | AAATYATAGRCAR (SEQ ID NO: 19084) |
| 163 | AAATYATA + GRCAR (SEQ ID NO: 19085) |
| 163 | AAATYATAG + RCAR (SEQ ID NO: 19086) |
| 163 | AAATYATAGRCA + R (SEQ ID NO: 19087) |
| 163 | AAA + TYAT + A + GRCAR (SEQ ID NO: 19088) |
| 163 | A + AATYAT + A + GRCAR (SEQ ID NO: 19089) |
| 163 | AAAT + YAT + A + GRCAR (SEQ ID NO: 19090) |
| 163 | AAATY + AT + A + GRCAR (SEQ ID NO: 19091) |
| 163 | AAATYAT + A + G + RCAR (SEQ ID NO: 19092) |
| 163 | AAATYAT + A + GRC + AR (SEQ ID NO: 19093) |
| 163 | AAATYAT + A + GR + CAR (SEQ ID NO: 19094) |
| 163 | AAATYAT + A + GRCA + R (SEQ ID NO: 19095) |
| 163 | AAAATYATAGRCARGTMA (SEQ ID NO: 19096) |
| 163 | AAATYATAGRCARGTMA (SEQ ID NO: 19097) |
| 163 | AAATYATAGRCARGT (SEQ ID NO: 19098) |
| 163 | AAATYATAGRCAR (SEQ ID NO: 19099) |
| 163 | ATTATAMGRCAGGTA (SEQ ID NO: 19100) |
| 163 | ATTATAAARCAGGTA (SEQ ID NO: 19101) |
| 230 | TACAGRGA + C + GCAGAGAYC (SEQ ID NO: 19102) |
| 230 | TACAGRGA + CGCAGAGAYC (SEQ ID NO: 19103) |
| 230 | TACAGR + GACGCAGAGAYC (SEQ ID NO: 19104) |
| 230 | TA + CAGRGACGCAGAGAYC (SEQ ID NO: 19105) |
| 230 | T + ACAGRGACGCAGAGAYC (SEQ ID NO: 19106) |
| 230 | TACAGRGAC + GCAGAGAYC (SEQ ID NO: 19107) |
| 230 | TACAGRGACG + CAGAGAYC (SEQ ID NO: 19108) |
| 230 | TACAGRGACGC + AGAGAYC (SEQ ID NO: 19109) |
| 230 | TACAGRGACGCAGAGA + YC (SEQ ID NO: 19110) |
| 230 | TACAGRG + A + C + GCAGAGAYC (SEQ ID NO: 19111) |
| 230 | TACAGR + GA + C + GCAGAGAYC (SEQ ID NO: 19112) |
| 230 | TAC + AGRGA + C + GCAGAGAYC (SEQ ID NO: 19113) |
| 230 | TACAG + RGA + C + GCAGAGAYC (SEQ ID NO: 19114) |

TABLE 13-continued

| | |
|---|---|
| 230 | TACAGRGA + C + GC + AGAGAYC (SEQ ID NO: 19115) |
| 230 | TACAGRGA + C + GCAGAGAY + C (SEQ ID NO: 19116) |
| 230 | TACAGRGA + C + G + CAGAGAYC (SEQ ID NO: 19117) |
| 230 | TACAGRGA + C + GCAGA + GAYC (SEQ ID NO: 19118) |
| 230 | ACAGRGA + C + GCAGAGAYC (SEQ ID NO: 19119) |
| 230 | ACAGRGA + CGCAGAGAYC (SEQ ID NO: 19120) |
| 230 | ACAGR + GACGCAGAGAYC (SEQ ID NO: 19121) |
| 230 | A + CAGRGACGCAGAGAYC (SEQ ID NO: 19122) |
| 230 | +ACAGRGACGCAGAGAYC (SEQ ID NO: 19123) |
| 230 | ACAGRGAC + GCAGAGAYC (SEQ ID NO: 19124) |
| 230 | ACAGRGACG + CAGAGAYC (SEQ ID NO: 19125) |
| 230 | ACAGRGACGC + AGAGAYC (SEQ ID NO: 19126) |
| 230 | ACAGRGACGCAGAGA + YC (SEQ ID NO: 19127) |
| 230 | ACAGRG + A + C + GCAGAGAYC (SEQ ID NO: 19128) |
| 230 | ACAGR + GA + C + GCAGAGAYC (SEQ ID NO: 19129) |
| 230 | AC + AGRGA + C + GCAGAGAYC (SEQ ID NO: 19130) |
| 230 | ACAG + RGA + C + GCAGAGAYC (SEQ ID NO: 19131) |
| 230 | ACAGRGA + C + GC + AGAGAYC (SEQ ID NO: 19132) |
| 230 | ACAGRGA + C + GCAGAGAY + C (SEQ ID NO: 19133) |
| 230 | ACAGRGA + C + G + CAGAGAYC (SEQ ID NO: 19134) |
| 230 | ACAGRGA + C + GCAGA + GAYC (SEQ ID NO: 19135) |
| 230 | ACAGRGA + C + GCAGAGA (SEQ ID NO: 19136) |
| 230 | ACAGRGA + CGCAGAGA (SEQ ID NO: 19137) |
| 230 | ACAGR + GACGCAGAGA (SEQ ID NO: 19138) |
| 230 | A + CAGRGACGCAGAGA (SEQ ID NO: 19139) |
| 230 | +ACAGRGACGCAGAGA (SEQ ID NO: 19140) |
| 230 | ACAGRGAC + GCAGAGA (SEQ ID NO: 19141) |
| 230 | ACAGRGACG + CAGAGA (SEQ ID NO: 19142) |
| 230 | ACAGRGACGC + AGAGA (SEQ ID NO: 19143) |
| 230 | ACAGRGACGCAGAGA (SEQ ID NO: 19144) |
| 230 | ACAGRG + A + C + GCAGAGA (SEQ ID NO: 19145) |
| 230 | ACAGR + GA + C + GCAGAGA (SEQ ID NO: 19146) |
| 230 | AC + AGRGA + C + GCAGAGA (SEQ ID NO: 19147) |
| 230 | ACAG + RGA + C + GCAGAGA (SEQ ID NO: 19148) |
| 230 | ACAGRGA + C + GC + AGAGA (SEQ ID NO: 19149) |
| 230 | ACAGRGA + C + GCAGAGAY (SEQ ID NO: 19150) |
| 230 | ACAGRGA + C + G + CAGAGA (SEQ ID NO: 19151) |
| 230 | ACAGRGA + C + GCAGA + GA (SEQ ID NO: 19152) |
| 230 | ACAGRGA + C + GCAGA (SEQ ID NO: 19153) |
| 230 | ACAGRGA + CGCAGA (SEQ ID NO: 19154) |
| 230 | ACAGR + GACGCAGA (SEQ ID NO: 19155) |
| 230 | A + CAGRGACGCAGA (SEQ ID NO: 19156) |
| 230 | +ACAGRGACGCAGA (SEQ ID NO: 19157) |
| 230 | ACAGRGAC + GCAGA (SEQ ID NO: 19158) |
| 230 | ACAGRGACG + CAGA (SEQ ID NO: 19159) |
| 230 | ACAGRGACGC + AGA (SEQ ID NO: 19160) |
| 230 | ACAGRGACGCAGAG (SEQ ID NO: 19161) |
| 230 | ACAGRG + A + C + GCAGA (SEQ ID NO: 19162) |
| 230 | ACAGR + GA + C + GCAGA (SEQ ID NO: 19163) |
| 230 | AC + AGRGA + C + GCAGA (SEQ ID NO: 19164) |
| 230 | ACAG + RGA + C + GCAGA (SEQ ID NO: 19165) |
| 230 | ACAGRGA + C + GC + AGA (SEQ ID NO: 19166) |
| 230 | ACAGRGA + C + GCAGAG (SEQ ID NO: 19167) |
| 230 | ACAGRGA + C + G + CAGA (SEQ ID NO: 19168) |
| 230 | ACAGRGA + C + GCAGA (SEQ ID NO: 19169) |
| 230 | TACAGRGACGCAGAGAYC (SEQ ID NO: 19170) |
| 230 | ACAGRGACGCAGAGAYC (SEQ ID NO: 19171) |
| 230 | ACAGRGACGCAGAGA (SEQ ID NO: 19172) |
| 230 | ACAGRGACGCAGAGAY (SEQ ID NO: 19173) |
| 230 | ACAGRGACGCAGA (SEQ ID NO: 19174) |
| 230 | AGGGACCGCAGAGAC (SEQ ID NO: 19175) |
| 263 | TRCCAAGR + A + RAAAGYAAA (SEQ ID NO: 19176) |
| 263 | TRCCAAG + RARAAAGYAAA (SEQ ID NO: 19177) |
| 263 | TRCCAA + GRARAAAGYAAA (SEQ ID NO: 19178) |
| 263 | TR + CCAAGRARAAAGYAAA (SEQ ID NO: 19179) |
| 263 | TRC + CAAGRARAAAGYAAA (SEQ ID NO: 19180) |
| 263 | TRCCAAGRARAAA + GYAAA (SEQ ID NO: 19181) |
| 263 | TRCCAAGRARAAAGY + AAA (SEQ ID NO: 19182) |
| 263 | TRCCAAGRARAA + AGYAAA (SEQ ID NO: 19183) |
| 263 | TRCCAAGRAR + AAAGYAAA (SEQ ID NO: 19184) |
| 263 | TR + CCAAGR + A + RAAAGYAAA (SEQ ID NO: 19185) |
| 263 | TRC + CAAGR + A + RAAAGYAAA (SEQ ID NO: 19186) |

TABLE 13-continued

| | |
|---|---|
| 263 | TRCCAA + GR + A + RAAAGYAAA (SEQ ID NO: 19187) |
| 263 | TRCCAAG + R + A + RAAAGYAAA (SEQ ID NO: 19188) |
| 263 | TRCCAAGR + A + RAAAG + YAAA (SEQ ID NO: 19189) |
| 263 | TRCCAAGR + A + RAA + AGYAAA (SEQ ID NO: 19190) |
| 263 | TRCCAAGR + A + RAAA + GYAAA (SEQ ID NO: 19191) |
| 263 | TRCCAAGR + A + R + AAAGYAAA (SEQ ID NO: 19192) |
| 263 | RCCAAGR + A + RAAAGYAAA (SEQ ID NO: 19193) |
| 263 | RCCAAG + RARAAAGYAAA (SEQ ID NO: 19194) |
| 263 | RCCAA + GRARAAAGYAAA (SEQ ID NO: 19195) |
| 263 | R + CCAAGRARAAAGYAAA (SEQ ID NO: 19196) |
| 263 | RC + CAAGRARAAAGYAAA (SEQ ID NO: 19197) |
| 263 | RCCAAGRARAAA + GYAAA (SEQ ID NO: 19198) |
| 263 | RCCAAGRARAAAGY + AAA (SEQ ID NO: 19199) |
| 263 | RCCAAGRARAAA + AGYAAA (SEQ ID NO: 19200) |
| 263 | RCCAAGRAR + AAAGYAAA (SEQ ID NO: 19201) |
| 263 | R + CCAAGR + A + RAAAGYAAA (SEQ ID NO: 19202) |
| 263 | RC + CAAGR + A + RAAAGYAAA (SEQ ID NO: 19203) |
| 263 | RCCAA + GR + A + RAAAGYAAA (SEQ ID NO: 19204) |
| 263 | RCCAAG + R + A + RAAAGYAAA (SEQ ID NO: 19205) |
| 263 | RCCAAGR + A + RAAAG + YAAA (SEQ ID NO: 19206) |
| 263 | RCCAAGR + A + RAA + AGYAAA (SEQ ID NO: 19207) |
| 263 | RCCAAGR + A + RAAA + GYAAA (SEQ ID NO: 19208) |
| 263 | RCCAAGR + A + R + AAAGYAAA (SEQ ID NO: 19209) |
| 263 | RCCAAGR + A + RAAAGYA (SEQ ID NO: 19210) |
| 263 | RCCAAG + RARAAAGYA (SEQ ID NO: 19211) |
| 263 | RCCAA + GRARAAAGYA (SEQ ID NO: 19212) |
| 263 | R + CCAAGRARAAAGYA (SEQ ID NO: 19213) |
| 263 | RC + CAAGRARAAAGYA (SEQ ID NO: 19214) |
| 263 | RCCAAGRARAAA + GYA (SEQ ID NO: 19215) |
| 263 | RCCAAGRARAAAGY + A (SEQ ID NO: 19216) |
| 263 | RCCAAGRARAAA + AGYA (SEQ ID NO: 19217) |
| 263 | RCCAAGRAR + AAAGYA (SEQ ID NO: 19218) |
| 263 | R + CCAAGR + A + RAAAGYA (SEQ ID NO: 19219) |
| 263 | RC + CAAGR + A + RAAAGYA (SEQ ID NO: 19220) |
| 263 | RCCAA + GR + A + RAAAGYA (SEQ ID NO: 19221) |
| 263 | RCCAAG + R + A + RAAAGYA (SEQ ID NO: 19222) |
| 263 | RCCAAGR + A + RAAAG + YA (SEQ ID NO: 19223) |
| 263 | RCCAAGR + A + RAA + AGYA (SEQ ID NO: 19224) |
| 263 | RCCAAGR + A + RAAA + GYA (SEQ ID NO: 19225) |
| 263 | RCCAAGR + A + R + AAAGYA (SEQ ID NO: 19226) |
| 263 | RCCAAGR + A + RAAAG (SEQ ID NO: 19227) |
| 263 | RCCAAG + RARAAAG (SEQ ID NO: 19228) |
| 263 | RCCAA + GRARAAAG (SEQ ID NO: 19229) |
| 263 | R + CCAAGRARAAAG (SEQ ID NO: 19230) |
| 263 | RC + CAAGRARAAAG (SEQ ID NO: 19231) |
| 263 | RCCAAGRARAAA + G (SEQ ID NO: 19232) |
| 263 | RCCAAGRARAAAGY (SEQ ID NO: 19233) |
| 263 | RCCAAGRARAA + AG (SEQ ID NO: 19234) |
| 263 | RCCAAGRAR + AAAG (SEQ ID NO: 19235) |
| 263 | R + CCAAGR + A + RAAAG (SEQ ID NO: 19236) |
| 263 | RC + CAAGR + A + RAAAG (SEQ ID NO: 19237) |
| 263 | RCCAA + GR + A + RAAAG (SEQ ID NO: 19238) |
| 263 | RCCAAG + R + A + RAAAG (SEQ ID NO: 19239) |
| 263 | RCCAAGR + A + RAAAG (SEQ ID NO: 19240) |
| 263 | RCCAAGR + A + RAA + AG (SEQ ID NO: 19241) |
| 263 | RCCAAGR + A + RAAA + G (SEQ ID NO: 19242) |
| 263 | RCCAAGR + A + R + AAAG (SEQ ID NO: 19243) |
| 263 | TRCCAAGRARAAAGYAAA (SEQ ID NO: 19244) |
| 263 | RCCAAGRARAAAGYAAA (SEQ ID NO: 19245) |
| 263 | RCCAAGRARAAAGYA (SEQ ID NO: 19246) |
| 263 | RCCAAGRARAAAG (SEQ ID NO: 19247) |
| 263 | CCAAGAARAAAGCA (SEQ ID NO: 19248) |

Other embodiments will be evident to those of skill in the art. It should be understood that the foregoing description is provided for clarity only and is merely exemplary. The spirit and scope of the present invention are not limited to the above examples, but are encompassed by the following claims. All publications and patent applications cited above are incorporated by reference herein in their entirety for all purposes to the same extent as if each individual publication or patent application were specifically indicated to be so incorporated by reference.

LENGTHY TABLES

The patent contains a lengthy table section. A copy of the table is available in electronic form from the USPTO web site (http://seqdata.uspto.gov/?pageRequest=docDetail&DocID=US10100349B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10100349B2). An electronic copy of the "Sequence Listing" will also be available from the USPTO upon request and payment of the fee set forth in 37 CFR 1.19(b)(3).

What is claimed is:

1. A method of determining the presence of a polymorphism at one or more of a target nucleotide position in a plurality of target nucleic acid sequences, with each target nucleic acid sequence having a sense strand sequence and an antisense strand sequence, wherein the one or more of a target nucleotide position is flanked by a 5' flanking region and a 3' flanking region in each of the sense strand sequence and the antisense strand sequence comprising amplifying the target nucleic acid sequences to produce amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the amplicons have a sense strand amplicon and an antisense strand amplicon, wherein the sense strand amplicon includes a probe binding site including one or more of a target nucleotide at the one or more of a target nucleotide position with a 5' flanking region being the 3' adapter region sequence of the forward primer and with a 3' flanking region being the complement of the 3' adapter region sequence of the reverse primer, wherein the antisense strand amplicon includes a probe binding site including one or more of a target nucleotide at the one or more of a target nucleotide position with a 5' flanking region being the 3' adapter region sequence of the reverse primer and with a 3' flanking region being the complement of the 3' adaptor region of the forward primer, contacting the amplicons with sense-oriented nucleic acid probes or antisense-oriented nucleic acid probes including a label and having a probe sequence identical to the complement of the probe binding site, and detecting the label of hybridized nucleic acid probes.

2. The method of claim 1, wherein the forward primer further includes a pan degenerate region.

3. The method of claim 1 wherein the reverse primer further includes a pan degenerate region.

4. The method of claim 1 wherein the plurality of target nucleotide sequences is a population of viral nucleic acids, bacterial nucleic acids, or fungal nucleic acids.

5. The method of claim 4 wherein the viral nucleic acids are viral RNA or viral DNA.

6. The method of claim 4 wherein the bacterial nucleic acids are bacterial RNA or bacterial DNA.

7. The method of claim 4 wherein the fungal nucleic acids are fungal RNA or fungal DNA.

8. The method of claim 1 wherein the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position.

9. The method of claim 1 wherein the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position, wherein the polymorphism provides drug resistance.

10. The method of claim 1 wherein the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position, and wherein the sense oriented nucleic acid probes or the antisense oriented nucleic acid probes include wild type probes with a first label and mutant detecting probes with a second label and where the first label and the second label are spectrally resolvable.

11. The method of claim 1 wherein the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position, and wherein the sense oriented nucleic acid probes or the antisense oriented nucleic acid probes include wild type probes with a first label and mutant detecting probes with a second label and where the first label and the second label are spectrally resolvable, wherein the method further includes determining the relative amount of the wild type viral nucleic acids versus the mutated viral nucleic acids by comparing the detected labels.

12. The method of claim 1 wherein the plurality of target nucleotide sequences is a population of viral nucleic acids including wild type viral nucleic acids with a wild type nucleotide at the one or more of a target nucleotide position and mutated viral nucleic acids with the polymorphism at the one or more of a target nucleotide position, and wherein the sense oriented nucleic acid probes or the antisense oriented nucleic acid probes include wild type probes with a first label and mutant detecting probes with a second label and where the first label and the second label are spectrally resolvable, wherein the method further includes determining the relative amount of the wild type viral nucleic acids versus the mutated viral nucleic acids by comparing the detected labels, wherein the relative amount is indicative of drug resistance of the population of viral nucleic acids.

13. The method of claim 1 wherein the plurality of target nucleotide sequences is a population of viral nucleic acids including wild type viral nucleic acids with a wild type nucleotide at the one or more of a target nucleotide position and mutated viral nucleic acid with the polymorphism at the one or more of a target nucleotide position, and wherein the sense oriented nucleic acid probes or the antisense oriented nucleic acid probes include wild type probes with a first label and mutant detecting probes with a second label and where the first label and the second label are spectrally resolvable, wherein the method further includes determining the relative amount of the wild type viral nucleic acids versus the mutated viral nucleic acids by comparing the detected labels, wherein the relative amount is indicative of the presence of virulent versus non-virulent strains of virus.

14. The method of claim 1 wherein the plurality of target nucleotide sequences is a population of viral nucleic acids with first viral nucleic acids having a first nucleotide at the one or more of a target nucleotide position indicative of a non-virulent strain of virus and mutated viral nucleic acids with the polymorphism at the one or more of a target nucleotide position indicative of a virulent strain of virus, and wherein the sense oriented nucleic acid probes or the antisense oriented nucleic acid probes include mutant detecting probes with a first label and wherein detecting the first label is indicative of the presence of the virulent strain of virus.

15. The method of claim 1 wherein the forward primers and the reverse primers have constant adaptor regions and variable pan degenerate regions.

16. The method of claim 1 wherein the nucleic acid probes include molecular beacons, hydrolysis probes, locked nucleic acid probes, or FRET probes.

17. The method of claim 1 wherein the plurality of target nucleotide sequences comprises a population of HIV viral DNA, Newcastle disease viral DNA, or hepatitis C viral DNA.

18. The method of claim 1 wherein the polymorphism at the one or more of a target nucleotide position is a single nucleotide polymorphism.

19. The method of claim 1 wherein the 5' flanking region to the one or more of a target nucleotide position is between about 1 to about 10 nucleotides in length and wherein the 3' flanking region to the one or more of a target nucleotide position is between about 1 to about 10 nucleotides in length.

20. The method of claim 1 wherein the 5' flanking region to the one or more of a target nucleotide position is between about 3 to about 8 nucleotides in length and wherein the 3' flanking region to the one or more of a target nucleotide position is between about 3 to about 8 nucleotides in length.

21. The method of claim 1 wherein the 5' flanking region to the one or more of a target nucleotide position is between about 6 to about 8 nucleotides in length and wherein the 3' flanking region to the one or more of a target nucleotide position is between about 6 to about 8 nucleotides in length.

22. The method of claim 1 wherein the 5' flanking region to the one or more of a target nucleotide position is about 7 nucleotides in length and wherein the 3' flanking region to the one or more of a target nucleotide position is about 7 nucleotides in length.

23. The method of claim 1 wherein the sense oriented nucleic acid probe or the antisense oriented nucleic acid probe includes a complement to the nucleotide at the one or more of a target nucleotide position which is flanked by a 5' flanking region and a 3' flanking region.

24. The method of claim 1 wherein the sense oriented nucleic acid probe or the antisense oriented nucleic acid probe is an exact complement of the probe binding site of the amplicons.

25. The method of claim 1 wherein the sense oriented nucleic acid probe or the antisense oriented nucleic acid probe is about 10 to about 20 nucleotides in length.

26. The method of claim 1 wherein the sense oriented nucleic acid probe or the antisense oriented nucleic acid probe is about 12 to about 15 nucleotides in length.

27. The method of claim 1 wherein the sense oriented nucleic acid probe or the antisense oriented nucleic acid probe is about 15 nucleotides in length.

28. The method of claim 2 wherein the pan degenerate region is between about 25 to about 35 nucleotides in length.

29. The method of claim 2 wherein the pan degenerate region is between about 28 to about 32 nucleotides in length.

30. The method of claim 2 wherein the pan degenerate region is about 30 nucleotides in length.

31. The method of claim 1 wherein the label is a fluorescent label.

32. A method of mutating flanking regions of one or more of a target nucleotide position in a plurality of target nucleic acid sequences to provide a known probe binding site on amplicons, with each target nucleic acid sequence having a sense strand sequence and an antisense strand sequence, wherein the one or more of a target nucleotide position is flanked by a 5' flanking region and a 3' flanking region in each of the sense strand sequence and the antisense strand sequence comprising
   amplifying the target nucleic acid sequence to produce the amplicons using a forward primer and a reverse primer, wherein the forward primer includes a 3' adaptor region, wherein the 3' adaptor region is a determined consensus sequence for the 5' flanking region of the sense strand,
   wherein the reverse primer includes a 3' adaptor region, wherein the 3' adaptor region is complementary to a determined consensus sequence for the 3' flanking region of the sense strand,
   wherein the amplicons have the known probe binding site determined by the determined consensus sequences from the forward and reverse primers and the target nucleotide at the one or more of a target nucleotide position.

33. The method of claim 32 wherein a polymorphism is present at the one or more of a target nucleotide position.

34. The method of claim 32 wherein a single nucleotide polymorphism is present at the one or more of a target nucleotide position.

35. A method of providing a known probe binding site sequence including one or more of a target nucleotide in amplicons of a plurality of target nucleic acid sequences, with each target nucleic acid sequence having a sense strand sequence and an antisense strand sequence, wherein one or more of a target nucleotide position is flanked by a 5' flanking region and a 3' flanking region in each of the sense strand sequence and the antisense strand sequence comprising amplifying the target nucleic acid sequence to produce the amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the known probe binding site of the amplicons is determined by the determined consensus sequences from the forward and reverse primers and the target nucleotide at the one or more of a target nucleotide position.

36. The method of claim 35, wherein the forward primer further includes a pan degenerate region.

37. The method of claim 35 wherein the reverse primer further includes a pan degenerate region.

38. The method of claim 35 wherein the one or more of a target nucleotide is a polymorphism.

39. The method of claim 35 wherein the one or more of a target nucleotide is a single nucleotide polymorphism.

40. A method of removing secondary polymorphisms flanking one or more of a target nucleotide position in a plurality of target nucleic acid sequences to provide a known probe binding site in amplicons, with each target nucleic acid sequence having a sense strand sequence and an antisense strand sequence, wherein the target nucleotide position is flanked by a 5' flanking region and a 3' flanking region in each of the sense strand sequence and the antisense strand sequence comprising amplifying the target nucleic acid sequence to produce the amplicons using a forward primer and a reverse primer, wherein the forward primer includes a 3' adaptor region, wherein the 3' adaptor region is a determined consensus sequence for the 5' flanking region of the sense strand, wherein the reverse primer includes a 3' adaptor region, wherein the 3' adaptor region is complementary to a determined consensus sequence for the 3' flanking region of the sense strand, wherein the amplicons have the known probe binding site determined by the determined consensus sequences from the forward and reverse primers and the target nucleotide at the one or more of a target nucleotide position.

41. The method of claim 40, wherein the forward primer further includes a pan degenerate region.

42. The method of claim 40 wherein the reverse primer further includes a pan degenerate region.

43. The method of claim 40 wherein a polymorphism is present at the one or more of a target nucleotide position.

44. The method of claim 40 wherein a single nucleotide polymorphism is present at the one or more of a target nucleotide position.

45. The method of claim 3 wherein the pan degenerate region is between about 25 to about 35 nucleotides in length.

46. The method of claim 3 wherein the pan degenerate region is between about 28 to about 32 nucleotides in length.

47. The method of claim 3 wherein the pan degenerate region is about 30 nucleotides in length.

\* \* \* \* \*